(12) United States Patent
Braendlin et al.

(10) Patent No.: US 12,421,211 B2
(45) Date of Patent: *Sep. 23, 2025

(54) HETEROCYCLIC COMPOUNDS

(71) Applicant: Hoffmann-La Roche Inc., Little Falls, NJ (US)

(72) Inventors: Mathis Braendlin, Basel (CH); Sandra Marie Joseph Grall-Ulsemer, Village-Neuf (FR); Xingchun Han, Shanghai (CN); Christian Lerner, Bottmingen (CH); Mingming Li, Shanghai (CN); Yongqiang Liu, Shanghai (CN); Sébastien Schmitt, Hagenthal-le-Bas (FR); Jianhua Wang, Shanghai (CN); Yongguang Wang, Shanghai (CN); Min Wang, Shanghai (CN); Song Yang, Shanghai (CN); Chengang Zhou, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/388,776

(22) Filed: Nov. 10, 2023

(65) Prior Publication Data

US 2024/0368117 A1    Nov. 7, 2024

Related U.S. Application Data

(63) Continuation of application No. 17/865,192, filed on Jul. 14, 2022, now Pat. No. 11,858,912.

(30) Foreign Application Priority Data

Jul. 15, 2021 (WO) ................ PCT/CN2021/106544

(51) Int. Cl.
| | |
|---|---|
| *C07D 401/14* | (2006.01) |
| *A61K 31/33* | (2006.01) |
| *A61P 31/04* | (2006.01) |
| *C07D 403/10* | (2006.01) |
| *C07D 403/14* | (2006.01) |

(52) U.S. Cl.
CPC ............ *C07D 401/14* (2013.01); *A61P 31/04* (2018.01); *C07D 403/10* (2013.01); *C07D 403/14* (2013.01)

(58) Field of Classification Search
CPC ........ C07D 401/14; A61K 31/33; A61P 31/04
See application file for complete search history.

*Primary Examiner* — Bruck Kifle
(74) *Attorney, Agent, or Firm* — Genentech, Inc.

(57) ABSTRACT

The invention provides novel heterocyclic compounds having the general formula (I), and pharmaceutically acceptable salts thereof, wherein X, D, $R^1$ to $R^4$, and $R^6$ to $R^{10}$ are as described herein.

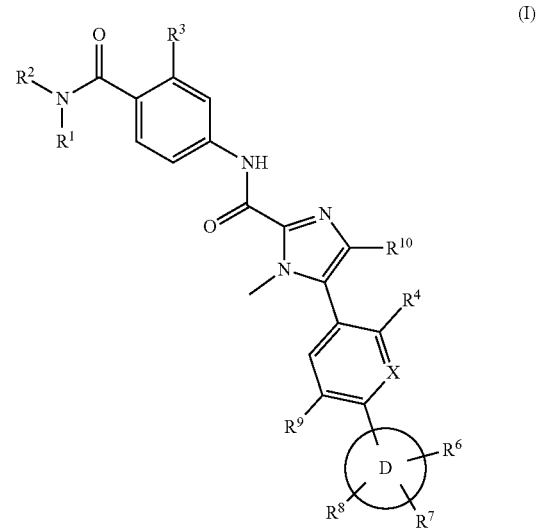

(I)

Further provided are pharmaceutical compositions including the compounds, processes of manufacturing the compounds and methods of using the compounds as medicaments, in particular methods of using the compounds as antibiotics for the treatment or prevention of bacterial infections and resulting diseases.

15 Claims, No Drawings

HETEROCYCLIC COMPOUNDS

CROSS-REFERENCE TO RELATED APPLICATIONS

This application is a Continuation of U.S. application Ser. No. 17/865,192, filed Jul. 14, 2022, which claims benefit of priority to International Patent Application No. PCT/CN2021/106544 filed Jul. 15, 2021, each of which is incorporated herein by reference in its entirety.

BACKGROUND

The present invention relates to novel heterocyclic compounds which exhibit antibacterial properties. The invention also relates to methods of using the compounds for the treatment or prevention of bacterial infections and resulting diseases, in particular for the treatment or prevention of infections with *Acinetobacter baumannii* and resulting diseases.

*Acinetobacter baumannii* is a Gram-negative, aerobic, nonfermenting bacterium recognized over the last decades as an emergining pathogen with very limited treatment options.

*A. baumannii* is considered to be a serious threat by the US Centers for Disease Control and Prevention and belongs to the so called 'ESKAPE' pathogens (*Enterococcus faecium, Staphylococcus aureus, Klebsiella pneumoniae, Acinetobacter baumannii, Pseudomonas aeruginosa* and *Enterobacter* species & *E. coli*) that currently cause the majority of nosocomial infections and effectively "escape" the activity of antimicrobial agents.

*A. baumannii* is most often encountered in intensive care units and surgical wards, where extensive antibiotic use has enabled selection for resistance against all known antimicrobials and where it causes infections that include bacteremia, pneumonia, meningitis, urinary tract infection, and wound infection.

*A. baumannii* has an exceptional ability to upregulate and acquire resistance determinants and shows an environmental persistance that allows its survival and spread in the nosocomial setting, making this organism a frequent cause of outbreaks of infection and an endemic, health care-associated pathogen.

Due to increasing antibiotic resistance to most if not all available therapeutic options, Muti-Drug Resistant (MDR) *A. baumanniii* infections, especially those caused by Carbapenem resistant *A. baumannii*, are extremely difficult or even impossible to treat with high mortality rate as well as increased morbidity and length of stay in intensive care unit.

*Acinetobacter baumannii* has been defined and still remains "a prime example of a mismatch between unmet medical needs and the current antimicrobial research and development pipeline" according to the Antimicrobial Availability Task Force (AATF) of the Infectious Diseases Society of America (IDSA). Thus, there is a high demand and need to identify compounds suitable for the treatment of diseases and infections caused by *Acinetobacter baumannii*.

The present invention provides novel compounds which exhibit activity against drug-susceptible as well as drug-resistant strains of *Acinetobacter baumannii*.

SUMMARY OF THE DISCLOSURE

In a first aspect, the present invention provides a compound of formula (I)

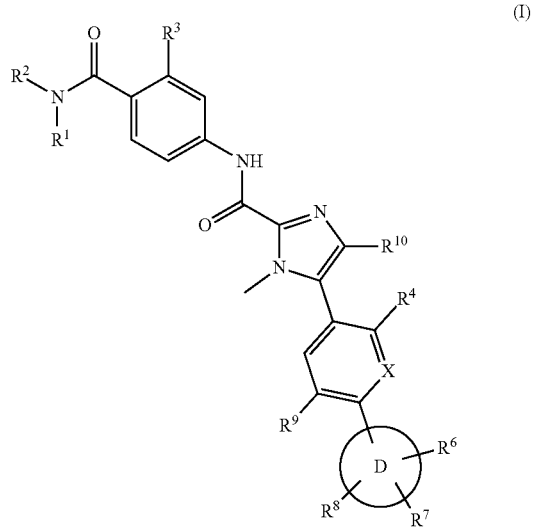

or a pharmaceutically acceptable salt thereof, wherein X, D, $R^1$ to $R^4$, and $R^6$ to $R^{10}$ are as defined herein.

In one aspect, the present invention provides a process of manufacturing the compounds of formula (I) described herein, wherein said process is as described in any one of Schemes 1 to 6 herein.

In a further aspect, the present invention provides a compound of formula (I) as described herein, when manufactured according to the processes described herein.

In a further aspect, the present invention provides a compound of formula (I) as described herein, or a pharmaceutically acceptable salt thereof, for use as therapeutically active substance.

In a further aspect, the present invention provides a pharmaceutical composition comprising a compound of formula (I) as described herein, or a pharmaceutically acceptable salt thereof, and a therapeutically inert carrier.

In a further aspect, the present invention provides a compound of formula (I) as described herein, or a pharmaceutically acceptable salt thereof, for use as antibiotic.

In a further aspect, the present invention provides a compound of formula (I) as described herein, or a pharmaceutically acceptable salt thereof, for use in the treatment or prevention of nosocomial infections and resulting diseases.

In a further aspect, the present invention provides a compound of formula (I) as described herein, or a pharmaceutically acceptable salt thereof, for use in the treatment or prevention of infections and resulting diseases caused by Gram-negative bacteria.

In a further aspect, the present invention provides a compound of formula (I) as described herein, or a pharmaceutically acceptable salt thereof, for use in the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination therof.

DETAILED DESCRIPTION OF THE DISCLOSURE

Definitions

Features, integers, characteristics, compounds, chemical moieties or groups described in conjunction with a particular aspect, embodiment or example of the invention are to be understood to be applicable to any other aspect, embodiment or example described herein, unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The following definitions are provided to facilitate understanding of certain terms used frequently herein and are not meant to limit the scope of the present disclosure. All references referred to herein are incorporated by reference in their entirety.

The term "alkyl" refers to a mono- or multivalent, e.g., a mono- or bivalent, linear or branched saturated hydrocarbon group of 1 to 6 carbon atoms ("$C_1$-$C_6$-alkyl"), e.g., 1, 2, 3, 4, 5, or 6 carbon atoms. In some embodiments, the alkyl group contains 1 to 3 carbon atoms, e.g., 1, 2 or 3 carbon atoms. Some non-limiting examples of alkyl include methyl, ethyl, propyl, 2-propyl (isopropyl), n-butyl, iso-butyl, sec-butyl, tert-butyl, and 2,2-dimethylpropyl. Particularly preferred, yet non-limiting examples of alkyl include methyl and ethyl.

The term "alkyldiyl" as used herein refers to a saturated linear or branched-chain divalent hydrocarbon radical of about one to to six carbon atoms ($C_1$-$C_6$). Examples of alkyldiyl groups include, but are not limited to, methylene (—$CH_2$—), ethylene (—$CH_2CH_2$—), propylene (—$CH_2CH_2CH_2$—), and the like. An alkyldiyl group may also be referred to as an "alkylene" group.

The term "alkoxy" refers to an alkyl group, as previously defined, attached to the parent molecular moiety via an oxygen atom. Unless otherwise specified, the alkoxy group contains 1 to 6 carbon atoms ("$C_1$-$C_6$-alkoxy"). In some preferred embodiments, the alkoxy group contains contains 1 to 4 carbon atoms. In still other embodiments, the alkoxy group contains 1 to 3 carbon atoms. Some non-limiting examples of alkoxy groups include methoxy, ethoxy, n-propoxy, isopropoxy, n-butoxy, isobutoxy and tert-butoxy. A particularly preferred, yet non-limiting example of alkoxy is methoxy.

The term "halogen" or "halo" refers to fluoro (F), chloro (Cl), bromo (Br), or iodo (I). Preferably, the term "halogen" or "halo" refers to fluoro (F), chloro (Cl) or bromo (Br). Particularly preferred, yet non-limiting examples of "halogen" or "halo" are fluoro (F) and chloro (Cl).

The term "cycloalkyl" as used herein refers to a saturated or partly unsaturated monocyclic or bicyclic hydrocarbon group of 3 to 10 ring carbon atoms ("$C_3$-$C_{10}$-cycloalkyl"). In some preferred embodiments, the cycloalkyl group is a saturated monocyclic hydrocarbon group of 3 to 8 ring carbon atoms. "Bicyclic cycloalkyl" refers to cycloalkyl moieties consisting of two saturated carbocycles having two carbon atoms in common, i.e., the bridge separating the two rings is either a single bond or a chain of one or two ring atoms, and to spirocyclic moieties, i.e., the two rings are connected via one common ring atom. Preferably, the cycloalkyl group is a saturated monocyclic hydrocarbon group of 3 to 6 ring carbon atoms, e.g., of 3, 4, 5 or 6 carbon atoms. Some non-limiting examples of cycloalkyl include cyclopropyl, cyclobutyl, cyclopentyl, cyclohexyl, cycloheptyl, and spiro[2.3]hexan-5-yl.

The term "aminoalkoxy" refers to an alkoxy group, wherein at least one of the hydrogen atoms of the alkoxy group has been replaced by an amino group. Preferably, "aminoalkoxy" refers to an alkoxy group wherein 1, 2 or 3 hydrogen atoms of the alkoxy group have been replaced by an amino group. Preferred, yet non-limiting examples of aminoalkoxy are aminomethoxy and 1-aminoethoxy.

The term "heterocyclyl" refers to a saturated or partly unsaturated mono- or bicyclic, preferably monocyclic ring system of 3 to 14 ring atoms, preferably 3 to 10 ring atoms, more preferably 3 to 8 ring atoms wherein 1, 2, or 3 of said ring atoms are heteroatoms selected from N, O and S, the remaining ring atoms being carbon. Preferably, 1 to 2 of said ring atoms are selected from N and O, the remaining ring atoms being carbon. "Bicyclic heterocyclyl" refers to heterocyclic moieties consisting of two cycles having two ring atoms in common, i.e., the bridge separating the two rings is either a single bond or a chain of one or two ring atoms, and to spirocyclic moieties, i.e., the two rings are connected via one common ring atom. Some non-limiting examples of heterocyclyl groups include azetidin-3-yl; azetidin-2-yl; oxetan-3-yl; oxetan-2-yl; piperidyl; piperazinyl; pyrrolidinyl; 2-oxopyrrolidin-1-yl; 2-oxopyrrolidin-3-yl; 5-oxopyrrolidin-2-yl; 5-oxopyrrolidin-3-yl; 2-oxo-1-piperidyl; 2-oxo-3-piperidyl; 2-oxo-4-piperidyl; 6-oxo-2-piperidyl; 6-oxo-3-piperidyl; 1-piperidinyl; 2-piperidinyl; 3-piperidinyl; 4-piperidinyl; morpholino; morpholin-2-yl; morpholin-3-yl; pyrrolidinyl (e.g., pyrrolidin-3-yl); 3-azabicyclo[3.1.0]hexan-6-yl; 2,5-diazabicyclo[2.2.1]heptan-2-yl; 2-azaspiro[3.3]heptan-2-yl; 2,6-diazaspiro[3.3]heptan-2-yl; 2,3,3a,4,6,6a-hexahydro-1H-pyrrolo[3,4-c]pyrrol-5-yl, and 3-aza-6-azoniaspiro[5.5]undecane.

The term "heterocyclylalkyl" refers to a heterocyclyl group that is bound to the parent moiety via an alkylene group. A preferred, yet non-limiting example of a heterocyclylalkyl group is azetidin-3-ylmethyl.

The term "aryl" refers to a monocyclic, bicyclic, or tricyclic carbocyclic ring system having a total of 6 to 10 ring members ("$C_6$-$C_{10}$-aryl") and wherein at least one ring in the system is aromatic. A particularly preferred, yet non-limiting example of aryl is phenyl.

The term "heteroaryl" refers to a mono- or multivalent, monocyclic or bicyclic, preferably bicyclic ring system having a total of 5 to 14 ring members, preferably, 5 to 12 ring members, and more preferably 5 to 10 ring members, wherein at least one ring in the system is aromatic, and at least one ring in the system contains one or more heteroatoms. Preferably, "heteroaryl" refers to a 5-10 membered heteroaryl comprising 1, 2, 3 or 4 heteroatoms independently selected from O, S and N. Most preferably, "heteroaryl" refers to a 5-10 membered heteroaryl comprising 1 to 2 heteroatoms independently selected from O and N. Some non-limiting examples of heteroaryl include 2-pyridyl, 3-pyridyl, 4-pyridyl, pyridazin-3-yl, pyridazin-4-yl, pyrimidin-2-yl, pyrimidin-4-yl, pyrimidin-5-yl, pyrimidin-6-yl, indol-1-yl, 1H-indol-2-yl, 1H-indol-3-yl, 1H-indol-4-yl, 1H-indol-5-yl, 1H-indol-6-yl, 1H-indol-7-yl, 1,2-benzoxazol-3-yl, 1,2-benzoxazol-4-yl, 1,2-benzoxazol-5-yl, 1,2-benzoxazol-6-yl, 1,2-benzoxazol-7-yl, 1H-indazol-3-yl, 1H-indazol-4-yl, 1H-indazol-5-yl, 1H-indazol-6-yl, 1H-indazol-7-yl, pyrazol-1-yl, 1H-pyrazol-3-yl, 1H-pyrazol-4-yl, 1H-pyrazol-5-yl, imidazol-1-yl, 1H-imidazol-2-yl, 1H-imidazol-4-yl, 1H-imidazol-5-yl, oxazol-2-yl, oxazol-4-yl, oxazol-5-yl, thiazol-4-yl, 1,2,4-oxadiazol-3-yl, 1H-triazol-5-yl, 1H-triazol-4-yl, and triazol-1-yl. Most preferably, "heteroaryl" refers to pyridyl and pyrimidinyl.

The term "hydroxy" refers to an —OH group.

The term "carboxy" refers to a group —C(O)$_2$H, i.e. a carboxylic acid group.

The term "oxo" refers to an oxygen atom that is bound to the parent moiety via a double bond (=O).

The term "amino" refers to an —NH$_2$ group.

The term "cyano" refers to a —CN (nitrile) group.

The term "carbamoyl" refers to a —C(O)NH$_2$ group.

The term "carbonyl" refers to a carbon radical having two of the four covalent bonds shared with an oxygen atom (C=O).

The term "haloalkyl" refers to an alkyl group, wherein at least one of the hydrogen atoms of the alkyl group has been replaced by a halogen atom, preferably fluoro. Preferably, "haloalkyl" refers to an alkyl group wherein 1, 2 or 3 hydrogen atoms of the alkyl group have been replaced by a halogen atom, most preferably fluoro. Non-limiting examples of haloalkyl are fluoromethyl, difluoromethyl, trifluoromethyl, trifluoroethyl, 2-fluoroethyl, and 2,2-difluoroethyl. A particularly preferred, yet non-limiting example of haloalkyl is trifluoromethyl.

The term "cyanoalkyl" refers to an alkyl group, wherein at least one of the hydrogen atoms of the alkyl group has been replaced by cyano group. Preferably, "cyanoalkyl" refers to an alkyl group wherein 1, 2 or 3 hydrogen atoms of the alkyl group have been replaced by a cyano group. Most preferably, "cyanoalkyl" refers to an alkyl group wherein 1 hydrogen atom of the alkyl group has been replaced by a cyano group. A preferred, yet non-limiting example of cyanoalkyl is cyanomethyl.

The term "alkoxyalkyl" refers to an alkyl group, wherein at least one of the hydrogen atoms of the alkyl group has been replaced by an alkoxy group. Preferably, "alkoxyalkyl" refers to an alkyl group wherein 1, 2 or 3 hydrogen atoms of the alkyl group have been replaced by an alkoxy group. Most preferably, "alkoxyalkyl" refers to an alkyl group wherein 1 hydrogen atom of the alkyl group has been replaced by an alkoxy group. A preferred, yet non-limiting example of alkoxyalkyl is 2-methoxyethyl.

The term "haloalkoxy" refers to an alkoxy group, wherein at least one of the hydrogen atoms of the alkoxy group has been replaced by a halogen atom, preferably fluoro. Preferably, "haloalkoxy" refers to an alkoxy group wherein 1, 2 or 3 hydrogen atoms of the alkoxy group have been replaced by a halogen atom, most preferably fluoro. Particularly preferred, yet non-limiting examples of haloalkoxy are fluoromethoxy (FCH$_2$O—), difluoromethoxy (F$_2$CHO—), and trifluoromethoxy (F$_3$CO—).

The term "carbamoylalkyl" refers to an alkyl group, wherein at least one of the hydrogen atoms of the alkyl group has been replaced by a carbamoyl group. Preferably, "carbamoylalkyl" refers to an alkyl group wherein 1, 2 or 3 hydrogen atoms of the alkyl group have been replaced by a carbamoyl group. Most preferably, "carbamoylalkyl" refers to an alkyl group wherein 1 hydrogen atom of the alkyl group has been replaced by a carbamoyl group. A preferred, yet non-limiting example of a carbamoylalkyl group is 2-amino-2-oxo-ethyl.

The term "carboxyalkyl" refers to an alkyl group, wherein at least one of the hydrogen atoms of the alkyl group has been replaced by a carboxy group. Preferably, "carboxyalkyl" refers to an alkyl group wherein 1, 2 or 3 hydrogen atoms of the alkyl group have been replaced by a carboxy group. Most preferably, "carboxyalkyl" refers to an alkyl group wherein 1 hydrogen atom of the alkyl group has been replaced by a carboxy group. A preferred, yet non-limiting example of a carboxyalkyl group is carboxymethyl.

The term "hydroxyalkyl" refers to an alkyl group, wherein at least one of the hydrogen atoms of the alkyl group has been replaced by a hydroxy group. Preferably, "hydroxyalkyl" refers to an alkyl group wherein 1, 2 or 3 hydrogen atoms, most preferably 1 hydrogen atom of the alkyl group have been replaced by a hydroxy group. Preferred, yet non-limiting examples of hydroxyalkyl are hydroxymethyl, hydroxyethyl (e.g. 2-hydroxyethyl), and 3-hydroxy-3-methyl-butyl.

The term "pharmaceutically acceptable salt" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as formic acid, acetic acid, trifluoroacetic acid, propionic acid, glycolic acid, pyruvic acid, oxalic acid, maleic acid, malonic acid, succinic acid, fumaric acid, tartaric acid, lactic acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are hydrochlorides, fumarates, formates, lactates (in particular derived from L-(+)-lactic acid), tartrates (in particular derived from L-(+)-tartaric acid) and trifluoroacetates.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention, the asymmetric carbon atom can be of the "R" or "S" configuration.

The term "treatment" as used herein includes: (1) inhibiting the state, disorder or condition (e.g. arresting, reducing or delaying the development of the disease, or a relapse thereof in case of maintenance treatment, of at least one clinical or subclinical symptom thereof); and/or (2) relieving the condition (i.e., causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

The term "mammal" as used herein includes both humans and non-humans and includes but is not limited to humans, non-human primates, canines, felines, murines, bovines, equines, and porcines. In a particularly preferred embodiment, the term "mammal" refers to humans.

The term "nosocomial infection" refers to a hospital-acquired infection (HAI), which is an infection that is acquired in a hospital or other health care facility. To emphasize both hospital and nonhospital settings, it is sometimes instead called a health care-associated infection (HAI or HCAI). Such an infection can be acquired in hospitals, nursing homes, rehabilitation facilities, outpatient clinics, or other clinical settings.

Compounds of the Invention

In a first aspect, the present invention provides a compound of formula (I)

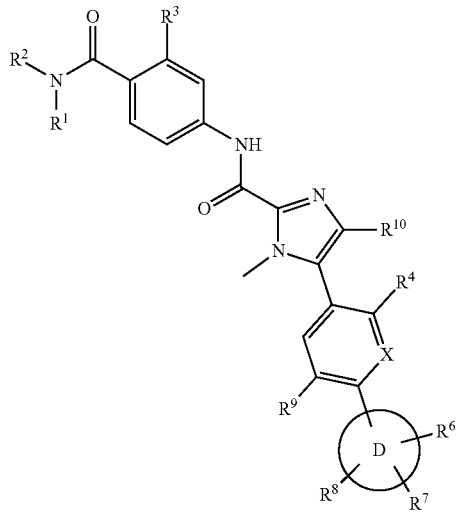

or a pharmaceutically acceptable salt thereof, wherein:

X is N or C—$R^5$;

$R^1$ and $R^2$, taken together with the nitrogen atom to which they are attached, form a group

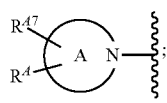

or
$R^1$ is a group

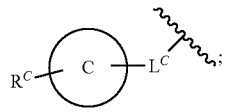

and $R^2$ is hydrogen;
$R^3$ is halogen or $C_1$-$C_6$-alkyl;
$R^4$ is selected from hydrogen, halogen, $C_1$-$C_6$-alkyl, and $C_1$-$C_6$-alkoxy;

$R^5$ is selected from hydrogen, halogen, and $C_1$-$C_6$-alkyl;
$R^6$ is selected from hydrogen, $C_1$-$C_6$-alkyl, carbamoyl-$C_1$-$C_6$-alkyl-NH—, amino, halogen, hydroxy-$C_1$-$C_6$-alkyl, halo-$C_1$-$C_6$-alkyl, and a group

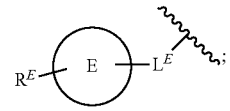

$R^7$ is selected from hydrogen, $C_1$-$C_6$-alkyl, $C_1$-$C_6$-alkoxy-$C_1$-$C_6$-alkyl-, hydroxy-$C_1$-$C_6$-alkyl, halo-$C_1$-$C_6$-alkyl, carbamoyl-$C_1$-$C_6$-alkyl, $C_1$-$C_6$-alkyl-NH—C(O)—$C_1$-$C_6$-alkyl-, $C_1$-$C_6$-alkyl-NH—C(O)—NH—$C_1$-$C_6$-alkyl-, cyano-$C_1$-$C_6$-alkyl, $C_1$-$C_6$-alkyl-SO$_2$—$C_1$-$C_6$-alkyl-, halo-$C_1$-$C_6$-alkoxy-$C_1$-$C_6$-alkyl-, amino-$C_1$-$C_6$-alkoxy-$C_1$-$C_6$-alkyl-, and a group

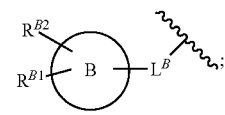

and $R^8$ is selected from hydrogen, halogen, $C_1$-$C_6$-alkyl, halo-$C_1$-$C_6$-alkyl, and $C_1$-$C_6$-alkoxy-$C_1$-$C_6$-alkyl; or
$R^7$ and $R^8$, taken together with the atoms to which they are attached, form a 3- to 14-membered heterocycle;
$R^9$ and $R^{10}$ are each independently hydrogen or halogen;
$R^A$ is selected from hydrogen, $(C_1$-$C_6$-alkyl)$_2$N—$C_1$-$C_6$-alkyl-C(O)—, $(R^{A6})_3$N$^+$—$C_1$-$C_6$-alkyl-C(O)—, and a group

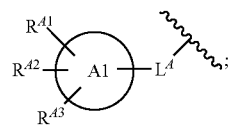

$R^{A1}$ is selected from hydrogen, hydroxy, amino, $C_1$-$C_6$-alkyl, halo-$C_1$-$C_6$-alkyl, hydoxy-$C_1$-$C_6$-alkyl, amino-$C_1$-$C_6$-alkyl, carbamoyl-$C_1$-$C_6$-alkyl, $C_1$-$C_6$-alkoxy-$C_1$-$C_6$-alkyl, H$_2$N—SO$_2$—$C_1$-$C_6$-alkyl-, H$_2$N—NH—C(O)—$C_1$-$C_6$-alkyl-, $C_1$-$C_6$-alkoxy, oxo, carbamoyl, and a group

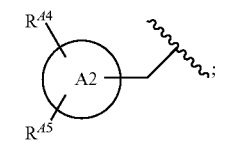

$R^{A2}$ is selected from hydrogen, hydroxy, amino, $C_1$-$C_6$-alkyl, carboxy-$C_1$-$C_6$-alkyl, and carbamoyl-$C_1$-$C_6$-alkyl;
$R^{A3}$, $R^{A4}$, $R^{A5}$, $R^{C2}$, and $R^{C3}$ are each independently selected from hydrogen and $C_1$-$C_6$-alkyl;
each $R^{A6}$ is independently selected from $C_1$-$C_6$-alkyl, amino-$C_1$-$C_6$-alkyl, $C_1$-$C_6$-alkyl-NH—$C_1$-$C_6$-alkyl-, $(C_1$-$C_6$-alkyl)$_2$N—$C_1$-$C_6$-alkyl-, carboxy-$C_1$-$C_6$-alkyl-, and (3- to 14-membered heterocyclyl)-$C_1$-$C_6$-alkyl-;
$R^{A7}$ is selected from hydrogen and $C_1$-$C_6$-alkyl;

$R^{B1}$ is selected from hydrogen, halogen, cyano, amino, oxo, $C_1$-$C_6$-alkyl, $C_1$-$C_6$-alkoxy, and 3- to 14-membered heterocyclyl;

$R^{B2}$ is selected from hydrogen, halogen, and $C_1$-$C_6$-alkyl;

$R^C$ is selected from hydrogen, $(C_1$-$C_6$-alkyl$)_2$N—$C_1$-$C_6$-alkyl-C(O)—, $(C_1$-$C_6$-alkyl$)_3$N$^+$—$C_1$-$C_6$-alkyl-C(O)—, and a group

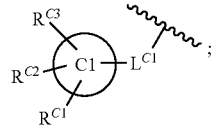

$R^{C1}$ is hydroxy;

$R^E$ is selected from $C_1$-$C_6$-alkyl, $C_1$-$C_6$-alkoxy, and halogen;

$L^A$ is selected from —$C_1$-$C_6$-alkyldiyl-, carbonyl, —C(O)—NH—, —NH—C(O)—, —C(O)—N($C_1$-$C_6$-alkyl)-, —N($C_1$-$C_6$-alkyl)-C(O)—, —$C_1$-$C_6$-alkyldiyl-NH—C(O)—, —SO$_2$—NH—, —NH—SO$_2$—, —$C_1$-$C_6$-alkyldiyl-C(O)—, and —C(O)—$C_1$-$C_6$-alkyldiyl-C(O)—;

$L^B$ is selected from a covalent bond, —$C_1$-$C_6$-alkyldiyl-, —NH—C(O)—$C_1$-$C_6$-alkyldiyl-, —C(O)—NH—$C_1$-$C_6$-alkyldiyl-, —NH—C(O)—NH—$C_1$-$C_6$-alkyldiyl-, —C(O)—$C_1$-$C_6$-alkyldiyl-, and —SO$_2$—NH—$C_1$-$C_6$-alkyldiyl-;

$L^C$ and $L^E$ are each independently a covalent bond or —$C_1$-$C_6$-alkyldiyl-;

$L^{C1}$ is —NH—C(O)— or carbonyl;

A, C, and C$_1$ are each independently a 3- to 14-membered heterocyclyl;

A2 is selected from 3- to 14-membered heterocyclyl and $C_6$-$C_{10}$-aryl;

A1 is selected from 3- to 14-membered heterocyclyl, 5- to 14-membered heteroaryl, and $C_3$-$C_{10}$-cycloalkyl;

B is selected from 5- to 14-membered heteroaryl, 3- to 14-membered heterocyclyl, $C_3$-$C_{10}$-cycloalkyl, and $C_6$-$C_{10}$-aryl;

D is a 5- to 14-membered heteroaryl;

E is selected from 5- to 14-membered heteroaryl, 3- to 14-membered heterocyclyl, and $C_6$-$C_{10}$-aryl; and a wavy line represents the point of attachment of the respective R group to the remainder of formula (I).

In one embodiment, the present invention provides a compound of formula (I) as defined herein, or a pharmaceutically acceptable salt thereof, wherein:

X is N or C—$R^5$;

$R^1$ and $R^2$, taken together with the nitrogen atom to which they are attached, form a group

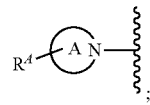

or $R^1$ is a group

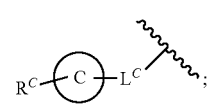

and $R^2$ is hydrogen;

$R^3$ is halogen or $C_1$-$C_6$-alkyl;

$R^4$ is selected from hydrogen, halogen, and $C_1$-$C_6$-alkyl, and $C_1$-$C_6$-alkoxy;

$R^5$ is selected from hydrogen, halogen, and $C_1$-$C_6$-alkyl;

$R^6$ is selected from hydrogen, $C_1$-$C_6$-alkyl, carbamoyl-$C_1$-$C_6$-alkyl-NH—, amino, halogen, hydroxy-$C_1$-$C_6$-alkyl, halo-$C_1$-$C_6$-alkyl, and a group

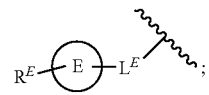

$R^7$ is selected from hydrogen, $C_1$-$C_6$-alkyl, $C_1$-$C_6$-alkoxy-$C_1$-$C_6$-alkyl-, hydroxy-$C_1$-$C_6$-alkyl, halo-$C_1$-$C_6$-alkyl, carbamoyl-$C_1$-$C_6$-alkyl, $C_1$-$C_6$-alkyl-NH—C(O)—$C_1$-$C_6$-alkyl-, $C_1$-$C_6$-alkyl-NH—C(O)—NH—$C_1$-$C_6$-alkyl-, cyano-$C_1$-$C_6$-alkyl, $C_1$-$C_6$-alkyl-SO$_2$—$C_1$-$C_6$-alkyl-, halo-$C_1$-$C_6$-alkoxy-$C_1$-$C_6$-alkyl-, amino-$C_1$-$C_6$-alkoxy-$C_1$-$C_6$-alkyl-, and a group

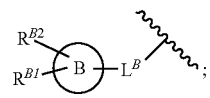

and $R^8$ is selected from hydrogen, halogen, $C_1$-$C_6$-alkyl, halo-$C_1$-$C_6$-alkyl, and $C_1$-$C_6$-alkoxy-$C_1$-$C_6$-alkyl; or $R^7$ and $R^8$, taken together with the atoms to which they are attached, form a 3- to 14-membered heterocycle;

$R^9$ and $R^{10}$ are each independently hydrogen or halogen;

$R^A$ is selected from hydrogen, $(C_1$-$C_6$-alkyl$)_2$N—$C_1$-$C_6$-alkyl-C(O)—, $(R^{A6})_3$N$^+$—$C_1$-$C_6$-alkyl-C(O)—, and a group

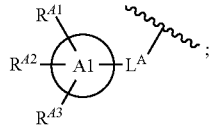

$R^{A1}$ is selected from hydrogen, hydroxy, amino, $C_1$-$C_6$-alkyl, halo-$C_1$-$C_6$-alkyl, hydoxy-$C_1$-$C_6$-alkyl, amino-$C_1$-$C_6$-alkyl, carbamoyl-$C_1$-$C_6$-alkyl, $C_1$-$C_6$-alkoxy-$C_1$-$C_6$-alkyl, H$_2$N—SO$_2$—$C_1$-$C_6$-alkyl-, H$_2$N—NH—C(O)—$C_1$-$C_6$-alkyl-, $C_1$-$C_6$-alkoxy, oxo, carbamoyl, and a group

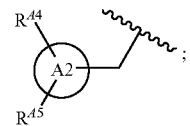

$R^{A2}$ is selected from hydrogen, hydroxy, amino, $C_1$-$C_6$-alkyl, carboxy-$C_1$-$C_6$-alkyl, and carbamoyl-$C_1$-$C_6$-alkyl;

$R^{A3}$, $R^{A4}$, $R^{A5}$, $R^{C2}$, and $R^{C3}$ are each independently selected from hydrogen and $C_1$-$C_6$-alkyl;

each $R^{A6}$ is independently selected from $C_1$-$C_6$-alkyl, amino-$C_1$-$C_6$-alkyl, carboxy-$C_1$-$C_6$-alkyl, and (3- to 14-membered heterocyclyl)-$C_1$-$C_6$-alkyl-;

$R^{B1}$ is selected from hydrogen, halogen, cyano, amino, oxo, $C_1$-$C_6$-alkyl, and $C_1$-$C_6$-alkoxy;

$R^{B2}$ is selected from hydrogen, halogen, and $C_1$-$C_6$-alkyl;

$R^C$ is selected from hydrogen, $(C_1$-$C_6$-alkyl$)_2$N—$C_1$-$C_6$-alkyl-C(O)—, $(C_1$-$C_6$-alkyl$)_3$N$^+$—$C_1$-$C_6$-alkyl-C(O)—, and a group

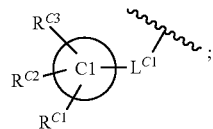

$R^{C1}$ is hydroxy;

$R^E$ is selected from $C_1$-$C_6$-alkyl, $C_1$-$C_6$-alkoxy, and halogen;

$L^A$ is selected from —$C_1$-$C_6$-alkyldiyl-, carbonyl, —C(O)—NH—, and —$C_1$-$C_6$-alkyldiyl-C(O)—;

$L^B$ is selected from a covalent bond, —$C_1$-$C_6$-alkyldiyl-, —NH—C(O)—$C_1$-$C_6$-alkyldiyl-, —C(O)—NH—$C_1$-$C_6$-alkyldiyl-, —NH—C(O)—NH—$C_1$-$C_6$-alkyldiyl-, —C(O)—$C_1$-$C_6$-alkyldiyl-, and —SO$_2$—NH—$C_1$-$C_6$-alkyldiyl-;

$L^C$ and $L^E$ are each independently a covalent bond or —$C_1$-$C_6$-alkyldiyl-;

$L^{C1}$ is —NH—C(O)— or carbonyl;

A, A2, C, and $C_1$ are each independently a 3- to 14-membered heterocyclyl;

A1 is selected from 3- to 14-membered heterocyclyl and $C_3$-$C_{10}$-cycloalkyl;

B is selected from 3- to 14-membered heteroaryl, 3- to 14-membered heterocyclyl, $C_3$-$C_{10}$-cycloalkyl, and $C_6$-$C_{10}$-aryl;

D is a 3- to 14-membered heteroaryl;

E is selected from 3- to 14-membered heteroaryl, 3- to 14-membered heterocyclyl, and $C_6$-$C_{10}$-aryl; and a wavy line represents the point of attachment of the respective R group to the remainder of formula (I).

In one embodiment, the present invention provides a compound of formula (I) as defined herein, or a pharmaceutically acceptable salt thereof, wherein:

$R^1$ and $R^2$, taken together with the nitrogen atom to which they are attached, form a group

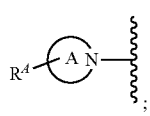

$R^A$ is selected from $(R^{A6})_3$N$^+$—$C_1$-$C_6$-alkyl-C(O)—, and a group

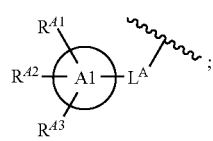

$R^{A1}$ is selected from hydroxy, $C_1$-$C_6$-alkyl, carbamoyl-$C_1$-$C_6$-alkyl, and a group

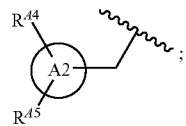

$R^{A2}$ is selected from $C_1$-$C_6$-alkyl, carboxy-$C_1$-$C_6$-alkyl, and carbamoyl-$C_1$-$C_6$-alkyl;

$R^{A3}$ is selected from hydrogen and $C_1$-$C_6$-alkyl;

$R^{A4}$ and $R^{A5}$ are hydrogen;

each $R^{A6}$ is independently selected from amino-$C_1$-$C_6$-alkyl and carboxy-$C_1$-$C_6$-alkyl;

$L^A$ is carbonyl; and

A, A1 and A2 are each independently a 3- to 14-membered heterocyclyl.

In a preferred embodiment, the present invention provides a compound of formula (I) as defined herein, or a pharmaceutically acceptable salt thereof, wherein:

$R^1$ and $R^2$, taken together with the nitrogen atom to which they are attached, form a group

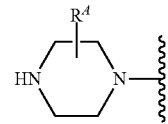

or a group

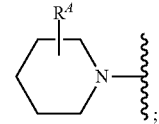

$R^A$ is selected from $(R^{A6})_3$N$^+$—(CH$_2$)$_3$—C(O)—, and a group

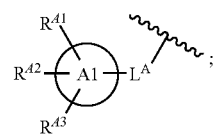

$R^{A1}$ is selected from hydroxy, methyl, 2-amino-2-oxo-ethyl, and a group

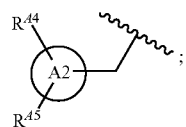

$R^{A2}$ is selected from methyl, carboxymethyl, and 2-amino-2-oxo-ethyl;

$R^{A3}$ is selected from hydrogen and methyl;

$R^{A4}$ and $R^{A5}$ are hydrogen;

each $R^{A6}$ is independently selected from aminopropyl and carboxymethyl;

$L^A$ is carbonyl;

A1 is selected from pyrrolidinyl, piperazinyl, piperidinyl, and 3-azabicyclo[3.1.0]hexan-6-yl; and A2 is azetidinyl.

In a particularly preferred embodiment, the present invention provides a compound of formula (I) as described herein, or a pharmaceutically acceptable salt thereof, wherein $R^1$ and $R^2$, taken together with the nitrogen atom to which they are attached, form a group

or a group

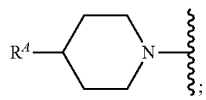

wherein $R^A$ is as defined herein.

In a preferred embodiment, the present invention provides a compound of formula (I) as described herein, or a pharmaceutically acceptable salt thereof, wherein $L^A$ is selected from —$C_1$-$C_6$-alkyldiyl-, carbonyl, —C(O)—NH—, —NH—C(O)—, —C(O)—N($C_1$-$C_6$-alkyl)-, —$C_1$-$C_6$-alkyldiyl-NH—C(O)—, —$SO_2$—NH—, —NH—$SO_2$—, —$C_1$-$C_6$-alkyldiyl-C(O)—, and —C(O)—$C_1$-$C_6$-alkyldiyl-C(O)—.

In a preferred embodiment, the present invention provides a compound of formula (I) as described herein, or a pharmaceutically acceptable salt thereof, wherein $L^A$ is selected from —$C_1$-$C_6$-alkyldiyl-, carbonyl, —C(O)—NH—, —$SO_2$—NH—, and —$C_1$-$C_6$-alkyldiyl-C(O)—.

In one embodiment, the present invention provides a compound of formula (I) as described herein, or a pharmaceutically acceptable salt thereof, wherein:

$R^1$ is a group

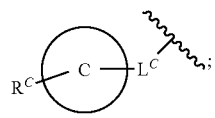

$R^2$ is hydrogen;

$R^C$ is selected from hydrogen, ($C_1$-$C_6$-alkyl)$_2$N—$C_1$-$C_6$-alkyl-C(O)—, ($C_1$-$C_6$-alkyl)$_3$N$^+$—$C_1$-$C_6$-alkyl-C(O)—, and a group

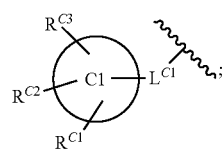

$R^{C1}$ is hydroxy;

$R^{C2}$ and $R^{C3}$ are each independently selected from hydrogen and $C_1$-$C_6$-alkyl;

$L^C$ is a covalent bond or —$C_1$-$C_6$-alkyldiyl-;

$L^{C1}$ is —NH—C(O)— or carbonyl; and

C and C1 are each independently a 3- to 14-membered heterocyclyl.

In a preferred embodiment, the present invention provides a compound of formula (I) as described herein, or a pharmaceutically acceptable salt thereof, wherein:

$R^1$ is a group

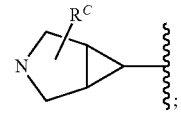

$R^2$ is hydrogen;

$R^C$ is selected from hydrogen, ($C_1$-$C_6$-alkyl)$_2$N—$C_1$-$C_6$-alkyl-C(O)—, ($C_1$-$C_6$-alkyl)$_3$N$^+$—$C_1$-$C_6$-alkyl-C(O)—, and a group

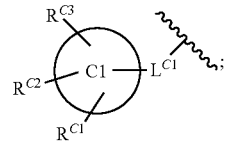

$R^{C1}$ is hydroxy;

$R^{C2}$ and $R^{C3}$ are each independently selected from hydrogen and $C_1$-$C_6$-alkyl;

$L^{C1}$ is —NH—C(O)— or carbonyl; and $C_1$ is a 3- to 14-membered heterocyclyl.

In a further preferred embodiment, the present invention provides a compound of formula (I) as defined herein, or a pharmaceutically acceptable salt thereof, wherein $R^1$ and $R^2$, taken together with the nitrogen atom to which they are attached, form a group

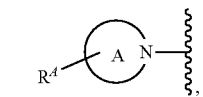

which is

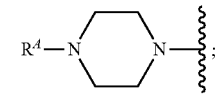

wherein $R^A$ is as defined herein.

In a further preferred embodiment, the present invention provides a compound of formula (I) as defined herein, or a pharmaceutically acceptable salt thereof, wherein $R^1$ and $R^2$, taken together with the nitrogen atom to which they are attached, form a group

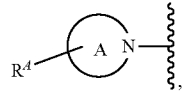

which is

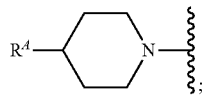

wherein $R^4$ is as defined herein.

In one embodiment, the present invention provides a compound of formula (I) as defined herein, or a pharmaceutically acceptable salt thereof, wherein $R^3$ is halogen.

In a preferred embodiment, the present invention provides a compound of formula (I) as defined herein, or a pharmaceutically acceptable salt thereof, wherein $R^3$ is chloro or fluoro.

In a particularly preferred embodiment, the present invention provides a compound of formula (I) as defined herein, or a pharmaceutically acceptable salt thereof, wherein $R^3$ is chloro.

In one embodiment, the present invention provides a compound of formula (I) as defined herein, or a pharmaceutically acceptable salt thereof, wherein $R^3$ is $C_1$-$C_6$-alkyl.

In a preferred embodiment, the present invention provides a compound of formula (I) as defined herein, or a pharmaceutically acceptable salt thereof, wherein $R^3$ is methyl.

In one embodiment, the present invention provides a compound of formula (I) as defined herein, or a pharmaceutically acceptable salt thereof, wherein:
X is C—$R^5$;
$R^4$ and $R^5$ are both halogen; and
$R^9$ is hydrogen.

In a preferred embodiment, the present invention provides a compound of formula (I) as defined herein, or a pharmaceutically acceptable salt thereof, wherein:
X is C—$R^5$;
$R^4$ is fluoro or chloro;
$R^5$ is fluoro; and
$R^9$ is hydrogen.

In one embodiment, the present invention provides a compound of formula (I) as defined herein, or a pharmaceutically acceptable salt thereof, wherein:
X is C—$R^5$;
$R^4$ is selected from halogen and $C_1$-$C_6$-alkyl;
$R^5$ is halogen; and
$R^9$ is hydrogen.

In a preferred embodiment, the present invention provides a compound of formula (I) as defined herein, or a pharmaceutically acceptable salt thereof, wherein:
X is C—$R^5$;
$R^4$ is selected from methyl, fluoro and chloro;
$R^5$ is fluoro; and
$R^9$ is hydrogen.

In one embodiment, the present invention provides a compound of formula (I) as defined herein, or a pharmaceutically acceptable salt thereof, wherein:
$R^6$ is selected from hydrogen, $C_1$-$C_6$-alkyl, and a group

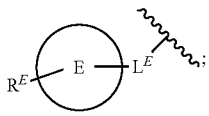

$R^7$ is selected from hydrogen, $C_1$-$C_6$-alkoxy-$C_1$-$C_6$-alkyl-, and a group

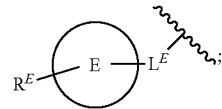

$R^8$ is selected from hydrogen, halogen, $C_1$-$C_6$-alkyl, and halo-$C_1$-$C_6$-alkyl;
$R^{B1}$ is selected from hydrogen and halogen;
$R^{B2}$ is hydrogen;
$R^E$ is halogen;
$L^B$ is selected from —$C_1$-$C_6$-alkyldiyl- and —NH—C(O)—$C_1$-$C_6$-alkyldiyl-;
$L^E$ is a covalent bond;
B and D are each independently a 3- to 14-membered heteroaryl; and
E is $C_6$-$C_{10}$-aryl.

In a preferred embodiment, the present invention provides a compound of formula (I) as defined herein, or a pharmaceutically acceptable salt thereof, wherein:
$R^6$ is selected from hydrogen, methyl, and a group

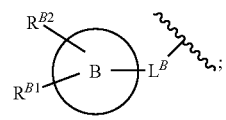

$R^7$ is selected from hydrogen, 2-methoxyethyl, and a group

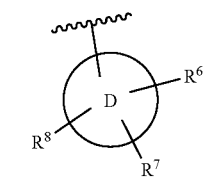

$R^8$ is selected from hydrogen, chloro, methyl, and difluoromethyl;
$R^{B1}$ is selected from hydrogen and fluoro;
$R^{B2}$ is hydrogen;
$R^E$ is fluoro;
$L^B$ is selected from —$CH_2$— and —NH—C(O)—$CH_2$—;
$L^E$ is a covalent bond;
B is selected from pyridyl and pyridazinyl;
D is pyrazolyl; and
E is phenyl.

In a preferred embodiment, the present invention provides a compound of formula (I) as defined herein, or a pharmaceutically acceptable salt thereof, wherein $R^{10}$ is hydrogen.

In a preferred embodiment, the present invention provides a compound of formula (I) as described herein, or a pharmaceutically acceptable salt thereof, wherein the group

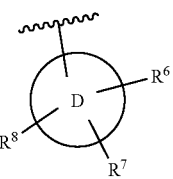

is a group

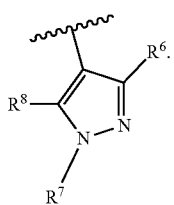

In one embodiment, the present invention provides a compound of formula (I) as described herein, or a pharmaceutically acceptable salt thereof, wherein:

X is C—$R^5$;

$R^1$ and $R^2$, taken together with the nitrogen atom to which they are attached, form a group

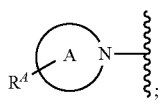

$R^3$, $R^4$, $R^5$ and $R^E$ are each independently halogen;

$R^6$ is selected from hydrogen, $C_1$-$C_6$-alkyl, and a group

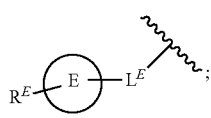

$R^7$ is selected from hydrogen, $C_1$-$C_6$-alkoxy-$C_1$-$C_6$-alkyl-, and a group

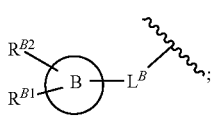

$R^8$ is selected from hydrogen, halogen, $C_1$-$C_6$-alkyl, and halo-$C_1$-$C_6$-alkyl;

$R^9$, $R^{10}$, $R^{44}$, $R^{45}$, and $R^{B2}$ are hydrogen;

$R^A$ is selected from $(R^{46})_3N^+$—$C_1$-$C_6$-alkyl-C(O)—, and a group

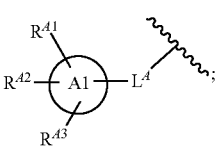

$R^{41}$ is selected from hydroxy, $C_1$-$C_6$-alkyl, carbamoyl-$C_1$-$C_6$-alkyl, and a group

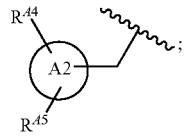

$R^{42}$ is selected from $C_1$-$C_6$-alkyl, carboxy-$C_1$-$C_6$-alkyl, and carbamoyl-$C_1$-$C_6$-alkyl;

$R^{43}$ is selected from hydrogen and $C_1$-$C_6$-alkyl;

each $R^{46}$ is independently selected from amino-$C_1$-$C_6$-alkyl and carboxy-$C_1$-$C_6$-alkyl;

$R^{B1}$ is selected from hydrogen and halogen;

$L^A$ is carbonyl;

$L^B$ is selected from —$C_1$-$C_6$-alkyldiyl- and —NH—C(O)—$C_1$-$C_6$-alkyldiyl-;

$L^E$ is a covalent bond;

A, A1 and A2 are each independently a 3- to 14-membered heterocyclyl;

B and D are each independently a 3- to 14-membered heteroaryl; and

E is $C_6$-$C_{10}$-aryl.

In a preferred embodiment, the present invention provides a compound of formula (I) as described herein, or a pharmaceutically acceptable salt thereof, wherein:

X is C—$R^5$;

$R^1$ and $R^2$, taken together with the nitrogen atom to which they are attached, form a group

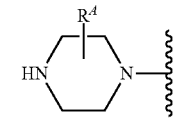

or a group

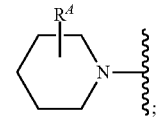

$R^3$ is chloro;

$R^4$ is fluoro or chloro;

$R^5$ and $R^E$ are fluoro;

$R^6$ is selected from hydrogen, methyl, and a group

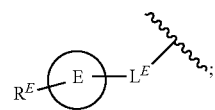

$R^7$ is selected from hydrogen, 2-methoxyethyl, and a group

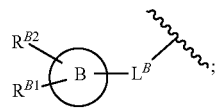

$R^8$ is selected from hydrogen, chloro, methyl, and difluoromethyl;
$R^9$, $R^{10}$, $R^{A4}$, $R^{A5}$, and $R^{B2}$ are hydrogen;
$R^A$ is selected from $(R^{A6})_3N^+$—$(CH_2)_3$—C(O)—, and a group

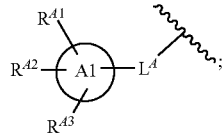

$R^{A1}$ is selected from hydroxy, methyl, 2-amino-2-oxoethyl, and a group

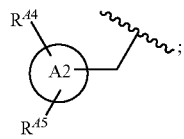

$R^{A2}$ is selected from methyl, carboxymethyl, and 2-amino-2-oxo-ethyl;
$R^{A3}$ is selected from hydrogen and methyl;
each $R^{A6}$ is independently selected from aminopropyl and carboxymethyl;
$R^{B1}$ is selected from hydrogen and fluoro;
$L^A$ is carbonyl;
$L^B$ is selected from —$CH_2$— and —NH—C(O)—$CH_2$—;
$L^E$ is a covalent bond;
A1 is selected from pyrrolidinyl, piperazinyl, piperidinyl, and 3-azabicyclo[3.1.0]hexan-6-yl;
A2 is azetidinyl;
B is selected from pyridyl and pyridazinyl;
D is pyrazolyl; and
E is phenyl.

In one embodiment, the present invention provides a compound of formula (I) as described herein, or a pharmaceutically acceptable salt thereof, wherein:
X is C—$R^5$;
$R^1$ and $R^2$, taken together with the nitrogen atom to which they are attached, form a group

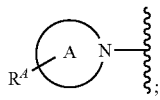

$R^3$, $R^4$, and $R^5$ are each independently halogen;
$R^7$ is $C_1$-$C_6$-alkoxy-$C_1$-$C_6$-alkyl-;
$R^8$ is $C_1$-$C_6$-alkyl;
$R^6$, $R^9$, $R^{10}$, $R^{A3}$, $R^{A4}$, and $R^{A5}$ are hydrogen;
$R^A$ is a group R

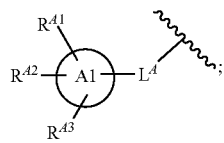

$R^{A1}$ is a group

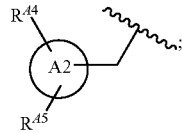

$R^{A2}$ is carboxy-$C_1$-$C_6$-alkyl;
$L^A$ is carbonyl;
A, A1 and A2 are each independently a 3- to 14-membered heterocyclyl; and
D is a 3- to 14-membered heteroaryl.

In a preferred embodiment, the present invention provides a compound of formula (I) as described herein, or a pharmaceutically acceptable salt thereof, wherein:
X is C—$R^5$;
$R^1$ and $R^2$, taken together with the nitrogen atom to which they are attached, form a group

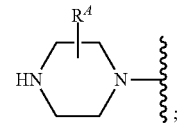

$R^3$ is chloro;
$R^4$ and $R^5$ are both fluoro;
$R^7$ is 2-methoxyethyl;
$R^8$ is methyl;
$R^6$, $R^9$, $R^{10}$, $R^{A3}$, $R^{A4}$, and $R^{A5}$ are hydrogen;
$R^A$ is a group

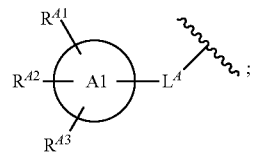

$R^{A1}$ is a group

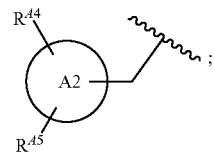

$R^{A2}$ is carboxymethyl;
$L^A$ is carbonyl;
A1 is piperidyl;
A2 is azetidinyl; and
D is a pyrazolyl.

In one embodiment, the present invention provides a compound of formula (I) as described herein, or a pharmaceutically acceptable salt thereof, wherein:
X is C—$R^5$;
$R^1$ and $R^2$, taken together with the nitrogen atom to which they are attached, form a group

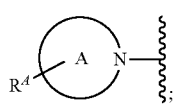

R³ and R⁵ are each independently halogen;
R⁴ is $C_1$-$C_6$-alkyl;
R⁷ is $C_1$-$C_6$-alkoxy-$C_1$-$C_6$-alkyl-;
R⁸ is $C_1$-$C_6$-alkyl;
R⁶, R⁹, R¹⁰, $R^{A3}$, $R^{A4}$, and $R^{A5}$ are hydrogen;
$R^A$ is a group

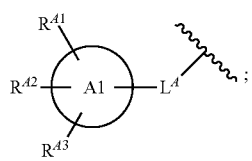

$R^{A1}$ is a group

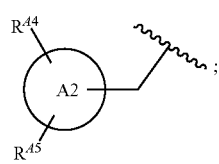

$R^{A2}$ is carboxy-$C_1$-$C_6$-alkyl;
$L^A$ is carbonyl;
A, A1 and A2 are each independently a 3- to 14-membered heterocyclyl; and
D is a 3- to 14-membered heteroaryl.

In a preferred embodiment, the present invention provides a compound of formula (I) as described herein, or a pharmaceutically acceptable salt thereof, wherein:
X is C—R⁵;
R¹ and R², taken together with the nitrogen atom to which they are attached, form a group

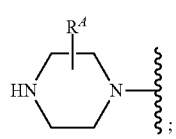

R³ is chloro;
R⁴ is methyl;
R⁵ is fluoro;
R⁷ is 2-methoxyethyl;
R⁸ is methyl;
R⁶, R⁹, R¹⁰, $R^{A3}$, $R^{A4}$, and $R^{A5}$ are hydrogen;
$R^A$ is a group R

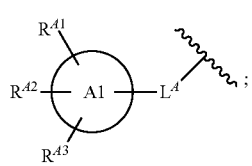

$R^{A1}$ is a group

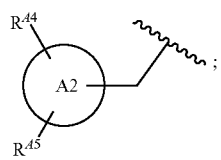

$R^{A2}$ is carboxymethyl;
$L^A$ is carbonyl;
A1 is piperidyl;
A2 is azetidinyl; and
D is a pyrazolyl.

In one embodiment, the present invention provides a compound of formula (I) as described herein, or a pharmaceutically acceptable salt thereof, wherein said compound of formula (I) is a compound of formula (II):

(II)

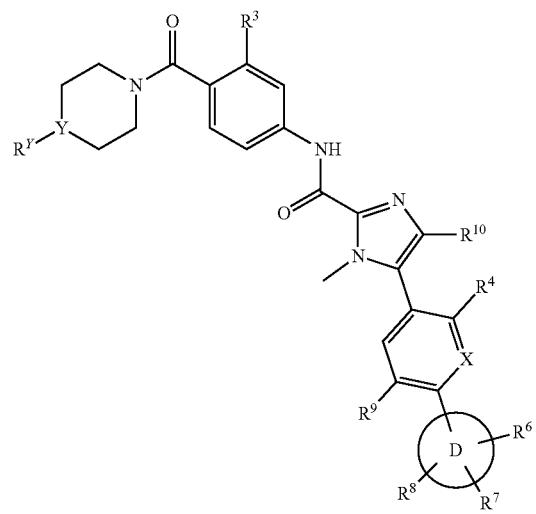

wherein:
X, D, R³, R⁴, and R⁶ to R¹⁰ are as defined herein;
Y is CH or N, most preferably N; and
$R^Y$ is selected from hydrogen,

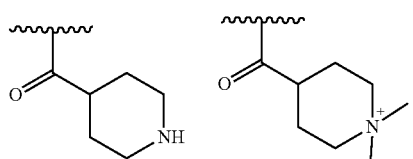

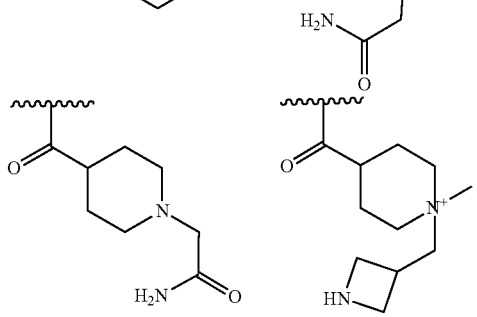

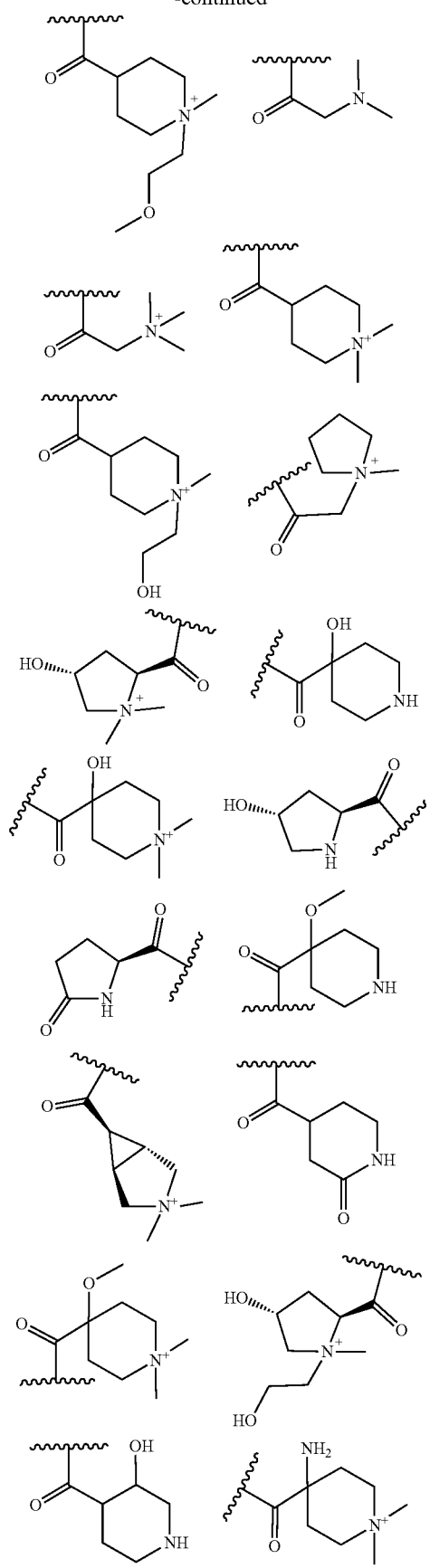
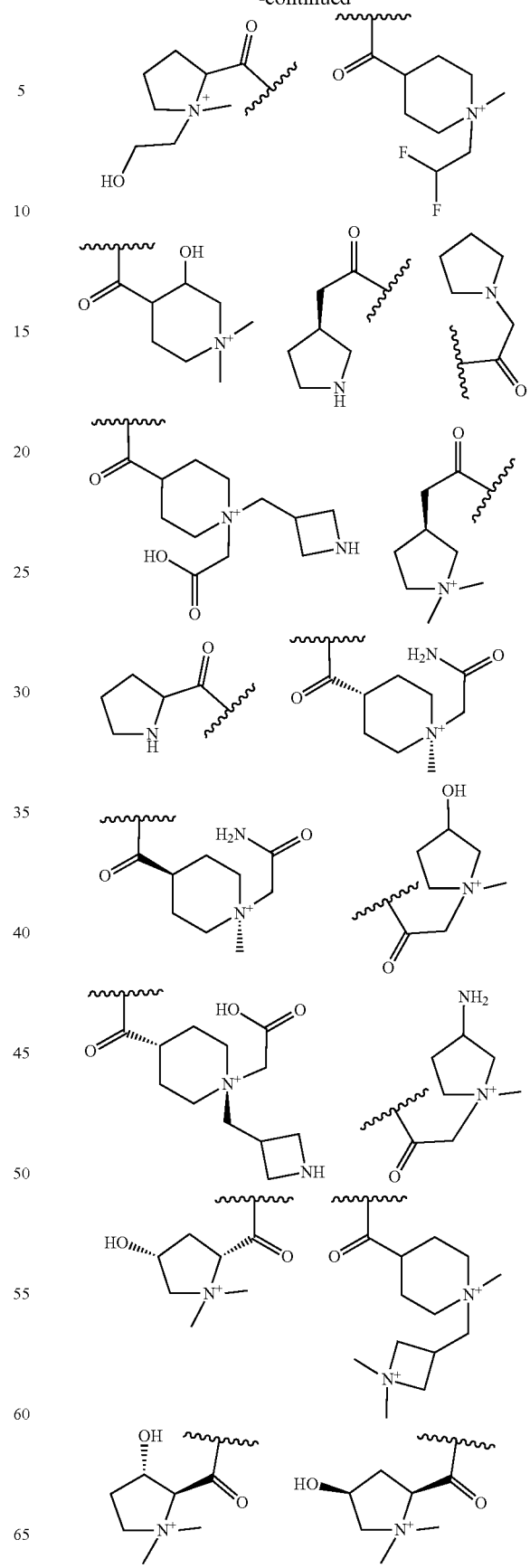

25
-continued
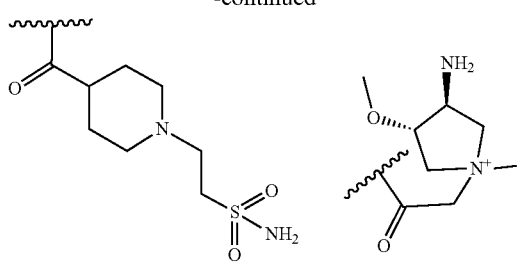
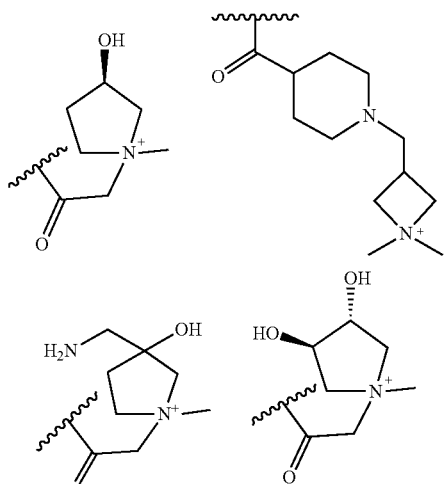
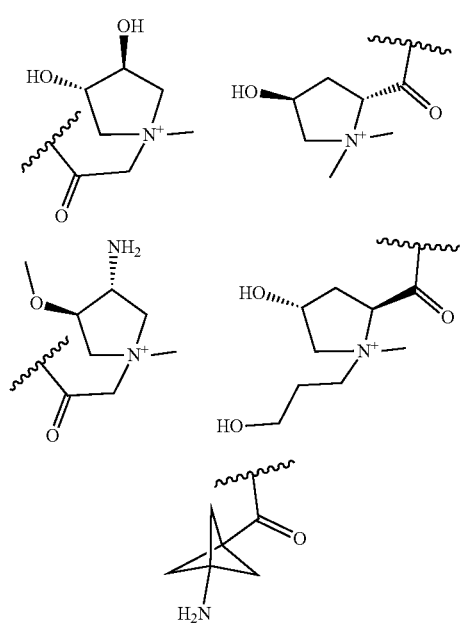
26
-continued
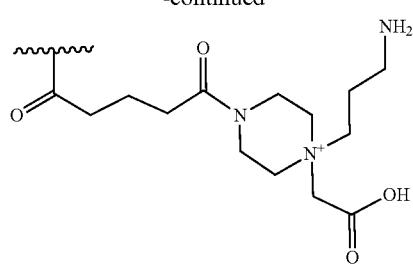
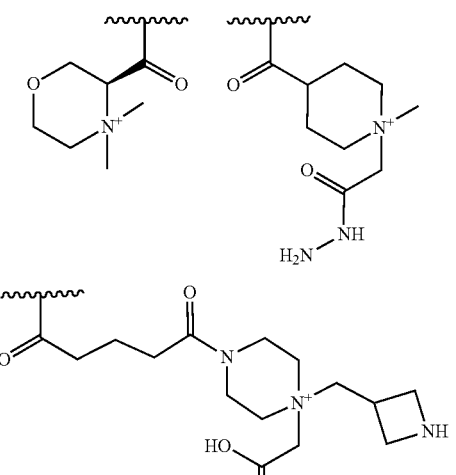
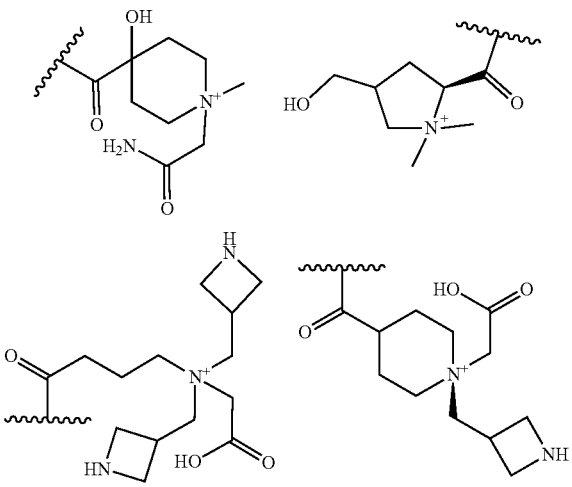

-continued

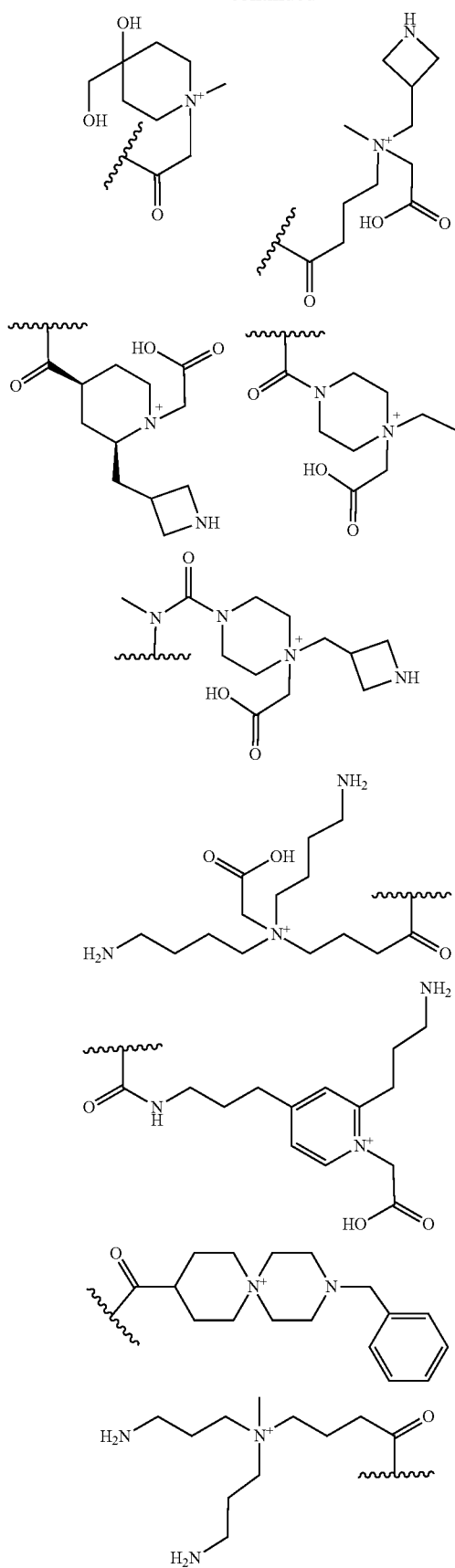
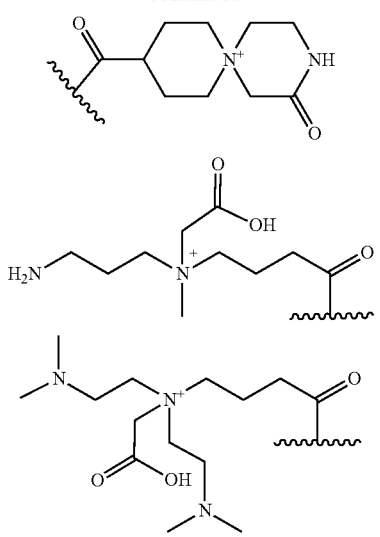

wherein a wavy line indicates the point of attachment of $R^Y$ to Y.

In one embodiment, the present invention provides a compound of formula (I) or (II) as described herein, or a pharmaceutically acceptable salt thereof, wherein said compound of formula (I) or (II) is a compound of formula (III):

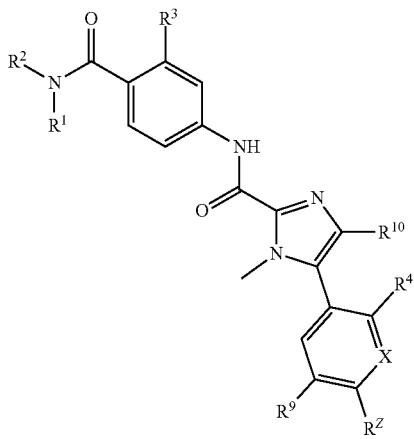

(III)

wherein:
X, $R^1$ to $R^4$, $R^9$ and $R^{10}$ are as defined herein; and
$R^Z$ is selected from:

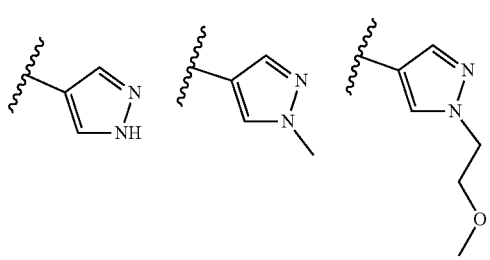

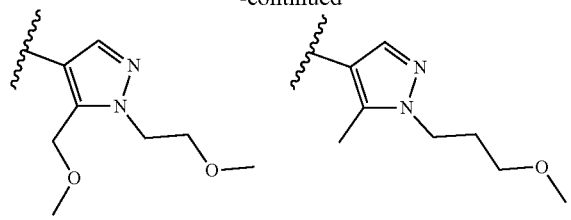
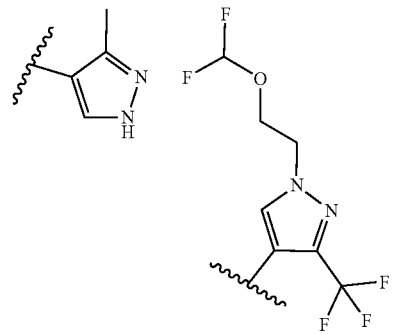
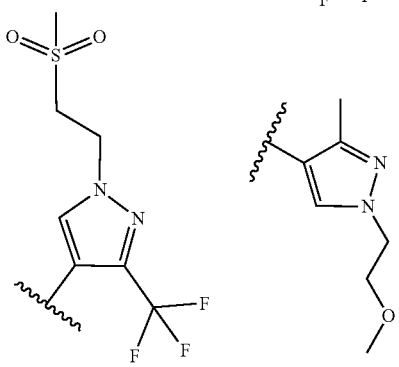
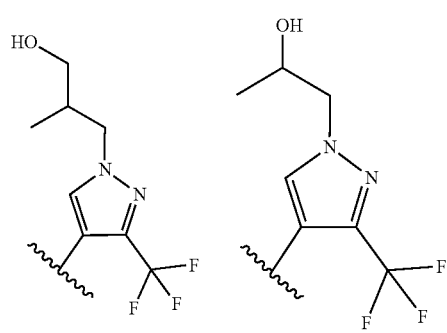
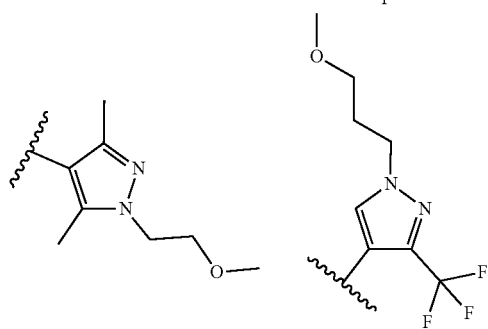
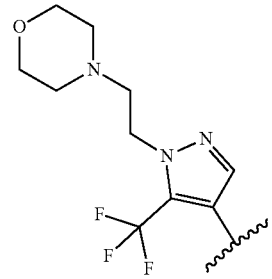
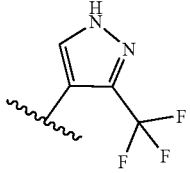
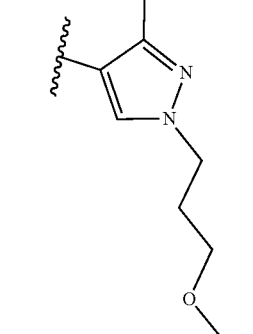
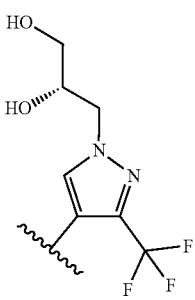
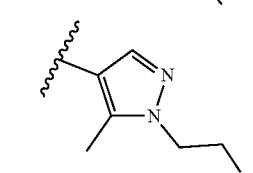
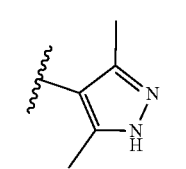
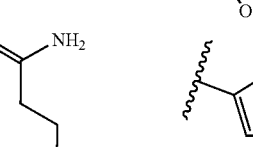
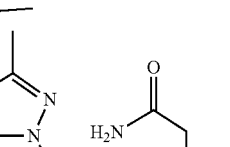
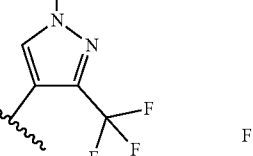
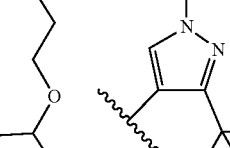
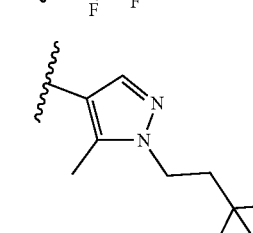
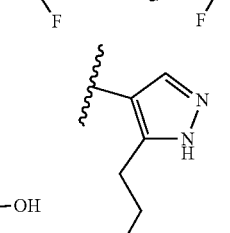
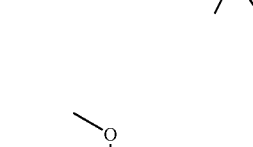
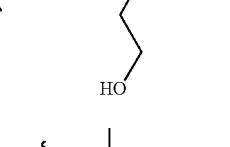
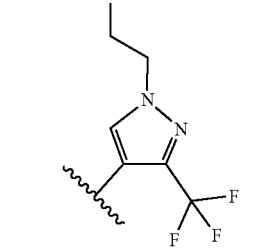
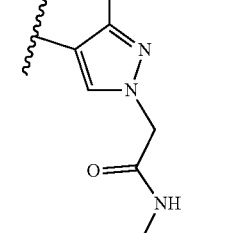

31
-continued
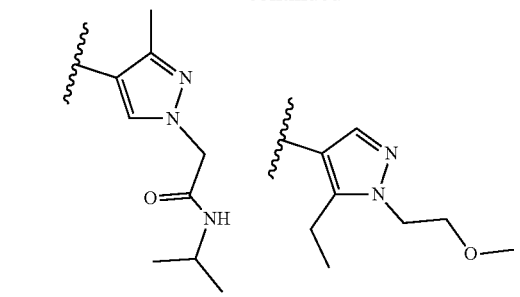
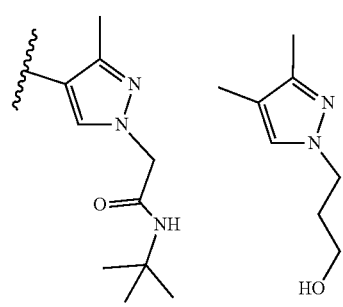
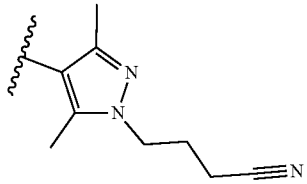
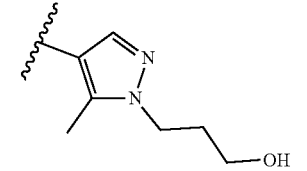
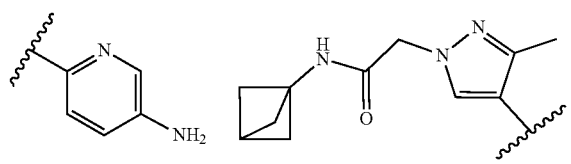
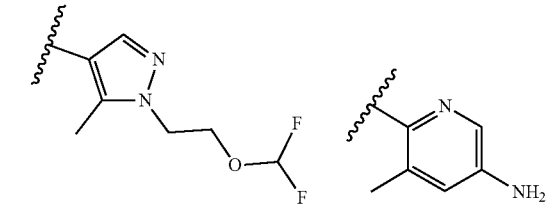
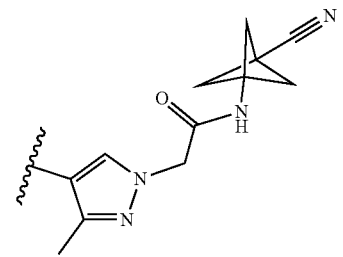
32
-continued
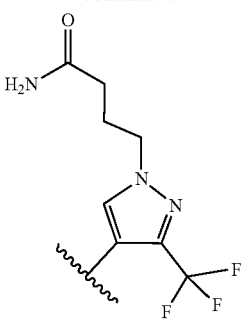
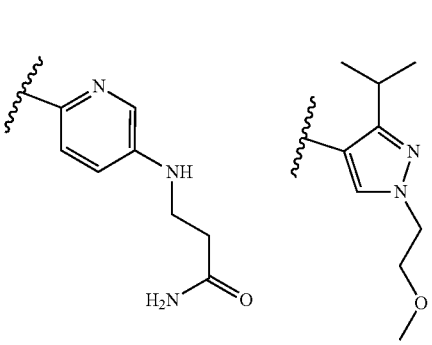
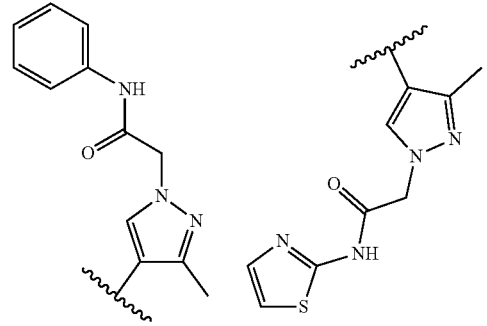
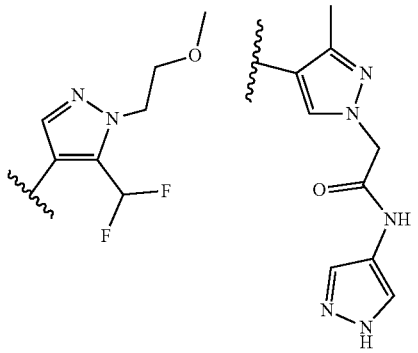
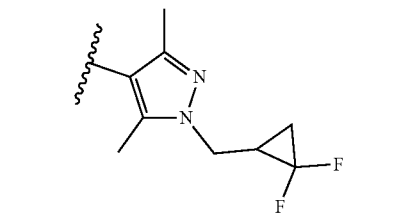

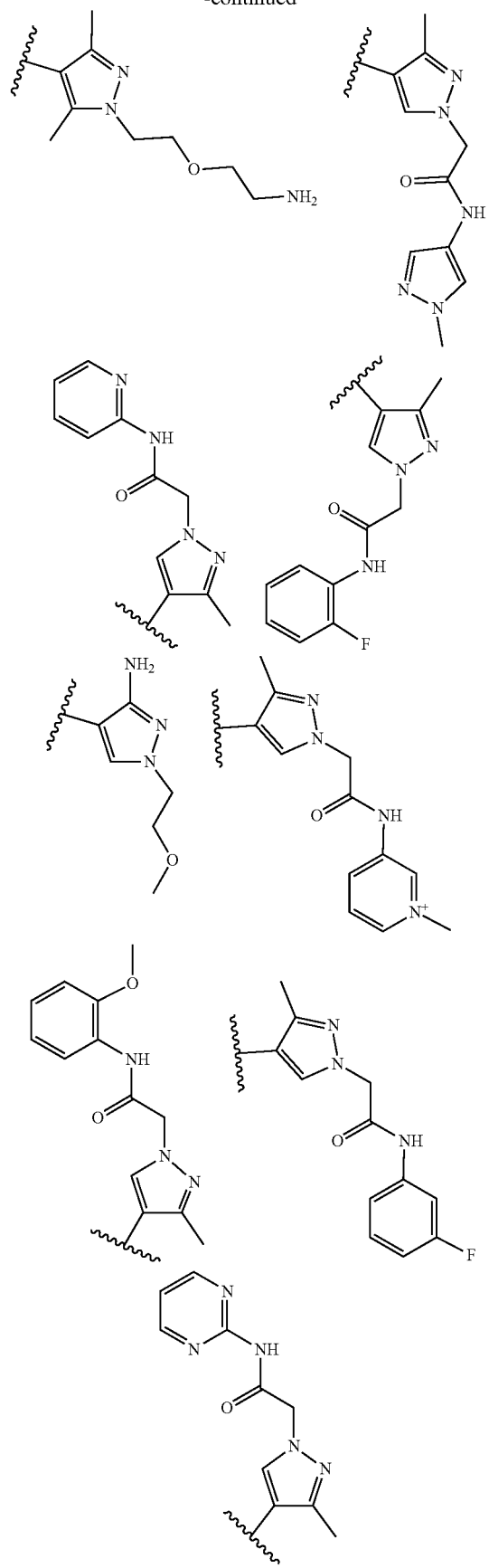
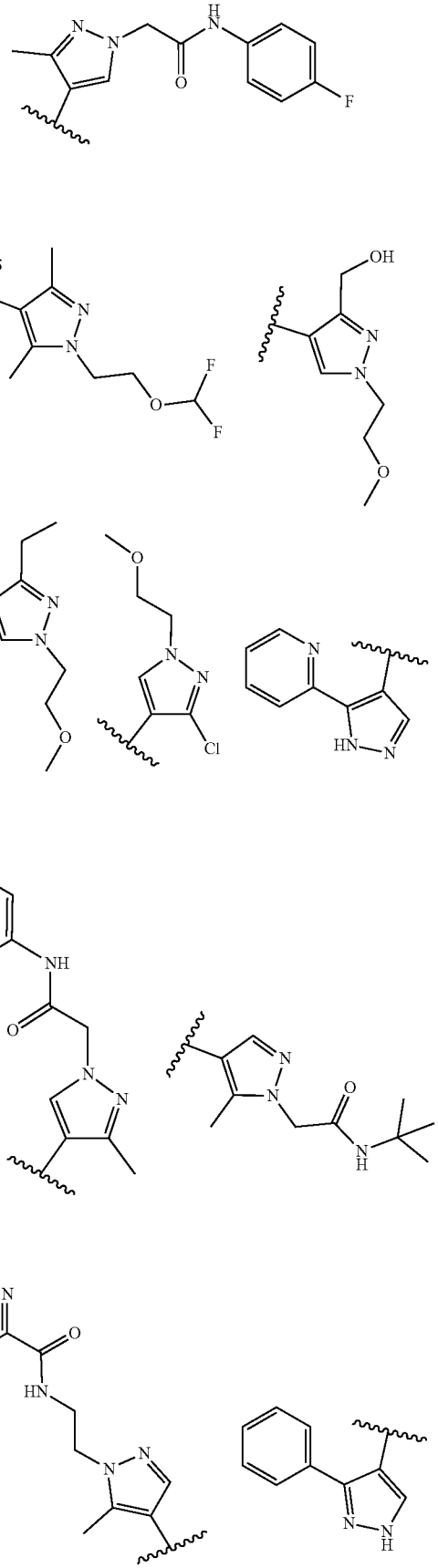

35
-continued
36
-continued
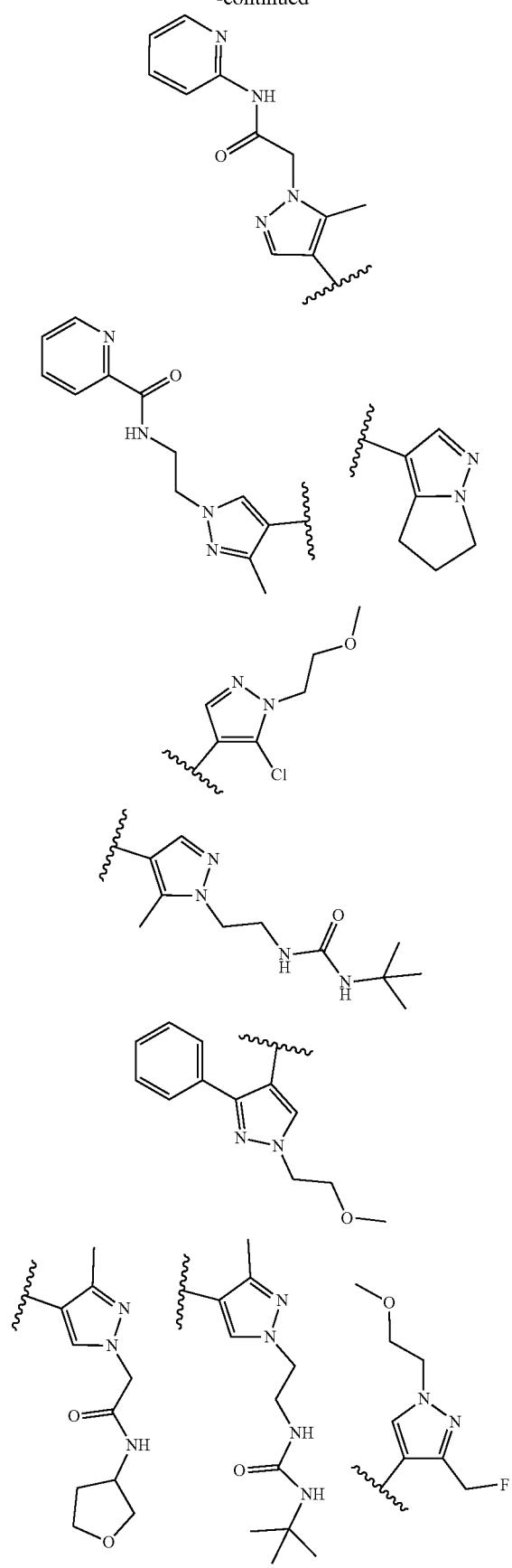
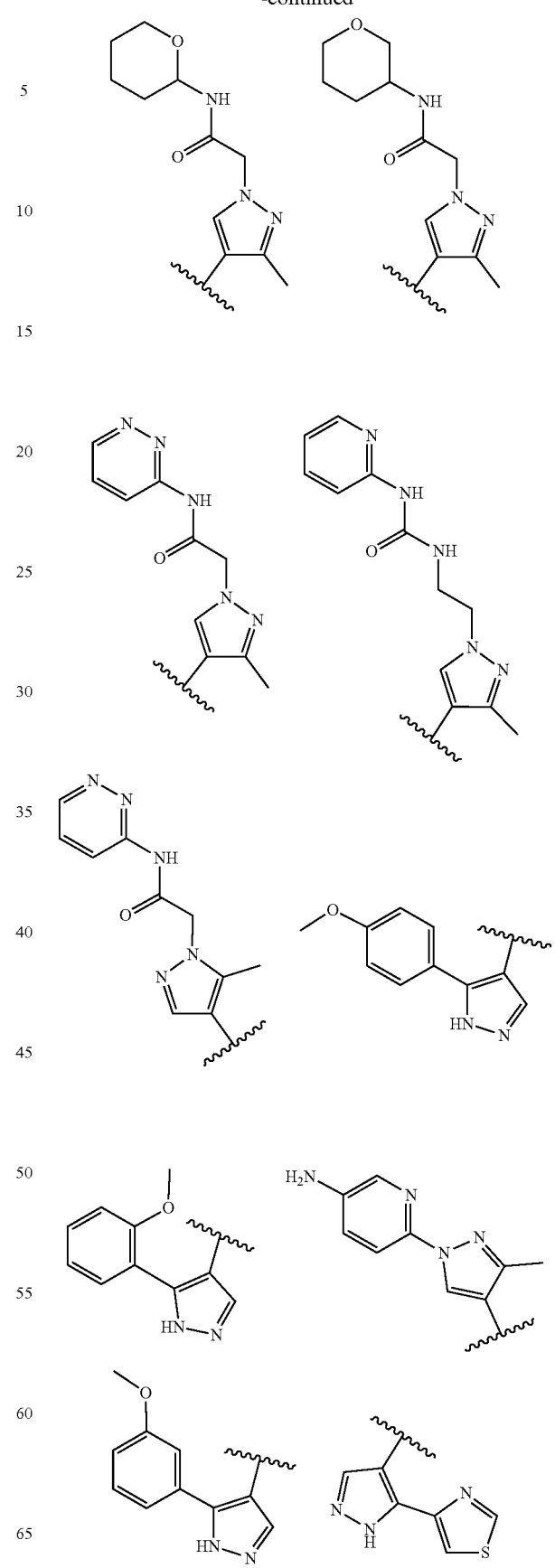

37
-continued
38
-continued
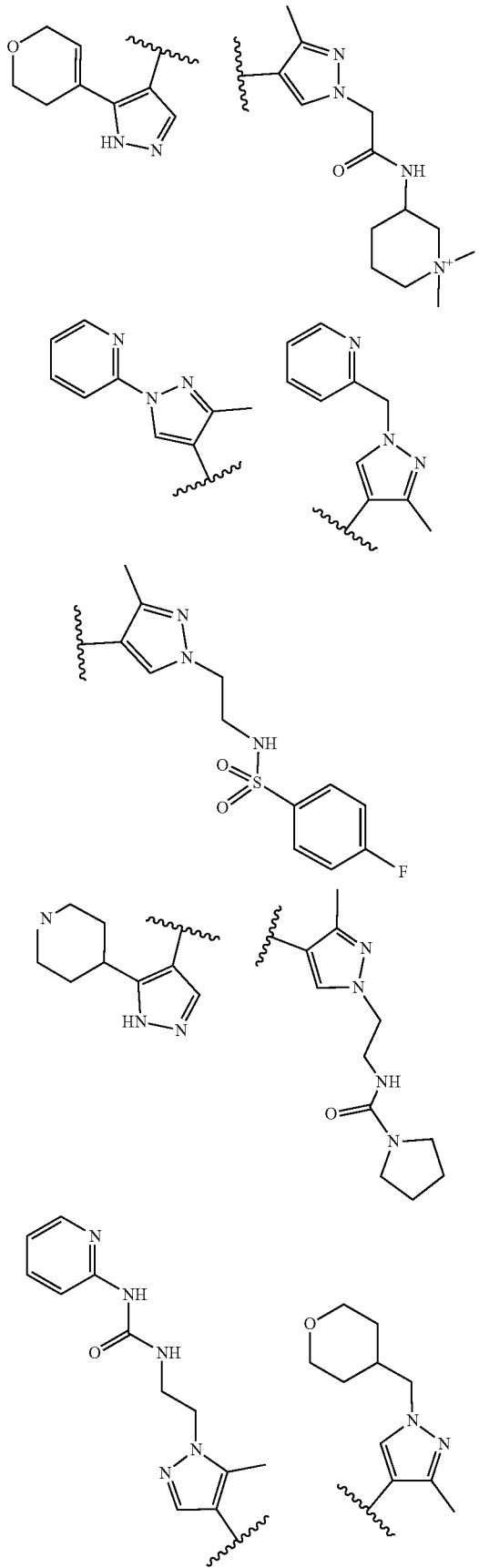
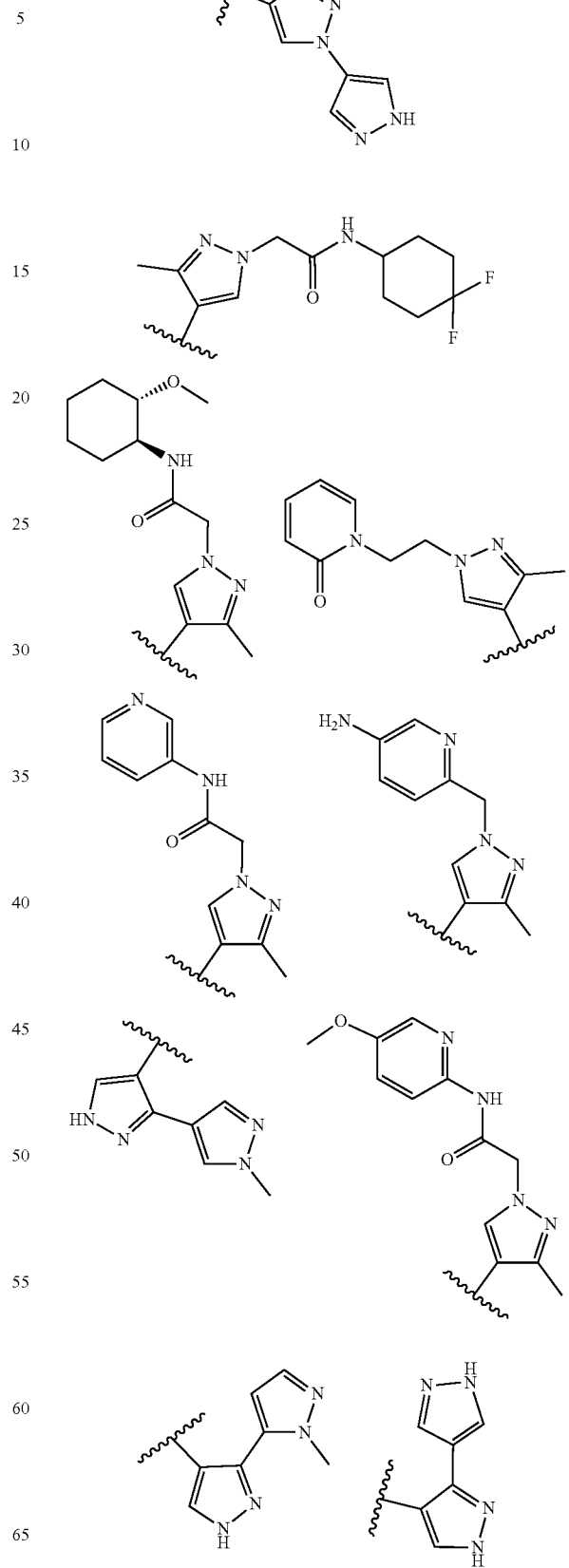

39
-continued
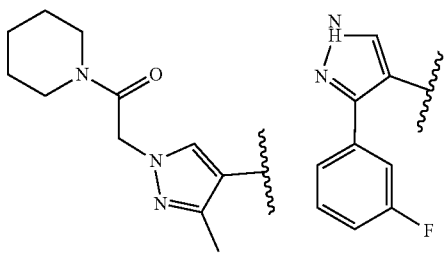
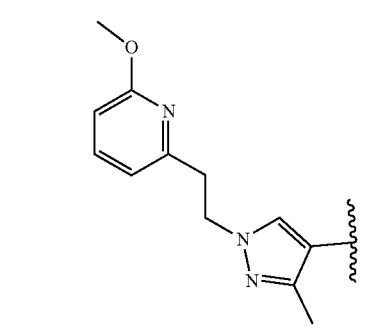
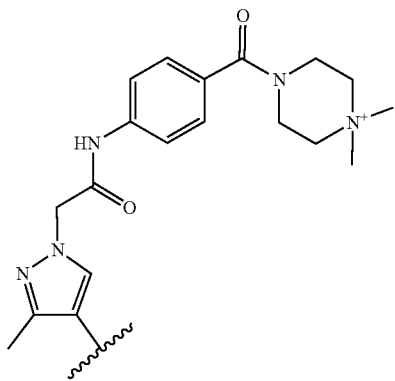
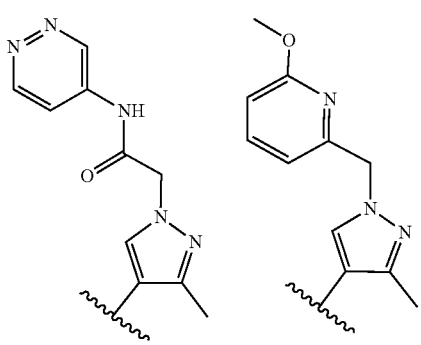
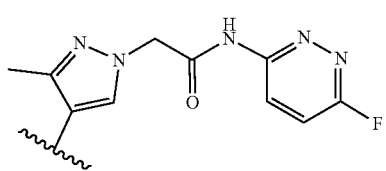
40
-continued
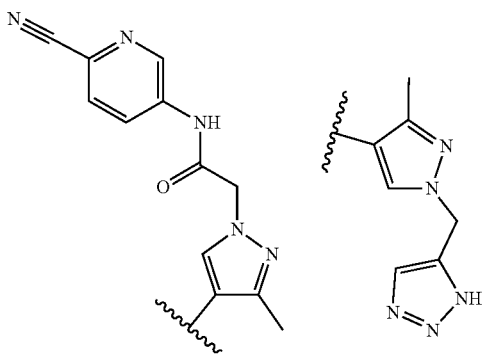
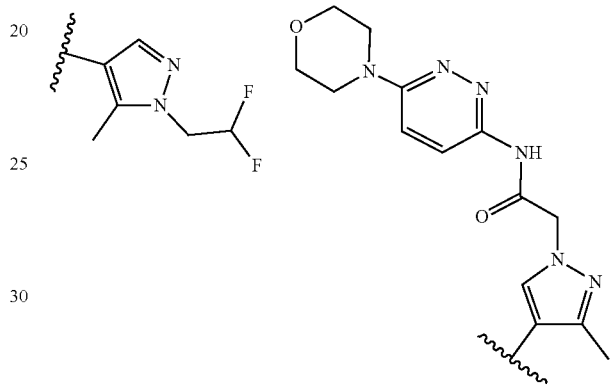
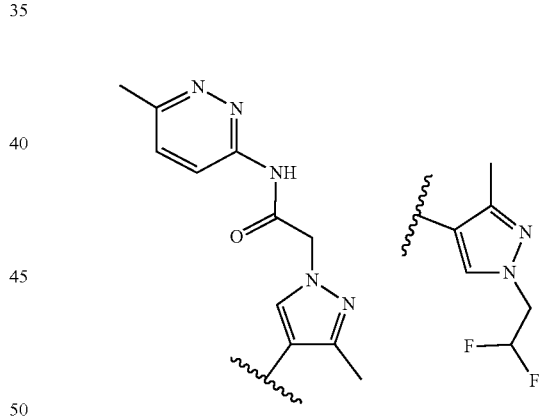
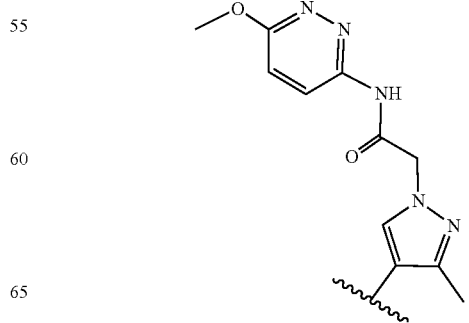

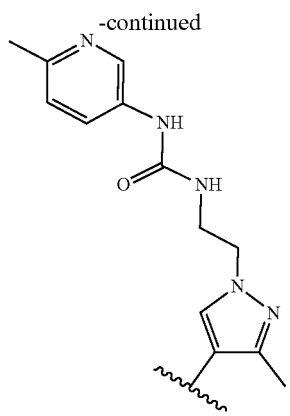

wherein a wavy line indicates the point of attachment of $R^Z$ to the remainder of formula (I).

In one embodiment, the present invention provides a compound of formula (I) as described herein, or a pharmaceutically acceptable salt thereof, wherein said compound of formula (I) is selected from:

N-[3-chloro-4-[4-(1,1-dimethylpiperidin-1-ium-4-carbonyl)piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[4-[1-(2-methoxyethyl)-3,5-dimethyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[2-[(3S)-1,1-dimethylpyrrolidin-1-ium-3-yl]acetyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-(4-hydroxy-1,1-dimethyl-piperidin-1-ium-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-(3-hydroxy-1,1-dimethyl-piperidin-1-ium-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

[2-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-2-oxo-ethyl]-trimethyl-ammonium;

[2-[4-[[[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]amino]methyl]-1-piperidyl]-2-oxo-ethyl]-trimethyl-ammonium;

N-[3-chloro-4-[4-(4,4-dimethylpiperazin-4-ium-1-carbonyl)piperidine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[(2S,3S)-3-hydroxy-1,1-dimethyl-pyrrolidin-1-ium-2-carbonyl]piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide;

N-[3-chloro-4-[4-[(2S)-4-(hydroxymethyl)-1,1-dimethyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-(4-methoxy-1,1-dimethyl-piperidin-1-ium-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[4-[4-[1-(2-amino-2-oxo-ethyl)-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide;

N-[4-[4-[1-(2-amino-2-oxo-ethyl)-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide;

N-[4-[4-[1-(2-amino-2-oxo-ethyl)-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[1-(2-hydroxyethyl)-1-methyl-piperidin-1-ium-4-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[4-[4-[1-(azetidin-3-ylmethyl)-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide;

N-[4-[4-[1-(2-amino-2-oxo-ethyl)-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide;

N-[4-[4-[1-(2-amino-2-oxo-ethyl)-1-methyl-piperidin-1-ium-4-carbonyl]piperazine-1-carbonyl]-3-chloro-phenyl]-5-[4-[1-(2,2-difluoroethyl)-3-methyl-pyrazol-4-yl]-2,3-difluoro-phenyl]-1-methyl-imidazole-2-carboxamide;

N-[3-chloro-4-[4-[1-(2-hydroxyethyl)-1-methyl-piperidin-1-ium-4-carbonyl]piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide;

N-[3-chloro-4-[4-[1-(2-hydroxyethyl)-1-methyl-piperidin-1-ium-4-carbonyl]piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide;

N-[3-chloro-4-[4-[1-(2-methoxyethyl)-1-methyl-piperidin-1-ium-4-carbonyl]piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide;

N-[4-[4-[1-(2-amino-2-oxo-ethyl)-1-methyl-piperidin-1-ium-4-carbonyl]piperazine-1-carbonyl]-3-chloro-phenyl]-5-[4-[1-(2-methoxyethyl)-3,5-dimethyl-pyrazol-4-yl]phenyl]-1-methyl-imidazole-2-carboxamide;

N-[3-chloro-4-[4-[1-(2-hydroxyethyl)-1-methyl-piperidin-1-ium-4-carbonyl]piperazine-1-carbonyl]phenyl]-5-[4-[1-(2-methoxyethyl)-3,5-dimethyl-pyrazol-4-yl]phenyl]-1-methyl-imidazole-2-carboxamide;

2-[4-[1-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperidine-4-carbonyl]-1-methyl-piperazin-1-ium-1-yl]acetic acid;

2-[1-(2-amino-2-oxo-ethyl)-4-[1-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperidine-4-carbonyl]piperazin-1-ium-1-yl]acetic acid;

N-[4-[4-[4-(2-amino-2-oxo-ethyl)-4-methyl-piperazin-4-ium-1-carbonyl]piperidine-1-carbonyl]-3-chloro-phenyl]-5-[2,3-difluoro-4-[1-(2-methoxyethyl)-5-methyl-pyrazol-4-yl]phenyl]-1-methyl-imidazole-2-carboxamide;

N-[4-[4-[1-(2-amino-2-oxo-ethyl)-4-hydroxy-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[1-(2-hydrazino-2-oxo-ethyl)-1-methyl-piperidin-1-ium-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

2-[1-(azetidin-3-ylmethyl)-4-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]piperidin-1-ium-1-yl]acetic acid;

N-[3-chloro-4-[4-[1-[(1,1-dimethylazetidin-1-ium-3-yl)methyl]-1-methyl-piperidin-1-ium-4-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;diformate;

2-[1-(azetidin-3-ylmethyl)-4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]piperidin-1-ium-1-yl]acetic acid;

N-[4-[4-[1-(azetidin-3-ylmethyl)-1-methyl-piperidin-1-ium-4-carbonyl]piperazine-1-carbonyl]-3-chloro-phenyl]-5-[2,3-difluoro-4-[1-(2-methoxyethyl)-5-methyl-pyrazol-4-yl]phenyl]-1-methyl-imidazole-2-carboxamide;

2-[1-(azetidin-3-ylmethyl)-4-[1-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperidine-4-carbonyl]piperazin-1-ium-1-yl]acetic acid;

N-[4-[4-[4-(azetidin-3-ylmethyl)-4-methyl-piperazin-4-ium-1-carbonyl]piperidine-1-carbonyl]-3-chloro-phenyl]-5-[2,3-difluoro-4-[1-(2-methoxyethyl)-5-methyl-pyrazol-4-yl]phenyl]-1-methyl-imidazole-2-carboxamide;

N-[4-[4-[4-(2-amino-2-oxo-ethyl)-4-(azetidin-3-ylmethyl)piperazin-4-ium-1-carbonyl]piperidine-1-carbonyl]-3-chloro-phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[(1R,5S)-3,3-dimethyl-3-azoniabicyclo[3.1.0]hexane-6-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[(1R,5S)-3,3-dimethyl-3-azoniabicyclo[3.1.0]hexane-6-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[(2S,4R)-4-hydroxy-1-(3-hydroxypropyl)-1-methyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;iodide;

2-[1-(azetidin-3-ylmethyl)-4-[4-[2-chloro-4-[[5-[3-chloro-2-fluoro-4-[1-(2-methoxyethyl)-5-methyl-pyrazol-4-yl]phenyl]-1-methyl-imidazole-2-carbonyl]amino]benzoyl]piperazine-1-carbonyl]piperidin-1-ium-1-yl]acetic acid;

2-[1-(azetidin-3-ylmethyl)-4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]piperidin-1-ium-1-yl]acetic acid;

N-[3-chloro-4-[4-[1-[(1,1-dimethylazetidin-1-ium-3-yl)methyl]piperidine-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[1-(2,2-difluoroethyl)-1-methyl-piperidin-1-ium-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[1-(2-sulfamoylethyl)piperidine-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[1-methyl-1-(2-sulfamoylethyl)piperidin-1-ium-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[1-(2-hydroxyethyl)-1-methyl-pyrrolidin-1-ium-2-carbonyl]piperazine-1-carbonyl]phenyl]-5-[2,3-difluoro-4-(3-methyl-1H-pyrazol-4-yl)phenyl]-1-methyl-imidazole-2-carboxamide;

N-[3-chloro-4-[4-[(2S,4R)-4-hydroxy-1-(2-hydroxyethyl)-1-methyl-pyrrolidin-1-ium-2-carbonyl]piperazine-1-carbonyl]phenyl]-5-[2,3-difluoro-4-(3-methyl-1H-pyrazol-4-yl)phenyl]-1-methyl-imidazole-2-carboxamide;

2-[1-(azetidin-3-ylmethyl)-4-[4-[2-chloro-4-[[5-[2-chloro-3-fluoro-4-[1-(2-methoxyethyl)-5-methyl-pyrazol-4-yl]phenyl]-1-methyl-imidazole-2-carbonyl]amino]benzoyl]piperazine-1-carbonyl]piperidin-1-ium-1-yl]acetic acid;

2-[1-(azetidin-3-ylmethyl)-4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]piperazin-1-ium-1-yl]acetic acid;

2-[1-(azetidin-3-ylmethyl)-4-[4-[2-chloro-4-[[5-[3-fluoro-4-[1-(2-methoxyethyl)-5-methyl-pyrazol-4-yl]-2-methyl-phenyl]-1-methyl-imidazole-2-carbonyl]amino]benzoyl]piperazine-1-carbonyl]piperidin-1-ium-1-yl]acetic acid;

2-[1-(azetidin-3-ylmethyl)-4-[4-[2-chloro-4-[[5-[5-chloro-4-[1-(2-methoxyethyl)-5-methyl-pyrazol-4-yl]-2-methyl-phenyl]-1-methyl-imidazole-2-carbonyl]amino]benzoyl]piperazine-1-carbonyl]piperidin-1-ium-1-yl]acetic acid;

N-[3-chloro-4-[4-[2-(3-hydroxy-1-methyl-pyrrolidin-1-ium-1-yl)acetyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[4-[4-[2-(3-amino-1-methyl-pyrrolidin-1-ium-1-yl)acetyl]piperazine-1-carbonyl]-3-chloro-phenyl]-5-[2,3-difluoro-4-[1-(2-methoxyethyl)-5-methyl-pyrazol-4-yl]phenyl]-1-methyl-imidazole-2-carboxamide;

N-[4-[4-[2-(3-amino-1-methyl-pyrrolidin-1-ium-1-yl)acetyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[2-(3-hydroxy-1-methyl-pyrrolidin-1-ium-1-yl)acetyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[4-[4-[2-[(3S,4S)-3-amino-4-methoxy-1-methyl-pyrrolidin-1-ium-1-yl]acetyl]piperazine-1-carbonyl]-3-chlorophenyl]-5-[2,3-difluoro-4-[1-(2-methoxyethyl)-3-methyl-pyrazol-4-yl]phenyl]-1-methyl-imidazole-2-carboxamide;

N-[4-[4-[2-[3-(aminomethyl)-3-hydroxy-1-methyl-pyrrolidin-1-ium-1-yl]acetyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide;

N-[4-[4-[2-(3-carbamoyl-1-methyl-pyrrolidin-1-ium-1-yl)acetyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[2-[(3R)-3-hydroxy-1-methyl-pyrrolidin-1-ium-1-yl]acetyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[2-[(3S)-3-hydroxy-1-methyl-pyrrolidin-1-ium-1-yl]acetyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[2-[(3R,4R)-3,4-dihydroxy-1-methyl-pyrrolidin-1-ium-1-yl]acetyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[2-(3-hydroxy-1-methyl-pyrrolidin-1-ium-1-yl)acetyl]piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide;

N-[3-chloro-4-[4-[2-[(3R,4R)-3,4-dihydroxy-1-methyl-pyrrolidin-1-ium-1-yl]acetyl]piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide;

N-[4-[4-[2-[(3R,4R)-3-amino-4-methoxy-1-methyl-pyrrolidin-1-ium-1-yl]acetyl]piperazine-1-carbonyl]-3-chloro-phenyl]-5-[2,3-difluoro-4-[1-(2-methoxyethyl)-3,5-dimethyl-pyrazol-4-yl]phenyl]-1-methyl-imidazole-2-carboxamide;

N-[3-chloro-4-[4-[2-(1-methylpyrrolidin-1-ium-1-yl)acetyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[(2S,3S)-3-hydroxy-1,1-dimethyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-(3-hydroxy-1,1-dimethyl-piperidin-1-ium-4-carbonyl)piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide;

N-[3-chloro-4-[4-(3-hydroxy-1,1-dimethyl-piperidin-1-ium-4-carbonyl)piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide;

N-[3-chloro-4-[4-[3-(hydroxymethyl)-4,4-dimethyl-piperazin-4-ium-1-carbonyl]piperidine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[(2R,4S)-4-hydroxy-1,1-dimethyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[(2R,4R)-4-hydroxy-1,1-dimethyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[(2S,4S)-4-hydroxy-1,1-dimethyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(3-methoxypropyl)-3-methyl-pyrazol-4-yl]phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(3-methoxypropyl)-5-methyl-pyrazol-4-yl]phenyl]-1-methyl-imidazole-2-carboxamide;

N-[3-chloro-4-[4-[(3S)-4,4-dimethylmorpholin-4-ium-3-carbonyl]piperazine-1-carbonyl]phenyl]-5-[2,3-difluoro-4-[1-(3-methoxypropyl)-3-methyl-pyrazol-4-yl]phenyl]-1-methyl-imidazole-2-carboxamide;

N-[3-chloro-4-[4-[(4,4-dimethyl-2-oxo-piperazin-4-ium-1-yl)methyl]piperidine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[2-(1-methylpyrrolidin-1-ium-1-yl)acetyl]piperazine-1-carbonyl]phenyl]-5-[2,3-difluoro-4-(3-methyl-1H-pyrazol-4-yl)phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-(3-methyl-1H-pyrazol-4-yl)phenyl]-1-methyl-imidazole-2-carboxamide;

N-[3-chloro-4-[4-[2-(4-hydroxy-1,1-dimethyl-piperidin-1-ium-4-yl)acetyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[2-[4-hydroxy-4-(hydroxymethyl)-1-methyl-piperidin-1-ium-1-yl]acetyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-(3-methyl-1H-pyrazol-4-yl)phenyl]-1-methyl-imidazole-2-carboxamide;

N-[4-[4-(4-amino-1,1-dimethyl-piperidin-1-ium-4-carbonyl)piperazine-1-carbonyl]-3-chloro-phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[(4,4-dimethyl-2-oxo-piperazin-4-ium-1-yl)methyl]piperidine-1-carbonyl]phenyl]-5-[2,3-difluoro-4-(3-methyl-1H-pyrazol-4-yl)phenyl]-1-methyl-imidazole-2-carboxamide;

5-[2,3-difluoro-4-[1-(2-methoxyethyl)-3-methyl-pyrazol-4-yl]phenyl]-N-[4-[4-(3-hydroxypiperidine-4-carbonyl)piperazine-1-carbonyl]-3-methyl-phenyl]-1-methyl-imidazole-2-carboxamide;

N-[3-chloro-4-[4-[[(2S,4R)-4-hydroxypyrrolidine-2-carbonyl]amino]piperidine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-(4-hydroxypiperidine-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-(3-hydroxypiperidine-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[(2S)-5-oxopyrrolidine-2-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-(2-oxopiperidine-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-(2-pyrrolidin-1-ylacetyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-(pyrrolidine-2-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[4-[4-(3-aminobicyclo[1.1.1]pentane-1-carbonyl)piperazine-1-carbonyl]-3-chloro-phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[(2S,4R)-4-hydroxypyrrolidine-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[2-(dimethylamino)acetyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[[1-[2-(dimethylamino)acetyl]-4-piperidyl]methylcarbamoyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[2-(dimethylamino)acetyl]piperazine-1-carbonyl]phenyl]-5-[2,3-difluoro-4-(3-methyl-1H-pyrazol-4-yl)phenyl]-1-methyl-imidazole-2-carboxamide;

[2-[4-[2-chloro-4-[[5-[2,3-difluoro-4-(3-methyl-1H-pyrazol-4-yl)phenyl]-1-methyl-imidazole-2-carbonyl]amino]benzoyl]piperazin-1-yl]-2-oxo-ethyl]-trimethyl-ammonium;

N-[3-chloro-4-[4-[(2S,4R)-4-hydroxypyrrolidine-2-carbonyl]piperazine-1-carbonyl]phenyl]-5-[2,3-difluoro-4-(3-methyl-1H-pyrazol-4-yl)phenyl]-1-methyl-imidazole-2-carboxamide;

N-[3-chloro-4-[4-[(1,1-dimethylpiperidin-1-ium-4-yl)sulfonylamino]piperidine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[[(1R,5S)-3-[(2S,4R)-4-hydroxy-1,1-dimethyl-pyrrolidin-1-ium-2-carbonyl]-3-azabicyclo[3.1.0]hexan-6-yl]carbamoyl]phenyl]-5-[2,3-difluoro-4-[1-(2-methoxyethyl)-3,5-dimethyl-pyrazol-4-yl]phenyl]-1-methyl-imidazole-2-carboxamide;

N-[3-chloro-4-[[(1S,5R)-3-[(2S,4R)-4-hydroxy-1,1-dimethyl-pyrrolidin-1-ium-2-carbonyl]-3-azabicyclo[3.1.0]hexan-6-yl]carbamoyl]phenyl]-5-[2,3-difluoro-4-[1-(2-methoxyethyl)-3,5-dimethyl-pyrazol-4-yl]phenyl]-1-methyl-imidazole-2-carboxamide;

bis(3-aminopropyl)-(carboxymethyl)-[4-[4-[2-chloro-4-[[5-[2,3-difluoro-4-(3-methyl-1H-pyrazol-4-yl)phenyl]-1-methyl-imidazole-2-carbonyl]amino]benzoyl]piperazin-1-yl]-4-oxo-butyl]ammonium;

bis(azetidin-3-ylmethyl)-(carboxymethyl)-[4-[4-[2-chloro-4-[[5-[2,3-difluoro-4-(3-methyl-1H-pyrazol-4-yl)phenyl]-1-methyl-imidazole-2-carbonyl]amino]benzoyl]piperazin-1-yl]-4-oxo-butyl]ammonium;

N-[3-chloro-4-[4-[(2S,4R)-4-hydroxy-1,1-dimethyl-pyrrolidin-1-ium-2-carbonyl]piperazine-1-carbonyl]phenyl]-5-[4-(3,5-dimethyl-1H-pyrazol-4-yl)-2,3-difluoro-phenyl]-1-methyl-imidazole-2-carboxamide;

N-[3-chloro-4-[4-(4-methoxypiperidine-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-(piperidine-4-carbonyl)piperazine-1-carbonyl]phenyl]-5-[4-[1-(2,2-difluoroethyl)-5-methyl-pyrazol-4-yl]-2,3-difluoro-phenyl]-1-methyl-imidazole-2-carboxamide;

N-[3-chloro-4-[4-[2-[(3S)-pyrrolidin-3-yl]acetyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-(piperidine-4-carbonyl)piperazine-1-carbonyl]phenyl]-5-[2-fluoro-4-[1-(2-methoxyethyl)-5-methyl-pyrazol-4-yl]-3-methyl-phenyl]-1-methyl-imidazole-2-carboxamide;

5-[2-chloro-3-fluoro-4-[1-(2-methoxyethyl)-5-methyl-pyrazol-4-yl]phenyl]-N-[3-chloro-4-[4-(piperidine-4-carbonyl)piperazine-1-carbonyl]phenyl]-1-methyl-imidazole-2-carboxamide;

N-[3-chloro-4-[4-(piperidine-4-carbonyl)piperazine-1-carbonyl]phenyl]-5-[3-fluoro-4-[1-(2-methoxyethyl)-5-methyl-pyrazol-4-yl]-2-methyl-phenyl]-1-methyl-imidazole-2-carboxamide;

N-[3-chloro-4-[4-(piperidine-4-carbonyl)piperazine-1-carbonyl]phenyl]-5-[4-[1-[2-(difluoromethoxy)ethyl]-3-(trifluoromethyl)pyrazol-4-yl]-2,3-difluoro-phenyl]-1-methyl-imidazole-2-carboxamide;

N-[3-chloro-4-(piperazine-1-carbonyl)phenyl]-5-[2,3-difluoro-4-[1-(2-methoxyethyl)-5-methyl-pyrazol-4-yl]phenyl]-1-methyl-imidazole-2-carboxamide;

5-[2,3-difluoro-4-[1-(2-methoxyethyl)-5-methyl-pyrazol-4-yl]phenyl]-N-[4-[4-[(2S,4R)-4-hydroxypyrrolidine-2-carbonyl]piperazine-1-carbonyl]-3-methyl-phenyl]-1-methyl-imidazole-2-carboxamide;

N-[3-chloro-4-[4-[(2S,4R)-4-hydroxypyrrolidine-2-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-(4-piperidylmethylcarbamoyl)phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-(piperidine-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[4-[4-[1-(2-amino-2-oxo-ethyl)piperidine-4-carbonyl]piperazine-1-carbonyl]-3-chloro-phenyl]-5-[3-fluoro-4-[3-(trifluoromethyl)-1H-pyrazol-4-yl]phenyl]-1-methyl-imidazole-2-carboxamide;

N-[3-chloro-4-[4-(piperidine-4-carbonyl)piperazine-1-carbonyl]phenyl]-5-[2,3-difluoro-4-[1-(2-methoxyethyl)-5-(methoxymethyl)pyrazol-4-yl]phenyl]-1-methyl-imidazole-2-carboxamide;

N-[4-[4-[2-(dimethylamino)acetyl]piperazine-1-carbonyl]-3-methyl-phenyl]-5-[4-[1-(2-methoxyethyl)-5-methyl-pyrazol-4-yl]phenyl]-1-methyl-imidazole-2-carboxamide;

N-[3-chloro-4-[4-[2-(dimethylamino)acetyl]piperazine-1-carbonyl]phenyl]-1-methyl-5-[4-(3-methyl-1H-pyrazol-4-yl)phenyl]imidazole-2-carboxamide;

N-[3-chloro-4-[4-[2-(dimethylamino)acetyl]piperazine-1-carbonyl]phenyl]-5-[4-(3,5-dimethyl-1H-pyrazol-4-yl)phenyl]-1-methyl-imidazole-2-carboxamide;

N-[3-chloro-4-[4-(piperidine-4-carbonyl)piperazine-1-carbonyl]phenyl]-5-[2-fluoro-6-[5-(4-methoxyphenyl)-1H-pyrazol-4-yl]-3-pyridyl]-1-methyl-imidazole-2-carboxamide;

N-[3-chloro-4-[4-(piperidine-4-carbonyl)piperazine-1-carbonyl]phenyl]-5-[2-fluoro-6-(1H-pyrazol-4-yl)-3-pyridyl]-1-methyl-imidazole-2-carboxamide;

N-[3-chloro-4-[4-(piperidine-4-carbonyl)piperazine-1-carbonyl]phenyl]-5-[2,3-difluoro-4-(3-methyl-1H-pyrazol-4-yl)phenyl]-1-methyl-imidazole-2-carboxamide;

N-[3-chloro-4-[4-(piperidine-4-carbonyl)piperazine-1-carbonyl]phenyl]-5-[2,3-difluoro-4-(1-methylpyrazol-4-yl)phenyl]-1-methyl-imidazole-2-carboxamide;

N-[3-chloro-4-[4-(piperidine-4-carbonyl)piperazine-1-carbonyl]phenyl]-5-[2,3-difluoro-4-[1-(2-methoxyethyl)pyrazol-4-yl]phenyl]-1-methyl-imidazole-2-carboxamide;

(1S,5R)-6-[[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]amino]-N-[(3R,4R)-4-hydroxypyrrolidin-3-yl]-3-azabicyclo[3.1.0]hexane-3-carboxamide;

N-[3-chloro-4-[4-(piperidine-4-carbonyl)piperazine-1-carbonyl]phenyl]-1-methyl-5-[4-(1H-pyrazol-4-yl)phenyl]imidazole-2-carboxamide;

5-[4-[1-(3-amino-3-oxo-propyl)-3-(trifluoromethyl)pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2-chloro-3-fluoro-4-[1-(2-methoxyethyl)-5-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[3-fluoro-4-[1-(2-methoxyethyl)-5-methyl-pyrazol-4-yl]-2-methyl-phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(3-hydroxy-3-methyl-butyl)-5-methyl-pyrazol-4-yl]phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[3-methyl-1-[2-(methylamino)-2-oxo-ethyl]pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[4-[1-[2-(difluoromethoxy)ethyl]-3-(trifluoromethyl)pyrazol-4-yl]-2,3-difluoro-phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-(3-hydroxy-2-methyl-propyl)-3-(trifluoromethyl)pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[4-[1-[(2S)-2,3-dihydroxypropyl]-3-(trifluoromethyl)pyrazol-4-yl]-2,3-difluoro-phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[4-[1-(2-(difluoromethoxy)ethyl]-3-methyl-pyrazol-4-yl]-2,3-difluoro-phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[4-[1-(2-(difluoromethoxy)ethyl]-5-methyl-pyrazol-4-yl]-2,3-difluoro-phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[3-isopropyl-1-(2-methoxyethyl)pyrazol-4-yl]phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[4-[5-(difluoromethyl)-1-(2-methoxyethyl)pyrazol-4-yl]-2,3-difluoro-phenyl]-1-methyl-imidazole-2-carboxamide;

5-[2,3-difluoro-4-[1-(2-methoxyethyl)-5-methyl-pyrazol-4-yl]phenyl]-N-[4-[4-[(2S,4R)-4-hydroxy-1,1-dimethyl-pyrrolidin-1-ium-2-carbonyl]piperazine-1-carbonyl]-3-methyl-phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(3-hydroxypropyl)-3-methyl-pyrazol-4-yl]phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(3-hydroxypropyl)-5-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2-methoxy-4-[1-(2-methoxyethyl)-5-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[4-[1-(2-methoxyethyl)-5-methyl-pyrazol-4-yl]-2-methyl-phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[4-[5-ethyl-1-(2-methoxyethyl)pyrazol-4-yl]-2,3-difluoro-phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[5-(4-hydroxybutyl)-1H-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2-chloro-4-[1-(2-methoxyethyl)-5-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[3-fluoro-2-methoxy-4-[1-(2-methoxyethyl)-5-methyl-pyrazol-4-yl]phenyl]-1-methyl-imidazole-2-carboxamide;

N-[3-chloro-4-[4-[2-(4-hydroxy-1,1-dimethyl-piperidin-1-ium-4-yl)acetyl]piperazine-1-carbonyl]phenyl]-5-[4-[3-ethyl-1-(2-methoxyethyl)pyrazol-4-yl]-2,3-difluoro-phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-(hydroxymethyl)-1-(2-methoxyethyl)pyrazol-4-yl]phenyl]-1-methyl-imidazole-2-carboxamide;

5-[4-[3-amino-1-(2-methoxyethyl)pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-(3-phenyl-1H-pyrazol-4-yl)phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[4-(5,6-dihydro-4H-pyrrolo[1,2-b]pyrazol-3-yl)-2,3-difluoro-phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-(fluoromethyl)-1-(2-methoxyethyl)pyrazol-4-yl]phenyl]-1-methyl-imidazole-2-carboxamide;chloride;

N-[3-chloro-4-[4-(1,1-dimethylpiperidin-1-ium-4-carbonyl)piperazine-1-carbonyl]phenyl]-5-[4-[3-chloro-1-(2-methoxyethyl)pyrazol-4-yl]-2,3-difluoro-phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[4-[5-chloro-1-(2-methoxyethyl)pyrazol-4-yl]-2,3-difluoro-phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-(2-methylsulfonylethyl)-3-(trifluoromethyl)pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-(2-hydroxypropyl)-3-(trifluoromethyl)pyrazol-4-yl]phenyl]-1-methyl-imidazole-2-carboxamide;

5-[4-[1-(4-amino-4-oxo-butyl)-3-(trifluoromethyl)pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;

5-[4-[1-(2-amino-2-oxo-ethyl)-3-(trifluoromethyl)pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-(2-methoxyethyl)-3-(trifluoromethyl)pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-(2-morpholinoethyl)-5-(trifluoromethyl)pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-(3-methoxypropyl)-3-(trifluoromethyl)pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-(tetrahydropyran-4-ylmethyl)pyrazol-4-yl]phenyl]-1-methyl-imidazole-2-carboxamide;

5-[4-[1-(5-amino-2-pyridyl)-3-methyl-pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;chloride;

N-[3-chloro-4-[4-(1,1-dimethylpiperidin-1-ium-4-carbonyl)piperazine-1-carbonyl]phenyl]-5-[2,3-difluoro-4-[3-methyl-1-(2-pyridylmethyl)pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-(1H-pyrazol-4-yl)pyrazol-4-yl]phenyl]-1-methyl-imidazole-2-carboxamide;

5-[4-[1-[(5-amino-2-pyridyl)methyl]-3-methyl-pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;chloride;

N-[3-chloro-4-[4-(1,1-dimethylpiperidin-1-ium-4-carbonyl)piperazine-1-carbonyl]phenyl]-5-[2,3-difluoro-4-[3-(2-methylpyrazol-3-yl)-1H-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-(3-fluorophenyl)-1H-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-[2-(2-oxo-1-pyridyl)ethyl]pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-(1-methylpyrazol-4-yl)-1H-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-(1H-pyrazol-4-yl)-1H-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-(2-methoxyethyl)-3-phenyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-(2-pyridyl)pyrazol-4-yl]phenyl]-1-methyl-imidazole-2-carboxamide;

[2-[4-[2-chloro-4-[[1-methyl-5-[4-(3-methyl-1H-pyrazol-4-yl)phenyl]imidazole-2-carbonyl]amino]benzoyl]piperazin-1-yl]-2-oxo-ethyl]-trimethyl-ammonium;

[2-[4-[2-chloro-4-[[5-[4-(3,5-dimethyl-1H-pyrazol-4-yl)phenyl]-1-methyl-imidazole-2-carbonyl]amino]benzoyl]piperazin-1-yl]-2-oxo-ethyl]-trimethyl-ammonium;

4-chloro-N-[3-chloro-4-[4-(1,1-dimethylpiperidin-1-ium-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-[2-(6-methoxy-2-pyridyl)ethyl]-3-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-[(6-methoxy-2-pyridyl)methyl]-3-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-(1H-triazol-4-ylmethyl)pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2-fluoro-6-[1-(2-methoxyethyl)-5-methyl-pyrazol-4-yl]-3-pyridyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[4-[1-(3-cyanopropyl)-3,5-dimethyl-pyrazol-4-yl]-2,3-difluoro-phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2-fluoro-6-[5-(4-methoxyphenyl)-1H-pyrazol-4-yl]-3-pyridyl]-1-methyl-imidazole-2-carboxamide;

(1R,5S)-6-[[2-chloro-4-[[5-[2,3-difluoro-4-[1-(2-methoxyethyl)-3,5-dimethyl-pyrazol-4-yl]phenyl]-1-methyl-imidazole-2-carbonyl]amino]benzoyl]amino]-N-[(3R,4R)-4-hydroxy-1,1-dimethyl-pyrrolidin-1-ium-3-yl]-3-azabicyclo[3.1.0]hexane-3-carboxamide;

5-[4-[5-[(3-amino-3-oxo-propyl)amino]-2-pyridyl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;

5-[4-(5-amino-3-methyl-2-pyridyl)-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;

5-[4-(5-amino-2-pyridyl)-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;

(1S,5R)-6-[[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]amino]-N-[(3R,4R)-4-hydroxy-1,1-dimethyl-pyrrolidin-1-ium-3-yl]-3-azabicyclo[3.1.0]hexane-3-carboxamide;

N-[3-chloro-4-[4-(1,1-dimethylpiperidin-1-ium-4-carbonyl)piperazine-1-carbonyl]phenyl]-5-[2-fluoro-6-[1-(2-methoxyethyl)-3,5-dimethyl-pyrazol-4-yl]-3-pyridyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-[2-(isopropylamino)-2-oxo-ethyl]-3-methyl-pyrazol-4-yl]phenyl]-1-methyl-imidazole-2-carboxamide;

5-[4-[1-[2-(tert-butylamino)-2-oxo-ethyl]-3-methyl-pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;

5-[4-[1-[2-(1-bicyclo[1.1.1]pentanylamino)-2-oxo-ethyl]-3-methyl-pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[4-[1-[2-[(3-cyano-1-bicyclo[1.1.1]pentanyl)amino]-2-oxo-ethyl]-3-methyl-pyrazol-4-yl]-2,3-difluoro-phenyl]-1-methyl-imidazole-2-carboxamide;

5-[4-[1-(2-anilino-2-oxo-ethyl)-3-methyl-pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-[2-(2-fluoroanilino)-2-oxo-ethyl]-3-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-[2-(2-methoxyanilino)-2-oxo-ethyl]-3-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-[2-(4-fluoroanilino)-2-oxo-ethyl]-3-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[4-[1-[2-(cyclohexylamino)-2-oxo-ethyl]-3-methyl-pyrazol-4-yl]-2,3-difluoro-phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(thiazol-2-ylamino)ethyl]pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(1H-pyrazol-4-ylamino)ethyl]pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-[2-[(1-methylpyrazol-4-yl)amino]-2-oxo-ethyl]pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-[2-(3-fluoroanilino)-2-oxo-ethyl]-3-methyl-pyrazol-4-yl]phenyl]-1-methyl-imidazole-2-carboxamide;chloride;

N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(2-pyridylamino)ethyl]pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-[2-[(1-methylpyridin-1-ium-3-yl)amino]-2-oxo-ethyl]pyrazol-4-yl]phenyl]-1-methyl-imidazole-2-carboxamide;diformate;

N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(pyrimidin-2-ylamino)ethyl]pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(4-pyridylamino)ethyl]pyrazol-4-yl]phenyl]-1-methyl-imidazole-2-carboxamide;chloride;

5-[4-[1-[2-(tert-butylamino)-2-oxo-ethyl]-5-methyl-pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[5-methyl-1-[2-oxo-2-(2-pyridylamino)ethyl]pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(tetrahydrofuran-3-ylamino)ethyl]pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(tetrahydropyran-2-ylamino)ethyl]pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(tetrahydropyran-3-ylamino)ethyl]pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(pyridazin-3-ylamino)ethyl]pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[4-[1-[2-[(1,1-dimethylpiperidin-1-ium-3-yl)amino]-2-oxo-ethyl]-3-methyl-pyrazol-4-yl]-2,3-difluoro-phenyl]-1-methyl-imidazole-2-carboxamide;diformate;

N-[3-chloro-4-[4-(1,1-dimethylpiperidin-1-ium-4-carbonyl) piperazine-1-carbonyl]phenyl]-5-[2,3-difluoro-4-[5-methyl-1-[2-oxo-2-(pyridazin-3-ylamino)ethyl]pyrazol-4-yl]phenyl]-1-methyl-imidazole-2-carboxamide;

N-[3-chloro-4-[4-(1,1-dimethylpiperidin-1-ium-4-carbonyl) piperazine-1-carbonyl]phenyl]-5-[4-[1-[2-[(4,4-difluorocyclohexyl)amino]-2-oxo-ethyl]-3-methyl-pyrazol-4-yl]-2,3-difluoro-phenyl]-1-methyl-imidazole-2-carboxamide;

N-[3-chloro-4-[4-(1,1-dimethylpiperidin-1-ium-4-carbonyl) piperazine-1-carbonyl]phenyl]-5-[2,3-difluoro-4-[3-methyl-1-[2-oxo-2-(3-pyridylamino)ethyl]pyrazol-4-yl]phenyl]-1-methyl-imidazole-2-carboxamide;

N-[3-chloro-4-[4-(1,1-dimethylpiperidin-1-ium-4-carbonyl) piperazine-1-carbonyl]phenyl]-5-[2,3-difluoro-4-[1-[2-[(5-methoxy-2-pyridyl)amino]-2-oxo-ethyl]-3-methyl-pyrazol-4-yl]phenyl]-1-methyl-imidazole-2-carboxamide;

N-[3-chloro-4-[4-(1,1-dimethylpiperidin-1-ium-4-carbonyl) piperazine-1-carbonyl]phenyl]-5-[2,3-difluoro-4-[3-methyl-1-[2-oxo-2-(1-piperidyl)ethyl]pyrazol-4-yl]phenyl]-1-methyl-imidazole-2-carboxamide;

N-[3-chloro-4-[4-(1,1-dimethylpiperidin-1-ium-4-carbonyl) piperazine-1-carbonyl]phenyl]-5-[4-[1-[2-[4-(4,4-dimethylpiperazin-4-ium-1-carbonyl)anilino]-2-oxo-ethyl]-3-methyl-pyrazol-4-yl]-2,3-difluoro-phenyl]-1-methyl-imidazole-2-carboxamide;

N-[3-chloro-4-[4-(1,1-dimethylpiperidin-1-ium-4-carbonyl) piperazine-1-carbonyl]phenyl]-5-[2,3-difluoro-4-[1-[2-[(6-fluoropyridazin-3-yl)amino]-2-oxo-ethyl]-3-methyl-pyrazol-4-yl]phenyl]-1-methyl-imidazole-2-carboxamide;

N-[3-chloro-4-[4-(1,1-dimethylpiperidin-1-ium-4-carbonyl) piperazine-1-carbonyl]phenyl]-5-[2,3-difluoro-4-[1-[2-[[(1S,2S)-2-methoxycyclohexyl]amino]-2-oxo-ethyl]-3-methyl-pyrazol-4-yl]phenyl]-1-methyl-imidazole-2-carboxamide;

N-[3-chloro-4-[4-(1,1-dimethylpiperidin-1-ium-4-carbonyl) piperazine-1-carbonyl]phenyl]-5-[2,3-difluoro-4-[3-methyl-1-[2-oxo-2-(pyridazin-4-ylamino)ethyl]pyrazol-4-yl]phenyl]-1-methyl-imidazole-2-carboxamide;

N-[3-chloro-4-[4-(1,1-dimethylpiperidin-1-ium-4-carbonyl) piperazine-1-carbonyl]phenyl]-5-[4-[1-[2-[(6-cyano-3-pyridyl)amino]-2-oxo-ethyl]-3-methyl-pyrazol-4-yl]-2,3-difluoro-phenyl]-1-methyl-imidazole-2-carboxamide;

N-[2-[4-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]-2,3-difluoro-phenyl]-5-methyl-pyrazol-1-yl]ethyl]pyridine-2-carboxamide;

N-[2-[4-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]-2,3-difluoro-phenyl]-3-methyl-pyrazol-1-yl]ethyl]pyridine-2-carboxamide;

N-[3-chloro-4-[4-(1,1-dimethylpiperidin-1-ium-4-carbonyl) piperazine-1-carbonyl]phenyl]-5-[2,3-difluoro-4-[1-[2-[(4-fluorophenyl)sulfonylamino]ethyl]-3-methyl-pyrazol-4-yl]phenyl]-1-methyl-imidazole-2-carboxamide;

5-[4-[1-[2-(tert-butylcarbamoylamino)ethyl]-5-methyl-pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;

5-[4-[1-[2-(tert-butylcarbamoylamino)ethyl]-3-methyl-pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;

N-[3-chloro-4-[4-(1,1-dimethylpiperidin-1-ium-4-carbonyl) piperazine-1-carbonyl]phenyl]-5-[2,3-difluoro-4-[5-methyl-1-[2-(2-pyridylcarbamoylamino)ethyl]pyrazol-4-yl]phenyl]-1-methyl-imidazole-2-carboxamide;

N-[3-chloro-4-[4-(1,1-dimethylpiperidin-1-ium-4-carbonyl) piperazine-1-carbonyl]phenyl]-5-[2,3-difluoro-4-[3-methyl-1-[2-(2-pyridylcarbamoylamino)ethyl]pyrazol-4-yl]phenyl]-1-methyl-imidazole-2-carboxamide;

N-[3-chloro-4-[4-(1,1-dimethylpiperidin-1-ium-4-carbonyl) piperazine-1-carbonyl]phenyl]-5-[2,3-difluoro-4-[3-methyl-1-[2-(pyrrolidine-1-carbonylamino)ethyl]pyrazol-4-yl]phenyl]-1-methyl-imidazole-2-carboxamide;

N-[3-chloro-4-[4-(1,1-dimethylpiperidin-1-ium-4-carbonyl) piperazine-1-carbonyl]phenyl]-5-[2,3-difluoro-4-[5-(2-pyridyl)-1H-pyrazol-4-yl]phenyl]-1-methyl-imidazole-2-carboxamide;

N-[3-chloro-4-[4-(1,1-dimethylpiperidin-1-ium-4-carbonyl) piperazine-1-carbonyl]phenyl]-5-[2,3-difluoro-4-[5-(4-methoxyphenyl)-1H-pyrazol-4-yl]phenyl]-1-methyl-imidazole-2-carboxamide;

N-[3-chloro-4-[4-(1,1-dimethylpiperidin-1-ium-4-carbonyl) piperazine-1-carbonyl]phenyl]-5-[2,3-difluoro-4-[5-(3-methoxyphenyl)-1H-pyrazol-4-yl]phenyl]-1-methyl-imidazole-2-carboxamide;

N-[3-chloro-4-[4-(1,1-dimethylpiperidin-1-ium-4-carbonyl) piperazine-1-carbonyl]phenyl]-5-[2,3-difluoro-4-[5-(2-methoxyphenyl)-1H-pyrazol-4-yl]phenyl]-1-methyl-imidazole-2-carboxamide;

N-[3-chloro-4-[4-(1,1-dimethylpiperidin-1-ium-4-carbonyl) piperazine-1-carbonyl]phenyl]-5-[2,3-difluoro-4-(5-thiazol-4-yl-1H-pyrazol-4-yl)phenyl]-1-methyl-imidazole-2-carboxamide;

N-[3-chloro-4-[4-(1,1-dimethylpiperidin-1-ium-4-carbonyl) piperazine-1-carbonyl]phenyl]-5-[2,3-difluoro-4-(5-tetrahydropyran-4-yl-1H-pyrazol-4-yl)phenyl]-1-methyl-imidazole-2-carboxamide;

N-[3-chloro-4-[4-(1,1-dimethylpiperidin-1-ium-4-carbonyl) piperazine-1-carbonyl]phenyl]-5-[4-[5-(3,6-dihydro-2H-pyran-4-yl)-1H-pyrazol-4-yl]-2,3-difluoro-phenyl]-1-methyl-imidazole-2-carboxamide;

N-[4-[4-[1-(azetidin-3-ylmethyl)-1-methyl-piperidin-1-ium-4-carbonyl]piperazine-1-carbonyl]-3-chloro-phenyl]-5-[2,3-difluoro-4-(3-methyl-1H-pyrazol-4-yl)phenyl]-1-methyl-imidazole-2-carboxamide;

5-[4-[1-[2-(2-aminoethoxy)ethyl]-3,5-dimethyl-pyrazol-4-yl]-2,3-difluoro-phenyl]-N-[3-chloro-4-[4-[(2S,4R)-4-hydroxy-1,1-dimethyl-pyrrolidin-1-ium-2-carbonyl]piperazine-1-carbonyl]phenyl]-1-methyl-imidazole-2-carboxamide;

N-[3-chloro-4-[4-[(2S,4R)-4-hydroxy-1,1-dimethyl-1$\lambda^5$-azolidine-2-carbonyl]piperazine-1-carbonyl]phenyl]-5-[4-[1-[2-(difluoromethoxy)ethyl]-3,5-dimethyl-pyrazol-4-yl]-2,3-difluoro-phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[4-[1-[(2,2-difluorocyclopropyl)methyl]-3,5-dimethyl-pyrazol-4-yl]-2,3-difluoro-phenyl]-1-methyl-imidazole-2-carboxamide;

N-[4-[4-(3-benzyl-3-aza-6-azoniaspiro[5.5]undecane-9-carbonyl)piperazine-1-carbonyl]-3-chloro-phenyl]-5-[2,3-difluoro-4-[1-(2-methoxyethyl)-3-methyl-pyrazol-4-yl] phenyl]-1-methyl-imidazole-2-carboxamide;

cis 2-[1-(azetidin-3-ylmethyl)-4-[4-[2-chloro-4-[[5-[2,3-difluoro-4-[1-[2-[(6-fluoropyridazin-3-yl)amino]-2-oxo-ethyl]-3-methyl-pyrazol-4-yl]phenyl]-1-methyl-imidazole-2-carbonyl]amino]benzoyl]piperazine-1-carbonyl]
piperidin-1-ium-1-yl]acetic acid;
N-[3-chloro-4-[4-(1,1-dimethylpiperidin-1-ium-4-carbonyl)
piperazine-1-carbonyl]phenyl]-5-[2,3-difluoro-4-[3-
methyl-1-[2-[(6-methyl-3-pyridyl)carbamoylamino]
ethyl]pyrazol-4-yl]phenyl]-1-methyl-imidazole-2-
carboxamide;
N-[3-chloro-4-[4-(4-oxo-3-aza-6-azoniaspiro[5.5]unde-
cane-9-carbonyl)piperazine-1-carbonyl]phenyl]-5-[2,3-
difluoro-4-[1-(2-methoxyethyl)-3-methyl-pyrazol-4-yl]
phenyl]-1-methyl-imidazole-2-carboxamide;
N-[3-chloro-4-[4-(1,1-dimethylpiperidin-1-ium-4-carbonyl)
piperazine-1-carbonyl]phenyl]-5-[3-fluoro-4-[1-[2-[(6-
fluoropyridazin-3-yl)amino]-2-oxo-ethyl]-3-methyl-
pyrazol-4-yl]phenyl]-1-methyl-imidazole-2-
carboxamide;
N-[3-chloro-4-[4-(1,1-dimethylpiperidin-1-ium-4-carbonyl)
piperazine-1-carbonyl]phenyl]-5-[4-[1-[2-[(6-fluoro-
pyridazin-3-yl)amino]-2-oxo-ethyl]-3-methyl-pyrazol-4-
yl]phenyl]-1-methyl-imidazole-2-carboxamide;
bis(4-aminobutyl)-(carboxymethyl)-[4-[4-[2-chloro-4-[[5-
[2,3-difluoro-4-[1-(2-methoxyethyl)-5-methyl-pyrazol-4-
yl]phenyl]-1-methyl-imidazole-2-carbonyl]amino]ben-
zoyl]-3-methyl-piperazino]-4-keto-butyl]ammonium;
N-[3-chloro-4-[4-(1,1-dimethylpiperidin-1-ium-4-carbonyl)
piperazine-1-carbonyl]phenyl]-5-[2,3-difluoro-4-[3-
methyl-1-[2-[(6-methylpyridazin-3-yl)amino]-2-oxo-
ethyl]pyrazol-4-yl]phenyl]-1-methyl-imidazole-2-
carboxamide;
N-[3-chloro-4-[4-(1,1-dimethylpiperidin-1-ium-4-carbonyl)
piperazine-1-carbonyl]phenyl]-5-[2,3-difluoro-4-[1-[2-
[(6-methoxypyridazin-3-yl)amino]-2-oxo-ethyl]-3-
methyl-pyrazol-4-yl]phenyl]-1-methyl-imidazole-2-
carboxamide;
N-[3-chloro-4-[4-(1,1-dimethylpiperidin-1-ium-4-carbonyl)
piperazine-1-carbonyl]phenyl]-5-[2,3-difluoro-4-[3-
methyl-1-[2-[(6-morpholinopyridazin-3-yl)amino]-2-
oxo-ethyl]pyrazol-4-yl]phenyl]-1-methyl-imidazole-2-
carboxamide;
cis 2-[1-(azetidin-3-ylmethyl)-4-[4-[2-chloro-4-[[5-[3-
fluoro-4-[1-(2-methoxyethyl)-3-methyl-pyrazol-4-yl]
phenyl]-1-methyl-imidazole-2-carbonyl]amino]benzoyl]
piperazine-1-carbonyl]piperidin-1-ium-1-yl]acetic acid;
cis 2-[1-(azetidin-3-ylmethyl)-4-[4-[2-chloro-4-[[5-[3-
fluoro-4-[1-(2-methoxyethyl)-5-methyl-pyrazol-4-yl]-2-
methyl-phenyl]-1-methyl-imidazole-2-carbonyl]amino]
benzoyl]piperazine-1-carbonyl]piperidin-1-ium-1-yl]
acetic acid;
2-[2-(3-aminopropyl)-4-[3-[[1-[2-chloro-4-[[5-[2,3-dif-
luoro-4-[1-(2-methoxyethyl)-5-methyl-pyrazol-4-yl]phe-
nyl]-1-methyl-imidazole-2-carbonyl]amino]benzoyl]
isonipecotoyl]amino]propyl]pyridin-1-ium-1-yl]acetic
acid;
azetidin-3-ylmethyl-(carboxymethyl)-[4-[4-[2-chloro-4-[[5-
[4-[1-[2-(difluoromethoxy)ethyl]-5-methyl-pyrazol-4-
yl]-3-fluoro-2-methyl-phenyl]-1-methyl-imidazole-2-car-
bonyl]amino]benzoyl]piperazin-1-yl]-4-oxo-butyl]-
methyl-ammonium;formic acid;
2-[1-(azetidin-3-ylmethyl)-4-[4-[2-chloro-4-[[5-[4-[1-[2-
(difluoromethoxy)ethyl]-5-methyl-pyrazol-4-yl]-3-
fluoro-2-methyl-phenyl]-1-methyl-imidazole-2-carbonyl]
amino]benzoyl]piperazine-1-carbonyl]piperidin-1-ium-1-
yl]acetic acid;
3-aminopropyl-(carboxymethyl)-[4-[4-[2-chloro-4-[[5-[4-
[1-[2-(difluoromethoxy)ethyl]-5-methyl-pyrazol-4-yl]-3-
fluoro-2-methyl-phenyl]-1-methyl-imidazole-2-carbonyl]
amino]benzoyl]piperazin-1-yl]-4-oxo-butyl]-methyl-
ammonium;
2-[1-(azetidin-3-ylmethyl)-4-[4-[2-chloro-4-[[5-[3-fluoro-
4-[1-(2-methoxyethyl)-5-methyl-pyrazol-4-yl]phenyl]-1-
methyl-imidazole-2-carbonyl]amino]benzoyl]piperazine-
1-carbonyl]piperidin-1-ium-1-yl]acetic acid;
carboxymethyl-[4-[4-[2-chloro-4-[[5-[2,3-difluoro-4-[1-(2-
methoxyethyl)-5-methyl-pyrazol-4-yl]phenyl]-1-methyl-
imidazole-2-carbonyl]amino]benzoyl]piperazin-1-yl]-4-
oxo-butyl]-bis[2-(dimethylamino)ethyl]ammonium;
cis 2-[1-(azetidin-3-ylmethyl)-4-[4-[2-chloro-4-[[5-[4-[1-
[2-(difluoromethoxy)ethyl]-3-methyl-pyrazol-4-yl]-2,3-
difluoro-phenyl]-1-methyl-imidazole-2-carbonyl]amino]
benzoyl]piperazine-1-carbonyl]piperidin-1-ium-1-yl]
acetate;
bis(3-aminopropyl)-[4-[4-[2-chloro-4-[[5-[2,3-difluoro-4-
[1-(2-methoxyethyl)-5-methyl-pyrazol-4-yl]phenyl]-1-
methyl-imidazole-2-carbonyl]amino]benzoyl]piperazin-
1-yl]-4-oxo-butyl]-methyl-ammonium;
N-[3-chloro-4-[4-[(2S,4R)-4-hydroxy-1,1-dimethyl-pyrroli-
din-1-ium-2-carbonyl]piperazine-1-carbonyl]phenyl]-5-
[3-fluoro-4-[1-(2-methoxyethyl)-5-methyl-pyrazol-4-yl]-
2-methyl-phenyl]-1-methyl-imidazole-2-carboxamide;
3-aminopropyl-(carboxymethyl)-[4-[4-[2-chloro-4-[[5-[3-
fluoro-4-[1-(2-methoxyethyl)-5-methyl-pyrazol-4-yl]-2-
methyl-phenyl]-1-methyl-imidazole-2-carbonyl]amino]
benzoyl]piperazino]-4-keto-butyl]-methyl-ammonium
0.1:1 2,2,2-trifluoroacetic acid;
bis(4-aminobutyl)-(carboxymethyl)-[4-[4-[2-chloro-4-[[5-
[2,3-difluoro-4-[1-(2-methoxyethyl)-5-methyl-pyrazol-4-
yl]phenyl]-1-methyl-imidazole-2-carbonyl]amino]ben-
zoyl]piperazin-1-yl]-4-oxo-butyl]ammonium;
cis 2-[1-(azetidin-3-ylmethyl)-4-[4-[2-chloro-4-[[5-[2,3-dif-
luoro-4-[1-(2-methoxyethyl)-3-methyl-pyrazol-4-yl]phe-
nyl]-1-methyl-imidazole-2-carbonyl]amino]benzoyl]pip-
erazine-1-carbonyl]piperidin-1-ium-1-yl]acetic acid;
trans 2-[1-(azetidin-3-ylmethyl)-4-[4-[2-chloro-4-[[5-[2,3-
difluoro-4-[1-(2-methoxyethyl)-3-methyl-pyrazol-4-yl]
phenyl]-1-methyl-imidazole-2-carbonyl]amino]benzoyl]
piperazine-1-carbonyl]piperidin-1-ium-1-yl]acetic acid;
2-[1-(azetidin-3-ylmethyl)-4-[5-[4-[2-chloro-4-[[5-[2,3-dif-
luoro-4-[1-(2-methoxyethyl)-5-methyl-pyrazol-4-yl]phe-
nyl]-1-methyl-imidazole-2-carbonyl]amino]benzoyl]pip-
erazino]-5-keto-pentanoyl]piperazin-1-ium-1-yl]acetic
acid;
2-[1-(3-aminopropyl)-4-[5-[4-[2-chloro-4-[[5-[2,3-difluoro-
4-[1-(2-methoxyethyl)-5-methyl-pyrazol-4-yl]phenyl]-1-
methyl-imidazole-2-carbonyl]amino]benzoyl]piper-
azino]-5-keto-pentanoyl]piperazin-1-ium-1-yl]acetic
acid;
2-[1-(azetidin-3-ylmethyl)-4-[(1S,5R)-6-[[2-chloro-4-[[5-
[2,3-difluoro-4-[1-(2-methoxyethyl)-5-methyl-pyrazol-4-
yl]phenyl]-1-methyl-imidazole-2-carbonyl]amino]ben-
zoyl]amino]-3-azabicyclo[3.1.0]hexane-3-carbonyl]
piperidin-1-ium-1-yl]acetic acid;
2-[1-(azetidin-3-ylmethyl)-4-[[1-[2-chloro-4-[[5-[2,3-dif-
luoro-4-[1-(2-methoxyethyl)-5-methyl-pyrazol-4-yl]phe-
nyl]-1-methyl-imidazole-2-carbonyl]amino]benzoyl]-4-
piperidyl]-methyl-carbamoyl]piperidin-1-ium-1-yl]acetic
acid;
azetidin-3-ylmethyl-(carboxymethyl)-[4-[4-[2-chloro-4-[[5-
[2,3-difluoro-4-[1-(2-methoxyethyl)-5-methyl-pyrazol-4-
yl]phenyl]-1-methyl-imidazole-2-carbonyl]amino]ben-
zoyl]piperazin-1-yl]-4-oxo-butyl]-methyl-ammonium;
cis 2-[1-(azetidin-3-ylmethyl)-4-[4-[[5-[2,3-difluoro-4-
[1-(2-methoxyethyl)-3-methylpyrazol-4-yl]phenyl]-1- methylimidazole-2-carbonyl]amino]-2-methylbenzoyl]
piperazine-1-carbonyl]piperidin-1-ium-1-yl]acetic acid;
cis 2-[1-(azetidin-3-ylmethyl)-4-[4-[4-[[5-[3-fluoro-4-[1-(2-methoxyethyl)-3-methyl-pyrazol-4-yl]phenyl]-1-methyl-imidazole-2-carbonyl]amino]-2-methyl-benzoyl]piperazine-1-carbonyl]piperidin-1-ium-1-yl]acetic acid; and
cis 2-[1-(azetidin-3-ylmethyl)-4-[4-[4-[[5-[3-fluoro-4-[1-(2-methoxyethyl)-5-methylpyrazol-4-yl]-2-methylphenyl]-1-methylimidazole-2-carbonyl]amino]-2-methylbenzoyl]piperazine-1-carbonyl]piperidin-1-ium-1-yl]acetic acid.

In a preferred embodiment, the present invention provides a compound of formula (I) as described herein, or a pharmaceutically acceptable salt thereof, wherein said compound of formula (I) is selected from:

N-[3-chloro-4-[4-(1,1-dimethylpiperidin-1-ium-4-carbonyl)piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-(4,4-dimethylpiperazin-4-ium-1-carbonyl)piperidine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[4-[4-[1-(2-amino-2-oxo-ethyl)-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide;

N-[4-[4-[1-(2-amino-2-oxo-ethyl)-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide;

N-[4-[4-[1-(2-amino-2-oxo-ethyl)-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide;

N-[4-[4-[4-(2-amino-2-oxo-ethyl)-4-(azetidin-3-ylmethyl)piperazin-4-ium-1-carbonyl]piperidine-1-carbonyl]-3-chloro-phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[(1R,5S)-3,3-dimethyl-3-azoniabicyclo[3.1.0]hexane-6-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

2-[1-(azetidin-3-ylmethyl)-4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]piperidin-1-ium-1-yl]acetic acid;

N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[(2R,4R)-4-hydroxy-1,1-dimethyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

bis(3-aminopropyl)-(carboxymethyl)-[4-[4-[2-chloro-4-[[5-[2,3-difluoro-4-(3-methyl-1H-pyrazol-4-yl)phenyl]-1-methyl-imidazole-2-carbonyl]amino]benzoyl]piperazin-1-yl]-4-oxo-butyl]ammonium;

N-[3-chloro-4-[4-(1,1-dimethylpiperidin-1-ium-4-carbonyl)piperazine-1-carbonyl]phenyl]-5-[2-chloro-3-fluoro-4-[1-(2-methoxyethyl)-5-methyl-pyrazol-4-yl]phenyl]-1-methyl-imidazole-2-carboxamide; and N-[3-chloro-4-[4-[(2S,4R)-4-hydroxy-1,1-dimethyl-pyrrolidin-1-ium-2-carbonyl]piperazine-1-carbonyl]phenyl]-5-[4-[5-(difluoromethyl)-1-(2-methoxyethyl)pyrazol-4-yl]-2,3-difluoro-phenyl]-1-methyl-imidazole-2-carboxamide.

In a particularly preferred embodiment, the present invention provides a compound of formula (I) as described herein, or a pharmaceutically acceptable salt thereof, wherein said compound of formula (I) is N-[4-[4-[1-(2-amino-2-oxo-ethyl)-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide.

In a particularly preferred embodiment, the present invention provides a compound of formula (I) as described herein, or a pharmaceutically acceptable salt thereof, wherein said compound of formula (I) is cis 2-[1-(azetidin-3-ylmethyl)-4-[4-[2-chloro-4-[[5-[3-fluoro-4-[1-(2-methoxyethyl)-5-methyl-pyrazol-4-yl]-2-methyl-phenyl]-1-methyl-imidazole-2-carbonyl]amino]benzoyl]piperazine-1-carbonyl]piperidin-1-ium-1-yl]acetic acid, in particular cis 2-[1-(azetidin-3-ylmethyl)-4-[4-[2-chloro-4-[[5-[3-fluoro-4-[1-(2-methoxyethyl)-5-methyl-pyrazol-4-yl]-2-methyl-phenyl]-1-methyl-imidazole-2-carbonyl]amino]benzoyl]piperazine-1-carbonyl]piperidin-1-ium-1-yl]acetic acid formate.

In a particularly preferred embodiment, the present invention provides a compound of formula (I) as described herein, or a pharmaceutically acceptable salt thereof, wherein said compound of formula (I) is N-[3-chloro-4-[4-[(2R,4R)-4-hydroxy-1,1-dimethyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide.

In a particularly preferred embodiment, the present invention provides a compound of formula (I) as described herein, or a pharmaceutically acceptable salt thereof, wherein said compound of formula (I) is N-[3-chloro-4-[4-(1,1-dimethylpiperidin-1-ium-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide.

In a particularly preferred embodiment, the present invention provides a compound of formula (I) as described herein, or a pharmaceutically acceptable salt thereof, wherein said compound of formula (I) is 2-[1-(azetidin-3-ylmethyl)-4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]piperidin-1-ium-1-yl]acetic acid.

In a particularly preferred embodiment, the present invention provides a compound of formula (I) as described herein, or a pharmaceutically acceptable salt thereof, wherein said compound of formula (I) is N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide.

In one embodiment, the present invention provides pharmaceutically acceptable salts of the compounds of formula (I) as described herein, especially pharmaceutically acceptable salts selected from hydrochlorides, fumarates, lactates (in particular derived from L-(+)-lactic acid), tartrates (in particular derived from L-(+)-tartaric acid) and trifluoroacetates. In yet a further particular embodiment, the present invention provides compounds according to formula (I) as described herein (i.e., as "free bases" or "free acids", respectively).

In some embodiments, the compounds of formula (I) are isotopically-labeled by having one or more atoms therein replaced by an atom having a different atomic mass or mass number. Such isotopically-labeled (i.e., radiolabeled) compounds of formula (I) are considered to be within the scope of this disclosure. Examples of isotopes that can be incorporated into the compounds of formula (I) include isotopes of hydrogen, carbon, nitrogen, oxygen, phosphorous, sulfur, fluorine, chlorine, and iodine, such as, but not limited to, $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. Certain isotopically-labeled compounds of formula (I), for example, those incorporating a radioactive isotope, are useful in drug and/or substrate tissue distribution studies. The radioactive isotopes tritium, i.e. $^3$H, and carbon-14, i.e., $^{14}$C, are particularly useful for this purpose in view of their ease of incorporation and ready means of detection. For example, a compound of formula (I) can be enriched with 1, 2, 5, 10, 25, 50, 75, 90, 95, or 99 percent of a given isotope.

Substitution with heavier isotopes such as deuterium, i.e. $^2$H, may afford certain therapeutic advantages resulting from greater metabolic stability, for example, increased in vivo half-life or reduced dosage requirements.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples as set out below using an appropriate isotopically-labeled reagent in place of the non-labeled reagent previously employed.

Processes of Manufacturing

The preparation of compounds of formula (I) of the present invention may be carried out in sequential or convergent synthetic routes. Syntheses of the compounds of the invention are shown in the following schemes. The skills required for carrying out the reactions and purifications of the resulting products are known to those skilled in the art. The substituents and indices used in the following description of the processes have the significance given herein before unless indicated to the contrary. In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations*, 3rd Edition, Richard C. Larock. John Wiley & Sons, New York, NY. 2018). We find it convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux temperature. The time required for the reaction may also vary widely, depending on many factors, notably the reaction temperature and the nature of the reagents. However, a period of from 0.5 h to several days will usually suffice to yield the described intermediates and compounds. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

All substituents, in particular, X, D, and $R^1$ to $R^9$ are as defined above and in the claims, unless otherwise indicated. Furthermore, and unless explicitly otherwise stated, all reactions, reaction conditions, abbreviations and symbols have the meanings well known to a person of ordinary skill in organic chemistry.

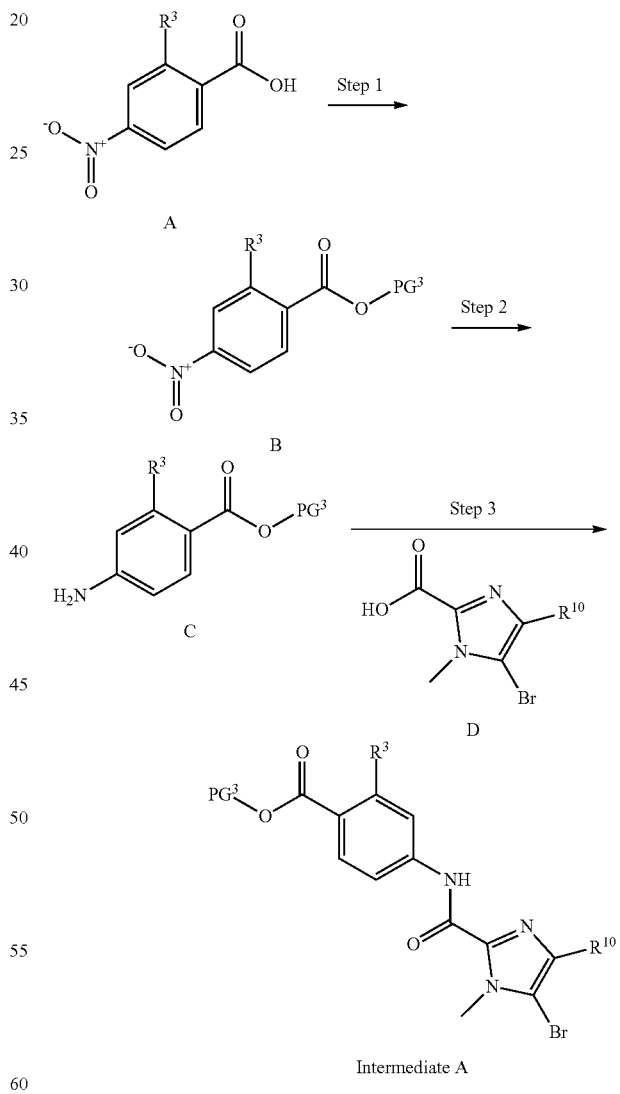

Wherein PG$^3$ is a protective group, such as Boc.

Intermediate A can be prepared according to Scheme 1. Protection of substituted 4-nitrobenzoic acid A, e.g. with (BOC)$_2$O, gives compound B. Reduction of the nitro group of compound B, for example using the well-known ammonium chloride/iron system at room temperature, yields amine C. Coupling of carboxylic acid D and amine C in the presence of a condensing agent, such as HATU/DIPEA in a solvent, such as DMSO, affords Intermediate A.

Scheme 2

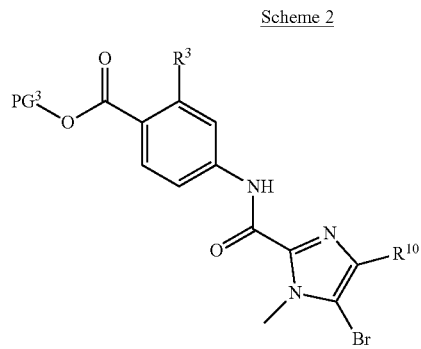

Intermediate A

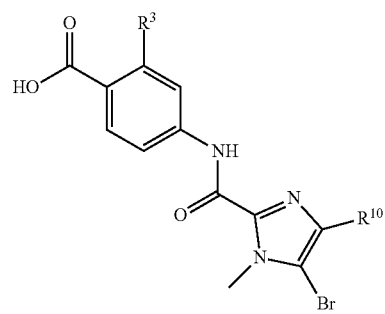

E

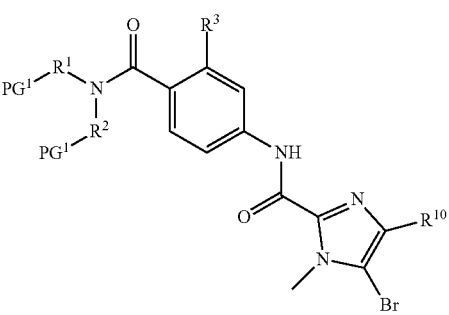

Intermediate B, C, D

Wherein PG¹ is a protective group, such as Boc, or PG¹ is H (no protection); and PG³ is a protective group, such as Boc.

Intermediates B, C, D can be prepared according to Scheme 2. Hydrolysis the Intermediate A gives carboxylic acid E, which can be coupled with diverse amines in the presence of a condensing agent, such as HATU/DIPEA in a solvent, such as DMSO, to afford Intermediates B, C, and D.

Scheme 3

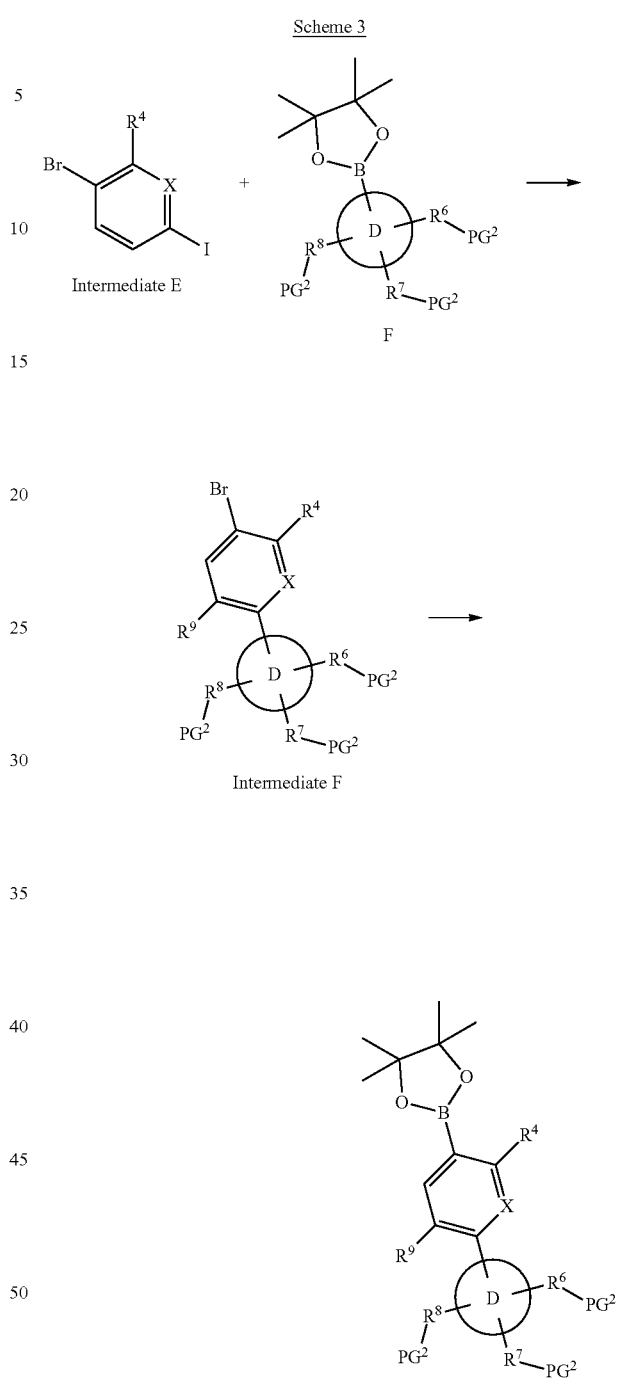

wherein: PG² is a protective group, such as Boc, SEM, TBS; or PG² H (no protection).

Intermediate G can be prepared according to Scheme 3. Thus, Suzuki coupling of Intermediate E with boronic acid esters F, e.g. using palladium catalysts and phosphine ligands, affords Intermediate F. Intermediate F is further reacted with Bis(pinacolato)diboron using palladium catalysts and phosphine ligands to afford Intermediate G (in some cases, the bronic acid ester will directly hydrolyse to the bronic acid in the reaction system).

Scheme 4

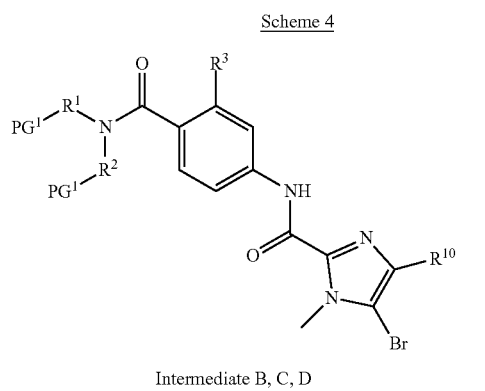

Scheme 5

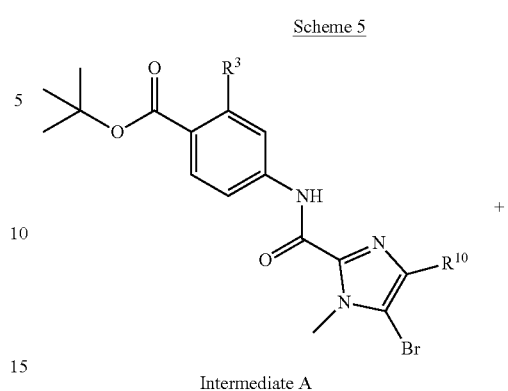

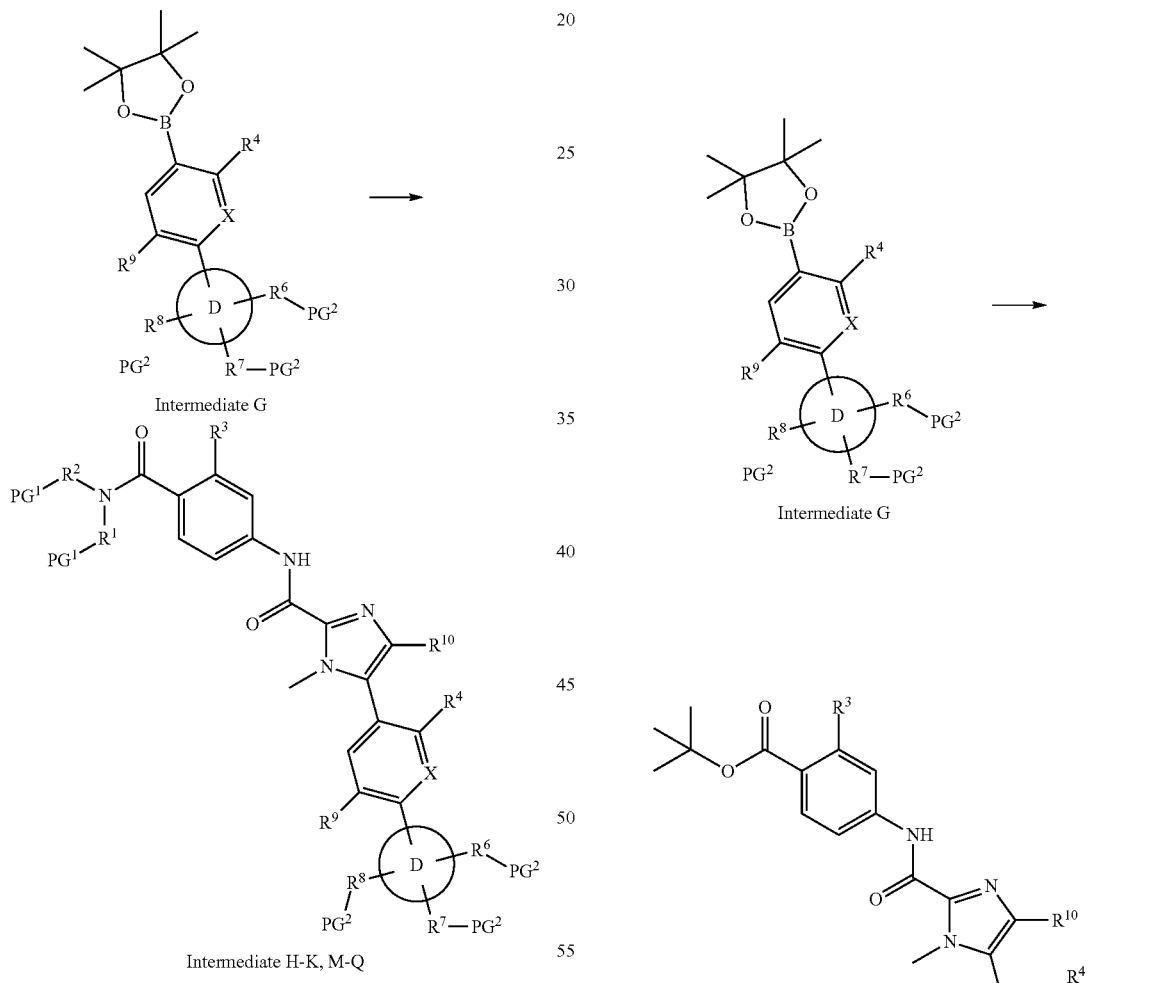

wherein: PG$^1$ is a protective group, such as Boc, or PG$^1$ is H (no protection); and PG$^2$ is a protective group, such as Boc, SEM, TBS, or PG$^2$ H (no protection).

Intermediate H—K, and M-Q can be prepared according to Scheme 4. Thus, Suzuki coupling of Intermediate B, C, D with bronic acid ester Intermediate G in the presence of a palladium catalyst and a phosphine ligand affords Intermediate H—K, and M-Q.

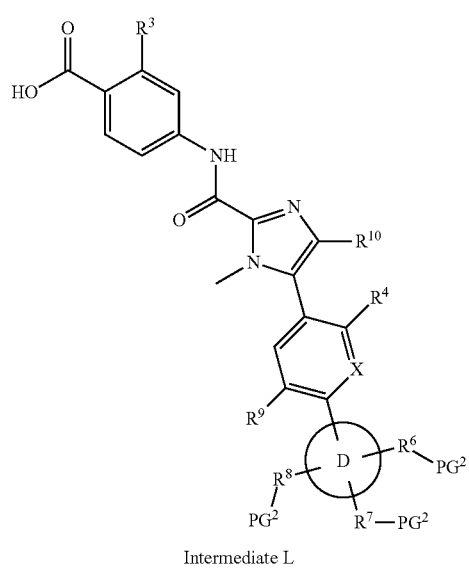

Intermediate L

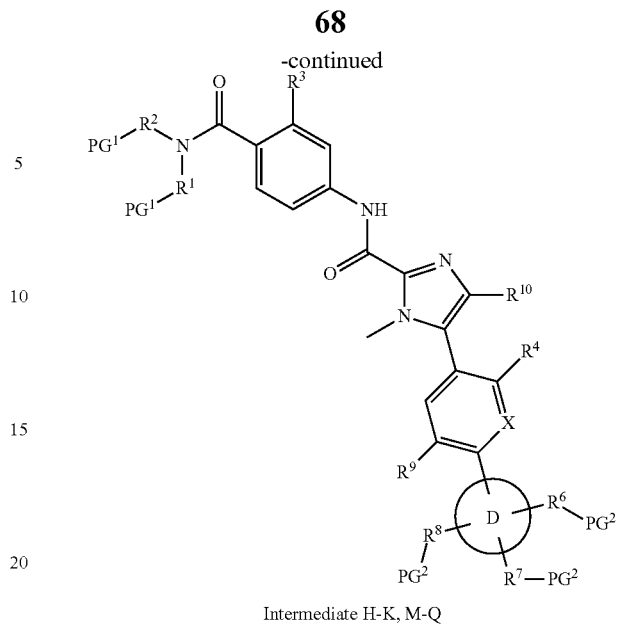

Intermediate H-K, M-Q wherein: PG$^1$ is a protective group, such as Boc, or PG$^1$ is H (no protection); and PG$^2$ is a protective group, such as Boc, SEM, TBS, or or PG$^2$ is H (no protection).

In addition to the procedure outlined in Scheme 4, Intermediate H—K, and M-Q also can be prepared according to Scheme 5. Thus, Suzuki coupling of Intermediate A with boronic acid ester Intermediate G in the presence of a palladium catalyst and a phosphine ligand affords compound G. Hydrolysis of compound G yields carboxylic acid Intermediate L, which is subsequently coupled with diverse amines in the presence of a condensing agent, such as HATU/DIPEA in a solvent, such as DMSO, to afford Intermediate H—K, and M-Q.

Scheme 6

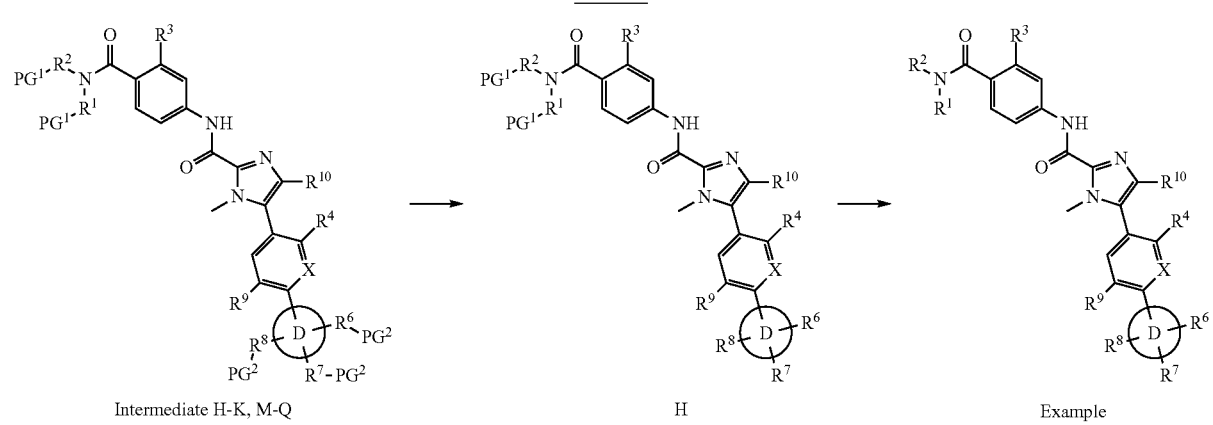

Intermediate H-K, M-Q        H        Example

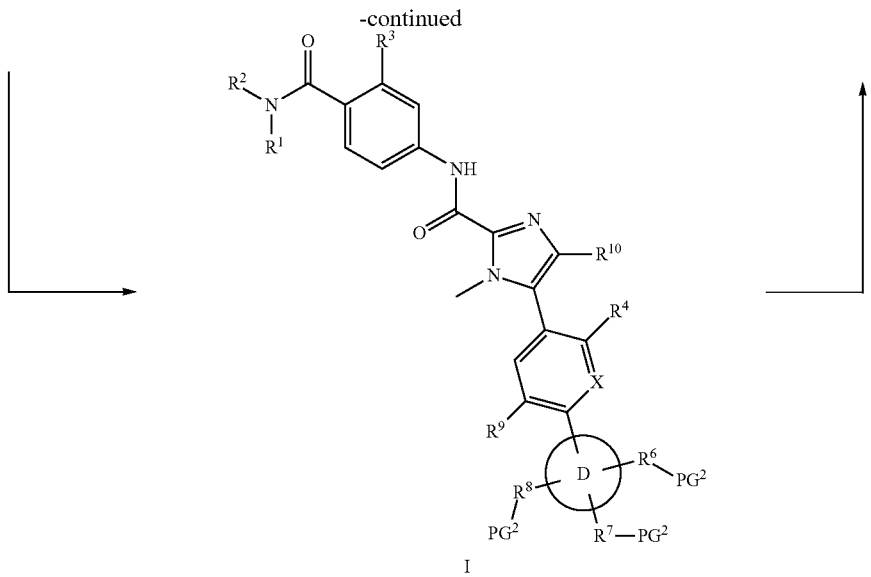

I wherein: PG¹ is a protective group, such as Boc, or PG¹ is H (no protection); and PG² is a protective group, such as Boc, SEM, TBS, or PG² is H (no protection).

The Examples can be prepared according to Scheme 6. Thus, removal of PG² (in case PG² is not hydrogen) from Intermediates H—K, and M-Q affords compound H. Subsequent removal of PG¹ (in case PG¹ is not hydrogen) finally affords Examples. The order of deprotection steps can also be reversed, going via compound I. In some cases, the final Examples are achieved by alkylation of certain intermediates, e.g. methylation using MeI in the presence of DIPEA in acetonitrile at room temperature. The removal of the protective groups PG¹ and PG² can occur before or after the alkylation step, based on the requirements of the substitution pattern.

In one aspect, the present invention provides a process of manufacturing the compounds of formula (I) described herein, wherein said process is as described in any one of Schemes 1 to 6 above.

In a further aspect, the present invention provides a compound of formula (I) as described herein, or a pharmaceutically acceptable salt thereof, when manufactured according to the processes disclosed herein.

Using the Compounds

As illustrated in the experimental section, the compounds of formula (I) and their pharmaceutically acceptable salts possess valuable pharmacological properties for the treatment or prevention of infections and resulting diseases, particularly bacteremia, pneumonia, meningitis, urinary tract infection, and wound infection, caused by pathogens, particularly by bacteria, more particularly by *Acinetobacter* species, most particularly by *Acinetobacter baumannii*.

The compounds of formula (I) and their pharmaceutically acceptable salts exhibit activity as antibiotics, particularly as antibiotics against *Acinetobacter* species, more particularly as antibiotics against *Acinetobacter baumannii*, most particularly as pathogen-specific antibiotics against *Acinetobacter baumannii*.

The compounds of formula (I) and their pharmaceutically acceptable salts can be used as antibiotics, i.e. as antibacterial pharmaceutical ingredients suitable in the treatment and prevention of bacterial infections, particularly in the treatment and prevention of bacterial infections caused by *Acinetobacter* species, more particularly in the treatment and prevention of bacterial infections caused by *Acinetobacter baumannii*.

The compounds of the present invention can be used, either alone or in combination with other drugs, for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*.

In one aspect, the present invention provides compounds of formula (I) or their pharmaceutically acceptable salts as described herein for use as therapeutically active substances.

In a further aspect, the present invention provides a compound of formula (I) as described herein, or a pharmaceutically acceptable salt thereof, for use as antibiotic.

In a further aspect, the present invention provides a compound of formula (I) as described herein, or a pharmaceutically acceptable salt thereof, for use in the treatment or prevention of nosocomial infections and resulting diseases.

In a particular embodiment, said nosocomial infections and resulting diseases are selected from bacteremia, pneumonia, meningitis, urinary tract infection and wound infection, or a combination thereof.

In a further aspect, the present invention provides a compound of formula (I) as described herein, or a pharmaceutically acceptable salt thereof, for use in the treatment or prevention of infections and resulting diseases caused by Gram-negative bacteria.

In a particular embodiment, said infections and resulting diseases caused by Gram-negative bacteria are selected from bacteremia, pneumonia, meningitis, urinary tract infection and wound infection, or a combination thereof.

In a further aspect, the present invention provides a compound of formula (I) as described herein, or a pharmaceutically acceptable salt thereof, for use in the treatment or prevention of infections and resulting diseases caused by *Enterococcus faecium, Staphylococcus aureus, Klebsiella*

*pneumoniae, Acinetobacter baumannii, Pseudomonas aeruginosa, Enterobacter* species or *E. coli*, or a combination therof.

In a further aspect, the present invention provides a method for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination therof, which method comprises administering a compound of formula (I) as described herein, or a pharmaceutically acceptable salt thereof, to a mammal.

In a further aspect, the present invention provides the use of a compound of formula (I) as described herein, or a pharmaceutically acceptable salt thereof, as an antibiotic.

In a further aspect, the present invention provides the use of a compound of formula (I) as described herein, or a pharmaceutically acceptable salt thereof, for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination therof.

In a further aspect, the present invention provides the use of a compound of formula (I) as described herein, or a pharmaceutically acceptable salt thereof, for the preparation of medicaments useful for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination therof.

In a particular embodiment, said infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination therof, are selected from bacteremia, pneumonia, meningitis, urinary tract infection and wound infection, or a combination thereof.

In a further aspect, the present invention provides compounds of formula (I) or their pharmaceutically acceptable salts as defined above for use in the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*.

In a further aspect, the present invention provides a method for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*, which method comprises administering a compound of formula (I) or a pharmaceutically acceptable salt thereof as defined above to a mammal.

In a further aspect, the present invention provides the use of compounds of formula (I) or their pharmaceutically acceptable salts as defined above for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*.

In a further aspect, the present invention provides the use of compounds of formula (I) or their pharmaceutically acceptable salts as defined above for the preparation of medicaments for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*. Such medicaments comprise compounds of formula (I) or their pharmaceutically acceptable salts as defined above.

Pharmaceutical Compositions and Administration

In one aspect, the present invention provides pharmaceutical compositions comprising compounds of formula (I) or their pharmaceutically acceptable salts as defined above and one or more pharmaceutically acceptable excipients. Exemplary pharmaceutical compositions are described in Examples 1-4.

In a further aspect, the present invention relates to pharmaceutical compositions comprising compounds of formula (I) or their pharmaceutically acceptable salts as defined above and one or more pharmaceutically acceptable excipients for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions or infusion solutions).

The compounds of formula (I) and their pharmaceutically acceptable salts can be processed with pharmaceutically inert, inorganic or organic excipients for the production of tablets, coated tablets, dragées and hard gelatin capsules. Lactose, corn starch or derivatives thereof, talc, stearic acid or its salts etc. can be used, for example, as such excipients for tablets, dragées and hard gelatin capsules.

Suitable excipients for soft gelatin capsules are, for example, vegetable oils, waxes, fats, semi-solid substances and liquid polyols, etc.

Suitable excipients for the production of solutions and syrups are, for example, water, polyols, saccharose, invert sugar, glucose, etc.

Suitable excipients for injection solutions are, for example, water, alcohols, polyols, glycerol, vegetable oils, etc.

Suitable excipients for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

Co-Administration of Compounds of Formula (I) and Other Agents

The compounds of formula (I) or salts thereof or a compound disclosed herein or a pharmaceutically acceptable salt thereof may be employed alone or in combination with other agents for treatment. For example, the second agent of the pharmaceutical combination formulation or dosing regimen may have complementary activities to the compound of formula (I) such that they do not adversely affect each other. The compounds may be administered together in a unitary pharmaceutical composition or separately. In one embodiment a compound or a pharmaceutically acceptable salt can be co-administered with an antibiotic, in particular with an antibiotic for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination therof.

The term "co-administering" refers to either simultaneous administration, or any manner of separate sequential administration, of a compound of formula (I) or a salt thereof or a compound disclosed herein or a pharmaceutically acceptable salt thereof and a further active pharmaceutical ingredient or ingredients, including antibiotic agents. If the administration is not simultaneous, the compounds are administered in a close time proximity to each other. Furthermore, it does not matter if the compounds are administered in the same dosage form, e.g. one compound may be administered intravenously and another compound may be administered orally.

Typically, any agent that has antimicrobial activity may be co-administered. Particular examples of such agents are Carbapenems (meropenem), Fluoroquinolone (Ciprofloxacin), Aminoglycoside (amikacin), Tetracyclines (tigecycline), Colistin, Sulbactam, Sulbactam+Durlobactam, Cefiderocol (Fetroja), macrocyclic peptides as exemplified e.g. in WO 2017072062 A1, WO 2019185572 A1 and WO 2019206853 A1, and Macrolides (erythromycin).

In one aspect, the present invention provides a pharmaceutical composition described herein, further comprising an additional therapeutic agent.

In one embodiment, said additional therapeutic agent is an antibiotic agent.

In one embodiment, said additional therapeutic agent is an antibiotic agent that is useful for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination therof.

In one embodiment, said additional therapeutic agent is an antibiotic agent selected from Carbapenems (meropenem), Fluoroquinolone (Ciprofloxacin), Aminoglycoside (amikacin), Tetracyclines (tigecycline), Colistin, Sulbactam, Sulbactam+Durlobactam, Cefiderocol (Fetroja), macrocyclic peptides as exemplified in WO 2017072062 A1, WO 2019185572 A1 and WO 2019206853 A1, and Macrolides (erythromycin).

EXAMPLES

The invention will be more fully understood by reference to the following examples. The claims should not, however, be construed as limited to the scope of the examples.

In case the preparative examples are obtained as a mixture of enantiomers, the pure enantiomers can be separated by methods described herein or by methods known to the man skilled in the art, such as e.g., chiral chromatography (e.g., chiral SFC) or crystallization.

All reaction examples and intermediates were prepared under an argon atmosphere if not specified otherwise.

Abbreviations Used Herein are as Follows:
ACN or MeCN acetonitrile
BINAP 2,2'-Bis(diphenylphosphino)-1,1'-binaphthalene
CFU colony-forming unit
d day
DCM dichloromethane
DIPEA N,N-diisopropylethylamine
EtOAc or EA ethyl acetate
FA formic acid
h(s) or hr(s) hour(s)
HATU: 1-[Bis(dimethylamino)methylene]-1H-1,2,3-triazolo[4,5-b]pyridinium 3-oxid hexafluorophosphate
HPLC: high performance liquid chromatography
HPLC-UV: high performance liquid chromatography with ultraviolet detector
IC50 half maximal inhibitory concentration
IC90 90% inhibitory concentration
PE petroleum ether
$PdCl_2(DPPF)$ [1,1'-Bis(diphenylphosphino)ferrocene]dichloropalladium(II)
$Pd_2(dba)_3$ Tris(dibenzylideneacetone)dipalladium(0)
PG Protecting group
Precat precatalyst
prep-HPLC preparative high performance liquid chromatography
RBF Round bottom flask
rt room temperature
sat saturated
SEM 2-methoxyethyl(trimethyl)silane
FA Formic acid
TFA Trifluoroacetic Acid
wt weight
X-PHOS 2-Dicyclohexylphosphino-2',4',6'-triisopropylbiphenyl Intermediate A1 tert-butyl 4-[(5-bromo-1-methyl-imidazole-2-carbonyl)amino]-2-chloro-benzoate

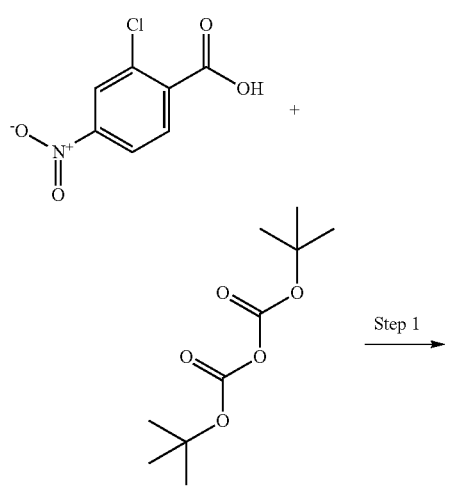

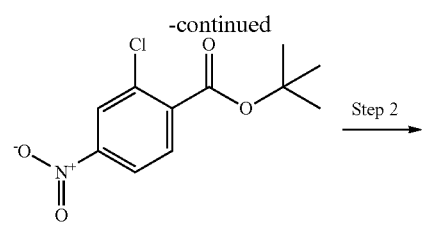

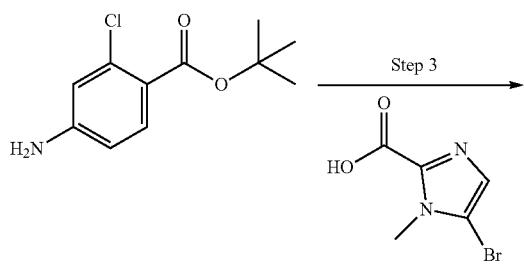

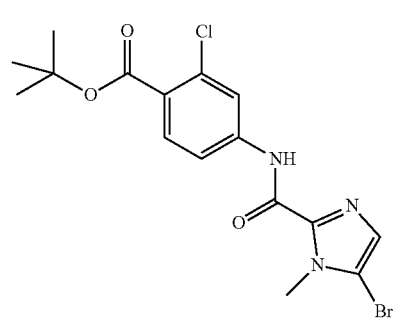

Intermediate A1

Step 1: tert-butyl 2-chloro-4-nitro-benzoate

To a mixture of 2-chloro-4-nitro-benzoic acid (15.0 g, 74.42 mmol), N,N-dimethylpyridin-4-amine (2.73 g, 22.33 mmol) and N,N-diethylethanamine (31.12 mL, 223.26 mmol) in THF (80 mL) was added a solution of tert-butoxycarbonyl tert-butyl carbonate (24.36 g, 111.63 mmol) in THF (20 mL) at −10° C. The resulting mixture was warmed to 25° C. and stirred for another 14 h. The mixture was concentrated. The residue was treated with EA (50 mL) and H₂O (50 mL). The mixture was extracted with EA. The combined organic layers were concentrated. The crude was then purified by flash column chromatography to afford tert-butyl 2-chloro-4-nitro-benzoate (18.8 g) as a colorless solid.

Step 2: tert-butyl 4-amino-2-chloro-benzoate

To a mixture of tert-butyl 2-chloro-4-nitro-benzoate (18.8 g, 72.96 mmol) and Ammonium chloride (19.51 g, 364.81 mmol) in ethanol (200 mL) and water (200 mL) was added Iron (20.37 g, 364.81 mmol). The mixture was stirred at 25° C. for 14 h. The mixture was filtered by Celite. The filtrate was concentrated to remove ethanol. The mixture was extracted with EA. The combined organic layers were dried over anhydrous Na₂SO₄ and concentrated to afford tert-butyl 4-amino-2-chloro-benzoate (16.31 g) as a light yellow solid. MS [M+H]⁺: 228.1.

Step 3: tert-butyl 4-[(5-bromo-1-methyl-imidazole-2-carbonyl)amino]-2-chloro-benzoate A mixture of 5-bromo-1-methyl-imidazole-2-carboxylic acid hydrochloride (7.0 g, 28.99 mmol), tert-butyl 4-amino-2-chloro-benzoate (6.0 g, 26.35 mmol), HATU (13.23 g, 34.79 mmol) and DIPEA (16.16 mL, 92.77 mmol) in DMF (15 mL) was stirred at 25° C. for 3 h. The mixture was added water (10 mL) and extracted with EA. The combined organic layers were concentrated. The crude was purified by FCC to afford tert-butyl 4-[(5-bromo-1-methyl-imidazole-2-carbonyl)amino]-2-chloro-benzoate (8 g, 19.29 mmol) as a white solid. MS [M+H]⁺: 414.0.

The following Intermediates were prepared in analogy to Intermediate A1.

| Ex# | Name | Structure | MS ESI [M + H]⁺ | Starting Material |
|---|---|---|---|---|
| Intermediate A2 | tert-butyl 4-[(5-bromo-1-methyl-imidazole-2-carbonyl)amino]-2-methyl-benzoate | 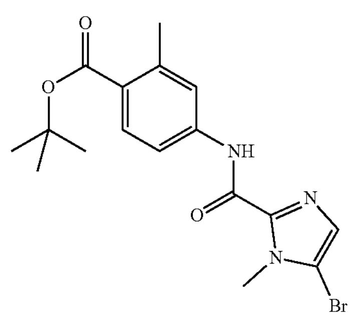 [SMILES: Cc1cc(NC(=O)c2ncc(Br)n2C)ccc1C(=O)OC(C)(C)C] | 394.2 | 2-methyl-4-nitro-benzoic acid and tert-butoxycarbonyl tert-butyl carbonate |

Intermediate B1

5-bromo-N-[3-chloro-4-(piperazine-1-carbonyl)phenyl]-1-methyl-imidazole-2-carboxamide

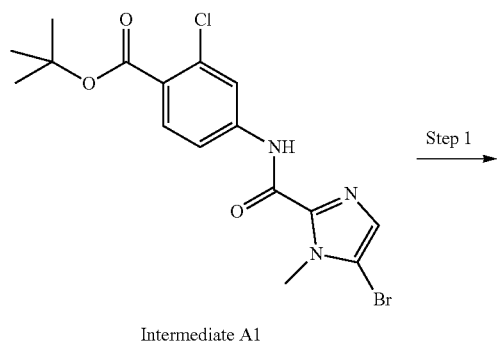

Intermediate A1

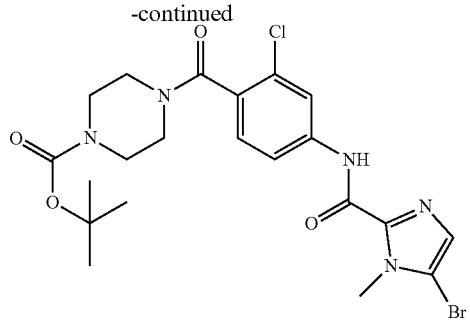

Intermediate B1

Step 1: 4-(5-bromo-1-methyl-1h-imidazole-2-carboxamido)-2-chlorobenzoic acid In a 250 mL round-bottomed flask, tert-butyl 4-(5-bromo-1-methyl-1h-imidazole-2-carboxamido)-2-chlorobenzoate (5 g, 12.1 mmol) was combined with $CH_2Cl_2$ (30 mL) to give a light brown solution. TFA (41.2 g, 27.9 mL, 362 mmol) was added. The reaction was stirred at room temperature for 1 h. The crude reaction mixture was concentrated in vacuum to afford 4-(5-bromo-1-methyl-1h-imidazole-2-carboxamido)-2-chlorobenzoic acid (4.32 g). MS [M+H]$^+$: 359.8.

Step 2: tert-butyl 4-(4-(5-bromo-1-methyl-1h-imidazole-2-carboxamido)-2-chlorobenzoyl)piperazine-2-carboxylate

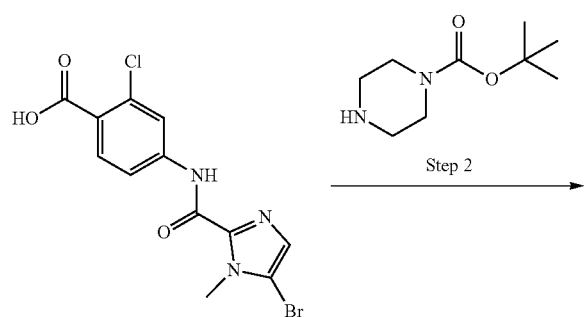

In a 100 mL round-bottomed flask, 4-(5-bromo-1-methyl-1h-imidazole-2-carboxamido)-2-chlorobenzoic acid (2 g, 5.58 mmol), tert-butyl piperazine-1-carboxylate (1.19 g, 6.41 mmol) and DIPEA (2.16 g, 16.7 mmol) were combined with DMF (15 mL) to give a colorless solution. HATU (2.76 g, 7.25 mmol) was added. The reaction was stirred at room temperature for 1 h. The reaction mixture was poured into 150 mL $H_2N$ and extracted with EtOAc (3×75 mL). The organic layers were combined, washed with sat. NaCl (1×75 mL). The organic layers were dried over $Na_2SO_4$ and concentrated in vacuum to afford tert-butyl 4-(4-(5-bromo-1-methyl-1h-imidazole-2-carboxamido)-2-chlorobenzoyl)piperazine-1-carboxylate (2.94 g). MS [M+H]$^+$: 527.9.

The following Intermediates were prepared in analogy to Intermediate B1.

| Ex# | Name | Structure | MS ESI [M + H]$^+$ | Starting Material |
|---|---|---|---|---|
| Intermediate B2 | tert-butyl 4-[4-[(5-bromo-1-methyl-imidazole-2-carbonyl)amino]-2-methyl-benzoyl]piperazine-1-carboxylate | 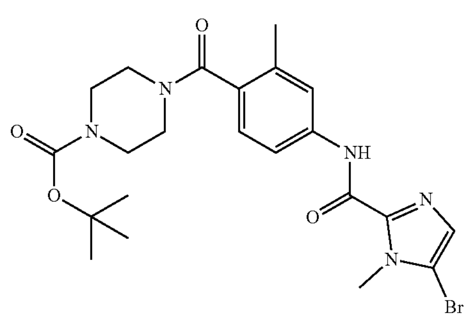 [SMILES: Cc1cc(NC(=O)c2ncc(Br)n2C)ccc1C(=O)N1CCN(C(=O)OC(C)(C)C)CC1] | 506.1 | Intermediate A2; tert-butyl piperazine-1-carboxylate |

-continued

| Ex# | Name | Structure | MS ESI [M + H]+ | Starting Material |
|---|---|---|---|---|
| Intermediate B3 | tert-butyl N-[1-[4-[(5-bromo-1-methyl-imidazole-2-carbonyl)amino]-2-chloro-benzoyl]-4-piperidyl]carbamate | 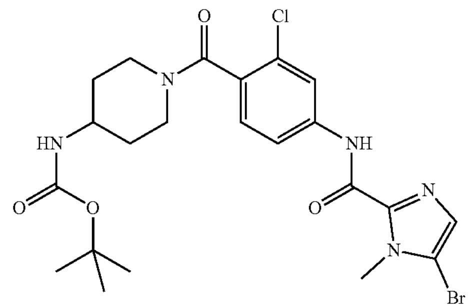 [SMILES: Cn1c(Br)cnc1C(=O)Nc1ccc(C(=O)N2CCC(NC(=O)OC(C)(C)C)CC2)c(Cl)c1] | 540.1 | Intermediate A1; tert-butyl N-(4-piperidyl)carbamate |
| Intermediate B4 | tert-butyl 1-[4-[(5-bromo-1-methyl-imidazole-2-carbonyl)amino]-2-chloro-benzoyl]piperidine-4-carboxylate | 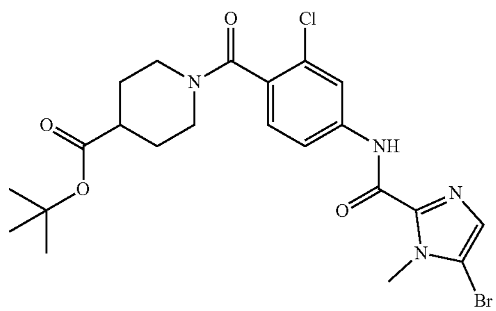 [SMILES: Cn1c(Br)cnc1C(=O)Nc1ccc(C(=O)N2CCC(C(=O)OC(C)(C)C)CC2)c(Cl)c1] | 525.1 | Intermediate A1; tert-butyl piperidine-4-carboxylate |
| Intermediate B5 | tert-butyl 4-[[[4-[(5-bromo-1-methyl-imidazole-2-carbonyl)amino]-2-chloro-benzoyl]amino]methyl]piperidine-1-carboxylate | 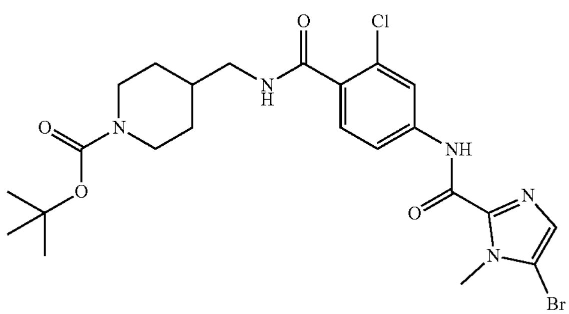 [SMILES: Cn1c(Br)cnc1C(=O)Nc1ccc(C(=O)NCC2CCN(C(=O)OC(C)(C)C)CC2)c(Cl)c1] | 554.1 | Intermediate A1; tert-butyl 4-(aminomethyl)piperidine-1-carboxylate |
| Intermediate B6 | tert-butyl (1S,5R)-6-[[4-[(5-bromo-1-methyl-imidazole-2-carbonyl)amino]-2-chloro-benzoyl]amino]-3-azabicyclo[3.1.0]hexane-3-carboxylate | 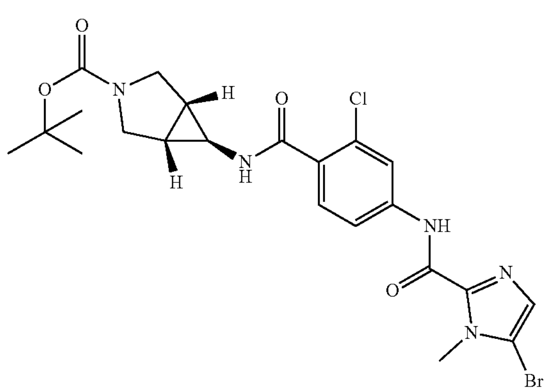 [SMILES: Cn1c(Br)cnc1C(=O)Nc1ccc(C(=O)N[C@H]2[C@@H]3CN(C(=O)OC(C)(C)C)C[C@@H]32)c(Cl)c1] | 538.8 | Intermediate A1; tert-butyl rac-(1R,5S)-6-amino-3-azabicyclo[3.1.0]hexane-3-carboxylate |

Intermediate C1

5-bromo-N-(3-chloro-4-(piperazine-1-carbonyl)phenyl)-1-methyl-1h-imidazole-2-carboxamide

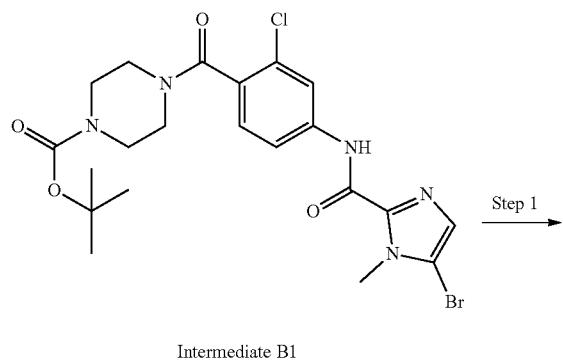

Intermediate B1

$\xrightarrow{\text{Step 1}}$

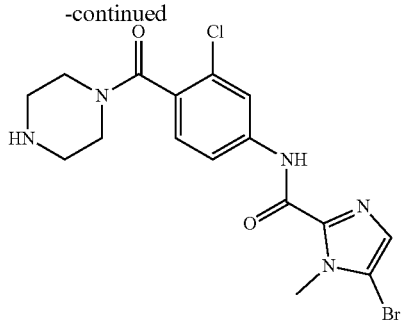

Intermediate C1

In a 100 mL round-bottomed flask, tert-butyl 4-(4-(5-bromo-1-methyl-1h-imidazole-2-carboxamido)-2-chlorobenzoyl)piperazine-1-carboxylate (2.94 g, 5.58 mmol) was combined with THF (20 mL) to give a light brown solution. HCl(in water) (11.6 mL, 140 mmol) was added. The reaction was stirred at room temperature for 1 h. The crude reaction mixture was concentrated in vacuum. The crude product was directly used to the next step to afford 5-bromo-N-(3-chloro-4-(piperazine-1-carbonyl)phenyl)-1-methyl-1h-imidazole-2-carboxamide (2.38 g). MS [M+H]$^+$: 427.8.

The following Intermediates were prepared in analogy to Intermediate C1.

| Ex# | Name | Structure | MS ESI [M + H]$^+$ | Starting Material |
|---|---|---|---|---|
| Intermediate C2 | 5-bromo-1-methyl-N-[3-methyl-4-(piperazine-1-carbonyl)phenyl]imidazole-2-carboxamide | 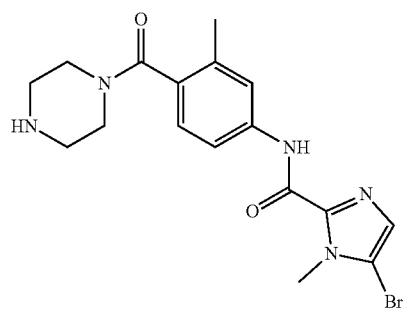 [SMILES: Cc1cc(NC(=O)c2ncc(Br)n2C)ccc1C(=O)N1CCNCC1] | 406.1 | Intermediate B2 and HCl |

| Ex# | Name | Structure | MS ESI [M + H]+ | Starting Material |
|---|---|---|---|---|
| Intermediate C3 | 1-[4-[(5-bromo-1-methyl-imidazole-2-carbonyl)amino]-2-chloro-benzoyl]piperidine-4-carboxylic acid | 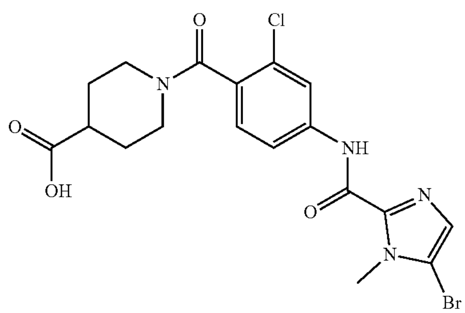 [SMILES: Cn1c(Br)cnc1C(=O)Nc1ccc(C(=O)N2CCC(C(=O)O)CC2)c(Cl)c1] | 469.1 | Intermediate B4 and HCl |
| Intermediate C4 | N-[4-[[(1S,5R)-3-azabicyclo[3.1.0]hexan-6-yl]carbamoyl]-3-chloro-phenyl]-5-bromo-1-methyl-imidazole-2-carboxamide | 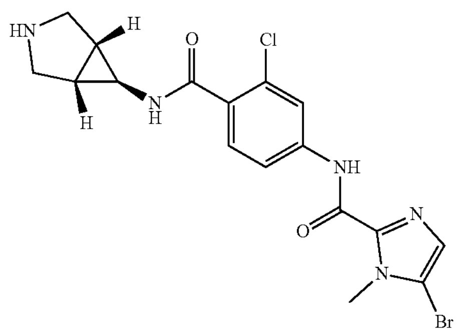 [SMILES: Cn1c(Br)cnc1C(=O)Nc1ccc(C(=O)N[C@H]2[C@@H]3CNC[C@@H]32)c(Cl)c1] | 438.7 | Intermediate B6 and HCl |

Intermediate D1 tert-butyl 4-(4-(4-(5-bromo-1-methyl-1h-imidazole-2-carboxamido)-2-chlorobenzoyl)piperazine-1-carbonyl)piperidine-1-carboxylate

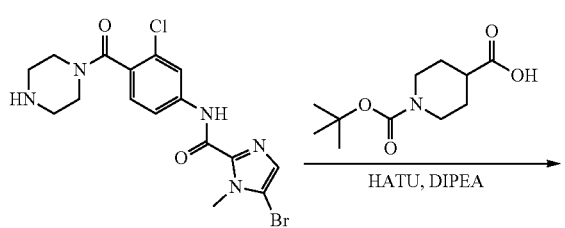

Intermediate C1

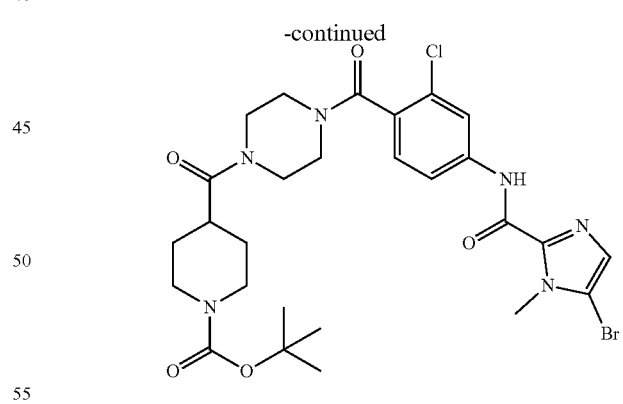

Intermediate D1

In a 100 mL round-bottomed flask, 5-bromo-N-(3-chloro-4-(piperazine-1-carbonyl)phenyl)-1-methyl-1h-imidazole-2-carboxamide (2.38 g, 5.58 mmol), 1-(tert-butoxycarbonyl)piperidine-4-carboxylic acid (2.05 g, 8.92 mmol) and DIPEA (2.16 g, 16.7 mmol) were combined with DMF (15 mL) to give a light brown solution. HATU (3.39 g, 8.92 mmol) was added. The reaction was stirred at room temperature for 1 h. The reaction mixture was poured into 150 mL H$_2$O and extracted with EtOAc (3×50 mL). The organic layers were combined, washed with sat NaCl (1×75 mL).

The organic layers were dried over Na₂SO₄ and concentrated in vacuum to afford tert-butyl 4-(4-(4-(5-bromo-1-methyl-1h-imidazole-2-carboxamido)-2-chlorobenzoyl)piperazine-1-carbonyl)piperidine-1-carboxylate (3.56 g). MS [M+H]⁺: 638.9.

The following intermediates were prepared in analogy to Intermediate D1.

| Ex# | Name | Structure | MS ESI [M + H]⁺ | Starting Material |
|---|---|---|---|---|
| Intermediate D2 | tert-butyl (3S)-3-[2-[4-[4-[(5-bromo-1-methyl-imidazole-2-carbonyl)amino]-2-chloro-benzoyl]piperazin-1-yl]-2-oxo-ethyl]pyrrolidine-1-carboxylate | 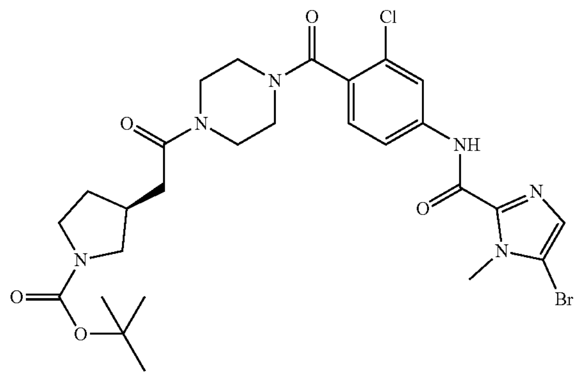 [SMILES: Cn1c(Br)cnc1C(=O)Nc1ccc(C(=O)N2CCN(C(=O)C[C@@H]3CCN(C(=O)OC(C)(C)C)C3)CC2)c(Cl)c1] | 637.9 | Intermediate C1 and 2-[(3 S)-1-tert-butoxycarbonyl-pyrrolidin-3-yl] acetic acid |
| Intermediate D3 | 5-bromo-N-[3-chloro-4-[4-[2-(dimethylamino)acetyl]piperazine-1-carbonyl]phenyl]-1-methyl-imidazole-2-carboxamide | 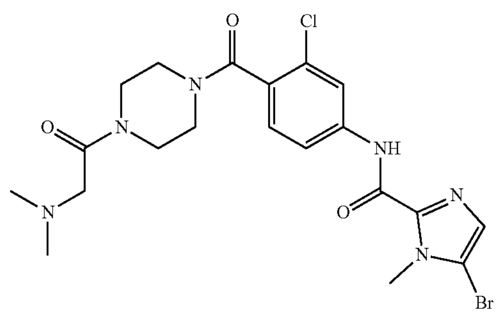 [SMILES: CN(C)CC(=O)N1CCN(C(=O)c2ccc(NC(=O)c3ncc(Br)n3C)cc2Cl)CC1] | 511.2 | Intermediate C1 and 2-(dimethylamino) acetic acid |
| Intermediate D4 | tert-butyl (2S,4R)-2-[4-[4-[(5-bromo-1-methyl-imidazole-2-carbonyl)amino]-2-methyl-benzoyl]piperazine-1-carbonyl]-4-hydroxy-pyrrolidine-1-carboxylate | 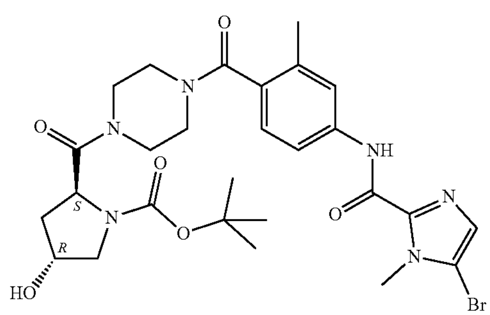 | 619.1 | Intermediate C2 and (2S,4R)-1-tert-butoxycarbonyl-4-hydroxy-pyrrolidine-2-carboxylic acid |
| Intermediate D5 | 5-bromo-N-[4-[4-[2-(dimethylamino)acetyl]piperazine-1-carbonyl]-3-methyl-phenyl]-1-methyl-imidazole-2-carboxamide | 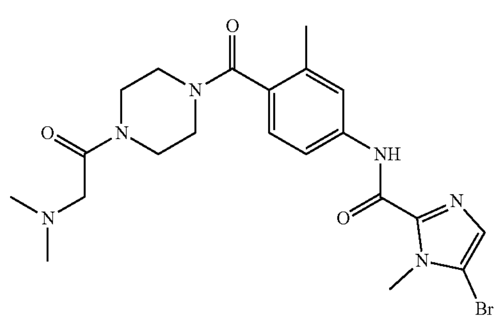 [SMILES: Cc1cc(NC(=O)c2ncc(Br)n2C)ccc1C(=O)N1CCN(C(=O)CN(C)C)CC1] | 491.2 | Intermediate C2 and 2-(dimethylamino) acetic acid |

| Ex# | Name | Structure | MS ESI [M + H]+ | Starting Material |
|---|---|---|---|---|
| Intermediate D6 | tert-butyl (2S,4R)-2-[4-[4-[(5-bromo-1-methyl-imidazole-2-carbonyl)amino]-2-chloro-benzoyl]piperazine-1-carbonyl]-4-hydroxy-pyrrolidine-1-carboxylate | 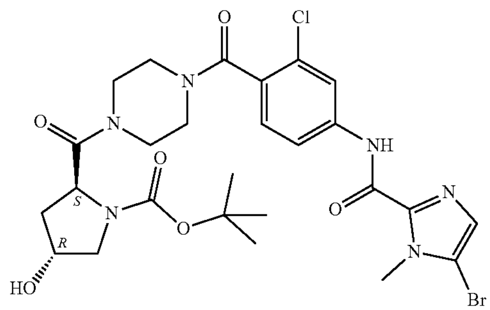 | 639.2 | Intermediate C1 and (2S,4R)-1-tert-butoxycarbonyl-4-hydroxy-pyrrolidine-2-carboxylic acid |
| Intermediate D7 | tert-butyl 4-[1-[4-[(5-bromo-1-methyl-imidazole-2-carbonyl)amino]-2-chloro-benzoyl]piperidine-4-carbonyl]piperazine-1-carboxylate | 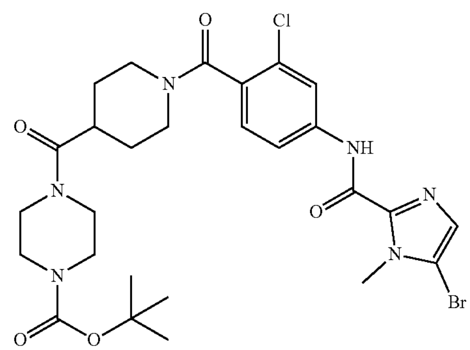 [SMILES: Cn1c(Br)cnc1C(=O)Nc1ccc(C(=O)N2CCC(C(=O)N3CCN(C(=O)OC(C)(C)C)CC3)CC2)c(Cl)c1] | 637.0 | Intermediate C3 and 1-Boc-piperazine |
| Intermediate D8 | tert-butyl 4-[2-[4-[4-[(5-bromo-1-methyl-imidazole-2-carbonyl)amino]-2-chloro-benzoyl]piperazin-1-yl]-2-oxo-ethyl]-4-hydroxy-piperidine-1-carboxylate | 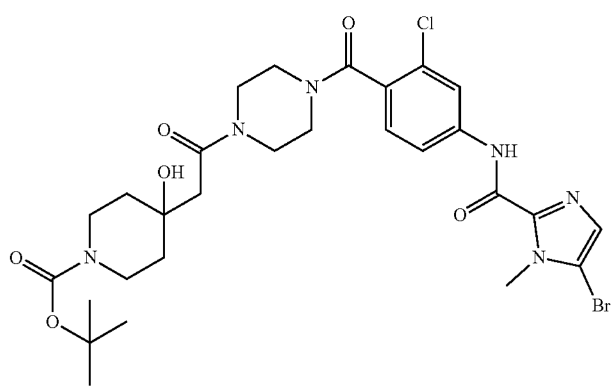 [SMILES: Cn1c(Br)cnc1C(=O)Nc1ccc(C(=O)N2CCN(C(=O)CC3(O)CCN(C(=O)OC(C)(C)C)CC3)CC2)c(Cl)c1] | 667.2 | Intermediate C1 and 2-(1-tert-butoxycarbonyl-4-hydroxy-4-piperidyl)acetic acid |
| Intermediate D9 | 5-bromo-N-[3-chloro-4-[4-(1-methylpiperidine-4-carbonyl)piperazine-1-carbonyl]phenyl]-1-methyl-imidazole-2-carboxamide | 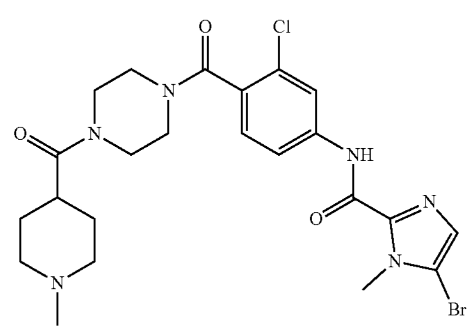 [SMILES: CN1CCC(C(=O)N2CCN(C(=O)c3ccc(NC(=O)c4ncc(Br)n4C)cc3Cl)CC2)CC1] | 551.2 | Intermediate C1 and 1-methylpiperidine-4-carboxylic acid |

Intermediate D10 tert-butyl 4-[4-[4-[(5-bromo-4-chloro-1-methyl-imidazole-2-carbonyl)amino]-2-chloro-benzoyl]piperazine-1-carbonyl]piperidine-1-carboxylate

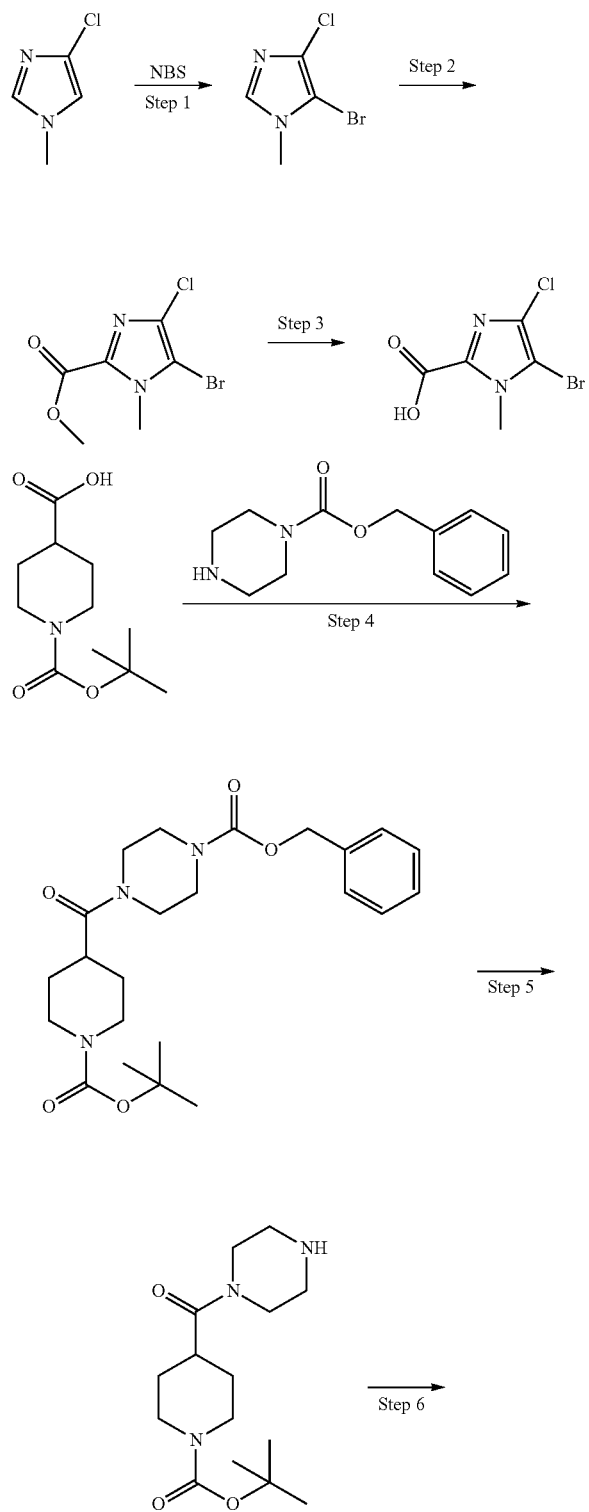

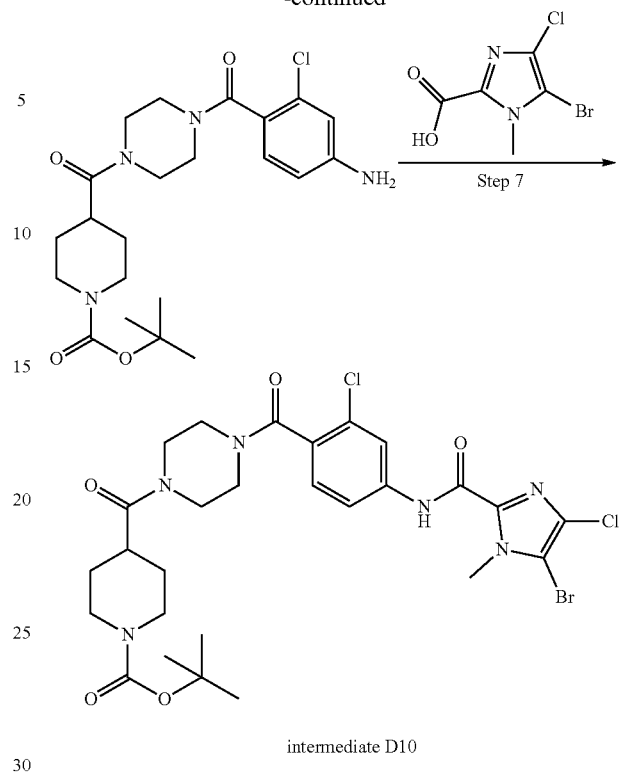

intermediate D10

Step 1: 5-bromo-4-chloro-1-methyl-imidazole 4-chloro-1-methyl-imidazole (466 mg, 4. mmol) was dissolved in N,N-dimethylformamide (8 mL), NBS (498.13 mg, 2.8 mmol) was added at rt. The mixture was stirred at room temperature for 1 h. The reaction mixture was diluted with sat. NaHCO$_3$-solution (20 mL) and extracted two times with EtOAc (30 mL). The organic layers were washed with brine (30 mL), dried over Na$_2$SO$_4$ and concentrated to dryness. The crude product was directly used to the next step, to afford 5-bromo-4-chloro-1-methyl-imidazole (284 mg, 36.34%) as light brown solid. MS [M+H]$^+$: 196.9.

Step 2: 5-bromo-4-chloro-1-methyl-imidazole-2-carboxylic acid methyl ester 5-bromo-4-chloro-1-methyl-imidazole (284 mg, 1.45 mmol) was dissolved in tetrahydrofuran (5 mL), 2 M lithium diisopropylamide (871.88 uL, 1.74 mmol) was added at −78° C., The reaction was stirred at −78° C. for 30 mins, methyl chloroformate (164.79 mg, 1.74 mmol) was added at −78° C. The mixture was warmed to room temperature with stirring for 1 h.

The reaction mixture was diluted with water (20 mL) and extracted two times with EtOAc (20 mL). The organic layers were washed with brine (20 mL), dried over Na$_2$SO$_4$ and concentrated to dryness. The crude product was directly used to the next step, to afford 5-bromo-4-chloro-1-methyl-imidazole-2-carboxylic acid methyl ester (360 mg) as light brown oil. MS [M+H]$^+$: 254.9.

Step 3: 5-bromo-4-chloro-1-methyl-imidazole-2-carboxylic acid 5-bromo-4-chloro-1-methyl-imidazole-2-carboxylic acid methyl ester (360 mg, 1.42 mmol) was dissolved in methanol (9 mL) and water (3 mL), NaOH (284.05 mg, 7.1 mmol) was added at rt. The mixture was stirred at room temperature for 1 h. The PH of the reaction mixture was adjusted to 6. The reaction was concentrated to dryness. The crude product was directly used to the next step, to afford 5-bromo-4-chloro-1-methyl-imidazole-2-carboxylic acid (340 mg) as light yellow solid. MS [M+H]+: 240.9.

Step 4: 4-(1-tert-butoxycarbonylisonipecotoyl)piperazine-1-carboxylic acid benzyl ester 1-tert-butoxycarbonylisonipecotic acid (2.5 g, 10.9 mmol) was dissolved in N,N-dimethylformamide (31.25 mL), benzyl 1-piperazinecarboxylate (2.64 g, 11.99 mmol), HATU (4.98 g, 13.09 mmol) and DIEA (2.82 g, 21.81 mmol) were added at rt. The mixture was stirred at room temperature for 2 h. The reaction mixture was diluted with water (30 mL) and extracted two times with EtOAc (30 mL). The organic layers were washed with brine (30 mL), dried over Na₂SO₄ and concentrated to dryness. The crude material was purified by flash chromatography on silica gel (5% MeOH in DCM). to afford 4-(1-tert-butoxycarbonylisonipecotoyl)piperazine-1-carboxylic acid benzyl ester (3 g, 63.76%) as colorless oil. MS [M+H]+: 454.2.

Step 5: 4-(piperazine-1-carbonyl)piperidine-1-carboxylic acid tert-butyl ester 4-(1-tert-butoxycarbonylisonipecotoyl)piperazine-1-carboxylic acid benzyl ester (3 g, 6.95 mmol) was dissolved in methanol (50 mL), palladium hydroxide on carbon (97.63 mg, 0.695 mmol) was added at rt. The mixture was purge from the H₂ ballon three times, and stirred at room temperature for 15 h. The reaction mixture was filtered, the filtrate was concentrated to dryness. The crude product was directly used to the next step to afford 4-(piperazine-1-carbonyl)piperidine-1-carboxylic acid tert-butyl ester (2.07 g) as colorless oil. MS [M+H]+: 298.2.

Step 6: 4-[4-(4-amino-2-chloro-benzoyl)piperazine-1-carbonyl]piperidine-1-carboxylic acid tert-butyl ester 4-(piperazine-1-carbonyl)piperidine-1-carboxylic acid tert-butyl ester (1 g, 3.36 mmol) was dissolved in N,N-dimethylformamide (7 mL), 4-amino-2-chloro-benzoic acid (576.95 mg, 3.36 mmol), HATU (1.53 g, 4.04 mmol) and DIEA (869.16 mg, 1.17 mL, 6.73 mmol) were added at rt. The mixture was stirred at room temperature for 1 h. The reaction mixture was diluted with water (40 mL) and extracted two times with EtOAc (30 mL). The organic layers were washed with brine (30 mL), dried over Na₂SO₄ and concentrated to dryness. The crude material was purified by flash chromatography on silica gel (10% MeOH in DCM). to afford 4-[4-(4-amino-2-chloro-benzoyl)piperazine-1-carbonyl]piperidine-1-carboxylic acid tert-butyl ester (1.09 g) as white solid. MS [M+H]+: 351.2.

Step 7: 4-[4-[4-[(5-bromo-4-chloro-1-methyl-imidazole-2-carbonyl)amino]-2-chloro-benzoyl]piperazine-1-carbonyl]piperidine-1-carboxylic acid tert-butyl ester 4-[4-(4-amino-2-chloro-benzoyl)piperazine-1-carbonyl]piperidine-1-carboxylic acid tert-butyl ester (400 mg, 0.887 mmol) was dissolved in N,N-dimethylformamide (5 mL), 5-bromo-4-chloro-1-methyl-imidazole-2-carboxylic acid (212.39 mg, 0.887 mmol), HATU (472.17 mg, 1.24 mmol) and DIEA (229.27 mg, 1.77 mmol) were added at rt. The mixture was stirred at room temperature for 2 h. The reaction mixture was diluted with water (30 mL) and extracted two times with EtOAc (30 mL). The organic layers were washed with brine (30 mL), dried over Na₂SO₄ and concentrated to dryness. The crude material was purified by flash chromatography on silica gel (10% MeOH in DCM). to afford 4-[4-[4-[(5-bromo-4-chloro-1-methyl-imidazole-2-carbonyl)amino]-2-chloro-benzoyl]piperazine-1-carbonyl]piperidine-1-carboxylic acid tert-butyl ester (277 mg) as light brown solid. MS [M+H]: 573.1.

Intermediate D11 tert-butyl (3R,4R)-3-[[(1S,5R)-6-[[4-[(5-bromo-1-methyl-imidazole-2-carbonyl)amino]-2-chloro-benzoyl]amino]-3-azabicyclo[3.1.0]hexane-3-carbonyl]amino]-4-hydroxy-pyrrolidine-1-carboxylate

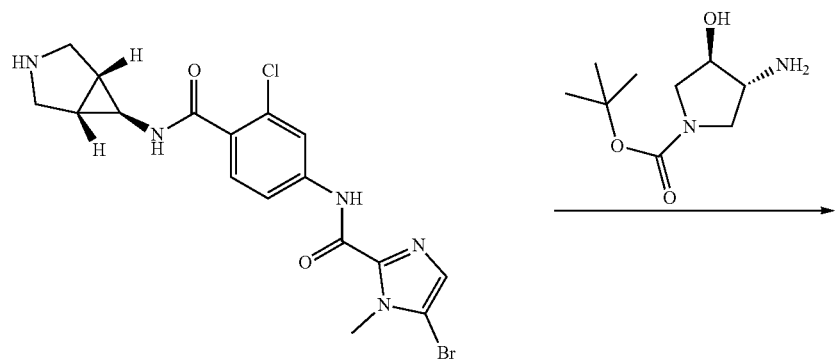

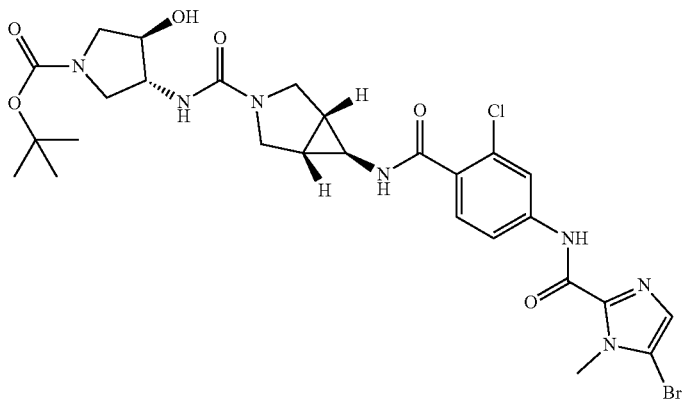

Intermediate D11

In a 25 mL round bottomed-flask equiped with a magnetic stirrer-bar, a $N_2$-balloon and a spetum-cap, tert-butyl (3R,4R)-3-amino-4-hydroxypyrrolidine-1-carboxylate (253 mg, 1.25 mmol) was dissolved in DMF (1 mL). TEA (211 mg, 2.08 mmol) and CDI (169 mg, 1.04 mmol) were added to the clear solution and stirred at RT. After 15 min, N-(4-(((1R,5S,6s)-3-azabicyclo[3.1.0]hexan-6-yl)carbamoyl)-3-chlorophenyl)-5-bromo-1-methyl-1H-imidazole-2-carboxamide hydrochloride (197.8 mg, 416 μmol) was added and the resulting light brownish reaction solution was stirred for 1.5 h. Water (7 mL) was added to the reaction mixture, but the product did not precipitate out. The aqueous layer was extracted with EA (2×10 mL). The organic layers were washed with LiCl-solution (5% in water) (10 mL each organic layer) and with sat. —NaCl solution (1×10 mL), dried over $Na_2SO_4$, filtered off and concentrated in vacuum at 40° C. Crude product purified by silica gel chromatography, to yield tert-butyl (3R,4R)-3-((1R,5S)-6-(4-(5-bromo-1-methyl-1H-imidazole-2-carboxamido)-2-chlorobenzamido)-3-azabicyclo[3.1.0]hexane-3-carboxamido)-4-hydroxypyrrolidine-1-carboxylate (216 mg). $[M+H]^+$: 668.3.

The following intermediates were prepared in analogy to Intermediate D11.

| Ex# | Name | Structure | MS ESI $[M + H]^+$ | Starting Material |
|---|---|---|---|---|
| Intermediate D12 | tert-butyl 4-[4-[4-[(5-bromo-1-methyl-imidazole-2-carbonyl)amino]-2-chloro-benzoyl]piperazine-1-carbonyl]piperazine-1-carboxylate | 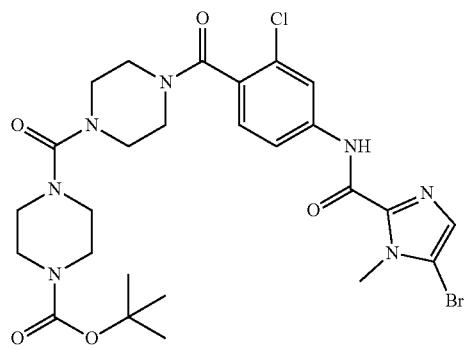 [SMILES: Cn1c(Br)cnc1C(=O)Nc1ccc(C(=O)N2CCN(C(=O)N3CCN(C(=O)OC(C)(C)C)CC3)CC2)c(Cl)c1] | 638.9 | Intermediate C1 and CDI; tert-butyl piperazine-1-carboxylate |

Intermediate E1 and Intermediate E2

1-(2-methoxyethyl)-3-methyl-4-(4,4,5,5-tetramethyl-1,3,2-dioxaborolan-2-yl)pyrazole (Intermediate E1)

1-(2-methoxyethyl)-5-methyl-4-(4,4,5,5-tetramethyl-1,3,2-dioxaborolan-2-yl)pyrazole (Intermediate E2)

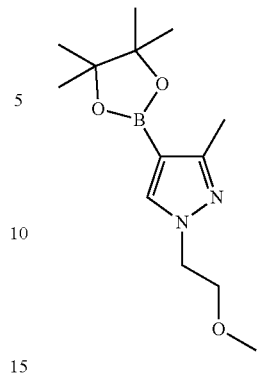 + 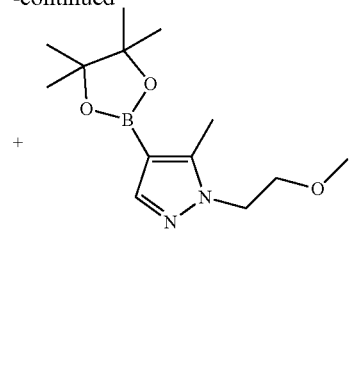

Intermediate E1      Intermediate E2

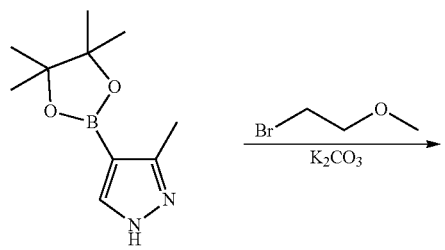

Intermediate SM1

To a 25 mL microwave vial was added 3-methyl-4-(4,4,5,5-tetramethyl-1,3,2-dioxaborolan-2-yl)-1H-pyrazole (2 g, 9.61 mmol), 1-bromo-2-methoxyethane (1.74 g, 12.5 mmol), $K_2CO_3$ (1.73 g, 12.5 mmol) and potassium iodide (319 mg, 1.92 mmol) in DMF (15 mL). The vial was capped and heated in the microwave at 100° C. for 15 h. The reaction mixture was filtered through glass fiber paper. The filtrate was concentrated in vacuum. The crude material was purified by flash chromatography to afford 2 g of crude product, The crude product was purified by preparative HPLC to afford 1-(2-methoxyethyl)-3-methyl-4-(4,4,5,5-tetramethyl-1,3,2-dioxaborolan-2-yl)pyrazole (550 mg)(Intermediate E1) and 1-(2-methoxyethyl)-5-methyl-4-(4,4,5,5-tetramethyl-1,3,2-dioxaborolan-2-yl)pyrazole (316 mg)) (Intermediate E2). MS [M+H]$^+$: 267.1.

The following intermediates were prepared in analogy to Intermediate E1.

| Ex# | Name | Structure | MS ESI [M + H]$^+$ | Starting Material |
|---|---|---|---|---|
| Intermediate E3 | 1-(2-methoxyethyl)-3,5-dimethyl-4-(4,4,5,5-tetramethyl-1,3,2-dioxaborolan-2-yl)pyrazole | 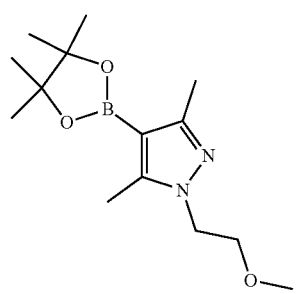 | 281.1 | Intermediate SM1 and 1-bromo-2-methoxyethane |

-continued

| Ex# | Name | Structure | MS ESI [M + H]+ | Starting Material |
|---|---|---|---|---|
| Intermediate E4 | trimethyl-[2-[[3-methyl-4-(4,4,5,5-tetramethyl-1,3,2-dioxaborolan-2-yl)pyrazol-1-yl]methoxy]ethyl]silane | 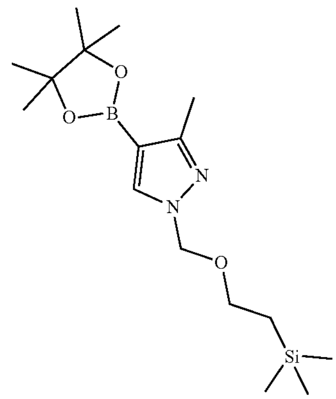 | 339.0 | Intermediate SM1 and 2-(chloromethoxy)ethyl-trimethyl-silane |
| Intermediate E5 | 2-[[3,5-dimethyl-4-(4,4,5,5-tetramethyl-1,3,2-dioxaborolan-2-yl)pyrazol-1-yl]methoxy]ethyl-trimethyl-silane | 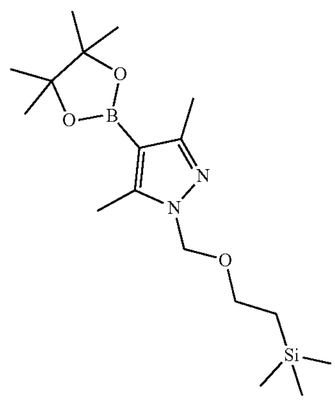 | 353.2 | Intermediate SM1 and 2-(chloromethoxy)ethyl-trimethyl-silane |
| Intermediate E6 | 2-methyl-4-[5-methyl-4-(4,4,5,5-tetramethyl-1,3,2-dioxaborolan-2-yl)pyrazol-1-yl]butan-2-ol | 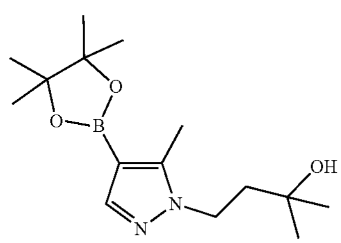 [SMILES: Cc1c(B2OC(C)(C)C(C)(C)O2)cnn1CCC(C)(C)O] | 295.2 | Intermediate SM1 and 4-bromo-2-methyl-butan-2-ol |
| Intermediate E7 | N-methyl-2-[3-methyl-4-(4,4,5,5-tetramethyl-1,3,2-dioxaborolan-2-yl)pyrazol-1-yl]acetamide | 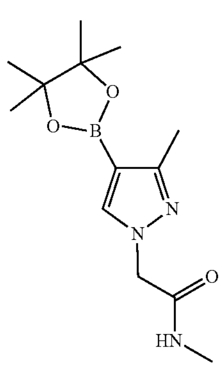 | 280.2 | Intermediate SM1 and 2-iodo-N-methyl-acetamide |

| Ex# | Name | Structure | MS ESI [M + H]+ | Starting Material |
|---|---|---|---|---|
| Intermediate E8 | methyl 2-[3-methyl-4-(4,4,5,5-tetramethyl-1,3,2-dioxaborolan-2-yl)pyrazol-1-yl]acetate | 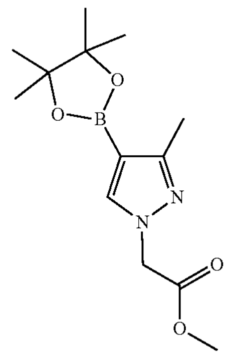 | 281.4 | Intermediate SM1 and methyl 2-bromoacetate |
| Intermediate E9 | tert-butyl-dimethyl-[2-[3-methyl-4-(4,4,5,5-tetramethyl-1,3,2-dioxaborolan-2-yl)pyrazol-1-yl]ethoxy]silane | 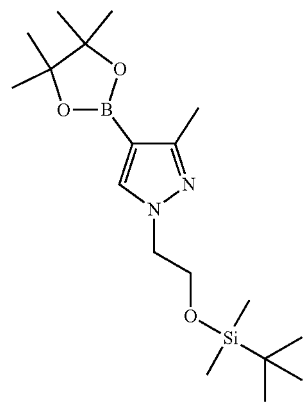 [SMILES: Cc1nn(CCO[Si](C)(C)C(C)(C)C)cc1B1OC(C)(C)C(C)(C)O1] | 367.3 | Intermediate SM1 and (2-bromo ethoxy)(tert-butyl) dimethylsilane |
| Intermediate E10 | tert-butyl-dimethyl-[2-[5-methyl-4-(4,4,5,5-tetramethyl-1,3,2-dioxaborolan-2-yl)pyrazol-1-yl]ethoxy]silane | 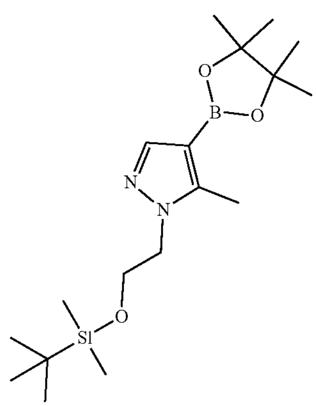 | 367.3 | Intermediate SM1 and (2-bromo ethoxy)(tert-butyl) dimethylsilane |
| Intermediate E11 | 1-(3-methoxypropyl)-3-methyl-4-(4,4,5,5-tetramethyl-1,3,2-dioxaborolan-2-yl)pyrazole | 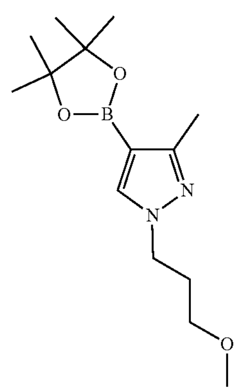 | 281.1 | Intermediate SM1 and 1-bromo-3-methoxypropane |

| Ex# | Name | Structure | MS ESI [M + H]+ | Starting Material |
|---|---|---|---|---|
| Intermediate E12 | 1-(3-methoxypropyl)-5-methyl-4-(4,4,5,5-tetramethyl-1,3,2-dioxaborolan-2-yl)pyrazole | 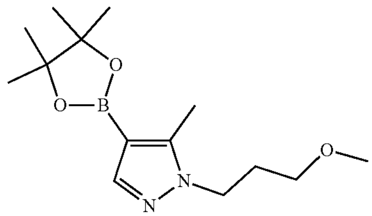 | 281.1 | Intermediate SM1 and 1-bromo-3-methoxypropane |
| Intermediate E13 | tert-butyl-dimethyl-[3-[3-methyl-4-(4,4,5,5-tetramethyl-1,3,2-dioxaborolan-2-yl)pyrazol-1-yl]propoxy]silane | 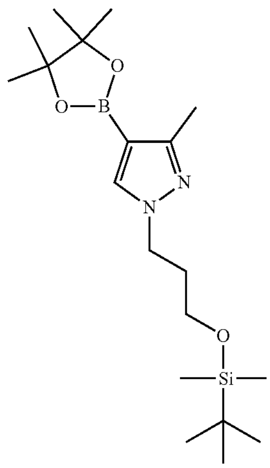 | 381.3 | Intermediate SM1 and (3-bromopropoxy)(tert-butyl)dimethylsilane |
| Intermediate E14 | tert-butyl-dimethyl-[3-[5-methyl-4-(4,4,5,5-tetramethyl-1,3,2-dioxaborolan-2-yl)pyrazol-1-yl]propoxy]silane | 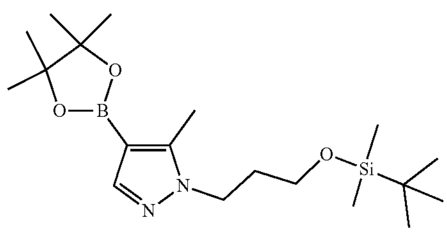 [SMILES: Cc1c(B2OC(C)(C)C(C)(C)O2)cnn1CCCO[Si](C)(C)C(C)(C)C] | 381.4 | Intermediate SM1 and (3-bromopropoxy)(tert-butyl)dimethylsilane |
| Intermediate E15 | methyl 2-[5-methyl-4-(4,4,5,5-tetramethyl-1,3,2-dioxaborolan-2-yl)pyrazol-1-yl]acetate | 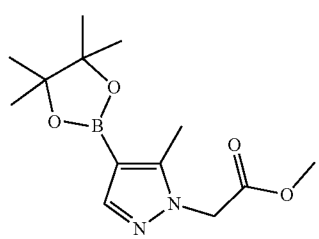 | 281.4 | Intermediate SM1 and methyl 2-bromoacetate |
| Intermediate E16 | 3-methyl-1-(tetrahydropyran-4-ylmethyl)-4-(4,4,5,5-tetramethyl-1,3,2-dioxaborolan-2-yl)pyrazole | 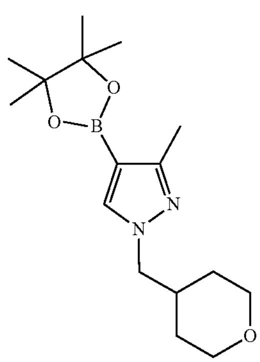 [SMILES: Cc1nn(CC2CCOCC2)cc1B1OC(C)(C)C(C)(C)O1] | 306.9 | Intermediate SM1 and bromomethyl cyclohexane |

-continued

| Ex# | Name | Structure | MS ESI [M + H]+ | Starting Material |
|---|---|---|---|---|
| Intermediate E17 | 2-[[3-methyl-4-(4,4,5,5-tetramethyl-1,3,2-dioxaborolan-2-yl)pyrazol-1-yl]methyl]pyridine | 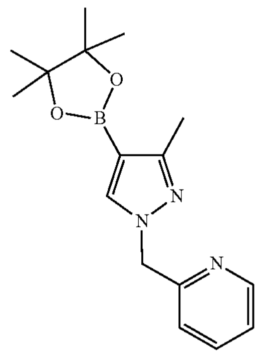 [SMILES: Cc1nn(Cc2ccccn2)cc1B1OC(C)(C)C(C)(C)O1] | 299.2 | Intermediate SM1 and bromomethyl benzene |
| Intermediate E21 | 2-methoxy-6-[[3-methyl-4-(4,4,5,5-tetramethyl-1,3,2-dioxaborolan-2-yl)pyrazol-1-yl]methyl]pyridine | 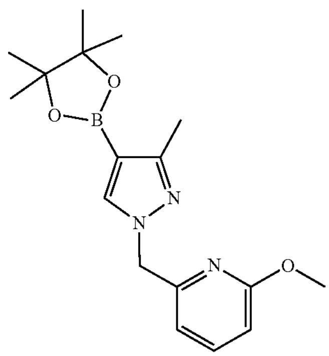 | 329.2 | Intermediate SM1 and 2-(bromomethyl)-6-methoxy-pyridine |
| Intermediate E22 | 4-[3,5-dimethyl-4-(4,4,5,5-tetramethyl-1,3,2-dioxaborolan-2-yl)pyrazol-1-yl]butanenitrile | 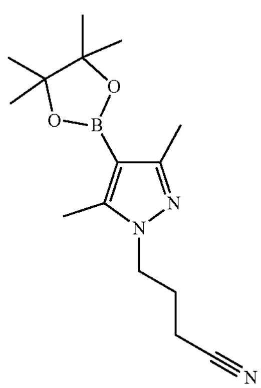 [SMILES: Cc1nn(CCCC#N)c(C)c1B1OC(C)(C)C(C)(C)O1] | 289.2 | 3,5-dimethyl-4-(4,4,5,5-tetramethyl-1,3,2-dioxaborolan-2-yl)-1H-pyrazole and 4-bromobutanenitrile |
| Intermediate E23 | 1-(2-methoxyethyl)-4-(4,4,5,5-tetramethyl-1,3,2-dioxaborolan-2-yl)pyrazole | 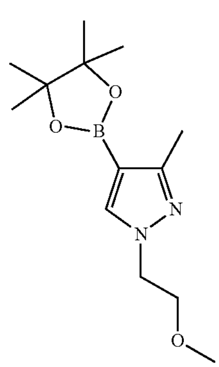 | 253.1 | 4-(4,4,5,5-tetramethyl-1,3,2-dioxaborolan-2-yl)-1H-pyrazole and 1-bromo-2-methoxy-ethane |

| Ex# | Name | Structure | MS ESI [M + H]+ | Starting Material |
|---|---|---|---|---|
| Intermediate E24 | tert-butyl-[2-[3,5-dimethyl-4-(4,4,5,5-tetramethyl-1,3,2-dioxaborolan-2-yl)pyrazol-1-yl]ethoxy]-dimethyl-silane | 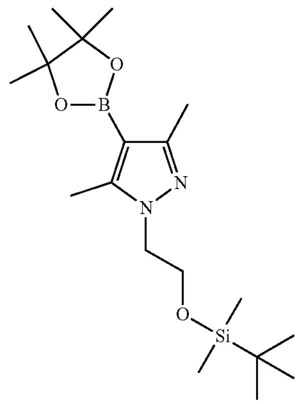 [SMILES: Cc1nn(CCO[Si](C)(C)C(C)(C)C)c(C)c1B1OC(C)(C)C(C)(C)O1] | 381.3 | 3,5-dimethyl-4-(4,4,5,5-tetramethyl-1,3,2-dioxaborolan-2-yl)-1H-pyrazole and (2-bromoethoxy)(tert-butyl)dimethylsilane |
| Intermediate E25 | 1-[(2,2-difluorocyclopropyl)methyl]-3,5-dimethyl-4-(4,4,5,5-tetramethyl-1,3,2-dioxaborolan-2-yl)pyrazole | 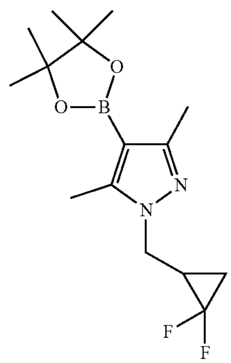 [SMILES: Cc1nn(CC2CC2(F)F)c(C)c1B1OC(C)(C)C(C)(C)O1] | 313.2 | 3,5-dimethyl-4-(4,4,5,5-tetramethyl-1,3,2-dioxaborolan-2-yl)-1H-pyrazole and 2-(bromomethyl)-1,1-difluorocyclopropane |

Intermediate E18

5-ethyl-1-(2-methoxyethyl)-4-(4,4,5,5-tetramethyl-1,3,2-dioxaborolan-2-yl)pyrazole

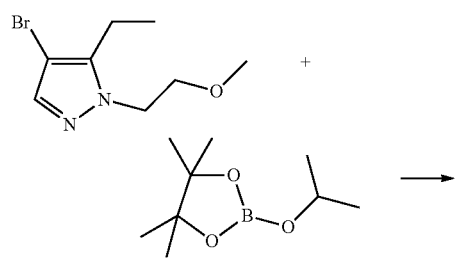

Intermediate E18

A solution of 4-bromo-5-ethyl-1-(2-methoxyethyl)-1H-pyrazole (0.47 g, 2.0 mmol) and 2-isopropoxy-4,4,5,5-tetramethyl-1,3,2-dioxaborolane (0.56 g, 3.0 mmol) were dissolved in THF (8.0 ml). The solution was cooled to −78° C. under argon atmosphere. N-butyllithium (2.0 mL, 3.0 mol) was then added dropwise to the solution. The resulting solution was stirred for 60 min at this temperature, and then the temperature was raise to room temperature gradually. The reaction mixture was quenched by methanol at 0° C. and evaporation of the solvent gave a crude product, which was purified by flash chromatography on silica gel to give 5-ethyl-1-(2-methoxyethyl)-4-(4,4,5,5-tetramethyl-1,3,2-dioxaborolan-2-yl)pyrazole (706 mg). MS [M+H]+: 281.1.

Intermediate E19 tert-butyl-dimethyl-[4-[4-(4,4,5,5-tetramethyl-1,3,2-dioxaborolan-2-yl)-2-(2-trimethylsilylethoxymethyl)pyrazol-3-yl]butoxy]silane

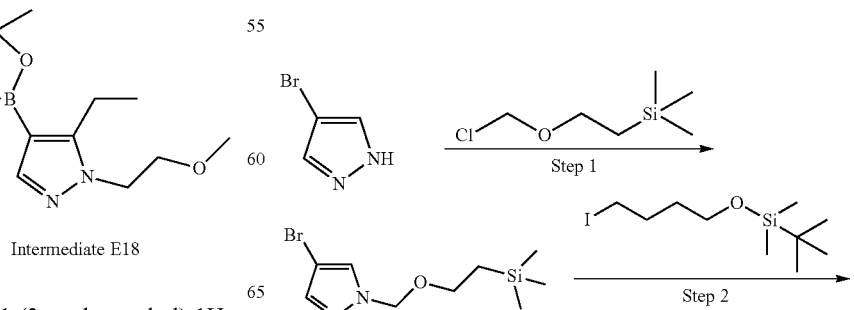

-continued

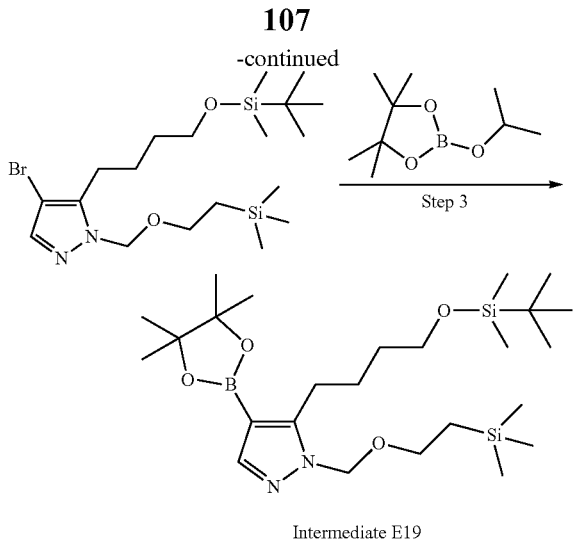

Intermediate E19

Step 1: 2-[(4-bromopyrazol-1-yl)methoxy]ethyl-trimethyl-silane 4-bromo-1H-pyrazole (7.35 g, 50 mmol) and DIPEA (13.0 g, 100 mmol) were dissolved in anhydrous $CH_2Cl_2$ (50 ml). The solution was cooled to 0° C. and (2-(chloromethoxy)ethyl)trimethylsilane (10 g, 60 mmol) was then added dropwise. The mixture was warmed to room tmperature and then stirred for 12.0 h. The mixture was poured into water and the aqueous solution was extracted with EtOAc (2×150 ml). The organic layers were combined and washed with water and brine, dried over anhydrous sodium sulfate and concentrated under reduced pressure to give a red oil which was purified by flash chromatography on silica gel to afford 2-[(4-bromopyrazol-1-yl)methoxy]ethyl-trimethyl-silane (8.6 g). MS [M+H]⁺: 277.1.

Step 2: 2-[[4-bromo-5-[4-[tert-butyl(dimethyl)silyl]oxybutyl]pyrazol-1-yl]methoxy]ethyl-trimethyl-silane To a solution of 2-[(4-bromopyrazol-1-yl)methoxy]ethyl-trimethyl-silane (1.4 g, 5.0 mmol) in anhydrous THF (15 mL) was added dropwise LDA (2.0 M in THF) (5.0 mmol) at −78° C. under argon. The resulting mixture was stirred for 1.0 h at −78° C., tert-butyl-(4-iodobutoxy)-dimethyl-silane (2.4 g, 7.5 mmol) was added. The reaction was stirred at −78° C. for 30 min. the reaction was warmed to room temperature with stirring. The reaction was quenched by saturated aqueous solution of ammonium chloride and followed by extracted with EtOAc (2×50 mL). The organic layers were combined, washed with water and brine, dried over anhydrous sodium sulfate and concentrated in vacuum. The crude material was purified by flash chromatography on silica gel to give 2-[[4-bromo-5-[4-[tert-butyl(dimethyl)silyl]oxybutyl]pyrazol-1-yl]methoxy]ethyl-trimethyl-silane (1.2 g). MS [M+H]⁺: 463.3.

Step 3: tert-butyl-dimethyl-[4-[4-(4,4,5,5-tetramethyl-1,3,2-dioxaborolan-2-yl)-2-(2-trimethylsilylethoxymethyl)pyrazol-3-yl]butoxy]silane To a solution of 2-[[4-bromo-5-[4-[tert-butyl(dimethyl)silyl]oxybutyl]pyrazol-1-yl]methoxy]ethyl-trimethyl-silane (0.46 g, 1.0 mmol) and 2-isopropoxy-4,4,5,5-tetramethyl-1,3,2-dioxaborolane (0.28 g, 1.5 mmol) in anhydrous THE (15 mL) was added dropwise n-BuLi (1.6 M in THF) (1.3 mL, 2.0 mmol) at −78° C. under argon. The resulting mixture was stirred for 1.0 h at −78° C. and then the reaction was warmed to room temperature, stirred overnight. The reaction was quenched by saturated aqueous solution of ammonium chloride and followed by extracted by EtOAc (2×50 mL). The organic layers were combined, washed with water and brine, dried over anhydrous sodium sulfate and concentrated in vacuum. The crude material was purified by flash chromatography on silica gel to give tert-butyl-dimethyl-[4-[4-(4,4,5,5-tetramethyl-1,3,2-dioxaborolan-2-yl)-2-(2-trimethylsilylethoxymethyl)pyrazol-3-yl]butoxy]silane the title compound. (400.0 mg). MS [M+H]⁺: 511.0.

Intermediate E20

1-(2-methoxyethyl)-5-(methoxymethyl)-4-(4,4,5,5-tetramethyl-1,3,2-dioxaborolan-2-yl)pyrazole

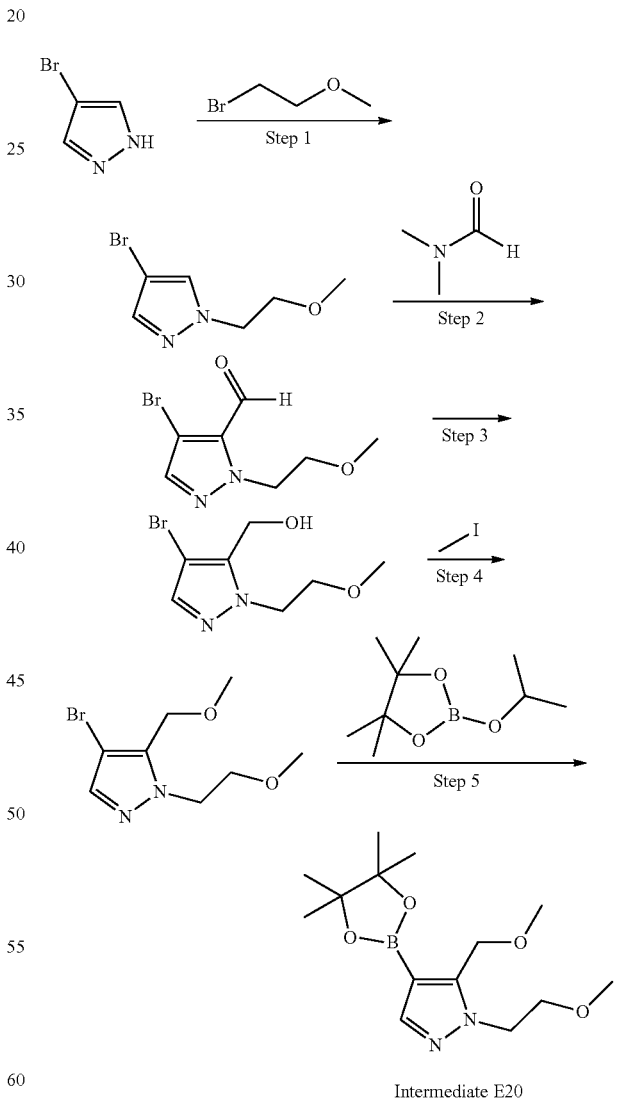

Intermediate E20

Step 1: 4-bromo-1-(2-methoxyethyl)pyrazole

To a solution of 4-bromo-1H-pyrazole (5.88 g, 40 mmol) in anhydrous DMF (25 ml) was added NaH (2.4 g, 60 mmol)

and then the mixture stirred at 0° C. for 1 h. 1-bromo-2-methoxyethane (8.34 g, 60 mmol) was added in batches to the mixture and then stirred for extra 2.0 h at room temperature. The reaction mixture was quenched by water at 0° C. and then acidified with 1N HCl to PH=7-8, the aqueous solution was extracted with EtOAc, the combined extracts were concentrated in vacuum. The crude material was purified by flash chromatography on silica gel to afford 4-bromo-1-(2-methoxyethyl)pyrazole (7.2 g).

Step 2:
4-bromo-2-(2-methoxyethyl)pyrazole-3-carbaldehyde

To a solution of 4-bromo-1-(2-methoxyethyl)pyrazole (3.1 g, 15 mmol) in anhydrous THE (20 mL) was added dropwise LDA (22.5 mmol) at −78° C. under argon. The resulting mixture was stirred for 1.0 h at −78° C. and then DMF (1.65 g, 22.5 mmol) was added dropwise into the mixture and stirred for extra 8.0 h at room temperature. The reaction mixture was quenched by water at 0° C. and then acidified with 1N HCl to PH=7-8. The aqueous solution was extracted with EtOAc, the combined extracts were concentrated in vacuum. The crude material was purified by flash chromatography on silica gel to afford afford 4-bromo-2-(2-methoxyethyl)pyrazole-3-carbaldehyde (3.0 g). MS [M+H]$^+$: 232.9.

Step 3: [4-bromo-2-(2-methoxyethyl)pyrazol-3-yl]methanol

To a solution of 4-bromo-2-(2-methoxyethyl)pyrazole-3-carbaldehyde (3.5 g, 15 mmol) in anhydrous THF (65 mL) was added dropwise borane (1.0 M in THF) (22.5 mmol) at −78° C. under argon. The resulting mixture was stirred for 2.0 h at −78° C. and then stirred for extra 5.0 h at room temperature. The reaction mixture was quenched by water at 0° C. and then extracted with EtOAc (75 mL×3), the combined extracts were concentrated in vacuum. The crude material was purified by flash chromatography on silica gel to afford [4-bromo-2-(2-methoxyethyl)pyrazol-3-yl]methanol (2.8 g). MS [M+H]$^+$: 235.0.

Step 4: 4-bromo-1-(2-methoxyethyl)-5-(methoxymethyl)pyrazole

To a solution of [4-bromo-2-(2-methoxyethyl)pyrazol-3-yl]methanol (1.2 g, 5.0 mmol) in anhydrous THF (25 mL) was added NaH (300 mg, 7.5 mmol) at 0° C. and then the suspension was stirred for 1 h. Iodomethane (1.1 g, 7.5 mmol) was added into the mixture, stirred for extra 2.0 h at room temperature. The mixture was quenched by water and then poured into water (50 mL) and the aqueous solution was extracted with EtOAC (100 mL×2). The organic layers were combined and washed with water and brine, dried over anhydrous sodium sulfate and concentrated under reduced pressure to give a red oil, the residue was purified by flash chromatography on silica gel to afford 4-bromo-1-(2-methoxyethyl)-5-(methoxymethyl)pyrazole (0.86 g). MS [M+H]$^+$: 249.0.

Step 5: 1-(2-methoxyethyl)-5-(methoxymethyl)-4-(4,4,5,5-tetramethyl-1,3,2-dioxaborolan-2-yl)pyrazole A solution of 4-bromo-1-(2-methoxyethyl)-5-(methoxymethyl)pyrazole (2.5 g, 10 mmol) and 2-isopropoxy-4,4,5,5-tetramethyl-1,3,2-dioxaborolane (2.3 g, 12 mmol) were dissolved in THE (20 mL). The solution was cooled to −78° C. under argon atmosphere, n-butyllithium (7.5 mL, 12 mmol) was then added dropwise to the solution. The resulting solution was stirred for 1.0 h at this temperature, and then the temperature was raised to room temperature.

The reaction mixture was quenched by methanol at 0° C. Evaporation of the solvent gave a crude product, which was purified by flash chromatography on silica gel to give 1-(2-methoxyethyl)-5-(methoxymethyl)-4-(4,4,5,5-tetramethyl-1,3,2-dioxaborolan-2-yl)pyrazole (1.0 g). MS [M+H]$^+$: 297.1.

Intermediate F1 and Intermediate F2

4-(4-bromo-2,3-difluoro-phenyl)-1-(2,2-difluoro-ethyl)-3-methyl-pyrazole (Intermediate F1)

4-(4-bromo-2,3-difluoro-phenyl)-1-(2,2-difluoro-ethyl)-3-methyl-pyrazole (Intermediate F2)

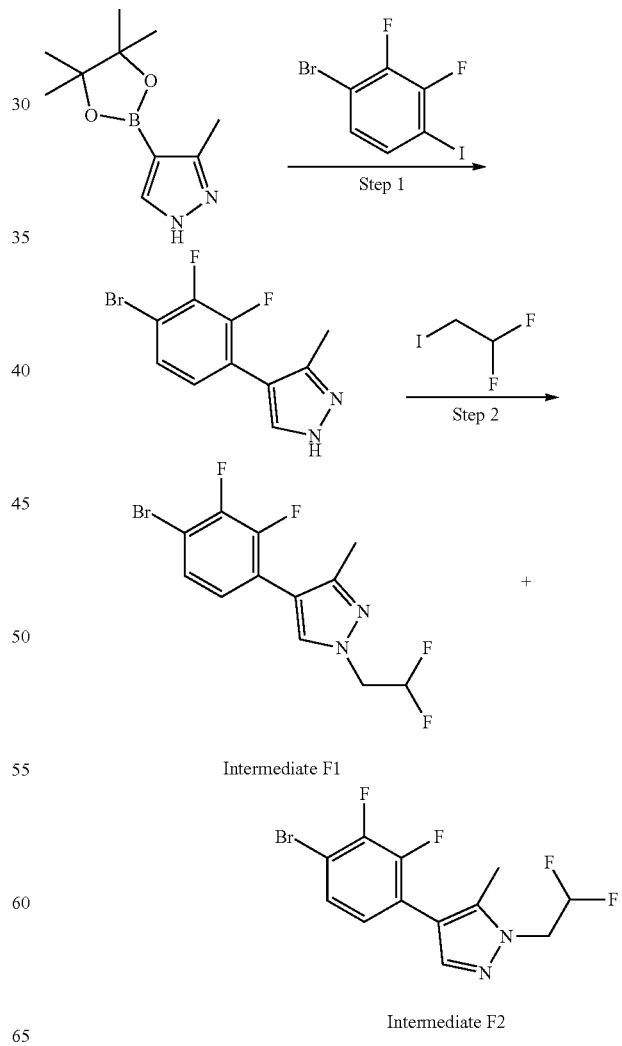

Step 1: 4-(4-bromo-2,3-difluoro-phenyl)-3-methyl-1H-pyrazole

To a 25 mL microwave vial was added 3-methyl-4-(4,4,5,5-tetramethyl-1,3,2-dioxaborolan-2-yl)-1H-pyrazole (1.7 g, 8.15 mmol), 1-bromo-2,3-difluoro-4-iodobenzene (2 g, 6.27 mmol), $Na_2CO_3$ (1.99 g, 18.8 mmol) and $PdCl_2$(dppf)-$CH_2Cl_2$ adduct (459 mg, 627 μmol) in Dioxane (50 mL)/Water (5 mL). The vial was capped and heated in the microwave at 100° C. for 15 h under $N_2$. The crude reaction mixture was concentrated in vacuum. The crude material was purified by flash chromatography to afford 4-(4-bromo-2,3-difluorophenyl)-3-methyl-1H-pyrazole (1.7 g). MS [M+H]$^+$: 275.0.

Step 2: 4-(4-bromo-2,3-difluoro-phenyl)-1-(2,2-difluoroethyl)-3-methyl-pyrazole and 4-(4-bromo-2,3-difluoro-phenyl)-1-(2,2-difluoroethyl)-3-methyl-pyrazole In a 50 mL round-bottomed flask, 4-(4-bromo-2,3-difluorophenyl)-3-methyl-1H-pyrazole (1 g, 3.66 mmol), $K_2CO_3$ (759 mg, 5.49 mmol) and 1,1-difluoro-2-iodoethane (914 mg, 4.76 mmol) were combined with DMF (10 mL) to give a light yellow solution. The reaction mixture was heated to 100° C. and stirred for 15 h. The reaction mixture was filtered through glass fiber paper. The filtrate was concentrated in vacuum. The crude material was purified by flash chromatography to afford 400 mg the mixture product. The mixture was purified by preparative chiral-HPLC to obtain 4-(4-bromo-2,3-difluoro-phenyl)-1-(2,2-difluoroethyl)-3-methyl-pyrazole (96.7 mg) and 4-(4-bromo-2,3-difluoro-phenyl)-1-(2,2-difluoroethyl)-5-methyl-pyrazole (60 mg). MS [M+H]$^+$: 337.1.

Intermediate F3

4-(4-bromo-2,3-difluoro-phenyl)-3-(trifluoromethyl)-1H-pyrazole

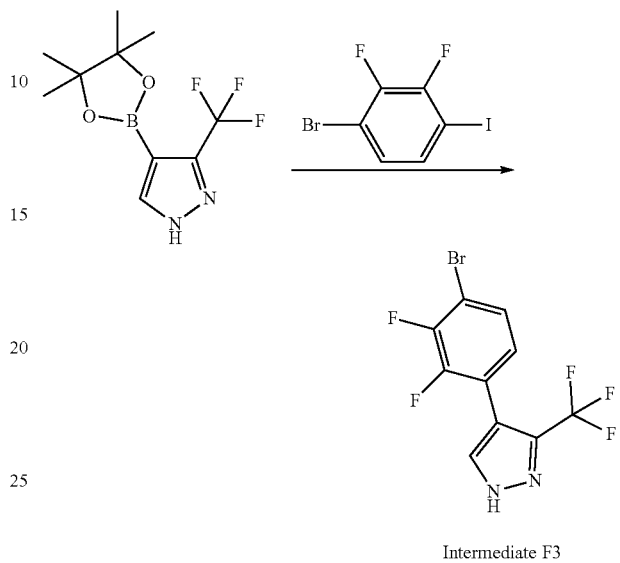

Intermediate F3

To a solution of 4-(4,4,5,5-tetramethyl-1,3,2-dioxaborolan-2-yl)-3-(trifluoromethyl)-1H-pyrazole (5 g, 19.1 mmol), 1-bromo-2,3-difluoro-4-iodobenzene (6.08 g, 19.1 mmol), sodium carbonate (6.07 g, 57.2 mmol) and $PdCl_2$(dppf)-$CH_2Cl_2$ adduct (1.56 g, 1.91 mmol) in dioxane (90 mL) and water (9. mL). The resultant mixture was heated at 100° C. for 10 h under $N_2$. The crude reaction mixture was concentrated in vacuum. The residue was purified by flash chromatography to afford 4-(4-bromo-2,3-difluoro-phenyl)-3-(trifluoromethyl)-1H-pyrazole (3.9 g). MS [M+H]$^+$: 327.0.

The following example was prepared in analogy to Intermediate F3.

| Ex# | Name | Structure | MS ESI [M + H]$^+$ | Starting Material |
|---|---|---|---|---|
| Intermediate F4 | 4-(4-bromo-2-fluoro-phenyl)-3-(trifluoromethyl)-1H-pyrazole | 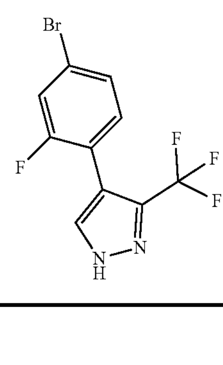 | 309.1 | 4-bromo-2-fluoro-1-iodobenzene and 4-(4,4,5,5-tetramethyl-1,3,2-dioxaborolan-2-yl)-3-(trifluoromethyl)-1H-pyrazole |

113

Intermediate G1

2-[[4-[2,3-difluoro-4-(4,4,5,5-tetramethyl-1,3,2-dioxaborolan-2-yl)phenyl]-3-methyl-pyrazol-1-yl]methoxy]ethyl-trimethyl-silane

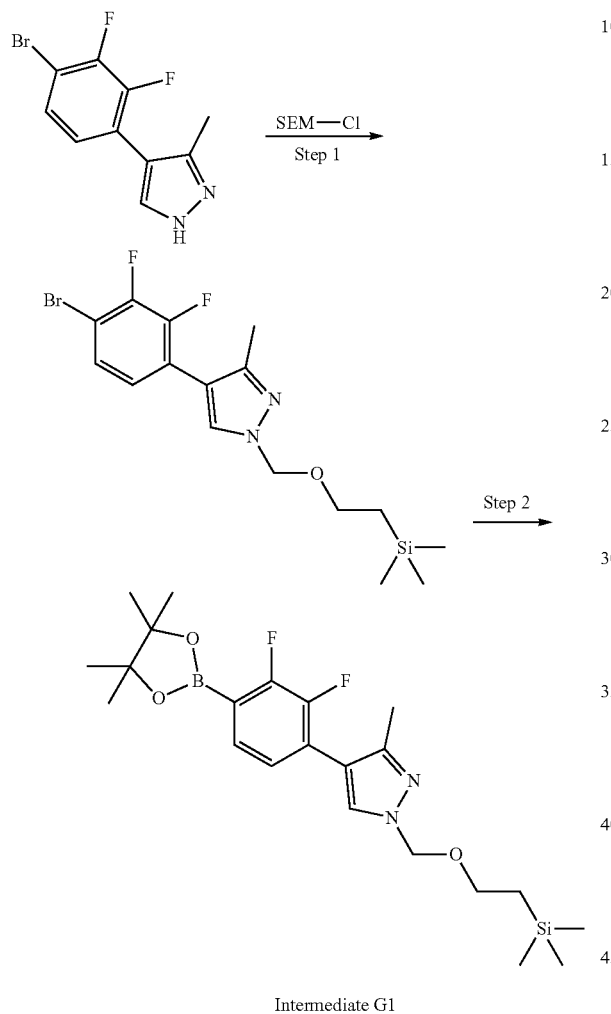

Intermediate G1

Step 1: 2-[[4-(4-bromo-2,3-difluoro-phenyl)-3-methyl-pyrazol-1-yl]methoxy]ethyl-trimethyl-silane In a 100 mL round-bottomed flask, 4-(4-bromo-2,3-difluorophenyl)-3-methyl-1H-pyrazole (1.7 g, 6.23 mmol) and DIPEA (1.21 g, 9.34 mmol) were combined with THF (30 mL) to give a light brown solution. SEM-Cl (1.56 g, 1.66 mL) was added. The reaction was stirred at room temperature for 1 h. The reaction mixture was poured into 50 mL H$_2$O and extracted with EtOAc (3×30 ml). The organic layers were combined, washed with sat NaCl (1×25 mL), The organic layers were dried over Na$_2$SO$_4$ and concentrated in vacuum to afford 2-[[4-(4-bromo-2,3-difluoro-phenyl)-3-methyl-pyrazol-1-yl]methoxy]ethyl-trimethyl-silane (1.51 g). MS [M+H]$^+$: 405.1.

114

Step 2: 2-[[4-[2,3-difluoro-4-(4,4,5,5-tetramethyl-1,3,2-dioxaborolan-2-yl)phenyl]-3-methyl-pyrazol-1-yl]methoxy]ethyl-trimethyl-silane In a 250 mL round-bottomed flask, bis(pinacolato)diboron (1.44 g, 5.65 mmol), 2-[4-(4-bromo-2,3-difluoro-phenyl)-3-methyl-pyrazol-1-yl]ethoxymethyl-trimethyl-silane (1.52 g, 3.77 mmol), PdCl$_2$(dppf)-CH$_2$Cl$_2$ adduct (276 mg, 377 μmol) and potassium acetate (1.11 g, 11.3 mmol) were combined with Dioxane (60 mL) to give a dark red solution. The reaction mixture was heated to 80° C. and stirred for 15 h under N$_2$. The crude reaction mixture was concentrated in vacuum. The reaction mixture was poured into 50 mL H$_2$O and extracted with EtOAc (3×50 mL). The organic layers were combined, washed with sat NaCl (1×50 mL), The organic layers were dried over Na$_2$SO$_4$ and concentrated in vacuum. The crude material was purified by flash chromatography to afford 2-[[4-[2,3-difluoro-4-(4,4,5,5-tetramethyl-1,3,2-dioxaborolan-2-yl)phenyl]-3-methyl-pyrazol-1-yl]methoxy]ethyl-trimethyl-silane (1 g).

Intermediate G2

4-[2,3-difluoro-4-(4,4,5,5-tetramethyl-1,3,2-dioxaborolan-2-yl)phenyl]-1-(2-methoxyethyl)-3-methyl-pyrazole

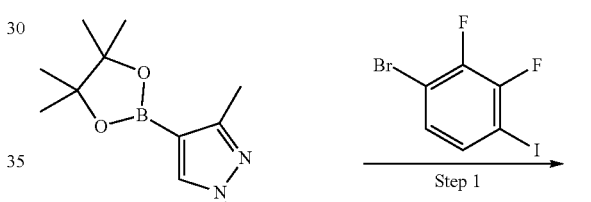

Intermediate G2

Step 1: 4-(4-bromo-2,3-difluoro-phenyl)-1-(2-methoxyethyl)-3-methyl-pyrazole In a 50 mL round-bottomed flask, 1-(2-methoxyethyl)-3-methyl-4-(4,4,5,5-tetramethyl-1,3,2-dioxaborolan-2-yl)-1H-pyrazole (459 mg, 1.72 mmol), 1-bromo-2,3-difluoro-4-iodobenzene (500 mg, 1.57 mmol), PdCl$_2$(dppf)-CH$_2$Cl$_2$ adduct (115 mg, 157 μmol) and Na$_2$CO$_3$ (499 mg, 4.7 mmol) were combined with Dioxane (10 mL)/Water (1 mL) to give a dark red solution. The reaction mixture was heated to 100° C. and stirred for 15 h under N$_2$. The reaction mixture was filtered through glass fiber paper. The filtrate was concentrated in vacuum. The crude material was purified by flash chromatography to afford 4-(4-bromo-2,3-difluoro-phenyl)-1-(2-methoxyethyl)-3-methyl-pyrazole (310 mg). MS [M+H]$^+$: 333.1.

Step 2: 4-[2,3-difluoro-4-(4,4,5,5-tetramethyl-1,3,2-dioxaborolan-2-yl)phenyl]-1-(2-methoxyethyl)-3-methyl-pyrazole In a 50 mL round-bottomed flask, 4-(4-bromo-2,3-difluoro-phenyl)-1-(2-methoxyethyl)-3-methyl-pyrazole (310 mg, 936 μmol), 4,4,4',4',5,5,5',5'-octamethyl-2,2'-bi(1,3,2-dioxaborolane) (357 mg, 1.4 mmol), PdCl$_2$(dppf)-CH$_2$Cl$_2$ adduct (68.5 mg, 93.6 μmol) and potassium acetate (276 mg, 2.81 mmol) were combined with dioxane (10 mL) to give a dark red solution. The reaction mixture was heated to 100° C. and stirred for 15 h under N$_2$. The reaction mixture was filtered through glass fiber paper. The crude reaction mixture was concentrated in vacuum. The crude material was purified by flash chromatography to afford 4-[2,3-difluoro-4-(4,4,5,5-tetramethyl-1,3,2-dioxaborolan-2-yl)phenyl]-1-(2-methoxyethyl)-3-methyl-pyrazole (350 mg). MS [M+H]$^+$: 379.1.

The following intermediates were prepared in analogy to Intermediate G2.

| Ex # | Name | Structure | MS ESI [M + H]$^+$ | Starting Material |
|---|---|---|---|---|
| Intermediate G3 | 4-[2,3-difluoro-4-(4,4,5,5-tetramethyl-1,3,2-dioxaborolan-2-yl)phenyl]-1-(2-methoxyethyl)-5-methyl-pyrazole | 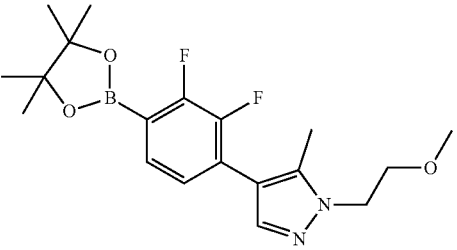 | 379.3 | Intermediate E2; 1-bromo-2,3-difluoro-4-iodobenzene and bis(pinacolato)diboron |
| Intermediate G4 | 1-(2,2-difluoroethyl)-4-[2,3-difluoro-4-(4,4,5,5-tetramethyl-1,3,2-dioxaborolan-2-yl)phenyl]-5-methyl-pyrazole | 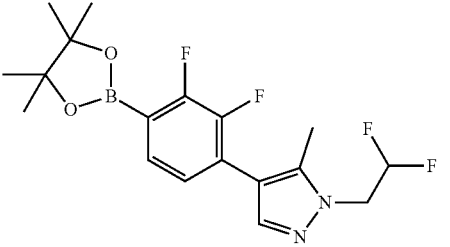 [SMILES: Cc1c(-c2ccc(B3OC(C)(C)C(C)(C)O3)c(F)c2F)cnn1CC(F)F] | 385.2 | Intermediate F2 and bis(pinacolato)diboron |
| Intermediate G5 | 1-(2,2-difluoroethyl)-4-[2,3-difluoro-4-(4,4,5,5-tetramethyl-1,3,2-dioxaborolan-2-yl)phenyl]-3-methyl-pyrazole | 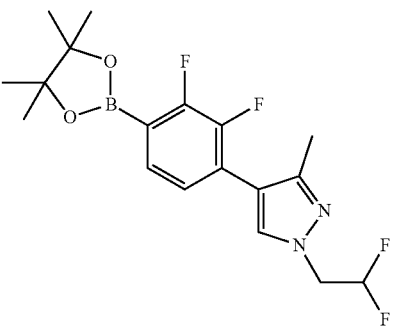 [SMILES: Cc1nn(CC(F)F)cc1-c1ccc(B2OC(C)(C)C(C)(C)O2)c(F)c1F] | 385.2 | Intermediate F1 and bis(pinacolato)diboron |

-continued

| Ex # | Name | Structure | MS ESI [M + H]+ | Starting Material |
|---|---|---|---|---|
| Intermediate G6 | 4-[2,3-difluoro-4-(4,4,5,5-tetramethyl-1,3,2-dioxaborolan-2-yl)phenyl]-1-(2-methoxyethyl)-3,5-dimethyl-pyrazole | 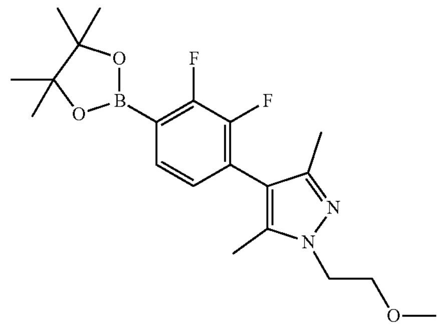 | 393.2 | Intermediate E3; 1-bromo-2,3-difluoro-4-iodobenzene and bis(pinacolato)diboron |
| Intermediate G7 | 1-(2-methoxyethyl)-3,5-dimethyl-4-[4-(4,4,5,5-tetramethyl-1,3,2-dioxaborolan-2-yl)phenyl]pyrazole | 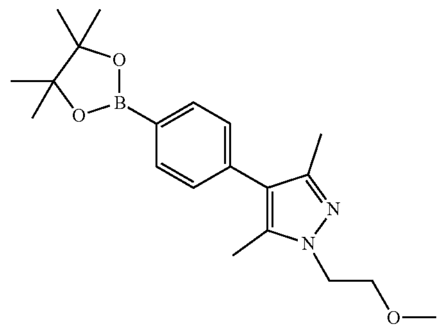 | 357.3 | Intermediate E3; 1-bromo-4-iodo-benzene and bis(pinacolato)diboron |
| Intermediate G8 | trimethyl-[2-[[3-methyl-4-[4-(4,4,5,5-tetramethyl-1,3,2-dioxaborolan-2-yl)phenyl]pyrazol-1-yl]methoxy]ethyl]silane | 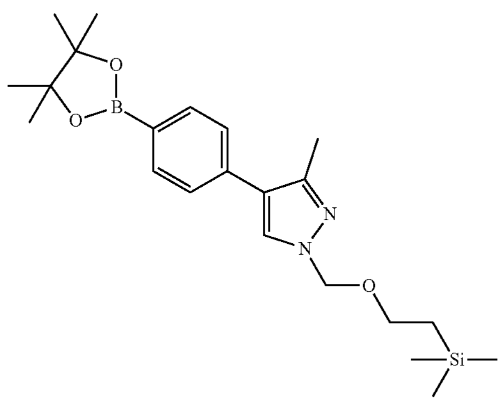 | 415.1 | Intermediate E4; 1-bromo-4-iodo-benzene and bis(pinacolato)diboron |
| Intermediate G9 | 2-[[3,5-dimethyl-4-[4-(4,4,5,5-tetramethyl-1,3,2-dioxaborolan-2-yl)phenyl]pyrazol-1-yl]methoxy]ethyl-trimethyl-silane | 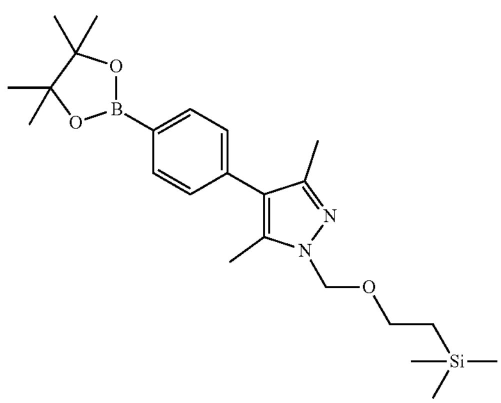 | 429.4 | Intermediate E5; 1-bromo-4-iodo-benzene and bis(pinacolato)diboron |

-continued

| Ex # | Name | Structure | MS ESI [M + H]+ | Starting Material |
|---|---|---|---|---|
| Intermediate G10 | 4-[3-fluoro-2-methyl-4-(4,4,5,5-tetramethyl-1,3,2-dioxaborolan-2-yl)phenyl]-1-(2-methoxyethyl)-5-methyl-pyrazole | 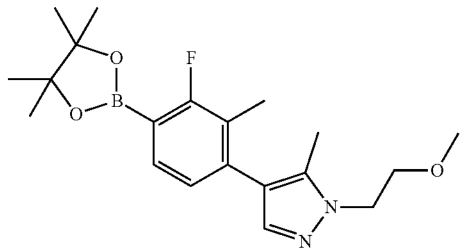 | 375.8 | Intermediate E2; 1-bromo-2-fluoro-4-iodo-3-methyl-benzene and bis(pinacolato)diboron |
| Intermediate G11 | 4-[3-chloro-2-fluoro-4-(4,4,5,5-tetramethyl-1,3,2-dioxaborolan-2-yl)phenyl]-1-(2-methoxyethyl)-5-methyl-pyrazole | 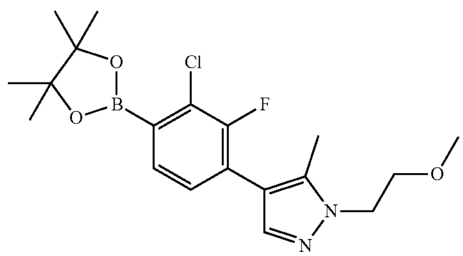 | 395.7 | Intermediate E2; 1-bromo-2-chloro-3-fluoro-4-iodo-benzene and bis(pinacolato)diboron |
| Intermediate G12 | 1-(2-methoxyethyl)-5-methyl-4-[4-(4,4,5,5-tetramethyl-1,3,2-dioxaborolan-2-yl)phenyl]pyrazole | 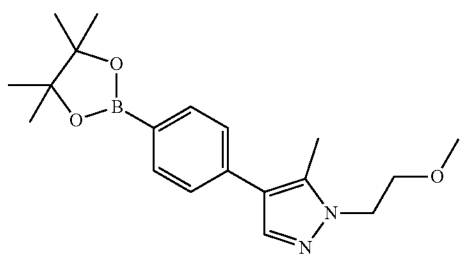 | 343.9 | Intermediate E2; 1-bromo-4-iodo-benzene and bis(pinacolato)diboron |
| Intermediate G13 | 4-[2-fluoro-3-methyl-4-(4,4,5,5-tetramethyl-1,3,2-dioxaborolan-2-yl)phenyl]-1-(2-methoxyethyl)-5-methyl-pyrazole | 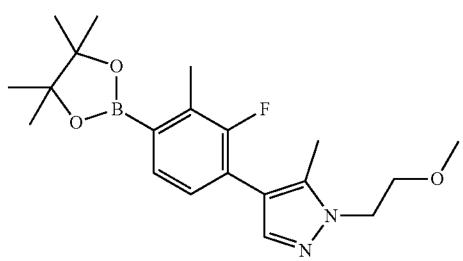 | 375.6 | Intermediate E2; 1-bromo-3-fluoro-4-iodo-2-methyl-benzene and bis(pinacolato)diboron |
| Intermediate G14 | 4-[4-[2,3-difluoro-4-(4,4,5,5-tetramethyl-1,3,2-dioxaborolan-2-yl)phenyl]-5-methyl-pyrazol-1-yl]-2-methyl-butan-2-ol | 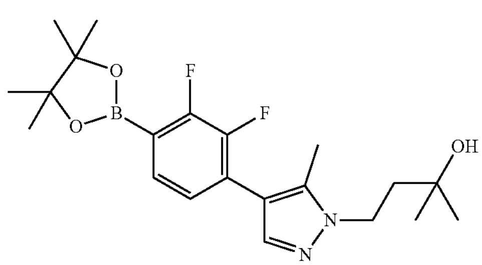 [SMILES: Cc1c(-c2ccc(B3OC(C)(C)C(C)(C)O3)c(F)c2F)cnn1CCC(C)(C)O] | 407.3 | Intermediate E6; 1-bromo-2,3-difluoro-4-iodobenzene and bis(pinacolato)diboron |

-continued

| Ex # | Name | Structure | MS ESI [M + H]+ | Starting Material |
|---|---|---|---|---|
| Intermediate G15 | 2-[4-[2,3-difluoro-4-(4,4,5,5-tetramethyl-1,3,2-dioxaborolan-2-yl)phenyl]-3-methyl-pyrazol-1-yl]-N-methyl-acetamide | | 392.2 | Intermediate E7; 1-bromo-2,3-difluoro-4-iodobenze and bis(pinacolato)diboron |
| Intermediate G16 | methyl 2-[4-[2,3-difluoro-4-(4,4,5,5-tetramethyl-1,3,2-dioxaborolan-2-yl)phenyl]-3-methyl-pyrazol-1-yl]acetate | | 393.4 | Intermediate E8; 1-bromo-2,3-difluoro-4-iodobenze and bis(pinacolato)diboron |
| Intermediate G17 | 4-[2,3-difluoro-4-(4,4,5,5-tetramethyl-1,3,2-dioxaborolan-2-yl)phenyl]-1-(3-methoxypropyl)-3-methyl-pyrazole | | 393.1 | Intermediate E11; 1-bromo-2,3-difluoro-4-iodobenze and bis(pinacolato)diboron |
| Intermediate G18 | 4-[2,3-difluoro-4-(4,4,5,5-tetramethyl-1,3,2-dioxaborolan-2-yl)phenyl]-1-(3-methoxypropyl)-5-methyl-pyrazole | | 393.2 | Intermediate E12; 1-bromo-2,3-difluoro-4-iodobenze and bis(pinacolato)diboron |

-continued

| Ex # | Name | Structure | MS ESI [M + H]+ | Starting Material |
|---|---|---|---|---|
| Intermediate G19 | tert-butyl-[3-[4-[2,3-difluoro-4-(4,4,5,5-tetramethyl-1,3,2-dioxaborolan-2-yl)phenyl]-3-methyl-pyrazol-1-yl]propoxy]-dimethyl-silane | 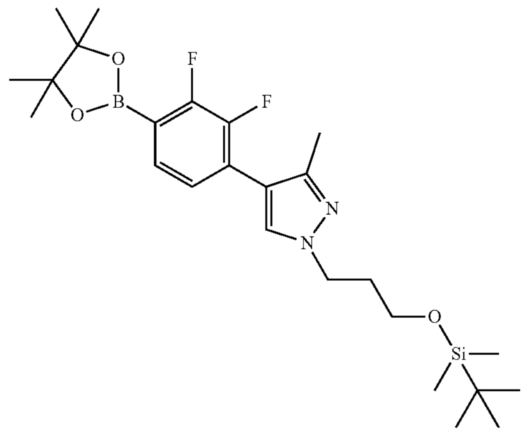 [SMILES: Cc1nn(CCCO[Si](C)(C)C(C)(C)C)cc1-c1ccc(B2OC(C)(C)C(C)(C)O2)c(F)c1F] | 493.3 | Intermediate E13; 1-bromo-2,3-difluoro-4-iodobenze and bis(pinacolato)diboron |
| Intermediate G20 | tert-butyl-[3-[4-[2,3-difluoro-4-(4,4,5,5-tetramethyl-1,3,2-dioxaborolan-2-yl)phenyl]-5-methyl-pyrazol-1-yl]propoxy]-dimethyl-silane | 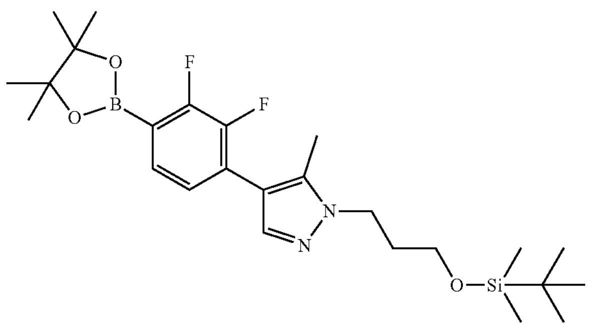 [SMILES: Cc1c(-c2ccc(B3OC(C)(C)C(C)(C)O3)c(F)c2F)cnn1CCCO[Si](C)(C)C(C)(C)C] | 493.3 | Intermediate E14; 1-bromo-2,3-difluoro-4-iodobenze and bis(pinacolato)diboron |
| Intermediate G21 | 1-(2-methoxyethyl)-4-[3-methoxy-4-(4,4,5,5-tetramethyl-1,3,2-dioxaborolan-2-yl)phenyl]-5-methyl-pyrazole | 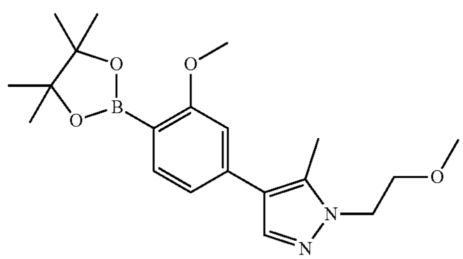 | 373.0 | Intermediate E2; 1-bromo-4-iodo-2-methoxybenzene and bis(pinacolato)diboron |
| Intermediate G22 | 1-(2-methoxyethyl)-5-methyl-4-[3-methyl-4-(4,4,5,5-tetramethyl-1,3,2-dioxaborolan-2-yl)phenyl]pyrazole | 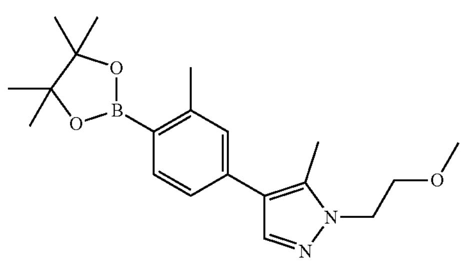 | 357.0 | Intermediate E2; 1-bromo-4-iodo-2-methylbenzene and bis(pinacolato)diboron |
| Intermediate G23 | 4-[2,3-difluoro-4-(4,4,5,5-tetramethyl-1,3,2-dioxaborolan-2-yl)phenyl]-5-ethyl-1-(2-methoxyethyl)pyrazole | 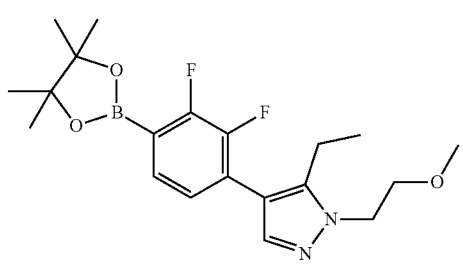 | 393.1 | Intermediate E18; 1-bromo-2,3-difluoro-4-iodobenzene and bis(pinacolato)diboron |

-continued

| Ex # | Name | Structure | MS ESI [M + H]+ | Starting Material |
|---|---|---|---|---|
| Intermediate G24 | tert-butyl-[4-[4-[2,3-difluoro-4-(4,4,5,5-tetramethyl-1,3,2-dioxaborolan-2-yl)phenyl]-2-(2-trimethylsilylethoxymethyl)pyrazol-3-yl]butoxy]-dimethyl-silane | 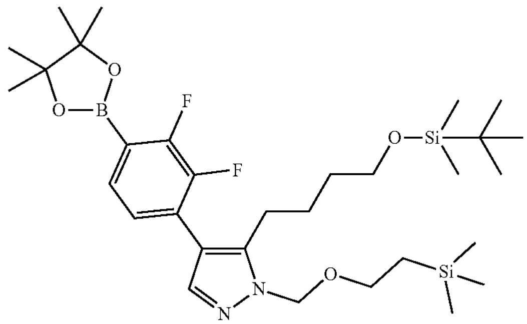 [SMILES: CC1(C)OB(c2ccc(-c3cnn(COCC[Si](C)(C)C)c3CCCCO[Si](C)(C)C(C)(C)C)c(F)c2F)OC1(C)C] | 623.4 | Intermediate E19; 1-bromo-2,3-difluoro-4-iodobenzene and bis(pinacolato)diboron |
| Intermediate G25 | 4-[2,3-difluoro-4-(4,4,5,5-tetramethyl-1,3,2-dioxaborolan-2-yl)phenyl]-1-(2-methoxyethyl)-5-(methoxymethyl)pyrazole | 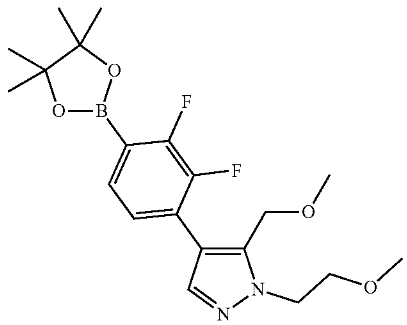 | 409.1 | Intermediate E20; 1-bromo-2,3-difluoro-4-iodobenzene and bis(pinacolato)diboron |
| Intermediate G26 | tert-butyl-[2-[4-[2,3-difluoro-4-(4,4,5,5-tetramethyl-1,3,2-dioxaborolan-2-yl)phenyl]-5-methyl-pyrazol-1-yl]ethoxy]-dimethyl-silane | 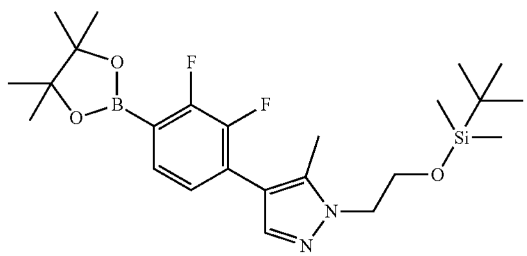 [SMILES: Cc1c(-c2ccc(B3OC(C)(C)C(C)(C)O3)c(F)c2F)cnn1CCO[Si](C)(C)C(C)(C)C] | 479.4 | Intermediate E10; 1-bromo-2,3-difluoro-4-iodobenzene and bis(pinacolato)diboron |
| Intermediate G27 | tert-butyl-[2-[4-[2,3-difluoro-4-(4,4,5,5-tetramethyl-1,3,2-dioxaborolan-2-yl)phenyl]-3-methyl-pyrazol-1-yl]ethoxy]-dimethyl-silane | 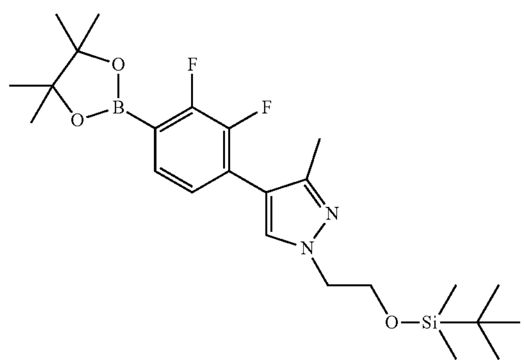 [SMILES: Cc1nn(CCO[Si](C)(C)C(C)(C)C)cc1-c1ccc(B2OC(C)(C)C(C)(C)O2)c(F)c1F] | 479.4 | Intermediate E9; 1-bromo-2,3-difluoro-4-iodobenzene and bis(pinacolato)diboron |
| Intermediate G28 | 4-[3-chloro-4-(4,4,5,5-tetramethyl-1,3,2-dioxaborolan-2-yl)phenyl]-1-(2-methoxyethyl)-5-methyl-pyrazole | 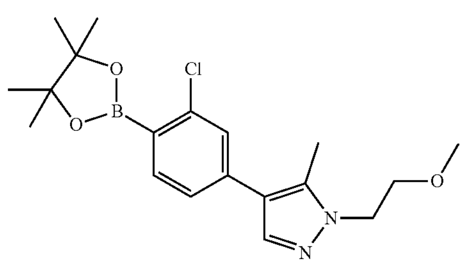 | 377.8 | Intermediate E2; 1-bromo-2-chloro-4-iodo-benzene and bis(pinacolato)diboron |

-continued

| Ex # | Name | Structure | MS ESI [M + H]+ | Starting Material |
|---|---|---|---|---|
| Intermediate G29 | 4-[2-fluoro-3-methoxy-4-(4,4,5,5-tetramethyl-1,3,2-dioxaborolan-2-yl)phenyl]-1-(2-methoxyethyl)-5-methyl-pyrazole | 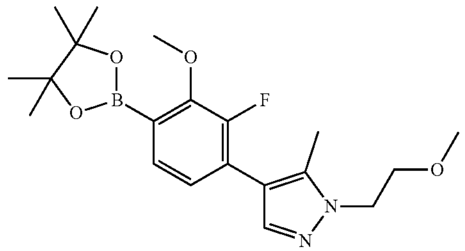 | 391.2 | Intermediate E2; 1-bromo-3-fluoro-4-iodo-2-methoxy-benzene and bis(pinacolato)diboron |
| Intermediate G30 | methyl 2-[4-[2,3-difluoro-4-(4,4,5,5-tetramethyl-1,3,2-dioxaborolan-2-yl)phenyl]-5-methyl-pyrazol-1-yl]acetate | 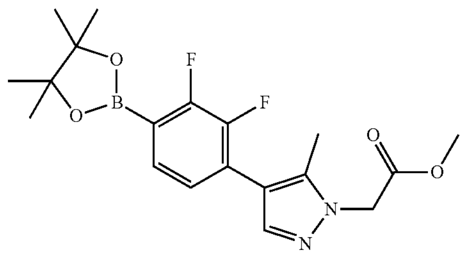 | 393.4 | Intermediate E15; 1-bromo-2,3-difluoro-4-iodobenze and bis(pinacolato)diboron |
| Intermediate G31 | 4-[2,3-difluoro-4-(4,4,5,5-tetramethyl-1,3,2-dioxaborolan-2-yl)phenyl]-3-methyl-1-(tetrahydropyran-4-ylmethyl)pyrazole | 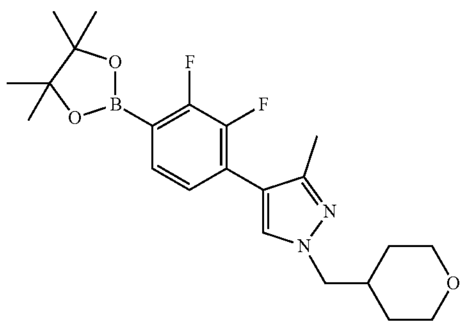 [SMILES: Cc1nn(CC2CCOCC2)cc1-c1ccc(B2OC(C)(C)C(C)(C)O2)c(F)c1F] | 419.0 | Intermediate E16; 1-bromo-2,3-difluoro-4-iodobenze and bis(pinacolato)diboron |
| Intermediate G32 | 2-[[4-[2,3-difluoro-4-(4,4,5,5-tetramethyl-1,3,2-dioxaborolan-2-yl)phenyl]-3-methyl-pyrazol-1-yl]methyl]pyridine | 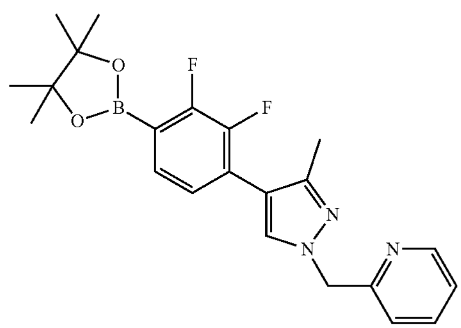 [SMILES: Cc1nn(Cc2ccccn2)cc1-c1ccc(B2OC(C)(C)C(C)(C)O2)c(F)c1F] | 330.0 | Intermediate E17; 1-bromo-2,3-difluoro-4-iodobenze and bis(pinacolato)diboron |
| Intermediate G77 | [2,3-difluoro-4-[1-[(6-methoxy-2-pyridyl)methyl]-3-methyl-pyrazol-4-yl]phenyl]boronic acid | 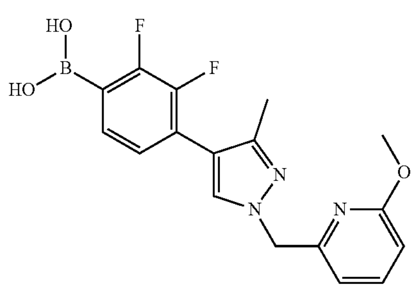 [SMILES: COc1cccc(Cn2cc(-c3ccc(B(O)O)c(F)c3F)c(C)n2)n1] | 360.1 | Intermediate E21; 1-bromo-2,3-difluoro-4-iodobenze and bis(pinacolato)diboron |

| Ex # | Name | Structure | MS ESI [M + H]+ | Starting Material |
|---|---|---|---|---|
| Intermediate G82 | 4-[2,3-difluoro-4-(4,4,5,5-tetramethyl-1,3,2-dioxaborolan-2-yl)phenyl]-1-methyl-pyrazole | 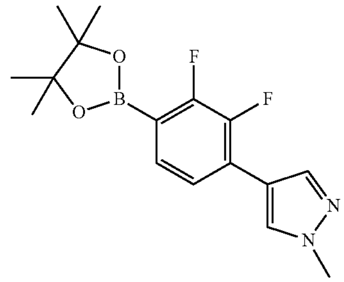 [SMILES: Cn1cc(-c2ccc(B3OC(C)(C)C(C)(C)O3)c(F)c2F)cn1] | 321.1 | 1-methyl-4-(4,4,5,5-tetramethyl-1,3,2-dioxaborolan-2-yl)pyrazole; 1-bromo-2,3-difluoro-4-iodobenze and bis(pinacolato)diboron |
| Intermediate G83 | 4-[2,3-difluoro-4-(4,4,5,5-tetramethyl-1,3,2-dioxaborolan-2-yl)phenyl]-1-(2-methoxyethyl)pyrazole | 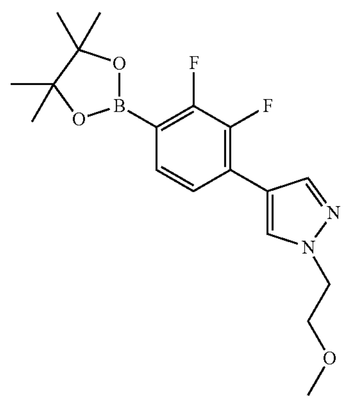 [SMILES: COCCn1cc(-c2ccc(B3OC(C)(C)C(C)(C)O3)c(F)c2F)cn1] | 365.2 | Intermediate E23; 1-bromo-2,3-difluoro-4-iodobenze and bis(pinacolato)diboron |
| Intermediate G89 | 2-[[4-[2,3-difluoro-4-(4,4,5,5-tetramethyl-1,3,2-dioxaborolan-2-yl)phenyl]-3,5-dimethyl-pyrazol-1-yl]methoxy]ethyl-trimethyl-silane | 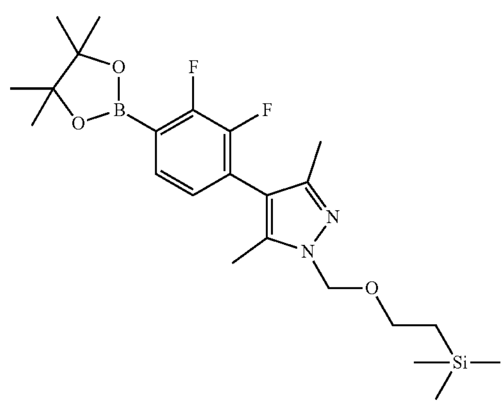 | 465.4 | 3,5-dimethyl-4-(4,4,5,5-tetramethyl-1,3,2-dioxaborolan-2-yl)-1H-pyrazole; 1-bromo-2,3-difluoro-4-iodobenze and bis(pinacolato)diboron |

-continued

| Ex # | Name | Structure | MS ESI [M + H]+ | Starting Material |
|---|---|---|---|---|
| Intermediate G90 | trimethyl-[2-[[4-[4-(4,4,5,5-tetramethyl-1,3,2-dioxaborolan-2-yl)phenyl]pyrazol-1-yl]methoxy]ethyl]silane | 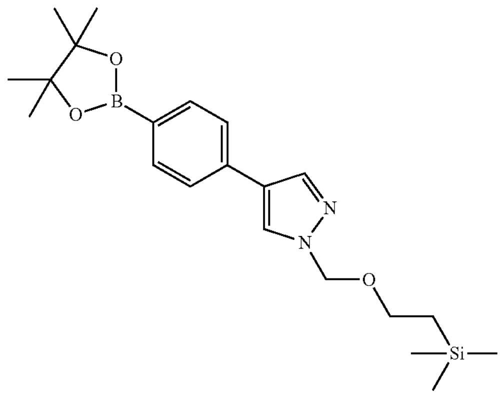 | 401.4 | trimethyl-[2-[[4-(4,4,5,5-tetramethyl-1,3,2-dioxaborolan-2-yl)pyrazol-1-yl]methoxy]ethyl]silane; 1-bromo-4-iodo-benzene and bis(pinacolato)diboron |
| Intermediate G92 | 4-[2-chloro-5-methyl-4-(4,4,5,5-tetramethyl-1,3,2-dioxaborolan-2-yl)phenyl]-1-(2-methoxyethyl)-5-methyl-pyrazole | 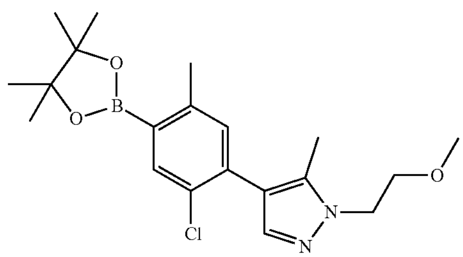 | 391.2 | Intermediate E2; 1-bromo-5-chloro-4-iodo-2-methyl-benzene and bis(pinacolato)diboron |
| Intermediate G93 | 4-[2-chloro-3-fluoro-4-(4,4,5,5-tetramethyl-1,3,2-dioxaborolan-2-yl)phenyl]-1-(2-methoxyethyl)-5-methyl-pyrazole | 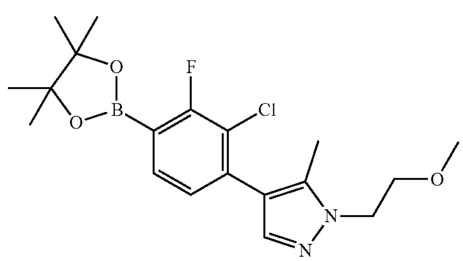 | 395.6 | Intermediate E2; 1-bromo-3-chloro-2-fluoro-4-iodo-benzene and bis(pinacolato)diboron |

Intermediate G33

1-[2-(difluoromethoxy)ethyl]-4-[2,3-difluoro-4-(4,4,5,5-tetramethyl-1,3,2-dioxaborolan-2-yl)phenyl]-3-methyl-pyrazole

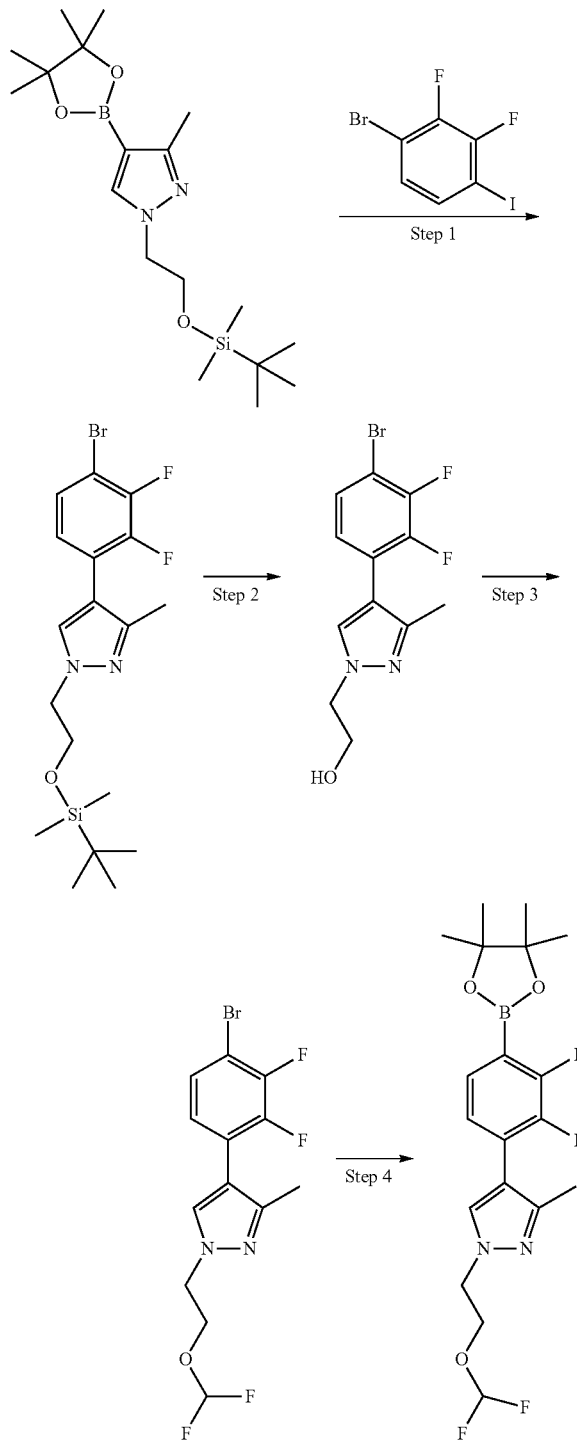

Intermediate G33

Step 1: 2-[4-(4-bromo-2,3-difluoro-phenyl)-3-methyl-pyrazol-1-yl]ethoxy-tert-butyl-dimethyl-silane To a solution of 1-bromo-2,3-difluoro-4-iodobenzene (1000 mg, 3.14 mmol) in the mixture solvent of dioxane (10 mL) and Water (2 mL) was added sodium carbonate (665 mg, 6.27 mmol), 1-(2-((tert-butyldimethylsilyl)oxy)ethyl)-3-methyl-4-(4,4,5,5-tetramethyl-1,3,2-dioxaborolan-2-yl)-1H-pyrazole (1.15 g, 3.14 mmol) and PdCl$_2$(dppf)-CH$_2$Cl$_2$ adduct (256 mg, 314 μmol). The reaction was stirred for 3 h at 130° C. under microwave irritation and atmosphere of argon. The mixture was filtered and the filtrate was concentrated in vacuum. The residue was purified by column chromatography to give 2-[4-(4-bromo-2,3-difluoro-phenyl)-3-methyl-pyrazol-1-yl]ethoxy-tert-butyl-dimethyl-silane (1 g). MS [M+H]$^+$: 431.1.

Step 2: 2-[4-(4-bromo-2,3-difluoro-phenyl)-3-methyl-pyrazol-1-yl]ethanol

To a solution of 4-(4-bromo-2,3-difluorophenyl)-1-(2-((tert-butyldimethylsilyl)oxy)ethyl)-3-methyl-1H-pyrazole (1 g, 2.32 mmol) in THF (10 mL) was added TBAF (6.95 mL, 6.95 mmol), the reaction was stirred for 1 h at room temperature. The reaction mixture was washed with brine (20 mL) and extracted in DCM (30 mL). The organic layer was dried over anhydrous Na$_2$SO$_4$ and concentrated in vacuum. The residue was purified by column chromatography to give 2-[4-(4-bromo-2,3-difluoro-phenyl)-3-methyl-pyrazol-1-yl]ethanol (500 mg). MS [M+H]$^+$: 317.0.

Step 3: 4-(4-bromo-2,3-difluoro-phenyl)-1-[2-(difluoromethoxy)ethyl]-3-methyl-pyrazole To a solution of 2-(4-(4-bromo-2,3-difluorophenyl)-3-methyl-1H-pyrazol-1-yl)ethan-1-ol (450 mg, 1.42 mmol) in Acetonitrile (5 mL) was added copper (I) iodide (54 mg, 284 μmol), the reaction was heated to 60° C., then the soution of 2,2-difluoro-2-(fluorosulfonyl)acetic acid (505 mg, 2.84 mmol) in Acetonitrile (5 mL) was addded dropwise over 5 min. The reaction was stirred for another 30 min. The reaction was cooled to room temperature and the mixture was concentrated in vacuum. The residue was purified by column chromatography to give 4-(4-bromo-2,3-difluoro-phenyl)-1-[2-(difluoromethoxy)ethyl]-3-methyl-pyrazole (200 mg). MS [M+H]$^+$: 367.0.

Step 4: 1-[2-(difluoromethoxy)ethyl]-4-[2,3-difluoro-4-(4,4,5,5-tetramethyl-1,3,2-dioxaborolan-2-yl)phenyl]-3-methyl-pyrazole To a solution of 4-(4-bromo-2,3-difluorophenyl)-1-(2-(difluoromethoxy)ethyl)-3-methyl-1H-pyrazole (200 mg, 545 μmol) in Dioxane (3 mL) was added potassium acetate (107 mg, 1.09 mmol), PdCl$_2$(dppf)-CH$_2$Cl$_2$ adduct (44.5 mg, 54.5 μmol) and bis(pinacolato)diboron (138 mg, 545 μmol), the reaction was stirred for 15 h at 80° C. under atmosphere of argon. The reaction mixture was cooled to room temperature and filtered. The filtrate was concentrated in vacuum and the residue was purified by column chromatography to give 1-[2-(difluoromethoxy)ethyl]-4-[2,3-difluoro-4-(4,4,5,5-tetramethyl-1,3,2-dioxaborolan-2-yl)phenyl]-3-methyl-pyrazole (150 mg). MS [M+H]$^+$: 415.2.

The following intermediates were prepared in analogy to Intermediate G33.

| Ex # | Name | Structure | MS ESI [M + H]+ | Starting Material |
|---|---|---|---|---|
| Intermediate G34 | 1-[2-(difluoromethoxy)ethyl]-4-[2,3-difluoro-4-(4,4,5,5-tetramethyl-1,3,2-dioxaborolan-2-yl)phenyl]-5-methyl-pyrazole | 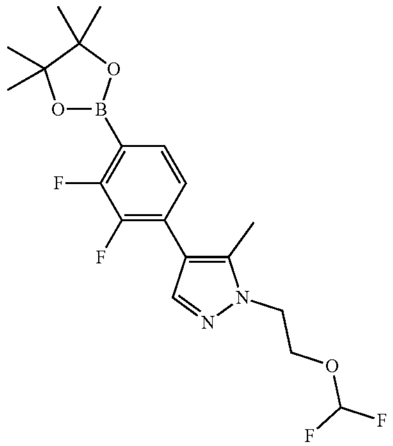 [SMILES: Cc1c(-c2ccc(B3OC(C)(C)C(C)(C)O3)c(F)c2F)cnn1CCOC(F)F] | 415.2 | Intermediate E10; 1-bromo-2,3-difluoro-4-iodobenzene; TBAF; 2,2-difluoro-2-(fluorosulfonyl) acetic acid and bis(pinacolato) diboron |

Intermediate G35

4-[2,3-difluoro-4-(4,4,5,5-tetramethyl-1,3,2-dioxaborolan-2-yl)phenyl]-3-isopropyl-1-(2-methoxyethyl)pyrazole

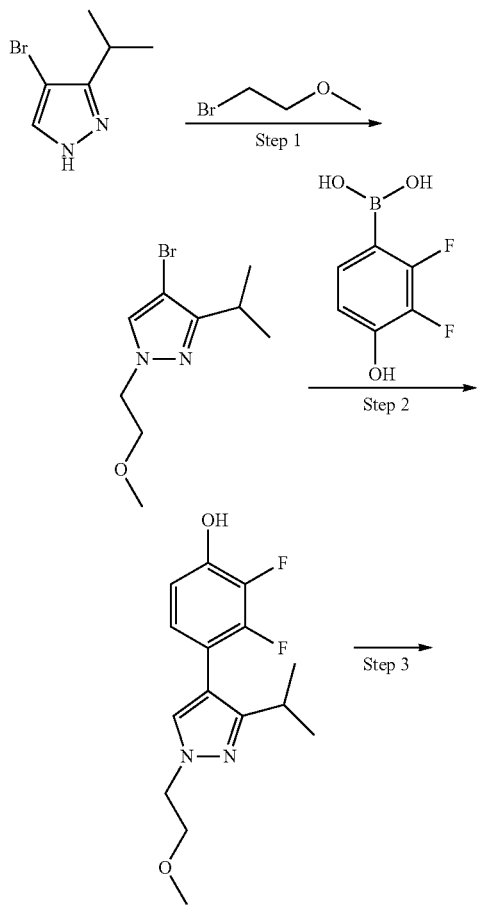

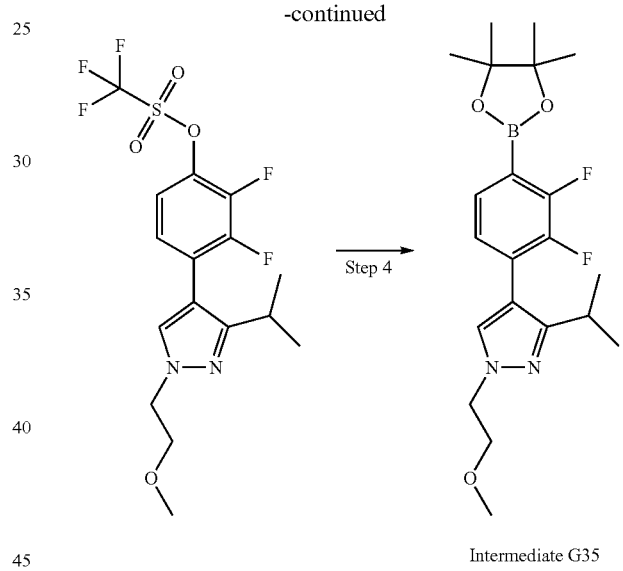

Intermediate G35

Step 1: 4-bromo-3-isopropyl-1-(2-methoxyethyl)pyrazole

To a solution of 4-bromo-3-isopropyl-1H-pyrazole (1000 mg, 5.29 mmol) in acetonitrile (10 mL) was added 1-bromo-2-methoxy-ethane (735.2 mg, 5.29 mmol) and cesium carbonate (3.45 g, 10.58 mmol), the reaction was stirred for 8 h at 100° C. The reaction was mixture was cooled to room temperature and filtered. The filtrate was concentrated in vacuum and the residue was purified by Chiral HPLC to give 4-bromo-3-isopropyl-1-(2-methoxyethyl)pyrazole (1.2 g). MS [M+H]+: 247.0.

Step 2: 2,3-difluoro-4-[3-isopropyl-1-(2-methoxyethyl)pyrazol-4-yl]phenol

To a solution of 4-bromo-3-isopropyl-1-(2-methoxyethyl) pyrazole (900 mg, 3.64 mmol) in the mixture solvent of 1,4-dioxane (12 mL) and water (2.4 mL) was added (2,3- difluoro-4-hydroxy-phenyl)boronic acid (1.27 g, 7.28 mmol), tetrakis(triphenylphosphine)palladium (420.83 mg, 0.364 mmol) and sodium carbonate (1.16 g, 10.93 mmol), the reaction was stirred for 3 h at 100° C. under atmosphere of nitrogen. The reaction mixture was cooled to room temperature and filtered. The filtrate was concentrated in vacuum. The residue was purified by column chromatography to give 2,3-difluoro-4-[3-isopropyl-1-(2-methoxyethyl)pyrazol-4-yl]phenol (210 mg). MS [M+H]⁺: 297.1.

Step 3: [2,3-difluoro-4-[3-isopropyl-1-(2-methoxyethyl)pyrazol-4-yl]phenyl]trifluoromethanesulfonate To a solution of 2,3-difluoro-4-[3-isopropyl-1-(2-methoxyethyl)pyrazol-4-yl]phenol (100 mg, 0.337 mmol) in N,N-dimethylformamide (3 mL) was added 1,1,1-trifluoro-N-phenyl-N-triflyl-methanesulfonamide (144.68 mg, 0.405 mmol), triethylamine (68.3 mg, 0.675 mmol) and n-(4-pyridyl)dimethylamine (4.12 mg, 0.034 mmol), the reaction was stirred for 1 h at room temperature. The reaction mixture was concentrated in vacuum. The residue was purified by flash column chromatography to give [2,3-difluoro-4-[3-isopropyl-1-(2-methoxyethyl)pyrazol-4-yl]phenyl] trifluoromethanesulfonate (135 mg). MS [M+H]⁺: 429.1.

Step 4: 4-[2,3-difluoro-4-(4,4,5,5-tetramethyl-1,3,2-dioxaborolan-2-yl)phenyl]-3-isopropyl-1-(2-methoxyethyl)pyrazole To a solution of trifluoromethanesulfonic acid [2,3-difluoro-4-[3-isopropyl-1-(2-methoxyethyl)pyrazol-4-yl]phenyl] ester (80 mg, 0.187 mmol) in anhydrous 1,4-dioxane (3 mL) was added 4,4,4',4',5,5,5',5'-octamethyl-2,2'-bi(1,3,2-dioxaborolane) (47.42 mg, 0.187 mmol), potassium acetate (36.66 mg, 0.374 mmol) and [1,1'-bis(diphenylphosphino)ferrocene]palladium(ii) dichloride dichloromethane adduct (15.25 mg, 0.019 mmol), the reaction was stirred for 5 h at 100° C. under atmosphere of nitrogen. The reaction mixture was cooled to room temperature and filtered. The filtrate was concentrated in vacuum. The residue was purified by column chromatography to give 4-[2,3-difluoro-4-(4,4,5,5-tetramethyl-1,3,2-dioxaborolan-2-yl)phenyl]-3-isopropyl-1-(2-methoxyethyl)pyrazole (60 mg). MS [M+H]⁺: 407.2.

The following intermediates were prepared in analogy to Intermediate G35.

| Ex # | Name | Structure | MS ESI [M + H]⁺ | Starting Material |
|---|---|---|---|---|
| Intermediate G36 | 5-(difluoromethyl)-4-[2,3-difluoro-4-(4,4,5,5-tetramethyl-1,3,2-dioxaborolan-2-yl)phenyl]-1-(2-methoxyethyl)pyrazole | 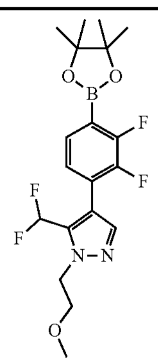 | 415.2 | Intermediate R4; 1,1,1-trifluoro-N-phenyl-N-triflyl-methanesulfonamide and bis(pinacolato)diboron |
| Intermediate G37 | 4-[2,3-difluoro-4-(4,4,5,5-tetramethyl-1,3,2-dioxaborolan-2-yl)phenyl]-3-fluoro-1-(2-methoxyethyl)pyrazole | 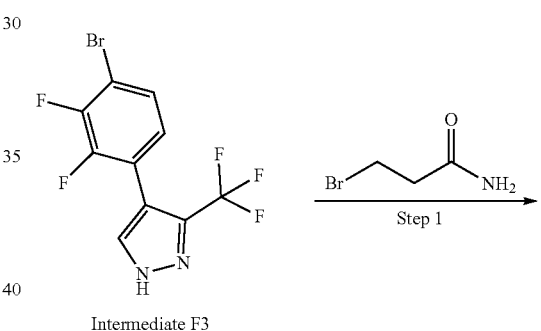 | 383.2 | 4-bromo-3-fluoro-1H-pyrazole; 1-bromo-2-methoxy-ethane; 1,1,1-trifluoro-N-phenyl-N-triflyl-methanesulfonamide and bis(pinacolato)diboron |

Intermediate G38

3-[4-[2,3-difluoro-4-(4,4,5,5-tetramethyl-1,3,2-dioxaborolan-2-yl)phenyl]-3-(trifluoromethyl)pyrazol-1-yl]propanamide

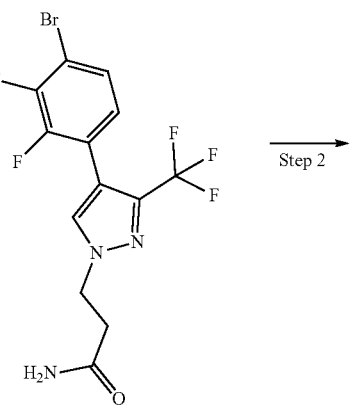

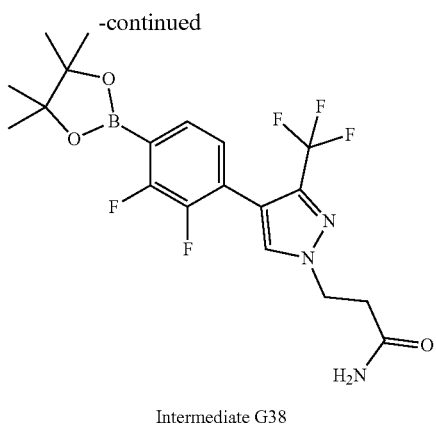

Intermediate G38

Step 1: 3-[4-(4-bromo-2,3-difluoro-phenyl)-3-(trifluoromethyl)pyrazol-1-yl]propanamide 4-(4-bromo-2,3-difluorophenyl)-3-(trifluoromethyl)-1H-pyrazole (500 mg, 1.53 mmol), 3-bromopropanamide (279 mg, 1.83 mmol) and potassium carbonate (634 mg, 4.59 mmol) were heated in anhydrous acetonitrile (7.64 mL) at 60° C. for 18 h. The mixture was cooled to room temperature, and 100-200 mesh silica gel was added to absorb the material. The loaded sample was purified by flash chromatography to afford the final compound as yellow oil (550 mg). MS [M+H]$^+$: 398.0.

Step 2: 3-[4-[2,3-difluoro-4-(4,4,5,5-tetramethyl-1,3,2-dioxaborolan-2-yl)phenyl]-3-(trifluoromethyl)pyrazol-1-yl]propanamide To a solution of 3-(4-(4-bromo-2,3-difluorophenyl)-3-(trifluoromethyl)-1H-pyrazol-1-yl)propanamide (590 mg, 1.48 mmol) in dioxane (14.8 mL) was added 4,4,4',4',5,5,5',5'-octamethyl-2,2'-bi(1,3,2-dioxaborolane) (452 mg, 1.78 mmol), potassium acetate (436 mg, 4.45 mmol) and PdCl$_2$(dppf)-CH$_2$Cl$_2$ (122 mg, 148 μmol), the reaction was stirred for 18 hours at 100° C. under atmosphere of argon. The reaction mixture was cooled to room temperature and filtered. The filtrate was concentrated in vacuum and the residue was purified by column chromatography to afford the product as yellow solid (390 mg). MS [M+H]$^+$: 446.2.

The following examples were prepared in analogy to Intermediate G38.

| Ex # | Name | Structure | MS ESI [M + H]$^+$ | Starting Material |
|---|---|---|---|---|
| Intermediate G39 | 4-[2,3-difluoro-4-(4,4,5,5-tetramethyl-1,3,2-dioxaborolan-2-yl)phenyl]-1-(2-methylsulfonylethyl)-3-(trifluoromethyl)pyrazole | 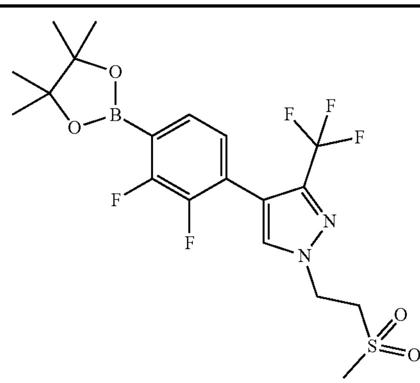 | 481.2 | Intermediate F3 and 1-methylsulfonylethylene |
| Intermediate G40 | 4-[4-[2,3-difluoro-4-(4,4,5,5-tetramethyl-1,3,2-dioxaborolan-2-yl)phenyl]-3-(trifluoromethyl)pyrazol-1-yl]butanamide | 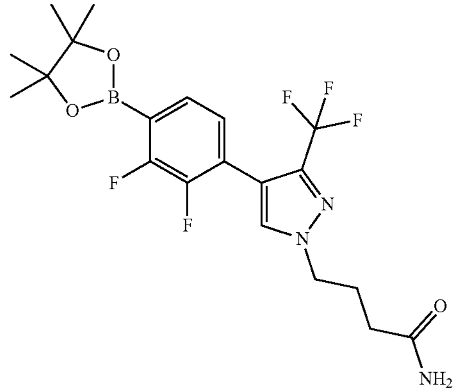 [SMILES: CC1(C)OB(c2ccc(-c3cn(CCCC(N)=O)nc3C(F)(F)F)c(F)c2F)OC1(C)C] | 460.2 | Intermediate F3 and 4-bromobutanamide |

| Ex # | Name | Structure | MS ESI [M + H]+ | Starting Material |
|---|---|---|---|---|
| Intermediate G41 | 2-[4-[2,3-difluoro-4-(4,4,5,5-tetramethyl-1,3,2-dioxaborolan-2-yl)phenyl]-3-(trifluoromethyl)pyrazol-1-yl]acetamide | 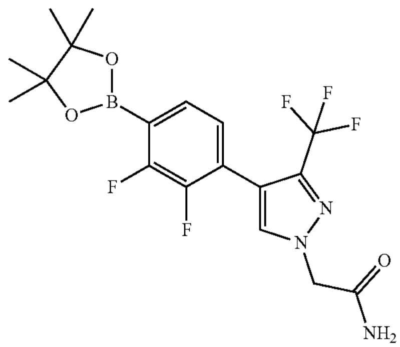 [SMILES: CC1(C)OB(c2ccc(-c3cn(CC(N)=O)nc3C(F)(F)F)c(F)c2F)OC1(C)C] | 432.1 | Intermediate F3 and 2-iodoacetamide |
| Intermediate G42 | 4-[2,3-difluoro-4-(4,4,5,5-tetramethyl-1,3,2-dioxaborolan-2-yl)phenyl]-1-(2-methoxyethyl)-3-(trifluoromethyl)pyrazole | 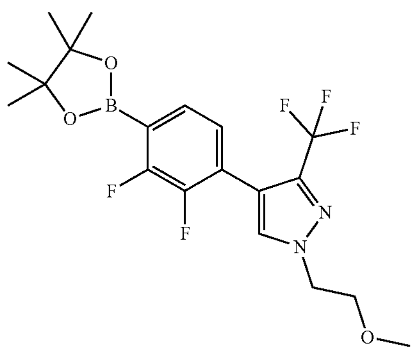 | 433.2 | Intermediate F3 and 1-bromo-2-methoxyethane |
| Intermediate G43 | 4-[2-[4-[2,3-difluoro-4-(4,4,5,5-tetramethyl-1,3,2-dioxaborolan-2-yl)phenyl]-5-(trifluoromethyl)pyrazol-1-yl]ethyl]morpholine | 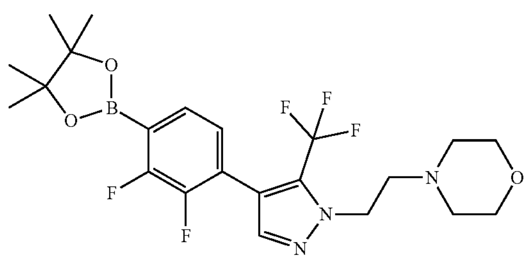 [SMILES: CC1(C)OB(c2ccc(-c3cnn(CCN4CCOCC4)c3C(F)(F)F)c(F)c2F)OC1(C)C] | 488.2 | Intermediate F3 and 4-(2-bromoethyl)morpholine |
| Intermediate G44 | 4-[2,3-difluoro-4-(4,4,5,5-tetramethyl-1,3,2-dioxaborolan-2-yl)phenyl]-1-(3-methoxypropyl)-3-(trifluoromethyl)pyrazole | 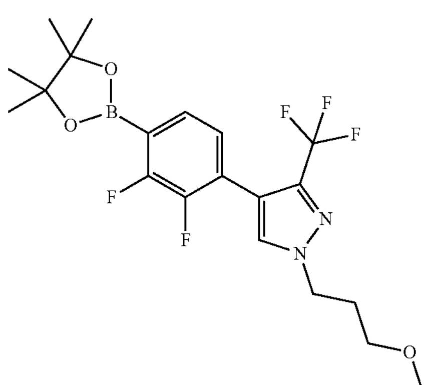 | 447.2 | Intermediate F3 and 1-bromo-3-methoxypropane |

| Ex # | Name | Structure | MS ESI [M + H]+ | Starting Material |
|---|---|---|---|---|
| Intermediate G45 | 4-[2,3-difluoro-4-(4,4,5,5-tetramethyl-1,3,2-dioxaborolan-2-yl)phenyl]-1-[[(4S)-2,2-dimethyl-1,3-dioxolan-4-yl]methyl]-3-(trifluoromethyl)pyrazole | 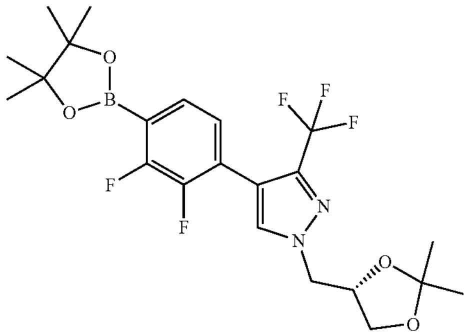 | 489.2 | Intermediate F3 and (S)-(2,2-dimethyl-1,3-dioxolan-4-yl)methyl 4-methylbenzenesulfonate |
| Intermediate G46 | 2-[[4-[2-fluoro-4-(4,4,5,5-tetramethyl-1,3,2-dioxaborolan-2-yl)phenyl]-3-(trifluoromethyl)pyrazol-1-yl]methoxy]ethyl-trimethyl-silane | 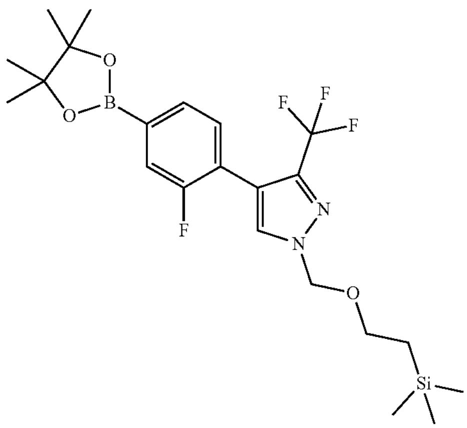 | 487.2 | Intermediate F4 and 2-(Trimethylsilyl)ethoxymethyl chloride |

Intermediate G47

1-[4-[2,3-difluoro-4-(4,4,5,5-tetramethyl-1,3,2-dioxaborolan-2-yl)phenyl]-3-(trifluoromethyl)pyrazol-1-yl]propan-2-ol

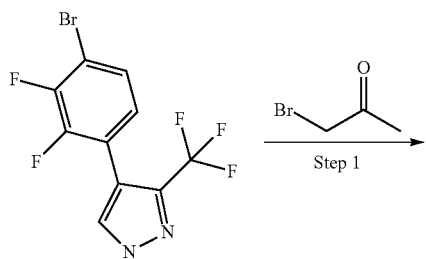

Intermediate F3

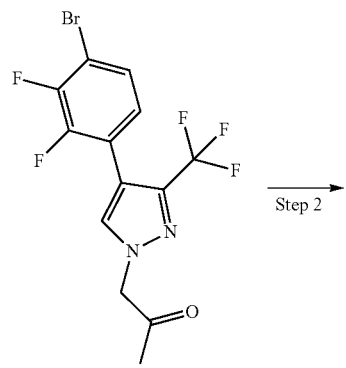

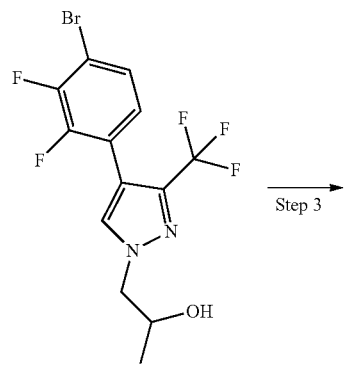

145

-continued

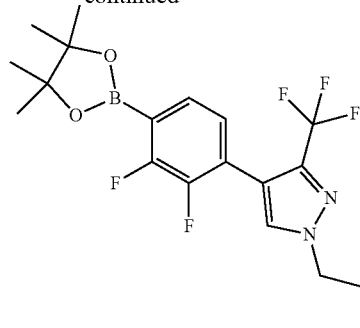

Intermediate G47

Step 1: 1-[4-(4-bromo-2,3-difluoro-phenyl)-3-(trifluoromethyl)pyrazol-1-yl]propan-2-one 4-(4-bromo-2,3-difluorophenyl)-3-(trifluoromethyl)-1H-pyrazole (110 mg, 336 μmol), 1-bromopropan-2-one (55.3 mg, 404 μmol) and potassium carbonate (139 mg, 1.01 mmol) were stirred in anhydrous acetonitrile (3.36 mL) at room temperature for 30 min. 100-200 mesh silica gel was added to absorb the material. The loaded sample was purified by flash chromatography to afford the final compound as light yellow oil (120 mg). MS [M+H]$^+$: 383.0.

Step 2: 1-[4-(4-bromo-2,3-difluoro-phenyl)-3-(trifluoromethyl)pyrazol-1-yl]propan-2-ol 1-(4-(4-bromo-2,3-difluorophenyl)-3-(trifluoromethyl)-1H-pyrazol-1-yl)propan-2-one (120 mg, 313 μmol) was dissolved in MeOH. The solution was cooled to 0° C. To this solution was added sodium tetrahydroborate (11.8 mg, 313 μmol), and the resulting mixture was stirred for 1 h at the same temperature. 100-200 mesh silica gel was added to absorb the material; the loaded sample was then purified by flash chromatography to afford the final compound as light yellow oil (110 mg). MS [M+H]$^+$: 385.0.

Step 3: 1-[4-[2,3-difluoro-4-(4,4,5,5-tetramethyl-1,3,2-dioxaborolan-2-yl)phenyl]-3-(trifluoromethyl)pyrazol-1-yl]propan-2-ol To a solution of 1-(4-(4-bromo-2,3-difluorophenyl)-3-(trifluoromethyl)-1H-pyrazol-1-yl)propan-2-ol (120 mg, 312 μmol) in dioxane (3.12 mL) was added 4,4,4',4',5,5,5',5'-octamethyl-2,2'-bi(1,3,2-dioxaborolane) (94.9 mg, 374 μmol), potassium acetate (91.7 mg, 935 μmol) and PdCl$_2$(dppf)-CH$_2$Cl$_2$ (25.5 mg, 31.2 μmol), the reaction was stirred for 18 hours at 100° C. under atmosphere of argon. The reaction mixture was cooled to room temperature and filtered. The filtrate was concentrated in vacuum and the residue was purified by column chromatography to afford the final compound as light brown oil (90 mg). MS [M+H]$^+$: 433.2.

146

Intermediate G48

1-[2-(difluoromethoxy)ethyl]-4-[2,3-difluoro-4-(4,4,5,5-tetramethyl-1,3,2-dioxaborolan-2-yl)phenyl]-3-(trifluoromethyl)pyrazole

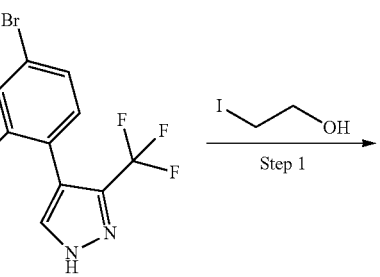

Intermediate F3

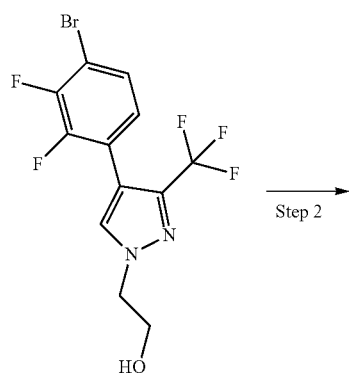

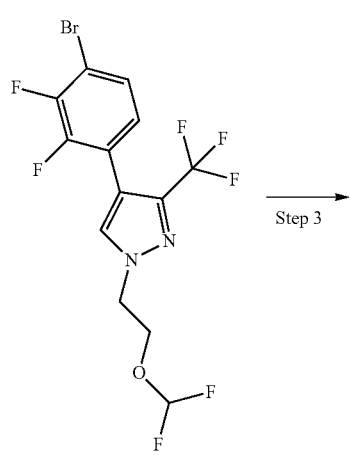

147
-continued

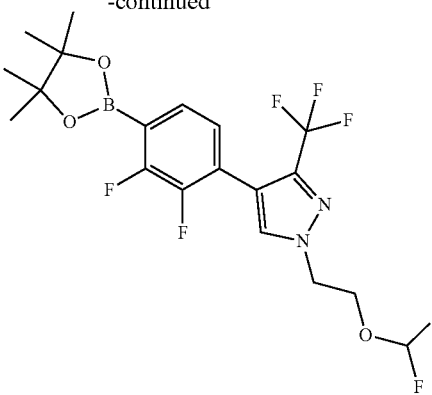

Intermediate G48

Step 1: 2-[4-(4-bromo-2,3-difluoro-phenyl)-3-(trifluoromethyl)pyrazol-1-yl]ethanol To a solution of 4-(4-bromo-2,3-difluorophenyl)-3-(trifluoromethyl)-1H-pyrazole (600 mg, 1.83 mmol) in DMF (15 mL) was added 2-iodoethan-1-ol (315 mg, 1.83 mmol) and potassium carbonate (761 mg, 5.5 mmol), the reaction was stirred for 3 hours at 90° C. The reaction mixture was cooled to room temperature and washed with brine, extracted in DCM. The organic layer was dried over anhydrous $Na_2SO_4$ and concentrated in vacuum. The residue was purified by column chromatography to give 2-[4-(4-bromo-2,3-difluoro-phenyl)-3-(trifluoromethyl)pyrazol-1-yl]ethanol (640 mg). MS $[M+H]^+$: 371.1.

Step 2: 4-(4-bromo-2,3-difluoro-phenyl)-1-[2-(difluoromethoxy)ethyl]-3-(trifluoromethyl)pyrazole To a solution of 2-(4-(4-bromo-2,3-difluorophenyl)-3-(trifluoromethyl)-1H-pyrazol-1-yl)ethan-1-ol (500 mg, 1.35 mmol) in Acetonitrile (5 mL) was added copper (I) iodide (51.3 mg, 269 μmol), the reaction was heated to 60° C., then the solution of 2,2-difluoro-2-(fluorosulfonyl)acetic acid (480 mg, 2.69 mmol) in Acetonitrile (5 mL) was addded dropwise over 5 min. The reaction was stirred for another 30 min. The reaction was cooled to room temperature and the mixture was concentrated in vacuum. The residue was purified by f column chromatgraphy to give 4-(4-bromo-2,3-difluoro-phenyl)-1-[2-(difluoromethoxy)ethyl]-3-(trifluoromethyl)pyrazole (260 mg). MS $[M+H]^+$: 421.1.

Step 3: 1-[2-(difluoromethoxy)ethyl]-4-[2,3-difluoro-4-(4,4,5,5-tetramethyl-1,3,2-dioxaborolan-2-yl)phenyl]-3-(trifluoromethyl)pyrazole To a solution of 4-(4-bromo-2,3-difluorophenyl)-1-(2-(difluoromethoxy)ethyl)-3-(trifluoromethyl)-1H-pyrazole (260 mg, 617 μmol) in Dioxane (3 mL) was added potassium acetate (121 mg, 1.23 mmol), $PdCl_2(dppf)-CH_2Cl_2$ (50.4 mg, 61.7 μmol) and bis(pinacolato)diboron (157 mg, 617 μmol), the reaction was stirred for 15 h at 80° C. under atmosphere of argon. The reaction mixture was cooled to room temperature and filtered. The filtrate was concentrated in vacuum and the residue was purified by column chromatography to give 1-[2-(difluoromethoxy)ethyl]-4-[2,3-difluoro-4-(4,4,5,5-tetramethyl-1,3,2-dioxaborolan-2-yl)phenyl]-3-(trifluoromethyl)pyrazole (205 mg). MS $[M+H]^+$: 469.1.

Intermediate G49

3-[4-[2,3-difluoro-4-(4,4,5,5-tetramethyl-1,3,2-dioxaborolan-2-yl)phenyl]-3-(trifluoromethyl)pyrazol-1-yl]-2-methyl-propan-1-ol

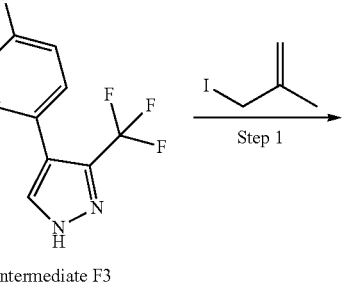

Intermediate F3

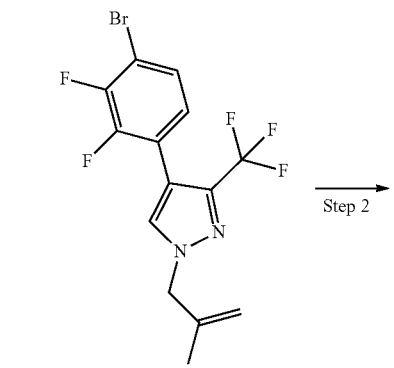

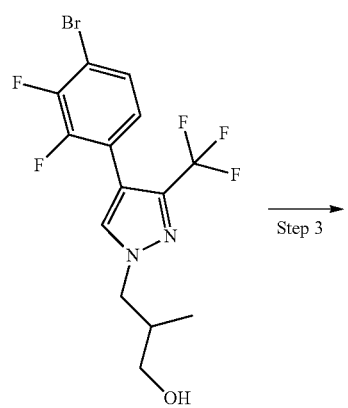

149

-continued

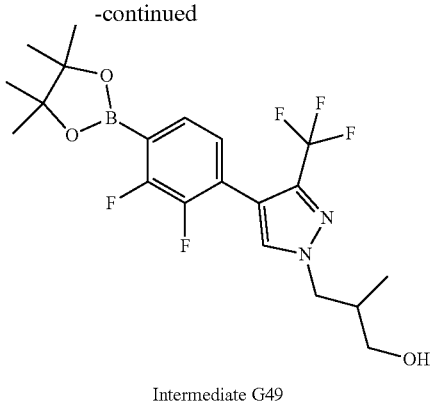

Intermediate G49

Step 1: 4-(4-bromo-2,3-difluoro-phenyl)-1-(2-methylallyl)-3-(trifluoromethyl)pyrazole To a solution of 4-(4-bromo-2,3-difluorophenyl)-3-(trifluoromethyl)-1H-pyrazole (600 mg, 1.83 mmol) in DMF (5 mL) was added 3-iodo-2-methylprop-1-ene (334 mg, 1.83 mmol) and potassium carbonate (761 mg, 5.5 mmol), the reaction was stirred for 3 h at 90° C. The reaction mixture was cooled to room temperature and washed with brine, extracted in DCM. The organic layer was dried over anhydrous $Na_2SO_4$ and concentrated in vacuum. The crude product was purified by column chromatography to give 4-(4-bromo-2,3-difluoro-phenyl)-1-(2-methylallyl)-3-(trifluoromethyl)pyrazole (400 mg). MS [M+H]$^+$: 381.1.

Step 2: 3-[4-(4-bromo-2,3-difluoro-phenyl)-3-(trifluoromethyl)pyrazol-1-yl]-2-methyl-propan-1-ol To a solution of 4-(4-bromo-2,3-difluorophenyl)-1-(2-methylallyl)-3-(trifluoromethyl)-1H-pyrazole (400 mg, 1.05 mmol) in THF (5 mL) was added Borane tetrahydrofuran complex solution (2.1 mL, 2.1 mmol) drop wise at room temperature under atmosphere of nitrogen. The reaction was stirred for 4 h, then water (0.5 mL) was added dropwise, followed by sodium hydroxide (2.1 mL, 3 mol/L) and hydrogen peroxide (2.1 mL, 30%). The reaction was stirred for another 4 h. The reaction mixture was concentrated in vacuum and the residue was purified by column chromatography to give 3-[4-(4-bromo-2,3-difluoro-phenyl)-3-(trifluoromethyl)pyrazol-1-yl]-2-methyl-propan-1-ol (320 mg). MS [M+H]$^+$: 399.1.

Step 3: 3-[4-[2,3-difluoro-4-(4,4,5,5-tetramethyl-1,3,2-dioxaborolan-2-yl)phenyl]-3-(trifluoromethyl)pyrazol-1-yl]-2-methyl-propan-1-ol To a solution of 3-(4-(4-bromo-2,3-difluorophenyl)-3-(trifluoromethyl)-1H-pyrazol-1-yl)-2-methylpropan-1-ol (400 mg, 1 mmol) in dioxane (5 mL) was added potassium acetate (197 mg, 2 mmol), $PdCl_2(dppf)$-$CH_2Cl_2$ (81.8 mg, 100 µmol) and bis(pinacolato)diboron (254 mg, 1 mmol), the reaction was stirred for 15 h at 80° C. under atmosphere of argon. The reaction mixture was cooled to room temperature and filtered. The filtrate was concentrated in vacuum and the residue was purified by column chromatography to give 3-[4-[2,3-difluoro-4-(4,4,5,5-tetramethyl-1,3,2-dioxaborolan-2-yl)phenyl]-3-(trifluoromethyl)pyrazol-1-yl]-2-methyl-propan-1-ol (260 mg). MS [M+H]$^+$: 447.1.

150

Intermediate G50

[4-[3-ethyl-1-(2-methoxyethyl)pyrazol-4-yl]-2,3-difluoro-phenyl]boronic acid

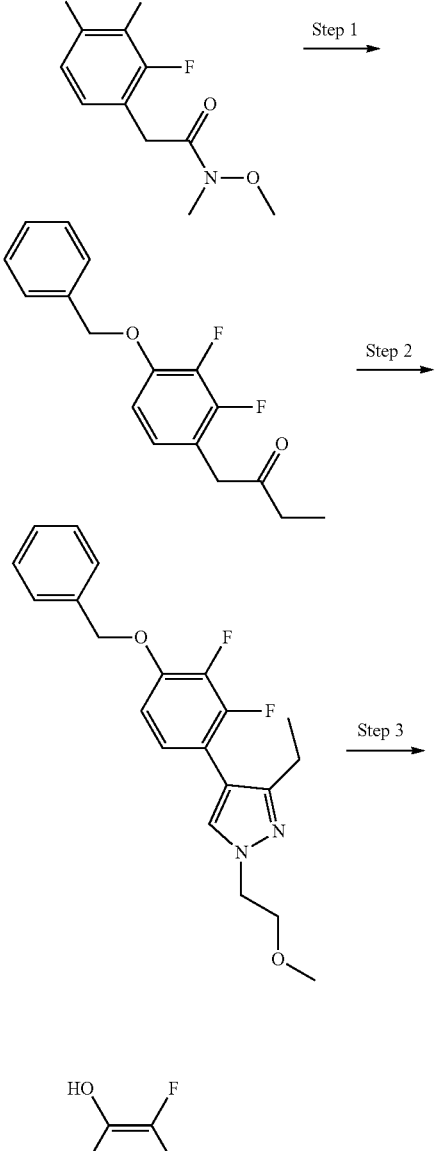

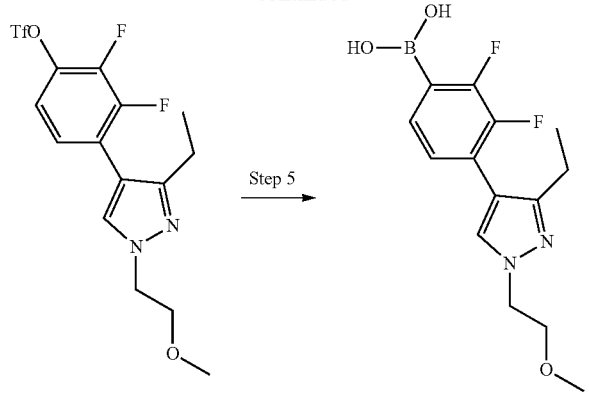

Intermediate G50

Step 1: 1-(4-benzyloxy-2,3-difluoro-phenyl)butan-2-one

To a solution of 2-(4-benzyloxy-2,3-difluoro-phenyl)-N-methoxy-N-methyl-acetamide (6.7 g, 20.85 mmol) in THF (50.0 mL) was added ethylmagnesium bromide in Et$_2$O (3M) (10.43 mL, 31.28 mmol) slowly at −40° C. under N$_2$. This reaction mixture was stirred at −10° C. for 2 h. This reaction was quenched by NH$_4$Cl (50.0 mL) and was extracted by EtOAc (50.0 mL×2). The combined organic layers were dried over Na$_2$SO$_4$ and concentrated to get the crude product. This crude product was purified by silica gel chromatography (PE:EtOAc=8:1) to get 1-(4-benzyloxy-2,3-difluoro-phenyl)butan-2-one (1.4 g) as yellow solid.

Step 2: 4-(4-benzyloxy-2,3-difluoro-phenyl)-3-ethyl-1-(2-methoxyethyl)pyrazole To a mixture of 1-(4-benzyloxy-2,3-difluoro-phenyl)butan-2-one (700.0 mg, 2.41 mmol) and molecular sieves 4 A (500.0 mg) in toluene (8.0 mL) was added 2-methoxyethylhydrazine (521.53 mg, 5.79 mmol) in one portion. The reaction mixture was stirred at 100° C. for 3 h. The mixture was filtered and concentrated under reduced pressure affording the residue. The mixture of residue and N,N-dimethylformamide dimethyl acetal (7.07 mL, 86.81 mmol) was stirred at 100° C. for 16 h. This reaction was quenched by H$_2$O (10.0 mL) and was extracted by EtOAc (10.0 mL×3). The combined organic layers were dried over Na$_2$SO$_4$ and concentrated to get the crude product. The crude product was purified by silica gel chromatography (PE:EtOAc=5:1) to get 4-(4-benzyloxy-2,3-difluoro-phenyl)-3-ethyl-1-(2-methoxyethyl)pyrazole (630.0 mg) as yellow oil. MS [M+H]$^+$: 373.2.

Step 3: 4-[3-ethyl-1-(2-methoxyethyl)pyrazol-4-yl]-2,3-difluoro-phenol

To a solution of 4-(4-benzyloxy-2,3-difluoro-phenyl)-3-ethyl-1-(2-methoxyethyl)pyrazole (630.0 mg, 1.69 mmol) in methanol (6 mL) was added palladium on carbon (180.03 mg) in one portion under N$_2$. This mixture was degassed and purged with N$_2$ for 3 times. Then H$_2$ (15 psi) was introduced into this system. The reaction mixture was stirred at 20° C. for 16 h under H$_2$ atmosphere. The mixture was filtered and concentrated under reduced pressure affording the crude product 4-[3-ethyl-1-(2-methoxyethyl)pyrazol-4-yl]-2,3-difluoro-phenol (470.0 mg) as a black oil. MS [M+H]$^+$: 283.2.

Step 4: [4-[3-ethyl-1-(2-methoxyethyl)pyrazol-4-yl]-2,3-difluoro-phenyl]trifluoromethanesulfonate A mixture of 4-[3-ethyl-1-(2-methoxyethyl)pyrazol-4-yl]-2,3-difluoro-phenol (220.0 mg, 0.78 mmol) and pyridine (0.09 mL, 1.17 mmol) in DCM (5 mL) was degassed and purged with N$_2$ for 3 times. Then trifluoromethanesulfonic anhydride (0.15 mL, 0.94 mmol) was added dropwise into the mixture at 0° C. The reaction mixture was stirred at 20° C. for 2 h under N$_2$ atmosphere. This reaction was quenched by NaHCO$_3$ (10 mL) and was extracted by DCM (10 mL×3). The combined organic layers were dried over Na$_2$SO$_4$ and concentrated to get the crude product [4-[3-ethyl-1-(2-methoxyethyl)pyrazol-4-yl]-2,3-difluoro-phenyl] trifluoromethanesulfonate (390.0 mg) as red oil. MS [M+H]$^+$: 415.1.

Step 5: [4-[3-ethyl-1-(2-methoxyethyl)pyrazol-4-yl]-2,3-difluoro-phenyl]boronic acid A mixture of bis(pinacolato)diboron (478.03 mg, 1.88 mmol), [4-[3-ethyl-1-(2-methoxyethyl)pyrazol-4-yl]-2,3-difluoro-phenyl] trifluoromethanesulfonate (390.0 mg, 0.94 mmol), potassium acetate (0.15 mL, 2.35 mmol) and X-PHOS (44.87 mg, 0.09 mmol) in 1,4-dioxane (5 mL) was degassed and purged with N$_2$ for 3 times. Then tris(dibenzylideneacetone)dipalladium (0) (43.1 mg, 0.05 mmol) was added into the mixture. The reaction mixture was stirred at 100° C. for 2 h under N$_2$ atmosphere. This reaction was extracted by EtOAc (10 mL×3). The combined organic layers were dried over Na$_2$SO$_4$ and concentrated to get the crude product. The crude product was purified by preparative HPLC (TFA) to get [4-[3-ethyl-1-(2-methoxyethyl)pyrazol-4-yl]-2,3-difluoro-phenyl]boronic acid (150.0 mg, 0.480 mmol, 49.46% yield) as brown oil. MS [M+H]$^+$: 311.2.

Intermediate G51

[4-[3-ethyl-1-(2-methoxyethyl)pyrazol-4-yl]-2,3-difluoro-phenyl]boronic acid

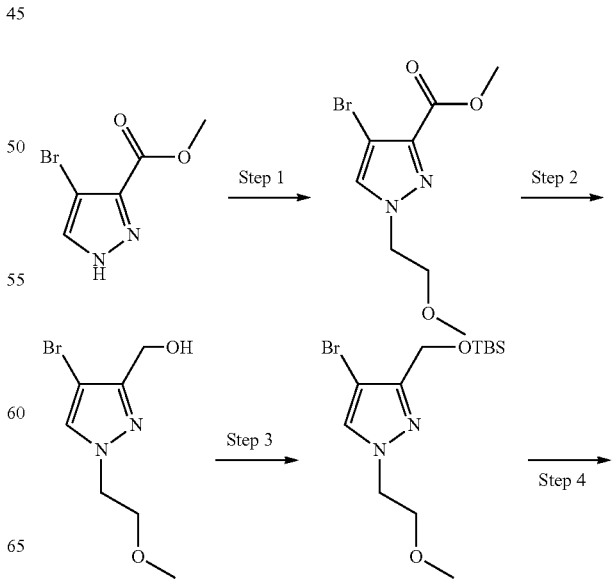

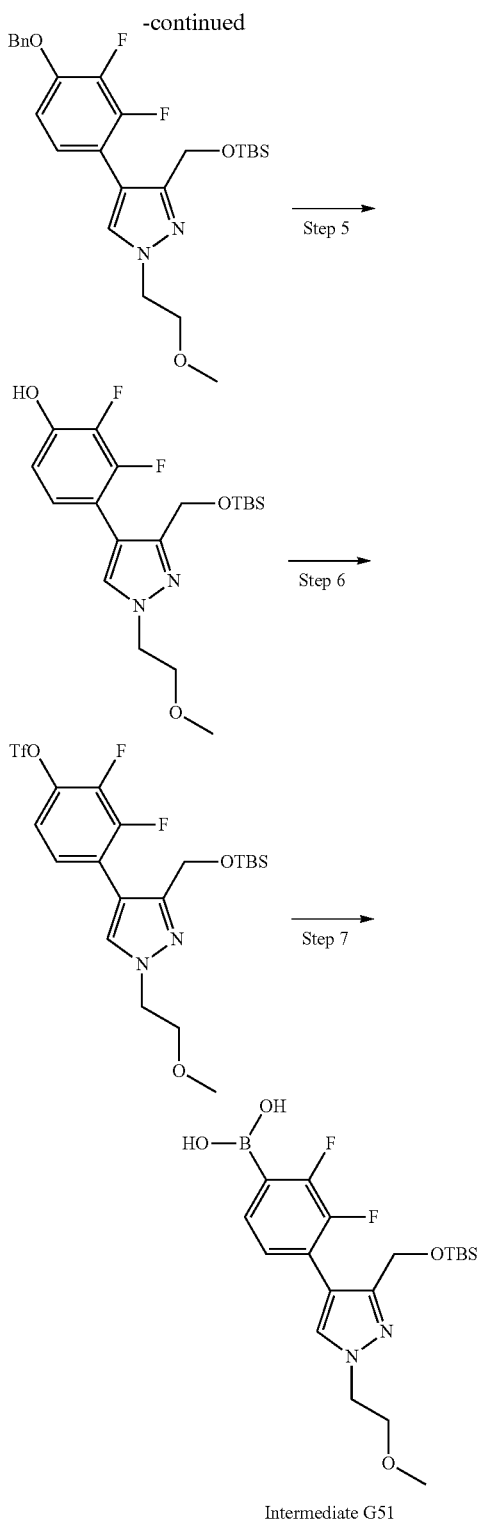

Intermediate G51

Step 1: methyl 4-bromo-1-(2-methoxyethyl)pyrazole-3-carboxylate

A mixture of methyl 4-bromo-1H-pyrazole-3-carboxylate (2.5 g, 12.19 mmol) and potassium carbonate (2.53 g, 18.29 mmol) in ACN (10 mL) was degassed and purged with $N_2$ for 3 times. Then 1-bromo-2-methoxy-ethane (3.44 mL, 36.58 mmol) was added into the mixture. The reaction mixture was stirred at 80° C. for 2 h under $N_2$ atmosphere. The mixture was filtered and concentrated under reduced pressure affording the crude product. The crude product (5 batches) was purified by Prep-HPLC to get methyl 4-bromo-1-(2-methoxyethyl)pyrazole-3-carboxylate (8.0 g). MS $[M+H]^+$: 263.0.

Step 2: [4-bromo-1-(2-methoxyethyl)pyrazol-3-yl]methanol

To a solution of methyl 4-bromo-1-(2-methoxyethyl)pyrazole-3-carboxylate (2.0 g, 7.6 mmol) in THF (20.0 mL) was added lithium borohydride (5.7 mL, 11.4 mmol) slowly at −40° C. under $N_2$. This reaction mixture was stirred at 20° C. for 16 h. This reaction was quenched by HCl (1 M, 20 mL) and was extracted by EtOAc (20 mL×3). The combined organic layers were dried over $Na_2SO_4$ and concentrated to get the crude product [4-bromo-1-(2-methoxyethyl)pyrazol-3-yl]methanol (1.6 g). MS $[M+H]^+$: 235.0.

Step 3: [4-bromo-1-(2-methoxyethyl)pyrazol-3-yl]methoxy-tert-butyl-dimethyl-silane To a solution of [4-bromo-1-(2-methoxyethyl)pyrazol-3-yl]methanol (1.2 g, 5.1 mmol) in DMF (10.0 mL) was added imidazole (0.48 mL, 7.15 mmol) and tert-butyldimethyl-chlorosilane (1.08 g, 7.15 mmol) in one portion. This reaction mixture was stirred at 20° C. for 16 h. This reaction was quenched by brine (10 mL) and was extracted by EtOAc (20 mL×3). The combined organic layers were dried over $Na_2SO_4$ and concentrated to get the crude product. The crude product was purified by silica gel chromatography (PE:EtOAc=5:1) to get [4-bromo-1-(2-methoxyethyl)pyrazol-3-yl]methoxy-tert-butyl-dimethyl-silane (1.36 g). MS $[M+H]^+$: 349.1.

Step 4: [4-(4-benzyloxy-2,3-difluoro-phenyl)-1-(2-methoxyethyl)pyrazol-3-yl]methoxy-tert-butyl-dimethyl-silane A mixture of 2,3-difluoro-4-(4,4,5,5-tetramethyl-1,3,2-dioxaborolan-2-yl)phenol (1.31 g, 3.78 mmol), [4-bromo-1-(2-methoxyethyl)pyrazol-3-yl]methoxy-tert-butyl-dimethyl-silane (1.36 g, 3.78 mmol) and potassium carbonate (1.04 g, 7.55 mmol) in 1,4-dioxane (10 mL) and water (1 mL) was degassed and purged with $N_2$ for 3 times. Then [1,1'-bis(diphenylphosphino)ferrocene]dichloropalladium (II) (276.36 mg, 0.38 mmol) was added into the mixture. The reaction mixture was stirred at 100° C. for 16 h under $N_2$ atmosphere. The mixture was filtered and concentrated under reduced pressure affording the crude product. The crude product was purified by silica gel chromatography (PE:EtOAc=5:1) to get [4-(4-benzyloxy-2,3-difluoro-phenyl)-1-(2-methoxyethyl)pyrazol-3-yl]methoxy-tert-butyl-dimethyl-silane (1.17 g). MS $[M+H]^+$: 489.2.

Step 5: 4-[3-[[tert-butyl(dimethyl)silyl]oxymethyl]-1-(2-methoxyethyl)pyrazol-4-yl]-2,3-difluoro-phenol To a solution of [4-(4-benzyloxy-2,3-difluoro-phenyl)-1-(2-methoxyethyl)pyrazol-3-yl]methoxy-tert-butyl-dimethyl-silane (1.0 g, 2.05 mmol) in methanol (10 mL) was added palladium on carbon (217.79 mg) in one portion under $N_2$. This mixture was degassed and purged with $N_2$ for 3 times. Then $H_2$ (15 psi) was introduced into this system. The reaction mixture was stirred at 20° C. for 2 h under $H_2$ atmosphere. The mixture was filtered and concentrated under reduced pressure affording the crude product. The crude product was purified by silica gel chromatography (PE:EtOAc=2:1) to get 4-[3-[[tert-butyl(dimethyl)silyl] oxymethyl]-1-(2-methoxyethyl)pyrazol-4-yl]-2,3-difluoro-phenol (480.0 mg). MS [M+H]⁺: 399.2.

Step 6: [4-[3-[[tert-butyl(dimethyl)silyl]oxymethyl]-1-(2-methoxyethyl)pyrazol-4-yl]-2,3-difluoro-phenyl] trifluoromethanesulfonate A mixture of 4-[3-[[tert-butyl(dimethyl)silyl]oxymethyl]-1-(2-methoxyethyl)pyrazol-4-yl]-2,3-difluoro-phenol (250.0 mg, 0.63 mmol) and pyridine (0.08 mL, 0.94 mmol) in DCM (5 mL) was degassed and purged with N₂ for 3 times. Then trifluoromethanesulfonic anhydride (0.12 mL, 0.75 mmol) was added dropwise into the mixture at 0° C. The reaction mixture was stirred at 20° C. for 2 h under N₂ atmosphere. This reaction was quenched by NaHCO₃ (10 mL) and was extracted by DCM (10 mL×3). The combined organic layers were dried over Na₂SO₄ and concentrated to get the crude product [4-[3-[[tert-butyl(dimethyl)silyl] oxymethyl]-1-(2-methoxyethyl)pyrazol-4-yl]-2,3-difluoro-phenyl] trifluoromethanesulfonate (370.0 mg). MS [M+H]⁺: 531.2.

Step 7: [4-[3-[[tert-butyl(dimethyl)silyl]oxymethyl]-1-(2-methoxyethyl)pyrazol-4-yl]-2,3-difluoro-phenyl]boronic acid A mixture of [4-[3-[[tert-butyl(dimethyl)silyl]oxymethyl]-1-(2-methoxyethyl)pyrazol-4-yl]-2,3-difluoro-phenyl] trifluoromethanesulfonate (330.0 mg, 0.62 mmol), bis(pinacolato) diboron (315.88 mg, 1.24 mmol), potassium acetate (0.1 mL, 1.55 mmol) and X-PHOS (29.65 mg, 0.06 mmol) in 1,4-dioxane (8 mL) was degassed and purged with N₂ for 3 times. Then tris(dibenzylideneacetone)dipalladium (0) (28.48 mg, 0.03 mmol) was added into the mixture. The reaction mixture was stirred at 100° C. for 3 h under N₂ atmosphere. This reaction was extracted by EtOAc (10 mL×3). The combined organic layers were dried over Na₂SO₄ and concentrated to get the crude product. The crude product was purified by preparative HPLC (TFA) to get [4-[3-[[tert-butyl(dimethyl)silyl]oxymethyl]-1-(2-methoxyethyl)pyrazol-4-yl]-2,3-difluoro-phenyl]boronic acid (210.0 mg). MS [M+H]⁺: 427.3.

Intermediate G52

[2,3-difluoro-4-[1-(2-methoxyethyl)-3-(methylamino)pyrazol-4-yl]phenyl]boronic acid

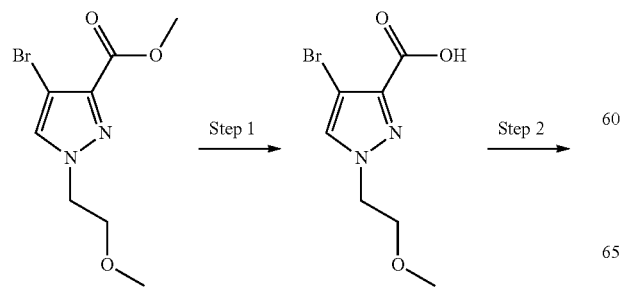

-continued

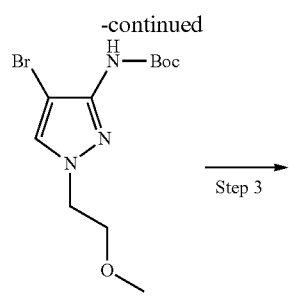

Step 3

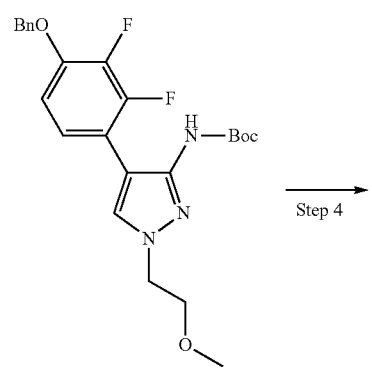

Step 4

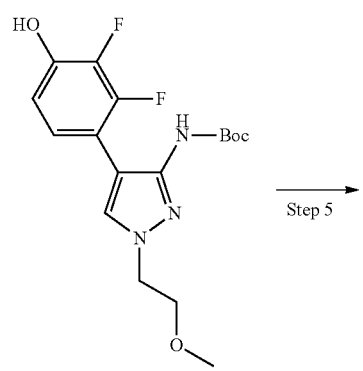

Step 5

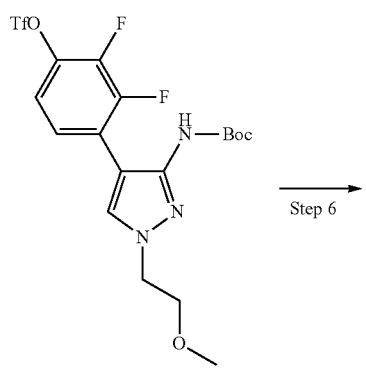

Step 6

-continued

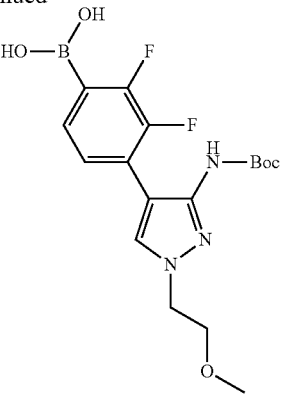

Intermediate G52

Step 1:
4-bromo-1-(2-methoxyethyl)pyrazole-3-carboxylic acid

To a solution of methyl 4-bromo-1-(2-methoxyethyl)pyrazole-3-carboxylate (1.0 g, 3.8 mmol) in THF (10.0 mL), methanol (10.0 mL) and water (2.5 mL) was added lithium hydroxide monohydrate (638.0 mg, 15.2 mmol) in one portion. This reaction mixture was stirred at 25° C. for 4 h. HCl (1 M) was added into this mixture to make pH<3. This mixture was extracted by EtOAc (30 mL×3). The combined organic layers were dried over Na$_2$SO$_4$ and concentrated to get 4-bromo-1-(2-methoxyethyl)pyrazole-3-carboxylic acid (900.0 mg), The crude product would be used in the next step directly without further purification. MS [M+H]$^+$: 249.0.

Step 2: tert-butyl N-[4-bromo-1-(2-methoxyethyl)pyrazol-3-yl]carbamate

To a solution of 4-bromo-1-(2-methoxyethyl)pyrazole-3-carboxylic acid (900.0 mg, 3.61 mmol) and triethylamine (1.01 mL, 7.23 mmol) in tert-butanol (20 mL) was added diphenylphosphonic azide (1.56 mL, 7.23 mmol) in one portion. This reaction mixture was stirred at 80° C. for 4 h. This reaction mixture was concentrated to get the residue. The residue was diluted with EtOAc (30 mL) and washed by saturated aqueous Na$_2$CO$_3$ (5 mL×2). The organic layer was dried over Na$_2$SO$_4$ and concentrated to get the crude product. This crude product was purified by silica gel chromatography (PE:EtOAc=1:1-1:2) to get tert-butyl N-[4-bromo-1-(2-methoxyethyl)pyrazol-3-yl]carbamate (1.0 g). MS [M+H]$^+$: 320.0.

Step 3: tert-butyl N-[4-(4-benzyloxy-2,3-difluoro-phenyl)-1-(2-methoxyethyl)pyrazol-3-yl]carbamate To a solution of tert-butyl N-[4-bromo-1-(2-methoxyethyl)pyrazol-3-yl]carbamate (1.0 g, 3.12 mmol), 2,3-difluoro-4-(4,4,5,5-tetramethyl-1,3,2-dioxaborolan-2-yl)phenol (1.08 g, 3.12 mmol) and potassium carbonate (0.86 g, 6.25 mmol) in 1,4-dioxane (20 mL) and water (2 mL) was added [1,1'-bis(diphenylphosphino)ferrocene]dichloropalladium(II) (228.53 mg, 0.31 mmol) in one portion under N$_2$. This reaction mixture was stirred at 100° C. for 16 h. This reaction mixture was filtered, and the filtrate was concentrated to get the residue. This residue was diluted with EtOAc (50 mL) and was washed by brine (10 mL×2). The organic layer was dried over Na$_2$SO$_4$ and concentrated to get the crude product. This crude product was purified by silica gel chromatography (PE:EtOAc=5:1-1:1) to get tert-butyl N-[4-(4-benzyloxy-2,3-difluoro-phenyl)-1-(2-methoxyethyl)pyrazol-3-yl]carbamate (1.1 g). MS [M+H]$^+$: 460.1.

Step 4: tert-butyl N-[4-(2,3-difluoro-4-hydroxy-phenyl)-1-(2-methoxyethyl)pyrazol-3-yl]carbamate To a solution of tert-butyl N-[4-(4-benzyloxy-2,3-difluoro-phenyl)-1-(2-methoxyethyl)pyrazol-3-yl]carbamate (800.0 mg, 1.74 mmol) in methanol (10 mL) was added palladium on carbon (185.28 mg) in one portion under N$_2$. Then H$_2$ (15 psi) was introduced into this system. The reaction mixture was stirred at 25° C. for 16 h. This reaction mixture was filtered, and the filtrate was concentrated to get tert-butyl N-[4-(2,3-difluoro-4-hydroxy-phenyl)-1-(2-methoxyethyl)pyrazol-3-yl]carbamate (600.0 mg), the crude product would be used in the next step directly without further purification. MS [M+H]$^+$: 370.0.

Step 5: [4-[3-(tert-butoxycarbonylamino)-1-(2-methoxyethyl)pyrazol-4-yl]-2,3-difluoro-phenyl] trifluoromethanesulfonate To a solution of tert-butyl N-[4-(2,3-difluoro-4-hydroxy-phenyl)-1-(2-methoxyethyl)pyrazol-3-yl]carbamate (600.0 mg, 1.62 mmol) and pyridine (0.2 mL, 2.44 mmol) in DCM (10 mL) was added trifluoromethanesulfonic anhydride (0.32 mL, 1.95 mmol) in one portion at 0° C. Then this reaction mixture was warmed to 25° C. and stirred for 1 h. This reaction was quenched by saturated aqueous NaHCO$_3$ (10 mL) and extracted by DCM (10 mL×2). The combined organic layers were dried over Na$_2$SO$_4$ and concentrated to get [4-[3-(tert-butoxycarbonylamino)-1-(2-methoxyethyl)pyrazol-4-yl]-2,3-difluoro-phenyl] trifluoromethanesulfonate (800.0 mg), MS [M+H]$^+$: 502.0.

Step 6: [4-[3-(tert-butoxycarbonylamino)-1-(2-methoxyethyl)pyrazol-4-yl]-2,3-difluoro-phenyl] boronic acid To a solution of bis(pinacolato)diboron (607.73 mg, 2.39 mmol), [4-[3-(tert-butoxycarbonylamino)-1-(2-methoxyethyl)pyrazol-4-yl]-2,3-difluoro-phenyl]trifluoromethanesulfonate (800.0 mg, 1.6 mmol) and potassium acetate (313.17 mg, 3.19 mmol) in 1,4-dioxane (10.0 mL) was added tris(dibenzylideneacetone)dipalladium (0) (146.1 mg, 0.16 mmol) and X-PHOS (76.06 mg, 0.16 mmol) in one portion under N$_2$. This reaction mixture was stirred at 100° C. for 2 h. This reaction mixture was filtered, and the filtrate was concentrated to get the crude product. This crude product was purified by Prep-HPLC (TFA) to get [4-[3-(tert-butoxycarbonylamino)-1-(2-methoxyethyl)pyrazol-4-yl]-2,3-difluoro-phenyl]boronic acid (190.0 mg). MS [M+H]$^+$: 342.1.

Intermediate G53

2-[[4-[2,3-difluoro-4-(4,4,5,5-tetramethyl-1,3,2-dioxaborolan-2-yl)phenyl]-3-phenyl-pyrazol-1-yl]methoxy]ethyl-trimethyl-silane

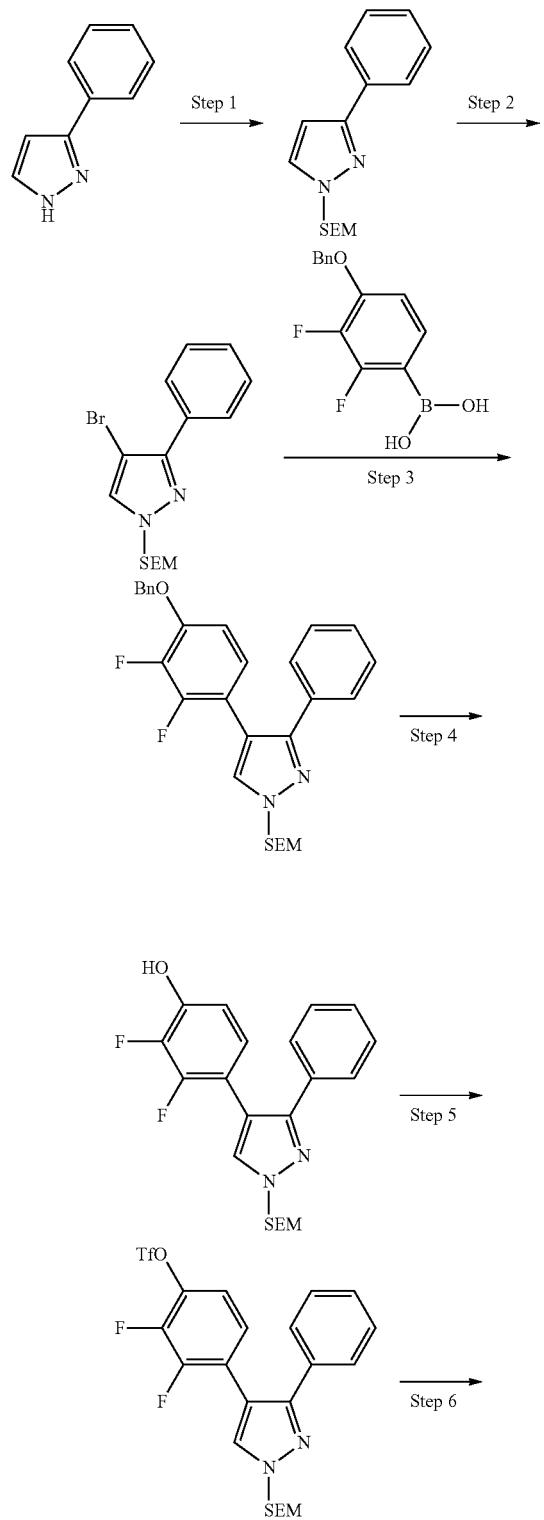

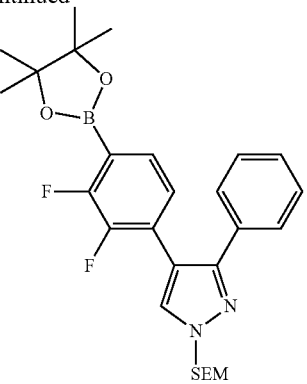

Intermediate G53

Step 1: 3-phenyl-1-((2-(trimethylsilyl)ethoxy)methyl)-1H-pyrazole

To a solution of 3-phenyl-1H-pyrazole (1.0 g, 6.94 mmol) in DMF (20 mL) was added sodium hydride (416.2 mg, 10.4 mmol) at 0° C. The mixture was stirred at 0° C. for 1 h. Then 2-(trimethylsilyl)ethoxymethyl chloride (1.6 mL, 9.02 mmol) was added and the mixture was stirred at 0° C. for 12 h. The reaction mixture was poured into water (100 mL) and extracted with EtOAc (100 mL×3), and the organics washed with water (50 mL×2) then saturated brine solution (50 mL×1). The organics were then separated and dried (MgSO$_4$) before concentration to dryness. The crude was then purified by flash column and dried by lyophilization to give trimethyl-[2-[(3-phenylpyrazol-1-yl)methoxy]ethyl]silane (1.85 g). MS [M+H]$^+$: 275.4.

Step 2: 4-bromo-3-phenyl-1-((2-(trimethylsilyl)ethoxy)methyl)-1H-pyrazole

To a solution of trimethyl-[2-[(3-phenylpyrazol-1-yl)methoxy]ethyl]silane (500.0 mg, 1.82 mmol) in DMF (10 mL) was added N-bromosuccinimide (0.45 mL, 2.37 mmol) at 20° C. The mixture was stirred at 20° C. for 1 h. The reaction was taken up in EtOAc (50 mL) and the organics washed with water (50 mL×2) then saturated brine solution (50 mL×1). The organics were then separated and dried (MgSO$_4$) before concentration to dryness to give 2-[(4-bromo-3-phenyl-pyrazol-1-yl)methoxy]ethyl-trimethyl-silane (300 mg). MS [M+H]$^+$: 353.1.

Step 3: 4-(4-(benzyloxy)-2,3-difluorophenyl)-3-phenyl-1-((2-(trimethylsilyl)ethoxy)methyl)-1H-pyrazole To a solution of 2-[(4-bromo-3-phenyl-pyrazol-1-yl)methoxy]ethyl-trimethyl-silane (1.0 g, 2.83 mmol) and 2-(4-benzyloxy-2,3-difluoro-phenyl)-4,4,5,5-tetramethyl-1,3,2-dioxaborolane (1.1 g, 3.11 mmol) in 1,4-dioxane (20 mL) and water (2 mL) was added potassium carbonate (782.3 mg, 5.66 mmol) and Pd(dppf)Cl$_2$ (206.9 mg, 0.28 mmol) under argon in glove box. The mixture was stirred at 90° C. for 2 h. The reaction mixture was filtered and the filtrate was concentrated in vacuum to give a residue, which was purified by flash column and dried by lyophilization to give 2-[[4-(4-benzyloxy-2,3-difluoro-phenyl)-3-phenyl-pyrazol-1-yl]methoxy]ethyl-trimethyl-silane (1 g). MS [M+H]$^+$: 493.2.

Step 4: 4-(4-(benzyloxy)-2,3-difluorophenyl)-3-phenyl-1-((2-(trimethylsilyl)ethoxy)methyl)-1H-pyrazole To a solution of 2-[[4-(4-benzyloxy-2,3-difluoro-phenyl)-3-phenyl-pyrazol-1-yl]methoxy]ethyl-trimethyl-silane (1.0 g, 2.03 mmol) in methanol (20.0 mL) was added Pd/C (1.0 g) under nitrogen. Then the mixture was stirred under hydrogen at 20° C. for 2 h. The reaction mixture was filtered and the filtrate was concentrated in vacuum to give 2,3-difluoro-4-[3-phenyl-1-(2-trimethylsilylethoxymethyl)pyrazol-4-yl]phenol (800.0 mg). MS [M+H]+: 403.1.

Step 5: 2,3-difluoro-4-(3-phenyl-1-((2-(trimethylsilyl)ethoxy)methyl)-1H-pyrazol-4-yl)phenyl trifluoromethanesulfonate To a solution of 2,3-difluoro-4-[3-phenyl-1-(2-trimethylsilylethoxymethyl)pyrazol-4-yl]phenol (350.0 mg, 0.87 mmol) in pyridine (10.0 mL) was added trifluoromethanesulfonic anhydride (490.7 mg, 1.74 mmol) at 0° C. The mixture was stirred at 0° C. for 1 h. The reaction was taken up in EtOAc (50 mL) and the organics washed with water (50 mL×2) then saturated brine solution (50 mL×1). The organics were then separated and dried (MgSO4) before concentration to dryness to give [2,3-difluoro-4-[3-phenyl-1-(2-trimethylsilylethoxymethyl)pyrazol-4-yl]phenyl] trifluoromethanesulfonate (400 mg). MS [M+H]+: 535.1.

Step 6: 4-(2,3-difluoro-4-(4,4,5,5-tetramethyl-1,3,2-dioxaborolan-2-yl)phenyl)-3-phenyl-1-((2-(trimethylsilyl)ethoxy)methyl)-1H-pyrazole To a solution of [2,3-difluoro-4-[3-phenyl-1-(2-trimethylsilylethoxymethyl)pyrazol-4-yl]phenyl]trifluoromethanesulfonate (400.0 mg, 0.75 mmol) and bis(pinacolato)diboron (228.0 mg, 0.90 mmol) in 1,4-dioxane (10 mL) was added Pd(dppf)Cl2 (54.7 mg, 0.07 mmol) and potassium acetate (110.1 mg, 1.12 mmol) under argon in glove box. The mixture was stirred at 100° C. for 1 h. The reaction mixture was filtered and the filtrate was concentrated in vacuum to give a residue, which was purified by flash column and dried by lyophilization to give 2-[[4-[2,3-difluoro-4-(4,4,5,5-tetramethyl-1,3,2-dioxaborolan-2-yl)phenyl]-3-phenyl-pyrazol-1-yl]methoxy]ethyl-trimethyl-silane (250.0 mg, 0.49 mmol, 65.2% yield) as a yellow solid. MS [M+H]+: 513.2.

Intermediate G54

3-[2,3-difluoro-4-(4,4,5,5-tetramethyl-1,3,2-dioxaborolan-2-yl)phenyl]-5,6-dihydro-4H-pyrrolo[1,2-b]pyrazole

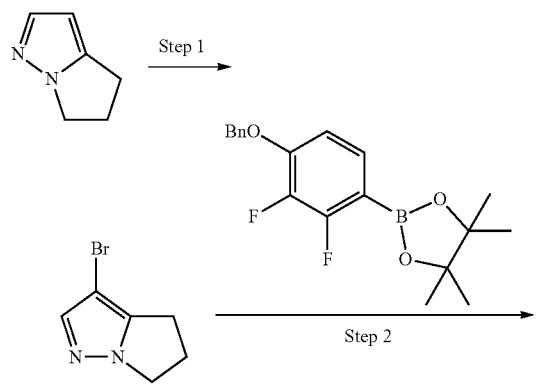

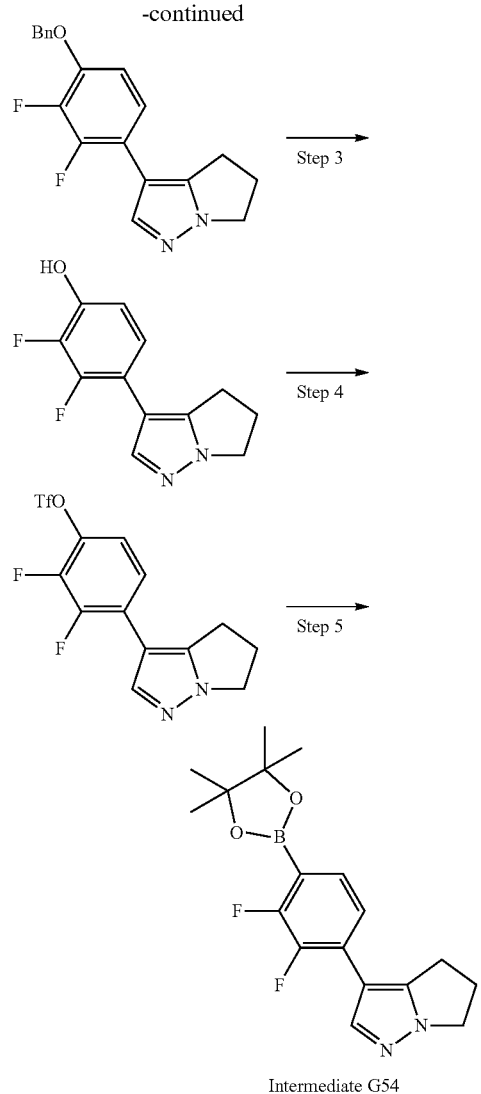

Intermediate G54

Step 1: 3-bromo-5,6-dihydro-4H-pyrrolo[1,2-b]pyrazole

To a solution of 5,6-dihydro-4H-pyrrolo[1,2-b]pyrazole (500.0 mg, 4.62 mmol) in DCM (5.0 mL) was added N-bromosuccinimide (905.2 mg, 5.09 mmol). The mixture was stirred at 20° C. for 12 h under N2. The reaction mixture was quenched by water (10 mL), extracted with DCM (20 mL×3). The combined organic layers were washed brine (20 mL), dried (Na2SO4) and concentrated to give crude product 3-bromo-5,6-dihydro-4H-pyrrolo[1,2-b]pyrazole (850.0 mg). MS [M+H]+: 187.0.

Step 2: 3-(4-benzyloxy-2,3-difluoro-phenyl)-5,6-dihydro-4H-pyrrolo[1,2-b]pyrazole A mixture of cpd 3-bromo-5,6-dihydro-4H-pyrrolo[1,2-b]pyrazole (0.8 g, 4.28 mmol), 2-(4-benzyloxy-2,3-difluoro-phenyl)-4,4,5,5-tetramethyl-1,3,2-dioxaborolane (1.6 g, 4.70 mmol), K2CO3 (1.2 g, 8.55 mmol) and 1,1'-bis(diphenylphosphino)ferrocene-palladium(II)dichloride dichloromethane complex (349.0 mg, 0.43 mmol) in a flask. The flask was degassed and purged with N2 gas for four times.

1,4-dioxane (5 mL) and water (1 mL) was added by injector to the mixture. The mixture was stirred at 90° C. for 2 h under $N_2$. The reaction mixture was filtered and the filtrate was concentrated under reduced pressure to remove the solvent, and the crude was purified by chromatography column flash and concentrated to give 3-(4-benzyloxy-2,3-difluoro-phenyl)-5,6-dihydro-4H-pyrrolo[1,2-b]pyrazole (900.0 mg). MS [M+H]$^+$: 327.1.

Step 3: 4-(5,6-dihydro-4H-pyrrolo[1,2-b]pyrazol-3-yl)-2,3-difluoro-phenol

To a solution of 3-(4-benzyloxy-2,3-difluoro-phenyl)-5,6-dihydro-4H-pyrrolo[1,2-b]pyrazole (900.0 mg, 2.76 mmol) in THF (20 mL) was added Pd/C (500.0 mg, 2.76 mmol) under $N_2$. The suspension was degassed under vacuum and purged with $H_2$ several times at 20° C. for 2 h. The reaction mixture was filtered and the filtrate was concentrated under reduced pressure to give 4-(5,6-dihydro-4H-pyrrolo[1,2-b]pyrazol-3-yl)-2,3-difluoro-phenol (600.0 mg) as orange oil. MS [M+H]$^+$: 237.0.

Step 4: [4-(5,6-dihydro-4H-pyrrolo[1,2-b]pyrazol-3-yl)-2,3-difluoro-phenyl]trifluoromethanesulfonate A solution of 4-(5,6-dihydro-4H-pyrrolo[1,2-b]pyrazol-3-yl)-2,3-difluoro-phenol (600.0 mg, 2.54 mmol) in Pyridine (6.0 mL) was added trifluoromethanesulfonic anhydride (1.3 mL, 5.08 mmol) under 0° C., The reaction was stirred at 20° C. for 1 h. The reaction was added water (20 mL), extracted with EtOAc (50 mL×3). The combined organic layers were washed by brine (30 mL×2), dried ($Na_2SO_4$) and concentrated to give crude product [4-(5,6-dihydro-4H-pyrrolo[1, 2-b]pyrazol-3-yl)-2,3-difluoro-phenyl] trifluoromethanesulfonate (900.0 mg). MS [M+H]$^+$: 369.0.

Step 5: [4-(5,6-dihydro-4H-pyrrolo[1,2-b]pyrazol-3-yl)-2,3-difluoro-phenyl]boronic acid A mixture of bis(pinacolato)diboron (703.3 mg, 2.77 mmol), 1,1'-bis(diphenylphosphino)ferrocene-palladium(II) dichloride dichloromethane complex (188.3 mg, 0.23 mmol), [4-(5,6-dihydro-4H-pyrrolo[1,2-b]pyrazol-3-yl)-2, 3-difluoro-phenyl]trifluoromethanesulfonate (850.0 mg, 2.31 mmol) and potassium acetate (453.0 mg, 4.62 mmol) in a flask. 1,4-dioxane (8 mL) was added by injector to the mixture. The flask was degassed and purged with $N_2$ gas for four times. The mixture was stirred at 100° C. for 2 h under $N_2$ atmosphere. The reaction mixture was filtered and the filtrate was concentrated under reduced pressure to remove the solvent, then the product was purified by reversed-phase chromatography (FA) to give [4-(5,6-dihydro-4H-pyrrolo[1, 2-b]pyrazol-3-yl)-2,3-difluoro-phenyl]boronic acid (210.0 mg). MS [M+H]$^+$: 265.0.

Intermediate G55

[2,3-difluoro-4-[3-(fluoromethyl)-1-(2-methoxy-ethyl)pyrazol-4-yl]phenyl]boronic acid

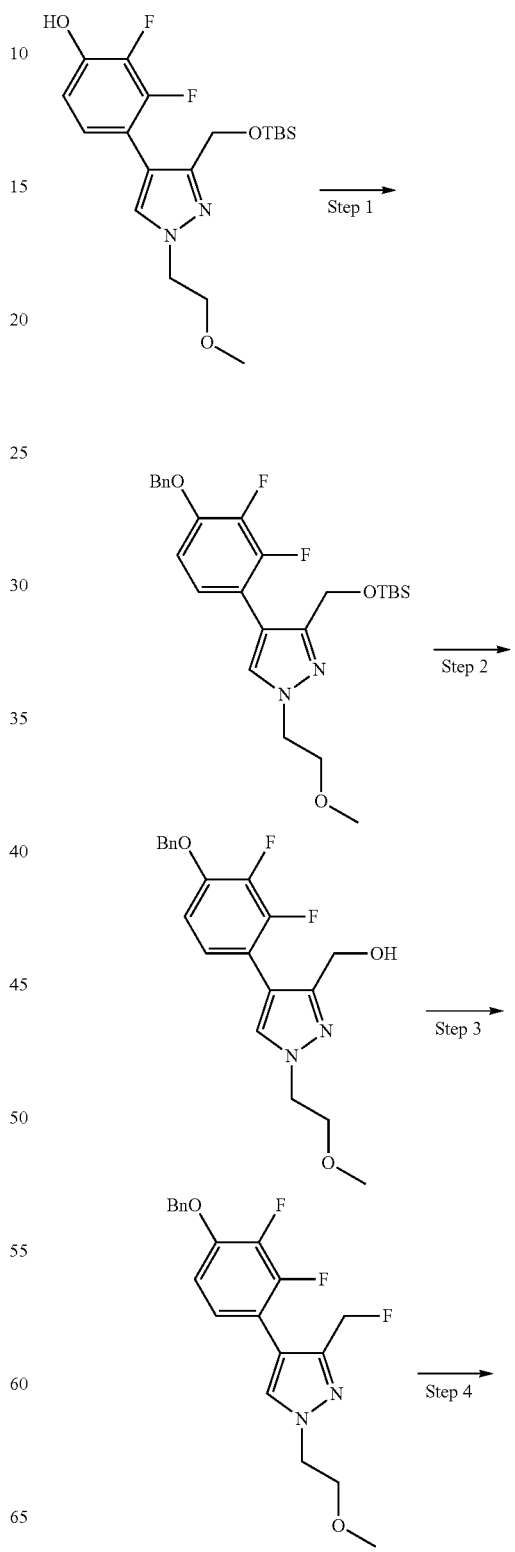

-continued

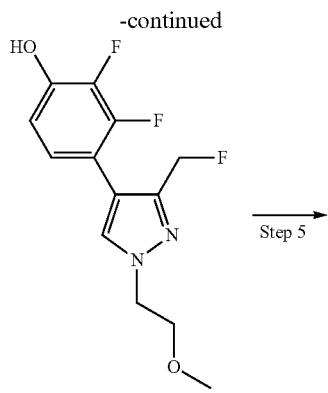

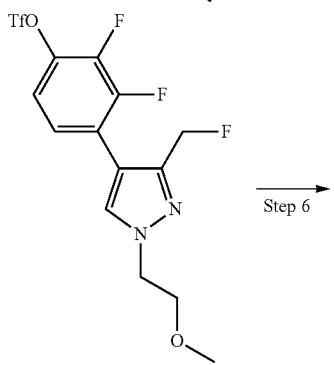

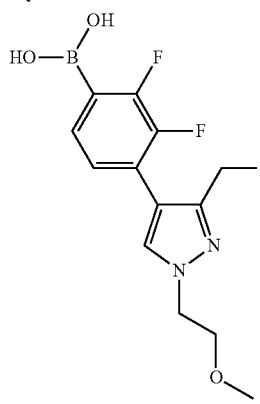

Intermediate 55

Step 1: [4-(4-benzyloxy-2,3-difluoro-phenyl)-1-(2-methoxyethyl)pyrazol-3-yl]methoxy-tert-butyl-dimethyl-silane To a solution of 4-[3-[[tert-butyl(dimethyl)silyl]oxymethyl]-1-(2-methoxyethyl)pyrazol-4-yl]-2,3-difluoro-phenol (200.0 mg, 0.5 mmol) in DMF (5 mL) was added potassium carbonate (138.7 mg, 1.0 mmol) and benzyl bromide (0.07 mL, 0.6 mmol). The reaction mixture was stirred at 20° C. for 4 h. The mixture was filtered and extracted with EtOAc (10 mL×3). The combined organic layers were washed with brine (10 mL), dried over Na$_2$SO$_4$, and concentrated under reduced pressure to afford the crude product. The crude product was purified by TLC (PE:EtOAc=3:1) to get [4-(4-benzyloxy-2,3-difluoro-phenyl)-1-(2-methoxyethyl)pyrazol-3-yl]methoxy-tert-butyl-dimethyl-silane (220.0 mg). MS [M+H]$^+$: 489.2.

Step 2: [4-(4-benzyloxy-2,3-difluoro-phenyl)-1-(2-methoxyethyl)pyrazol-3-yl]methanol To a solution of compound [4-(4-benzyloxy-2,3-difluoro-phenyl)-1-(2-methoxyethyl)pyrazol-3-yl]methoxy-tert-butyl-dimethyl-silane (220.0 mg, 0.45 mmol) in DCM (5 mL) was added hydrochloric acid in MeOH (4M) (1.8 mL, 7.2 mmol). The reaction mixture was stirred at 20° C. for 2 h. The mixture was concentrated under reduced pressure to afford the crude product [4-(4-benzyloxy-2,3-difluoro-phenyl)-1-(2-methoxyethyl)pyrazol-3-yl]methanol (170.0 mg). MS [M+H]$^+$: 375.2.

Step 3: 4-(4-benzyloxy-2,3-difluoro-phenyl)-3-(fluoromethyl)-1-(2-methoxyethyl)pyrazole To a solution of [4-(4-benzyloxy-2,3-difluoro-phenyl)-1-(2-methoxyethyl)pyrazol-3-yl]methanol (150.0 mg, 0.4 mmol) in DCM (5 mL) was added diethylaminosulfur trifluoride (0.21 mL, 1.6 mmol) slowly at −60° C. under N$_2$. This reaction mixture was stirred at −60° C. for 1 h. This reaction was quenched by NaHCO$_3$ (20 mL) and was extracted by EtOAc (10 mL×3). The combined organic layers were dried over Na$_2$SO$_4$ and concentrated to get the crude product. The crude product was purified by TLC (PE:EtOAc=1:1) to get 4-(4-benzyloxy-2,3-difluoro-phenyl)-3-(fluoromethyl)-1-(2-methoxyethyl)pyrazole (130.0 mg). MS [M+H]$^+$: 377.1.

Step 4: 2,3-difluoro-4-[3-(fluoromethyl)-1-(2-methoxyethyl)pyrazol-4-yl]phenol

To a solution of 4-(4-benzyloxy-2,3-difluoro-phenyl)-3-(fluoromethyl)-1-(2-methoxyethyl)pyrazole (130.0 mg, 0.35 mmol) in methanol (10 mL) was added palladium on carbon (0.04 mL, 0.03 mmol) in one portion under N$_2$. This mixture was degassed and purged with N$_2$ for three times. Then H$_2$ (15 psi) was introduced into this system. The reaction mixture was stirred at 20° C. for 2 h under H$_2$ atmosphere. The mixture was filtered and concentrated under reduced pressure to afford the crude product. The crude product was purified by TLC (PE:EtOAc=1:1) to get 2,3-difluoro-4-[3-(fluoromethyl)-1-(2-methoxyethyl)pyrazol-4-yl]phenol (90.0 mg). MS [M+H]$^+$: 287.1.

Step 5: [2,3-difluoro-4-[3-(fluoromethyl)-1-(2-methoxyethyl)pyrazol-4-yl]phenyl]trifluoromethanesulfonate A mixture of 2,3-difluoro-4-[3-(fluoromethyl)-1-(2-methoxyethyl)pyrazol-4-yl]phenol (90.0 mg, 0.31 mmol) and pyridine (0.05 mL, 0.63 mmol) in DCM (5.0 mL) was degassed and purged with N$_2$ for three times. Then trifluoromethanesulfonic anhydride (0.07 mL, 0.44 mmol) was added into the mixture at 0° C. The reaction mixture was stirred at 20° C. for 2 h under N$_2$ atmosphere. This reaction was quenched by NaHCO$_3$ (10 mL) and was extracted by DCM (10 mL×3). The combined organic layers were dried over Na$_2$SO$_4$ and concentrated to get the crude product [2,3-difluoro-4-[3-(fluoromethyl)-1-(2-methoxyethyl)pyrazol-4-yl]phenyl] trifluoromethanesulfonate (130.0 mg). MS [M+H]$^+$: 419.1.

Step 6: [2,3-difluoro-4-[3-(fluoromethyl)-1-(2-methoxyethyl)pyrazol-4-yl]phenyl]boronic acid A mixture of [2,3-difluoro-4-[3-(fluoromethyl)-1-(2-methoxyethyl)pyrazol-4-yl]phenyl]trifluoromethanesulfonate (130.0 mg, 0.31 mmol), bis(pinacolato)diboron (157.8 mg, 0.62 mmol), potassium acetate (76.3 mg, 0.78 mmol) and X-PHOS (14.8 mg, 0.03 mmol) in 1,4-dioxane (5.0 mL) was degassed and purged with N₂ for three times. Then tris(dibenzylideneacetone)dipalladium (28.46 mg, 0.03 mmol) was added into the mixture. The reaction mixture was stirred at 100° C. for 2 h under N₂ atmosphere. This reaction was filtered and concentrated to get the crude product. The crude product was purified by TLC (PE: EtOAc=3:1) to get [2,3-difluoro-4-[3-(fluoromethyl)-1-(2-methoxyethyl)pyrazol-4-yl]phenyl]boronic acid (70.0 mg). MS [M+H]⁺: 315.1.

Intermediate G56

[4-[3-chloro-1-(2-methoxyethyl)pyrazol-4-yl]-2,3-difluoro-phenyl]boronic acid

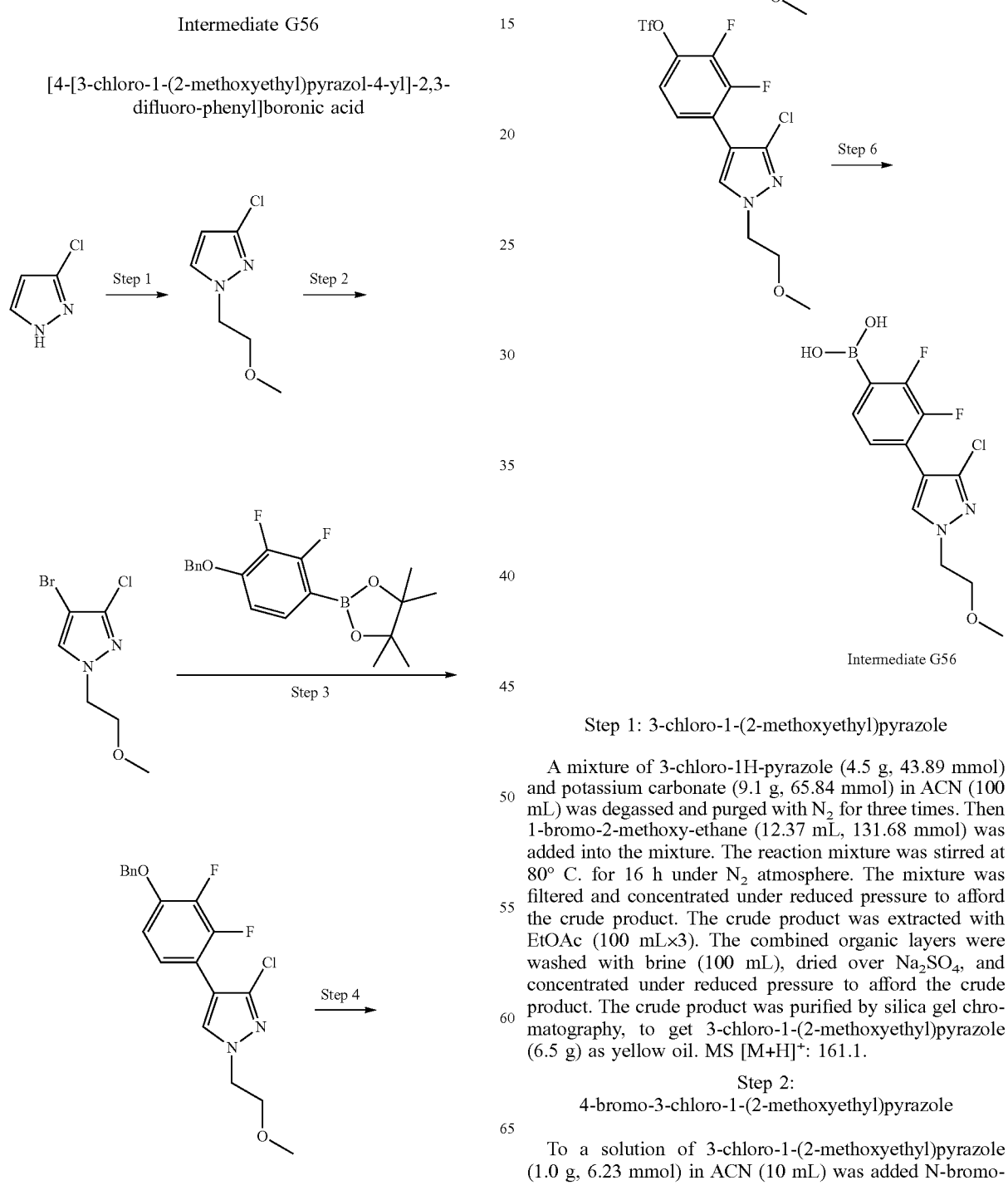

Intermediate G56

Step 1: 3-chloro-1-(2-methoxyethyl)pyrazole

A mixture of 3-chloro-1H-pyrazole (4.5 g, 43.89 mmol) and potassium carbonate (9.1 g, 65.84 mmol) in ACN (100 mL) was degassed and purged with N₂ for three times. Then 1-bromo-2-methoxy-ethane (12.37 mL, 131.68 mmol) was added into the mixture. The reaction mixture was stirred at 80° C. for 16 h under N₂ atmosphere. The mixture was filtered and concentrated under reduced pressure to afford the crude product. The crude product was extracted with EtOAc (100 mL×3). The combined organic layers were washed with brine (100 mL), dried over Na₂SO₄, and concentrated under reduced pressure to afford the crude product. The crude product was purified by silica gel chromatography, to get 3-chloro-1-(2-methoxyethyl)pyrazole (6.5 g) as yellow oil. MS [M+H]⁺: 161.1.

Step 2: 4-bromo-3-chloro-1-(2-methoxyethyl)pyrazole

To a solution of 3-chloro-1-(2-methoxyethyl)pyrazole (1.0 g, 6.23 mmol) in ACN (10 mL) was added N-bromosuccinimide (1.22 g, 6.85 mmol). The reaction mixture was stirred at 20° C. for 6 h. This reaction was quenched by Na$_2$SO$_3$ (40 mL) and was extracted by EtOAc (40 mL×3). The combined organic layers were dried over Na$_2$SO$_4$ and concentrated to get the crude product 4-bromo-3-chloro-1-(2-methoxyethyl)pyrazole (1.8 g). MS ([M+H]$^+$/[M+2+H]$^+$): 239.0/241.0.

Step 3: 4-(4-benzyloxy-2,3-difluoro-phenyl)-3-chloro-1-(2-methoxyethyl)pyrazole A mixture of 4-bromo-3-chloro-1-(2-methoxyethyl)pyrazole (1.8 g, 7.52 mmol), 2-(4-benzyloxy-2,3-difluoro-phenyl)-4,4,5,5-tetramethyl-1,3,2-dioxaborolane (3.9 g, 11.27 mmol) and potassium carbonate (2.08 g, 15.03 mmol) in 1,4-dioxane (20 mL) and water (2 mL) was degassed and purged with N$_2$ for three times. Then [1,1'-bis(diphenylphosphino) ferrocene]dichloropalladium(II) (274.97 mg, 0.38 mmol) was added dropwise into the mixture. The reaction mixture was stirred at 80° C. for 9 h under N$_2$ atmosphere. The mixture was filtered and concentrated under reduced pressure to afford the crude product. The crude product was purified by silica gel chromatography (PE:EtOAc=10:1-2:1) to get 4-(4-benzyloxy-2,3-difluoro-phenyl)-3-chloro-1-(2-methoxyethyl)pyrazole (1.7 g). MS [M+H]$^+$: 379.1.

Step 4: 4-[3-chloro-1-(2-methoxyethyl)pyrazol-4-yl]-2,3-difluoro-phenol

To a solution of 4-(4-benzyloxy-2,3-difluoro-phenyl)-3-chloro-1-(2-methoxyethyl)pyrazole (3.4 g, 8.98 mmol) in methanol (30 mL) was added platinum(IV) oxide (101.91 mg, 0.45 mmol) in one portion under Ar$_2$. This mixture was degassed and purged with Ar$_2$ for 3 times. Then H$_2$ (15 psi) was introduced into this system. The reaction mixture was stirred at 20° C. for 6 h under H$_2$ atmosphere. This reaction was filtered carefully and concentrated to get the crude product. The crude product was purified by silica gel chromatography (PE:EtOAc=4:1-1:1) to get 4-[3-chloro-1-(2-methoxyethyl)pyrazol-4-yl]-2,3-difluoro-phenol (2.4 g). MS [M+H]$^+$: 289.1.

Step 5: [4-[3-chloro-1-(2-methoxyethyl)pyrazol-4-yl]-2,3-difluoro-phenyl]trifluoromethanesulfonate A mixture of 4-[3-chloro-1-(2-methoxyethyl)pyrazol-4-yl]-2,3-difluoro-phenol (500.0 mg, 1.73 mmol) and pyridine (0.28 mL, 3.46 mmol) in DCM (5 mL) was degassed and purged with N$_2$ for 3 times. Then trifluoromethanesulfonic anhydride (0.4 mL, 2.42 mmol) was added into the mixture at 0° C. The reaction mixture was stirred at 20° C. for 2 h under N$_2$ atmosphere. This reaction was quenched by NaHCO$_3$ (10 mL) and was extracted by DCM (10 mL×3). The combined organic layers were dried over Na$_2$SO$_4$ and concentrated to get the crude product [4-[3-chloro-1-(2-methoxyethyl)pyrazol-4-yl]-2,3-difluoro-phenyl] trifluoromethanesulfonate (750.0 mg). MS [M+H]$^+$: 421.0.

Step 6: [4-[3-chloro-1-(2-methoxyethyl)pyrazol-4-yl]-2,3-difluoro-phenyl]boronic acid A mixture of [4-[3-chloro-1-(2-methoxyethyl)pyrazol-4-yl]-2,3-difluoro-phenyl]trifluoromethanesulfonate (900.0 mg, 2.14 mmol), bis(pinacolato)diboron (1.09 g, 4.28 mmol), potassium acetate (524.84 mg, 5.35 mmol) and X-PHOS (50.99 mg, 0.11 mmol) in 1,4-dioxane (5 mL) was degassed and purged with N$_2$ for 3 times. Then tris(dibenzylideneacetone)dipalladium (0) (97.94 mg, 0.11 mmol) was added into the mixture. The reaction mixture was stirred at 90° C. for 2 h under N$_2$ atmosphere. This reaction was filtered and concentrated to get the crude product. The crude product was purified by TLC (PE:EA=3:1) to get [4-[3-chloro-1-(2-methoxyethyl)pyrazol-4-yl]-2,3-difluoro-phenyl]boronic acid (450.0 mg). MS [M+H]$^+$: 317.0.

The following examples were prepared in analogy to Intermediate G54.

| Ex # | Name | Structure | MS ESI [M + H]$^+$ | Starting Material |
|---|---|---|---|---|
| Intermediate G57 | [4-[5-chloro-1-(2-methoxyethyl) pyrazol-4-yl]-2,3-difluoro-phenyl]boronic acid | 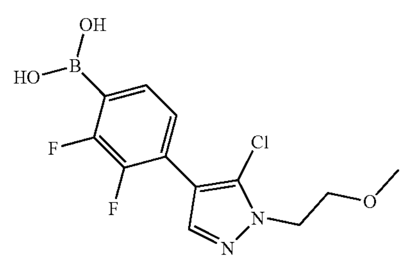 [SMILES: COCCn1ncc(-c2ccc(B(O)O)c(F)c2F)c1Cl] | 481.2 | 3-chloro-1H-pyrazole; 1-bromo-2-methoxy-ethane, 2-(4-benzyloxy-2,3-difluoro-phenyl)-4,4,5,5-tetramethyl-1,3,2-dioxaborolane |

Intermediate G58

[2,3-difluoro-4-[5-(2-pyridyl)-1-(2-trimethylsilylethoxymethyl)pyrazol-4-yl]phenyl]boronic acid

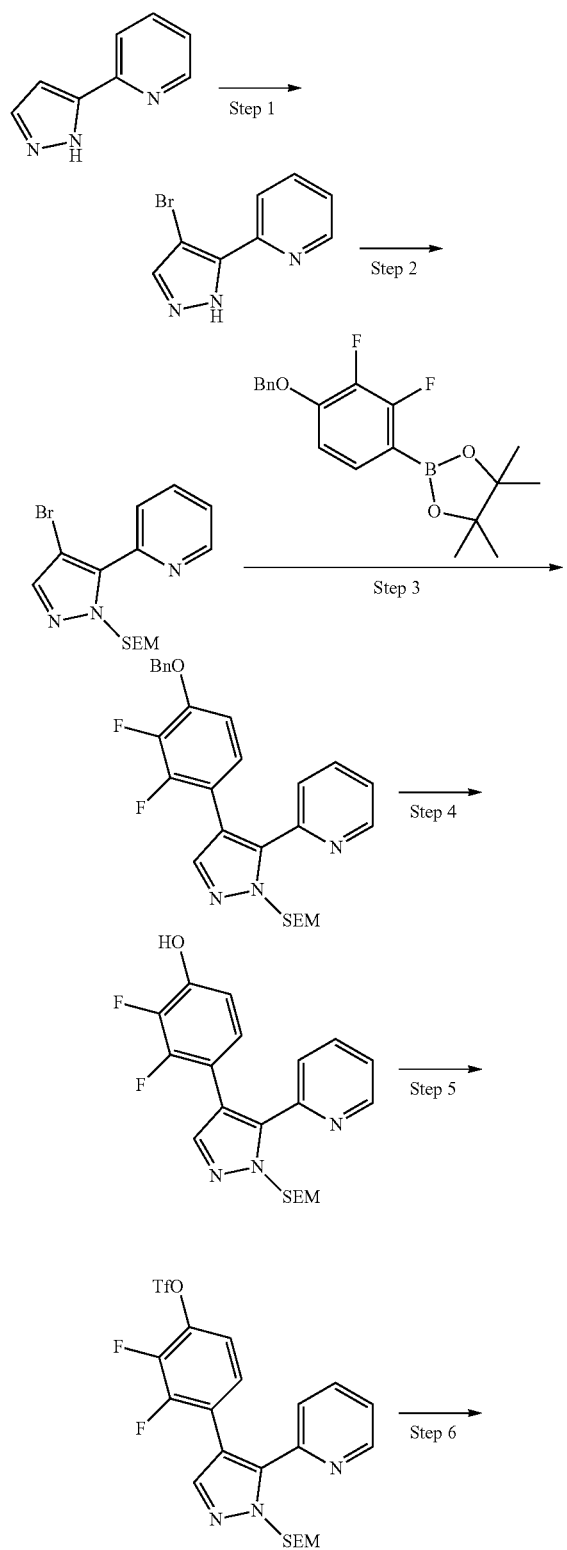

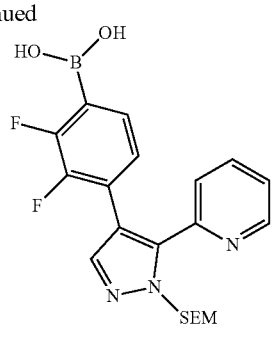

Intermediate G58

Step 1: 2-(4-bromo-1H-pyrazol-5-yl)pyridine

To a solution of 2-(1H-pyrazol-5-yl)pyridine (3.0 g, 20.7 mmol) in acetic acid (20 mL) was added and bromine (3.6 g, 22.7 mmol), the mixture was stirred at 20° C. for 0.5 h. The mixture was concentrated, the residue was diluted with 20 mL of water, the solution was added to the solution of NaOH in water (30 mL, 1 M), the precipitate was filtered off and dried in vacuum to give 2-(4-bromo-1H-pyrazol-5-yl)pyridine (4.6 g). MS [M+H]$^+$: 223.9.

Step 2: 2-(4-bromo-1-((2-(trimethylsilyl)ethoxy)methyl)-1H-pyrazol-5-yl)pyridine To a solution of 2-(4-bromo-1H-pyrazol-5-yl)pyridine (4.5 g, 20.08 mmol) in ACN (50.0 mL) was added cesium carbonate (13.1 g, 40.17 mmol) and 2-(trimethylsilyl)ethoxymethyl chloride (4.27 mL, 24.1 mmol), the mixture was stirred at 70° C. for 1 h. The mixture was filtered off, the filtrate was concentrated, the residue was purified by prep-HPLC to give 2-[[4-bromo-5-(2-pyridyl)pyrazol-1-yl]methoxy]ethyl-trimethyl-silane (3.82 g). MS [M+H]$^+$: 354.0.

Step 3: 2-(4-(4-(benzyloxy)-2,3-difluorophenyl)-1-((2-(trimethylsilyl)ethoxy)methyl)-1H-pyrazol-5-yl)pyridine To a solution of 2-[[4-bromo-5-(2-pyridyl)pyrazol-1-yl]methoxy]ethyl-trimethyl-silane (1.0 g, 2.82 mmol) in 1,4-dioxane (10 mL) was added 2-(4-benzyloxy-2,3-difluorophenyl)-4,4,5,5-tetramethyl-1,3,2-dioxaborolane (1.2 g, 3.39 mmol), [1,1'-bis(diphenylphosphino)ferrocene]dichloropalladium(II) (206.5 mg, 0.28 mmol), potassium carbonate (780.2 mg, 5.64 mmol) and dioxane (10 mL)/water (1 mL) in glove box, the mixture was stirred at 100° C. for 16 h under Ar$_2$. The mixture was diluted with 10 mL of ethyl acetate and filtered off, the filtrated was concentrated, the residue was purified by Flash-HPLC to give 2-[[4-(4-benzyloxy-2,3-difluoro-phenyl)-5-(2-pyridyl)pyrazol-1-yl]methoxy]ethyl-trimethyl-silane (520 mg). MS [M+H]$^+$: 494.2.

Step 4: 2,3-difluoro-4-(5-(pyridin-2-yl)-1-((2-(trimethylsilyl)ethoxy)methyl)-1H-pyrazol-4-yl)phenol To a solution of 2-[[4-(4-benzyloxy-2,3-difluoro-phenyl)-5-(2-pyridyl)pyrazol-1-yl]methoxy]ethyl-trimethyl-silane (470.0 mg, 0.95 mmol) in Methanol (10 mL) was added Pd/C (80.0 mg) under N$_2$, then the mixture was flashed with H₂ and stirred with a H₂ balloon at 20° C. for 2 h. The mixture was filtered off, the filtrate was concentrated to give 2,3-difluoro-4-[5-(2-pyridyl)-1-(2-trimethylsilylethoxymethyl)pyrazol-4-yl]phenol (290.0 mg). MS [M+H]⁺: 404.1.

Step 5: 2,3-difluoro-4-(5-(pyridin-2-yl)-1-((2-(trimethylsilyl)ethoxy)methyl)-1H-pyrazol-4-yl)phenyl trifluoromethanesulfonate To solution of 2,3-difluoro-4-[5-(2-pyridyl)-1-(2-trimethylsilylethoxymethyl)pyrazol-4-yl]phenol (290.0 mg, 0.72 mmol) in pyridine (4.0 mL) was added trifluoromethanesulfonic anhydride (405.5 mg, 1.44 mmol) at 0° C. under N₂. The mixture was stirred at 20° C. for 0.5 h. the mixture was diluted with 50 mL of ethyl acetate, washed with 20 mL of water and 20 mL of brine, the organic layer was dried over Na₂SO₄ and concentrated to give [2,3-difluoro-4-[5-(2-pyridyl)-1-(2-trimethylsilylethoxymethyl)pyrazol-4-yl]phenyl] trifluoromethanesulfonate (384.0 mg). MS [M+H]⁺: 536.1.

Step 6: (2,3-difluoro-4-(5-(pyridin-2-yl)-1-((2-(trimethylsilyl)ethoxy)methyl)-1H-pyrazol-4-yl)phenyl) boronic acid To a solution of [2,3-difluoro-4-[5-(2-pyridyl)-1-(2-trimethylsilylethoxymethyl)pyrazol-4-yl]phenyl] trifluoromethanesulfonate (350.0 mg, 0.65 mmol) in 1,4-dioxane (2.0 mL) was added potassium acetate (0.08 mL, 1.31 mmol), bis(pinacolato)diboron (331.9 mg, 1.31 mmol) and [1,1'-bis(diphenylphosphino)ferrocene]dichloropalladium(II) (47.8 mg, 0.07 mmol) in glove box. The mixture was stirred at 100° C. for 8 h. The mixture was filtered off, the filtrate was concentrated, the residue was purified by Prep-HPLC to give [2,3-difluoro-4-[5-(2-pyridyl)-1-(2-trimethylsilylethoxymethyl)pyrazol-4-yl]phenyl]boronic acid (500.0 mg). MS [M+H]⁺: 432.1.

Intermediate G59

2-[[4-[2,3-difluoro-4-(4,4,5,5-tetramethyl-1,3,2-dioxaborolan-2-yl)phenyl]-5-(4-methoxyphenyl)pyrazol-1-yl]methoxy]ethyl-trimethyl-silane

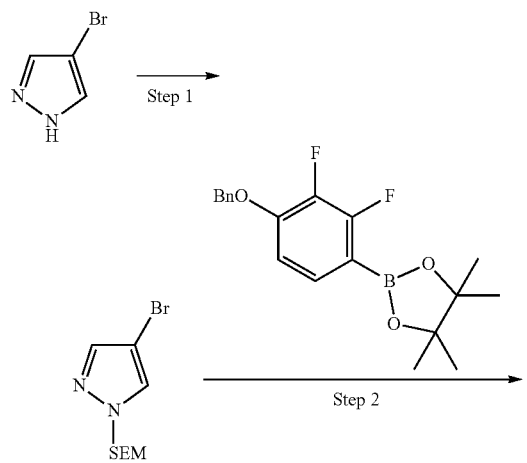

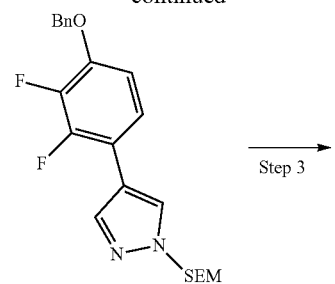

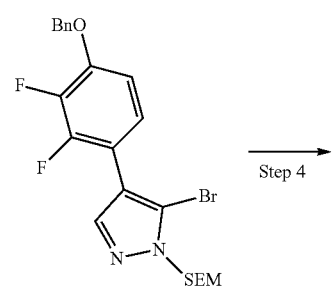

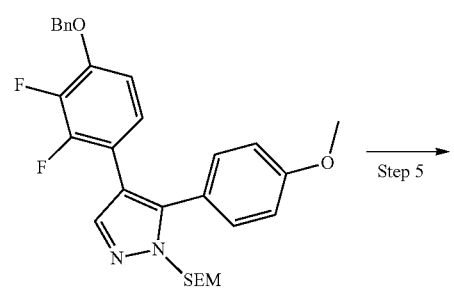

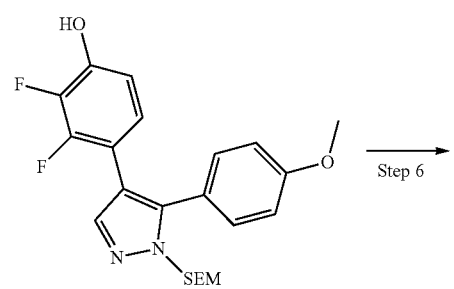

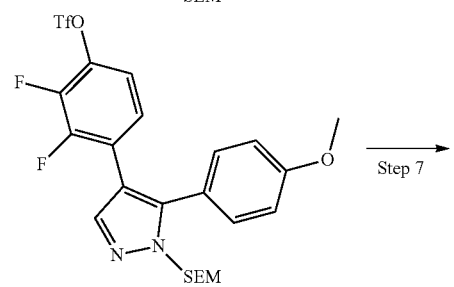

-continued

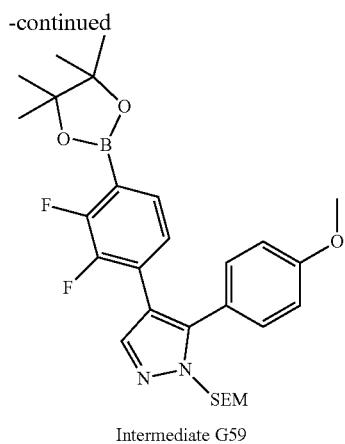

Intermediate G59

Step 1: 2-[(4-bromopyrazol-1-yl)methoxy]ethyl-trimethyl-silane

To a solution of 4-bromo-1H-pyrazole (20.0 g, 136.08 mmol) in THF (500 mL) was added sodium hydride, 60% in oil (6.5 g, 163.3 mmol) slowly at 0° C. After addition, this reaction mixture was stirred at 0° C. for 1 h. Then 2-(trimethylsilyl)ethoxymethyl chloride (36.1 mL, 204.12 mmol) was added into this mixture slowly at 0° C. This reaction mixture was warmed to 20° C. and stirred for 15 h. This reaction was quenched by saturated aqueous NH$_4$Cl (50 mL) and extracted by EtOAc (50 mL×3). The combined organic layers were dried over Na$_2$SO$_4$ and concentrated to get 2-[(4-bromopyrazol-1-yl)methoxy]ethyl-trimethyl-silane (32.0 g).

Step 2: 2-[[4-(4-benzyloxy-2,3-difluoro-phenyl)pyrazol-1-yl]methoxy]ethyl-trimethyl-silane To a solution of 2-(4-benzyloxy-2,3-difluoro-phenyl)-4,4,5,5-tetramethyl-1,3,2-dioxaborolane (12.5 g, 36.07 mmol), 2-[(4-bromopyrazol-1-yl)methoxy]ethyl-trimethyl-silane (10.0 g, 36.07 mmol) and potassium carbonate (7.5 g, 54.11 mmol) in 1,4-dioxane (200 mL) and water (20 mL) was added [1,1'-bis(diphenylphosphino)ferrocene]dichloropalladium(II) (1.3 g, 1.8 mmol) in one portion under N$_2$. This reaction mixture was stirred at 100° C. for 4 h. and the filtrate was concentrated to get the residue. This residue was diluted with EtOAc (200 mL) and was washed by brine (50 mL×2). The organic layer was dried over Na$_2$SO$_4$ and concentrated to get the crude product. This crude product was purified by silica gel chromatography (PE:EtOAc=5:1~1:1) to get 2-[[4-(4-benzyloxy-2,3-difluoro-phenyl)pyrazol-1-yl]methoxy]ethyl-trimethyl-silane (10.0 g). MS [M+H]$^+$: 417.2.

Step 3: 2-[[4-(4-benzyloxy-2,3-difluoro-phenyl)-5-bromo-pyrazol-1-yl]methoxy]ethyl-trimethyl-silane To a solution of 2-[[4-(4-benzyloxy-2,3-difluoro-phenyl)pyrazol-1-yl]methoxy]ethyl-trimethyl-silane (9.0 g, 21.61 mmol) in DMF (100 mL) was added N-bromosuccinimide (4.6 g, 25.93 mmol) in one portion. This reaction mixture was stirred at 80° C. for 16 h. This reaction was quenched by saturated aqueous Na$_2$SO$_3$ (100 mL) and extracted by EtOAc (50 mL×3). The combined organic layers were dried over Na$_2$SO$_4$ and concentrated to get the crude product. This crude product was purified by Prep-HPLC to get 2-[[4-(4-benzyloxy-2,3-difluoro-phenyl)-5-bromo-pyrazol-1-yl]methoxy]ethyl-trimethyl-silane (3.0 g). MS [M+H]$^+$: 496.9.

Step 4: 2-[[4-(4-benzyloxy-2,3-difluoro-phenyl)-5-(4-methoxyphenyl)pyrazol-1-yl]methoxy]ethyl-trimethyl-silane To a solution of 2-[[4-(4-benzyloxy-2,3-difluoro-phenyl)-5-bromo-pyrazol-1-yl]methoxy]ethyl-trimethyl-silane (184.0 mg, 1.21 mmol), compound 5 (400.0 mg, 0.81 mmol) and potassium carbonate (223.2 mg, 1.61 mmol) in 1,4-dioxane (10 mL) and water (1 mL) was added [1,1'-bis(diphenylphosphino)ferrocene]dichloropalladium(II) (59.1 mg, 0.08 mmol) in one portion under N$_2$. This reaction mixture was stirred at 100° C. for 4 h. This reaction mixture was filtered, and the filtrate was concentrated to get the residue. This residue was diluted with EtOAc (50 mL) and was washed by brine (10 mL×2). The organic phase was dried over Na$_2$SO$_4$ and concentrated to get the crude product. This crude product was purified by silica gel chromatography to get 2-[[4-(4-benzyloxy-2,3-difluoro-phenyl)-5-(4-methoxyphenyl)pyrazol-1-yl]methoxy]ethyl-trimethyl-silane (330.0 mg). MS [M+H]$^+$: 523.2.

Step 5: 2,3-difluoro-4-[5-(4-methoxyphenyl)-1-(2-trimethylsilylethoxymethyl)pyrazol-4-yl]phenol To a solution of 2-[[4-(4-benzyloxy-2,3-difluoro-phenyl)-5-(4-methoxyphenyl)pyrazol-1-yl]methoxy]ethyl-trimethyl-silane (280.0 mg, 0.54 mmol) in methanol (20 mL) was added palladium on carbon (10%, 57.0 mg) in one portion under N$_2$. Then H$_2$ (15 psi) was introduced into this system. This reaction mixture was stirred at 20° C. for 16 h. This reaction mixture was filtered, and the filtrate was concentrated to get 2,3-difluoro-4-[5-(4-methoxyphenyl)-1-(2-trimethylsilylethoxymethyl)pyrazol-4-yl]phenol (230.0 mg, 0.53 mmol), which would be used in the next step directly without further purification. MS [M+H]$^+$: 433.2.

Step 6: [2,3-difluoro-4-[5-(4-methoxyphenyl)-1-(2-trimethylsilylethoxymethyl)pyrazol-4-yl]phenyl] trifluoromethanesulfonate To a solution of 2,3-difluoro-4-[5-(4-methoxyphenyl)-1-(2-trimethylsilylethoxymethyl) pyrazol-4-yl]phenol (230.0 mg, 0.53 mmol) and pyridine (0.06 mL, 0.8 mmol) in DCM (10 mL) was added trifluoromethanesulfonic anhydride (0.11 mL, 0.64 mmol) in one portion at 0° C. Then reaction mixture was warmed to 20° C. and stirred for 2 h. This reaction was quenched by saturated aqueous Na$_2$CO$_3$ (10 mL) and extracted by DCM (10 mL×2). The combined organic layers were dried over Na$_2$SO$_4$ and concentrated to get [2,3-difluoro-4-[5-(4-methoxyphenyl)-1-(2-trimethylsilylethoxymethyl)pyrazol-4-yl]phenyl] trifluoromethanesulfonate (320.0 mg). MS [M+H]$^+$: 565.0.

Step 7: 2-[[4-[2,3-difluoro-4-(4,4,5,5-tetramethyl-1,3,2-dioxaborolan-2-yl)phenyl]-5-(4-methoxyphenyl)pyrazol-1-yl]methoxy]ethyl-trimethyl-silane To a solution of [2,3-difluoro-4-[5-(4-methoxyphenyl)-1-(2-trimethylsilylethoxymethyl) pyrazol-4-yl]phenyl] trifluoromethanesulfonate (320.0 mg, 0.57 mmol), bis(pinacolato)diboron (287.8 mg, 1.13 mmol) and potassium acetate (139.06 mg, 1.42 mmol) in 1,4-dioxane (10 mL) was added X-PHOS (27.0 mg, 0.06 mmol) and tris(dibenzylideneacetone)dipalladium (0) (51.9 mg, 0.06 mmol) in one portion under N$_2$. This reaction mixture was stirred at 100° C. for 2 h. This reaction mixture was filtered, and the filtrate was concentrated to get the crude product. This crude product was purified by silica gel chromatography to get 2-[[4-[2,3-difluoro-4-(4,4,5,5-tetramethyl-1,3,2-dioxaborolan-2-yl)phenyl]-5-(4-methoxyphenyl)pyrazol-1-yl]methoxy]ethyl-trimethyl-silane (250.0 mg, 0.46 mmol). MS [M+H]$^+$: 543.3. The following examples were prepared in analogy to Intermediate G59

| Ex # | Name | Structure | MS ESI [M + H]+ | Starting Material |
|---|---|---|---|---|
| Intermediate G60 | 2-[[4-[2,3-difluoro-4-(4,4,5,5-tetramethyl-1,3,2-dioxaborolan-2-yl)phenyl]-5-(3-methoxyphenyl)pyrazol-1-yl]methoxy]ethyl-trimethyl-silane | 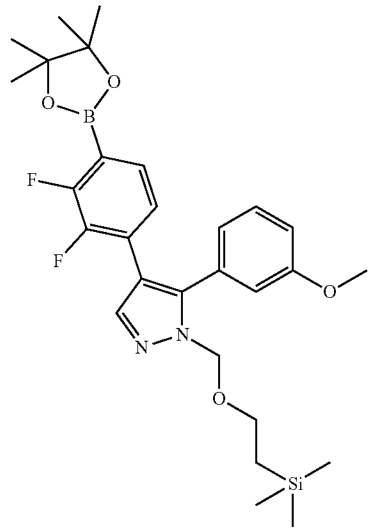 | 543.2 | 2-[[4-(4-benzyloxy-2,3-difluoro-phenyl)-5-bromo-pyrazol-1-yl]methoxy]ethyl-trimethyl-silane and (3-methoxyphenyl)boronic acid |
| Intermediate G61 | 2-[[4-[2,3-difluoro-4-(4,4,5,5-tetramethyl-1,3,2-dioxaborolan-2-yl)phenyl]-5-(2-methoxyphenyl)pyrazol-1-yl]methoxy]ethyl-trimethyl-silane | 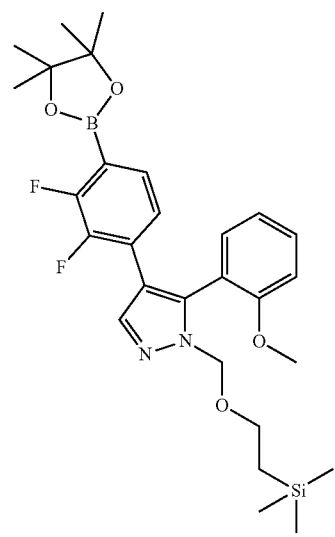 | 543.3 | 2-[[4-(4-benzyloxy-2,3-difluoro-phenyl)-5-bromo-pyrazol-1-yl]methoxy]ethyl-trimethyl-silane and (2-methoxyphenyl)boronic acid |

| Ex # | Name | Structure | MS ESI [M + H]+ | Starting Material |
|---|---|---|---|---|
| Intermediate G62 | 2-[[4-[2,3-difluoro-4-(4,4,5,5-tetramethyl-1,3,2-dioxaborolan-2-yl)phenyl]-5-thiazol-4-yl-pyrazol-1-yl]methoxy]ethyl-trimethyl-silane | 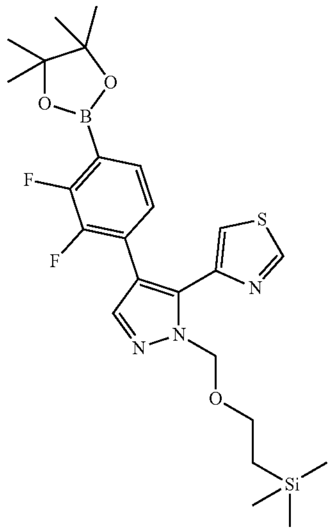 | 520.2 | 2-[[4-(4-benzyloxy-2,3-difluoro-phenyl)-5-bromo-pyrazol-1-yl]methoxy]ethyl-trimethyl-silane and tributyl(thiazol-4-yl)stannane |
| Intermediate G63 | 2-[[4-[2,3-difluoro-4-(4,4,5,5-tetramethyl-1,3,2-dioxaborolan-2-yl)phenyl]-5-tetrahydropyran-4-yl-pyrazol-1-yl]methoxy]ethyl-trimethyl-silane | 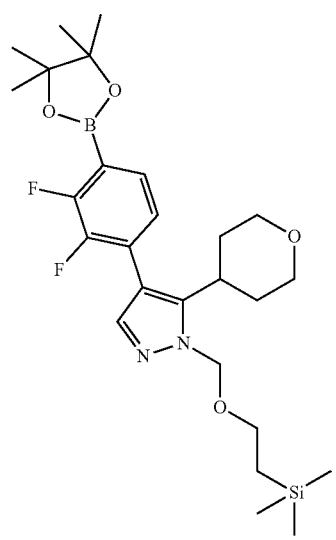 | 521.3 | 2-[[4-(4-benzyloxy-2,3-difluoro-phenyl)-5-bromo-pyrazol-1-yl]methoxy]ethyl-trimethyl-silane and Intermediate R9 |

| Ex # | Name | Structure | MS ESI [M + H]+ | Starting Material |
|---|---|---|---|---|
| Intermediate G64 | 2-[[4-[2,3-difluoro-4-(4,4,5,5-tetramethyl-1,3,2-dioxaborolan-2-yl)phenyl]-5-(3,6-dihydro-2H-pyran-4-yl)pyrazol-1-yl]methoxy]ethyl-trimethyl-silane | | 519.3 | 2-[[4-(4-benzyloxy-2,3-difluoro-phenyl)-5-bromo-pyrazol-1-yl]methoxy]ethyl-trimethyl-silane and Intermediate R9 |
| Intermediate G65 | 2-[[4-[2,3-difluoro-4-(4,4,5,5-tetramethyl-1,3,2-dioxaborolan-2-yl)phenyl]-3-(2-methylpyrazol-3-yl)pyrazol-1-yl]methoxy]ethyl-trimethyl-silane | | 517.7 | 2-[[4-(4-benzyloxy-2,3-difluoro-phenyl)-5-bromo-pyrazol-1-yl]methoxy]ethyl-trimethyl-silane and 1-methyl-5-(4,4,5,5-tetramethyl-1,3,2-dioxaborolan-2-yl)pyrazole |
| Intermediate G66 | 2-[[4-[2,3-difluoro-4-(4,4,5,5-tetramethyl-1,3,2-dioxaborolan-2-yl)phenyl]-3-(3-fluorophenyl)pyrazol-1-yl]methoxy]ethyl-trimethyl-silane | | 531.4 | 2-[[4-(4-benzyloxy-2,3-difluoro-phenyl)-5-bromo-pyrazol-1-yl]methoxy]ethyl-trimethyl-silane and (3-fluorophenyl)boronic acid |

| Ex # | Name | Structure | MS ESI [M + H]+ | Starting Material |
|---|---|---|---|---|
| Intermediate G67 | [2,3-difluoro-4-[3-(1-methylpyrazol-4-yl)-1-(2-trimethylsilylethoxymethyl)pyrazol-4-yl]phenyl]boronic acid | 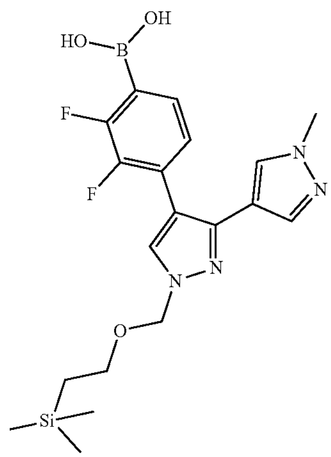 [SMILES: Cn1cc(-c2nn(COCC[Si](C)(C)C)cc2-c2ccc(B(O)O)c(F)c2F)cn1] | 435.2 | 2-[[4-(4-benzyloxy-2,3-difluorophenyl)-5-bromo-pyrazol-1-yl]methoxy]ethyl-trimethyl-silane and 1-methyl-4-(4,4,5,5-tetramethyl-1,3,2-dioxaborolan-2-yl)pyrazole |
| Intermediate G68 | [2,3-difluoro-4-[1-(2-trimethylsilylethoxymethyl)-3-[1-(2-trimethylsilylethoxymethyl)pyrazol-4-yl]pyrazol-4-yl]phenyl]boronic acid | 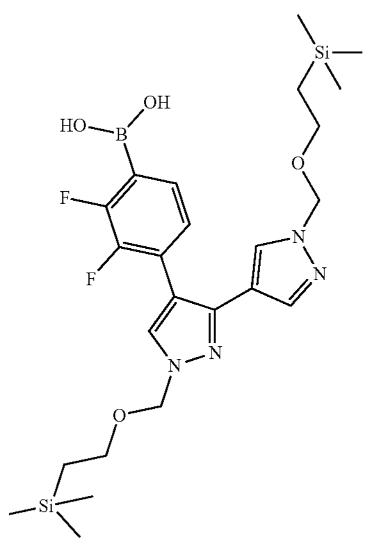 | 644.4 | 2-[[4-(4-benzyloxy-2,3-difluorophenyl)-5-bromo-pyrazol-1-yl]methoxy]ethyl-trimethyl-silane and trimethyl-[2-[[4-(4,4,5,5-tetramethyl-1,3,2-dioxaborolan-2-yl)pyrazol-1-yl]methoxy]ethyl]silane |
| Intermediate G69 | [2,3-difluoro-4-[1-(2-methoxyethyl)-3-phenyl-pyrazol-4-yl]phenyl]boronic acid | 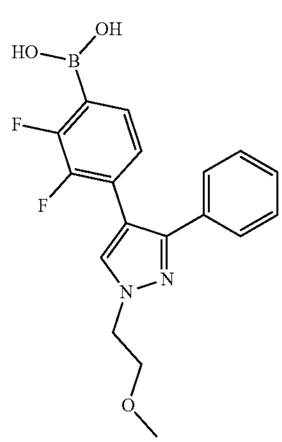 [SMILES: COCCn1cc(-c2ccc(B(O)O)c(F)c2F)c(-c2ccccc2)n1] | 359.0 | 2-[[4-(4-benzyloxy-2,3-difluorophenyl)-5-bromo-pyrazol-1-yl]methoxy]ethyl-trimethyl-silane and phenylboronic acid |

Intermediate G70 tert-butyl N-[6-[4-[2,3-difluoro-4-(4,4,5,5-tetramethyl-1,3,2-dioxaborolan-2-yl)phenyl]-3-methyl-pyrazol-1-yl]-3-pyridyl]carbamate

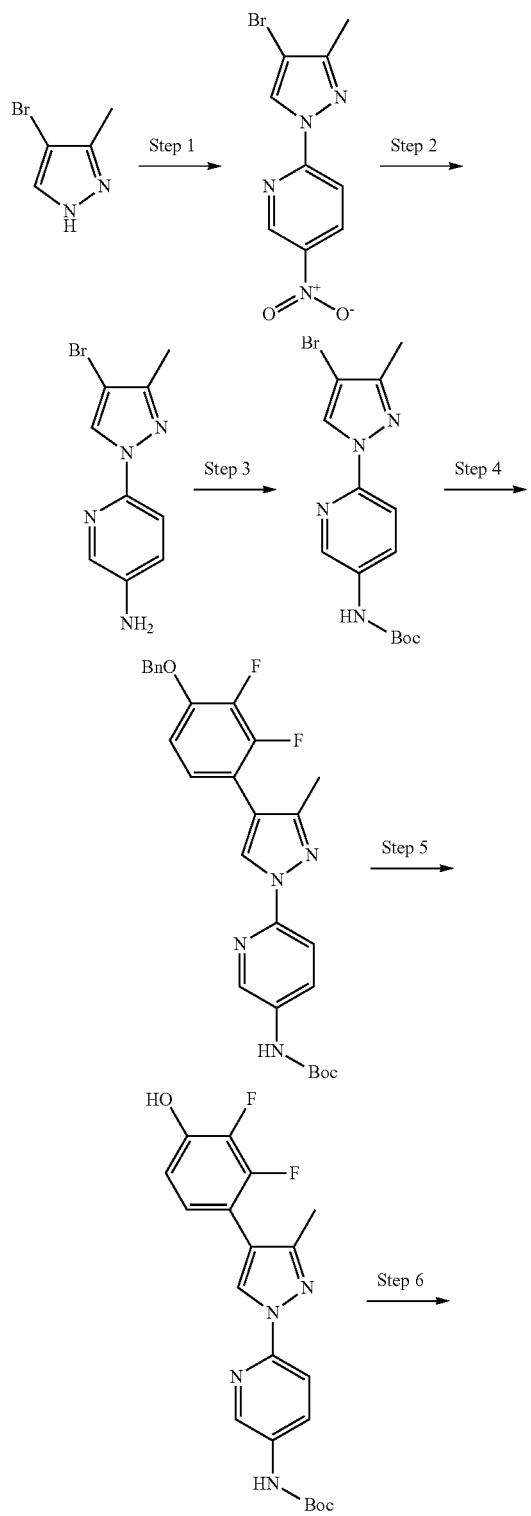

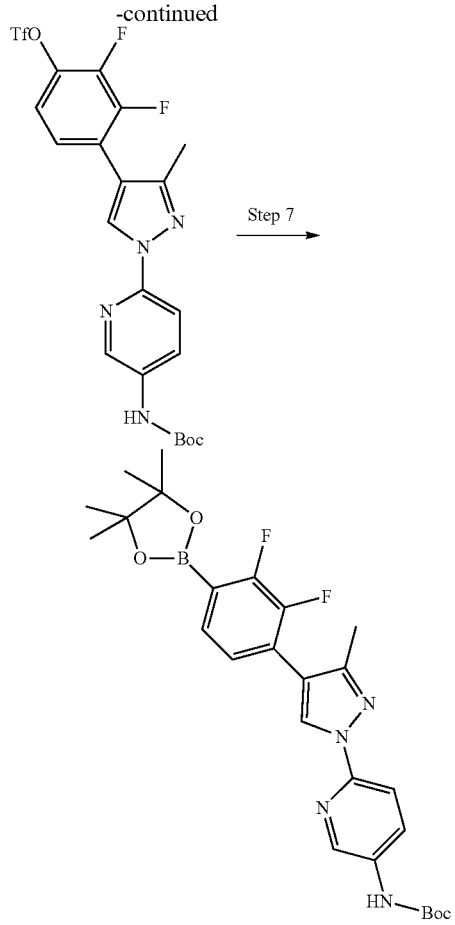

Intermediate G70

Step 1: 2-(4-bromo-3-methyl-1H-pyrazol-1-yl)-5-nitropyridine

To a solution of 4-bromo-3-methyl-1H-pyrazole (2.5 g, 15.53 mmol) in DMF (100 mL) was added sodium hydride (750.0 mg, 18.75 mmol) at 0° C. portionwise under $N_2$, after the addition was complete, the mixture was stirred at 0° C. for 0.5 h. Then 2-chloro-5-nitropyridine (2.5 g, 15.77 mmol) was added to the above mixture at 0° C. and the resultant mixture was warmed to 20° C. gradually and stirred for 11.5 h. Then the mixture was quenched with saturated $NH_4Cl$ (800 mL), filtered, the filter cake was washed with ACN (50 mL), dried under vacuum to afford 2-(4-bromo-3-methyl-pyrazol-1-yl)-5-nitro-pyridine (3.8 g). MS [M+H]$^+$: 283.0.

Step 2: 6-(4-bromo-3-methyl-1H-pyrazol-1-yl)pyridin-3-amine

To a solution of 2-(4-bromo-3-methyl-pyrazol-1-yl)-5-nitro-pyridine (3.8 g, 13.42 mmol) and ammonium chloride (8.6 g, 161.09 mmol) in ethanol (70 mL) and water (20 mL) was added Fe powder (2.5 g, 44.29 mmol) at 20° C. under $N_2$, the resultant mixture was stirred at 80° C. for 3 h under $N_2$. TLC (PE:EA=1:1) indicated the desired product was formed. After the reaction mixture was cooled down to 20° C., the mixture was added saturated $NaHCO_3$ (60 mL), extracted with brine (150 mL) and EtOAc (120 mL×3). The combined organics were dried over $Na_2SO_4$, filtered, concentrated in vacuo to afford 6-(4-bromo-3-methyl-pyrazol-1-yl)pyridin-3-amine (3.2 g).

Step 3: tert-butyl (6-(4-bromo-3-methyl-1H-pyrazol-1-yl)pyridin-3-yl)carbamate(4)

To a solution of afford 6-(4-bromo-3-methyl-pyrazol-1-yl)pyridin-3-amine (3.2 g, 12.64 mmol) and Boc$_2$O (5.5 g, 25.30 mmol) in methanol (50 mL) was added triethylamine (3.5 mL, 25.29 mmol), the resultant mixture was stirred at 20° C. for 14 h. Then the mixture was concentrated in vacuum to give a residue, which was purified by HPLC and evaporated under vacuum to afford tert-butyl N-[6-(4-bromo-3-methyl-pyrazol-1-yl)-3-pyridyl]carbamate (2.8 g). MS [M+H]$^+$: 353.0.

Step 4: tert-butyl (6-(4-(4-(benzyloxy)-2,3-difluoro-phenyl)-3-methyl-1H-pyrazol-1-yl)pyridin-3-yl)carbamate To a solution of tert-butyl N-[6-(4-bromo-3-methyl-pyrazol-1-yl)-3-pyridyl]carbamate (1.0 g, 2.83 mmol), 2-(4-benzyloxy-2,3-difluoro-phenyl)-4,4,5,5-tetramethyl-1,3,2-dioxaborolane (1.5 g, 4.33 mmol) and potassium carbonate (800.0 mg, 5.79 mmol) in 1,4-dioxane (25 mL) and water (5.0 mL) was added Pd(dppf)Cl$_2$ (207.0 mg, 0.28 mmol) under N$_2$ at 20° C., then the mixture was stirred at 85° C. for 15 h under N$_2$. After the mixture was cooled down to 20° C., the mixture was filtered through celite, the filtrate was extracted with brine (200 mL) and EtOAc (100 mL×3). The combined organics were dried over Na$_2$SO$_4$, filtered, concentrated in vacuum to give a residue, which was purified by HPLC and evaporated under vacuum to afford tert-butyl N-[6-[4-(4-benzyloxy-2,3-difluoro-phenyl)-3-methyl-pyrazol-1-yl]-3-pyridyl]carbamate (1.1 g) as yellow solid. MS [M+H]$^+$: 493.1.

Step 5: tert-butyl (6-(4-(2,3-difluoro-4-hydroxyphenyl)-3-methyl-1H-pyrazol-1-yl)pyridin-3-yl)carbamate To a solution of tert-butyl N-[6-[4-(4-benzyloxy-2,3-difluoro-phenyl)-3-methyl-pyrazol-1-yl]-3-pyridyl]carbamate (500.0 mg, 1.02 mmol) in methanol (15 mL) and ethyl acetate (15 mL) was added Pd/C (500.0 mg) at 20° C. under H$_2$, the resultant mixture was stirred at 20° C. for 12 h under a balloon of H$_2$. Then the mixture was filtered through celite, the filtrate was concentrated in vacuum to afford tert-butyl N-[6-[4-(2,3-difluoro-4-hydroxy-phenyl)-3-methyl-pyrazol-1-yl]-3-pyridyl]carbamate (325.0 mg). MS [M+H]$^+$: 403.1.

Step 6: 4-(1-(5-((tert-butoxycarbonyl)amino)pyridin-2-yl)-3-methyl-1H-pyrazol-4-yl)-2,3-difluorophenyl trifluoromethanesulfonate To a solution of tert-butyl N-[6-[4-(2,3-difluoro-4-hydroxy-phenyl)-3-methyl-pyrazol-1-yl]-3-pyridyl]carbamate (325.0 mg, 0.81 mmol) and pyridine (0.4 mL, 4.95 mmol) in DCM (15 mL) was added trifluoromethanesulfonic anhydride (290.0 mg, 1.03 mmol) at 20° C., the resultant mixture was stirred at 20° C. for 2 h. Then the mixture was extracted with saturated NH$_4$Cl (70.0 mL) and EtOAc (60 mL×3). The combined organics were dried over Na$_2$SO$_4$, filtered, concentrated in vacuo to afford [4-[1-[5-(tert-butoxycarbonylamino)-2-pyridyl]-3-methyl-pyrazol-4-yl]-2,3-difluoro-phenyl] trifluoromethanesulfonate (390.0 mg). MS [M+H]$^+$: 534.9.

Step 7: tert-butyl (6-(4-(2,3-difluoro-4-(4,4,5,5-tetramethyl-1,3,2-dioxaborolan-2-yl)phenyl)-3-methyl-1H-pyrazol-1-yl)pyridin-3-yl)carbamate To a solution of [4-[1-[5-(tert-butoxycarbonylamino)-2-pyridyl]-3-methyl-pyrazol-4-yl]-2,3-difluoro-phenyl] trifluoromethanesulfonate (300.0 mg, 0.56 mmol), bis(pinacolato)diboron (280.0 mg, 1.10 mmol) and potassium acetate (0.07 mL, 1.12 mmol) in 1,4-dioxane (8.0 mL) was added Pd(dppf)Cl$_2$ (42.0 mg, 0.06 mmol) at 20° C. under N$_2$, the resultant mixture was stirred at 100° C. for 14 h under N$_2$. After the mixture was cooled down, filtered through celite, the filtrate was concentrated in vacuum to give a residue, which was purified by prep-HPLC (FA) and concentrated under vacuum to afford tert-butyl N-[6-[4-[2,3-difluoro-4-(4,4,5,5-tetramethyl-1,3,2-dioxaborolan-2-yl)phenyl]-3-methyl-pyrazol-1-yl]-3-pyridyl]carbamate (160.0 mg). MS [M+H]$^+$: 513.2.

The following examples were prepared in analogy to Intermediate G70.

| Ex # | Name | Structure | MS ESI [M + H]$^+$ | Starting Material |
|---|---|---|---|---|
| Intermediate G71 | 2-[[4-[4-[2,3-difluoro-4-(4,4,5,5-tetramethyl-1,3,2-dioxaborolan-2-yl)phenyl]-3-methyl-pyrazol-1-yl]pyrazol-1-yl]methoxy]ethyl-trimethyl-silane | 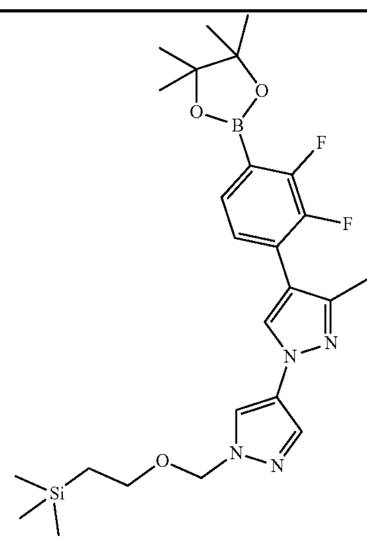 | 517.1 | 4-bromo-3-methyl-1H-pyrazole and 2-[(4-iodopyrazol-1-yl)methoxy]ethyl-trimethyl-silane; bis(pinacolato)diboron |

-continued

| Ex # | Name | Structure | MS ESI [M + H]+ | Starting Material |
|---|---|---|---|---|
| Intermediate G72 | [4-[1-[[5-(tert-butoxycarbonyl-amino)-2-pyridyl]methyl]-3-methyl-pyrazol-4-yl]-2,3-difluoro-phenyl]boronic acid | | 445.2 | 4-bromo-3-methyl-1H-pyrazole and tert-butyl N-[6-(bromomethyl)-3-pyridyl] carbamate; bis(pinacolato) diboron |
| Intermediate G73 | [2,3-difluoro-4-[3-methyl-1-[2-(2-oxo-1-pyridyl)ethyl]pyrazol-4-yl]phenyl]boronic acid | | 360.1 | 4-bromo-3-methyl-1H-pyrazole, piperidin-2-one and 1,2-dibromoethane; bis(pinacolato) diboron |
| Intermediate G74 | 2-[4-[2,3-difluoro-4-(4,4,5,5-tetramethyl-1,3,2-dioxaborolan-2-yl)phenyl]-3-methyl-pyrazol-1-yl]pyridine | | 398.2 | 4-bromo-3-methyl-1H-pyrazole and 2-chloropyridine; bis(pinacolato) diboron |

Intermediate G75

2-[[4-[6-fluoro-5-(4,4,5,5-tetramethyl-1,3,2-dioxaborolan-2-yl)-2-pyridyl]-3-(4-methoxyphenyl)pyrazol-1-yl]methoxy]ethyl-trimethyl-silane

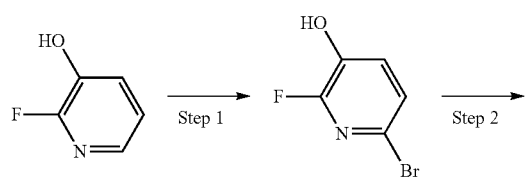

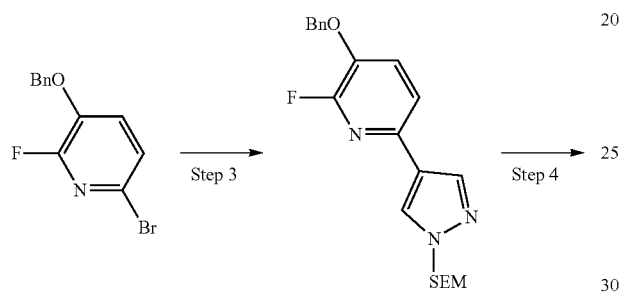

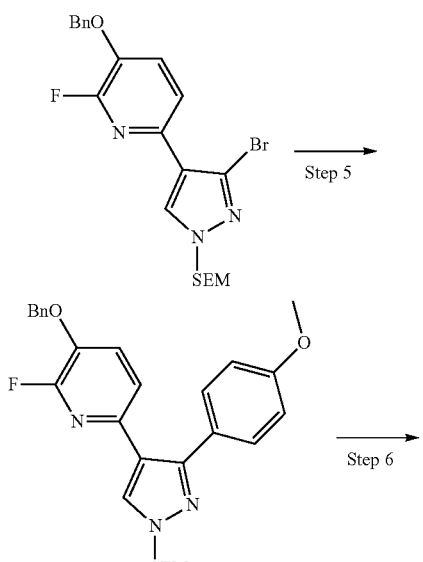

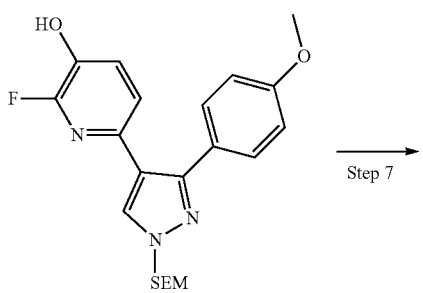

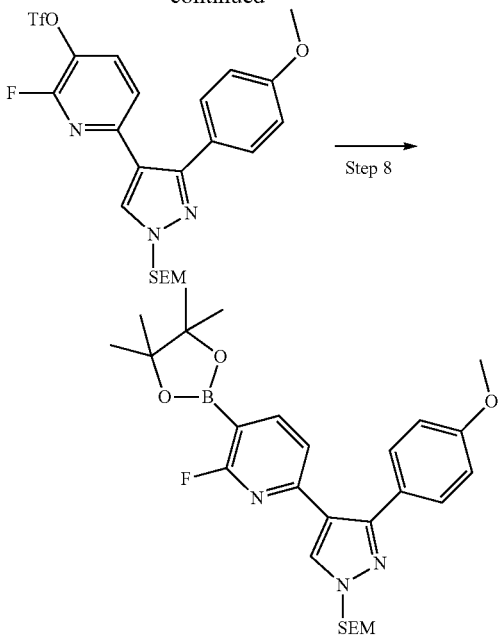

Intermediate G75

Step 1: 6-bromo-2-fluoropyridin-3-ol

To a solution of 2-fluoropyridin-3-ol (2.0 g, 17.69 mmol) in acetic acid (20.0 mL) was added sodium acetate (1.3 mL, 17.69 mmol), after the solid was dissolved, bromine (2.8 g, 17.69 mmol) was added by drops at 0° C. The mixture was stirred at 20° C. for 3 h. 1 g of sodium sulfite was added to the reaction mixture, then the mixture was concentrated. The residue was diluted with 20 mL of water and neutralized with 2 M NaOH solution, the solid was filtered off and dried in vacuum to give 6-bromo-2-fluoro-pyridin-3-ol (1.8 g). MS [M+H]$^+$: 191.9.

Step 2: 3-(benzyloxy)-6-bromo-2-fluoropyridine

To a solution of 6-bromo-2-fluoro-pyridin-3-ol (1.5 g, 7.81 mmol) in DMF (20.0 mL) was added NaH (375.0 mg, 9.38 mmol) at 0° C., the mixture was stirred at 0° C. for 0.5 h, then benzyl bromide (0.9 mL, 7.81 mmol) was added, the mixture was stirred at 20° C. for 16 h. The mixture was quenched with 30 mL of NH$_4$Cl water solution at 0° C., then the mixture was extracted with ethyl acetate (30 mL×3), the organic layer was concentrated, the residue was purified by Prep-HPLC to give 3-benzyloxy-6-bromo-2-fluoro-pyridine (1.7 g). MS [M+H]$^+$: 281.9.

Step 3: 3-(benzyloxy)-2-fluoro-6-(1-((2-(trimethylsilyl)ethoxy)methyl)-1H-pyrazol-4-yl)pyridine To a solution of 3-benzyloxy-6-bromo-2-fluoro-pyridine (1.5 g, 5.32 mmol) in 1,4-dioxane (60.0 mL) and water (6.0 mL) was added trimethyl-[2-[[4-(4,4,5,5-tetramethyl-1,3,2-dioxaborolan-2-yl)pyrazol]-1-yl]methoxy]ethyl]silane (3.8 g, 5.85 mmol), [1,1'-bis(diphenylphosphino) ferrocene]dichloropalladium(II) (389.1 mg, 0.53 mmol), K$_2$CO$_3$ (1.1 g, 10.63 mmol) in glovebox, the mixture was stirred at 60° C. for 16 h under Ar$_2$. The mixture was filtered off, the filtrate was concentrated, the residue was purified by silica gel column to give 2-[[4-(5-benzyloxy-6-fluoro-2-pyridyl)pyrazol-1-yl]methoxy]ethyl-trimethyl-silane (1.55 g) as a yellow solid. MS [M+H]$^+$: 400.1.

Step 4: 3-(benzyloxy)-6-(5-bromo-1-((2-(trimethylsilyl)ethoxy)methyl)-1H-pyrazol-4-yl)-2-fluoropyridine To a solution of 2-[[4-(5-benzyloxy-6-fluoro-2-pyridyl)pyrazol-1-yl]methoxy]ethyl-trimethyl-silane (1.5 g, 3.75 mmol) in DMF (15 mL) was added NBS (1.34 g, 7.51 mmol), the mixture was stirred at 60° C. for 16 h. The mixture was purified by Prep-HPLC to give 2-[[4-(5-benzyloxy-6-fluoro-2-pyridyl)-5-bromo-pyrazol-1-yl]methoxy]ethyl-trimethyl-silane (800.0 mg). MS [M+H]$^+$: 478.1.

Step 5: 3-(benzyloxy)-2-fluoro-6-(5-(4-methoxyphenyl)-1-((2-(trimethylsilyl)ethoxy)-methyl)-1H-pyrazol-4-yl)pyridine To a solution of (4-methoxyphenyl)boronic acid (297.3 mg, 1.96 mmol) in 1,4-dioxane (1.0 mL) and water (0.1 mL) was added 2-[[4-(5-benzyloxy-6-fluoro-2-pyridyl)-5-bromo-pyrazol-1-yl]methoxy]ethyl-trimethyl-silane (780.0 mg, 1.63 mmol), [1,1'-bis(diphenylphosphino) ferrocene] dichloropalladium(II) (119.3 mg, 0.16 mmol), $K_2CO_3$ (518.4 mg, 4.89 mmol) in glovebox, the mixture was stirred at 60° C. for 4 h under $Ar_2$. The mixture was filtered off, the filtrate was concentrated, the residue was purified by silica gel column to give 2-[[4-(5-benzyloxy-6-fluoro-2-pyridyl)-5-(4-methoxyphenyl)pyrazol-1-yl]methoxy]ethyl-trimethyl-silane (550.0 mg). MS [M+H]$^+$: 506.2.

Step 6: 2-fluoro-6-(5-(4-methoxyphenyl)-1-((2-(trimethylsilyl)ethoxy)methyl)-1H-pyrazol-4-yl)pyridin-3-ol A mixture of 2-[[4-(5-benzyloxy-6-fluoro-2-pyridyl)-5-(4-methoxyphenyl)pyrazol-1-yl]methoxy]ethyl-trimethyl-silane (550.0 mg, 1.09 mmol) in methanol (100 mL) was added Pd/C (50.0 mg) under $N_2$, then the miture flushed with $H_2$ and stirred with a $H_2$ balloon for 6 h at 15° C. The mixture was filtered off, the filtrate was concentrated to give 2-fluoro-6-[5-(4-methoxyphenyl)-1-(2-trimethylsilylethoxymethyl)pyrazol-4-yl]pyridin-3-ol (450.0 mg). MS [M+H]$^+$: 416.1.

Step 7: tert-butyl 2-fluoro-6-(5-(4-methoxyphenyl)-1-((2-(trimethylsilyl)ethoxy)methyl)-1H-pyrazol-4-yl)pyridin-3-yl trifluoromethanesulfonate A mixture of 2-fluoro-6-[5-(4-methoxyphenyl)-1-(2-trimethylsilylethoxymethyl)pyrazol-4-yl]pyridin-3-ol (450.0 mg, 1.08 mmol) in pyridine (15 mL) was added trifluoromethanesulfonic anhydride (611.1 mg, 2.17 mmol) at 0° C., then the mixture was stirred at 15° C. for 1 h. The mixture was diluted with 50 mL of ethyl acetate, washed with 30 mL of water and 30 mL of brine. The organic layer was dried over $Na_2SO_4$ and concentrated to give [2-fluoro-6-[5-(4-methoxyphenyl)-1-(2-trimethylsilylethoxymethyl)pyrazol-4-yl]-3-pyridyl]trifluoromethanesulfonate (580.0 mg). MS [M+H]$^+$: 548.1.

Step 8: 2-fluoro-6-(5-(4-methoxyphenyl)-1-((2-(trimethylsilyl)ethoxy)methyl)-1H-pyrazol-4-yl)-3-(4,4,5,5-tetramethyl-1,3,2-dioxaborolan-2-yl)pyridine To a solution of [2-fluoro-6-[5-(4-methoxyphenyl)-1-(2-trimethylsilylethoxymethyl)pyrazol-4-yl]-3-pyridyl] trifluoromethanesulfonate (560.0 mg, 1.02 mmol) in 1,4-dioxane (1.0 mL) was added bis(pinacolato)diboron (389.5 mg, 1.53 mmol), [1,1'-bis(diphenylphosphino)ferrocene]-dichloropalladium(II) (74.8 mg, 0.10 mmol) and potassium acetate (300.9 mg, 3.07 mmol) in glovebox, the mixture was stirred at 90° C. for 16 h. The mixture was filtered off, the filtrate was concentrated, the residue was purified by Prep-HPLC to give 2-[[4-[6-fluoro-5-(4,4,5,5-tetramethyl-1,3,2-dioxaborolan-2-yl)-2-pyridyl]-5-(4-methoxyphenyl)pyrazol-1-yl]methoxy]ethyl-trimethyl-silane (530.0 mg). MS [M+H]$^+$: 526.3.

Intermediate G76

2-[2-[4-[2,3-difluoro-4-(4,4,5,5-tetramethyl-1,3,2-dioxaborolan-2-yl)phenyl]-3-methyl-pyrazol-1-yl]ethyl]-6-methoxy-pyridine

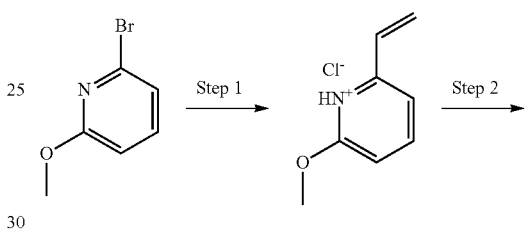

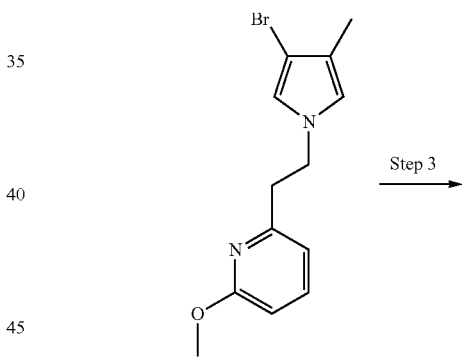

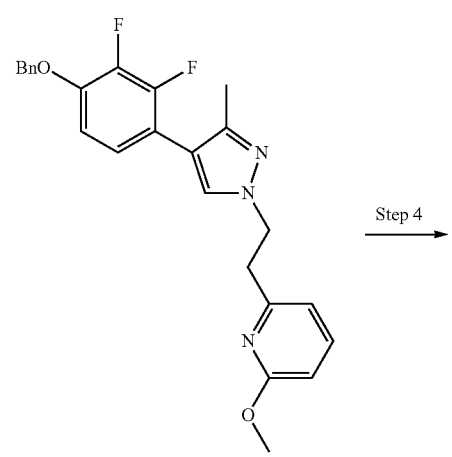

-continued

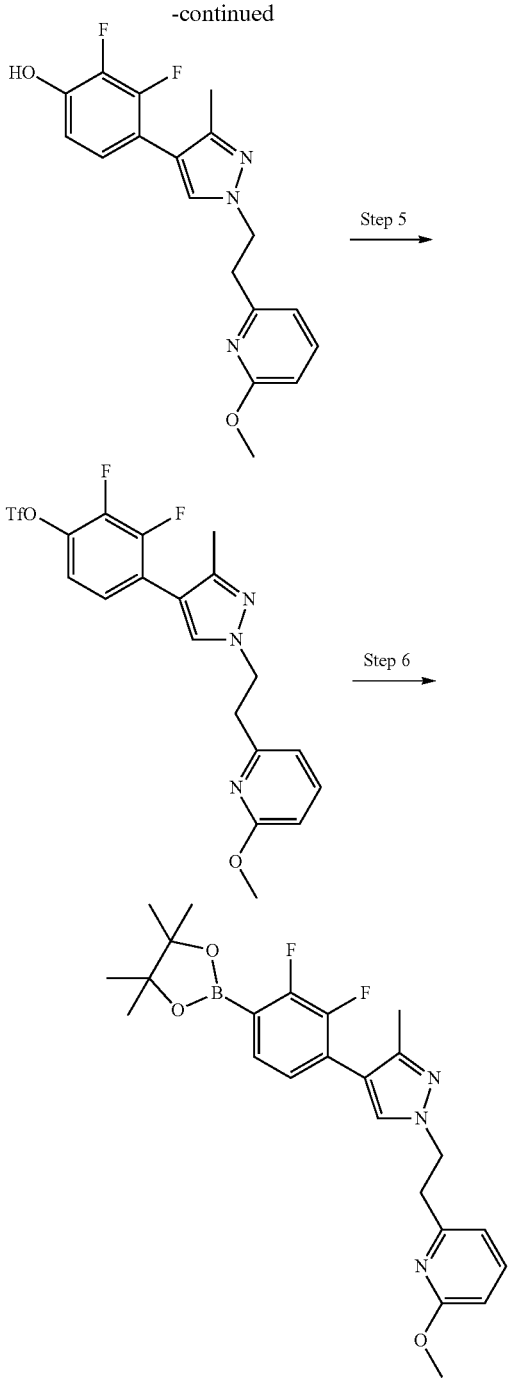

intermediate G76

Step 1: 2-methoxy-6-vinylpyridine

A mixture of 2-bromo-6-methoxy-pyridine (6.5 mL, 53.19 mmol) and potassium;trifluoro(vinyl)boranuide (8.6 g, 63.82 mmol) in 1,4-dioxane (120 mL) was added [1,1'-bis(diphenylphosphino)ferrocene]dichloropalladium(II) (0.8 g, 1.06 mmol), Potassium carbonate (20.6 g, 149.31 mmol) and Water (12 mL) in glove box. The mixture was stirred at 100° C. for 16 h under Ar. The mixture was distilled in vacuum, the collector was cooled with dry ice, the distillment was added 20 mL of HCl/1,4-dioxane (4 M), stirred at 60° C. for 2 h, then the mixture was concentrated to give 2-methoxy-6-vinyl-pyridine;hydrochloride (2.6 g) as a yellow gum. MS [M+H]$^+$: 136.1.

Step 2: 2-(2-(4-bromo-3-methyl-1H-pyrazol-1-yl)ethyl)-6-methoxypyridine

A mixture of 2-methoxy-6-vinyl-pyridine;hydrochloride (2.5 g, 18.5 mmol) in DMSO (20.0 mL) was added Potassium carbonate (5.1 g, 36.99 mmol) and 4-bromo-3-methylpyrazole (3.6 g, 22.20 mmol) the mixture was stirred at 80° C. for 12 h. The mixture was filtered off, the filtrate was purified by Prep-HPLC (TFA as additive) to give 2-[2-(4-bromo-3-methyl-pyrazol-1-yl) ethyl]-6-methoxy-pyridine (2.0 g) as a yellow oil. MS [M+H]$^+$: 296.0.

Step 3: 2-(2-(4-(4-(benzyloxy)-2,3-difluorophenyl)-3-methyl-1H-pyrazol-1-yl)ethyl)-6-methoxypyridine To a solution of 2-[2-(4-bromo-3-methyl-pyrazol-1-yl) ethyl]-6-methoxy-pyridine (2.2 g, 6.36 mmol), Pd(dppf)$_2$Cl$_2$ (0.9 g, 0.70 mmol), 2-(4-benzyloxy-2,3-difluoro-phenyl)-4,4,5,5-tetramethyl-1,3,2-dioxaborolane (1.8 g, 6.08 mmol) and K$_2$CO$_3$ (1.8 g, 13.02 mmol) in 1,4-dioxane (10 mL) and water (3 mL) was stirred at 80° C. for 12 h. The reaction mixture was dried by vacuum, the residue was purified by column and dried by vacuum to obtain 2-[2-[4-(4-benzyloxy-2,3-difluoro-phenyl)-3-methyl-pyrazol-1-yl]ethyl]-6-methoxy-pyridine (1.7 g, 3.81 mmol, 62.6% yield) as off-white solid. MS [M+H]$^+$: 435.9.

Step 4: 2,3-difluoro-4-(1-(2-(6-methoxypyridin-2-yl)ethyl)-3-methyl-1H-pyrazol-4-yl)phenol A solution of 2-[2-[4-(4-benzyloxy-2,3-difluoro-phenyl)-3-methyl-pyrazol-1-yl]ethyl]-6-methoxy-pyridine (2.1 g, 4.82 mmol) and Pd/C (200.0 mg) in methanol (0.2 mL) was stirred at 25° C. for 2 h. It was filtered and dried by vacuum to get 2,3-difluoro-4-[1-[2-(6-methoxy-2-pyridyl)ethyl]-3-methyl-pyrazol-4-yl]phenol (560.0 mg) as off-white solid. MS [M+H]$^+$: 345.8.

Step 5: 2,3-difluoro-4-(1-(2-(6-methoxypyridin-2-yl)ethyl)-3-methyl-1H-pyrazol-4-yl)phenyl trifluoromethanesulfonate A mixture of 2,3-difluoro-4-[1-[2-(6-methoxy-2-pyridyl)ethyl]-3-methyl-pyrazol-4-yl]phenol (500.0 mg, 1.45 mmol) and pyridine (0.5 mL) in DCM (2.0 mL) was added trifluoromethanesulfonic anhydride (408.5 mg, 1.45 mmol) at 0° C., it was stirred at 0° C. for 2 h. The reaction mixture was poured into ice-water (50 mL), extracted by EA (50 mL), and dried by Na$_2$SO$_4$, the organic phase was concentrated under reduced pressure to obtian [2,3-difluoro-4-[1-[2-(6-methoxy-2-pyridyl)ethyl]-3-methyl-pyrazol-4-yl]phenyl] trifluoromethanesulfonate (803.0 mg, 1.68 mmol, 116.2% yield) as light yellow gum. MS [M+H]$^+$: 478.1.

Step 6: 2-(2-(4-(2,3-difluoro-4-(4,4,5,5-tetramethyl-1,3,2-dioxaborolan-2-yl)phenyl)-3-methyl-1H-pyrazol-1-yl)ethyl)-6-methoxypyridine A mixture of [2,3-difluoro-4-[1-[2-(6-methoxy-2-pyridyl)ethyl]-3-methyl-pyrazol-4-yl]phenyl]trifluoromethanesulfonate (600.0 mg, 2.36 mmol), bis(pinacolato)diboron (800.0 mg, 1.68 mmol), Pd(dppf)Cl$_2$ (200.0 mg, 0.25 mmol) and AcOK (400.0 mg, 4.08 mmol) in 1,4-dioxane (0.3 mL)

was stirred at 80° C. for 2 h. The reaction mixture was Prep-HPLC (FA) to obtain 2-[2-[4-[2,3-difluoro-4-(4,4,5,5-tetramethyl-1,3,2-dioxaborolan-2-yl)phenyl]-3-methyl-pyrazol-1-yl]ethyl]-6-methoxy-pyridine (402.0 mg). MS [M+H]⁺: 373.9.

Intermediate G78

2-[[4-[[4-[2,3-difluoro-4-(4,4,5,5-tetramethyl-1,3,2-dioxaborolan-2-yl)phenyl]-3-methyl-pyrazol-1-yl]methyl]triazol-1-yl]methoxy]ethyl-trimethyl-silane

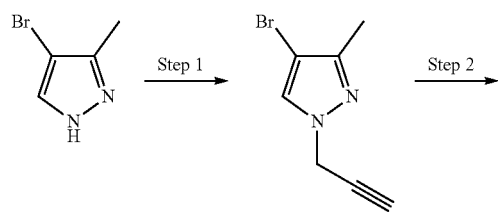

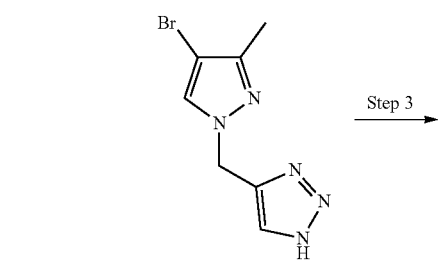

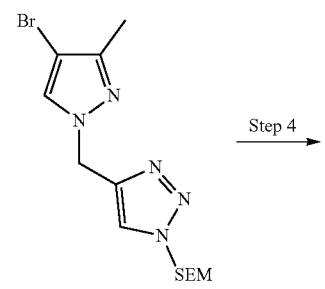

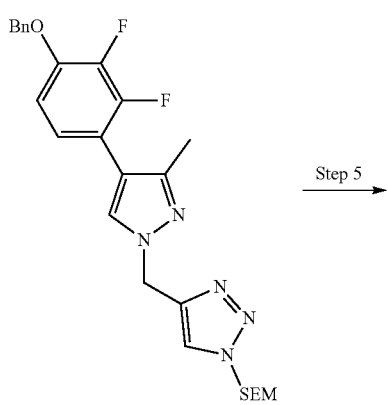

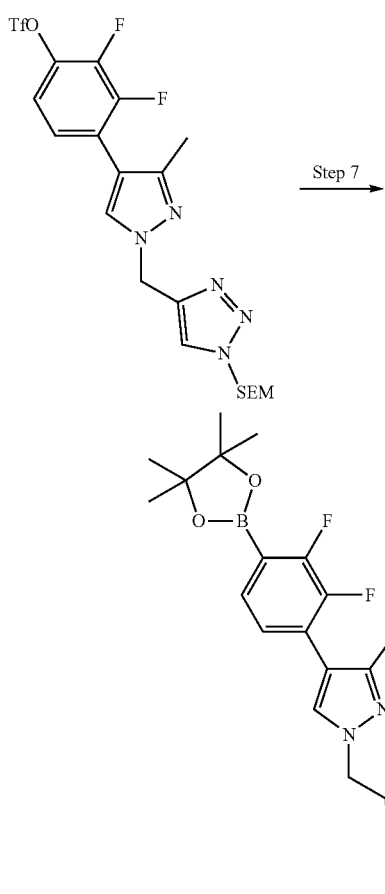

Intermediate G78

Step 1: 4-bromo-3-methyl-1-prop-2-ynyl-pyrazole

A mixture of propargyl bromide (11.1 g, 93.17 mmol) in NMP (100.0 mL) was addded 4-bromo-3-methyl-1H-pyrazole (10.0 g, 62.11 mmol) and potassium carbonate (17.2 g, 124.22 mmol), The mixture was stirred at 100° C. for 16 h. This reaction mixture was poured into water (300 mL) and EtOAc (200 mL) and was washed by brine (200 mL×2). The organic layer was dried over Na₂SO₄ and concentrated to give crude product which was further purified by prep-HPLC(FA) to get the mixture of 4-bromo-3-methyl-1-prop-2-ynyl-pyrazole (2) (8.0 g). MS [M+H]⁺: 198.7.

Step 2: 4-[(4-bromo-3-methyl-pyrazol-1-yl)methyl]-1H-triazole

A mixture of 4-bromo-3-methyl-1-prop-2-ynyl-pyrazole (5.0 g, 25.12 mmol) in azidotrimethylsilane (33.3 mL, 251.19 mmol) was stirred at 100° C. for 16 h. This reaction mixture was diluted with EtOAc (100 mL) and was washed by saturated aqueous Na$_2$CO$_3$ (200 mL×2). The organic layer was dried over Na$_2$SO$_4$ and concentrated to give crude product which was further purified by prep-HPLC (FA) to give a mixture of isomers which was further purified by chiral separation to get 4-[(4-bromo-3-methyl-pyrazol-1-yl)methyl]-1H-triazole (1.7 g). MS [M+H]$^+$: 242.0.

Step 3: 2-[[4-[(4-bromo-3-methyl-pyrazol-1-yl)methyl]triazol-1-yl]methoxy]ethyl-trimethyl-silane To a solution of 4-[(4-bromo-3-methyl-pyrazol-1-yl)methyl]-1H-triazole (1.6 g, 6.61 mmol) in DMF (20 mL) was added NaH (396.6 mg, 9.91 mmol) and 2-(trimethylsilyl) ethoxymethyl chloride (1.2 mL, 6.94 mmol) at 0° C., The mixture was stirred at 25° C. for 12 h under N$_2$. The reaction mixture was quenched by (30 mL) NH$_4$Cl (aq), extracted with EtOAc (80 mL×3), the organic phase was washed with brine (50 mL×2), dried over anhydrous Na$_2$SO$_4$ and concentrated in vacuum to give 2-[[4-[(4-bromo-3-methyl-pyrazol-1-yl)methyl]triazol-1-yl]methoxy]ethyl-trimethyl-silane (2200.0 mg). MS [M+H]$^+$: 372.0.

Step 4: 2-[[4-[[4-(4-benzyloxy-2,3-difluoro-phenyl)-3-methyl-pyrazol-1-yl]methyl]triazol-1-yl]methoxy]ethyl-trimethyl-silane A mixture of 2-[[4-[(4-bromo-3-methyl-pyrazol-1-yl)methyl]triazol-1-yl]methoxy]ethyl-trimethyl-silane (1300.0 mg, 3.49 mmol), 2-(4-benzyloxy-2,3-difluoro-phenyl)-4,4,5,5-tetramethyl-1,3,2-dioxaborolane (1208.7 mg, 3.49 mmol), Na$_2$CO$_3$ (740.1 mg, 6.98 mmol) and Pd(dppf)Cl$_2$ (307.6 mg, 0.35 mmol) in a flask. The flask was degassed and purged with N$_2$ gas for four times. 1,4-dioxane (15.0 mL) and water (2.0 mL) was added by injector to the mixture. The mixture was stirred at 80° C. for 2 h under N$_2$. The reaction mixture was filterrd and the filtrate was concentrated under reduced pressure to remove the solvent, then the product was purified by chromatography column flash (petroleum/EtOAc=20/1-1/1) and concentrated to give 2-[[4-[[4-(4-benzyloxy-2,3-difluoro-phenyl)-3-methyl-pyrazol-1-yl]methyl]triazol-1-yl]methoxy]ethyl-trimethyl-silane (1.7 g). MS [M+H]$^+$: 512.2.

Step 5: 2,3-difluoro-4-[3-methyl-1-[[1-(2-trimethylsilylethoxymethyl)triazol-4-yl]methyl]pyrazol-4-yl]phenol To a solution of 2-[[4-[[4-(4-benzyloxy-2,3-difluoro-phenyl)-3-methyl-pyrazol-1-yl]methyl]triazol-1-yl]methoxy]ethyl-trimethyl-silane (1.65 g, 3.22 mmol) in methanol (20.0 mL) was added Pd/C (300.0 mg) under N$_2$. The suspension was degassed under vacuum and purged with H$_2$ several times at 20° C. for 2 h. The reaction mixture was filterrd and the filtrate was concentrated under reduced pressure to give 2,3-difluoro-4-[3-methyl-1-[[1-(2-trimethylsilylethoxymethyl)triazol-4-yl]methyl]pyrazol-4-yl]phenol (1.35 g). MS [M+H]$^+$: 422.1.

Step 6: [2,3-difluoro-4-[3-methyl-1-[[1-(2-trimethylsilylethoxymethyl)triazol-4-yl]methyl]pyrazol-4-yl]phenyl] trifluoromethanesulfonate A solution of 2,3-difluoro-4-[3-methyl-1-[[1-(2-trimethylsilylethoxymethyl)triazol-4-yl]methyl]pyrazol-4-yl]phenol (1.3 g, 3.08 mmol) in pyridine (15.0 mL) was added trifluoromethanesulfonic anhydride (1.0 mL, 6.17 mmol) under 0° C., The reaction was stirred at 20° C. for 2 h. The mixture was poured into ice water (20 mL) and extracted with EtOAc (50 mL×2). The mixture was combined and washed with brine (20 mL). The organic layer was dried and concentrated under vacuum to give [2,3-difluoro-4-[3-methyl-1-[[1-(2-trimethylsilylethoxymethyl)triazol-4-yl]methyl]pyrazol-4-yl]phenyl] trifluoromethanesulfonate (1700.0 mg). MS [M+H]$^+$: 554.0.

Step 7: 2-[[4-[[4-[2,3-difluoro-4-(4,4,5,5-tetramethyl-1,3,2-dioxaborolan-2-yl)phenyl]-3-methyl-pyrazol-1-yl]methyl]triazol-1-yl]methoxy]ethyl-trimethyl-silane A mixture of 4,4,5,5-tetramethyl-2-(4,4,5,5-tetramethyl-1,3,2-dioxaborolan-2-yl)-1,3,2-dioxaborolane (908.3 mg, 3.58 mmol), Pd(dppf)Cl$_2$ (243.2 mg, 0.30 mmol), [2,3-difluoro-4-[3-methyl-1-[[1-(2-trimethylsilylethoxymethyl)triazol-4-yl]methyl]pyrazol-4-yl]phenyl]trifluoromethanesulfonate (1650.0 mg, 2.98 mmol) and potassium acetate (585.1 mg, 5.96 mmol) in a flask. 1,4-dioxane (20 mL) was added by injector to the mixture. The flask was degassed and purged with N$_2$ gas for four times. The mixture was stirred at 80° C. for 2 h under N$_2$ atmosphere. The reaction mixture was filterrd and the filtrate was concentrated under reduced pressure to remove the solvent, then the product was purified by reversed-phase chromatography (FA as additive) to give 2-[[4-[[4-[2,3-difluoro-4-(4,4,5,5-tetramethyl-1,3,2-dioxaborolan-2-yl)phenyl]-3-methyl-pyrazol-1-yl]methyl]triazol-1-yl]methoxy]ethyl-trimethyl-silane (800.0 mg). MS [M+H]$^+$: 532.3.

Intermediate G79

[2-fluoro-6-[1-(2-methoxyethyl)-5-methyl-pyrazol-4-yl]-3-pyridyl]boronic acid

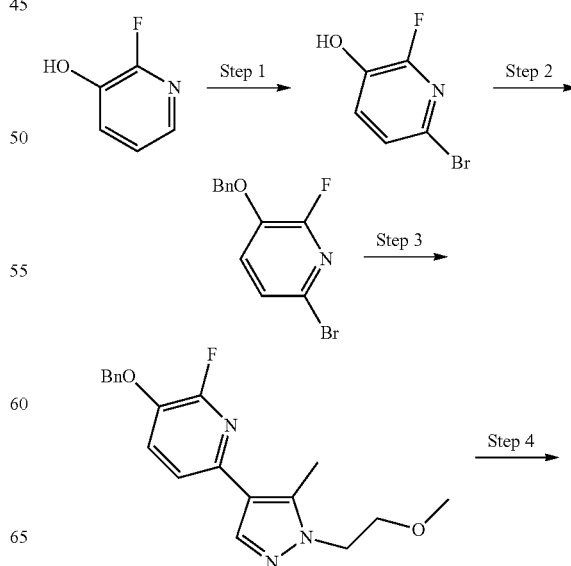

-continued

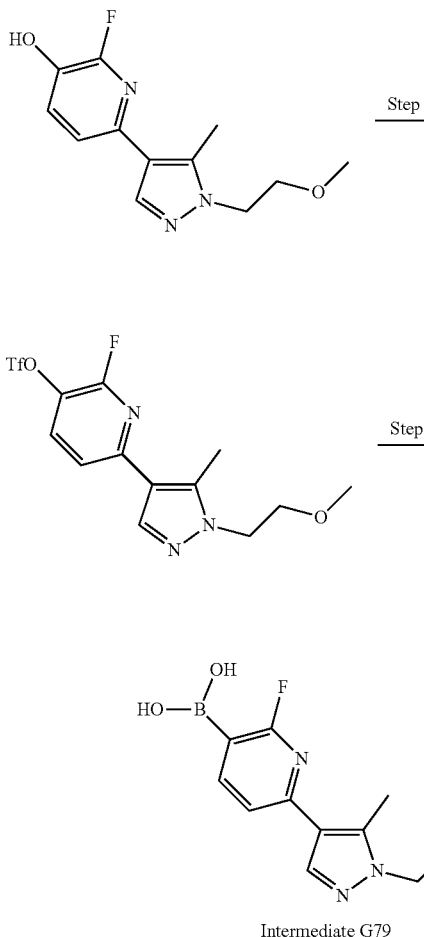

Intermediate G79

Step 1: 6-bromo-2-fluoropyridin-3-ol

To a solution of 2-fluoropyridin-3-ol (2.5 g, 22.11 mmol) in acetic acid (25 mL) was added sodium acetate (1.67 mL, 22.11 mmol), after the solid was dissolved, bromine (3.5 g, 22.11 mmol) was added by drops at 0° C., then the mixture was stirred at 20° C. for 3 h. The reaction mixture was poured into ice-water, it was extracted by EtOAc (2×200 mL). The reaction mixture was washed by 100 mL solution of sodium sulfite in water, and then organid layer was dried in vacuum to give 6-bromo-2-fluoro-pyridin-3-ol (3.15 g). MS [M+H]$^+$: 191.6.

Step 2: 3-(benzyloxy)-6-bromo-2-fluoropyridine

A solution of 6-bromo-2-fluoro-pyridin-3-ol (3.1 g, 16.15 mmol, 1.0 eq), benzyl bromide (1.95 mL, 16.37 mmol, 1.0 eq) and K$_2$CO$_3$ (3.1 g, 22.43 mmol, 1.39 eq) in ACN (30 mL) was stirred at 25° C. for 12 h. The reation mixture was filtred and washed by EtOAc (100 mL), then the filter was washed by brine (2×200 mL), it was dried by vacuum to obtain 3-benzyloxy-6-bromo-2-fluoro-pyridine (4.1 g). MS [M+H]$^+$: 281.6.

Step 3: 3-(benzyloxy)-2-fluoro-6-(1-(2-methoxyethyl)-5-methyl-1H-pyrazol-4-yl)pyridine To a solution of 3-benzyloxy-6-bromo-2-fluoro-pyridine (1.0 g, 3.54 mmol), 1-(2-methoxyethyl)-5-methyl-4-(4,4,5,5-tetramethyl-1,3,2-dioxaborolan-2-yl)pyrazole (1.0 g, 3.76 mmol) in 1,4-dioxane (10 mL) and water (3 mL) was added Pd(dppf)Cl$_2$ (300.0 mg, 0.37 mmol) and Na$_2$CO$_3$ (0.8 g, 7.55 mmol). The reaction mixture was stirred at 80° C. for 2 h. The reaction mixture was purified by Pre-HPLC (FA as additive) and dried by vacuum to obtain 3-benzyloxy-2-fluoro-6-[1-(2-methoxyethyl)-5-methyl-pyrazol-4-yl]pyridine (340 mg). MS [M+H]$^+$: 342.1.

Step 4: 2-fluoro-6-(1-(2-methoxyethyl)-5-methyl-1H-pyrazol-4-yl)pyridin-3-ol A solution of 3-benzyloxy-2-fluoro-6-[1-(2-methoxyethyl)-5-methyl-pyrazol-4-yl]pyridine (320.0 mg, 0.94 mmol) and Pd/C (100.0 mg) in methanol (0.5 mL) was stirred at 25° C. for 12 h under H$_2$ balloon. The reaction mixture was filtered and it was dried by vacuum to obtain 2-fluoro-6-[1-(2-methoxyethyl)-5-methyl-pyrazol-4-yl]pyridin-3-ol (236.0 mg). MS [M+H]$^+$: 251.8.

Step 5: 2-fluoro-6-(1-(2-methoxyethyl)-5-methyl-1H-pyrazol-4-yl)pyridin-3-yl trifluoromethanesulfonate A mixture of 2-fluoro-6-[1-(2-methoxyethyl)-5-methyl-pyrazol-4-yl]pyridin-3-ol (300.0 mg, 1.19 mmol) in pyridine (1.0 mL) was added trifluoromethanesulfonic anhydride (336.8 mg, 1.19 mmol) at 0° C., The reaction mixture was stirred at 0° C. for 2 h. This reaction mixture was poured into ice-water (50 mL), it was extracted by EA (50 mL), organic layer was dried over Na$_2$SO$_4$, filtered and then evaporated to give [2-fluoro-6-[1-(2-methoxyethyl)-5-methyl-pyrazol-4-yl]-3-pyridyl]trifluoromethanesulfonate (320.0 mg). MS [M+H]$^+$: 383.8.

Step 6: [2-fluoro-6-[1-(2-methoxyethyl)-5-methyl-pyrazol-4-yl]-3-pyridyl]boronic acid A mixture of 4,4,5,5-tetramethyl-2-(4,4,5,5-tetramethyl-1,3,2-dioxaborolan-2-yl)-1,3,2-dioxaborolane (260.0 mg, 1.02 mmol), [2-fluoro-6-[1-(2-methoxyethyl)-5-methyl-pyrazol-4-yl]-3-pyridyl]trifluoromethanesulfonate (320.0 mg, 0.83 mmol), Pd(dppf)Cl$_2$ (96.0 mg, 0.12 mmol) and KOAc (200.0 mg, 2.06 mmol) in 1,4-dioxane (5 mL) was stirred at 80° C. for 2 h. The reaction mxiture was purified by Pre-HPLC (FA) and dried by vacuum to obtain [2-fluoro-6-[1-(2-methoxyethyl)-5-methyl-pyrazol-4-yl]-3-pyridyl]boronic acid (126.0 mg). MS [M+H]$^+$: 279.8.

The following examples were prepared in analogy to Intermediate G79.

| Ex # | Name | Structure | MS ESI [M + H]+ | Starting Material |
|---|---|---|---|---|
| Intermediate G81 | 2-[[4-[6-fluoro-5-(4,4,5,5-tetramethyl-1,3,2-dioxaborolan-2-yl)-2-pyridyl]pyrazol-1-yl]methoxy]ethyl-trimethyl-silane | 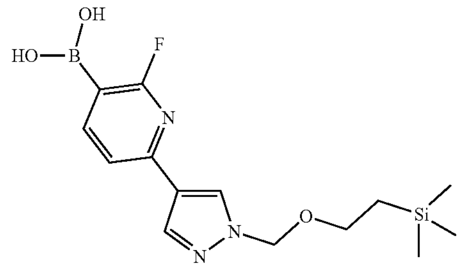 [SMILES: C[Si](C)(C)CCOCn1cc(-c2ccc(B(O)O)c(F)n2)cn1] | 338.2 | 2-fluoropyridin-3-ol and trimethyl-[2-[[4-(4,4,5,5-tetramethyl-1,3,2-dioxaborolan-2-yl)pyrazol-1-yl]methoxy]ethyl]silane; bis(pinacolato)diboron |
| Intermediate G91 | 2-fluoro-6-[1-(2-methoxyethyl)-3,5-dimethyl-pyrazol-4-yl]-3-(4,4,5,5-tetramethyl-1,3,2-dioxaborolan-2-yl)pyridine | 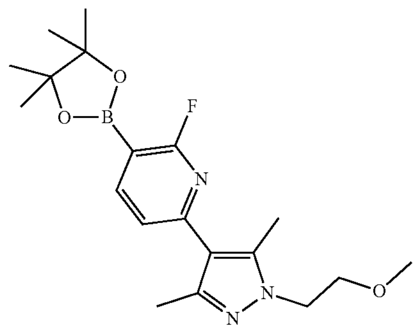 | 293.8 | 2-fluoropyridin-3-ol and 1-(2-methoxyethyl)-3,5-dimethyl-4-(4,4,5,5-tetramethyl-1,3,2-dioxaborolan-2-yl)pyrazole; bis(pinacolato)diboron |

Intermediate G86

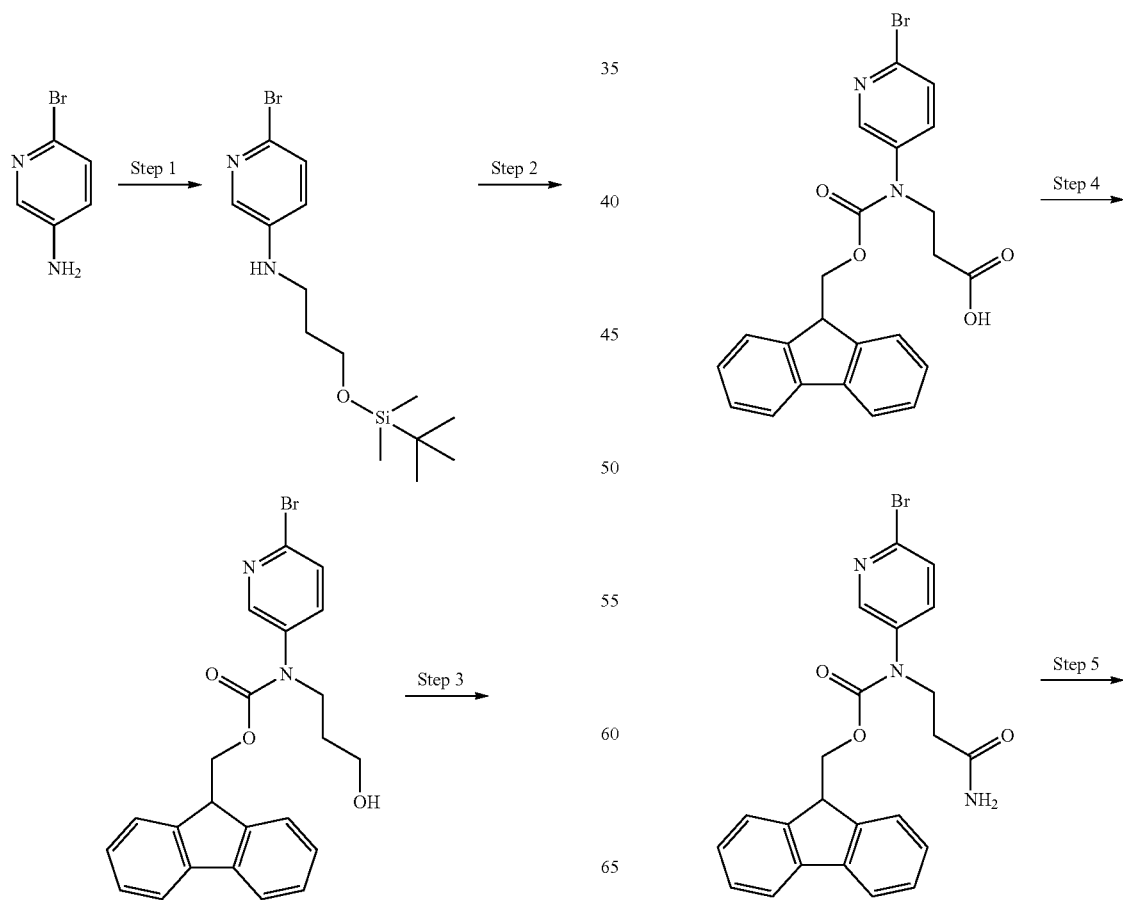

205
-continued

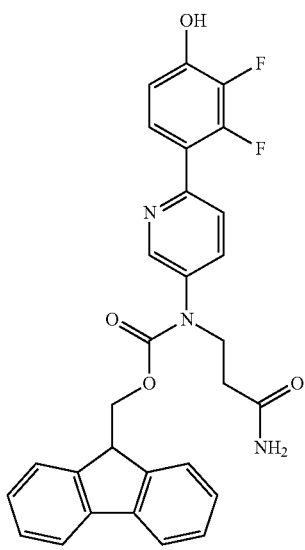

Step 6 →

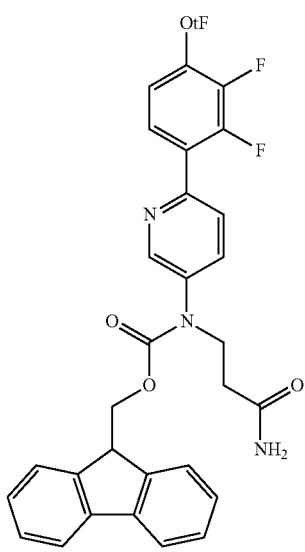

Step 7 →

206
-continued

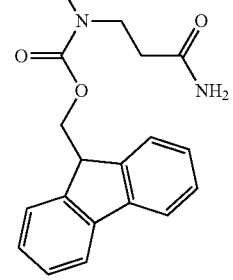

Intermediate G86

Step 1: (6-bromo-3-pyridyl)-[3-[tert-butyl(dimethyl) silyl]oxypropyl]amine (6-bromo-3-pyridyl)amine (2.45 g, 14.16 mmol), 3-[tert-butyl(dimethyl)silyl]oxypropion-aldehyde (2.67 g, 14.16 mmol) and acetic acid (170.07 mg, 2.83 mmol) were dissolved in dichloromethane (50 mL). To this solution was added sodium triacetoxyborohydride (3.6 g, 16.99 mmol) portionwise. The mixture was stirred at rt for 1 h after addition. The mixture was poured into 100 mL water and extracted with DCM (50 mL×2). The extracts were combined, washed with brine and dried over sodium sulfate. The solvent was removed in vacuum and the residue was purified by flash chromatography (silica gel; EtOAc:PE=0:1 to 1:1). To afford (6-bromo-3-pyridyl)-[3-[tert-butyl(dimethyl)silyl]oxypropyl]amine (3 g). MS [M+H]$^+$: 345.6.

Step 2: N-(6-bromo-3-pyridyl)-N-(3-hydroxypropyl) carbamic acid 9H-fluoren-9-ylmethyl ester (6-bromo-3-pyridyl)-[3-[tert-butyl(dimethyl)silyl]oxypropyl]amine (3.00 g, 8.69 mmol) was dissolved in 5 mL toluene and this solution was added dropwise to a solution of chlorocarbonic acid 9H-fluoren-9-ylmethyl ester (2.25 g, 8.69 mmol) in anhydrous toluene, extra dry (20 mL) at 0° C. After addition, the mixture was stirred at 0° C. for 1 h and then at rt for another 1 h. yellow precipitate formed. The mixture was left overnight. The solvent was removed in vacuum, and the residue was purified by flash chromatography (silica gel; EtOAc:PE=0:1 to 1:0). To afford N-(6-bromo-3-pyridyl)-N-(3-hydroxypropyl)carbamic acid 9H-fluoren-9-ylmethyl ester (2 g). MS [M+H]$^+$: 453.1.

Step 3: 3-[(6-bromo-3-pyridyl)-(9H-fluoren-9-yl-methoxycarbonyl)amino]propionic acid iodobenzene diacetate (703.41 mg, 2.18 mmol), TEMPO (62.44 mg, 0.397 mmol) and N-(6-bromo-3-pyridyl)-N-(3-hydroxypropyl)carbamic acid 9H-fluoren-9-ylmethyl ester (900 mg, 1.99 mmol) were combined in a reaction vessel, and to this mixture was added acetonitrile (10.99 mL) and water (5.99 mL). The reaction mixtures were stirred for 3 h before another batch of iodobenzene diacetate (703.41 mg, 2.18 mmol) was added. The stirring was continued 18 h. The solvent was removed in vacuo and the residue was purified by flash chromatography (silica gel; EtOAc:PE=0:1 to 1:0), to afford 3-[(6-bromo-3-pyridyl)-(9H-fluoren-9-ylmethoxycarbonyl)amino]propionic acid (778 mg). MS [M+H]$^+$: 467.1.

Step 4: N-(3-amino-3-keto-propyl)-N-(6-bromo-3-pyridyl)carbamic acid 9H-fluoren-9-ylmethyl ester 3-[(6-bromo-3-pyridyl)-(9H-fluoren-9-ylmethoxycarbonyl)amino]propionic acid (770 mg, 1.65 mmol), ammonium chloride (176.27 mg, 3.3 mmol) and DIEA (1.06 g, 8.24 mmol) were stirred in N,N-dimethylacetamide (27.11 mL) for 1 min. HATU (751.82 mg, 1.98 mmol) was added to the mixture, and the resulting solution was stirred at 25° C. for 1 h. The mixture was poured into 100 mL water and extracted with EtOAc (50 mL×3). The extracts were combined, washed with 50 mL brine, dried over sodium sulfate and concentrated in vacuum. The residue was purified by flash chromatography (silica gel; EtOAc:PE=0:1 to 1:0), to afford N-(3-amino-3-keto-propyl)-N-(6-bromo-3-pyridyl)carbamic acid 9H-fluoren-9-ylmethyl ester (725 mg). MS [M+H]$^+$: 466.2.

Step 5: N-(3-amino-3-keto-propyl)-N-[6-(2,3-difluoro-4-hydroxy-phenyl)-3-pyridyl]carbamic acid 9H-fluoren-9-ylmethyl ester In a microwave tube were placed N-(3-amino-3-keto-propyl)-N-(6-bromo-3-pyridyl)carbamic acid 9H-fluoren-9-ylmethyl ester (400 mg, 0.858 mmol), palladiumtetrakis (99.12 mg, 0.086 mmol), Na$_2$CO$_3$ (272.74 mg, 2.57 mmol) and (2,3-difluoro-4-hydroxy-phenyl)boronic acid (223.76 mg, 1.29 mmol) in water (0.351 mL) and 1,4-dioxane (3.51 mL). The vial was sealed with a rubber septum, evacuated and backfilled with nitrogen for 5 times. The mixture was then heated at 100° C. for 0.5 h. The mixture was cooled to rt, 100-200 mesh silica gel was added to absorb the material. The loaded sample was purified by flash chromatography (silica gel; MeOH:DCM=0:1 to 1:10), to afford N-(3-amino-3-keto-propyl)-N-[6-(2,3-difluoro-4-hydroxy-phenyl)-3-pyridyl]carbamic acid 9H-fluoren-9-ylmethyl ester (166 mg). MS [M+H]$^+$: 516.8.

Step 6: trifluoromethanesulfonic acid [4-[5-[(3-amino-3-keto-propyl)-(9H-fluoren-9-ylmethoxycarbonyl)amino]-2-pyridyl]-2,3-difluoro-phenyl] ester N-(3-amino-3-keto-propyl)-N-[6-(2,3-difluoro-4-hydroxy-phenyl)-3-pyridyl]carbamic acid 9H-fluoren-9-ylmethyl ester (165 mg, 0.320 mmol) and pyridine (75.95 mg, 0.960 mmol) were dissolved in anhydrous dichloromethane, extra dry (3.3 mL). Tf$_2$O (108.37 mg, 0.384 mmol) was added dropwise at 0° C. The solution was stirred at the same temperature for 1 h. 100-200 mesh silica gel was added to absorb the material. The loaded sample was purified by flash chromatography (silica gel; EtOAc:PE=0:1 to 1:0), to afford trifluoromethanesulfonic acid [4-[5-[(3-amino-3-keto-propyl)-(9H-fluoren-9-ylmethoxycarbonyl)amino]-2-pyridyl]-2,3-difluoro-phenyl] ester (168 mg). MS [M+H]$^+$: 648.3.

Step 7: N-(3-amino-3-keto-propyl)-N-[6-[2,3-difluoro-4-(4,4,5,5-tetramethyl-1,3,2-dioxaborolan-2-yl)phenyl]-3-pyridyl]carbamic acid 9H-fluoren-9-ylmethyl ester trifluoromethanesulfonic acid [4-[5-[(3-amino-3-keto-propyl)-(9H-fluoren-9-ylmethoxycarbonyl)amino]-2-pyridyl]-2,3-difluoro-phenyl] ester (165 mg, 0.255 mmol), 1,1'-bis(diphenylphosphino)ferrocene-palladium(II)dichloride dichloromethane complex (21.06 mg, 0.025 mmol), bis(pinacolato)diboron (77.64 mg, 0.306 mmol) and potassium acetate (75.02 mg, 0.764 mmol) were placed in 1,4-dioxane, extra dry (3.61 mL) in a microwave tube. The tube was sealed with a rubber septum, evacuated and backfilled with nitrogen for 5 times. The mixture was heated at 100° C. for 1 h. The mixture was cooled to rt and absorbed to 100-200 mesh silica gel. The loaded sample was purified by flash chromatography (silica gel; MeOH:DCM=0:1 to 1:10), to afford N-(3-amino-3-keto-propyl)-N-[6-[2,3-difluoro-4-(4,4,5,5-tetramethyl-1,3,2-dioxaborolan-2-yl)phenyl]-3-pyridyl]carbamic acid 9H-fluoren-9-ylmethyl ester (90 mg). MS [M+H]$^+$: 648.3.

The following examples were prepared in analogy to Intermediate G86.

| Ex # | Name | Structure | MS ESI [M + H]+ | Starting Material |
|---|---|---|---|---|
| Intermediate G87 | 9H-fluoren-9-ylmethyl N-[6-[2,3-difluoro-4-(4,4,5,5-tetramethyl-1,3,2-dioxaborolan-2-yl)phenyl]-5-methyl-3-pyridyl]carbamate | 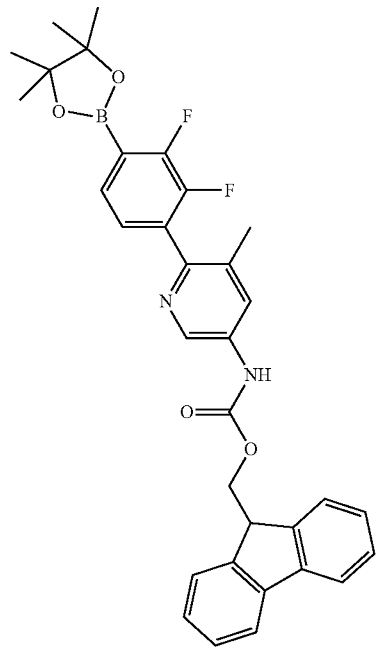 [SMILES: Cc1cc(NC(=O)OCC2c3ccccc3-c3ccccc32)cnc1-c1ccc(B2OC(C)(C)C(C)(C)O2)c(F)c1F] | 569.1 | 6-bromo-5-methyl-pyridin-3-amine and 9H-fluoren-9-ylmethyl carbonochloridate; (2,3-difluoro-4-hydroxy-phenyl)boronic acid; bis(pinacolato) diboron |
| Intermediate G88 | 9H-fluoren-9-ylmethyl N-[6-[2,3-difluoro-4-(4,4,5,5-tetramethyl-1,3,2-dioxaborolan-2-yl)phenyl]-3-pyridyl]carbamate | 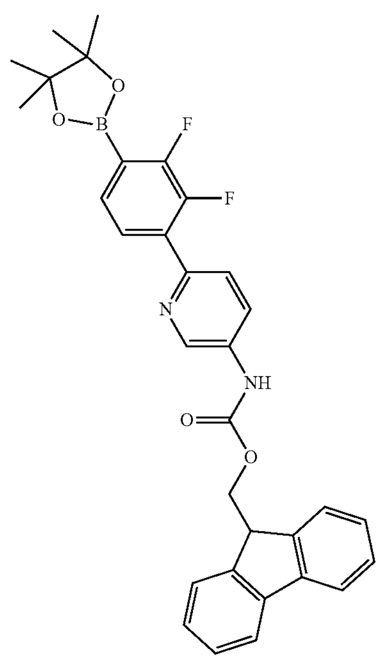 [SMILES: CC1(C)OB(c2ccc(-c3ccc(NC(=O)OCC4c5ccccc5-c5ccccc54)cn3)c(F)c2F)OC1(C)C] | 555.2 | 6-bromopyridin-3-amine and 9H-fluoren-9-ylmethyl carbonochloridate; (2,3-difluoro-4-hydroxy-phenyl)boronic acid; bis(pinacolato) diboron |

Intermediate H1
N-[3-chloro-4-[4-(piperidine-4-carbonyl)piperazine-1-carbonyl]phenyl]-5-[2,3-difluoro-4-[1-(2-methoxyethyl)-3-methyl-pyrazol-4-yl]phenyl]-1-methyl-imidazole-2-carboxamide
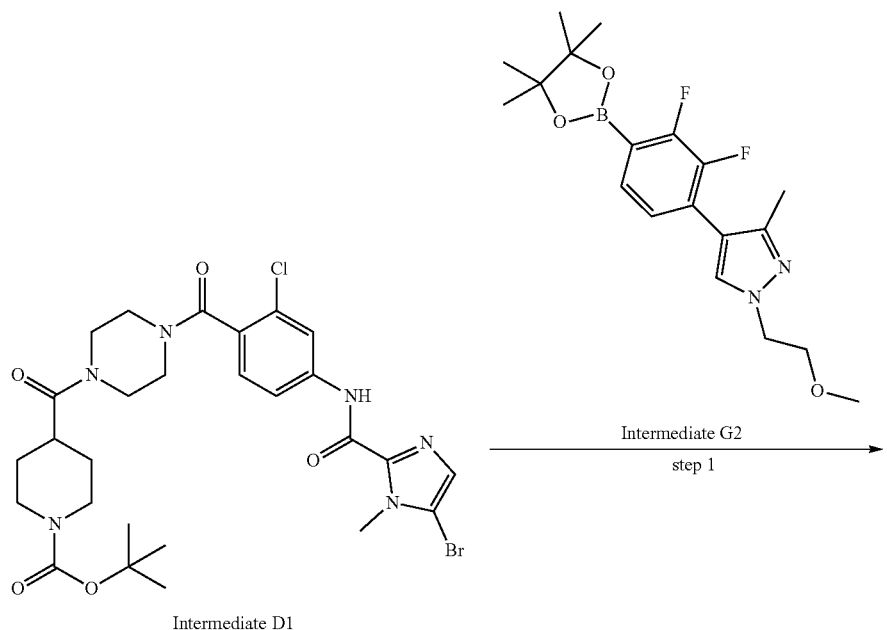
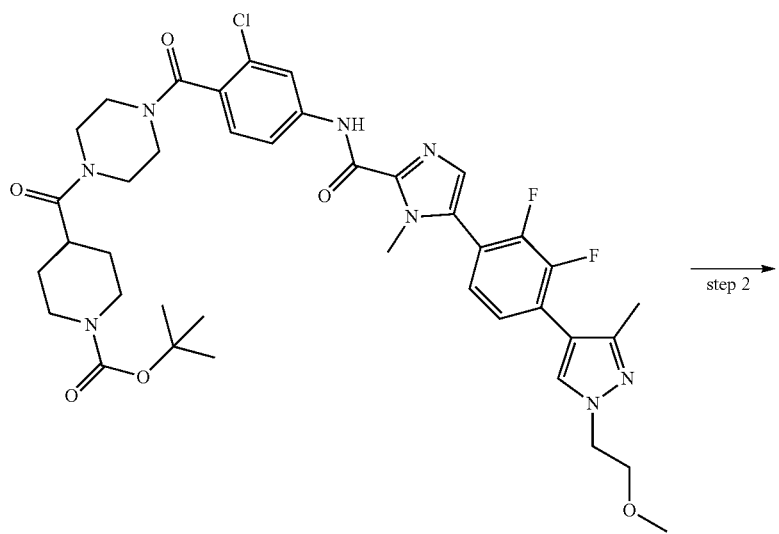

-continued

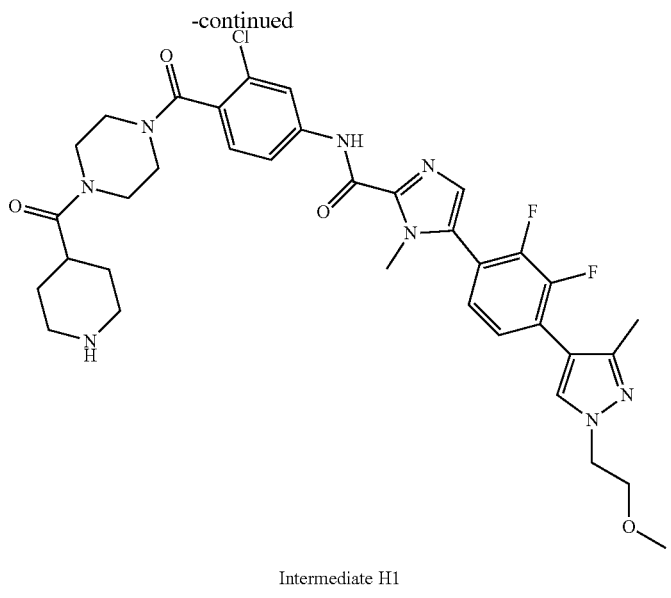

Intermediate H1

1: tert-butyl 4-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]piperidine-1-carboxylate To a 25 mL microwave vial was added tert-butyl 4-[4-[4-[(5-bromo-1-methyl-imidazole-2-carbonyl)amino]-2-chloro-benzoyl] piperazine-1-carbonyl]piperidine-11-carboxylate (180 mg, 282 μmol), 4-[2,3-difluoro-4-(4,4,5,5-tetramethyl-1,3,2-dioxaborolan-2-yl)phenyl]-1-(2-methoxyethyl)-3-methyl-pyrazole (160 mg, 423 μmol), 1,1'-bis(di-tert-butylphosphino)ferrocene palladium dichloride (18.4 mg, 28.2 μmol) and Na$_2$CO$_3$ (89.7 mg, 846 μmol) in 1,4-Dioxane (15 mL)/Water (1.5 mL). The vial was capped and heated in the microwave at 100° C. for 3 h under N$_2$. The reaction mixture was filtered through glass fiber paper. The filtrate was concentrated in vacuum. The crude material was purified by flash chromatography to afford tert-butyl 4-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]piperidine-1-carboxylate (150 mg). MS [M+H]$^+$: 809.5.

Step 2: N-[3-chloro-4-[4-(piperidine-4-carbonyl)piperazine-1-carbonyl]phenyl]-5-[2,3-difluoro-4-[1-(2-methoxyethyl)-3-methyl-pyrazol-4-yl]phenyl]-1-methyl-imidazole-2-carboxamide In a 50 mL round-bottomed flask, tert-butyl 4-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]piperidine-1-carboxylate (150 mg, 185 μmol) was combined with THE (2 mL) to give a light brown solution. HCl water solution (1.24 mL, 14.8 mmol) was added. The reaction was stirred at room temperature for 1 h. The crude reaction mixture was concentrated in vacuum. The crude product was directly used to the next step to afford N-[3-chloro-4-[4-(piperidine-4-carbonyl)piperazine-1-carbonyl]phenyl]-5-[2,3-difluoro-4-[1-(2-methoxyethyl)-3-methyl-pyrazol-4-yl]phenyl]-1-methyl-imidazole-2-carboxamide (131 mg). MS [M+H]$^+$: 709.3.

The following intermediates were prepared in analogy to Intermediate H1.

| Ex # | Name | Structure | MS ESI [M + H]$^+$ | Starting Material |
|---|---|---|---|---|
| Intermediate H2 | N-[3-chloro-4-[4-(piperidine-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide | 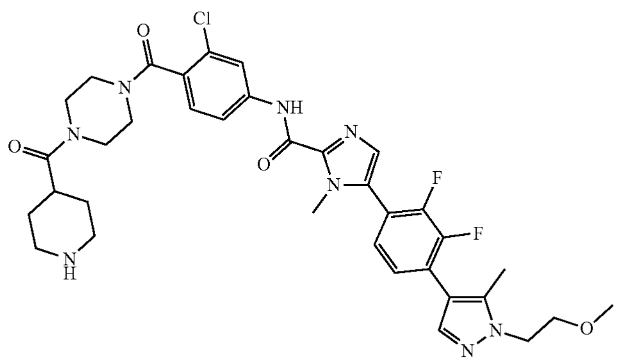 [SMILES: COCCn1ncc(-c2ccc(-c3cnc(C(=O)Nc4ccc(C(=O)N5CCN(C(=O)C6CCNCC6)CC5)c(Cl)c4)n3C)c(F)c2F)c1C] | 709.3 | Intermediate D1 and Intermediate G3; HCl |

-continued

| Ex # | Name | Structure | MS ESI [M + H]+ | Starting Material |
|---|---|---|---|---|
| Intermediate H3 | N-[3-chloro-4-[4-(piperidine-4-carbonyl)piperazine-1-carbonyl]phenyl]-5-[4-[1-(2,2-difluoroethyl)-3-methyl-pyrazol-4-yl]-2,3-difluoro-phenyl]-1-methyl-imidazole-2-carboxamide | 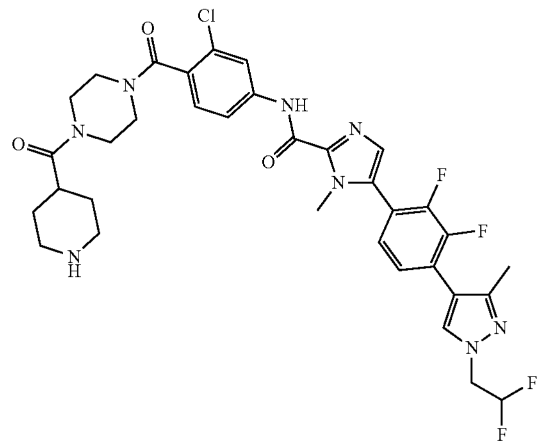 [SMILES: Cc1nn(CC(F)F)cc1-c1ccc(-c2cnc(C(=O)Nc3ccc(C(=O)N4CCN(C(=O)C5CCNCC5)CC4)c(Cl)c3)n2C)c(F)c1F] | 715.8 | Intermediate D1 and Intermediate G5; HCl |
| Intermediate H4 | N-[3-chloro-4-[4-(piperidine-4-carbonyl)piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide | 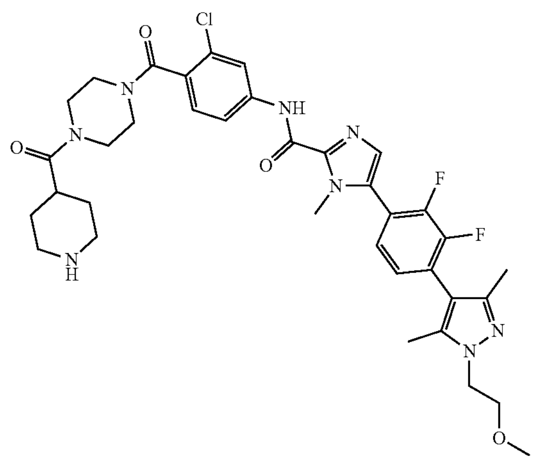 [SMILES: COCCn1nc(C)c(-c2ccc(-c3cnc(C(=O)Nc4ccc(C(=O)N5CCN(C(=O)C6CCNCC6)CC5)c(Cl)c4)n3C)c(F)c2F)c1C] | 723.7 | Intermediate D1 and Intermediate G6; HCl |
| Intermediate H5 | N-[3-chloro-4-[4-(piperidine-4-carbonyl)piperazine-1-carbonyl]phenyl]-5-[4-[1-(2-methoxyethyl)-3,5-dimethyl-pyrazol-4-yl]phenyl]-1-methyl-imidazole-2-carboxamide | 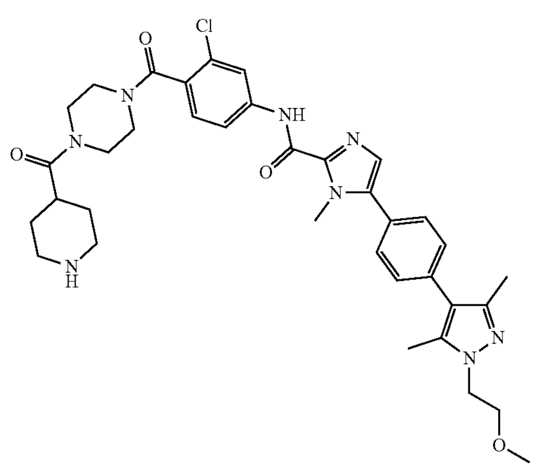 [SMILES: COCCn1nc(C)c(-c2ccc(-c3cnc(C(=O)Nc4ccc(C(=O)N5CCN(C(=O)C6CCNCC6)CC5)c(Cl)c4)n3C)cc2)c1C] | 687.3 | Intermediate D1 and Intermediate G7; HCl |

| Ex # | Name | Structure | MS ESI [M + H]+ | Starting Material |
|---|---|---|---|---|
| Intermediate H6 | N-[3-chloro-4-[4-(piperazine-1-carbonyl)piperidine-1-carbonyl]phenyl]-5-[2,3-difluoro-4-[1-(2-methoxyethyl)-5-methyl-pyrazol-4-yl]phenyl]-1-methyl-imidazole-2-carboxamide | 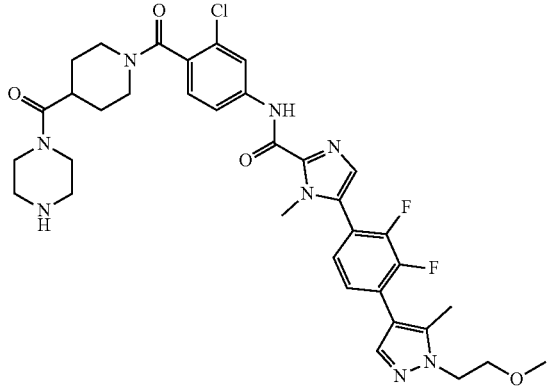 [SMILES: COCCn1ncc(-c2ccc(-c3cnc(C(=O)Nc4ccc(C(=O)N5CCC(C(=O)N6CCNCC6)CC5)c(Cl)c4)n3C)c(F)c2F)c1C] | 709.6 | Intermediate D7 and Intermediate G3; HCl |
| Intermediate H7 | 5-[2-chloro-3-fluoro-4-[1-(2-methoxyethyl)-5-methyl-pyrazol-4-yl]phenyl]-N-[3-chloro-4-(piperazine-1-carbonyl)phenyl]-1-methyl-imidazole-2-carboxamide | 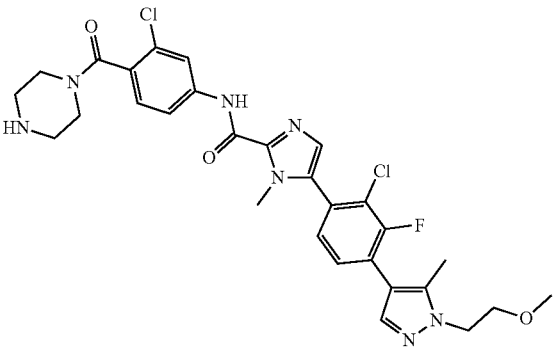 [SMILES: COCCn1ncc(-c2ccc(-c3cnc(C(=O)Nc4ccc(C(=O)N5CCNCC5)c(Cl)c4)n3C)c(Cl)c2F)c1C] | 613.2 | Intermediate A1 and Intermediate G11; HCl |
| Intermediate H8 | N-[3-chloro-4-(piperazine-1-carbonyl)phenyl]-5-[2,3-difluoro-4-[1-(2-methoxyethyl)-5-methyl-pyrazol-4-yl]phenyl]-1-methyl-imidazole-2-carboxamide | 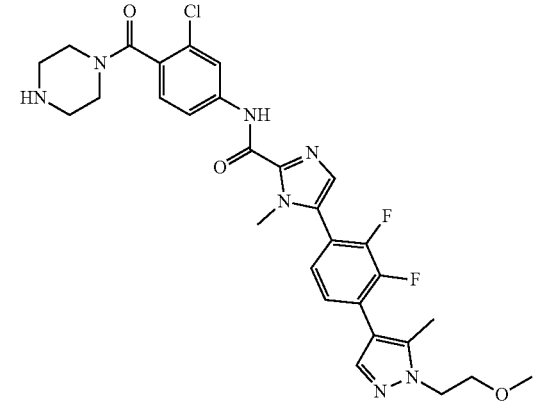 [SMILES: COCCn1ncc(-c2ccc(-c3cnc(C(=O)Nc4ccc(C(=O)N5CCNCC5)c(Cl)c4)n3C)c(F)c2F)c1C] | 597.3 | Intermediate A1 and Intermediate G3; HCl |
| Intermediate H9 | N-[3-chloro-4-(piperazine-1-carbonyl)phenyl]-5-[3-fluoro-4-[1-(2-methoxyethyl)-5-methyl-pyrazol-4-yl]-2-methyl-phenyl]-1-methyl-imidazole-2-carboxamide | 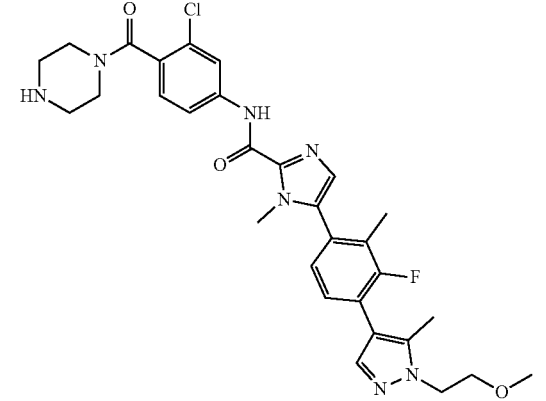 [SMILES: COCCn1ncc(-c2ccc(-c3cnc(C(=O)Nc4ccc(C(=O)N5CCNCC5)c(Cl)c4)n3C)c(C)c2F)c1C] | 593.3 | Intermediate A1 and Intermediate G13; HCl |

-continued

| Ex # | Name | Structure | MS ESI [M + H]+ | Starting Material |
|---|---|---|---|---|
| Intermediate H10 | 5-[5-chloro-4-[1-(2-methoxyethyl)-5-methyl-pyrazol-4-yl]-2-methyl-phenyl]-N-[3-chloro-4-[4-(piperidine-4-carbonyl)piperazine-1-carbonyl]phenyl]-1-methyl-imidazole-2-carboxamide | 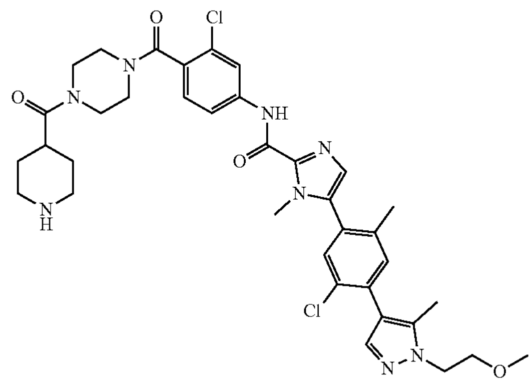 [SMILES: COCCn1ncc(-c2cc(C)c(-c3cnc(C(=O)Nc4ccc(C(=O)N5CCN(C(=O)C6CCNCC6)CC5)c(Cl)c4)n3C)cc2Cl)c1C] | 721.7 | Intermediate D1 and Intermediate G92; HCl |
| Intermediate H11 | 5-[3-chloro-2-fluoro-4-[1-(2-methoxyethyl)-5-methyl-pyrazol-4-yl]phenyl]-N-[3-chloro-4-(piperazine-1-carbonyl)phenyl]-1-methyl-imidazole-2-carboxamide | 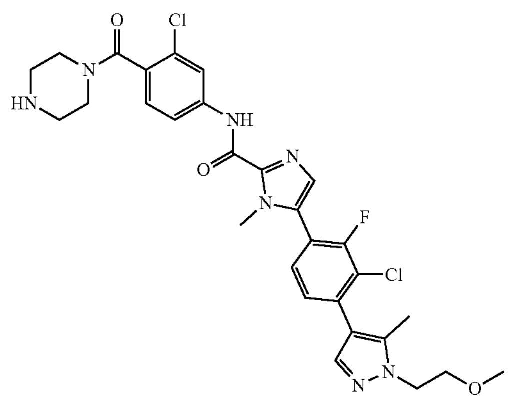 | 613.2 | Intermediate A1 and Intermediate G93; HCl |

Intermediate I1

N-[3-chloro-4-(piperazine-1-carbonyl)phenyl]-5-[2,3-difluoro-4-[1-(2-methoxyethyl)-5-methyl-pyrazol-4-yl]phenyl]-1-methyl-imidazole-2-carboxamide

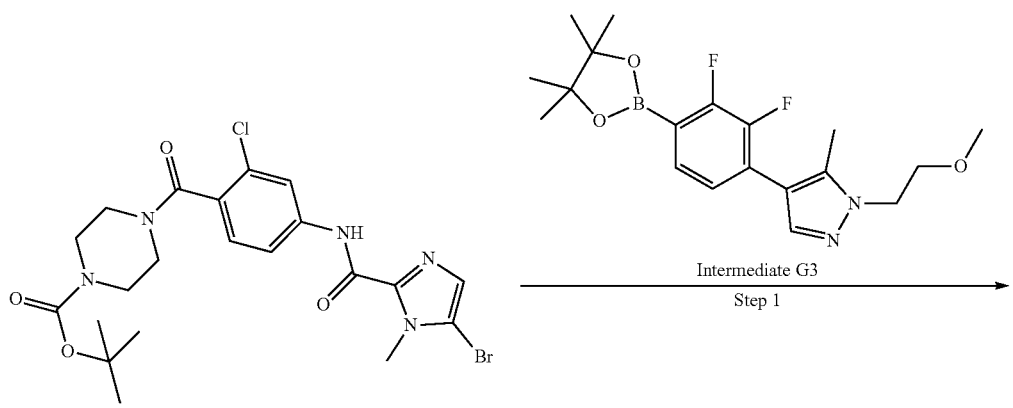

Intermediate B1

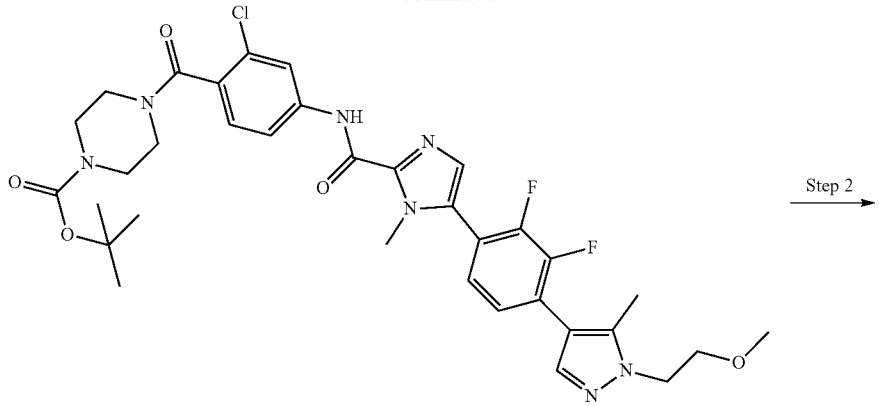

-continued

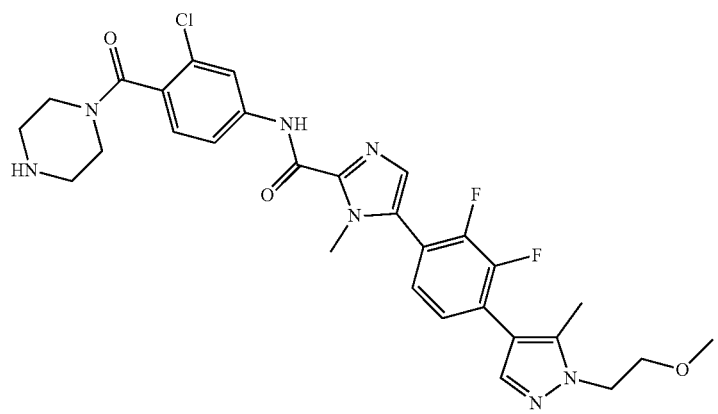

Intermediate I1

Step 1: tert-butyl 4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carboxylate In a 100 mL round-bottomed flask, tert-butyl 4-[4-[(5-bromo-1-methyl-imidazole-2-carbonyl)amino]-2-chloro-benzoyl]piperazine-1-carboxylate (150 mg, 285 μmol), 4-(2,3-difluoro-4-(4,4,5,5-tetramethyl-1,3,2-dioxaborolan-2-yl)phenyl)-1-(2-methoxyethyl)-5-methyl-1H-pyrazole (151 mg, 399 μmol), 1,1′-bis(di-tert-butylphosphino)ferrocene palladium dichloride (18.6 mg, 28.5 μmol) and Na₂CO₃ (90.5 mg, 854 μmol) were combined with dioxane (10 mL)/Water (1 mL) to give a dark red solution. The reaction mixture was heated to 100° C. and stirred for 15 h under N₂. The crude reaction mixture was concentrated in vacuum. The crude product was directly used to the next step to afford tert-butyl 4-[2-chloro-4-[[5-[2,3-difluoro-4-[1-(2-methoxy-ethyl)-5-methyl-pyrazol-4-yl]phenyl]-1-methyl-imidazole-2-carbonyl]amino]benzoyl]piperazine-1-carboxylate (160 mg). MS [M+H]⁺: 698.2.

Step 2: N-[3-chloro-4-(piperazine-1-carbonyl)phenyl]-5-[2,3-difluoro-4-[1-(2-methoxyethyl)-5-methyl-pyrazol-4-yl]phenyl]-1-methyl-imidazole-2-carboxamide In a 50 mL round-bottomed flask, tert-butyl 4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carboxylate (160 mg, 229 μmol) was combined with THF (2 mL) to give a light brown solution. HCl water solution (1.15 ml, 13.8 mmol) was added. The reaction was stirred at room temperature for 1 h. The crude reaction mixture was concentrated in vacuum. The crude product was directly used to the next step, To afford N-[3-chloro-4-(piperazine-1-carbonyl)phenyl]-5-[2,3-difluoro-4-[1-(2-methoxyethyl)-5-methyl-pyrazol-4-yl]phenyl]-1-methyl-imidazole-2-carboxamide (137 mg). MS [M+H]⁺: 598.1.

The following intermediates were prepared in analogy to Intermediate I1.

| Ex # | Name | Structure | MS ESI [M + H]+ | Starting Material |
|---|---|---|---|---|
| Intermediate I2 | N-[3-chloro-4-(piperazine-1-carbonyl)phenyl]-5-[2,3-difluoro-4-[1-(2-methoxyethyl)-3-methyl-pyrazol-4-yl]phenyl]-1-methyl-imidazole-2-carboxamide | 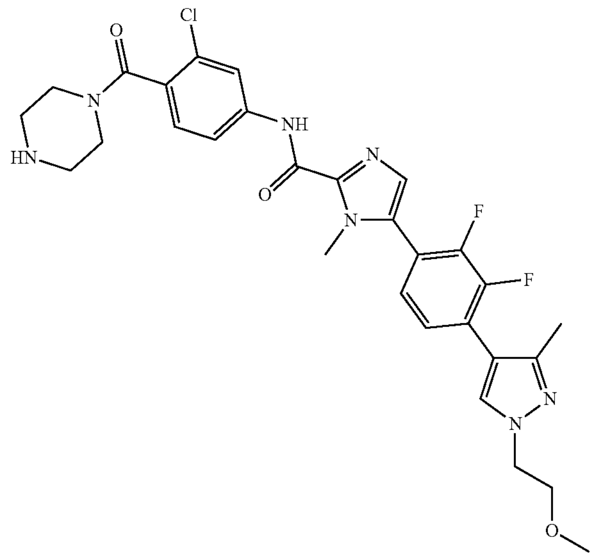 [SMILES: COCCn1cc(-c2ccc(-c3cnc(C(=O)Nc4ccc(C(=O)N5CCNCC5)c(Cl)c4)n3C)c(F)c2F)c(C)n1] | 598.1 | Intermediate B1 and Intermediate G2; HCl |
| Intermediate I3 | N-[3-chloro-4-(piperazine-1-carbonyl)phenyl]-5-[2,3-difluoro-4-[1-(2-methoxyethyl)-3-methyl-pyrazol-4-yl]phenyl]-1-methyl-imidazole-2-carboxamide | 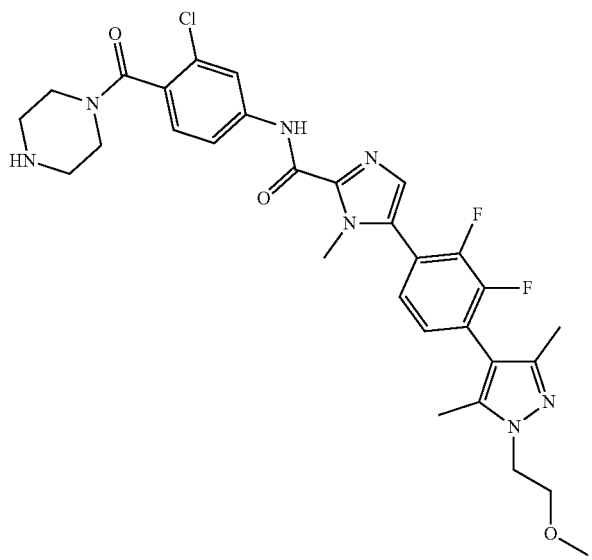 [SMILES: COCCn1nc(C)c(-c2ccc(-c3cnc(C(=O)Nc4ccc(C(=O)N5CCNCC5)c(Cl)c4)n3C)c(F)c2F)c1C] | 612.2 | Intermediate B1 and Intermediate G6; HCl |

-continued

| Ex # | Name | Structure | MS ESI [M + H]+ | Starting Material |
|---|---|---|---|---|
| Intermediate I4 | 5-[2,3-difluoro-4-[1-(2-methoxyethyl)-3-methyl-pyrazol-4-yl]phenyl]-1-methyl-N-[3-methyl-4-(piperazine-1-carbonyl)phenyl]imidazole-2-carboxamide | 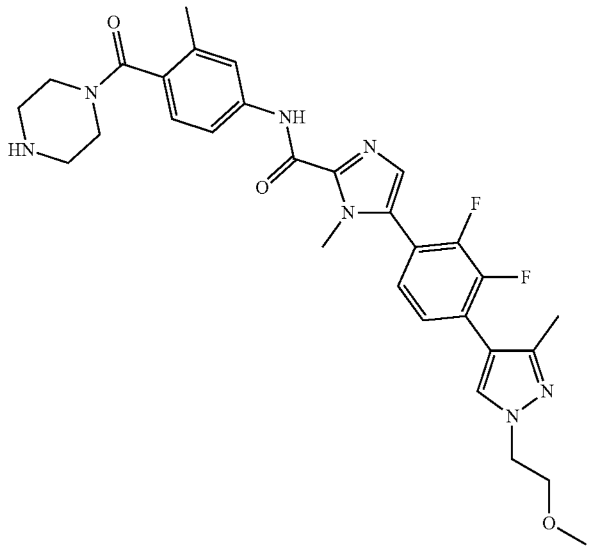 [SMILES: COCCn1cc(-c2ccc(-c3cnc(C(=O)Nc4ccc(C(=O)N5CCNCC5)c(C)c4)n3C)c(F)c2F)c(C)n1] | 578.3 | Intermediate B2 and Intermediate G2; HCl |
| Intermediate I5 | N-[4-(4-aminopiperidine-1-carbonyl)-3-chloro-phenyl]-5-[2,3-difluoro-4-[1-(2-methoxyethyl)-3-methyl-pyrazol-4-yl]phenyl]-1-methyl-imidazole-2-carboxamide | 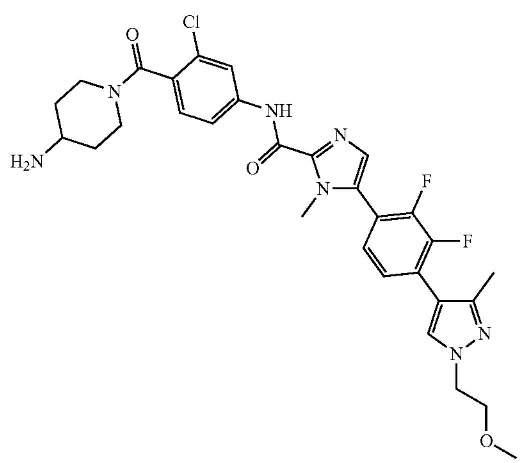 [SMILES: COCCn1cc(-c2ccc(-c3cnc(C(=O)Nc4ccc(C(=O)N5CCC(N)CC5)c(Cl)c4)n3C)c(F)c2F)c(C)n1] | 612.3 | Intermediate B3 and Intermediate G2; HCl |
| Intermediate I6 | 1-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperidine-4-carboxylic acid | 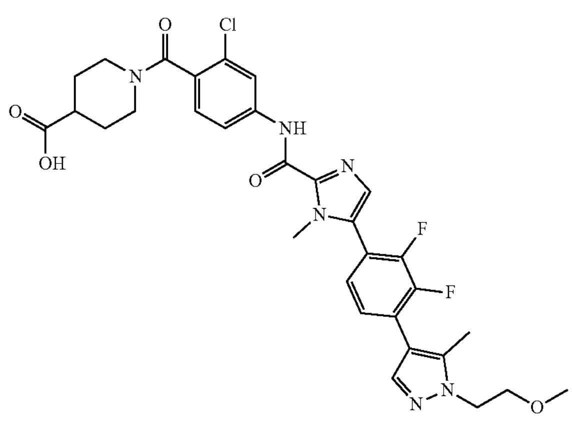 [SMILES: COCCn1ncc(-c2ccc(-c3cnc(C(=O)Nc4ccc(C(=O)N5CCC(C(=O)O)CC5)c(Cl)c4)n3C)c(F)c2F)c1C] | 641.2 | Intermediate B4 and Intermediate G3; TFA |

| Ex # | Name | Structure | MS ESI [M + H]+ | Starting Material |
|---|---|---|---|---|
| Intermediate I7 | N-[3-chloro-4-(4-piperidylmethylcarbamoyl)phenyl]-5-[2,3-difluoro-4-[1-(2-methoxyethyl)-5-methyl-pyrazol-4-yl]phenyl]-1-methyl-imidazole-2-carboxamide | 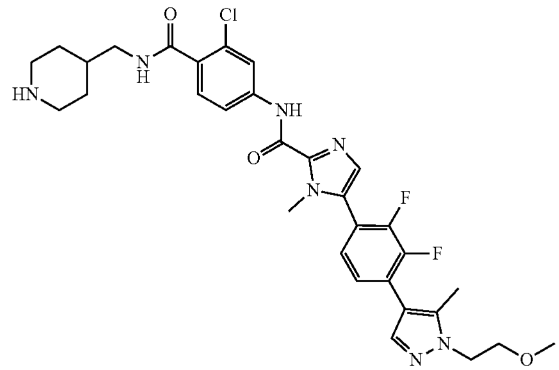 [SMILES: COCCn1ncc(-c2ccc(-c3cnc(C(=O)Nc4ccc(C(=O)NCC5CCNCC5)c(Cl)c4)n3C)c(F)c2F)c1C] | 626.4 | Intermediate B5 and Intermediate G3; HCl |
| Intermediate I8 | N-[3-chloro-4-(piperazine-1-carbonyl)phenyl]-5-[2,3-difluoro-4-[1-(3-methoxypropyl)-3-methyl-pyrazol-4-yl]phenyl]-1-methyl-imidazole-2-carboxamide | 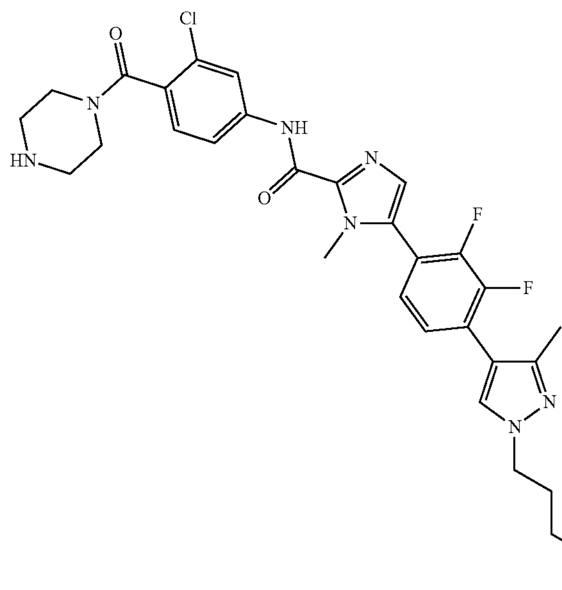 | 612.3 | Intermediate B1 and Intermediate G17; HCl |
| Intermediate I9 | N-[3-chloro-4-(piperazine-1-carbonyl)phenyl]-5-[2,3-difluoro-4-[1-(3-methoxypropyl)-5-methyl-pyrazol-4-yl]phenyl]-1-methyl-imidazole-2-carboxamide | 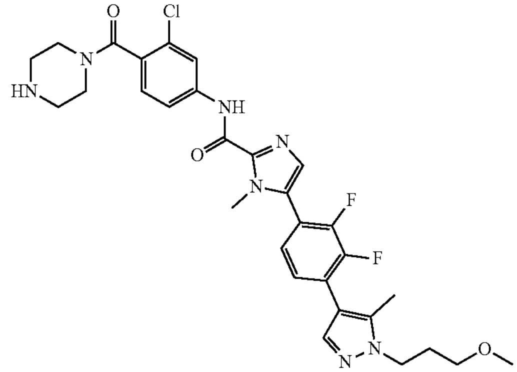 [SMILES: COCCCn1ncc(-c2ccc(-c3cnc(C(=O)Nc4ccc(C(=O)N5CCNCC5)c(Cl)c4)n3C)c(F)c2F)c1C] | 612.3 | Intermediate B1 and Intermediate G18; HCl |

-continued

| Ex # | Name | Structure | MS ESI [M + H]+ | Starting Material |
|---|---|---|---|---|
| Intermediate I10 | N-[4-(4-aminopiperidine-1-carbonyl)-3-chloro-phenyl]-5-[2,3-difluoro-4-[1-(2-methoxyethyl)-5-methyl-pyrazol-4-yl]phenyl]-1-methyl-imidazole-2-carboxamide | 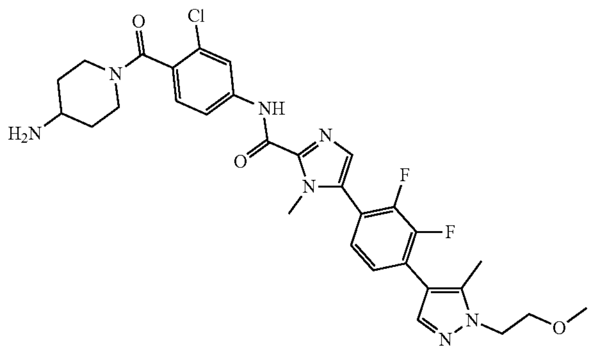 [SMILES: COCCn1ncc(-c2ccc(-c3cnc(C(=O)Nc4ccc(C(=O)N5CCC(N)CC5)c(Cl)c4)n3C)c(F)c2F)c1C] | 612.3 | Intermediate B3 and Intermediate G3; HCl |
| Intermediate I11 | N-[4-[[(1R,5S)-3-azabicyclo[3.1.0]hexan-6-yl]carbamoyl]-3-chloro-phenyl]-5-[2,3-difluoro-4-[1-(2-methoxyethyl)-3,5-dimethyl-pyrazol-4-yl]phenyl]-1-methyl-imidazole-2-carboxamide | 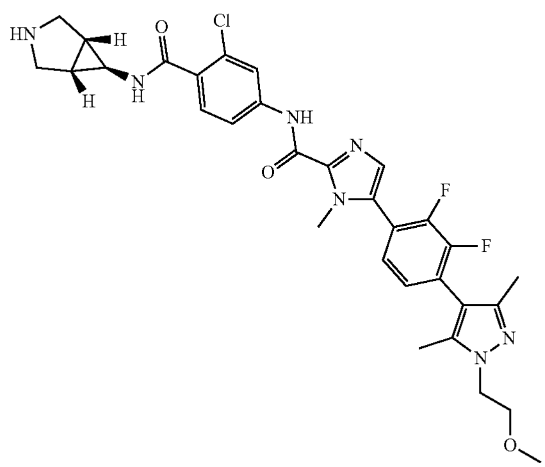 [SMILES: COCCn1nc(C)c(-c2ccc(-c3cnc(C(=O)Nc4ccc(C(=O)N[C@H]5[C@@H]6CNC[C@@H]65)c(Cl)c4)n3C)c(F)c2F)c1C] | 624.0 | Intermediate B6 and Intermediate G6; HCl |
| Intermediate I12 | N-[4-[[(1S,5R)-3-azabicyclo[3.1.0]hexan-6-yl]carbamoyl]-3-chloro-phenyl]-5-[2,3-difluoro-4-[1-(2-methoxyethyl)-5-methyl-pyrazol-4-yl]phenyl]-1-methyl-imidazole-2-carboxamide | 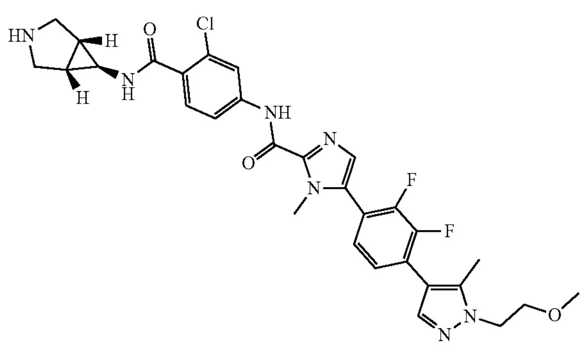 [SMILES: COCCn1ncc(-c2ccc(-c3cnc(C(=O)Nc4ccc(C(=O)N[C@H]5[C@@H]6CNC[C@@H]65)c(Cl)c4)n3C)c(F)c2F)c1C] | 610.0 | Intermediate B6 and Intermediate G3; HCl |

Intermediate J1
N-[3-chloro-4-[4-[2-(dimethylamino)acetyl]piperazine-1-carbonyl]phenyl]-1-methyl-5-[4-[3-methyl-1-(2-trimethylsilylethoxymethyl)pyrazol-4-yl]phenyl]imidazole-2-carboxamide
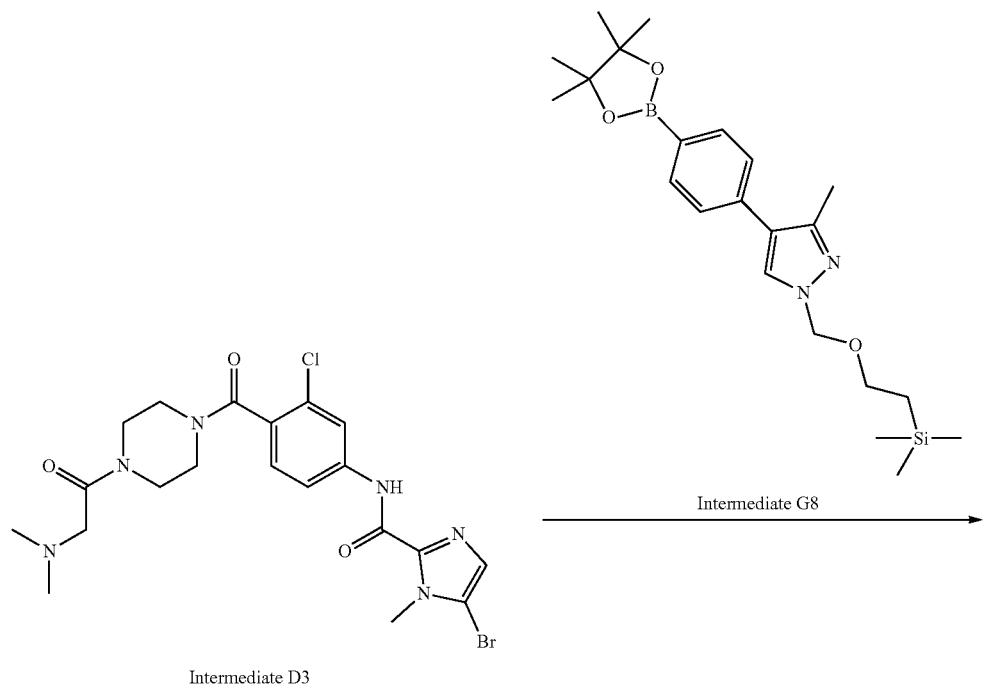

Under N₂ protection, a mixture of trimethyl-[2-[[3-methyl-4-[4-(4,4,5,5-tetramethyl-1,3,2-dioxaborolan-2-yl)phenyl]pyrazol-1-yl]methoxy]ethyl]silane (323.9 mg, 0.782 mmol), 5-bromo-N-[3-chloro-4-[4-[2-(dimethylamino)acetyl]piperazine-1-carbonyl]phenyl]-1-methyl-imidazole-2-carboxamide (400 mg, 782 μmol), Na₂CO₃ (249 mg, 2.34 mmol) and 1,1-bis(di-tert-butylphosphino)ferrocene palladium dichloride (25.5 mg, 39.1 μmol) in 1,4-dioxane (7 mL) and water (0.7 mL) was heated at 95° C. for 15 h. Then the mixture was filtered and concentrated in vacuum. The crude product was purified by flash column to afford N-[3-chloro-4-[4-[2-(dimethylamino)acetyl]piperazine-1-carbonyl]phenyl]-1-methyl-5-[4-[3-methyl-1-(2-trimethylsilylethoxymethyl)pyrazol-4-yl]phenyl]imidazole-2-carboxamide (50 mg) as a yellow solid. MS [M+H]⁺: 719.2.

The following examples were prepared in analogy to Intermediate J1.

| Ex # | Name | Structure | MS ESI [M + H]⁺ | Starting Material |
|---|---|---|---|---|
| Intermediate J2 | N-[3-chloro-4-[4-[2-(dimethylamino)acetyl]piperazine-1-carbonyl]phenyl]-5-[4-[3,5-dimethyl-1-(2-trimethylsilylethoxymethyl)pyrazol-4-yl]phenyl]-1-methyl-imidazole-2-carboxamide | 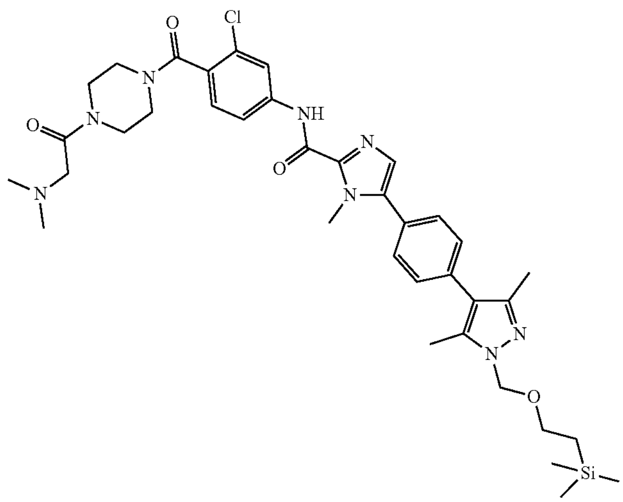 | 733.5 | Intermediate D3 and Intermediate G9 |

Intermediate K1

N-[3-chloro-4-[4-[(2,4R)-4-hydroxypyrrolidine-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide

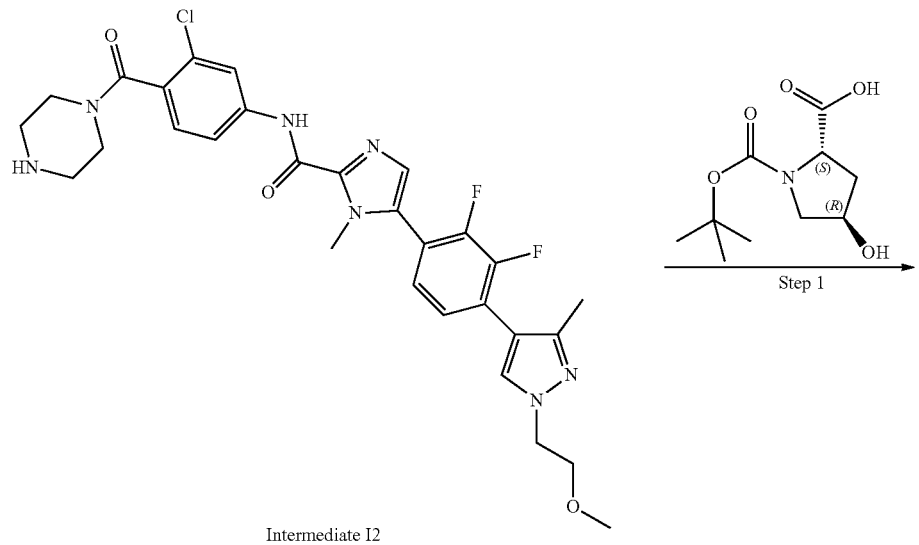

Intermediate I2

Step 1

-continued

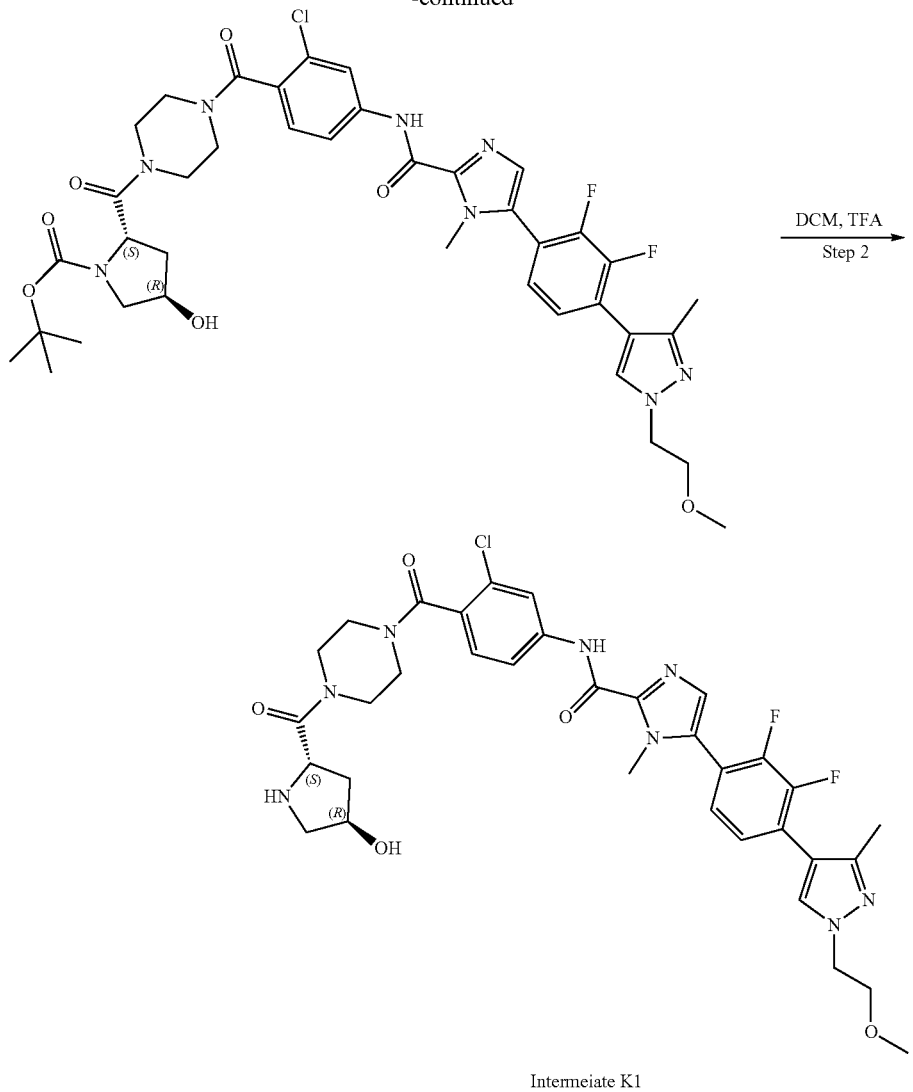

Intermeiate K1

Step 1: tert-butyl (2S,4R)-2-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]-4-hydroxy-pyrrolidine-1-carboxylate At room temperature, a mixture of N-[3-chloro-4-(piperazine-1-carbonyl)phenyl]-5-[2,3-difluoro-4-[1-(2-methoxyethyl)-3-methyl-pyrazol-4-yl]phenyl]-1-methyl-imidazole-2-carboxamide (350 mg, 585 μmol), (2S,4R)-1-tert-butoxycarbonyl-4-hydroxy-pyrrolidine-2-carboxylic acid (176 mg, 761 μmol), HATU (334 mg, 878 μmol) and DIPEA (227 mg, 1.76 mmol) in DMF (5 mL) was stirred for 16 h. Then the mixture was poured into water. The water layer was extracted with DCM. The combined organic layers were washed with water and concentrated in vacuum. The residue was purified by flash column to afford tert-butyl (2S,4R)-2-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]-4-hydroxy-pyrrolidine-1-carboxylate (310 mg) as a brown solid. MS [M+H]+: 811.2.

Step 2: N-[3-chloro-4-[4-[(2S,4R)-4-hydroxypyrrolidine-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide At room temperature, a solution of tert-butyl (2S,4R)-2-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]-4-hydroxy-pyrrolidine-1-carboxylate (310 mg, 382 μmol) in DCM (10 mL) and TFA (5 mL) was stirred for 1 h. Then the mixture was concentrated in vacuum. The residue was basified by NH$_3$·H$_2$O to PH 8-9. The water layer was extracted with DCM. The organic layer was dried over anhydrous Na$_2$SO$_4$ and concentrated in vacuum to afford the crude product N-[3-chloro-4-[4-[(2S,4R)-4-hydroxypyrrolidine-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide (240 mg) as a brown oil. MS [M+H]+: 711.3.

The following examples were prepared in analogy to Intermeiate K1.

| Ex # | Name | Structure | MS ESI [M + H]+ | Starting Material |
|---|---|---|---|---|
| Intermediate K2 | N-[3-chloro-4-[4-(4-hydroxypiperidine-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide | 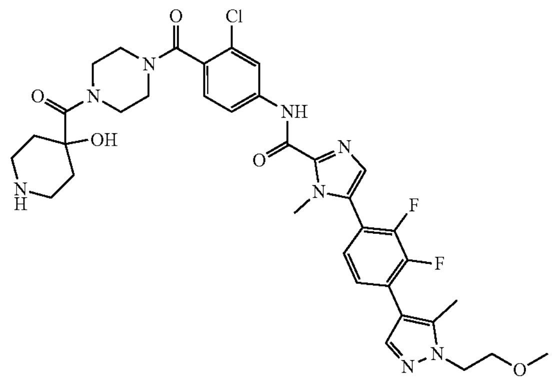 [SMILES: COCCn1ncc(-c2ccc(-c3cnc(C(=O)Nc4ccc(C(=O)N5CCN(C(=O)C6(O)CCNCC6)CC5)c(Cl)c4)n3C)c(F)c2F)c1C] | 725.2 | Intermediate I1 and 1-(tert-butoxycarbonyl)-4-hydroxypiperidine-4-carboxylic acid and HCl |
| Intermediate K3 | N-[3-chloro-4-[4-(3-hydroxypiperidine-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide | 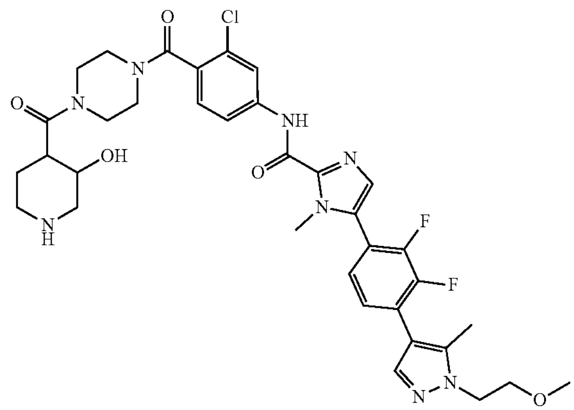 [SMILES: COCCn1ncc(-c2ccc(-c3cnc(C(=O)Nc4ccc(C(=O)N5CCN(C(=O)C6CCNCC6O)CC5)c(Cl)c4)n3C)c(F)c2F)c1C] | 725.2 | Intermediate I1 and 1-(tert-butoxycarbonyl)-3-hydroxypiperidine-4-carboxylic acid and HCl |
| Intermediate K4 | N-[3-chloro-4-[4-[2-(dimethylamino)acetyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide | 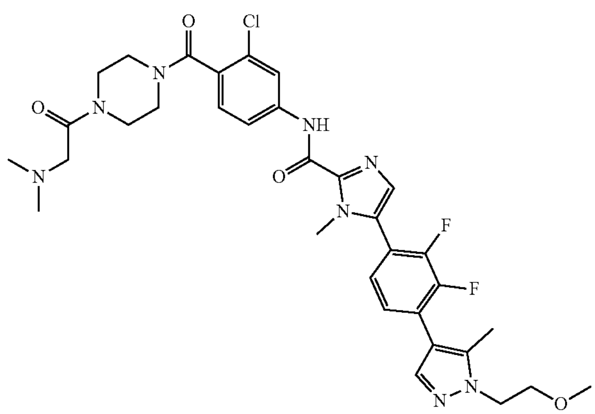 | 683.4 | Intermediate I1 and dimethylglycine |
| Intermediate K5 | N-[3-chloro-4-[[1-[2-(dimethylamino)acetyl]-4-piperidyl]methylcarbamoyl]phenyl]-5-[2,3-difluoro-4-[1-(2-methoxyethyl)-5-methyl-pyrazol-4-yl]phenyl]-1-methyl-imidazole-2-carboxamide | 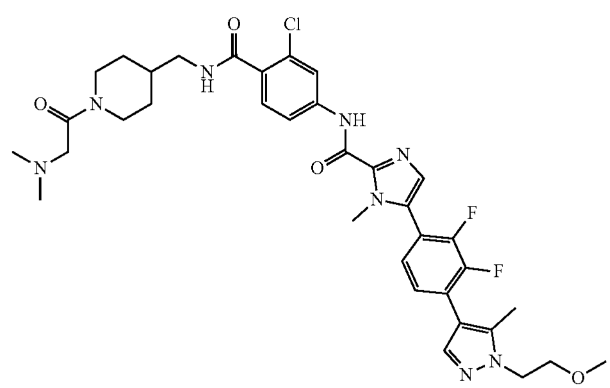 | 711.3 | Intermediate I7 and dimethylglycine |

-continued

| Ex # | Name | Structure | MS ESI [M + H]+ | Starting Material |
|---|---|---|---|---|
| Intermediate K6 | N-[3-chloro-4-[4-[(2S,3S)-3-hydroxypyrrolidine-2-carbonyl]piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide | 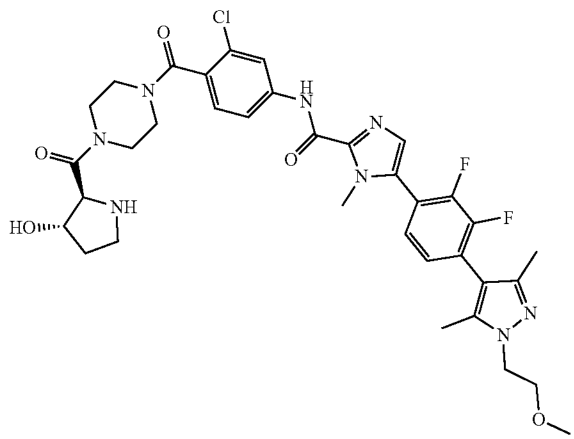 [SMILES: COCCn1nc(C)c(-c2ccc(-c3cnc(C(=O)Nc4ccc(C(=O)N5CCN(C(=O)[C@H]6NCC[C@@H]6O)CC5)c(Cl)c4)n3C)c(F)c2F)c1C] | 725.2 | Intermediate I3 and rac-(2S,3S)-1-tert-butoxycarbonyl-3-hydroxy-pyrrolidine-2-carboxylic acid and HCl |
| Intermediate K7 | N-[3-chloro-4-[4-(4-hydroxypiperidine-4-carbonyl)piperazine-1-carbonyl]phenyl]-5-[2,3-difluoro-4-[1-(2-methoxyethyl)-3-methyl-pyrazol-4-yl]phenyl]-1-methyl-imidazole-2-carboxamide | | 725.2 | Intermediate I2 and 1-(tert-butoxycarbonyl)-4-hydroxypiperidine-4-carboxylic acid and HCl |

| Ex # | Name | Structure | MS ESI [M + H]+ | Starting Material |
|---|---|---|---|---|
| Intermediate K8 | N-[3-chloro-4-[4-[(2S)-4-(hydroxymethyl) pyrrolidine-2-carbonyl] piperazine-1-carbonyl]phenyl]-5-[2,3-difluoro-4-[1-(2-methoxyethyl)-3-methyl-pyrazol-4-yl]phenyl]-1-methyl-imidazole-2-carboxamide | 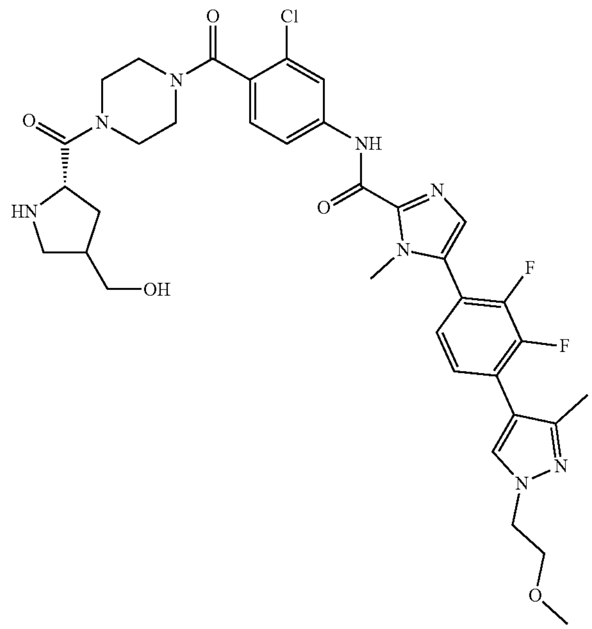 [SMILES: COCCn1cc(-c2ccc(-c3cnc(C(=O)Nc4ccc(C(=O)N5CCN(C(=O)[C@@H]6CC(CO)CN6)CC5)c(Cl)c4)n3C)c(F)c2F)c(C)n1] | 725.2 | Intermediate I2 and Intermediate R6 and HCl |
| Intermediate K9 | N-[3-chloro-4-[4-(piperidine-4-carbonyl) piperazine-1-carbonyl]phenyl]-5-[2,3-difluoro-4-(3-methyl-1H-pyrazol-4-yl)phenyl]-1-methyl-imidazole-2-carboxamide | 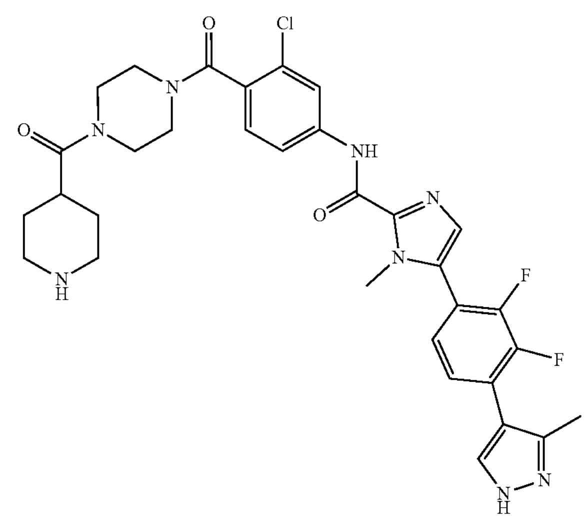 [SMILES: Cc1n[nH]cc1-c1ccc(-c2cnc(C(=O)Nc3ccc(C(=O)N4CCN(C(=O)C5CCNCC5)CC4)c(Cl)c3)n2C)c(F)c1F] | 651.2 | Intermediate M1 and 1-tert-butoxycarbonyl piperidine-4-carboxylic acid; HCl |

| Ex # | Name | Structure | MS ESI [M + H]+ | Starting Material |
|---|---|---|---|---|
| Intermediate K10 | N-[3-chloro-4-[4-[(2S,4R)-4-hydroxypyrrolidine-2-carbonyl]piperazine-1-carbonyl]phenyl]-5-[2,3-difluoro-4-(3-methyl-1H-pyrazol-4-yl)phenyl]-1-methyl-imidazole-2-carboxamide | 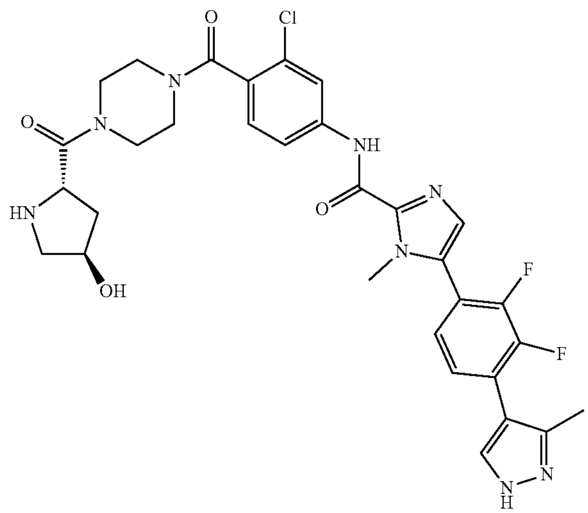 [SMILES: Cc1n[nH]cc1-c1ccc(-c2cnc(C(=O)Nc3ccc(C(=O)N4CCN(C(=O)[C@@H]5C[C@@H](O)CN5)CC4)c(Cl)c3)n2C)c(F)c1F] | 653.2 | Intermediate M1 and intermediate R3; HCl |
| Intermediate K11 | N-[3-chloro-4-[4-(pyrrolidine-2-carbonyl)piperazine-1-carbonyl]phenyl]-5-[2,3-difluoro-4-(3-methyl-1H-pyrazol-4-yl)phenyl]-1-methyl-imidazole-2-carboxamide | 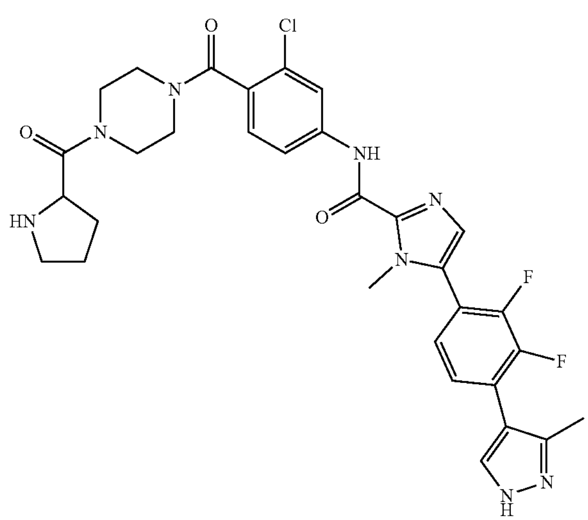 [SMILES: Cc1n[nH]cc1-c1ccc(-c2cnc(C(=O)Nc3ccc(C(=O)N4CCN(C(=O)C5CCCN5)CC4)c(Cl)c3)n2C)c(F)c1F] | 637.2 | Intermediate M1 and 1-tert-butoxycarbonylpyrrolidine-2-carboxylic acid; HCl |

Intermediate L1
2-chloro-4-[[5-[2,3-difluoro-4-(3-methyl-1H-pyrazol-4-yl)phenyl]-1-methyl-imidazole-2-carbonyl]amino]benzoic acid
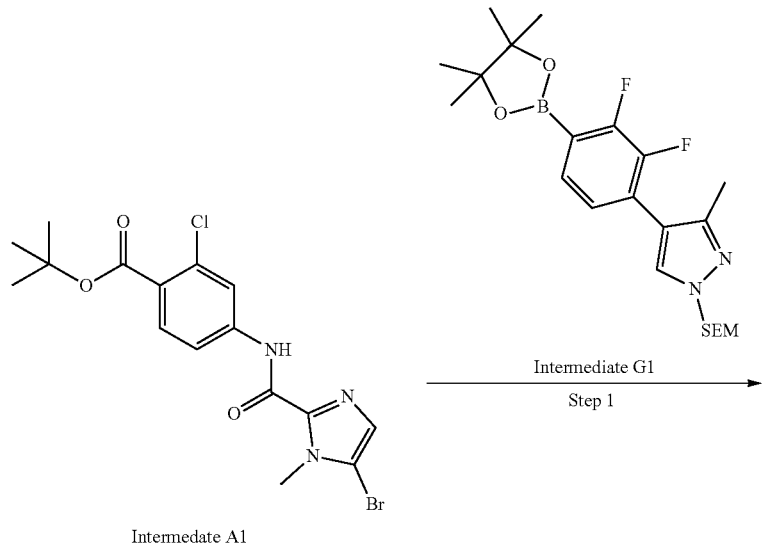

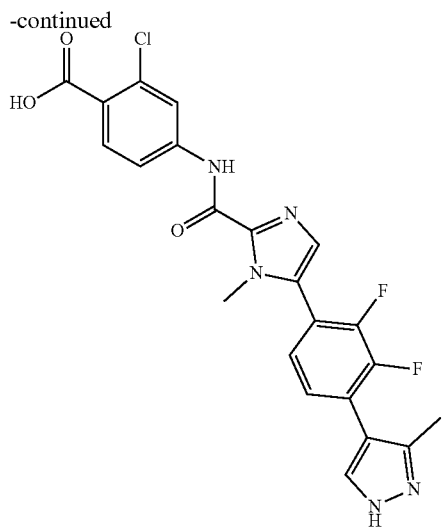

Intermediate L1

Step 1: tert-butyl 2-chloro-4-[[5-[2,3-difluoro-4-[3-methyl-1-(2-trimethylsilylethoxymethyl)pyrazol-4-yl]phenyl]-1-methyl-imidazole-2-carbonyl]amino]benzoate In a round bottomed flask were placed tert-butyl 4-(5-bromo-1-methyl-1H-imidazole-2-carboxamido)-2-chlorobenzoate (3.3 g, 7.96 mmol), 4-(2,3-difluoro-4-(4,4,5,5-tetramethyl-1,3,2-dioxaborolan-2-yl)phenyl)-3-methyl-1-((2-(trimethylsilyl)ethoxy)methyl)-1H-pyrazole (4.29 g, 9.52 mmol), PdCl$_2$(dtbpf) (259 mg, 398 μmol) and potassium carbonate (3.3 g, 23.9 mmol). Water (7.23 mL) and dioxane (72.3 mL) were added, and the flask was evacuated and backfilled with argon for 5 times. The mixture was heated at 100° C. for 18 h. The reaction was cooled to room temperature and poured into 100 mL water. The aqueous phase was extracted with EtOAc (50 mL×3). The organic layers were combined, washed with brine (50 mL), dried over sodium sulfate and concentrated in vacuo. The residue was purified by flash chromatography to afford the product (2.46 g). MS [M+H]$^+$: 658.2.

Step 2: 2-chloro-4-[[5-[2,3-difluoro-4-(3-methyl-1H-pyrazol-4-yl)phenyl]-1-methyl-imidazole-2-carbonyl]amino]benzoic acid tert-butyl 2-chloro-4-(5-(2,3-difluoro-4-(3-methyl-1-((2-(trimethylsilyl)ethoxy)methyl)-1H-pyrazol-4-yl)phenyl)-1-methyl-1H-imidazole-2-carboxamido)benzoate (2.45 g, 3.72 mmol) was stirred in TFA (3.72 mL) and CH$_2$Cl$_2$ (14.9 mL) for 5 h. The solvent was removed in vacuum and the residue was azeotroped with toluene (50 mL×3) to give the product which was used next without further purification (1.74 g). MS [M+H]$^+$: 472.2.

The following examples were prepared in analogy to Intermediate L1.

| Ex # | Name | Structure | MS ESI [M + H]$^+$ | Starting Material |
|---|---|---|---|---|
| Intermediate L2 | 2-chloro-4-[[5-[2,3-difluoro-4-[1-(2-methoxyethyl)-5-methyl-pyrazol-4-yl]phenyl]-1-methyl-imidazole-2-carbonyl]amino]benzoic acid | 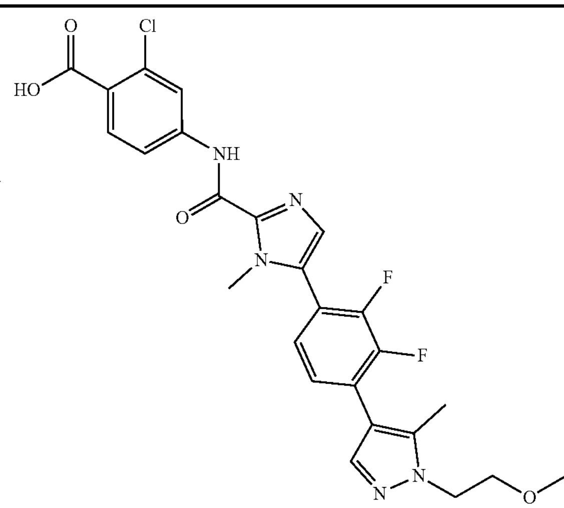 | 530.2 | Intermediate A1; Intermediate G3 and TFA |

| Ex # | Name | Structure | MS ESI [M + H]+ | Starting Material |
|---|---|---|---|---|
| Intermediate L3 | 2-chloro-4-[[5-[2,3-difluoro-4-[1-(2-methoxyethyl)-3-methyl-pyrazol-4-yl]phenyl]-1-methyl-imidazole-2-carbonyl]-amino]benzoic acid | 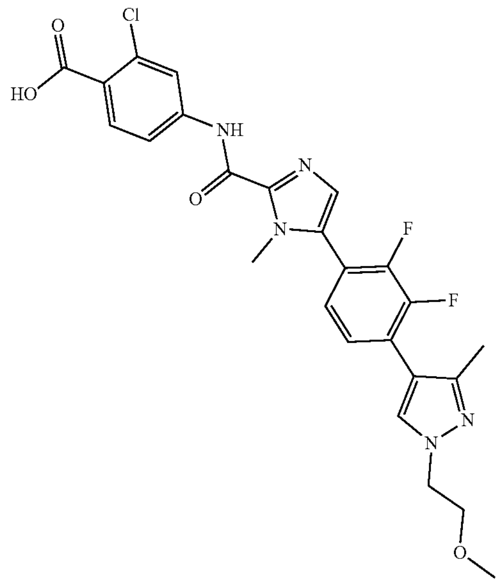 [SMILES: COCCn1cc(-c2ccc(-c3cnc(C(=O)Nc4ccc(C(=O)O)c(Cl)c4)n3C)c(F)c2F)c(C)n1] | 530.2 | Intermediate A1; Intermediate G2 and TFA |
| Intermediate L4 | 2-chloro-4-[[5-[4-(3,5-dimethyl-1H-pyrazol-4-yl)-2,3-difluoro-phenyl]-1-methyl-imidazole-2-carbonyl]amino]benzoic acid | 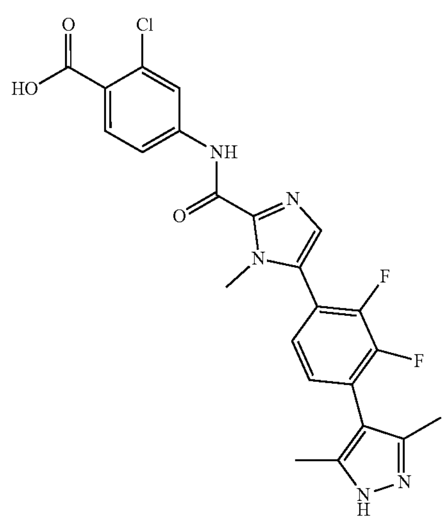 [SMILES: Cc1n[nH]c(C)c1-c1ccc(-c2cnc(C(=O)Nc3ccc(C(=O)O)c(Cl)c3)n2C)c(F)c1F] | 486.1 | Intermediate A1; Intermediate G89 and TFA |

251

Intermediate M1

N-[3-chloro-4-(piperazine-1-carbonyl)phenyl]-5-[2,3-difluoro-4-(3-methyl-1H-pyrazol-4-yl)phenyl]-1-methyl-imidazole-2-carboxamide; hydrochloride

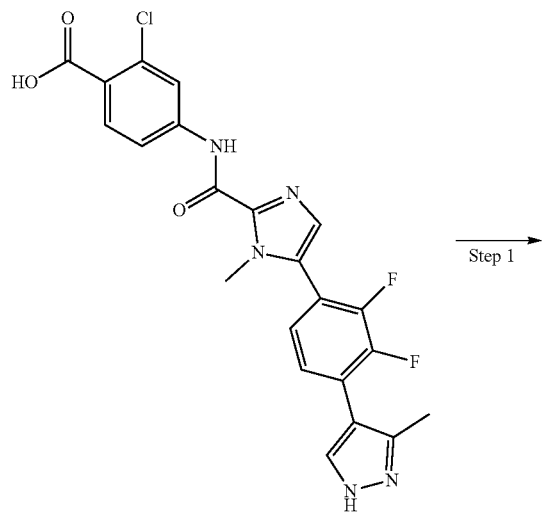

Intermediate L1

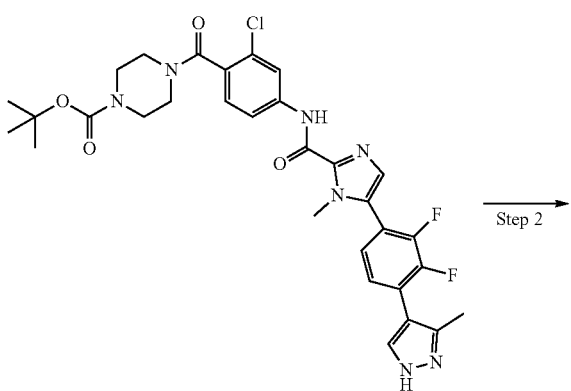

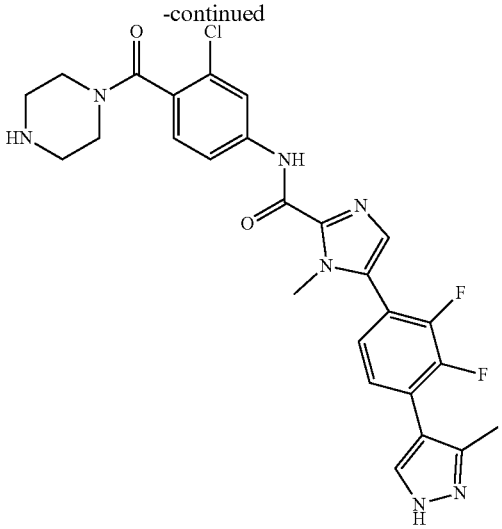

Intermediate M1

Step 1: tert-butyl 4-[2-chloro-4-[[5-[2,3-difluoro-4-(3-methyl-1H-pyrazol-4-yl)phenyl]-1-methyl-imidazole-2-carbonyl]amino]benzoyl]piperazine-1-carboxylate 1-((dimethylamino)(dimethyliminio)methyl)-1H-[1,2,3]triazolo[4,5-b]pyridine 3-oxide hexafluorophosphate(V) (96.7 mg, 254 μmol) was added to a solution of N-ethyl-N-isopropylpropan-2-amine (137 mg, 1.06 mmol), 2-chloro-4-(5-(2,3-difluoro-4-(3-methyl-1H-pyrazol-4-yl)phenyl)-1-methyl-1H-imidazole-2-carboxamido)benzoic acid (100 mg, 212 μmol) and tert-butyl piperazine-1-carboxylate (47.4 mg, 254 μmol) in DMA (4.24 mL) and stirred for 2 h at room temperature. The mixture was poured into 100 mL water and extracted with EtOAc (50 mL×4). The organic layer was washed with 50 mL brine, dried over sodium sulfate, and concentrated in vacuum. The residue was purified by flash chromatography to afford the product (105 mg). MS [M+H]$^+$: 640.2.

Step 2: N-[3-chloro-4-(piperazine-1-carbonyl)phenyl]-5-[2,3-difluoro-4-(3-methyl-1H-pyrazol-4-yl)phenyl]-1-methyl-imidazole-2-carboxamide; hydrochloride tert-butyl 4-(2-chloro-4-(5-(2,3-difluoro-4-(3-methyl-1H-pyrazol-4-yl)phenyl)-1-methyl-1H-imidazole-2-carboxamido)benzoyl)piperazine-1-carboxylate (1.38 g, 2.16 mmol) was dissolved in 4M HCl/MeOH (10.8 mL) solution. The solution was stirred at room temperature for 1 h. The solvent was removed in vacuum and the residue was azeotroped with toluene (50 mL×3) to give the product, which was used in the next step without purification (1.17 g). MS [M+H]$^+$: 540.2.

The following examples were prepared in analogy to Intermediate M1.

| Ex # | Name | Structure | MS ESI [M + H]+ | Starting Material |
|---|---|---|---|---|
| Intermediate M2 | N-[3-chloro-4-(piperazine-1-carbonyl)phenyl]-5-[4-(3,5-dimethyl-1H-pyrazol-4-yl)-2,3-difluoro-phenyl]-1-methyl-imidazole-2-carboxamide | 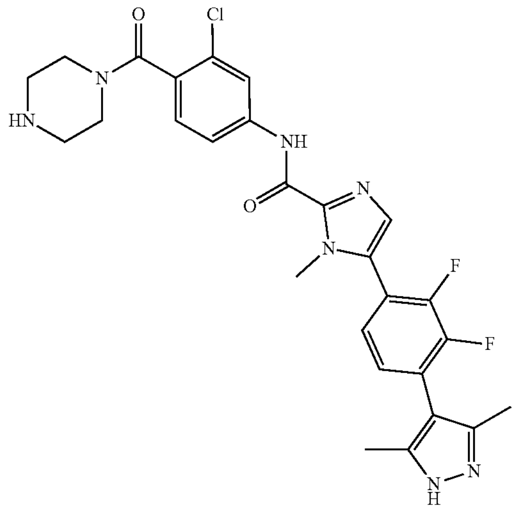 [SMILES: Cc1n[nH]c(C)c1-c1ccc(-c2cnc(C(=O)Nc3ccc(C(=O)N4CCNCC4)c(Cl)c3)n2C)c(F)c1F] | 554.2 | Intermediate L4 and tert-butyl piperazine-1-carboxylate and HCl |

Intermediate N1 and Intermediate N2 tert-butyl (1R,5S)-6-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]-3-azabicyclo[3.1.0]hexane-3-carboxylate (Intermediate N1), and tert-butyl (1R,5S)-6-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]-3-azabicyclo[3.1.0]hexane-3-carboxylate (Intermediate N2)

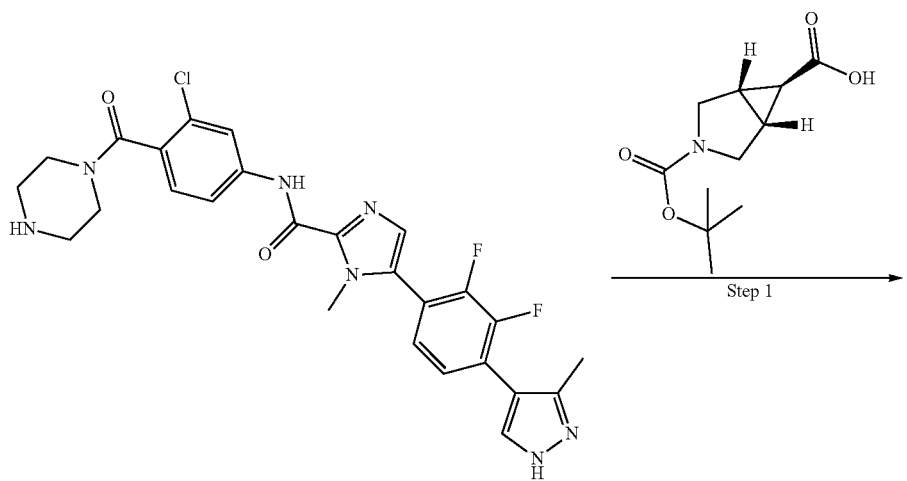

Intermediate M1

Step 1

-continued

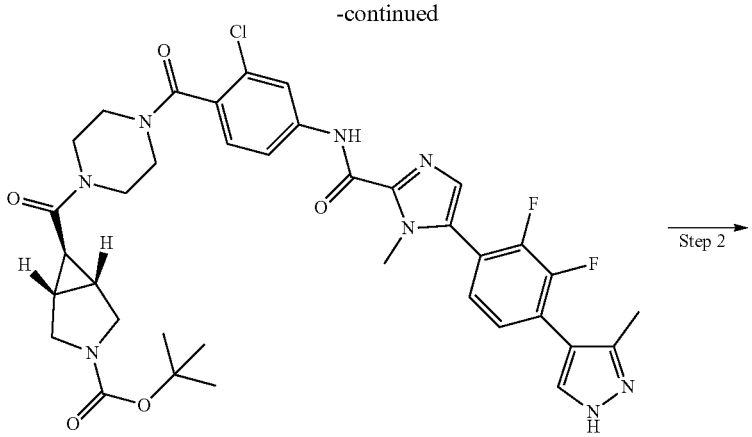

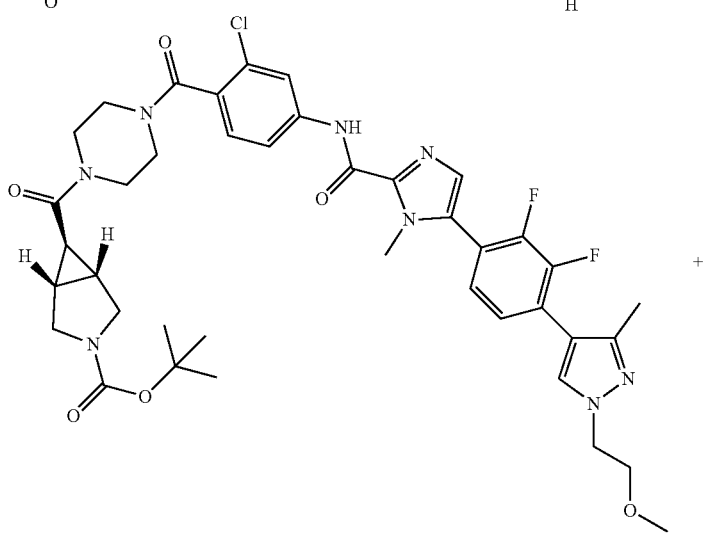

Intermediate N1

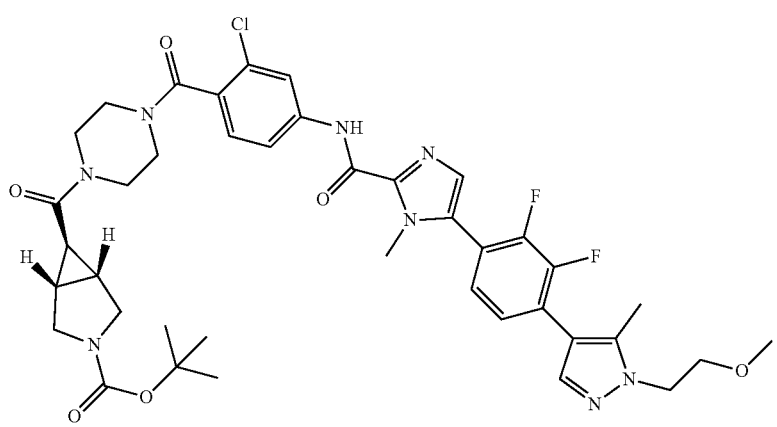

Intermediate N2

Step 1: tert-butyl (1S,5R)-6-[4-[2-chloro-4-[[5-[2,3-difluoro-4-(3-methyl-1H-pyrazol-4-yl)phenyl]-1-methyl-imidazole-2-carbonyl]amino]benzoyl]piperazine-1-carbonyl]-3-azabicyclo[3.1.0]hexane-3-carboxylate In a 100 mL round-bottomed flask, (1R,5S,6r)-3-(tert-butoxycarbonyl)-3-azabicyclo[3.1.0]hexane-6-carboxylic acid (248 mg, 1.09 mmol), N-[3-chloro-4-(piperazine-1-carbonyl)phenyl]-5-[2,3-difluoro-4-(3-methyl-1H-pyrazol-4-yl)phenyl]-1-methyl-imidazole-2-carboxamide (491 mg, 909 µmol), HATU (415 mg, 1.09 mmol) and DIPEA (235 mg, 1.82 mmol) were combined with DMF (6 mL) to give a light brown solution. The reaction was stirred at room temperature for 1 h. The reaction mixture was poured into 25 mL H₂O and extracted with EtOAc (3×25 mL). The organic layers were combined, washed with sat NaCl (1×25 mL), The organic layers were dried over Na₂SO₄ and concentrated in vacuum. The crude material was purified by flash chromatography to afford tert-butyl (1S,5R)-6-[4-[2-chloro- 4-[[5-[2,3-difluoro-4-(3-methyl-1H-pyrazol-4-yl)phenyl]-1-methyl-imidazole-2-carbonyl]amino]benzoyl]piperazine-1-carbonyl]-3-azabicyclo[3.1.0]hexane-3-carboxylate (520 mg). MS [M+H]$^+$: 749.3.

Step 2: tert-butyl (1R,5S)-6-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]-3-azabicyclo[3.1.0]hexane-3-carboxylate (Intermediate N1), and tert-butyl (1R,5S)-6-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]-3-azabicyclo[3.1.0]hexane-3-carboxylate (Intermediate N2)

To a 5 mL microwave vial was added tert-butyl (1S,5R)-6-[4-[2-chloro-4-[[5-[2,3-difluoro-4-(3-methyl-1H-pyrazol-4-yl)phenyl]-1-methyl-imidazole-2-carbonyl]amino]benzoyl]piperazine-1-carbonyl]-3-azabicyclo[3.1.0]hexane-3-carboxylate (330 mg, 440 µmol), 1-bromo-2-methoxyethane (91.8 mg, 661 µmol) and K$_2$CO$_3$ (122 mg, 881 µmol) in DMF (3 mL). The vial was capped and heated in the microwave at 70° C. for 1 h. The reaction mixture was poured into 50 mL H$_2$O and extracted with EtOAc (3×25 mL). The organic layers were combined, washed with sat NaCl (1×25 mL), The organic layers were dried over Na$_2$SO$_4$ and concentrated in vacuum. The crude material was purified by flash chromatography to afford 220 mg crude product, The crude product was purified by preparative chiral-HPLC to afford tert-butyl (1R,5S)-6-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]-3-azabicyclo[3.1.0]hexane-3-carboxylate (60 mg) and tert-butyl (1R,5S)-6-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]-3-azabicyclo[3.1.0]hexane-3-carboxylate (36 mg). MS [M+H]$^+$: 807.4.

Intermediate O1

2-[4-[4-[2-[[4-[4-(1-tert-butoxycarbonylpiperidine-4-carbonyl)piperazine-1-carbonyl]-3-chloro-phenyl]carbamoyl]-3-methyl-imidazol-4-yl]-2,3-difluoro-phenyl]-3-methyl-pyrazol-1-yl]acetic acid

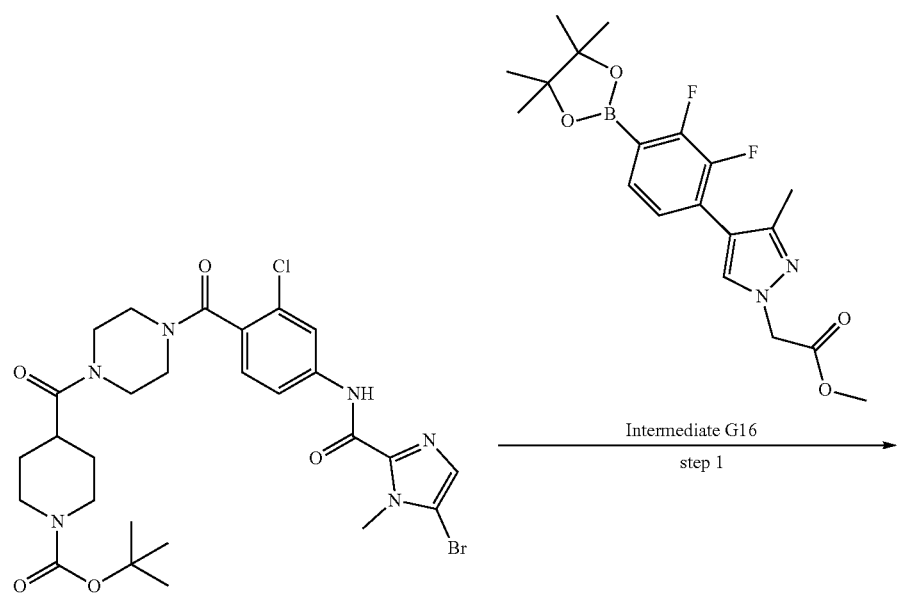

-continued

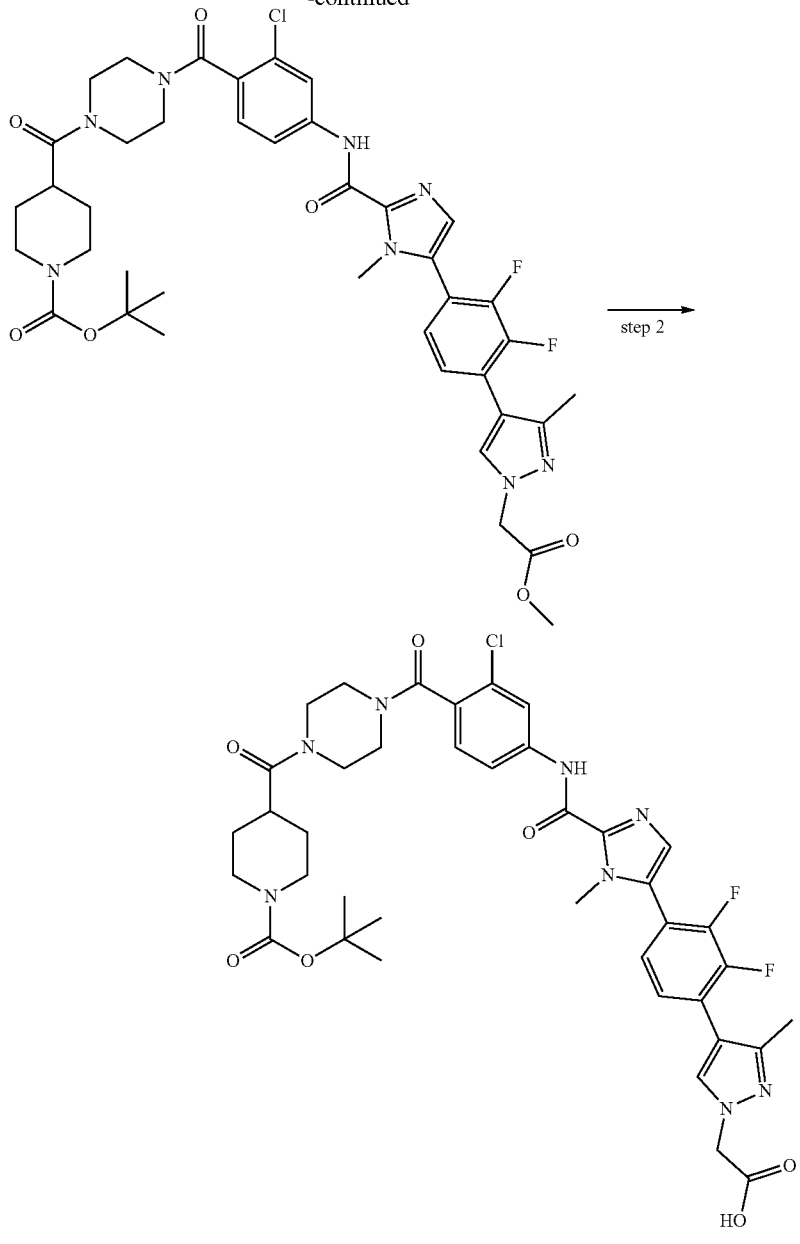

Intermediate O1

Step 1: tert-butyl 4-[4-[2-chloro-4-[[5-[4-[1-(2-ethoxy-2-oxo-ethyl)-3-methyl-pyrazol-4-yl]-2,3-difluoro-phenyl]-1-methyl-imidazole-2-carbonyl]amino]benzoyl]piperazine-1-carbonyl]piperidine-1-carboxylate A mixture of tert-butyl 4-[4-[4-[(5-bromo-1-methyl-imidazole-2-carbonyl)amino]-2-chloro-benzoyl]piperazine-1-carbonyl]piperidine-1-carboxylate (4554.2 mg, 7.14 mmol), ethyl 2-[4-[2,3-difluoro-4-(4,4,5,5-tetramethyl-1,3,2-dioxaborolan-2-yl)phenyl]-3-methyl-pyrazol-1-yl]acetate (2900.0 mg, 7.14 mmol), Na$_2$CO$_3$ (1513.3 mg, 14.28 mmol) and[1,1-Bis(di-tert-butylphosphino)ferrocene]palladium(II) Dichloride (943.4 mg, 1.07 mmol) in a flask. The flask was degassed and purged with N$_2$ gas for four times. 1,4-dioxane (30 mL) and water (6 mL) was added by injector to the mixture. The mixture was stirred at 90° C. for 2 h under N$_2$. The reaction mixture was filterrd and the filtrate was concentrated under reduced pressure to remove the solvent, then the product was purified by reversed-phase chromatography and dried by lyophilization to give tert-butyl 4-[4-[2-chloro-4-[[5-[4-[1-(2-ethoxy-2-oxo-ethyl)-3-methyl-pyrazol-4-yl]-2,3-difluoro-phenyl]-1-methyl-imidazole-2-carbonyl]amino]benzoyl]piperazine-1-carbonyl]piperidine-1-carboxylate (2750.0 mg). MS [M+H]$^+$: 837.3.

2-[4-[4-[2-[[4-[4-(1-tert-butoxycarbonylpiperidine-4-carbonyl)piperazine-1-carbonyl-3-chloro-phenyl]carbamoyl]-3-methyl-imidazol-4-yl]-2,3-difluoro-phenyl]-3-methyl-pyrazol-1-yl]acetic acid To a solution of tert-butyl 4-[4-[2-chloro-4-[[5-[4-[1-(2-ethoxy-2-oxo-ethyl)-3-methyl-pyrazol-4-yl]-2,3-difluorophenyl]-1-methyl-imidazole-2-carbonyl]amino]benzoyl] piperazine-1-carbonyl]piperdine-1-carboxylate (2740.0 mg, 3.27 mmol) in Methanol (30.0 mL) and water (10.0 mL) was added LiOH (235.1 mg, 9.82 mmol). The mixture was stirred at 20° C. for 12 h under $N_2$. The reaction mixture was quenched by water (50 mL), extracted with EtOAc (100×3 mL). The combined organic layers were washed brine (50 mL), dried ($Na_2SO_4$) and concentrated to give 2-[4-[4-[2-[[4-[4-(1-tert-butoxycarbonylpiperidine-4-carbonyl)piperazine-1-carbonyl]-3-chloro-phenyl] carbamoyl]-3-methyl-imidazol-4-yl]-2,3-difluoro-phenyl]-3-methyl-pyrazol-1l-yl]acetic acid (2500.0 mg). MS $[M+H]^+$: 809.3.

The following examples were prepared in analogy to Intermediate 01.

| Ex # | Name | Structure | MS ESI $[M + H]^+$ | Starting Material |
|---|---|---|---|---|
| Intermediate O2 | 2-[4-[4-[2-[[4-[4-(1-tert-butoxycarbonyl piperidine-4-carbonyl)piperazine-1-carbonyl]-3-chloro-phenyl]carbamoyl]-3-methyl-imidazol-4-yl]-2,3-difluoro-phenyl]-5-methyl-pyrazol-1-yl]acetic acid | 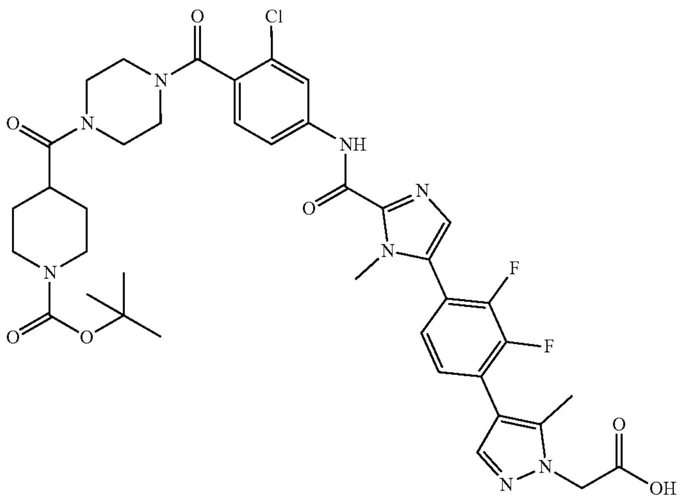 [SMILES: Cc1c(-c2ccc(-c3cnc(C(=O)Nc4ccc(C(=O)N5CCN(C(=O)C6CCN(C(=O)OC(C)(C)C)CC6)CC5)c(Cl)c4)n3C)c(F)c2F)cnn1CC(=O)O] | 809.6 | Intermediate D1; Intermediate G30 and LiOH |

Intermediate P1

N-[4-[4-[1-(2-amino-2-oxo-ethyl)piperidine-4-carbonyl]piperazine-1-carbonyl]-3-chloro-phenyl]-5-bromo-1-methyl-imidazole-2-carboxamide

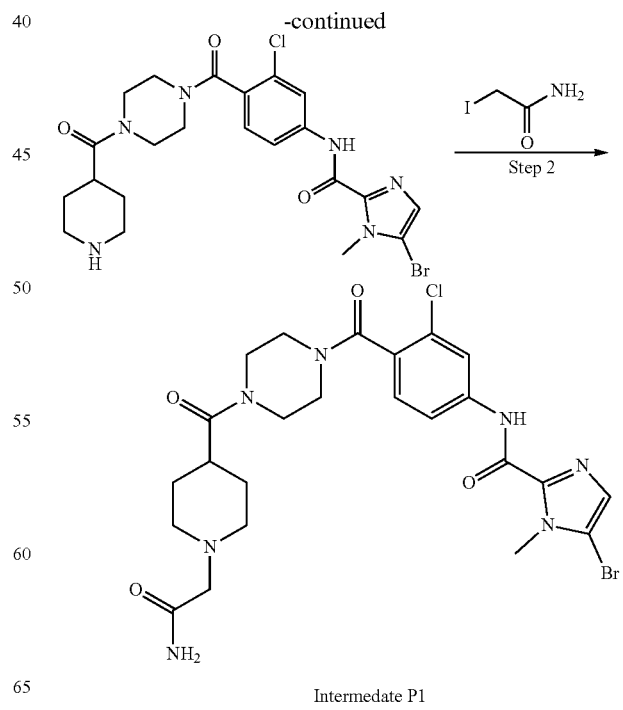

Step 1: 5-bromo-N-[3-chloro-4-[4-(piperidine-4-carbonyl)piperazine-1-carbonyl]phenyl]-1-methyl-imidazole-2-carboxamide To a solution of tert-butyl 4-(4-(4-(5-bromo-1-methyl-1H-imidazole-2-carboxamido)-2-chlorobenzoyl)piperazine-1-carbonyl)piperidine-1-carboxylate (1.9 g, 3.0 mmol) in DCM (25 mL) and was TFA (5 mL) then the resultant mixture was stirred for 1.0 h at room temperature. The mixture was basified with aqueous ammonia to pH=9-10 and then the mixture was poured into water (50 mL) and then extracted with dichloromethane/isopropanol (100/10 mL), the organic layer was concentrated in vacuum to give 5-bromo-N-[3-chloro-4-[4-(piperidine-4-carbonyl)piperazine-1-carbonyl]phenyl]-1-methyl-imidazole-2-carboxamide (1.2 g), which was used in next step without purification. MS [M+H]$^+$: 537.3.

Step 2: N-[4-[4-[1-(2-amino-2-oxo-ethyl)piperidine-4-carbonyl]piperazine-1-carbonyl]-3-chloro-phenyl]-5-bromo-1-methyl-imidazole-2-carboxamide To a solution of 5-bromo-N-[3-chloro-4-[4-(piperidine-4-carbonyl)piperazine-1-carbonyl]phenyl]-1-methyl-imidazole-2-carboxamide (2.15 g, 4.0 mmol) and DIPEA (1.55 g, 12 mmol) in acetonitrile (25 ml) was added 2-iodoacetamide (888 mg, 4.8 mmol) at room temperature, and then the resultant mixture was stirred overnight. The mixture was poured into water (50 mL) and then extracted with dichloromethane/isopropanol (100/10 mL), the organic layer was concentrated to give a red oil, which was purified by flash chromatography on silica gel to afford N-[4-[4-[1-(2-amino-2-oxo-ethyl)piperidine-4-carbonyl]piperazine-1-carbonyl]-3-chloro-phenyl]-5-bromo-1-methyl-imidazole-2-carboxamide (1.8 g). MS [M+H]$^+$: 594.2.

Intermediate Q1 tert-butyl 4-[4-[4-[[5-[4-[1-(2-aminoethyl)-5-methyl-pyrazol-4-yl]-2,3-difluoro-phenyl]-1-methyl-imidazole-2-carbonyl]amino]-2-chloro-benzoyl]piperazine-1-carbonyl]piperidine-1-carboxylate

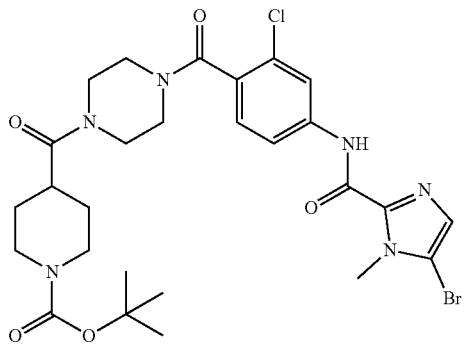

Intermedate D1

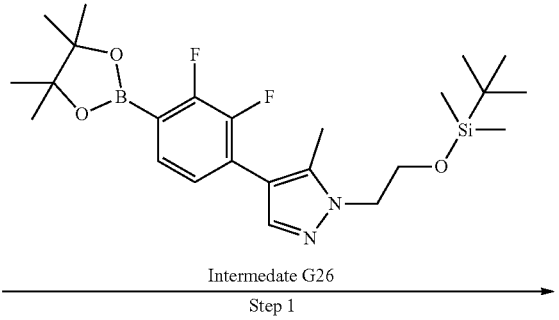

Intermediate G26

Step 1

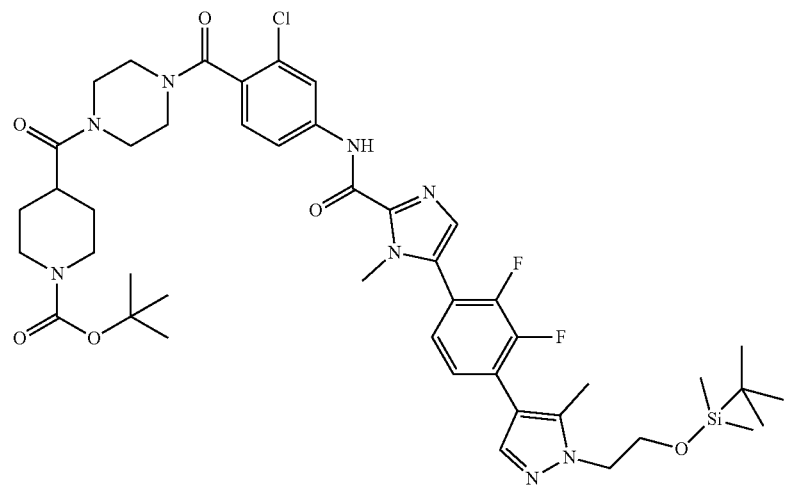

Step 2

-continued

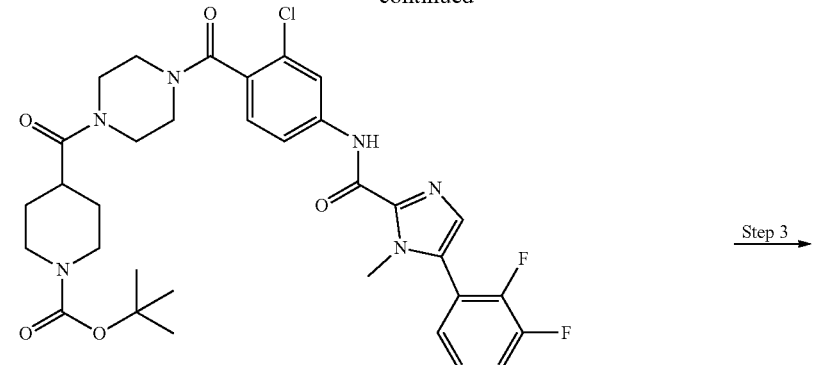

Step 3

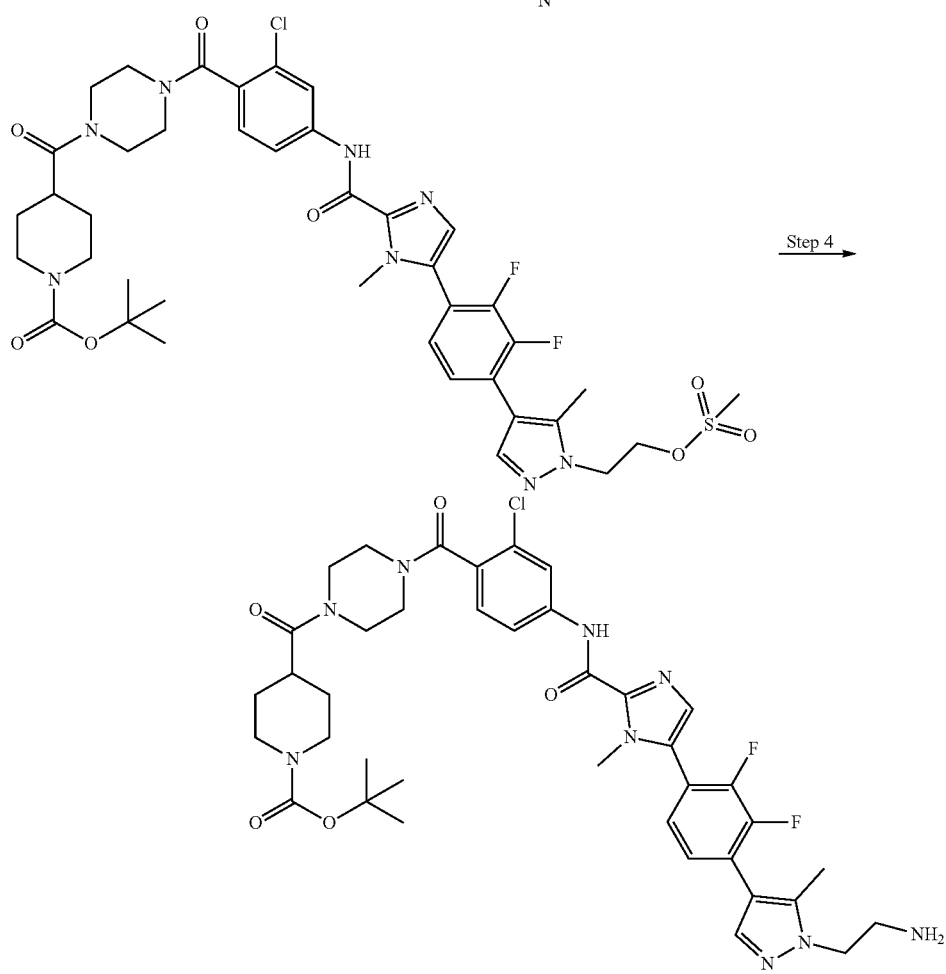

intermediate Q1

Step 1: tert-butyl 4-[4-[4-[[5-[4-[1-[2-tert-butyl(dimethyl)silyl]oxyethyl]-5-methyl-pyrazol-4-yl]-2,3-difluoro-phenyl]-1-methyl-imidazole-2-carbonyl]amino]-2-chloro-benzoyl]piperazine-1-carbonyl]piperidine-1-carboxylate 4-[4-[4-[(5-bromo-1-methyl-imidazole-2-carbonyl)amino]-2-chloro-benzoyl]piperazine-1-carbonyl]piperidine-1-carboxylic acid tert-butyl ester (1.5 g, 2.35 mmol) was dissolved in 1,4-dioxane (15 mL) and water (1.5 mL). tert-butyl-[2-[4-[2,3-difluoro-4-(4,4,5,5-tetramethyl-1,3,2-dioxaborolan-2-yl)phenyl]-5-methyl-pyrazol-1-yl]ethoxy]-dimethyl-silane (1.46 g, 3.06 mmol), 1,1'-bis(di-tert-butylphosphino)ferrocene palladium dichloride (153.24 mg, 0.235 mmol) and Na$_2$CO$_3$ (747.64 mg, 7.05 mmol) were added at rt. The mixture was stirred at 100° C. for 15 h under N₂. The reaction was filtered, the filtrate was concentrated under vacuum, The crude compound was purified by flash chromatography on silica gel, to afford 4-[4-[4-[[5-[4-[1-[2-[tert-butyl(dimethyl)silyl]oxyethyl]-5-methyl-pyrazol-4-yl]-2,3-difluoro-phenyl]-1-methyl-imidazole-2-carbonyl]amino]-2-chloro-benzoyl]piperazine-1-carbonyl]piperidine-1-carboxylic acid tert-butyl ester (1.2 g). MS [M+H]⁺. 910.1.

Step 2: tert-butyl 4-[4-[2-chloro-4-[[5-[2,3-difluoro-4-[1-(2-hydroxyethyl)-5-methyl-pyrazol-4-yl]phenyl]-1-methyl-imidazole-2-carbonyl]amino]benzoyl]piperazine-1-carbonyl]piperidine-1-carboxylate tert-butyl 4-[4-[4-[[5-[4-[1-[2-[tert-butyl(dimethyl)silyl]oxyethyl]-5-methyl-pyrazol-4-yl]-2,3-difluoro-phenyl]-1-methyl-imidazole-2-carbonyl]amino]-2-chloro-benzoyl]piperazine-1-carbonyl]piperidine-1-carboxylate (1.2 g, 1.32 mmol) was dissolved in N,N-dimethylformamide (20 mL) and water (5 mL), ammonium fluoride ((NH₄)F) (977.37 mg, 26.39 mmol) was added at rt. The reaction was stirred at 60° C. for 1 h. The reaction mixture was diluted with water (80 mL) and extracted two times with EtOAc (40 mL). The organic layers were washed with brine (30 mL), dried over Na₂SO₄ and concentrated to dryness. The crude product was directly used to the next step, to afford tert-butyl 4-[4-[2-chloro-4-[[5-[2,3-difluoro-4-[1-(2-hydroxyethyl)-5-methyl-pyrazol-4-yl]phenyl]-1-methyl-imidazole-2-carbonyl]amino]benzoyl]piperazine-1-carbonyl]piperidine-1-carboxylate (1.04 g). MS [M+H]⁺: 795.9.

Step 3: tert-butyl 4-[4-[2-chloro-4-[[5-[2,3-difluoro-4-[5-methyl-1-(2-methylsulfonyloxyethyl)pyrazol-4-yl]phenyl]-1-methyl-imidazole-2-carbonyl]amino]benzoyl]piperazine-1-carbonyl]piperidine-1-carboxylate tert-butyl 4-[4-[2-chloro-4-[[5-[2,3-difluoro-4-[1-(2-hydroxyethyl)-5-methyl-pyrazol-4-yl]phenyl]-1-methyl-imidazole-2-carbonyl]amino]benzoyl]piperazine-1-carbonyl]piperidine-1-carboxylate (1 g, 1.26 mmol) was dissolved in dichloromethane (30 mL), Methanesulfonic anhydride (328.57 mg, 1.89 mmol) and DIEA (325.02 mg, 2.51 mmol) were added at rt. The mixture was stirred at room temperature for 3 h. The reaction was concentrated under vacuum, The crude material was purified by flash chromatography on silica gel to afford tert-butyl 4-[4-[2-chloro-4-[[5-[2,3-difluoro-4-[5-methyl-1-(2-methylsulfonyloxyethyl)pyrazol-4-yl]phenyl]-1-methyl-imidazole-2-carbonyl]amino]benzoyl]piperazine-1-carbonyl]piperidine-1-carboxylate (580 mg). MS [M+H]⁺: 873.8.

Step 4: tert-butyl 4-[4-[4-[[5-[4-[1-(2-aminoethyl)-5-methyl-pyrazol-4-yl]-2,3-difluoro-phenyl]-1-methyl-imidazole-2-carbonyl]amino]-2-chloro-benzoyl]piperazine-1-carbonyl]piperidine-1-carboxylate tert-butyl 4-[4-[2-chloro-4-[[5-[2,3-difluoro-4-[5-methyl-1-(2-methylsulfonyloxyethyl)pyrazol-4-yl]phenyl]-1-methyl-imidazole-2-carbonyl]amino]benzoyl]piperazine-1-carbonyl]piperidine-1-carboxylate (580 mg, 0.664 mmol) was dissolved in methanol (10 mL), 7 M ammonia (3.73 g, 33.21 mmol) was added at rt. The mixture was stirred at 80° C. for 15 h. The reaction was concentrated under vacuum, the crude product was directly used to the next step, to afford tert-butyl 4-[4-[4-[[5-[4-[1-(2-aminoethyl)-5-methyl-pyrazol-4-yl]-2,3-difluoro-phenyl]-1-methyl-imidazole-2-carbonyl]amino]-2-chloro-benzoyl]piperazine-1-carbonyl]piperidine-1l-carboxylate (527 mg). MS [M+H]⁺: 794.8.

The following examples were prepared in analogy to Intermediate Q1.

| Ex # | Name | Structure | MS ESI [M + H]⁺ | Starting Material |
|---|---|---|---|---|
| Intermediate Q2 | tert-butyl 4-[4-[4-[[5-[4-[1-(2-aminoethyl)-3-methyl-pyrazol-4-yl]-2,3-difluoro-phenyl]-1-methyl-imidazole-2-carbonyl]amino]-2-chloro-benzoyl]piperazine-1-carbonyl]piperidine-1-carboxylate | 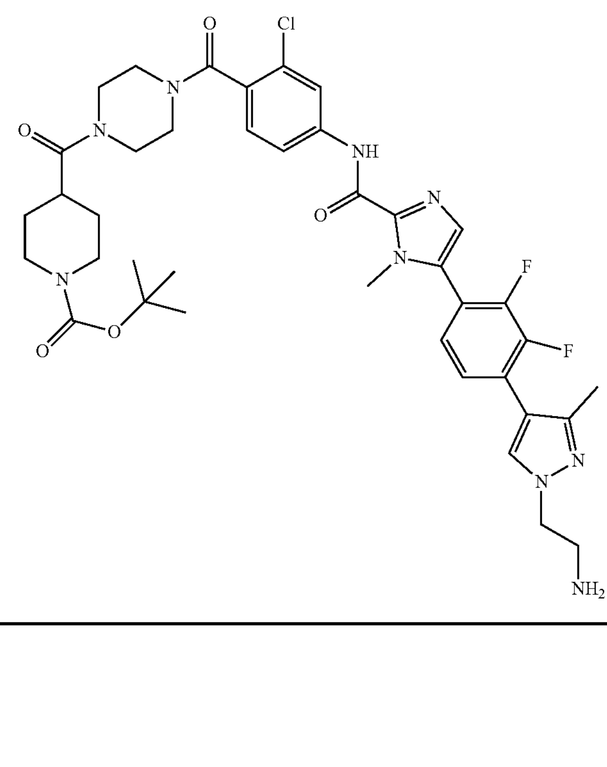 | 530.2 | Intermediate D1 and Intermediate G27; ammonium fluoride; Methanesulfonic anhydride; ammonia |

Intermediate R1

O1-tert-butyl O2-methyl (2S,4R)-4-[tert-butyl(diphenyl)silyl]oxypyrrolidine-1,2-dicarboxylate

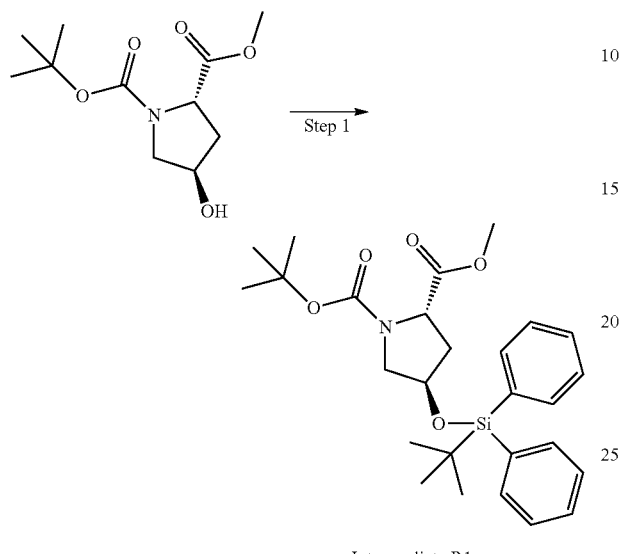

Intermediate R1

1-(tert-butyl) 2-methyl (2S,4R)-4-hydroxypyrrolidine-1,2-dicarboxylate (500 mg, 2.04 mmol), tert-butylchlorodiphenylsilane (672 mg, 2.45 mmol), 1H-imidazole (278 mg, 4.08 mmol) and N,N-dimethylpyridin-4-amine (24.9 mg, 204 μmol) were stirred in $CH_2Cl_2$ (10.2 mL) for 18 h. The reaction mixture was quenched with a saturated aqueous $Na_2CO_3$ solution until pH=10. The aqueous layer was extracted with $CH_2Cl_2$ and the combined organic phases were dried over $Na_2SO_4$ and filtered. The solvent was removed in vacuum to afford an oil, which was purified by flash column chromatography on silica gel to afford the product (902 mg). MS $[M+H]^+$: 484.2.

Intermediate R2

(2S,4R)-4-[tert-butyl(diphenyl)silyl]oxy-1-methyl-pyrrolidine-2-carboxylic acid

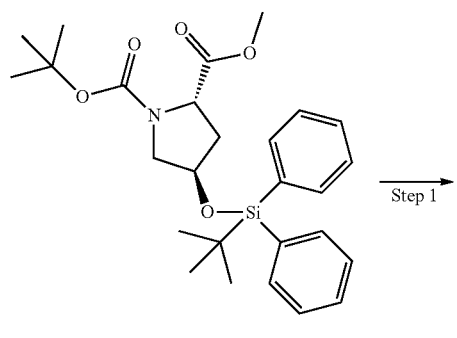

Intermediate R1

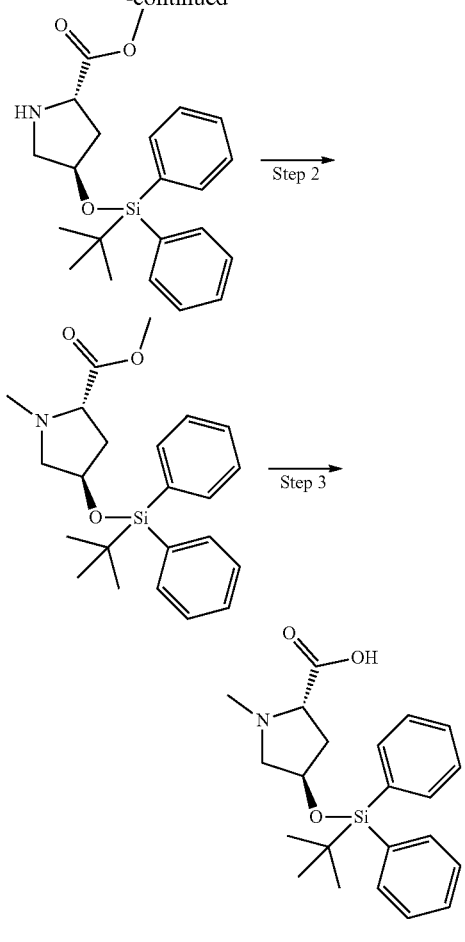

Intermediate R2

Step 1: methyl (2S,4R)-4-[tert-butyl(diphenyl)silyl]oxypyrrolidine-2-carboxylate O1-tert-butyl O2-methyl (2S,4R)-4-[tert-butyl(diphenyl)silyl]oxypyrrolidine-1,2-dicarboxylate (700 mg, 1.45 mmol) was dissolved in 5 mL 20% TFA/DCM solution and stirred at room temperature for 1 h. The solvent was removed in vacuum. The residue was neutralized with 100 mL sat. $K_2CO_3$, extracted with MeOH/DCM (50 mL×4, v/v=1:10), dried over sodium sulfate and concentrated in vacuo to afford the product (545 mg). MS $[M+H]^+$: 384.2.

Step 2: methyl (2S,4R)-4-[tert-butyl(diphenyl)silyl]oxy-1-methyl-pyrrolidine-2-carboxylate methyl (2S,4R)-4-((tert-butyldiphenylsilyl)oxy)pyrrolidine-2-carboxylate (270 mg, 704 μmol) and formaldehyde (85.7 mg, 1.06 mmol) (37% aqueous solution) was dissolved in 1,2-dichloroethane (3.52 mL) and stirred at room temperature for 30 min before adding of $NaBH_3CN$ (66.4 mg, 1.06 mmol). The mixture was then continued for 3 h. The mixture was poured into 100 mL water and extracted with DCM (50 mL×3). The organic layers were combined, washed with 50 mL brine, dried over sodium sulfate and concentrated in vacuum. The residue was purified by flash chromatography to afford the product (230 mg) as colorless oil. MS $[M+H]^+$: 398.2.

Step 3: (2S,4R)-4-[tert-butyl(diphenyl)silyl]oxy-1-methyl-pyrrolidine-2-carboxylic acid methyl (2S,4R)-4-[tert-butyl(diphenyl)silyl]oxy-1-methyl-pyrrolidine-2-carboxylate (230 mg) was dissolved in 5 mL MeOH and 1 mL water. To this solution was added 100 mg LiOH. The resulting mixture was stirred at room temperature for 48 h. The solution was poured into 100 mL 1N HCl and extracted with DCM (50 mL×4). The organic layers were combined, washed with 50 mL brine, dried over sodium sulfate and concentrated in vacuum. The crude product (200 mg) was used in the next step without purification. MS [M+H]$^+$: 384.2.

Intermediate R3

(2S,4R)-1-tert-butoxycarbonyl-4-[tert-butyl(diphenyl)silyl]oxy-pyrrolidine-2-carboxylic acid

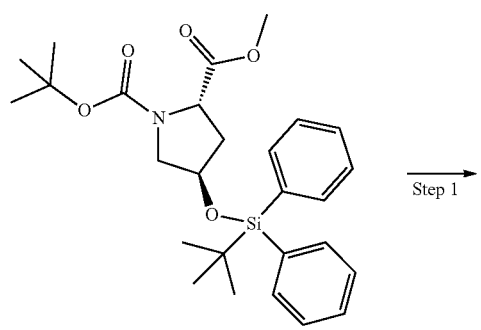

Intermediate R1

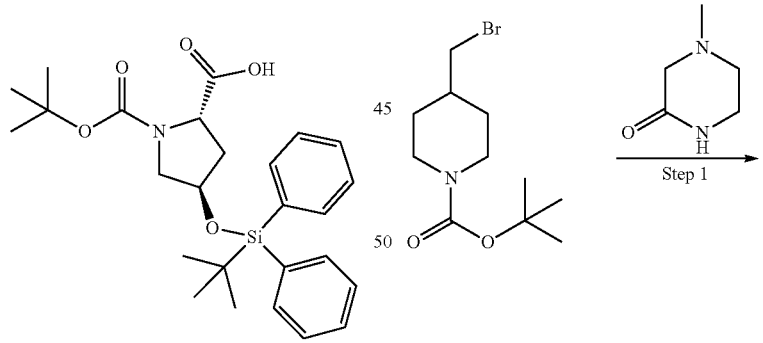

Intermediate R3

1-(tert-butyl) 2-methyl (2S,4R)-4-((tert-butyldiphenylsilyl)oxy)pyrrolidine-1,2-dicarboxylate (200 mg, 413 μmol) and lithium hydroxide (99 mg, 4.13 mmol) were stirred in water (345 μL) and MeOH (1.72 mL) for 18 h. After completion, the mixture was poured into 100 mL 1M HCl. The aqueous phase was extracted with DCM (50 mL×3). The organic layers were combined, washed with 50 mL brine, dried over sodium sulfate and concentrated in vacuum. The crude product was used in the coming step without purification. MS [M+H]$^+$: 470.3.

Intermediate R4

5-(difluoromethyl)-4-iodo-1-(2-methoxyethyl)pyrazole

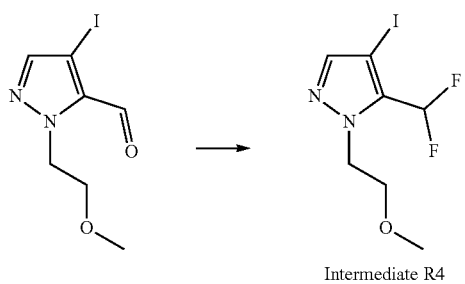

Intermediate R4

To a solution of 4-iodo-2-(2-methoxyethyl)pyrazole-3-carbaldehyde (1000 mg, 3.57 mmol) in dichloromethane (10 mL) was added dast (748.22 mg, 613.3 uL, 4.64 mmol) slowly at 0° C., the reaction was gradually warmed to room temperature and stirred for 18 h. The reaction was quenched with water. The reaction mixture was washed with brine and extracted in DCM. The organic layer was dried over anhydrous Na$_2$SO$_4$ and concentrated in vacuum The residue was purified by column chromatography to give 5-(difluoromethyl)-4-iodo-1-(2-methoxyethyl)pyrazole (800 mg). MS [M+H]$^+$: 303.0.

Intermediate R5

4-methyl-1-(4-piperidylmethyl)piperazin-2-one

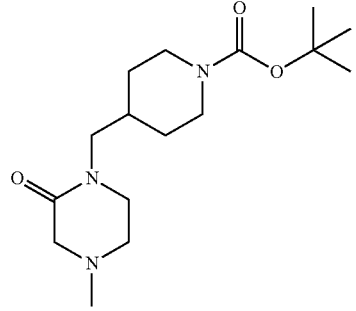

-continued

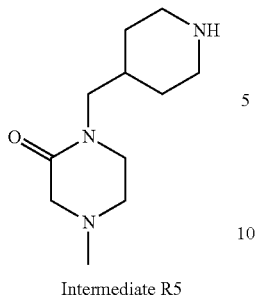

Intermediate R5

Step 1: tert-butyl 4-[(4-methyl-2-oxo-piperazin-1-yl)methyl]piperidine-1-carboxylate sodium hydride (275 mg, 6.84 mmol) was added to a solution of 4-methylpiperazin-2-one (650 mg, 5.7 mmol) in anhydrous DMF (15 ml). After 30 min, tert-butyl 4-(bromomethyl)piperidine-1-carboxylate (1.60 g, 5.7 mmol) was added and the mixture was stirred for 12 h at room temperature. The mixture was poured into water (80 mL) and extracted with EtOAc (50 mL×3). The organic layers were combined, washed with water and brine, dried over sodium sulfate and concentrated in vacuum to give tert-butyl 4-[(4-methyl-2-oxo-piperazin-1-yl)methyl]piperidine-1-carboxylate (1.2 g), which was directly used in the next step without further purification. MS [M+H]+: 312.2.

Step 2: 4-methyl-1-(4-piperidylmethyl)piperazin-2-one

To a solution of tert-butyl 4-((4-methyl-2-oxopiperazin-1-yl)methyl)piperidine-1-carboxylate (1.2 g, 3.8 mmol) in DCM (10 mL) and was added TFA (3 mL) then the resultant mixture was stirred for 1.0 h at room temperature. The solvent was concentrated under reduced pressure to give 4-methyl-1-(4-piperidylmethyl)piperazin-2-one (600 mg). MS [M+H]+: 212.2.

Intermediate R6 rac-(2S)-1-tert-butoxycarbonyl-4-(hydroxymethyl)pyrrolidine-2-carboxylic acid

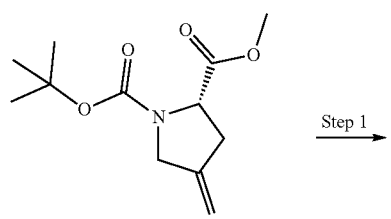

Step 1

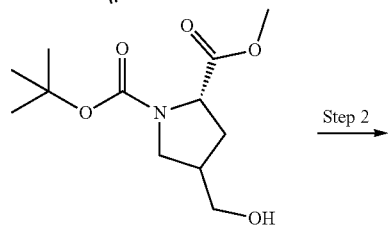

Step 2

-continued

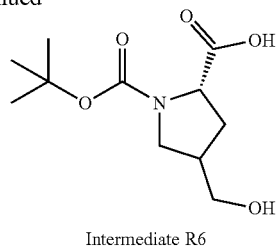

Intermediate R6

Step 1: 01-tert-butyl 02-methyl rac-(2S)-4-(hydroxymethyl)pyrrolidine-1,2-dicarboxylate To a solution of 01-tert-butyl 02-methyl (2S)-4-methylenepyrrolidine-1,2-dicarboxylate (1.0 g, 4.14 mmol) in THF (20.0 mL) was added 9-borabicyclo[3.3.1]nonane (0.5 M in THF) (9.95 mL, 4.97 mmol) slowly under N₂ at 0° C. After addition, this reaction mixture was warmed to 20° C. and stirred for 4 h. Then sodium hydroxide (2 M) (5.18 mL, 10.36 mmol) and hydrogen peroxide (1.46 g, 12.85 mmol) were added into this mixture slowly at 0° C. This reaction mixture was stirred at 0° C. for 1 h. Then the reaction mixture was warmed to 20° C. and stirred for further 2 h. This reaction was quenched by saturated aqueous Na₂SO₃ (50 mL) and extracted by EtOAc (20 mL×2). The combined organic layers were dried over Na₂SO₄ and concentrated to get the crude product. This crude product was purified by silica gel chromatography (PE:EtOAc=1:1) to get 01-tert-butyl 02-methyl rac-(2S)-4-(hydroxymethyl)pyrrolidine-1, 2-dicarboxylate (500.0 mg) as colorless oil. MS [M+H]+: 260.2.

Step 2: rac-(2S)-1-tert-butoxycarbonyl-4-(hydroxymethyl)pyrrolidine-2-carboxylic acid To a solution of rac-(2S)-4-(hydroxymethyl)pyrrolidine-1,2-dicarboxylate (400.0 mg, 1.54 mmol) in methanol (5.0 mL), THF (5 mL) and water (1 mL) was added lithium hydroxide monohydrate (97.1 mg, 2.31 mmol) in one portion. This reaction mixture was stirred at 25° C. for 1 h. This reaction mixture was concentrated to get the crude product. This crude product was purified by Prep-HPLC (FA) to get rac-(2S)-1-tert-butoxycarbonyl-4-(hydroxymethyl)pyrrolidine-2-carboxylic acid (160.0 mg, 0.65 mmol, 34.34% yield) as yellow oil. MS [M+H]+: 146.0.

Intermediate R7

2-[4-hydroxy-4-(hydroxymethyl)-1-piperidyl]-1-piperazin-1-yl-ethanone; 2,2,2-trifluoroacetic acid

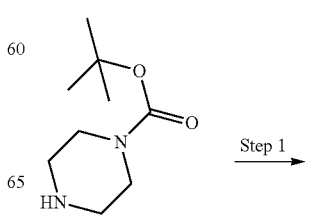

Step 1

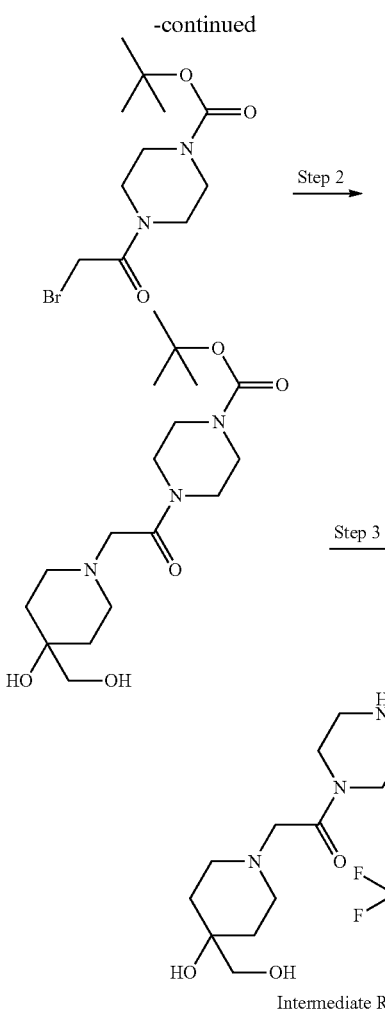

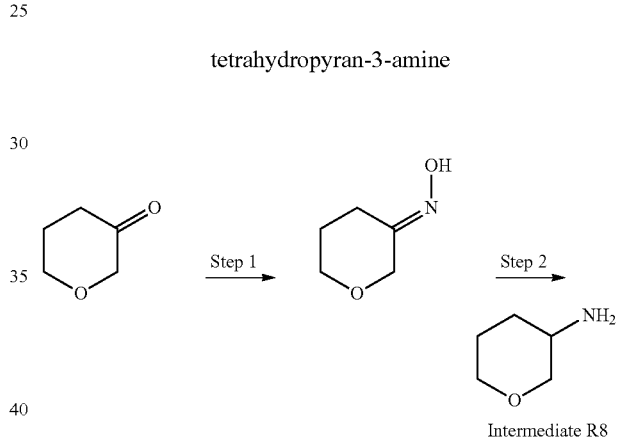

Intermediate R8 tetrahydropyran-3-amine

Intermediate R8 purified by Prep-HPLC (FA). The solution of desired product in ACN/H$_2$O was lyophilized to get tert-butyl 4-[2-[4-hydroxy-4-(hydroxymethyl)-1-piperidyl]acetyl]piperazine-1-carboxylate (180.0 mg). MS [M+H]$^+$: 358.1.

Step 3: 2-[4-hydroxy-4-(hydroxymethyl)-1-piperidyl]-1-piperazin-1-yl-ethanone; 2,2,2-trifluoroacetic acid To a solution of tert-butyl 4-[2-[4-hydroxy-4-(hydroxymethyl)-1-piperidyl]acetyl]piperazine-1-carboxylate (180.0 mg, 0.5 mmol) in DCM (5 mL) was added trifluoroacetic acid (0.5 mL, 6.49 mmol) in one portion. This reaction mixture was stirred at 25° C. for 1 h. This reaction mixture was concentrated to get 2-[4-hydroxy-4-(hydroxymethyl)-1-piperidyl]-1-piperazin-1-yl-ethanone;2,2,2-trifluoroacetic acid (190.0 mg), The crude product would be used in the next step directly without further purification. MS [M+H]$^+$: 258.1.

Intermediate R8 tetrahydropyran-3-amine

Step 1: tert-butyl 4-(2-bromoacetyl)piperazine-1-carboxylate

To a solution of tert-butyl piperazine-1-carboxylate (500.0 mg, 2.68 mmol) and in DCM (10.0 mL) was added 2-bromoacetyl chloride (464.78 mg, 2.95 mmol) slowly at 0° C. After addition, the reaction mixture was stirred at 0° C. for 2 h. This reaction was quenched by saturated aqueous NaHCO$_3$ (20 mL) and extracted by DCM (10 mL×2). The combined organic layers were dried over Na$_2$SO$_4$ and concentrated to get tert-butyl 4-(2-bromoacetyl)piperazine-1-carboxylate (800.0 mg), the crude product would be used in the next step directly without further purification. MS [M+H—C$_4$H$_8$]$^+$:251.0.

Step 2: tert-butyl 4-[2-[4-hydroxy-4-(hydroxymethyl)-1-piperidyl]acetyl]piperazine-1-carboxylate To a solution of 4-(hydroxymethyl)piperidin-4-ol (100.0 mg, 0.76 mmol) and potassium carbonate (210.73 mg, 1.52 mmol) in ACN (5.0 mL) was added tert-butyl 4-(2-bromoacetyl)piperazine-1-carboxylate (100.0 mg, 0.76 mmol) and potassium carbonate (351.28 mg, 1.14 mmol) in one portion. The reaction was stirred at room temperature for 1 h. This reaction mixture was filtered, and the filtrate was concentrated to get the crude product. This crude product was Step 1: tetrahydropyran-3-one oxime To a solution of tetrahydropyran-3-one (400.0 mg, 4.0 mmol) and potassium carbonate (828.2 mg, 5.99 mmol) in ACN (5 mL) was added hydroxylamine hydrochloride (555.3 mg, 7.99 mmol). The reaction mixture was stirred at 15° C. for 2 h. This reaction mixture was filtered and concentrated under reduced pressure to afford the crude product. The crude product was purified by silica gel chromatography to get tetrahydropyran-3-one oxime (400.0 mg).

Step 2: tetrahydropyran-3-amine

To a solution of tetrahydropyran-3-one oxime (350.0 mg, 3.04 mmol) in methanol (5.0 mL) was added palladium on carbon (161.7 mg) in one portion under N$_2$. This mixture was degassed and purged with N$_2$ for 3 times. Then H$_2$ (15 psi) was introduced into this system. The reaction mixture was stirred at 30° C. for 6 h under H$_2$ atmosphere. This reaction was filtered carefully and concentrated to get the crude product tetrahydropyran-3-amine (150.0 mg).

Intermediate R9

4-methyl-N-(tetrahydropyran-4-ylideneamino)benzenesulfonamide

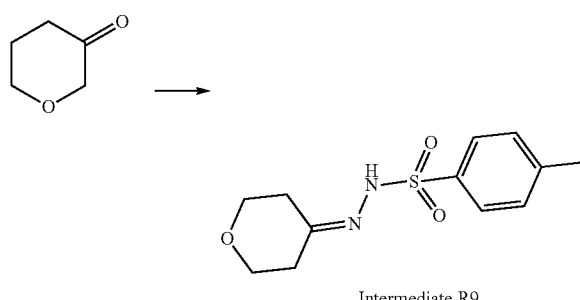

Intermediate R9

To a solution of tetrahydropyran-4-one (2.0 g, 19.98 mmol) in methanol (30.0 mL) was added 4-methylbenzenesulfonhydrazide (3.7 g, 19.98 mmol) the mixture was stirred at 20° C. for 3 h. The mixture was concentrated to give 4-methyl-N-(tetrahydropyran-4-ylideneamino)benzenesulfonamide (5.3 g, 19.75 mmol) as a white solid. MS [M+H]$^+$: 269.0.

Intermediate R10

4-(tert-butoxycarbonylamino)-1,1-dimethyl-piperidin-1-ium-4-carboxylic acid; chloride

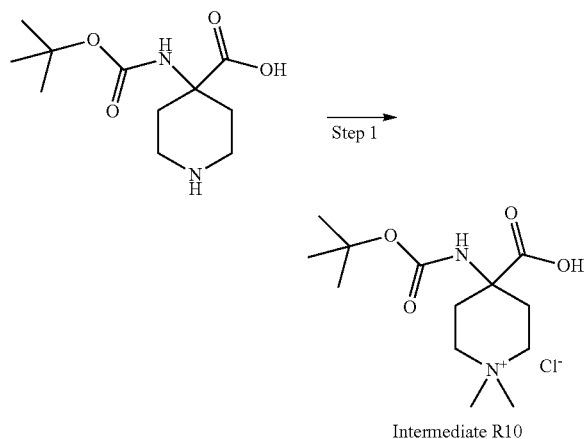

Intermediate R10

To a solution of 4-((tert-butoxycarbonyl)amino)piperidine-4-carboxylic acid (300 mg, 1.23 mmol) in MeOH (5 mL) was added sodium hydroxide (147 mg, 3.68 mmol) and methyl iodide (872 mg, 6.14 mmol), the reaction was stirred for two hours at room temperature. The reaction mixture was acidified with 3N HCl and concentrated in vacuum to give 4-(tert-butoxycarbonylamino)-1,1-dimethyl-piperidin-1-ium-4-carboxylic acid;chloride, the crude product was directly used for the next step without further purification. MS [M]$^+$: 273.2.

Intermediate R11

(2-tert-butoxy-2-oxo-ethyl)-(3-carboxypropyl)-bis[3-(methylamino)propyl]ammonium; bromide

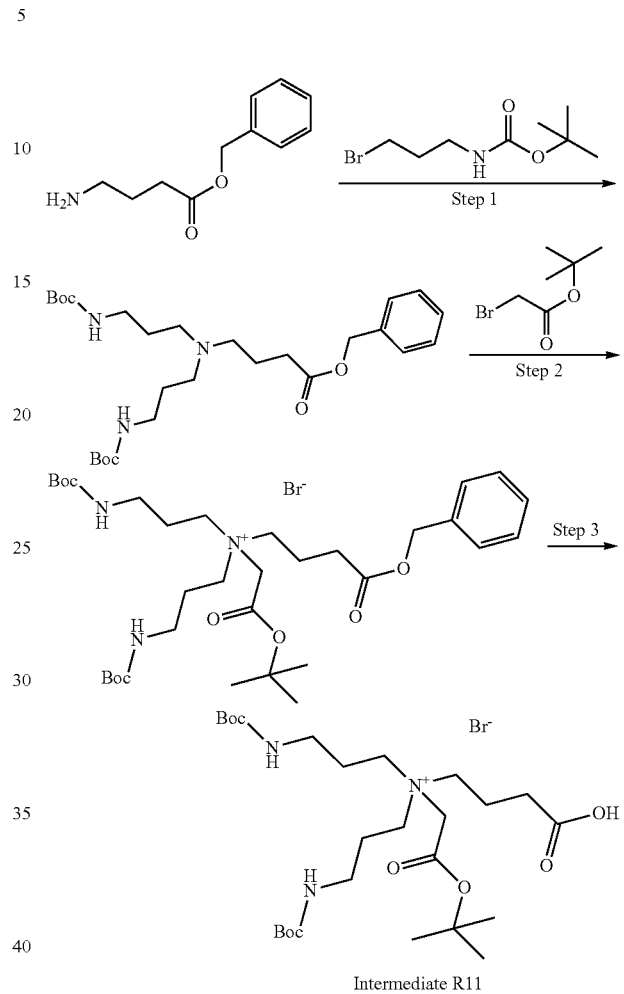

Intermediate R11

Step 1: benzyl 4-[bis[3-(tert-butoxycarbonylamino)propyl]amino]butanoate

To a solution of 3-(BOC-amino)propyl bromide (4.56 g, 19.16 mmol) in ACN (30 mL) was added benzyl 4-aminobutanoate;hydrochloride (2.0 g, 8.71 mmol) at 10° C., then the mixture was stirred at 70° C. for 16 h. The solution was concentrated, the residue was purified by reversed phase-HPLC (FA) to afford benzyl 4-[bis[3-(tert-butoxycarbonylamino)propyl]amino]butanoate (2.2 g). MS [M+H]$^+$: 508.4.

Step 2: (4-benzyloxy-4-oxo-butyl)-bis[3-(tert-butoxycarbonylamino)propyl]-(2-tert-butoxy-2-oxo-ethyl)ammonium; bromide To a solution of tert-butyl bromoacetate (1.27 mL, 7.88 mmol) in ACN (20 mL) was added benzyl 4-[bis[3-(tert-butoxycarbonylamino)propyl]amino]butanoate (2.0 g, 3.94 mmol) at 10° C., then the mixture was stirred at 80° C. for 16 h. The solution was concentrated, the residue was purified by reversed phase-HPLC (TFA) to afford (4-benzyloxy-4oxo-butyl)-bis[3-(tert-butoxycarbonylamino)propyl]-(2-tert-butoxy-2-oxo-ethyl)ammonium; bromide (1 g) as colorless oil. MS [M]$^+$: 622.5.

Step 3: bis[3-(tert-butoxycarbonylamino)propyl]-(2-tert-butoxy-2-oxo-ethyl)-(3-carboxypropyl)ammonium; bromide A solution of palladium on actived caobon (151.44 mg, 0.140 mmol) in Methanol (10 mL) was added (4-benzyloxy-4-oxo-butyl)-bis[3-(tert-butoxycarbonylamino)propyl]-(2-tert-butoxy-2-oxo-ethyl)ammonium;bromide (1.0 g, 1.42 mmol) under $N_2$, then the mixture was stirred under $H_2$ at 10° C. for 16 h. The strating materials were consumed completed. The mixture was filtered and concentrated to afford bis[3-(tert-butoxycarbonylamino)propyl]-(2-tert-butoxy-2-oxo-ethyl)-(3-carboxypropyl)ammonium; bromide (700 mg). MS $[M]^+$: 532.4.

The following examples were prepared in analogy to Intermediate R11

| Ex# | Name | Structure | MS ESI $[M + H]^+$ | Starting Material |
|---|---|---|---|---|
| Intermediate R12 | bis[(1-tert-butoxy-carbonylazetidin-3-yl)methyl]-(2-tert-butoxy-2-oxo-ethyl)-(3-carboxypropyl)ammonium; bromide | 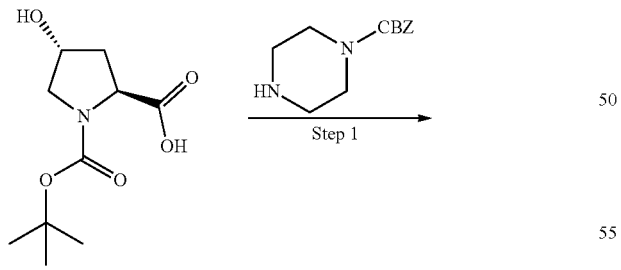 | 556.4 | benzyl 4-aminobutanoate and tert-butyl 3-(bromomethyl)azetidine-1-carboxylate; tert-butyl bromoacetate |

Intermediate R13

[(2S,4R)-4-hydroxy-1,1-dimethyl-pyrrolidin-1-ium-2-yl]-piperazin-1-yl-methanone

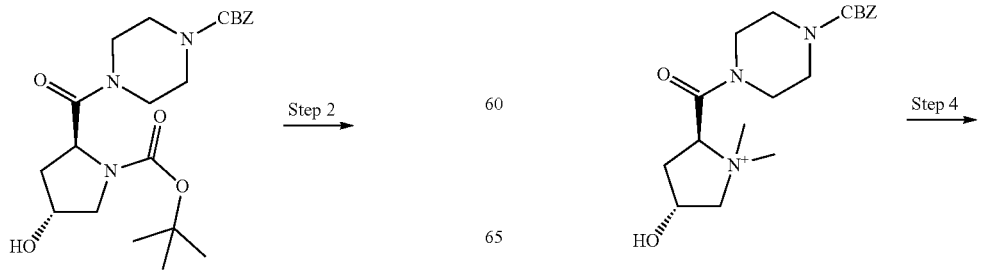

-continued

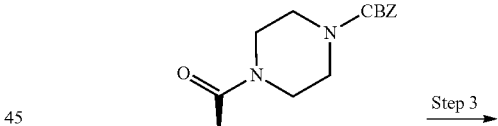

Step 3 →

Step 4 →

281
-continued

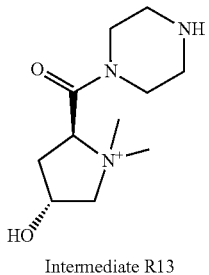

Intermediate R13

Step 1: benzyl 4-[(2S,4R)-1-tert-butoxycarbonyl-4-hydroxy-pyrrolidine-2-carbonyl]piperazine-1-carboxylate To a mixture of 1-CBZ-piperazine (5.0 g, 22.7 mmol) in THF (25 mL) and DMF (25 mL) was added N,N-diisopropylethylamine (17.57 g, 136.2 mmol) and BOC—HYP—OH (5.25 g, 22.7 mmol). Then the mixture was added propylphosphonic anhydride (18.78 g, 29.51 mmol) after 10 min. The reaction mixture was stirred at 25° C. for 16 h. The solution was extracted with water (50 mL) and EA (100 mL) and washed with sat.aq NaCl (50 mL), dried by anhydrous $Na_2SO_4$. The crude was purified by prep-HPLC(FA) to obtain the title compound (9.8 g). MS $[M+H]^+$: 434.5.

Step 2: benzyl 4-[(2S,4R)-4-hydroxypyrrolidine-2-carbonyl]piperazine-1-carboxylate To a mixture of benzyl 4-[rac-(2S,4R)-1-tert-butoxycarbonyl-4-hydroxy-pyrrolidine-2-carbonyl]piperazine-1-carboxylate (9.84 g, 22.7 mmol) in methanol (20 mL) was added HCl/dioxane (20 mL). The reaction mixture was stirred at 25° C. for 16 h. The solution was not purified and used next step directly to obtain the title compound (7.56 g). MS $[M+H]^+$: 334.5.

Step 3: benzyl 4-[(2S,4R)-4-hydroxy-1,1-dimethyl-pyrrolidin-1-ium-2-carbonyl]piperazine-1-carboxylate To a mixture of benzyl 4-[(2S,4R)-4-hydroxypyrrolidine-2-carbonyl]piperazine-1-carboxylate (7.56 g, 22.68 mmol) in MeCN (70 mL) and water (7 mL) was added iodomethane (32.19 g, 226.77 mmol) and triethylamine (63.21 mL, 453.54 mmol). The reaction mixture was stirred at 25° C. for 16 h. The mixture was concentrated to remove solvent, purified by prep-HPLC (0.1% FA) to afford the title compound (4 g). MS $[M]^+$: 362.4.

Step 4: piperazin-1-yl-[(2S,4R)-4-hydroxy-1,1-dimethyl-pyrrolidin-1-ium-2-yl]methanone To a mixture of benzyl 4-[(2S,4R)-4-hydroxy-1,1-dimethyl-pyrrolidin-1-ium-2-carbonyl]piperazine-1-carboxylate (1600.0 mg, 4.41 mmol) in methanol (20 mL) and were added ammonium hydroxide (2.0 mL, 4.41 mmol) and wet palladium 10% on active carbon (0.140 mmol, 0.030 eq). The reaction mixture was stirred at 25° C. for 16 h under hydrogen at 15 psi. The mixture was filtered and filtrate was concentrated to remove solvent, to afford the title compound (1 g). MS $[M]^+$: 228.2.

282

Intermediate R14

1-[(1-tert-butoxycarbonylazetidin-3-yl)methyl]-1-(2-tert-butoxy-2-oxo-ethyl)piperidin-1-ium-4-carboxylate

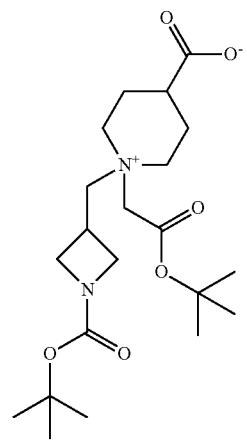 [SMILES: CC(C)(C)OC(=O)C[N+]1(CC2CN(C(=O)OC(C)(C)C)C2)CCC(C(=O)[O-])CC1]

Step 1: benzyl 1-[(1-tert-butoxycarbonylazetidin-3-yl)methyl]piperidine-4-carboxylate To a solution of benzyl piperidine-4-carboxylate hydrochloride (500.0 mg, 1.96 mmol) and potassium carbonate (811 mg, 5.87 mmol) in DMF (10 mL) was added 1-BOC-3-(bromomethyl)azetidine (587 mg, 2.35 mmol). The mixture was stirred at 25° C. for 16 h. Then the mixture was stirred at 50° C. for another 16 h. The mixture was diluted with EtOAc (100 mL) and then washed with brine (30 mL×3). The organic layer was dried over sodium sulfate, filtered and the filtrate was concentrated under vacuum. The residue was purified by column chromatography (PE:EA=2:1-0:1) to give the title compound (710 mg, 1.83 mmol, 74.17% yield) as light yellow gum. MS $[M+H]^+$: 389.1.

Step 2: benzyl 1-[(1-tert-butoxycarbonylazetidin-3-yl)methyl]-1-(2-tert-butoxy-2-oxo-ethyl)piperidin-1-ium-4-carboxylate; formate To a solution of benzyl 1-[(1-tert-butoxycarbonylazetidin-3-yl)methyl]piperidine-4-carboxylate (4.7 g, 12.1 mmol) and sodium iodide (181 mg, 1.21 mmol) in DMF (50 mL) was added tert-butyl bromoacetate (4.72 g, 24.2 mmol) and N,N-diisopropylethylamine (6.32 mL, 36.29 mmol). The mixture was stirred at 60° C. for 16 h. The mixture was concentrated under vacuum. The residue was purified twice by prep-HPLC (FA condition) to give the title compound (5 g, 9.93 mmol, 82.06% yield) as a yellow solid. MS $[M]^+$: 503.2.

Step 3: 1-[(1-tert-butoxycarbonylazetidin-3-yl)methyl]-1-(2-tert-butoxy-2-oxo-ethyl)piperidin-1-ium-4-carboxylate To a solution of benzyl 1-[(1-tert-butoxycarbonylazetidin-3-yl)methyl]-1-(2-tert-butoxy-2-oxo-ethyl)piperidin-1-ium-4-carboxylate formate (4.7 g, 8.57 mmol) in methanol (150 mL) was added palladium on charcoal (400 mg, 10% purity) and palladium hydroxide on charcoal (400.0 mg, 10% wt)

under nitrogen atmosphere. The mixture was degassed and then stirred at 15° C. for 4 h under hydrogen (760 mmHg). The mixture was filtered through celit pad, the solid was washed with MeOH (20 mL×4). The combined filtrate was concentrated under vacuum. The solid was dissolved in water (100 mL) and then lyophilized to give 1-[(1-tert-butoxycarbonylazetidin-3-yl)methyl]-1-(2-tert-butoxy-2-oxo-ethyl)piperidin-1-ium-4-carboxylate (3.5 g, 8.48 mmol, 93.86% yield) as a white solid. MS [M]⁺: 413.2.

Intermediate R15

Tert-butyl 2-[1-[3-(tert-butoxycarbonylamino)propyl]piperazin-1-ium-1-yl]acetate; formate

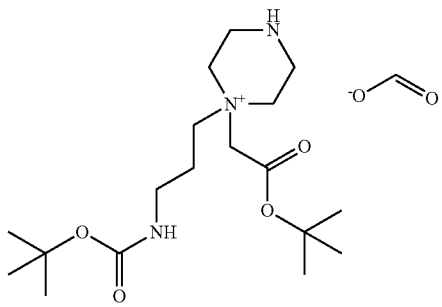

Step 1: benzyl 4-[3-(tert-butoxycarbonylamino)propyl]piperazine-1-carboxylate

To a solution of 1-CBZ-piperazine (5.0 g, 22.7 mmol) in MeCN (100 mL) was added triethylamine (3.16 mL, 22.7 mmol) and 3-(BOC-amino)propyl bromide (5.68 g, 23.83 mmol), then the mixture was stirred at 25° C. for 16 h. The mixture was concentrated in vacuum and purified by silica gel column (PE/EA=100:1-1:2) to obtain the title compound (5.2 g, 13.78 mmol, 60.69% yield) as light brown solid. MS [M+H]⁺: 378.3.

Step 2: benzyl 4-[3-(tert-butoxycarbonylamino)propyl]-4-(2-tert-butoxy-2-oxo-ethyl)piperazin-4-ium-1-carboxylate; formate To a solution of benzyl 4-[3-(tert-butoxycarbonylamino)propyl]piperazine-1-carboxylate (5.2 g, 13.78 mmol) in MeCN (100 mL) was added triethylamine (1.92 mL, 13.78 mmol) and tert-butyl bromoacetate (5.37 g, 27.55 mmol), then the mixture was stirred at 50° C. for 16 h. The mixture was concentrated in vacuum and purified by prep-HPLC (0.1% FA)-MeOH to obtain the title compound (4 g, 59% yield) as light yellow solid. MS [M+H]⁺: 492.4.

Step 3: tert-butyl 2-[1-[3-(tert-butoxycarbonylamino)propyl]piperazin-1-ium-1-yl]acetate; formate To a solution of benzyl 4-[3-(tert-butoxycarbonylamino)propyl]-4-(2-tert-butoxy-2-oxo-ethyl)piperazin-4-ium-1-carboxylate formate (4.0 g, 8.12 mmol) in THF (40 mL) was added 10% palladium on charcoal (400 mg) and the reaction stirred under hydrogen atmosphere at 25° C. for 16 h. The mixture was concentrated in vacuum and purified by prep-HPLC (0.1% FA)-ACN to obtain tert-butyl 2-[1-[3-(tert-butoxycarbonylamino)propyl]piperazin-1-ium-1-yl]acetate; formate (1.5 g, 4.18 mmol, 51.53% yield) as white solid. MS [M]⁺: 358.3.

Example A1

N-[3-chloro-4-[4-(1,1-dimethylpiperidin-1-ium-4-carbonyl)piperazine-1-carbonyl]phenyl]-5-[2,3-difluoro-4-[1-(2-methoxyethyl)-3-methyl-pyrazol-4-yl]phenyl]-1-methyl-imidazole-2-carboxamide; formate

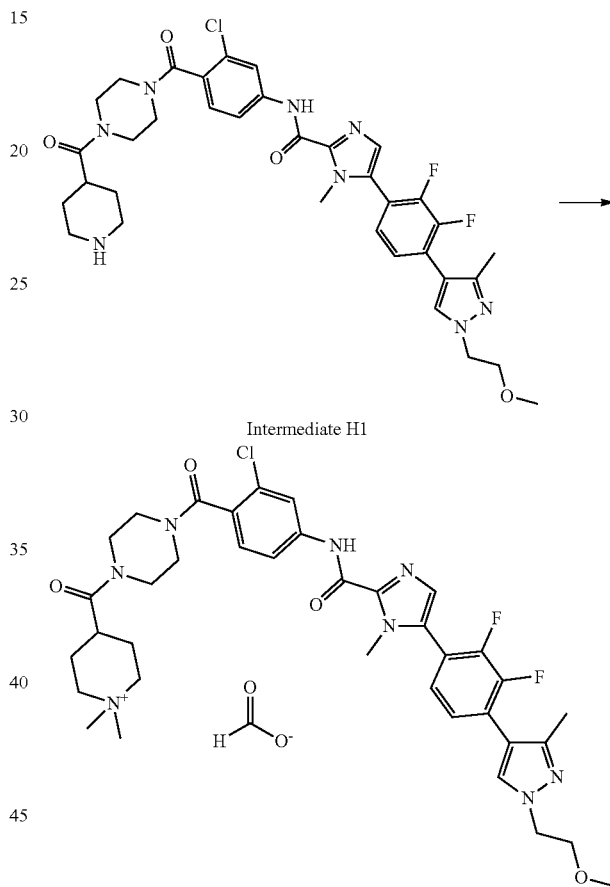

Example A1

In a 50 mL round-bottomed flask, afford N-[3-chloro-4-[4-(piperidine-4-carbonyl)piperazine-1-carbonyl]phenyl]-5-[2,3-difluoro-4-[1-(2-methoxyethyl)-3-methyl-pyrazol-4-yl]phenyl]-1-methyl-imidazole-2-carboxamide (131 mg, 185 μmol), MeI (105 mg, 739 μmol) and DIPEA (95.5 mg, 739 μmol) were combined with MeCN (6 mL) to give a light brown solution. The reaction was stirred at room temperature for 15 h. The crude reaction mixture was concentrated in vacuum. The crude material was purified by preparative HPLC to afford N-[3-chloro-4-[4-(1,1-dimethylpiperidin-1-ium-4-carbonyl)piperazine-1-carbonyl]phenyl]-5-[2,3-difluoro-4-[1-(2-methoxyethyl)-3-methyl-pyrazol-4-yl]phenyl]-1-methyl-imidazole-2-carboxamide; formate (80 mg). MS [M]⁺: 737.3.

The following examples were prepared in analogy to Examples A1.

| Ex# | Name | Structure | MS ESI [M]+ | Starting Material |
|---|---|---|---|---|
| Example A2 | N-[3-chloro-4-[4-(1,1-dimethylpiperidin-1-ium-4-carbonyl)piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide; formate | 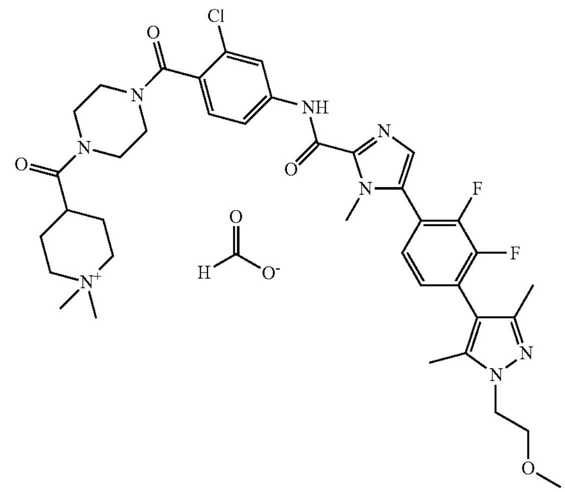 | 751.3 | Intermediate H4 and iodomethane |
| Example A3 | N-[3-chloro-4-[4-(1,1-dimethylpiperidin-1-ium-4-carbonyl)piperazine-1-carbonyl]phenyl]-5-[4-[1-(2-methoxyethyl)-3,5-dimethyl-pyrazol-4-yl]phenyl]-1-methyl-imidazole-2-carboxamide; formate | 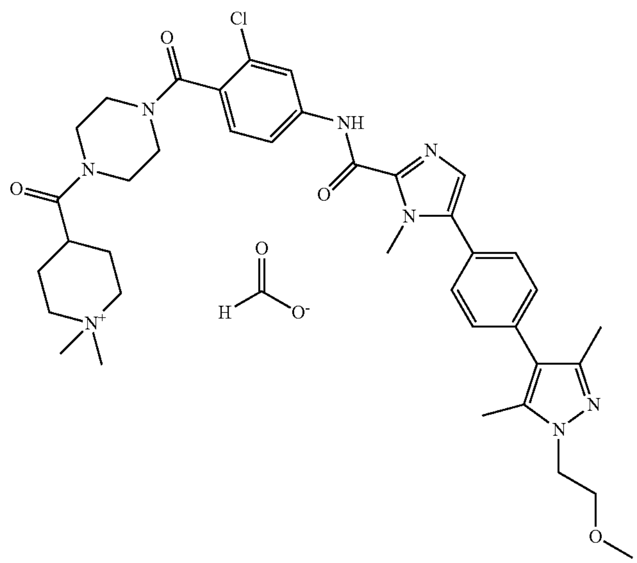 | 715.2 | Intermediate H5 and iodomethane |
| Example A4 | N-[3-chloro-4-[4-(1,1-dimethylpiperidin-1-ium-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; formate | 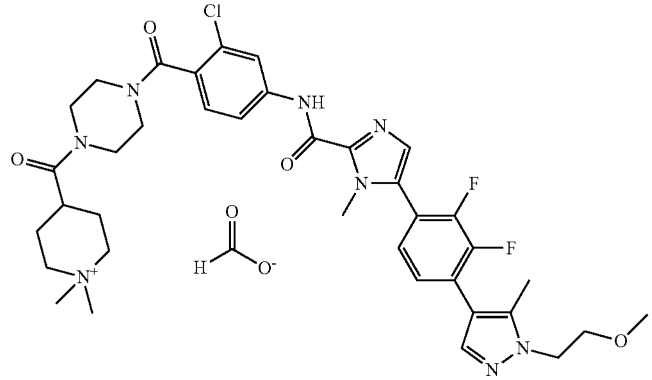 | 737.4 | Intermediate H2 and iodomethane |

| Ex# | Name | Structure | MS ESI [M]+ | Starting Material |
|---|---|---|---|---|
| Example A5 | N-[3-chloro-4-[4-[2-[(3S)-1,1-dimethylpyrrolidin-1-ium-3-yl]acetyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; formate | 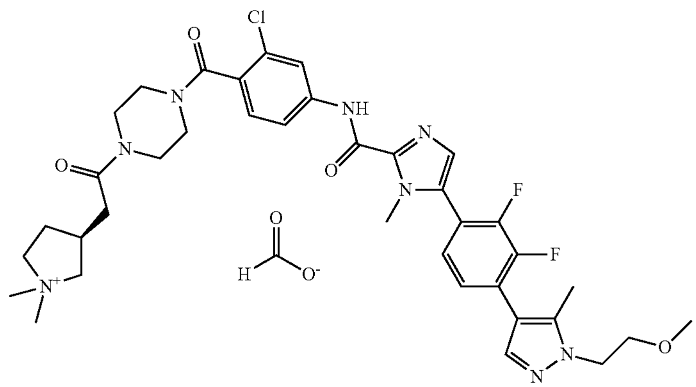 | 737.2 | Example 12 and iodomethane |
| Example A6 | N-[3-chloro-4-[4-(4-hydroxy-1,1-dimethyl-piperidin-1-ium-4-carbonyl)piperazne-1-carbonyl]phenyl]-5-[2,3-difluoro-4-[1-(2-methoxyethyl)-5-methyl-pyrazol-4-yl]phenyl]-1-methyl-imidazole-2-carboxamide; formate | 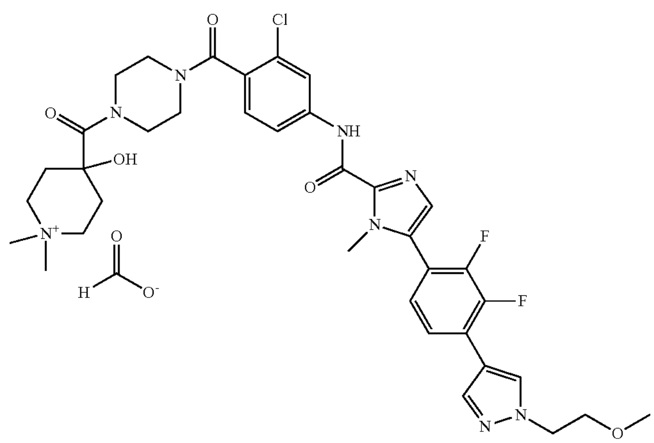 | 753.3 | Intermediate K2 and iodomethane |
| Example A7 | N-[3-chloro-4-[4-(3-hydroxy-1,1-dimethyl-piperidin-1-ium-4-carbonyl)piperazine-1-carbonyl]phenyl]-5-[2,3-difluoro-4-[1-(2-methoxyethyl)-5-methyl pyrazol-4-yl]phenyl]-1-methyl-imidazole-2-carboxamide; formate | 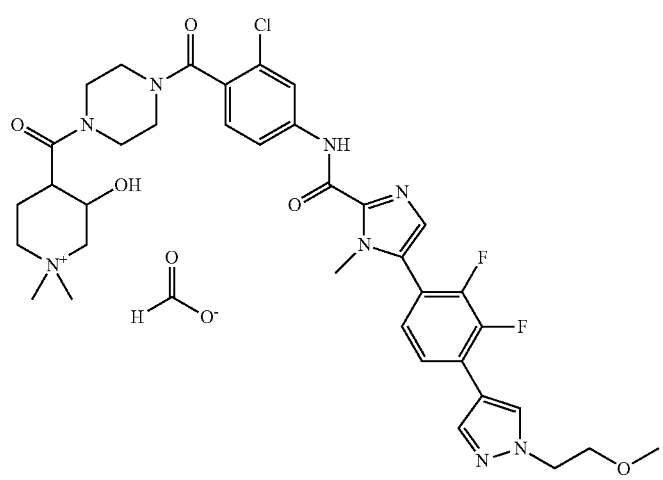 | 753.3 | Intermediate K3 and iodomethane |

-continued

| Ex# | Name | Structure | MS ESI [M]+ | Starting Material |
|---|---|---|---|---|
| Example A8 | [2-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-2-oxo-ethyl]-trimethyl-ammonium; 2,2,2-trifluoroacetate | 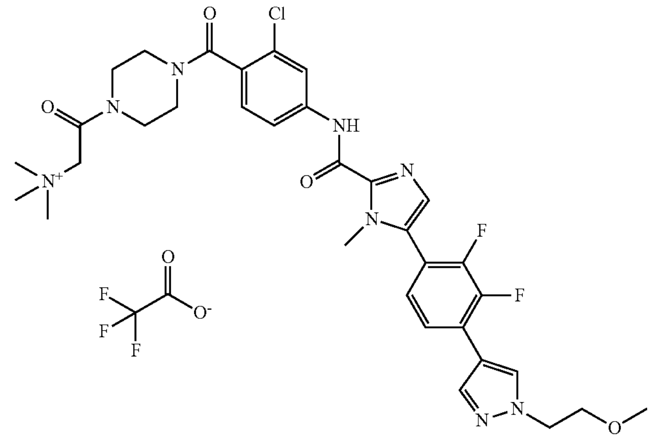 | 697.3 | Intermediate K4 and iodo-methane |
| Example A9 | [2-[4-[[[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]amino]methyl]-1-piperidyl]-2-oxo-ethyl]-trimethyl-ammonium; 2,2,2-trifluoroacetate | 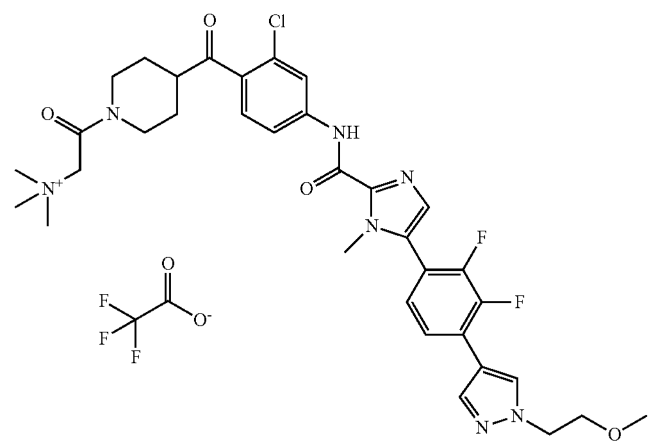 | 725.3 | Intermediate K5 and iodo-methane |
| Example A10 | N-[3-chloro-4-[4-(4,4-dimethylpiperazin-4-ium-1-carbonyl)piperidine-1-carbonyl]phenyl]-5-[2,3-difluoro-4-[1-(2-methoxyethyl)-5-methyl-pyrazol-4-yl]phenyl]-1-methyl-imidazole-2-carboxamide; formate | 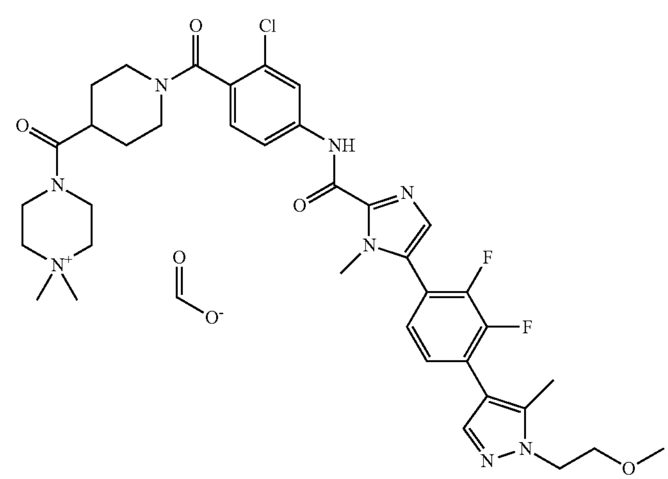 | 737.1 | Intermediate H6 and iodo-methane |

-continued

| Ex# | Name | Structure | MS ESI [M]+ | Starting Material |
|---|---|---|---|---|
| Example A11 | N-[3-chloro-4-[4-[(2S,3S)-3-hydroxy-1,1-dimethyl-pyrrolidin-1-ium-2-carbonyl]piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide; formate | 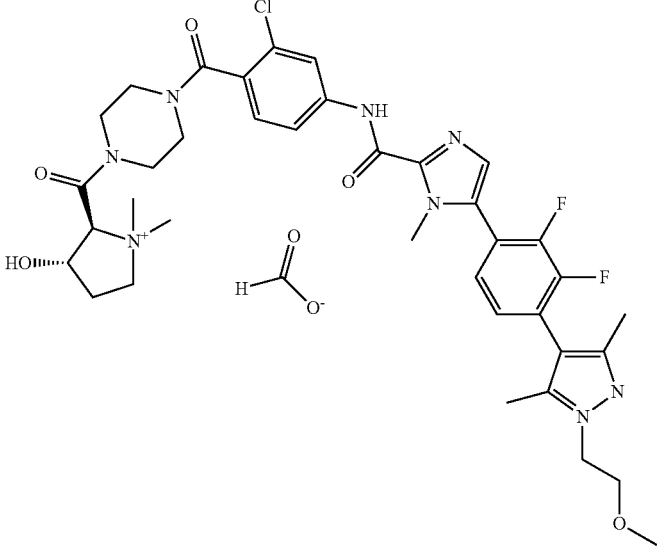 | 753.4 | Intermediate K6 and iodomethane |
| Example A12 | N-[3-chloro-4-[4-[(2S)-4-(hydroxymethyl)-1,1-dimethyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide; formate | 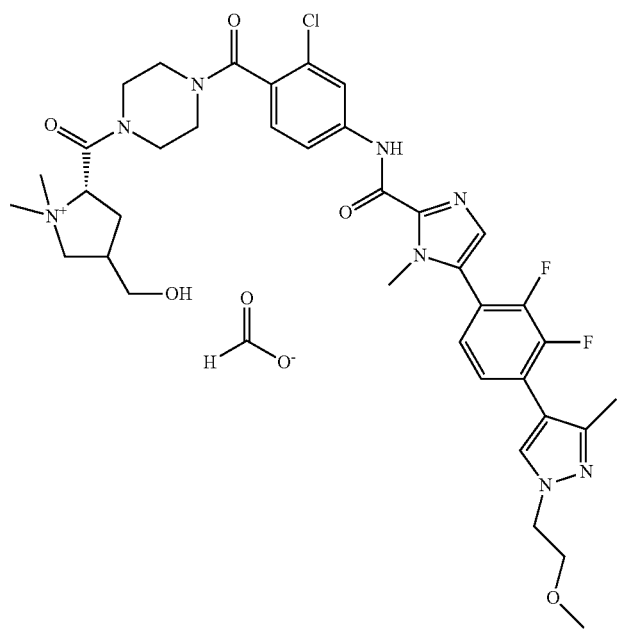 | 753.4 | Intermediate K8 and iodomethane |

| Ex# | Name | Structure | MS ESI [M]+ | Starting Material |
|---|---|---|---|---|
| Example A13 | N-[3-chloro-4-[4-(4-methoxy-1,1-dimethyl-piperidin-1-ium-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; formate | 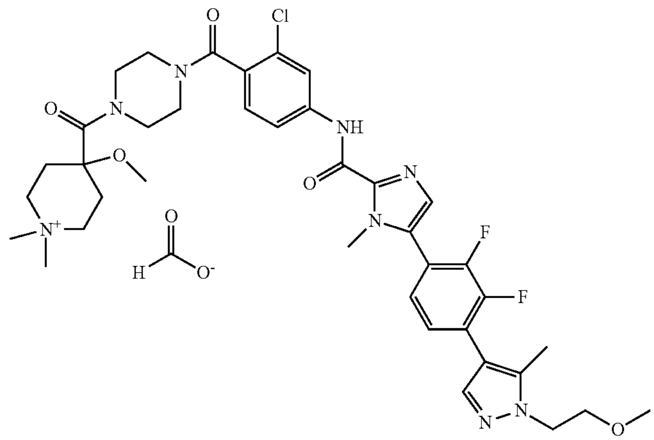 | 767.3 | Example D44 and iodomethane |

Example B1

N-[4-[4-[1-(2-amino-2-oxo-ethyl)-1-methyl-piperidin-1-ium-4-carbonyl]piperazine-1-carbonyl]-3-chloro-phenyl]-5-[2,3-difluoro-4-[1-(2-methoxy-ethyl)-3-methyl-pyrazol-4-yl]phenyl]-1-methyl-imidazole-2-carboxamide; formate

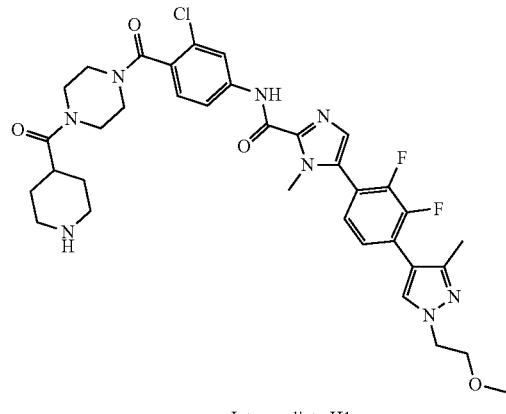

Intermediate H1

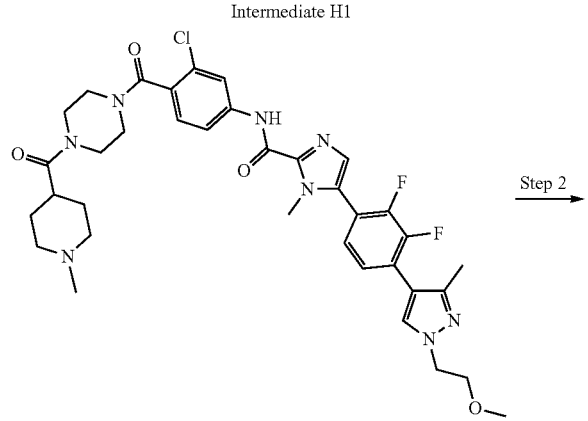

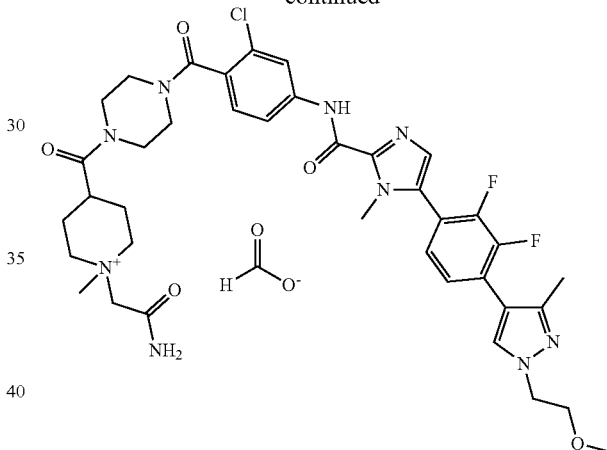

Example B1

Step 1: N-[3-chloro-4-[4-(1-methylpiperidine-4-carbonyl)piperazine-1-carbonyl]phenyl]-5-[2,3-difluoro-4-[1-(2-methoxyethyl)-3-methyl-pyrazol-4-yl]phenyl]-1-methyl-imidazole-2-carboxamide In a 100 mL round-bottomed flask, afford N-[3-chloro-4-[4-(piperidine-4-carbonyl)piperazine-1-carbonyl]phenyl]-5-[2,3-difluoro-4-[1-(2-methoxyethyl)-3-methyl-pyrazol-4-yl]phenyl]-1-methyl-imidazole-2-carboxamide (350 mg, 494 μmol), formaldehyde (74.1 mg, 2.47 mmol) and NaBH₃CN (155 mg, 2.47 mmol) were combined with MeOH (12 mL) to give a light brown solution. The reaction mixture was heated to 50° C. and stirred for 1 h. The crude reaction mixture was concentrated in vacuum. The reaction mixture was poured into 25 mL sat NaHCO₃ and extracted with EtOAc (3×25 mL). The organic layers were combined, washed with sat NaCl (1×25 mL), The organic layers were dried over Na₂SO₄ and concentrated in vacuum to afford N-[3-chloro-4-[4-(1-methylpiperidine-4-carbonyl)piperazine-1-carbonyl]phenyl]-5-[2,3-difluoro-4-[1-(2-methoxyethyl)-3-methyl-pyrazol-4-yl]phenyl]-1-methyl-imidazole-2-carboxamide (357 mg). MS [M+H]+: 723.4.

Step 2: N-[4-[4-[1-(2-amino-2-oxo-ethyl)-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide; formate In a 50 mL round-bottomed flask, N-[3-chloro-4-[4-(1-methylpiperidine-4-carbonyl)piperazine-1-carbonyl]phenyl]-5-[2,3-difluoro-4-[1-(2-methoxyethyl)-3-methyl-pyrazol-4-yl]phenyl]-1-methyl-imidazole-2-carboxamide (89 mg, 123 µmol), 2-iodoacetamide (45.5 mg, 246 µmol) and DIPEA (79.5 mg, 615 µmol) were combined with MeCN (5 mL) to give a light brown solution. The reaction was stirred at room temperature for 15 h. The crude reaction mixture was concentrated in vacuum. The crude material was purified by preparative HPLC to afford N-[4-[4-[1-(2-amino-2-oxo-ethyl)-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide; formate (22.6 mg). MS [M]+: 780.3.

Example B2 & Example B3

N-[4-[4-[1-(2-amino-2-oxo-ethyl)-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide; formate (Example B2)

N-[4-[4-[1-(2-amino-2-oxo-ethyl)-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide; formate (Example B3)

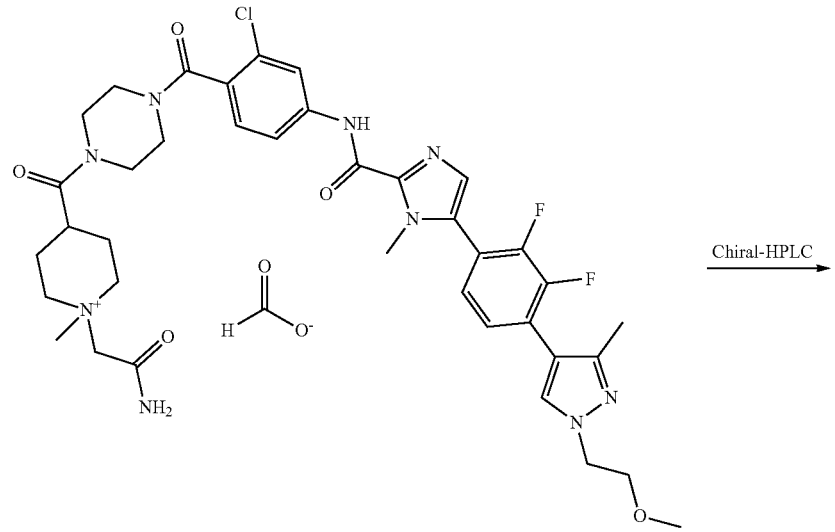

Example B1

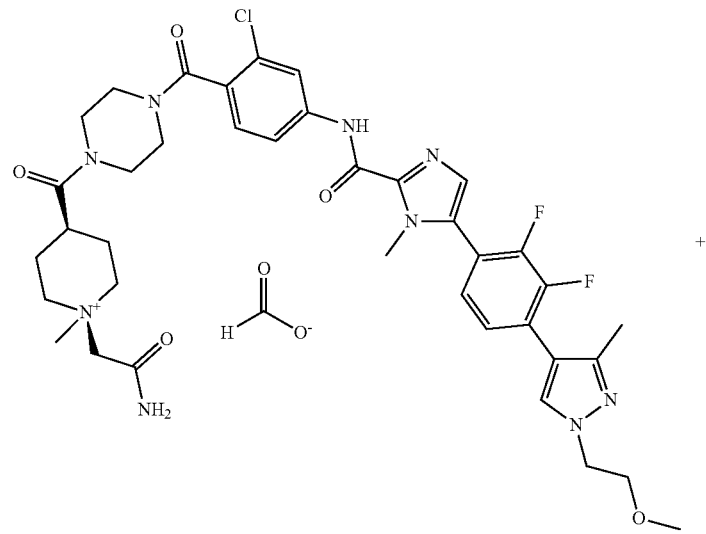

Example B2

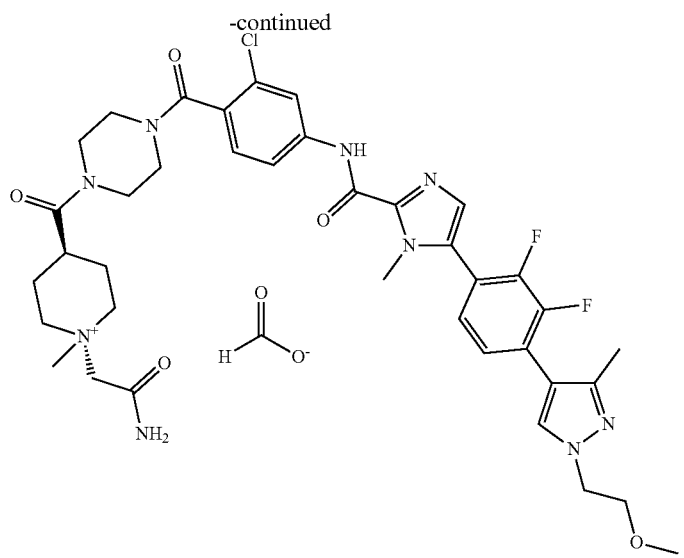

Example B3

N-[4-[4-[1-(2-amino-2-oxo-ethyl)-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide;formate was purified by preparative chial-HPLC. To afford N-[4-[4-[1-(2-amino-2-oxo-ethyl)-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide; formate (42.6 mg) and N-[4-[4-[1-(2-amino-2-oxo-ethyl)-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide; formate (38 mg). MS [M]+: 780.2.

The following examples were prepared in analogy to Examples B1.

| Ex# | Name | Structure | MS ESI [M + H]+ | Starting Material |
|---|---|---|---|---|
| Example B4 | N-[3-chloro-4-[4-[1-(2-hydroxyethyl)-1-methyl-piperidin-1-ium-4-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide; formate | 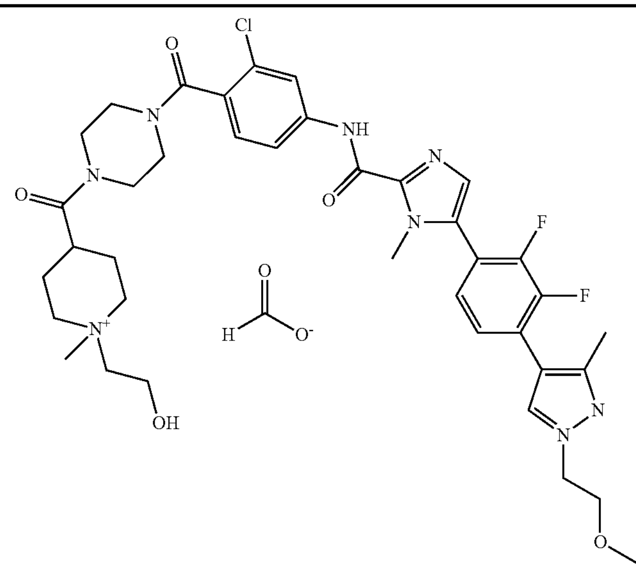 | 767.4 | Intermediate H1; formaldehyde and 2-bromoethanol |

| Ex# | Name | Structure | MS ESI [M + H]+ | Starting Material |
|---|---|---|---|---|
| Example B5 | N-[4-[4-[1-(azetidin-3-ylmethyl)-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide; formic acid; formate | 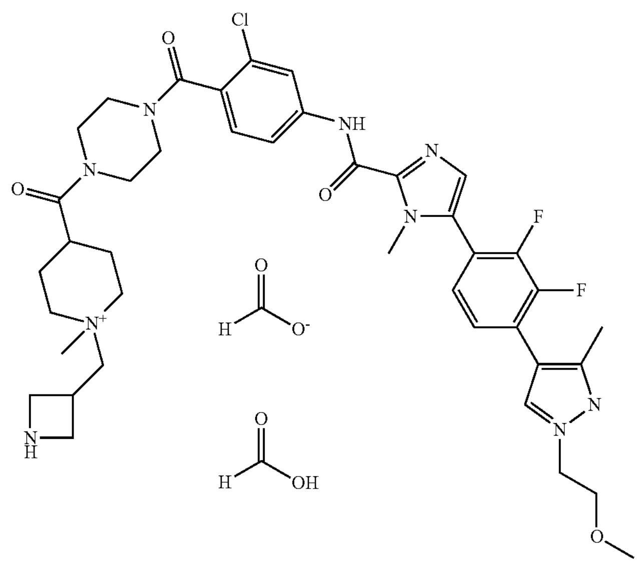 | 792.2 | Intermediate H1; formaldehyde and tert-butyl 3-(iodomethyl)azetidine-1-carboxylate |
| Example B6 | N-[4-[4-[1-(2-amino-2-oxo-ethyl)-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide; formate | 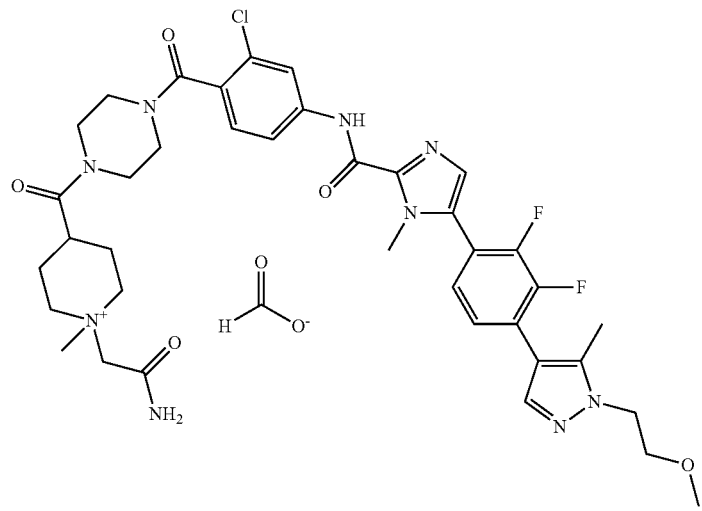 | 780.3 | Intermediate H2; formaldehyde and 2-iodoacetamide |

-continued

| Ex# | Name | Structure | MS ESI [M + H]+ | Starting Material |
|---|---|---|---|---|
| Example B7 | N-[4-[4-[1-(2-amino-2-oxo-ethyl)-1-methyl-piperidin-1-ium-4-carbonyl]piperazine-1-carbonyl]-3-chloro-phenyl]-5-[4-[1-(2,2-difluoroethyl)-3-methyl-pyrazol-4-yl]-2,3-difluoro-phenyl]-1-methyl-imidazole-2-carboxamide; formate | 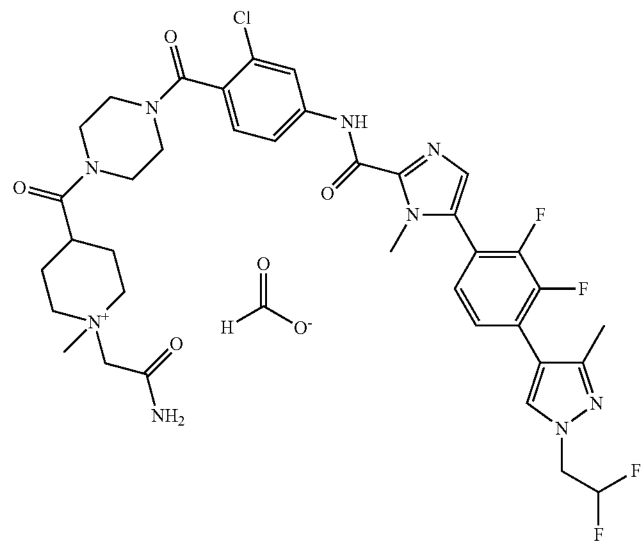 | 786.3 | Intermediate H3; formaldehyde and 2-iodo-acetamide |
| Example B8 | N-[3-chloro-4-[4-[1-(2-hydroxyethyl)-1-methyl-piperidin-1-ium-4-carbonyl]piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide; formate | 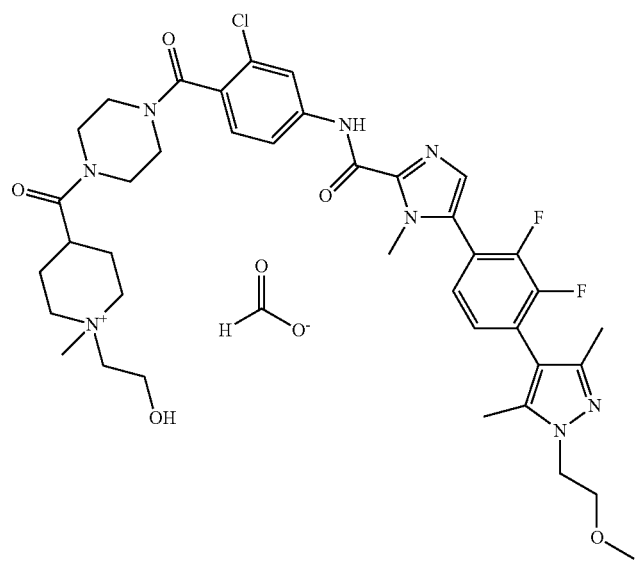 | 781.3 | Intermediate H4; formaldehyde and 2-bromo-ethanol |

-continued

| Ex# | Name | Structure | MS ESI [M + H]+ | Starting Material |
|---|---|---|---|---|
| Example B9 | N-[3-chloro-4-[4-[1-(2-methoxyethyl)-1-methyl-piperidin-1-ium-4-carbonyl]piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide; formate | 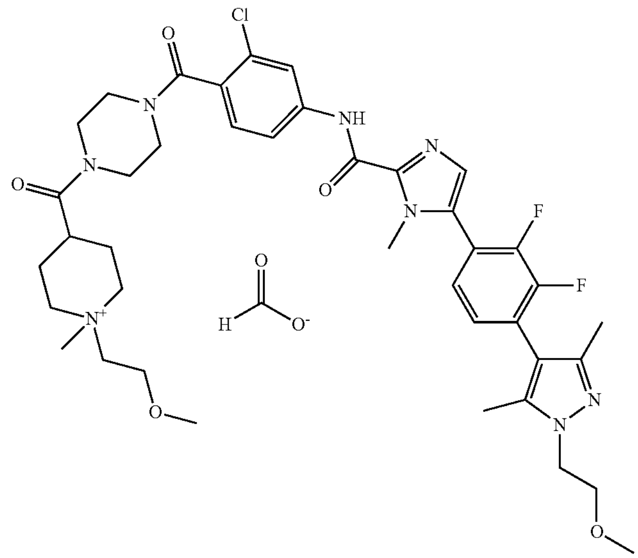 | 795.3 | Intermediate H4; formaldehyde and 1-bromo-2-methoxyethane |
| Example B10 | N-[4-[4-[1-(2-amino-2-oxo-ethyl)-1-methyl-piperidin-1-ium-4-carbonyl]piperazine-1-carbonyl]-3-chloro-phenyl]-5-[4-[1-(2-methoxyethyl)-3,5-dimethyl-pyrazol-4-yl]phenyl]-1-methyl-imidazole-2-carboxamide; formate | 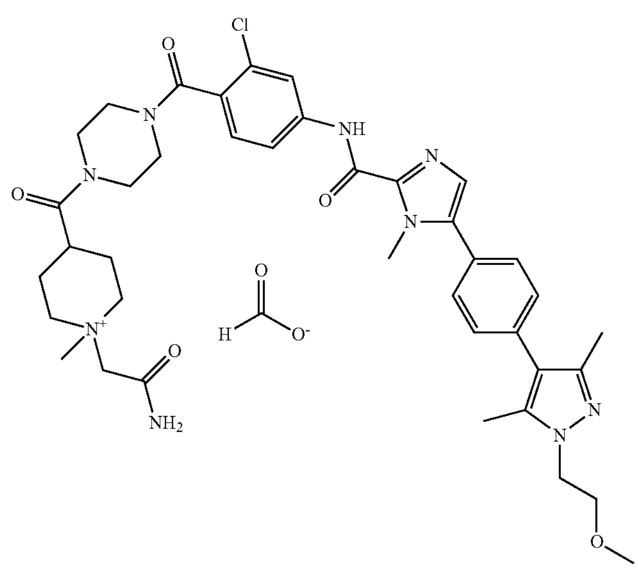 | 758.3 | Intermediate H5; formaldehyde and 2-iodo-acetamide |

| Ex# | Name | Structure | MS ESI [M + H]+ | Starting Material |
|---|---|---|---|---|
| Example B11 | N-[3-chloro-4-[4-[1-(2-hydroxyethyl)-1-methyl-piperidin-1-ium-4-carbonyl]piperazine-1-carbonyl]phenyl]-5-[4-[1-(2-methoxyethyl)-3,5-dimethyl-pyrazol-4-yl]phenyl]-1-methyl-imidazole-2-carboxamide; formate | 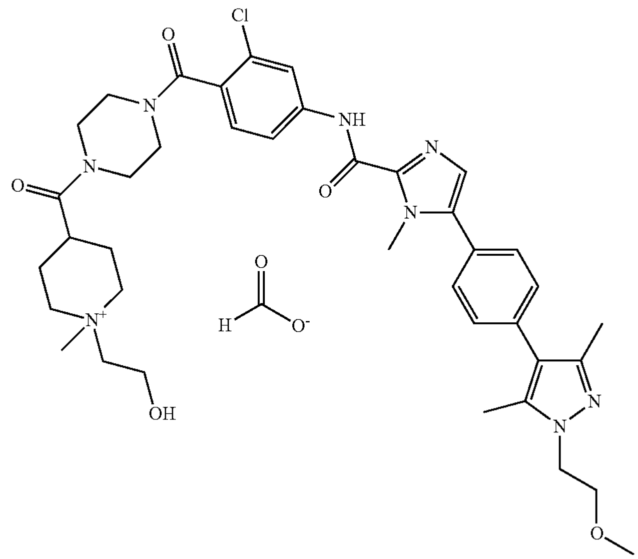 | 745.4 | Intermediate H5; formaldehyde and 2-bromoethanol |
| Example B12 | N-[3-chloro-4-[4-[1-(2-hydroxyethyl)-1-methyl-piperidin-1-ium-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; formate | 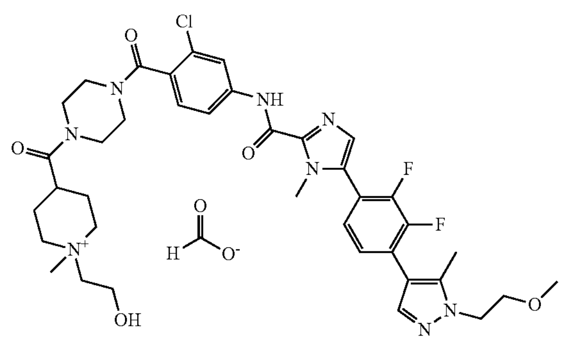 | 767.4 | Intermediate H2; formaldehyde and 2-bromoethanol |
| Example B13 | 2-[4-[1-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperidine-4-carbonyl]-1-methyl-piperazin-1-ium-1-yl]acetic acid; 2,2,2-trifluoroacetate | 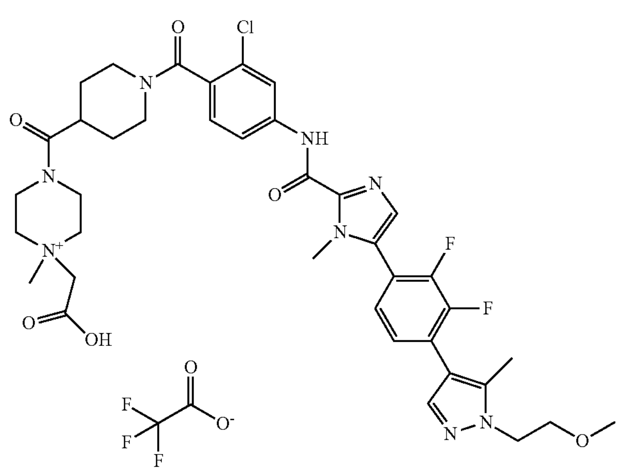 [SMILES: COCCn1ncc(-c2ccc(-c3cnc(C(=O)Nc4ccc(C(=O)N5CCC(C(=O)N6CC[N+](C)(CC(=O)O)CC6)CC5)c(Cl)c4)n3C)c(F)c2F)c1C ; O=C([O-])C(F)(F)F] | 781.3 | Intermediate H6; formaldehyde and tert-butyl 2-bromoacetate |

-continued

| Ex# | Name | Structure | MS ESI [M + H]+ | Starting Material |
|---|---|---|---|---|
| Example B14 | 2-[1-(2-amino-2-oxo-ethyl)-4-[1-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperidine-4-carbonyl]piperazin-1-ium-1-yl]acetic acid; 2,2,2-trifluoroacetate | 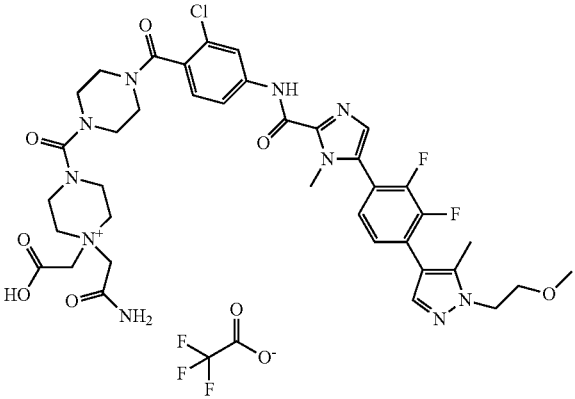 [SMILES: COCCn1ncc(-c2ccc(-c3cnc(C(=O)Nc4ccc(C(=O)N5CCN(C(=O)N6CC[N+](CC(N)=O)(CC(=O)O)CC6)CC5)c(Cl)c4)n3C)c(F)c2F)c1C ; O=C([O-])C(F)(F)F] | 824.3 | Intermediate H6; 2-iodo-acetamide and tert-butyl 2-bromo-acetate |
| Example B15 | N-[4-[4-[4-(2-amino-2-oxo-ethyl)-4-methyl-piperazin-4-ium-1-carbonyl]piperidine-1-carbonyl]-3-chloro-phenyl]-5-[2,3-difluoro-4-[1-(2-methoxyethyl)-5-methyl-pyrazol-4-yl]phenyl]-1-methyl-imidazole-2-carboxamide; formate | 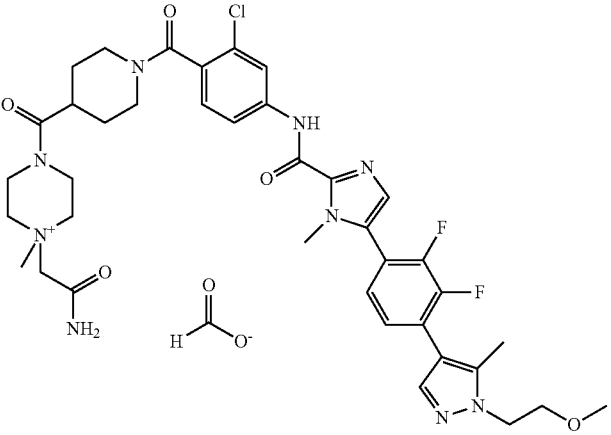 | 780.4 | Intermediate H6; form-aldehyde and 2-iodo-acetamide |
| Example B16 | N-[4-[4-[1-(2-amino-2-oxo-ethyl)-4-hydroxy-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide; formate | 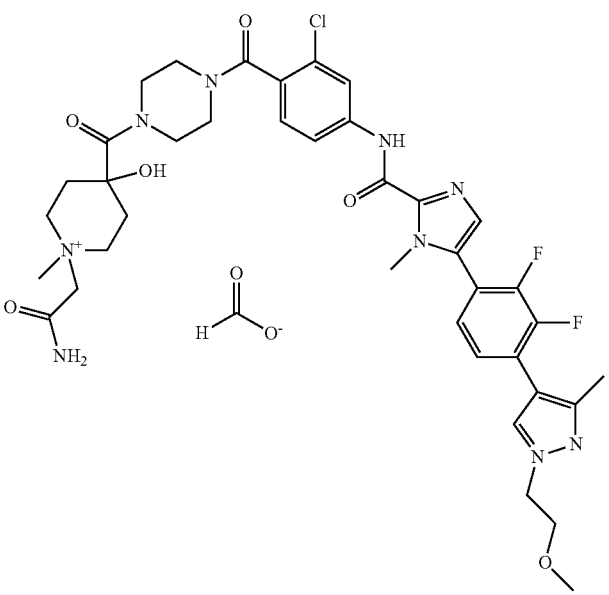 | 796.4 | Intermediate K7; form-aldehyde and 2-iodo-acetamide |

Example B17
N-[3-chloro-4-[4-[1-(2-hydrazino-2-oxo-ethyl)-1-methyl-piperidin-1-ium-4-carbonyl]piperazine-1-carbonyl]phenyl]-5-[2,3-difluoro-4-[1-(2-m ethoxy-ethyl)-5-methyl-pyrazol-4-yl]phenyl]-1-methyl-imidazole-2-carboxamide; formic acid; formate
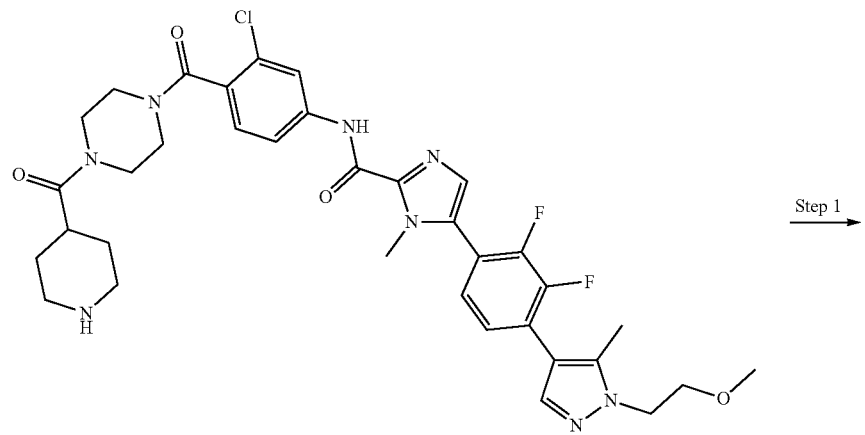
Intermediate H2
Step 1
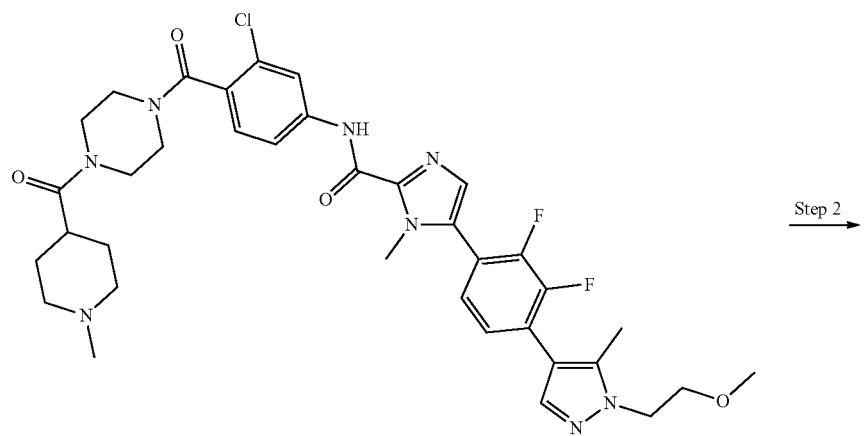
Step 2
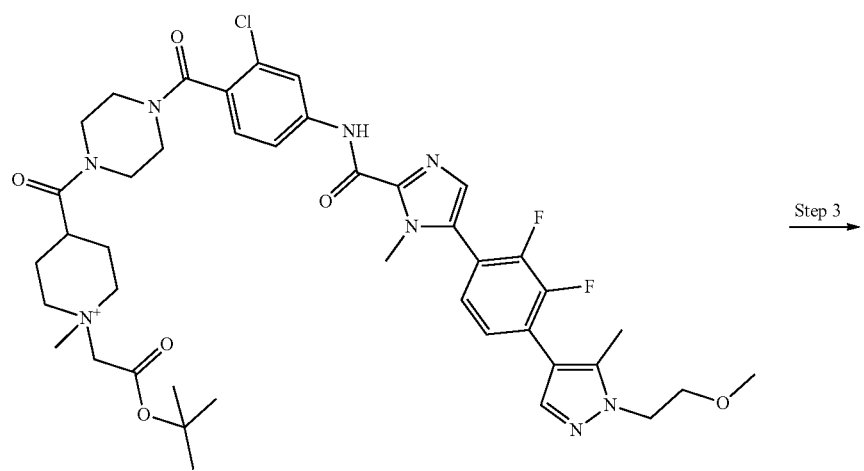
Step 3

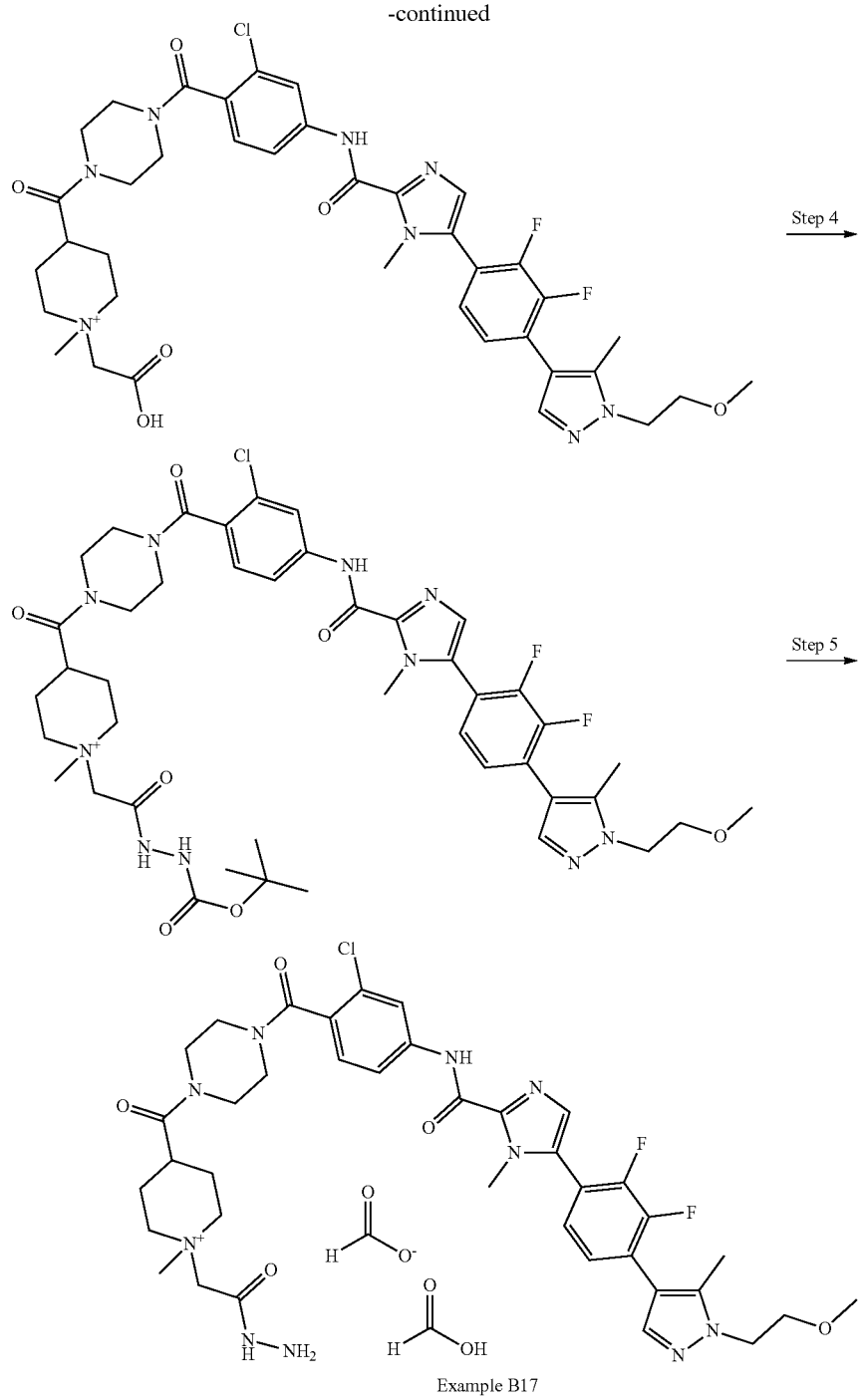

Example B17

Step 1: N-[3-chloro-4-[4-(1-methylpiperidine-4-carbonyl)piperazine-1-carbonyl]phenyl]5-[2,3-difluoro-4-[1-(2-methoxyethyl)-5-methyl-pyrazol-4-yl]phenyl]-1-methyl-imidazole-2-carboxamide N-[3-chloro-4-[4-(piperidine-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide (420 mg, 0.592 mmol) was dissolved in methanol (10 mL), formaldehyde (88.92 mg, 2.96 mmol) and sodium cyanoborohydride (186.08 mg, 2.96 mmol) were added at rt. The mixture was stirred at 50° C. for 2 h. The reaction mixture was concentrated and diluted with water (20 mL) and extracted two times with EtOAc (20 mL). The organic layers were washed with brine (20 mL), dried over Na$_2$SO$_4$ and concentrated to dryness. The crude product was directly used to the next step to afford N-[3-chloro-4-[4-(1-methylisonipecotoyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide (400 mg). MS [M+H]$^+$: 723.6.

Step 2: tert-butyl 2-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]-1-methyl-piperidin-1-ium-1-yl]acetate N-[3-chloro-4-[4-(1-methylisonipecotoyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide (100 mg, 0.138 mmol) was dissolved in acetonitrile (10 mL), and tert-butyl bromoacetate (107.88 mg, 0.553 mmol) and DIEA (71.48 mg, 0.553 mmol) were added at rt. The mixture was stirred at room temperature for 1 h. The reaction was concentrated under vacuum, the crude product was directly used to the next step to afford tert-butyl 2-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]-1-methyl-piperidin-1-ium-1-yl]acetate (115 mg). MS [M]⁺: 837.7.

Step 3: 2-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]-1-methyl-piperidin-1-ium-1-yl]acetic acid tert-butyl 2-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]-1-methyl-piperidin-1-ium-1-yl]acetate (115 mg, 0.137 mmol) was dissolved in tetrahydrofuran (2 mL) and 4 M HCl (in dioxane) (2.06 g, 6.86 mmol) was added at rt. The mixture was stirred at room temperature for 2 h. The reaction was concentrated under vacuum, the crude product was directly used to the next step to afford 2-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]-1-methyl-piperidin-1-ium-1-yl]acetic acid (107 mg). MS [M]⁺: 781.7.

Step 4: tert-butyl N-[[2-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]-1-methyl-piperidin-1-ium-1-yl]acetyl]amino]carbamate 2-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]-1-methyl-piperidin-1-ium-1-yl]acetic acid (107 mg, 0.137 mmol) was dissolved in N,N-dimethylformamide (3 mL), N-aminocarbamic acid tert-butyl ester (126.54 mg, 0.957 mmol), DIEA (35.36 mg, 0.274 mmol) and HATU (364.06 mg, 0.957 mmol) were added at rt. The mixture was stirred at room temperature for 1h. The reaction was directly used to the next step to afford tert-butyl N-[[2-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]-1-methyl-piperidin-1-ium-1-yl]acetyl]amino]carbamate (122.61 mg) as light brown solid. MS [M]⁺: 895.8.

Step 5: N-[3-chloro-4-[4-[1-(2-hydrazino-2-oxo-ethyl)-1-methyl-piperidin-1-ium-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; formic acid; formate N-[[2-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]-1-methyl-piperidin-1-ium-1-yl]acetyl]amino]carbamate (122.61 mg, 0.137 mmol) was dissolved in N,N-dimethylformamide (2 mL), and TFA (779.79 mg, 6.84 mmol) was added at rt. The mixture was stirred at room temperature for 1h. The reaction was concentrated under vacuum, the crude product was purified by HPLC to afford N-[3-chloro-4-[4-[1-(2-hydrazino-2-oxo-ethyl)-1-methyl-piperidin-1-ium-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; formic acid; formate (12.7 mg, 10.25%) as white powder. MS [M]⁺: 795.7.

Example B18

2-[1-(azetidin-3-ylmethyl)-4-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]piperidin-1-ium-1-yl] acetic acid; formic acid; formate

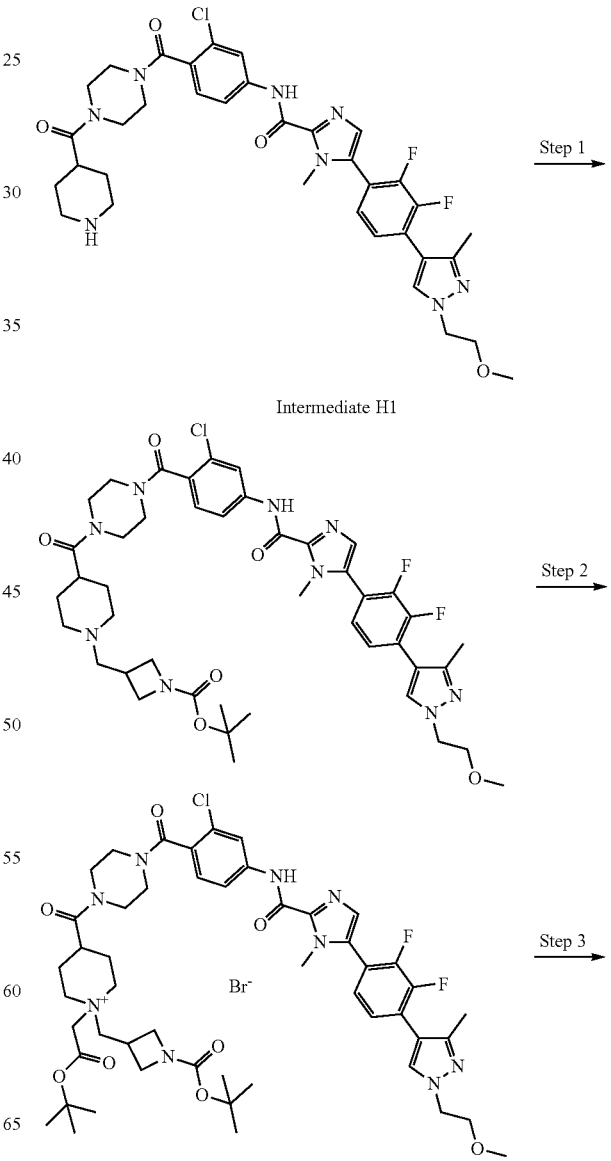

-continued

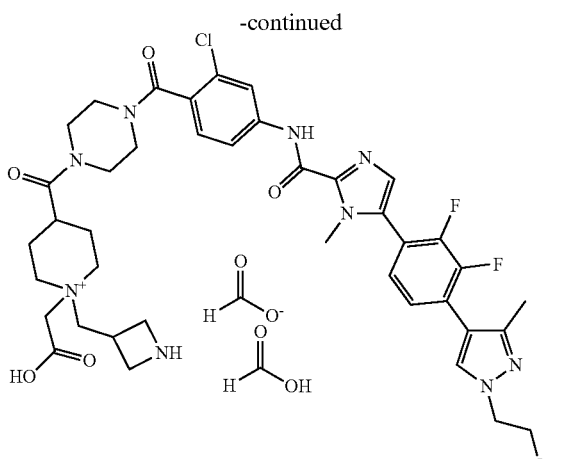

Example B18

Step 1: tert-butyl 3-[[4-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]-1-piperidyl]methyl]azetidine-1-carboxylate In a 100 mL round-bottomed flask, N-[3-chloro-4-[4-(piperidine-4-carbonyl)piperazine-1-carbonyl]phenyl]-5-[2,3-difluoro-4-[1-(2-methoxyethyl)-3-methyl-pyrazol-4-yl]phenyl]-1-methyl-imidazole-2-carboxamide (175 mg, 247 µmol), tert-butyl 3-formylazetidine-1-carboxylate (91.4 mg, 494 µmol) and NaBH$_3$CN (77.5 mg, 1.23 mmol) were combined with MeOH (12 mL) to give a light brown solution. The reaction mixture was heated to 50° C. and stirred for 1 h. The crude reaction mixture was concentrated in vacuum. The reaction mixture was poured into 25 mL sat NaHCO$_3$ and extracted with EtOAc (3×25 mL). The organic layers were combined, washed with sat NaCl (1×25 mL), The organic layers were dried over Na$_2$SO$_4$ and concentrated in vacuum to afford tert-butyl 3-[[4-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]-1-piperidyl]methyl]azetidine-1-carboxylate (217 mg). MS [M]: 879.0.

Step 2: tert-butyl 3-[[1-(2-tert-butoxy-2-oxo-ethyl)-4-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]piperidin-1-ium-1-yl]methyl]azetidine-1-carboxylate; bromide In a 50 mL round-bottomed flask, tert-butyl 3-[[4-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]-1-piperidyl]methyl]azetidine-1-carboxylate (108 mg, 123 µmol), tert-butyl 2-bromoacetate (36 mg, 184 µmol) and DIPEA (31.8 mg, 42.9 µl, 246 µmol) were combined with MeCN (3 mL) to give a light brown solution. The reaction mixture was heated to 40° C. and stirred for 15 h. The crude reaction mixture was concentrated in vacuum. The crude product was directly used to the next step to afford tert-butyl 3-[[1-(2-tert-butoxy-2-oxo-ethyl)-4-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]piperidin-1-ium-1-yl]methyl]azetidine-1-carboxylate; bromide (122 mg). MS [M]$^+$: 993.1.

Step 3: 2-[1-(azetidin-3-ylmethyl)-4-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]piperidin-1-ium-1-yl]acetic acid; formic acid; formate In a 50 mL round-bottomed flask, tert-butyl 3-[[1-(2-tert-butoxy-2-oxo-ethyl)-4-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]piperidin-1-ium-1-yl]methyl]azetidine-1-carboxylate;bromide (122 mg, 123 µmol) was combined with THF (2 mL) to give a light brown solution. HCl water solution (1.53 ml, 18.4 mmol) was added. The reaction was stirred at room temperature for 1 h. The crude reaction mixture was concentrated in vacuum. The crude material was purified by preparative HPLC to afford 2-[1-(azetidin-3-ylmethyl)-4-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]piperidin-1-ium-1-yl]acetic acid; formic acid; formate (23.7 mg). MS [M]$^+$: 836.7.

The following examples were prepared in analogy to Examples B18.

| Ex# | Name | Structure | MS ESI [M + H]$^+$ | Starting Material |
|---|---|---|---|---|
| Example B19 | N-[3-chloro-4-[4-[1-[(1,1-dimethylazetidin-1-ium-3-yl)methyl]-1-methyl-piperidin-1-ium-4-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide; diformate | 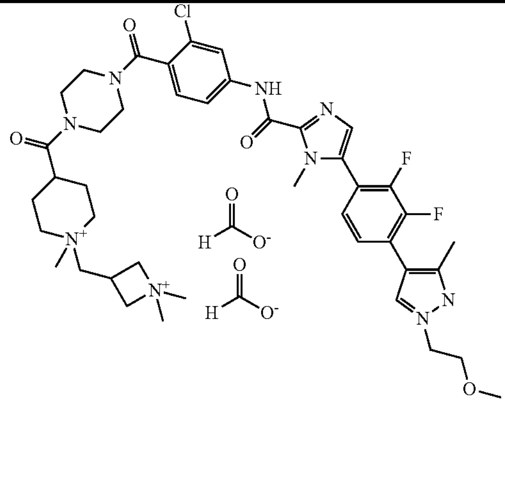 | 778.4 | Intermediate H1; tert-butyl 3-formylazetidine-1-carboxylate and iodomethane |

| Ex# | Name | Structure | MS ESI [M + H]+ | Starting Material |
|---|---|---|---|---|
| Example B20 | 2-[1-(azetidin-3-ylmethyl)-4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]piperidin-1-ium-1-yl]acetic acid; formic acid; formate | 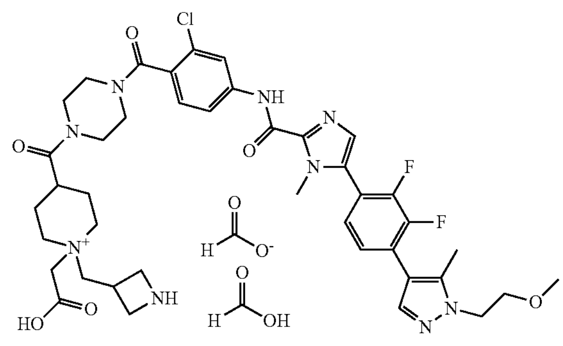 | 836.7 | Intermediate H2; tert-butyl 3-formylazetidine-1-carboxylate and tert-butyl 2-bromoacetate |
| Example B21 | N-[4-[4-[1-(azetidin-3-yl methyl)-1-methyl-piperidin-1-ium-4-carbonyl]piperazine-1-carbonyl]-3-chloro-phenyl]-5-[2,3-difluoro-4-[1-(2-methoxyethyl)-5-methyl-pyrazol-4-yl]phenyl]-1-methyl-imidazole-2-carboxamide; formic acid; formate | 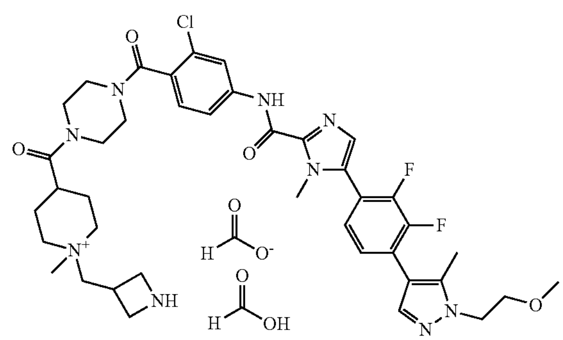 | 792.1 | Intermediate H2; tert-butyl 3-formylazetidine-1-carboxylate and iodomethane |
| Example B22 | 2-[1-(azetidin-3-ylmethyl)-4-[1-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperidine-4-carbonyl]piperazin-1-ium-1-yl]acetic acid; formate | 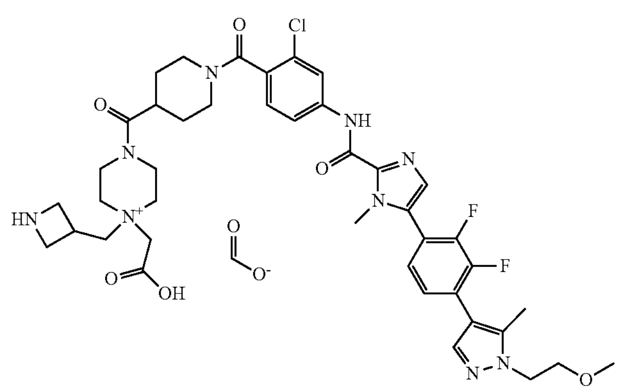 | 836.2 | Intermediate H6; tert-butyl 3-formylazetidine-1-carboxylate and tert-butyl 2-bromoacetate |
| Example B23 | N-[4-[4-[4-(azetidin-3-ylmethyl)-4-methyl-piperazin-4-ium-1-carbonyl]piperidine-1-carbonyl]-3-chloro-phenyl]-5-[2,3-difluoro-4-[1-(2-methoxyethyl)-5-methyl-pyrazol-4-yl]phenyl]-1-methyl-imidazole-2-carboxamide; formate | 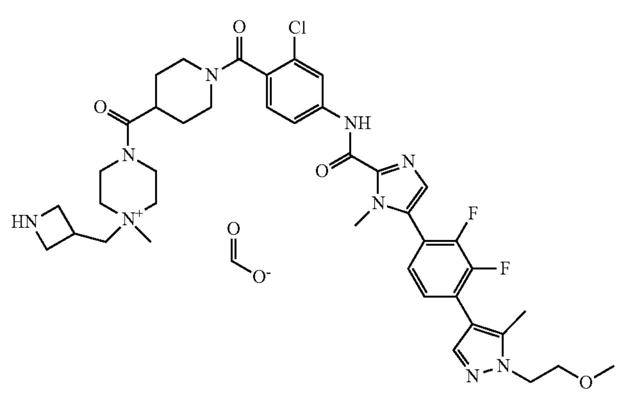 | 792.2 | Intermediate H6; tert-butyl 3-formylazetidine-1-carboxylate and iodomethane |

-continued

| Ex# | Name | Structure | MS ESI [M + H]+ | Starting Material |
|---|---|---|---|---|
| Example B24 | N-[4-[4-[4-(2-amino-2-oxo-ethyl)-4-(azetidin-3-ylmethyl)piperazin-4-ium-1-carbonyl]piperidine-1-carbonyl]-3-chloro-phenyl]-5-[2,3-difluoro-4-[1-(2-methoxyethyl)-5-methyl-pyrazol-4-yl]phenyl]-1-methyl-imidazole-2-carboxamide; 2,2,2-trifluoroacetate; 2,2,2-trifluoroacetic acid | 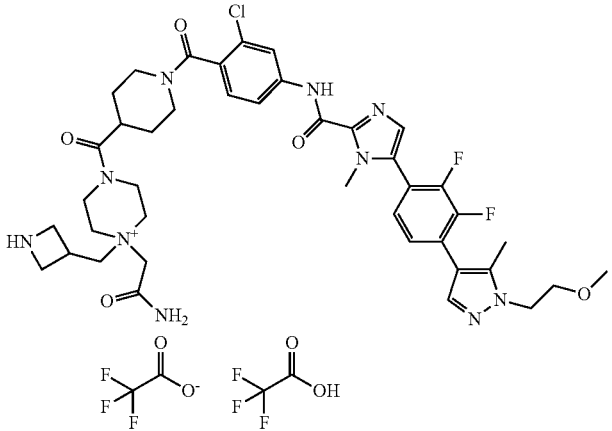 [SMILES: COCCn1ncc(-c2ccc(-c3cnc(C(=O)Nc4ccc(C(=O)N5CCC(C(=O)N6CC[N+](CC(N)=O)(CC7CNC7)CC6)CC5)c(Cl)c4)n3C)c(F)c2F)c1C ; O=C([O-])C(F)(F)F ; O=C(O)C(F)(F)F] | 835.2 | Intermediate H6; tert-butyl 3-formylazetidine-1-carboxylate and 2-iodoacetamide |
| Example B25 | N-[3-chloro-4-[4-[(1R,5S)-3,3-dimethyl-3-azoniabicyclo[3.10]hexane-6-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide; formate | 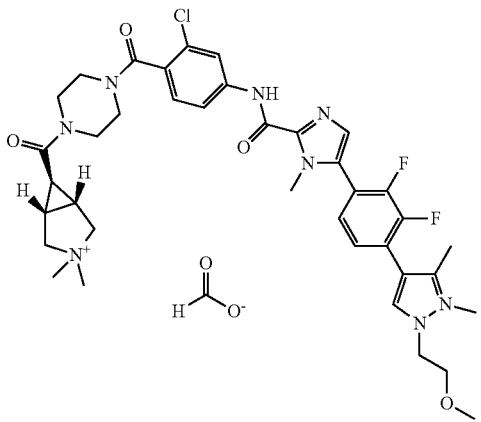 | 735.4 | Intermediate N1; HCl and iodomethane |
| Example B26 | N-[3-chloro-4-[4-[(1R,5S)-3,3-dimethyl-3-azoniabicyclo[3.10]hexane-6-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; formate | 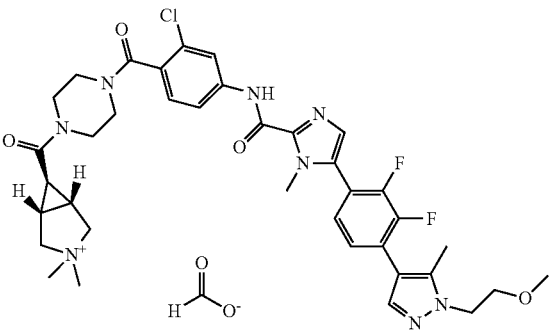 | 735.4 | Intermediate N2; HCl and iodomethane |

-continued

| Ex# | Name | Structure | MS ESI [M + H]+ | Starting Material |
|---|---|---|---|---|
| Example B27 | N-[3-chloro-4-[4-[(2S,4R)-4-hydroxy-1-(3-hydroxypropyl)-1-methyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide; iodide | 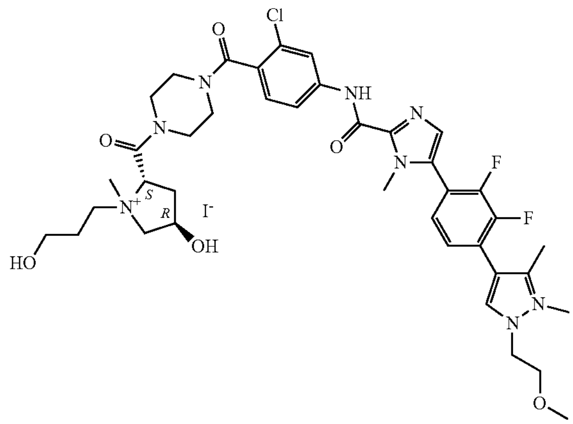 | 783.3 | Intermediate K1; 3-[tert-butyl(dimethyl)silyl]oxypropanal and iodomethane |
| Example B40 | 2-[1-(azetidin-3-ylmethyl)-4-[4-[2-chloro-4-[[5-[5-chloro-4-[1-(2-methoxyethyl)-5-methyl-pyrazol-4-yl]-2-methyl-phenyl]-1-methyl-imidazole-2-carbonyl]amino]benzoyl]piperazine-1-carbonyl]piperidin-1-ium-1-yl]acetic acid; formate | 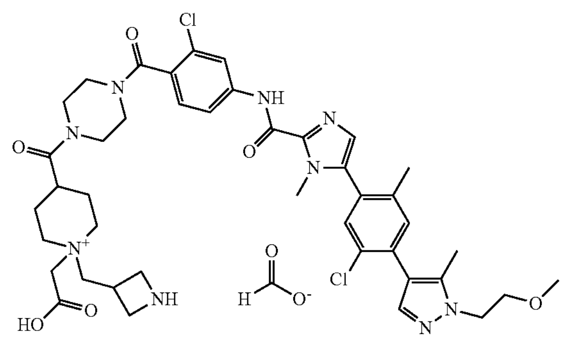 | 848.3 | Intermediate H10; tert-butyl 3-formylazetidine-1-carboxylate and tert-butyl 2-bromoacetate |

Example B28

2-[1-(azetidin-3-ylmethyl)-4-[4-[2-chloro-4-[[5-[3-chloro-2-fluoro-4-[1-(2-methoxyethyl)-5-methyl-pyrazol-4-yl]phenyl]-1-methyl-imidazole-2-carbonyl]amino]benzoyl]piperazine-1-carbonyl]piperidin-1-ium-1-yl]acetic acid; formate

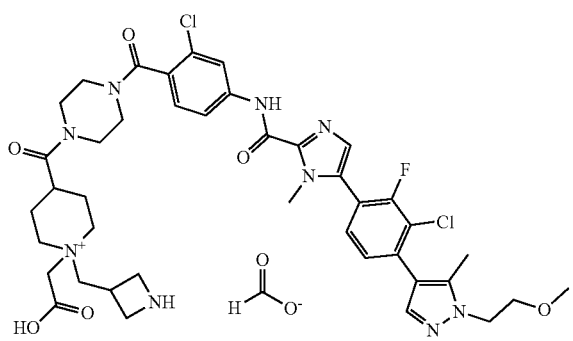

1-[(1-tert-butoxycarbonylazetidin-3-yl)methyl]-1-(2-tert-butoxy-2-keto-ethyl)piperidin-1-ium-4-carboxylate (28 mg, 0.068 mmol, Intermediate R14) was dissolved in dichloromethane, extra dry (1 mL) (purged with Ar) and 5-[3-chloro-2-fluoro-4-[1-(2-methoxyethyl)-5-methyl-pyrazol-4-yl]phenyl]-N-[3-chloro-4-(piperazine-1-carbonyl)phenyl]-1-methyl-imidazole-2-carboxamide. 1:1 hydrogen chloride (30 mg, 0.045 mmol), Intemediate H11 was added. DIEA (34.78 mg, 47 μL, 0.269 mmol) and (7-azabenzotriazol-1-yloxy)tripyrrolidino-phosphonium hexafluorophosphate (33 mg, 0.063 mmol) were added to the reaction mixture which was then stirred at rt for 1.5 h under Ar. 4 M HCl (1.2 g, 1 mL, 4 mmol) in dioxane was added (slowly, reaction is slightly exothermic) and the mixture was stirred at rt for 30 min. The volatiles were removed under reduced pressure to give a colourless solid (in some brownish oil). The crude reaction mixture was purified by prepHPLC and lyophilized to get 10 mg of a colourless foam, purity (LC/MS, UV) 96%, yield 24%. MS: [M]+: 852.3.

The following examples were prepared in analogy to Examples B28.

| Ex# | Name | Structure | MS ESI [M + H]+ | Starting Material |
|---|---|---|---|---|
| Example B37 | 2-[1-(azetidin-3-ylmethyl)-4-[4-[2-chloro-4-[[5-[2-chloro-3-fluoro-4-[1-(2-methoxyethyl)-5-methyl-pyrazol-4-yl]phenyl]-1-methyl-imidazole-2-carbonyl]amino]benzoyl]piperazine-1-carbonyl]piperidin-1-ium-1-yl]acetic acid; formate | 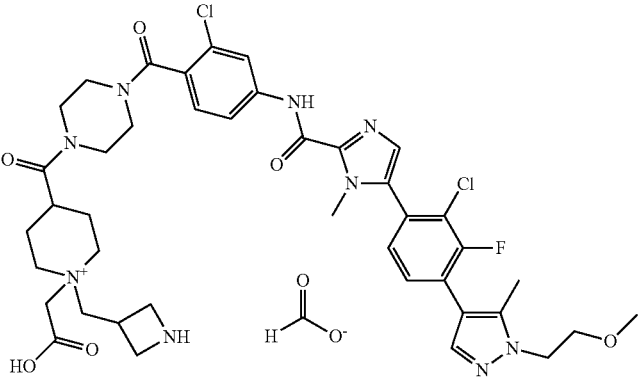 | 852.3 | Intermediate H7 and Intermediate R14 |
| Example B39 | 2-[1-(azetidin-3-ylmethyl)-4-[4-[2-chloro-4-[[5-[3-fluoro-4-[1-(2-methoxyethyl)-5-methyl-pyrazol-4-yl]-2-methyl-phenyl]-1-methyl-imidazole-2-carbonyl]amino]benzoyl]piperazine-1-carbonyl]piperidin-1-ium-1-yl]acetic acid; formate | 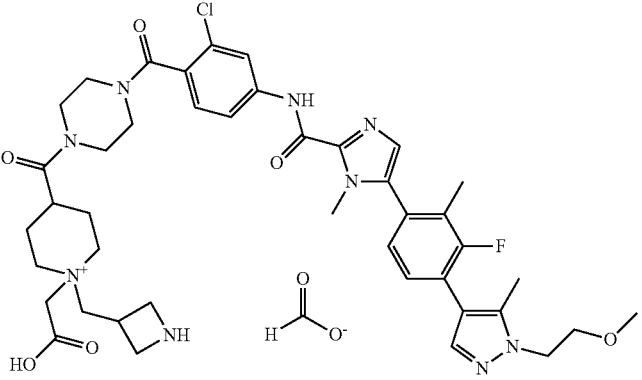 | 832.4 | Intermediate H9 and Intermediate R14 |

Example B29 & Example B30

2-[1-(azetidin-3-ylmethyl)-4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]piperidin-1-ium-1-yl]acetic acid; formic acid; formate (Example B29)

2-[1-(azetidin-3-ylmethyl)-4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]piperidin-1-ium-1-yl]acetic acid; formic acid; formate (Example B30)

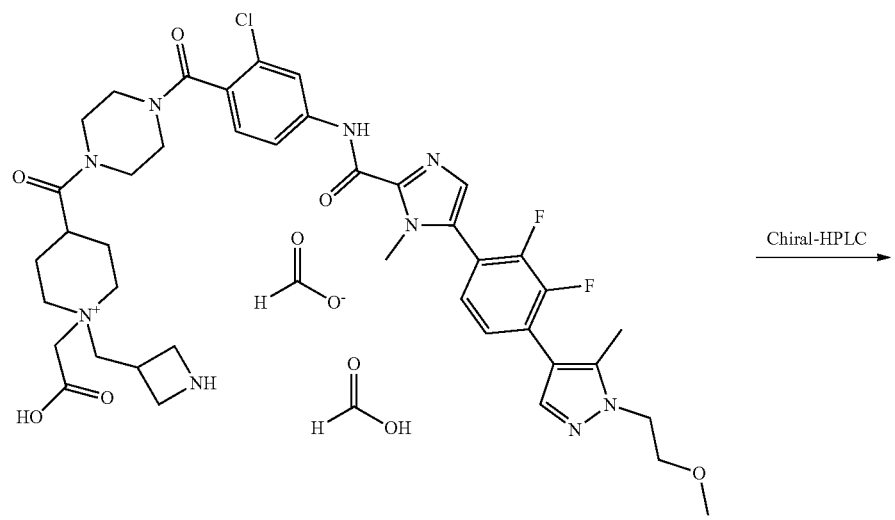

Example B20

Chiral-HPLC →

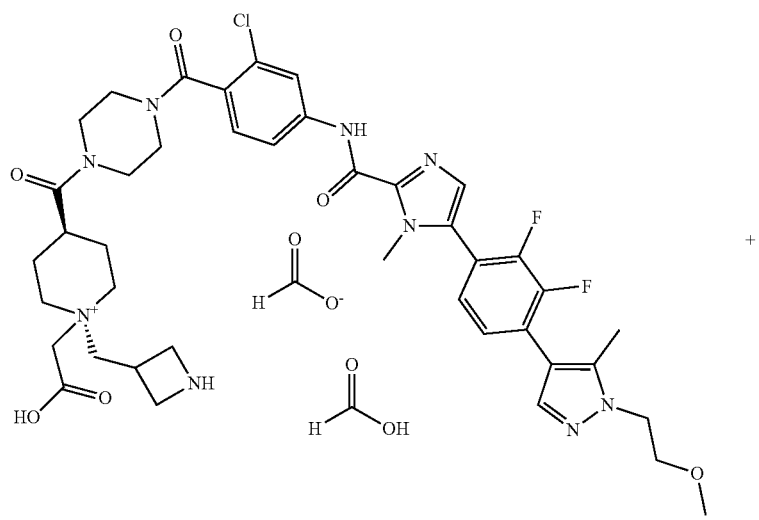

Example B29

+

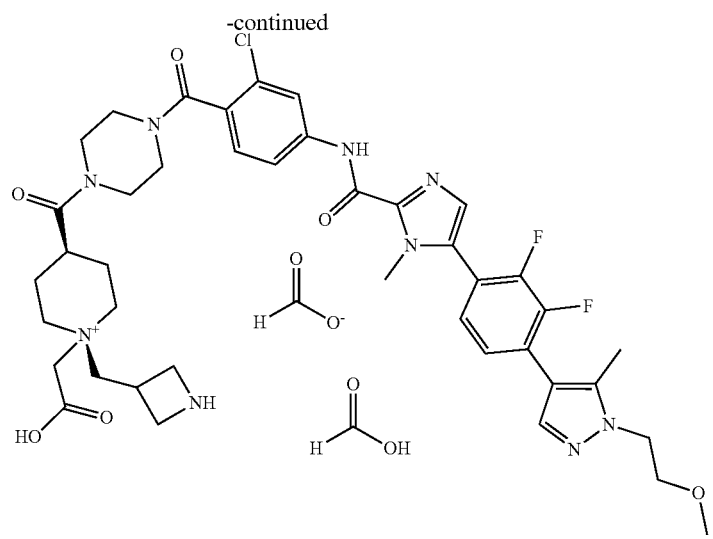

Example B30

2-[1-(azetidin-3-ylmethyl)-4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]piperidin-1-ium-1-yl]acetic acid; formic acid; formate (80 mg) was purified by preparative chial-HPLC to afford 2-[1-(azetidin-3-ylmethyl)-4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]piperidin-1-ium-1-yl]acetic acid;formic acid;formate (19.4 mg) and 2-[1-(azetidin-3-ylmethyl)-4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]piperidin-1-ium-1-yl]acetic acid; formic acid; formate (28.3 mg). MS [M]$^+$: 836.0.

Example B31

N-[3-chloro-4-[4-[1-[(1,1-dimethylazetidin-1-ium-3-yl)methyl]piperidine-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide

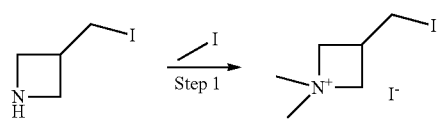

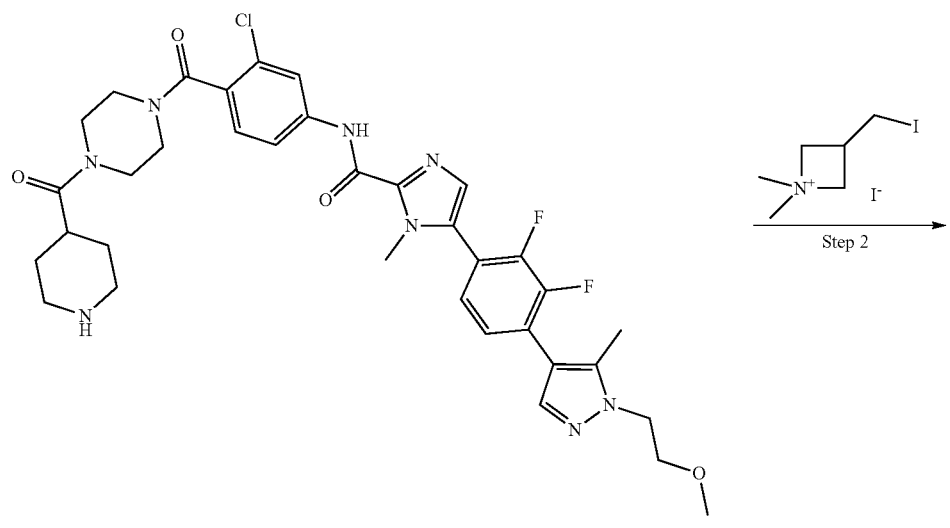

Intermediate H2

-continued

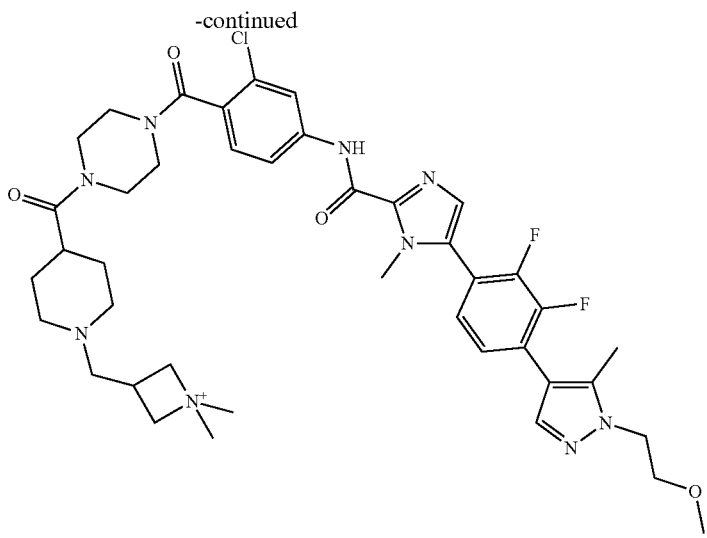

Example B31

Step 1: 3-(iodomethyl)-1,1-dimethyl-azetidin-1-ium

In a 50 mL round-bottomed flask, 3-(iodomethyl)azetidine (126 mg, 640 µmol), MeI (454 mg, 3.2 mmol) and DIPEA (413 mg, 3.2 mmol) were combined with MeCN (6 mL) to give a light brown solution. The reaction was stirred at room temperature for 2 h. The crude reaction mixture was concentrated in vacuum. The crude product was directly used to the next step to afford 3-(iodomethyl)-1,1-dimethylazetidin-1-ium (145 mg). MS [M]+: 225.9.

Step 2: N-[3-chloro-4-[4-[1-[(1,1-dimethylazetidin-1-ium-3-yl)methyl]piperidine-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide In a 50 mL round-bottomed flask, N-[3-chloro-4-[4-(piperidine-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide (70 mg, 98.7 µmol), 3-(iodomethyl)-1,1-dimethyl-114-azetidine (22.3 mg, 98.7 µmol) and DIPEA (63.8 mg, 494 µmol) were combined with MeCN (6 mL) to give a light brown solution. The reaction mixture was heated to 50° C. and stirred for 15 h. The crude reaction mixture was concentrated in vacuum. The crude material was purified by preparative HPLC to afford Product 1 (17.8 mg). MS [M]+: 806.7.

Example B32

N-[3-chloro-4-[4-[1-(2,2-difluoroethyl)-1-methyl-piperidin-1-ium-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; 2,2,2-trifluoroacetate

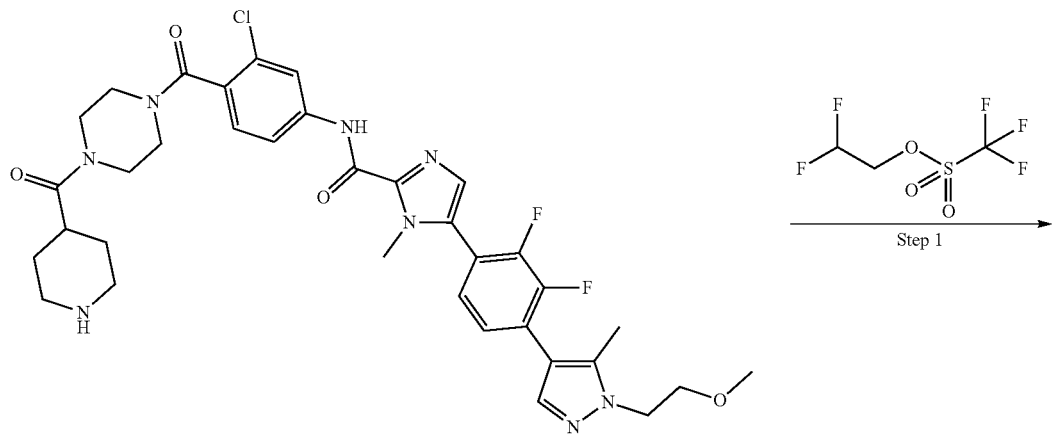

Intermediate H2

331

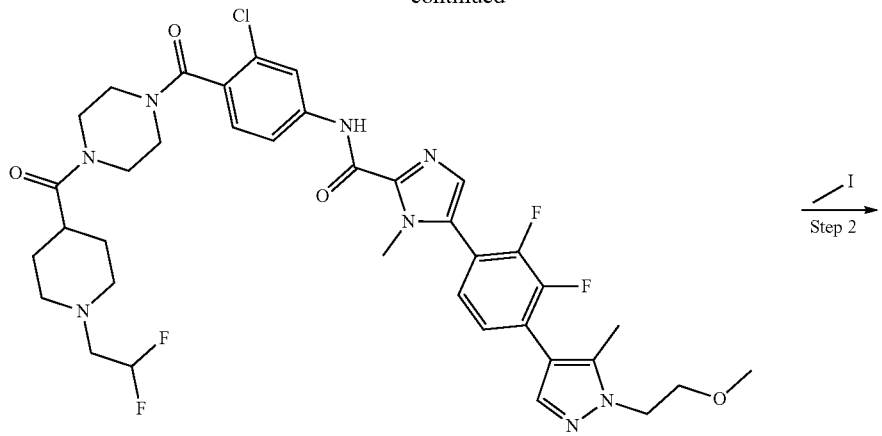

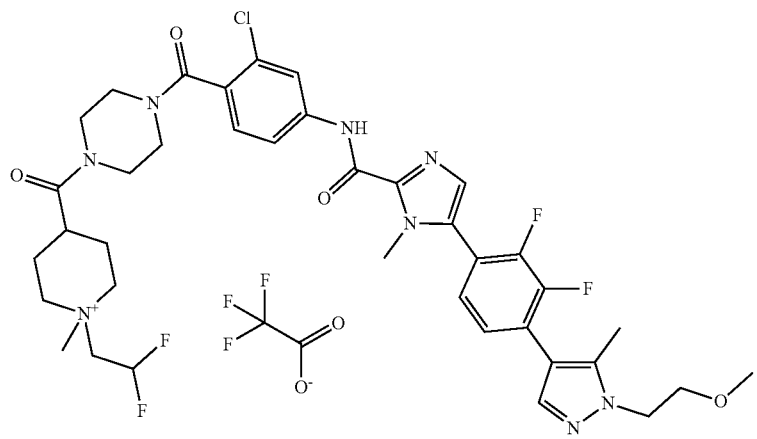

Example B32

Step 1: N-[3-chloro-4-[4-[1-(2,2-difluoroethyl)piperidine-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide To a solution of N-[3-chloro-4-[4-(piperidine-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide (300 mg, 423 μmol) and DIPEA (164 mg, 1.27 mmol) in DCM (2 mL) was added slowly a solution of 2,2-difluoroethyl trifluoromethanesulfonate (272 mg, 1.27 mmol) in DCM (1 mL) at 0° C. The ice bath was removed after 1 h and the mixture was stirred for another 16 h. Then the solution was concentrated in vacuum to afford the crude product N-[3-chloro-4-[4-[1-(2,2-difluoroethyl)piperidine-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide. MS [M+H]$^+$: 773.0.

Step 2: N-[3-chloro-4-[4-[1-(2,2-difluoroethyl)-1-methyl-piperidin-1-ium-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; 2,2,2-trifluoroacetate A mixture of N-[3-chloro-4-[4-[1-(2,2-difluoroethyl)piperidine-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide (150 mg, 194 μmol), iodomethane (551 mg, 3.88 mmol) and DIPEA (501 mg, 3.88 mmol) in acetonitrile (5 mL) was stirred at room temperature for 48 h. Then the mixture was concentrated in vacuum and the residue was purified by Prep-HPLC to afford N-[3-chloro-4-[4-[1-(2,2-difluoroethyl)-1-methyl-piperidin-1-ium-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; 2,2,2-trifluoroacetate (46 mg). MS [M]$^+$: 787.2.

Example B33
N-[3-chloro-4-[4-[1-(2-sulfamoylethyl)piperidine-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide
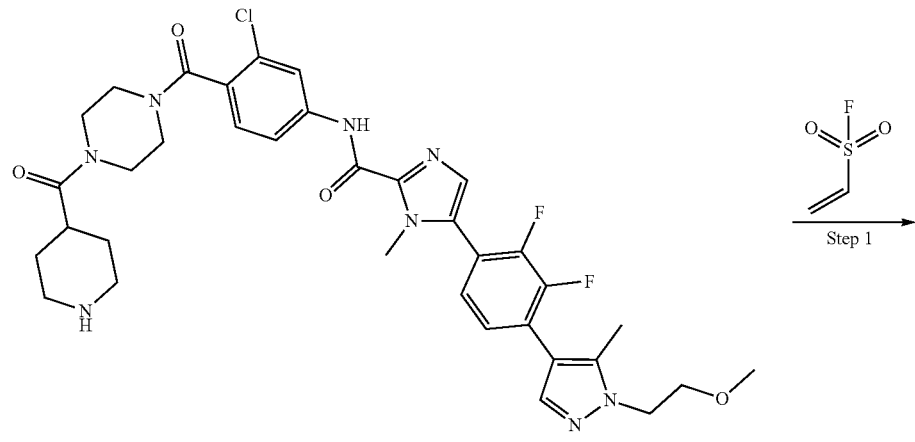
Intermediate H2
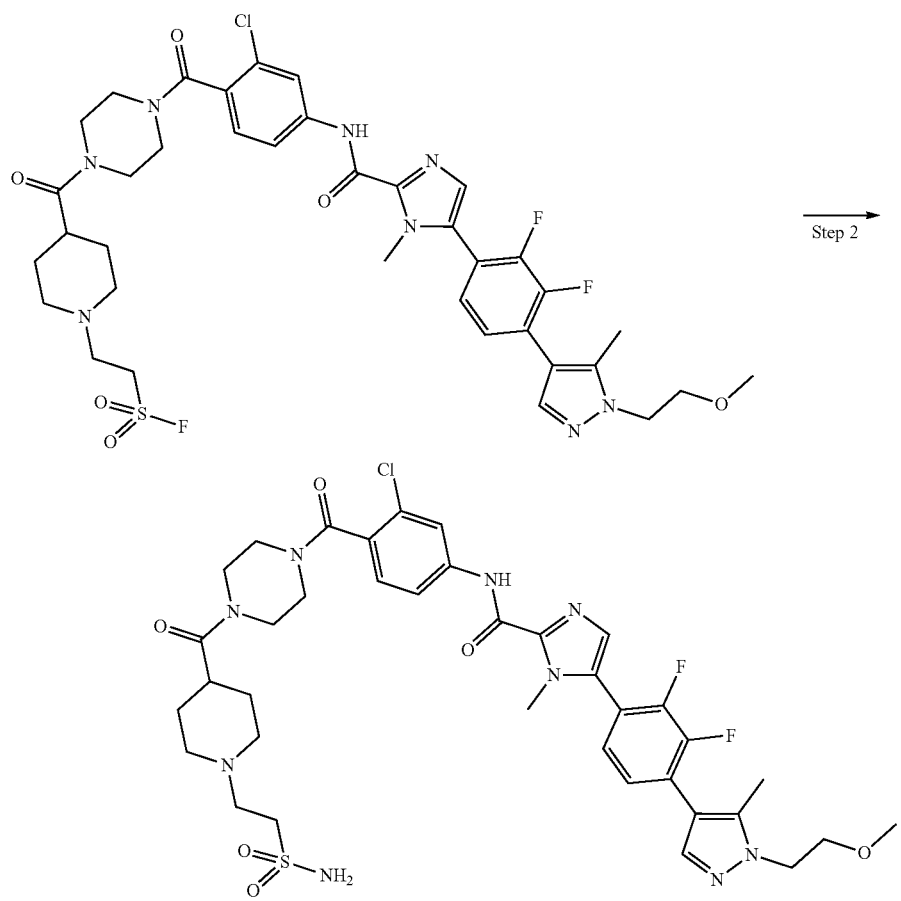
Example B33

Step 1: 2-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]-1-piperidyl]ethanesulfonyl fluoride A mixture of N-[3-chloro-4-[4-(piperidine-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide (150 mg, 212 µmol) and ethenesulfonyl fluoride (27.9 mg, 254 µmol) in DMF (2 mL) was stirred at room temperature for 3 h. Then the mixture was heated at 50° C. for 1 h. The mixture was concentrated in vacuum to afford the crude material 2-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]-1-piperidyl]ethanesulfonyl fluoride. The crude material was used into next step reaction without further purification. MS [M+H]$^+$: 819.4.

Step 2: N-[3-chloro-4-[4-[1-(2-sulfamoylethyl)piperidine-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide At room temperature, 2-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]-1-piperidyl]ethanesulfonyl fluoride was dissolved in DMF (2 mL). Then 7 M NH$_3$ (3 mL) in methanol solution was added. The mixture was stirred for 16 h. Then the mixture was concentrated in vacuum. The crude material was purified by Prep-HPLC to afford N-[3-chloro-4-[4-[1-(2-sulfamoylethyl)piperidine-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide (10 mg). MS [M+H]$^+$: 816.1.

Example B34

N-[3-chloro-4-[4-[1-methyl-1-(2-sulfamoylethyl)piperidin-1-ium-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; formate

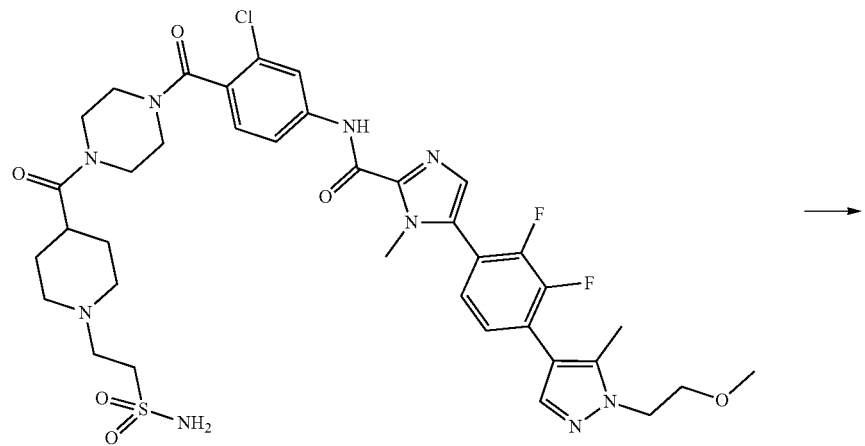

Example B33

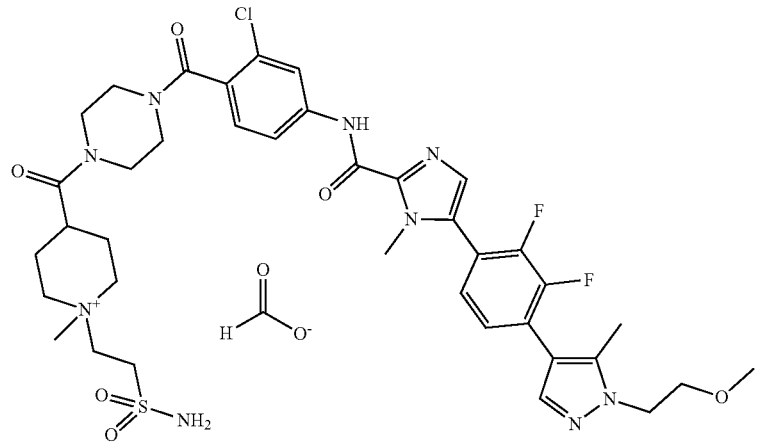

Example B34

At room temperature, iodomethane (2 mL) was added into a solution of N-[3-chloro-4-[4-[1-(2-sulfamoylethyl)piperidine-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide (150 mg, 184 µmol) in DMF (2 mL). The mixture was stirred for 16 h. Then the mixture was purified by Prep-HPLC to afford N-[3-chloro-4-[4-[1-methyl-1-(2-sulfamoylethyl)piperidin-1-ium-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; formate (6 mg). MS [M]$^+$: 830.4.

Example B35

N-[3-chloro-4-[4-[1-(2-hydroxyethyl)-1-methyl-pyrrolidin-1-ium-2-carbonyl]piperazine-1-carbonyl]phenyl]-5-[2,3-difluoro-4-(3-methyl-1H-pyrazol-4-yl)phenyl]-1-methyl-imidazole-2-carboxamide; 2,2,2-trifluoroacetate

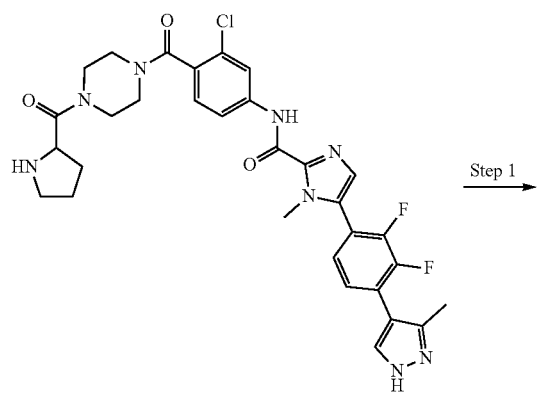

Intermediate K11

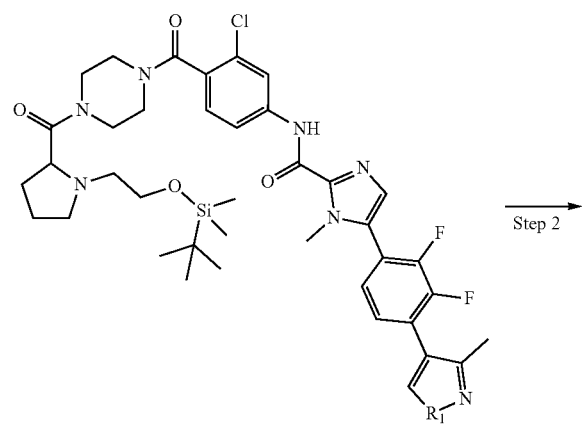

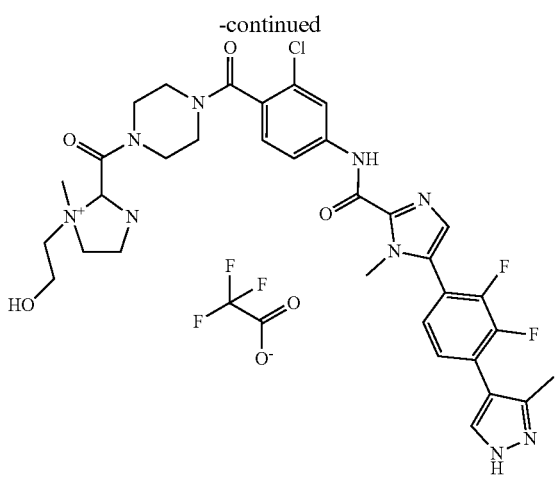

Example B35

Step 1: N-[4-[4-[1-[2-[tert-butyl(dimethyl)silyl]oxyethyl]pyrrolidine-2-carbonyl]piperazine-1-carbonyl]-3-chloro-phenyl]-5-[2,3-difluoro-4-(3-methyl-1H-pyrazol-4-yl)phenyl]-1-methyl-imidazole-2-carboxamide N-(3-chloro-4-(4-prolylpiperazine-1-carbonyl)phenyl)-5-(2,3-difluoro-4-(3-methyl-1H-pyrazol-4-yl)phenyl)-1-methyl-1H-imidazole-2-carboxamide (83 mg, 130 µmol) and 2-((tert-butyldimethylsilyl)oxy)acetaldehyde (34.1 mg, 195 µmol) were stirred in dry THF (2.61 mL) before adding of NaBH(OAc)$_3$ (41.4 mg, 195 µmol). The resulting mixture was stirred at room temperature for 1 h. Silica gel was added to absorb the material. The solid sample was purified by flash chromatography to afford the product (59 mg). MS [M]$^+$: 795.4.

Step 2: N-[3-chloro-4-[4-[1-(2-hydroxyethyl)-1-methyl-pyrrolidin-1-ium-2-carbonyl]piperazine-1-carbonyl]phenyl]-5-[2,3-difluoro-4-(3-methyl-1H-pyrazol-4-yl)phenyl]-1-methyl-imidazole-2-carboxamide; 2,2,2-trifluoroacetate N-(4-(4-((2-((tert-butyldimethylsilyl)oxy)ethyl)prolyl)piperazine-1-carbonyl)-3-chlorophenyl)-5-(2,3-difluoro-4-(3-methyl-1H-pyrazol-4-yl)phenyl)-1-methyl-1H-imidazole-2-carboxamide (59 mg, 74.2 µmol) and iodomethane (52.6 mg, 23.1 µL, 371 µmol) were stirred in MeCN (1.48 mL) for 5 h. The solvent was removed in vacuum and the residue was treated with tetrabutylammonium fluoride (223 µL, 223 µmol, 1M in THF) at room temperature. After completion, the product was purified directly by prep. HPLC to afford the product (59 mg) as white powder. MS [M]$^+$: 695.2.

The following examples were prepared in analogy to Example B35.

| Ex# | Name | Structure | MS ESI [M]+ | Starting Material |
|---|---|---|---|---|
| Example B36 | N-[3-chloro-4-[4-[(2S,4R)-4-hydroxy-1-(2-hydroxyethyl)-1-methyl-pyrrolidin-1-ium-2-carbonyl]piperazine-1-carbonyl]phenyl]-5-[2,3-difluoro-4-(3-methyl-1H-pyrazol-4-yl)phenyl]-1-methyl-imidazole-2-carboxamide; 2,2,2-trifluoroacetate | 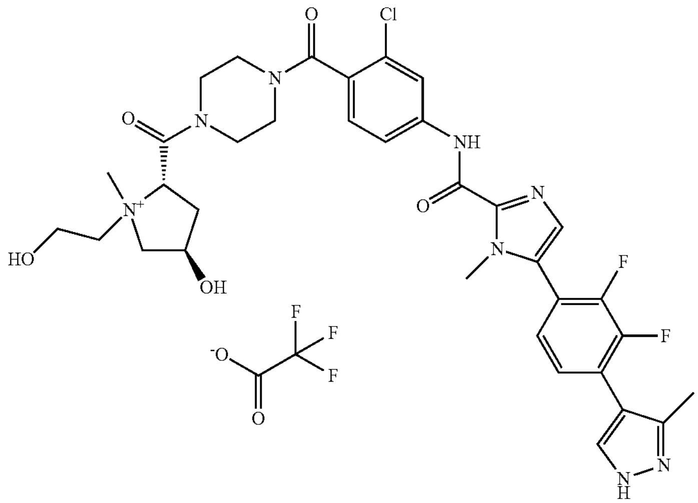 | 711.4 | Intermediate K10 and tert-butyl-(2-iodoethoxy)-dimethyl-silane; TBAF; iodomethane |

Example B38

2-[1-(azetidin-3-ylmethyl)-4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]piperazin-1-ium-1-yl]acetic acid; formate

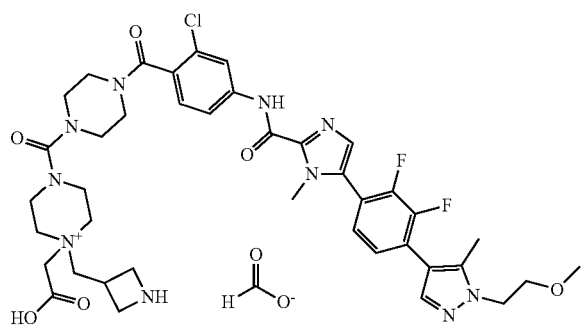

Step 1: tert-butyl 3-[[1-(2-tert-butoxy-2-oxo-ethyl)-4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]piperazin-1-ium-1-yl]methyl]azetidine-1-carboxylate; formate To a mixture of tert-butyl 3-[[1-(2-tert-butoxy-2-oxo-ethyl)piperazin-1-ium-1-yl]methyl]azetidine-1-carboxylate (100.0 mg, 0.270 mmol) Intermediate R15 and bis(trichloromethyl)carbonate (27.23 mg, 0.090 mmol) in DCM (2 mL) was stirred at 20° C. for 1 h. Then, N,N-diisopropylethylamine (0.1 mL, 0.590 mmol) and N-[3-chloro-4-(piperazine-1-carbonyl)phenyl]-5-[2,3-difluoro-4-[1-(2-methoxyethyl)-5-methyl-pyrazol-4-yl]phenyl]-1-methyl-imidazole-2-carboxamide (161.41 mg, 0.270 mmol) in DCM (1 mL) was added to the above solution. The reaction mixture was stirred at 20° C. for 2 h. The reaction mixture was concentrated in vacuum to give the residue, which was purified by prep-HPLC (FA) to afford the title compound (100 mg, 0.100 mmol, 37.25% yield) as yellow solid. MS [M−56]+: 937.6.

Step 2: 2-[1-(azetidin-3-ylmethyl)-4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]piperazin-1-ium-1-yl]acetic acid; formate To a solution of tert-butyl 3-[[1-(2-tert-butoxy-2-oxo-ethyl)-4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]piperazin-1-ium-1-yl]methyl]azetidine-1-carboxylate; formate (49.33 mg, 0.050 mmol, 1 eq) in DCM (1 mL) was added trifluoroacetic acid (1.0 mL, 12.98 mmol, 273.51 eq). The reaction mixture was stirred at 20° C. for 16 h. The reaction mixture was concentrated in vacuo. The residue was then purified by prep-HPLC (FA) to afford the title compound (19.3 mg, 0.020 mmol, 45.03% yield) as yellow solid. MS 837.2, [M]+, ESI+

Example C1
N-[3-chloro-4-[4-[2-(3-hydroxy-1-methyl-pyrrolidin-1-ium-1-yl)acetyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; formate
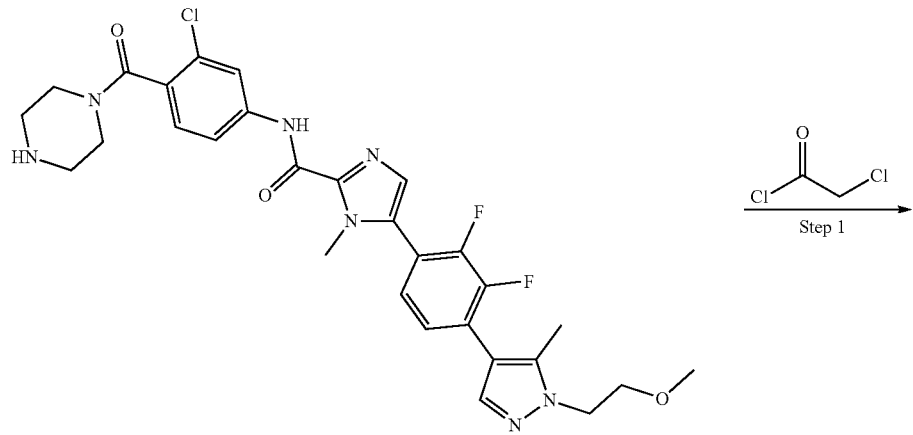
Intermediate I1
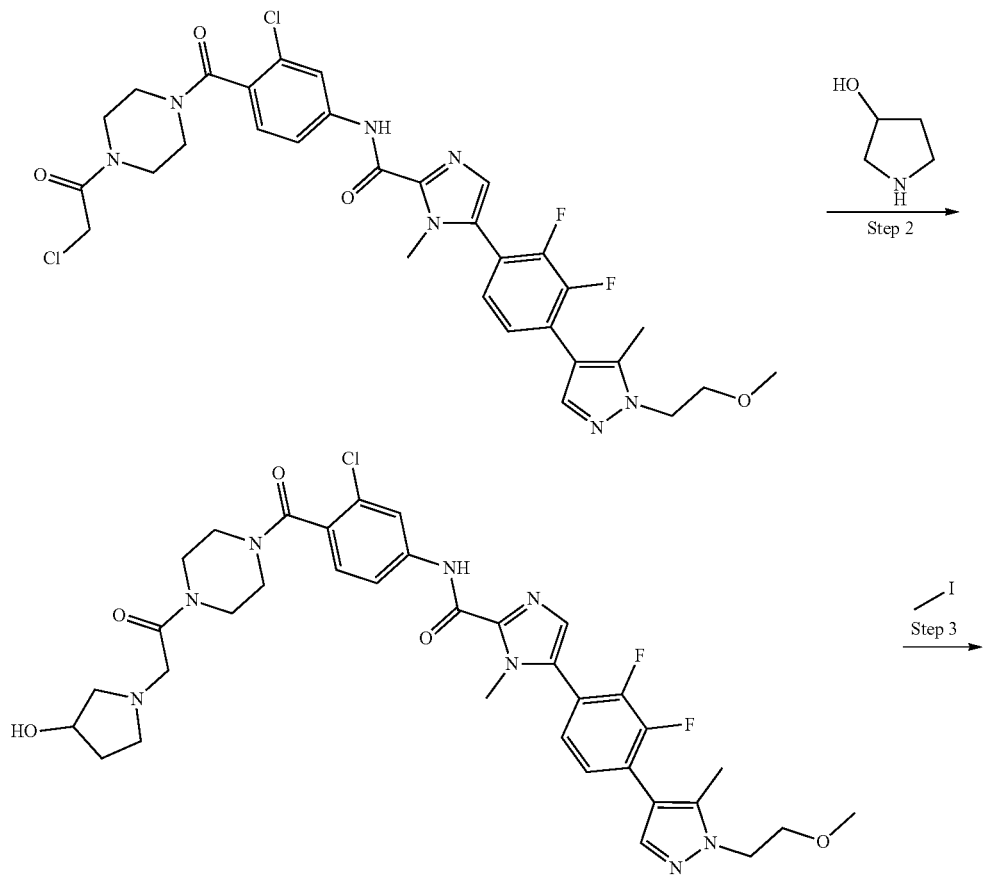

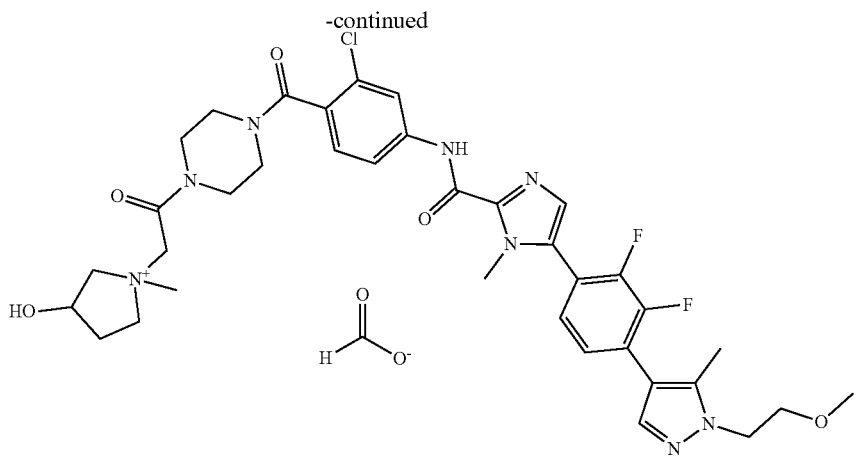

Example C1

Step 1: N-[3-chloro-4-[4-(2-chloroacetyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide In a 50 mL round-bottomed flask, N-[3-chloro-4-(piperazine-1-carbonyl)phenyl]-5-[2,3-difluoro-4-[1-(2-methoxyethyl)-5-methyl-pyrazol-4-yl]phenyl]-1-methyl-imidazole-2-carboxamide (137 mg, 229 μmol) and DIPEA (88.8 mg, 687 μmol) were combined with MeCN (5 mL) to give a light yellow solution. 2-chloroacetyl chloride (51.7 mg, 458 μmol) was added. The reaction was stirred at room temperature for 1 h. The crude reaction mixture was concentrated in vacuum. The crude material was purified by flash chromatography to afford N-[3-chloro-4-[4-(2-chloroacetyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide (150 mg). MS [M+H]⁺: 674.2.

Step 2: N-[3-chloro-4-[4-[2-(3-hydroxypyrrolidin-1-yl)acetyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide To a 5 mL microwave vial was added N-[3-chloro-4-[4-(2-chloroacetyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide (70 mg, 104 μmol), pyrrolidin-3-ol (18.1 mg, 208 μmol) and DIPEA (40.2 mg, 311 μmol) in MeCN (3 mL). The vial was capped and heated in the microwave at 70° C. for 30 min. The reaction was directly used the next step to afford N-[3-chloro-4-[4-[2-(3-hydroxypyrrolidin-1-yl)acetyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide (75.3 mg). MS [M+H]⁺: 725.2.

Step 3: N-[3-chloro-4-[4-[2-(3-hydroxy-1-methyl-pyrrolidin-1-ium-1-yl)acetyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; formate In a 50 mL round-bottomed flask, N-[3-chloro-4-[4-[2-(3-hydroxypyrrolidin-1-yl)acetyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide (75.3 mg, 104 μmol), MeI (73.7 mg, 519 μmol) and DIPEA (67.1 mg, 519 μmol) were combined with MeCN (3 mL) to give a light yellow solution. The reaction mixture was heated to 40° C. and stirred for 2 h. The crude reaction mixture was concentrated in vacuum. The crude material was purified by preparative HPLC to afford N-[3-chloro-4-[4-[2-(3-hydroxy-1-methyl-pyrrolidin-1-ium-1-yl)acetyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; formate (16.6 mg). MS [M]⁺: 739.3.

The following examples were prepared in analogy to Examples C1.

| Ex# | Name | Structure | MS ESI [M]⁺ | Starting Material |
|---|---|---|---|---|
| Example C2 | N-[4-[4-[2-(3-amino-1-methyl-pyrrolidin-1-ium-1-yl)acetyl]piperazine-1-carbonyl]-3-chloro-phenyl]-5-[2,3-difluoro-4-[1-(2-methoxyethyl)-5-methyl-pyrazol-4-yl]phenyl]-1-methyl-imidazole-2-carboxamide; formic acid; formate | 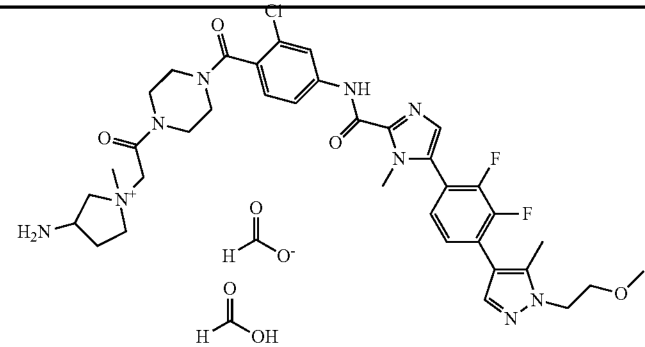 | 738.4 | Intermediate I1; 2-chloroacetyl chloride; tert-butyl N-pyrrolidin-3-ylcarbamate and iodomethane |

-continued

| Ex# | Name | Structure | MS ESI [M]+ | Starting Material |
|---|---|---|---|---|
| Example C3 | N-[4-[4-[2-(3-amino-1-methyl-pyrrolidin-1-ium-1-yl)acetyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide; formic acid; formate | 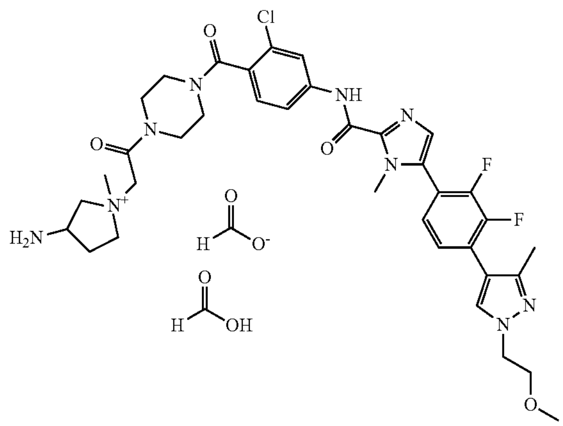 | 738.3 | Intermediate I2; 2-chloroacetyl chloride; tert-butyl N-pyrrolidin-3-ylcarbamate and iodomethane |
| Example C4 | N-[3-chloro-4-[4-[2-(3-hydroxy-1-methyl-pyrrolidin-1-ium-1-yl)acetyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide: formate | 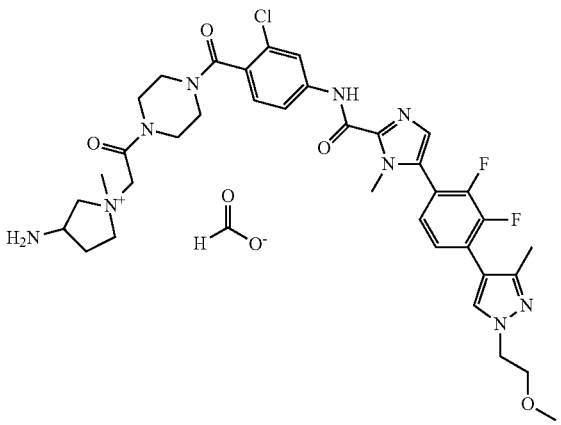 | 739.2 | Intermediate I2; 2-chloroacetyl chloride; pyrrolidin-3-ol and iodomethane |
| Example C5 | N-[4-[4-[2-[(3S,4S)-3-amino-4-methoxy-1-methyl-pyrrolidin-1-ium-1-yl]acetyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide; formic acid; formate | 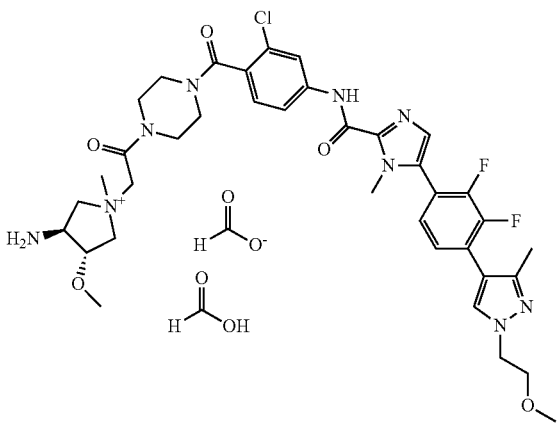 | 768.0 | Intermediate I2; 2-chloroacetyl chloride; tert-butyl N-[(3S,4S)-4-methoxypyrrolidin-3-yl]carbamate and iodomethane |

| Ex# | Name | Structure | MS ESI [M]+ | Starting Material |
|---|---|---|---|---|
| Example C6 | N-[4-[4-[2-[3-(aminomethyl)-3-hydroxy-1-methyl-pyrrolidin-1-ium-1-yl]acetyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide; formic acid; formate | 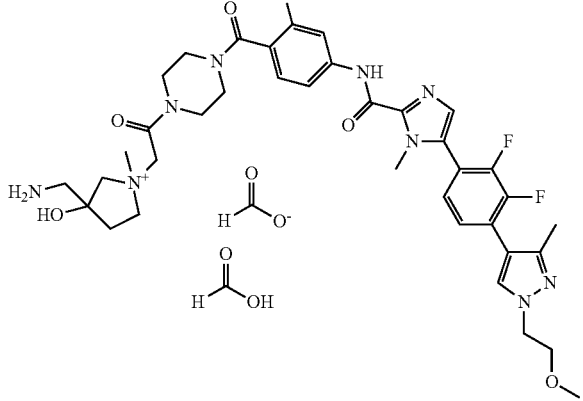 | 768.1 | Intermediate I2; 2-chloroacetyl chloride; tert-butyl N-[(3-hydroxypyrrolidin-3-yl)methyl]carbamate and iodomethane |
| Example C7 | N-[4-[4-[2-(3-carbamoyl-1-methyl-pyrrolidin-1-ium-1-yl)acetyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide; formate | 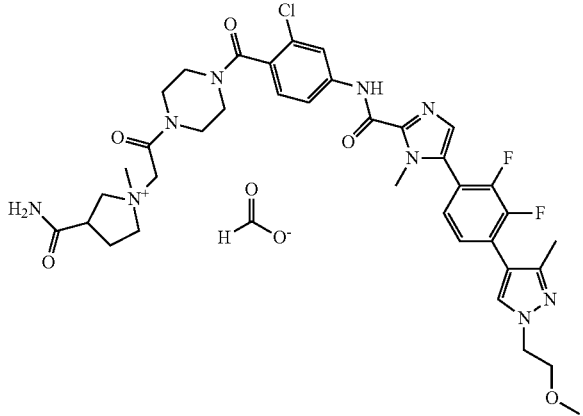 | 766.4 | Intermediate I2; 2-chloroacetyl chloride; pyrrolidine-3-carboxamide and iodomethane |
| Example C8 | N-[3-chloro-4-[4-[2-[(3R)-3-hydroxy-1-methyl-pyrrolidin-1-ium-1-yl]acetyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide; formate | 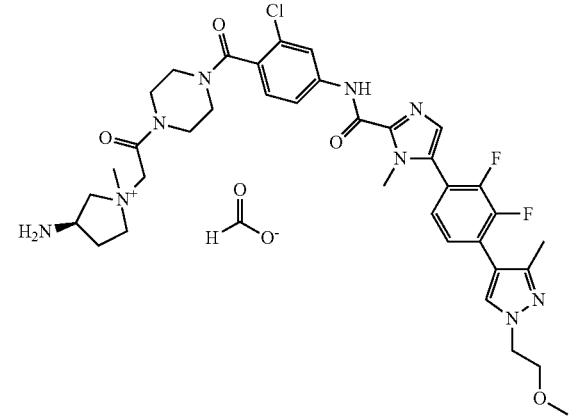 | 739.2 | Intermediate I2; 2-chloroacetyl chloride; rac-(3R)-pyrrolidin-3-ol and iodomethane |

| Ex# | Name | Structure | MS ESI [M]+ | Starting Material |
|---|---|---|---|---|
| Example C9 | N-[3-chloro-4-[4-[2-[(3S)-3-hydroxy-1-methyl-pyrrolidin-1-ium-1-yl]acetyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide; formate | 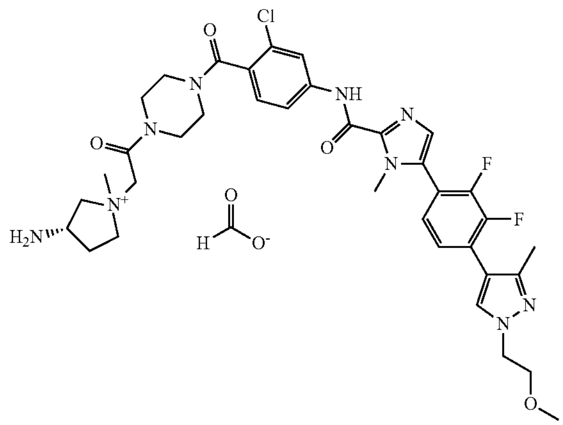 | 739.2 | Intermediate I2; 2-chloroacetyl chloride; rac-(3S)-pyrrolidin-3-ol and iodomethane |
| Example C10 | N-[3-chloro-4-[4-[2-[(3R,4R)-3,4-dihydroxy-1-methyl-pyrrolidin-1-ium-1-yl]acetyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide; formate | 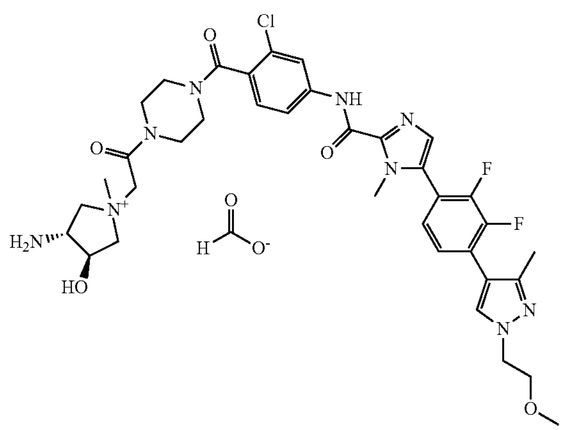 | 755.1 | Intermediate I2; 2-chloroacetyl chloride; rac-(3R,4R)-pyrrolidine-3,4-diol and iodomethane |
| Example C11 | N-[3-chloro-4-[4-[2-(3-hydroxy-1-methyl-pyrrolidin-1-ium-1-yl)acetyl]piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide; formate | 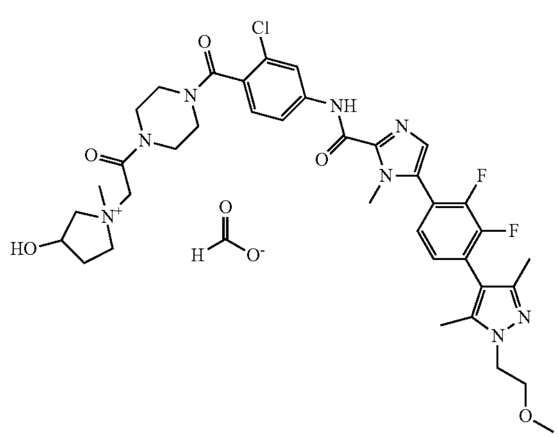 | 753.1 | Intermediate I3; 2-chloroacetyl chloride; pyrrolidin-3-ol and iodomethane |

-continued

| Ex# | Name | Structure | MS ESI [M]+ | Starting Material |
|---|---|---|---|---|
| Example C12 | N-[3-chloro-4-[4-[2-[(3R,4R)-3,4-dihydroxy-1-methyl-pyrrolidin-1-ium-1-yl]acetyl]piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide; formate | 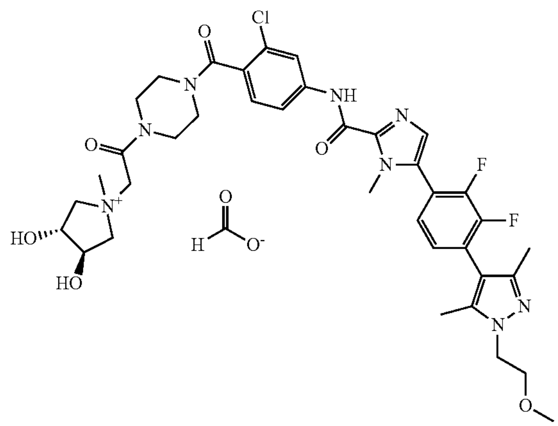 | 769.2 | Intermediate I3; 2-chloroacetyl chloride; rac-(3R,4R)-pyrrolidine-3,4-diol and iodomethane |
| Example C13 | N-[4-[4-[2-[(3R,4R)-3-amino-4-methoxy-1-methyl-pyrrolidin-1-ium-1-yl]acetyl]piperazine-1-carbonyl]-3-chloro-phenyl]-5-[2,3-difluoro-4-[1-(2-methoxyethyl)-3,5-dimethyl-pyrazol-4-yl]phenyl]-1-methyl-imidazole-2-carboxamide; formic acid; formate | 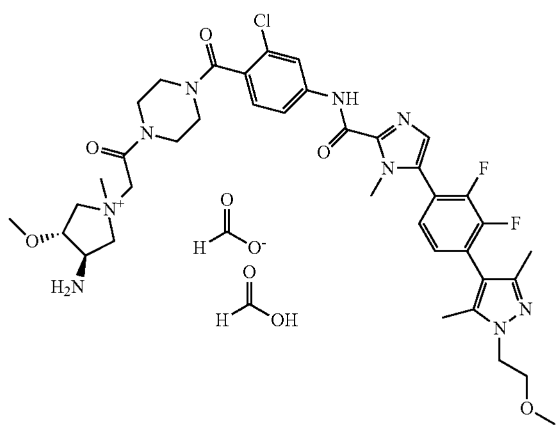 | 782.1 | Intermediate I3; 2-chloroacetyl chloride; rac-(3R,4R)-4-methoxypyrrolidin-3-amine and iodomethane |
| Example C14 | N-[3-chloro-4-[4-[2-(1-methylpyrrolidin-1-ium-1-yl)acetyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; 2,2,2-trifluoroacetate | 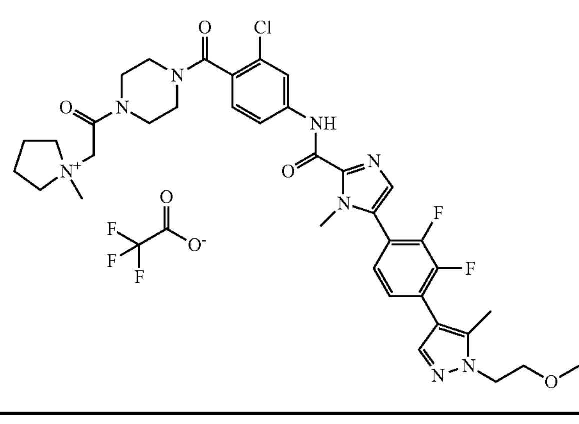 | 723.3 | Intermediate I-1; 2-(pyrrolidin-1-yl)acetic acid and iodomethane |

Example D1
N-[3-chloro-4-[4-[(2S,3S)-3-hydroxy-1,1-dimethyl-pyrrolidin-1-ium-2-carbonyl]piperazine-1-carbonyl]phenyl]-5-[2,3-difluoro-4-[1l-(2-methoxyethyl)-3-methyl-pyrazol-4-yl]phenyl]-1-methyl-imidazole-2-carboxamide; formate
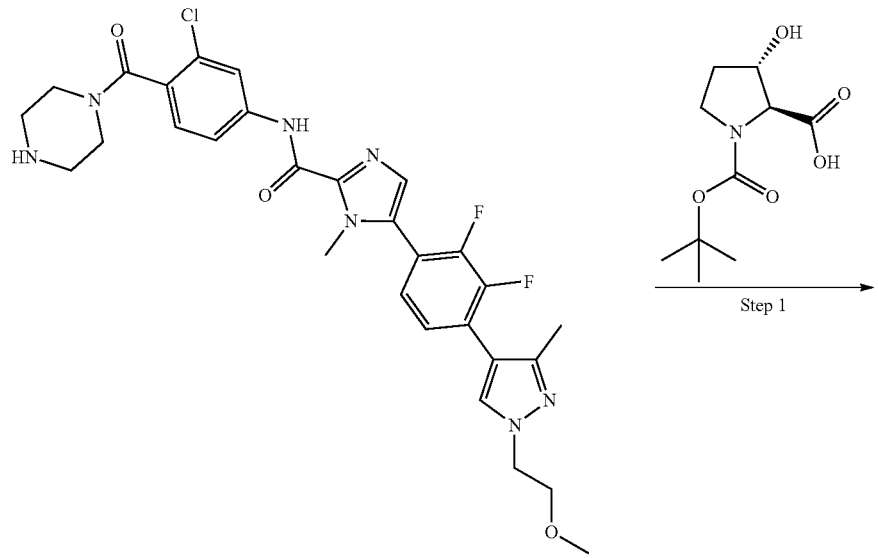
Intermediate I2
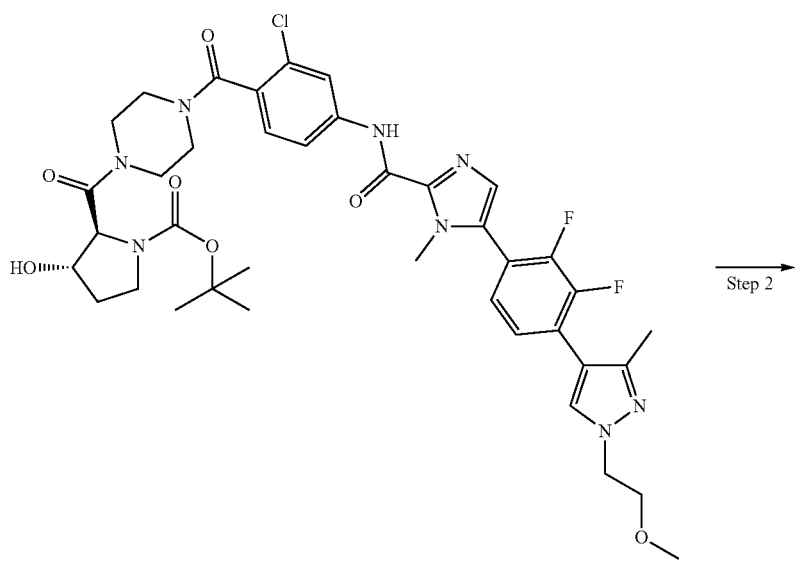

-continued

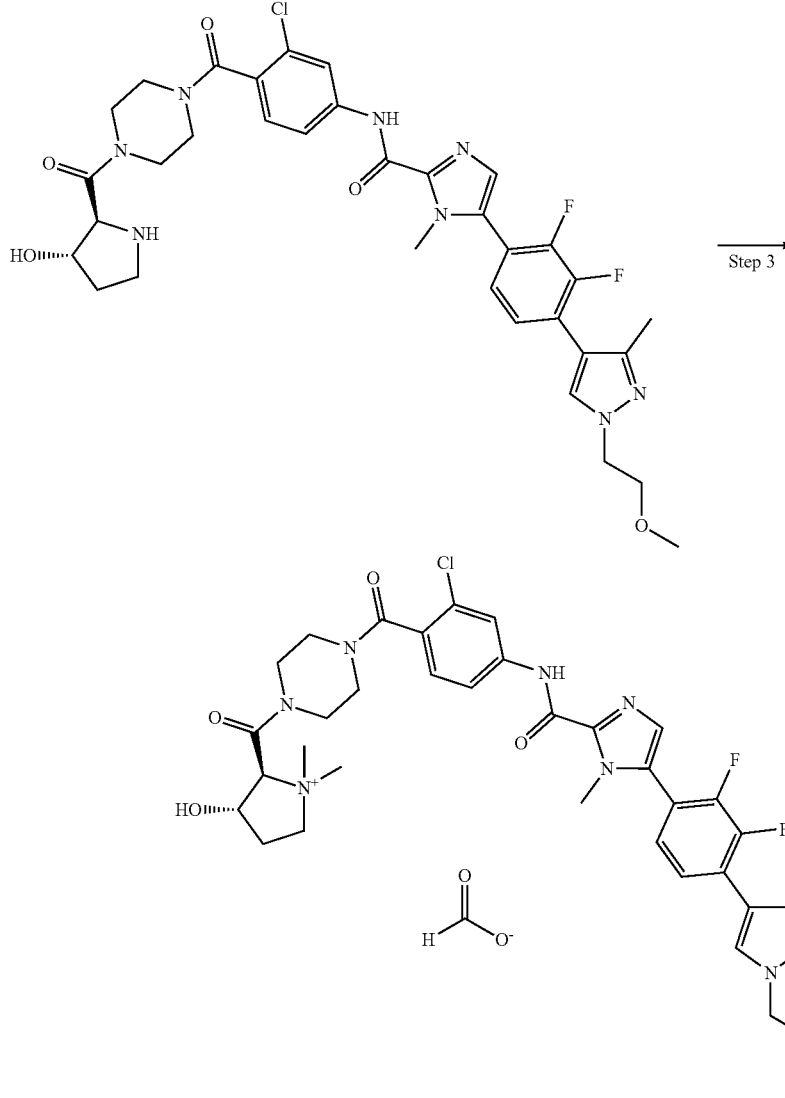

Example D1

Step 1: tert-butyl (2S,3S)-2-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]-3-hydroxy-pyrrolidine-1-carboxylate In a 50 mL round-bottomed flask, (2S,3S)-1-tert-butoxycarbonyl-3-hydroxy-pyrrolidine-2-carboxylic acid (40.2 mg, 174 μmol), N-[3-chloro-4-(piperazine-1-carbonyl)phenyl]-5-[2,3-difluoro-4-[1-(2-methoxyethyl)-3-methyl-pyrazol-4-yl]phenyl]-1-methyl-imidazole-2-carboxamide (80 mg, 134 μmol), HATU (66.1 mg, 174 μmol) and DIPEA (17.3 mg, 134 μmol) were combined with DMF (3 mL) to give a light brown solution. The reaction was stirred at room temperature for 1 h. The crude reaction mixture was concentrated in vacuum. The crude product was directly used to the next step to afford tert-butyl (2S,3 S)-2-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]-3-hydroxy-pyrrolidine-1-carboxylate (100 mg). MS [M+H]⁺. 811.3.

Step 2: N-[3-chloro-4-[4-[(2S,3S)-3-hydroxypyrrolidine-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide In a 50 mL round-bottomed flask, tert-butyl (2S,3S)-2-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]-piperazine-1-carbonyl]-3-hydroxypyrrolidine-1-carboxylate (100 mg, 123 μmol) was combined with THF (2 mL) to give a light brown solution. HCl (1.03 ml, 12.3 mmol) was added. The reaction was stirred at room temperature for 1 h. The crude reaction mixture was concentrated in vacuum. The crude product was directly used to the next step to afford N-[3-chloro-4-[4-[(2S,3S)-3-hydroxypyrrolidine-2-carbonyl]piperazine-1-carbonyl]phenyl]-5-[2,3-difluoro-4-[1-(2-methoxyethyl)-3- methyl-pyrazol-4-yl]phenyl]-1-methyl-imidazole-2-carboxamide (87.7 mg). MS [M+H]⁺: 711.2.

Step 3: N-[3-chloro-4-[4-[(2S,3S)-3-hydroxy-1,1-dimethyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide; formate In a 50 mL round-bottomed flask, tert-butyl (2S,3S)-2-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]-3-hydroxy-pyrrolidine-1-carboxylate (87 mg, 122 µmol), MeI (86.8 mg, 612 µmol) and DIPEA (79.1 mg, 612 µmol) were combined with MeCN (5 mL) to give a light red solution. The reaction mixture was heated to 40° C. and stirred for 15 h. The crude reaction mixture was concentrated in vacuum. The crude material was purified by preparative HPLC to afford N-[3-chloro-4-[4-[(2S,3S)-3-hydroxy-1,1-dimethyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide; formate (16.1 mg). MS [M]⁺: 739.1.

The following examples were prepared in analogy to Examples D1.

| Ex# | Name | Structure | MS ESI [M]⁺ | Starting Material |
|---|---|---|---|---|
| Example D2 | N-[3-chloro-4-[4-(3-hydroxy-1,1-dimethyl-piperidin-1-ium-4-carbonyl)piperazine-1-carbonyl]phenyl]-5-[2,3-difluoro-4-[1-(2-methoxyethyl)-3-methyl-pyrazol-4-yl]phenyl]-1-methyl-imidazole-2-carboxamide; formate | 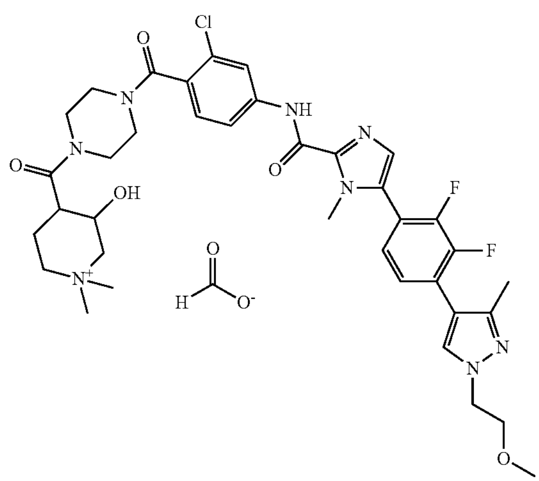 | 753.2 | Intermediate I2; 1-tert-butoxycarbonyl-3-hydroxy-piperidine-4-carboxylic acid; iodomethane |
| Example D3 | N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide; formate | 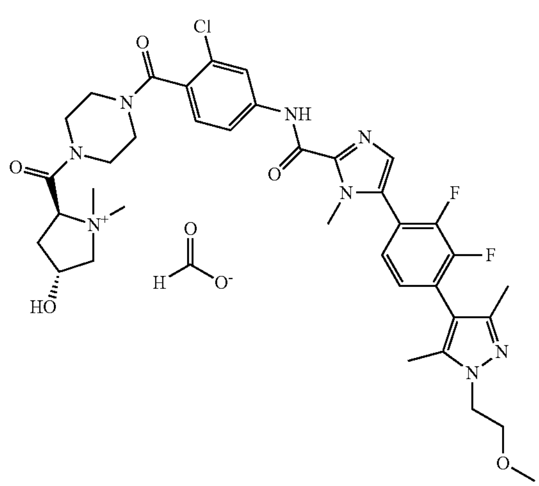 | 753.4 | Intermediate I3; rac-(2S,4R)-1-tert-butoxycarbonyl-4-hydroxy-pyrrolidine-2-carboxylic acid; iodomethane |

-continued

| Ex# | Name | Structure | MS ESI [M]+ | Starting Material |
|---|---|---|---|---|
| Example D4 | N-[3-chloro-4-[4-(3-hydroxy-1,1-dimethyl-piperidin-1-ium-4-carbonyl)piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide; formate | 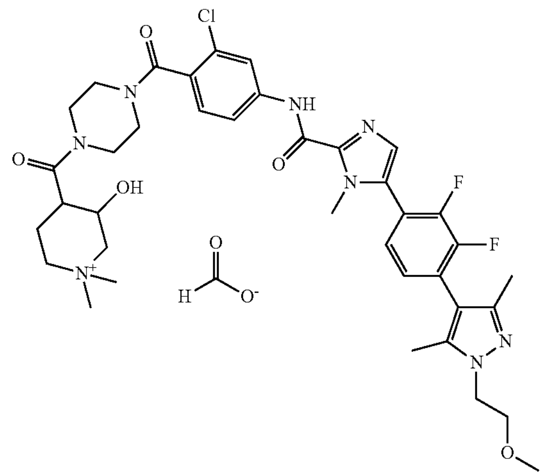 | 767.3 | Intermediate I3; 1-tert-butoxycarbonyl-3-hydroxy-piperidine-4-carboxylic acid; iodomethane |
| Example D6 | N-[3-chloro-4-[4-[3-(hydroxymethyl)-4,4-dimethyl-piperazin-4-ium-1-carbonyl]piperidine-1-carbonyl]phenyl]-5-[2,3-difluoro-4-[1-(2-methoxyethyl)-5-methyl-pyrazol-4-yl]phenyl]-1-methyl-imidazole-2-carboxamide; formate | 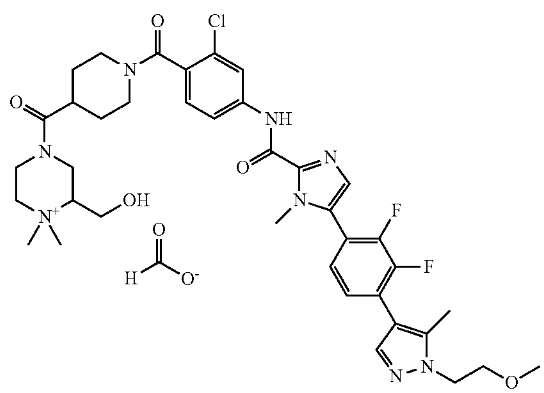 | 767.2 | Intermediate I6; tert-butyl 2-(hydroxymethyl)piperazine-1-carboxylate; iodomethane |
| Example D7 | N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide; formate | 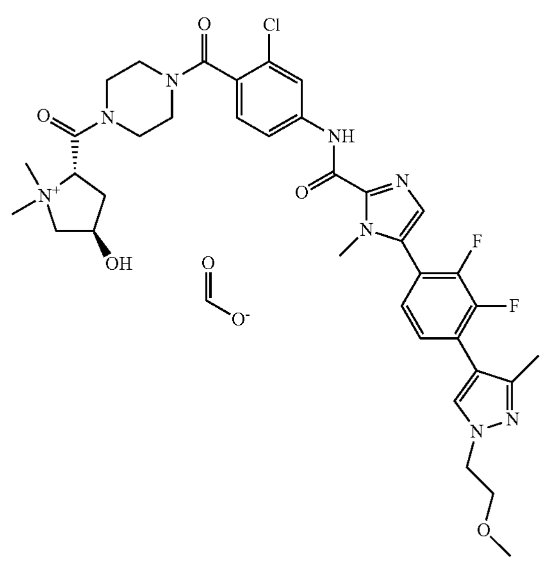 | 739.2 | Intermediate I2; (2S,4R)-1-tert-butoxycarbonyl-4-hydroxy-pyrrolidine-2-carboxylic acid; iodomethane |

-continued

| Ex# | Name | Structure | MS ESI [M]+ | Starting Material |
|---|---|---|---|---|
| Example D8 | N-[3-chloro-4-[4-[(2R,4S)-4-hydroxy-1,1-dimethyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide; formate | 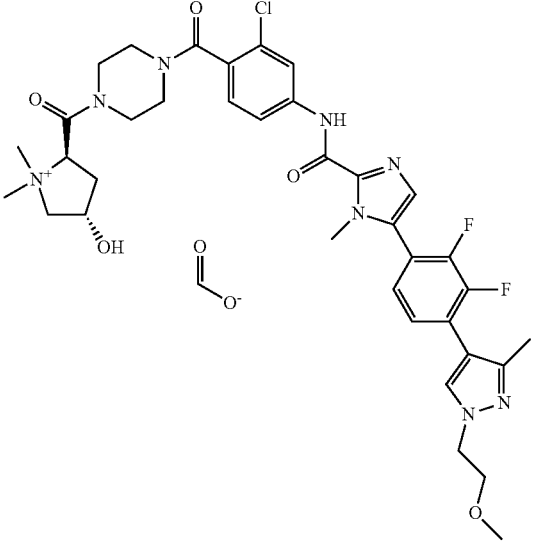 | 739.2 | Intermediate I2; (2R,4S)-1-tert-butoxycarbonyl-4-hydroxy-pyrrolidine-2-carboxylic acid; iodomethane |
| Example D9 | N-[3-chloro-4-[4-[(2R,4R)-4-hydroxy-1,1-dimethyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide; formate | 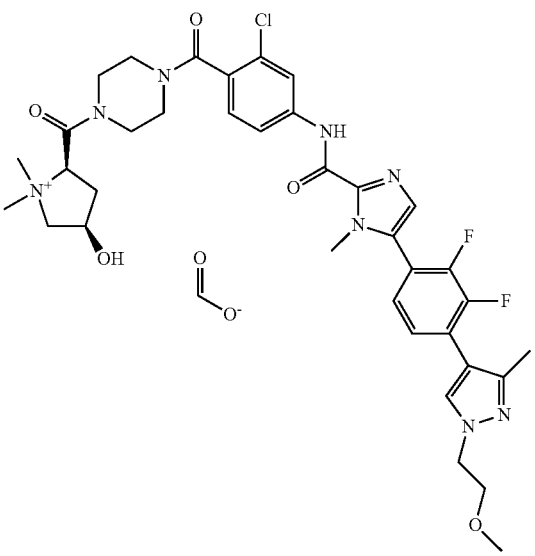 | 739.2 | Intermediate I2; (2R,4R)-1-tert-butoxycarbonyl-4-hydroxy-pyrrolidine-2-carboxylic acid; iodomethane |

-continued

| Ex# | Name | Structure | MS ESI [M]+ | Starting Material |
|---|---|---|---|---|
| Example D10 | N-[3-chloro-4-[4-[(2S,4S)-4-hydroxy-1,1-dimethyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide; formate | 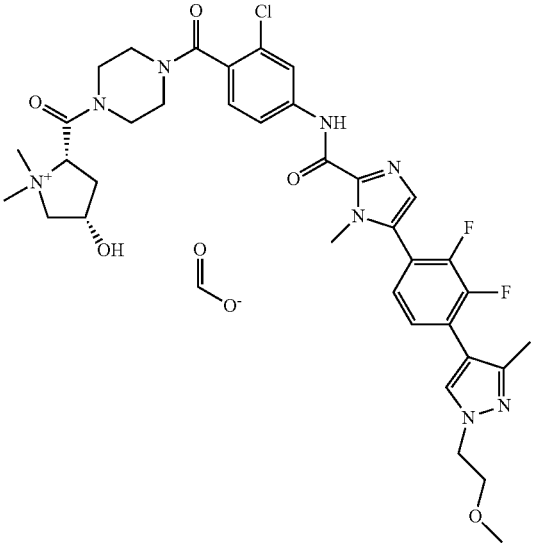 | 739.2 | Intermediate I2; (2S,4S)-1-tert-butoxycarbonyl-4-hydroxy-pyrrolidine-2-carboxylic acid; iodomethane |
| Example D11 | N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(3-methoxypropyl)-3-methyl-pyrazol-4-yl]phenyl]-1-methyl-imidazole-2-carboxamide; formate | 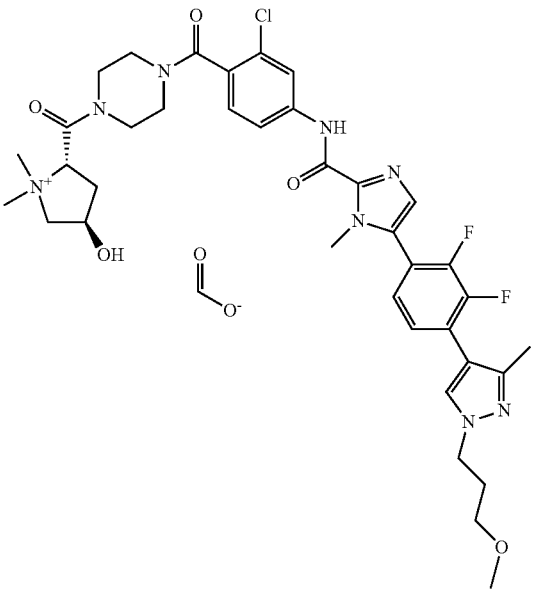 | 753.1 | Intermediate I8; (2S,4R)-1-tert-butoxycarbonyl-4-hydroxy-pyrrolidine-2-carboxylic acid; iodomethane |
| Example D12 | N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(3-methoxypropyl)-5-methyl-pyrazol-4-yl]phenyl]-1-methyl-imidazole-2-carboxamide; formate | 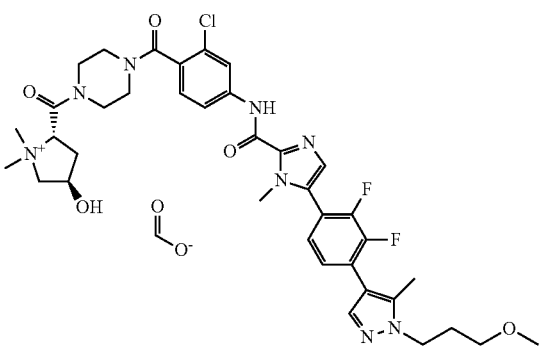 | 753.4 | Intermediate I9; (2S,4R)-1-tert-butoxycarbonyl-4-hydroxy-pyrrolidine-2-carboxylic acid; iodomethane |

-continued

| Ex# | Name | Structure | MS ESI [M]+ | Starting Material |
|---|---|---|---|---|
| Example D13 | N-[3-chloro-4-[4-[(3S)-4,4-dimethylmorpholin-4-ium-3-carbonyl]piperazine-1-carbonyl]phenyl]-5-[2,3-difluoro-4-[1-(3-methoxypropyl)-3-methyl-pyrazol-4-yl]phenyl]-1-methyl-imidazole-2-carboxamide; formate | 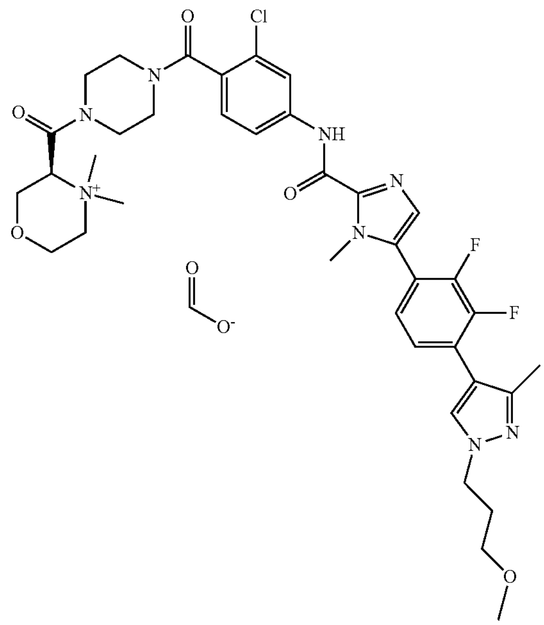 | 753.4 | Intermediate I2; (S)-4-(tert-butoxycarbonyl)morpholine-3-carboxylic acid; iodomethane |
| Example D14 | N-[3-chloro-4-[4-[(4,4-dimethyl-2-oxo-piperazin-4-ium-1-yl)methyl]piperidine-1-carbonyl]phenyl]-5-[2,3-difluoro-4-[1-(2-methoxyethyl)-5-methyl-pyrazol-4-yl]phenyl]-1-methyl-imidazole-2-carboxamide; 2,2,2-trifluoroacetate | 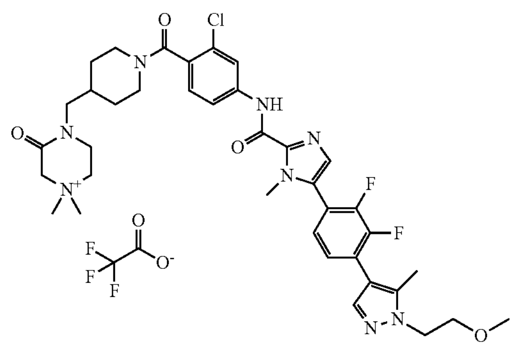 [SMILES: COCCn1ncc(-c2ccc(-c3cnc(C(=O)Nc4ccc(C(=O)N5CCC(CN6CC[N+](C)(C)CC6=O)CC5)c(Cl)c4)n3C)c(F)c2F)c1C ; O=C([O-])C(F)(F)F] | 737.2 | Intermediate L2; intermediate R5; iodomethane |
| Example D15 | N-[3-chloro-4-[2-(1-methylpyrrolidin-1-ium-1-yl)acetyl]piperazine-1-carbonyl]phenyl]-5-[2,3-difluoro-4-(3-methyl-1H-pyrazol-4-yl)phenyl]-1-methyl-imidazole-2-carboxamide; formate | 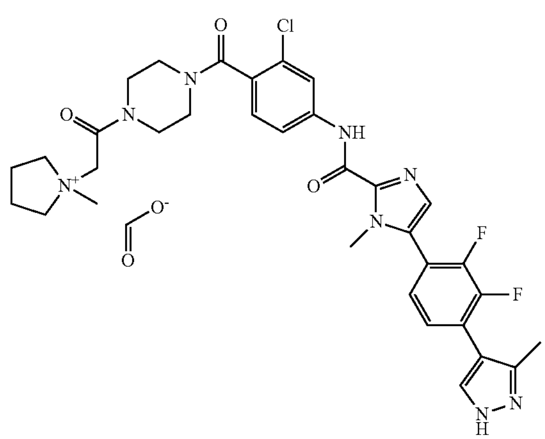 | 665.2 | Intermediate M1; 2-(pyrrolidin-1-yl)acetic acid; iodomethane |

| Ex# | Name | Structure | MS ESI [M]+ | Starting Material |
|---|---|---|---|---|
| Example D16 | N-[3-chloro-4-[4-(1,1-dimethylpiperidin-1-ium-4-carbonyl)piperazine-1-carbonyl]phenyl]-5-[2,3-difluoro-4-(3-methyl-1H-pyrazol-4-yl)phenyl]-1-methyl-imidazole-2-carboxamide; formate | 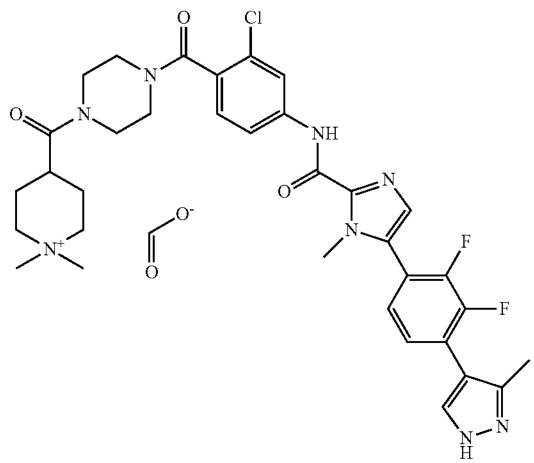 | 679.3 | Intermediate M1 and 1-tert-butoxycarbonyl-piperidine-4-carboxylic acid; then iodomethane |
| Example D17 | N-[3-chloro-4-[4-[2-(4-hydroxy-1,1-dimethyl-piperidin-1-ium-4-yl)acetyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide; formate | 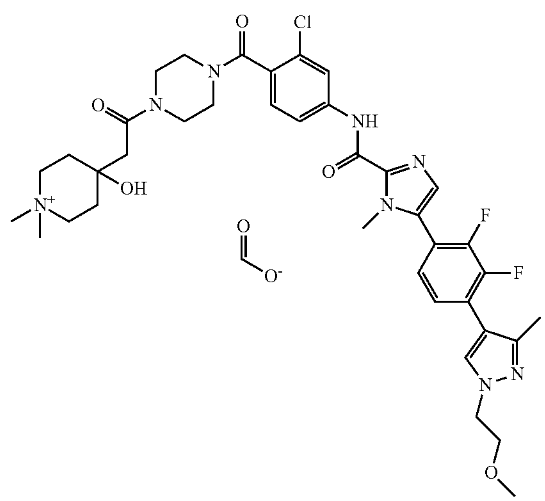 | 767.3 | Intermediate I2; 2-(1-tert-butoxycarbonyl-4-hydroxy-4-piperidyl)acetic acid; iodomethane |
| Example D18 | N-[3-chloro-4-[4-[2-[4-hydroxy-4-(hydroxymethyl)-1-methyl-piperidin-1-ium-1-yl]acetyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide; formate | 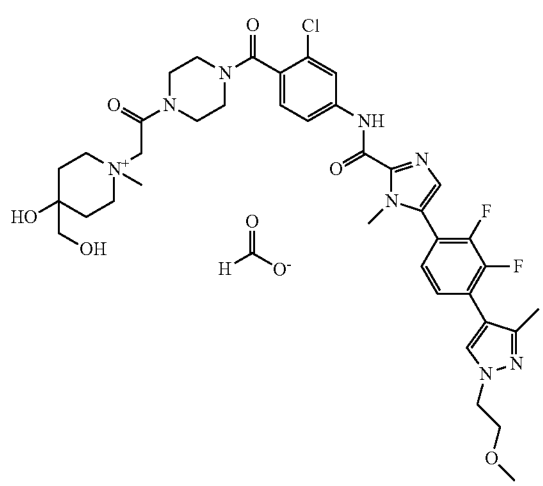 | 783.4 | Intermediate L3; Intermediate R7; iodomethane |

-continued

| Ex# | Name | Structure | MS ESI [M]+ | Starting Material |
|---|---|---|---|---|
| Example D19 | N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-(3-methyl-1H-pyrazol-4-yl)phenyl]-1-methyl-imidazole-2-carboxamide; formate | 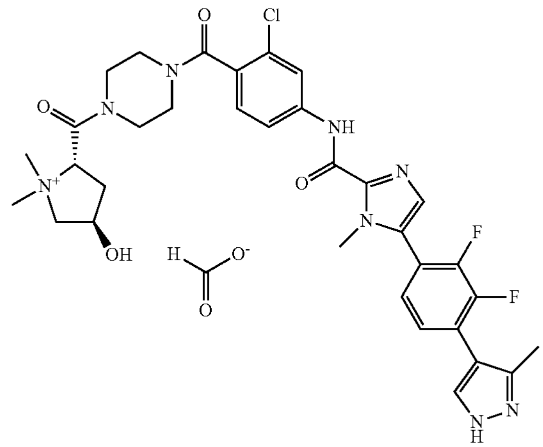 | 681.3 | Intermediate M1 and Intermediate R2; HCl; iodomethane |
| Example D20 | N-[4-[4-(4-amino-1,1-dimethyl-piperidin-1-ium-4-carbonyl)piperazine-1-carbonyl]-3-chloro-phenyl]-5-[2,3-difluoro-4-[1-(2-methoxyethyl)-5-methyl-pyrazol-4-yl]phenyl]-1-methyl-imidazole-2-carboxamide; formate | 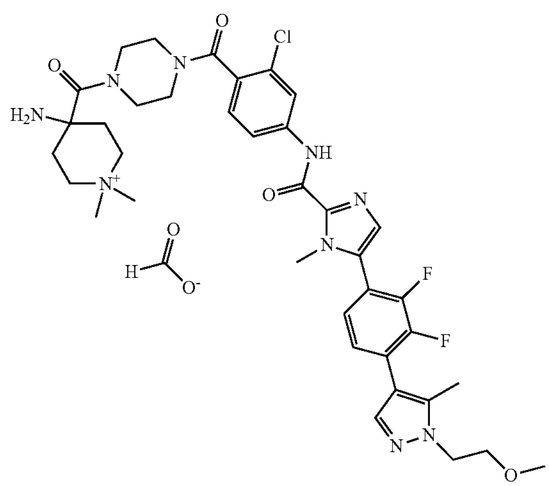 | 752.3 | Intermediate I1 and Intermediate R10; HCl |
| Example D21 | N-[3-chloro-4-[4-[(4,4-dimethyl-2-oxo-piperazin-4-ium-1-yl)methyl]piperidine-1-carbonyl]phenyl]-5-[2,3-difluoro-4-(3-methyl-1H-pyrazol-4-yl)phenyl]-1-methyl-imidazole-2-carboxamide; formate | 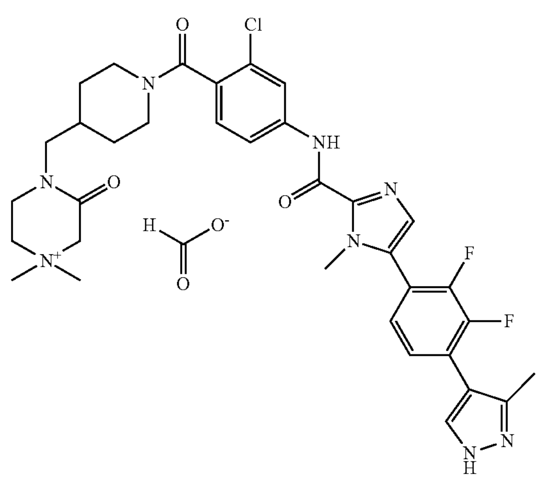 | 679.3 | Intermediate L1; intermediate R5; iodomethane |

| Ex# | Name | Structure | MS ESI [M]+ | Starting Material |
|---|---|---|---|---|
| Example D35 | [2-[4-[2-chloro-4-[[5-[2,3-difluoro-4-(3-methyl-1H-pyrazol-4-yl)phenyl]-1-methyl-imidazole-2-carbonyl]amino]benzoyl]piperazin-1-yl]-2-oxo-ethyl]-trimethyl-ammonium; formate | 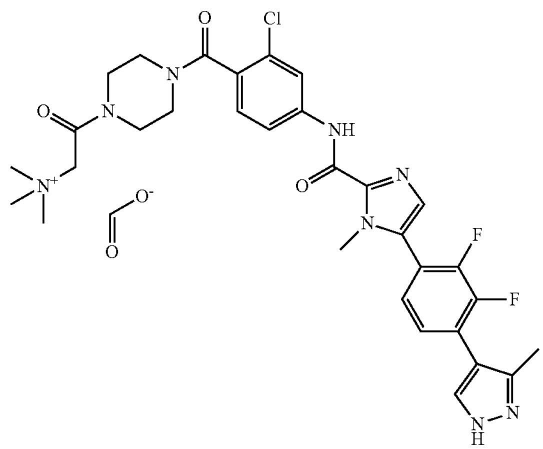 | 639.4 | Example D34 and iodomethane |
| Example D37 | N-[3-chloro-4-[4-[(1,1-dimethylpiperidin-1-ium-4-yl)sulfonylamino]piperidine-1-carbonyl]phenyl]-5-[2,3-difluoro-4-[1-(2-methoxyethyl)-5-methyl-pyrazol-4-yl]phenyl]-1-methyl-imidazole-2-carboxamide; formate | 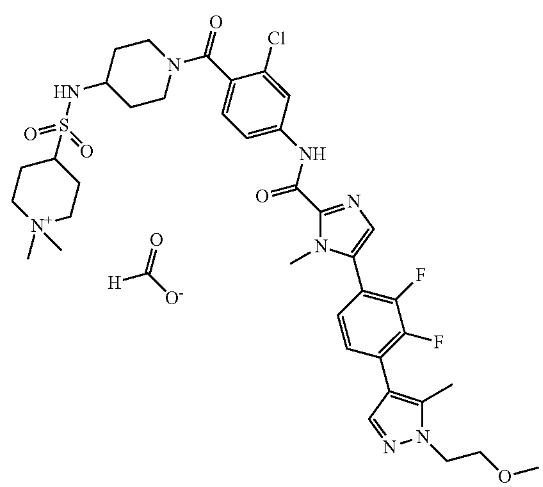 | 787.3 | Intermediate I10 and tert-butyl 4-chlorosulfonyl-piperidine-1-carboxylate; HCl; iodomethane |
| Example D38 | N-[3-chloro-4-[[(1R,5S)-3-[(2S,4R)-4-hydroxy-1,1-dimethyl-pyrrolidin-1-ium-2-carbonyl]-3-azabicyclo[3.1.0]hexan-6-yl]carbamoyl]phenyl]-5-[2,3-difluoro-4-[1-(2-methoxyethyl)-3,5-dimethyl-pyrazol-4-yl]phenyl]-1-methyl-imidazole-2-carboxamide; formate | 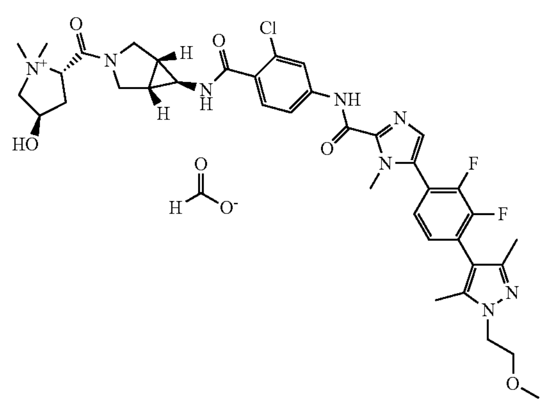 | 765.3 | Intermediate I11 and (2S,4R)-1-tert-butoxycarbonyl-4-hydroxy-pyrrolidine-2-carboxylic acid; HCl; iodomethane |

-continued

| Ex# | Name | Structure | MS ESI [M]+ | Starting Material |
|---|---|---|---|---|
| Example D40 | N-[3-chloro-4-[[(1S,5R)-3-[(2S,4R)-4-hydroxy-1,1-dimethyl-pyrrolidin-1-ium-2-carbonyl]-3-azabicyclo[3.1.0]hexan-6-yl]carbamoyl]phenyl]-5-[2,3-difluoro-4-[1-(2-methoxyethyl)-3,5-dimethyl-pyrazol-4-yl]phenyl]-1-methyl-imidazole-2-carboxamide; formate | 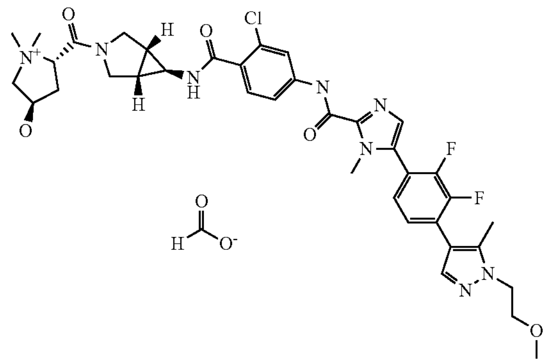 | 751.3 | Intermediate I12 and (2S,4R)-1-tert-butoxycarbonyl-4-hydroxy-pyrrolidine-2-carboxylic acid; HCl; iodomethane |
| Example D41 | bis(3-aminopropyl)-(carboxymethyl)-[4-[4-[2-chloro-4-[[5-[2,3-difluoro-4-(3-methyl-1H-pyrazol-4-yl)phenyl]-1-methyl-imidazole-2-carbonyl]amino]benzoyl]piperazin-1-yl]-4-oxo-butyl] ammonium; formic acid; formate | 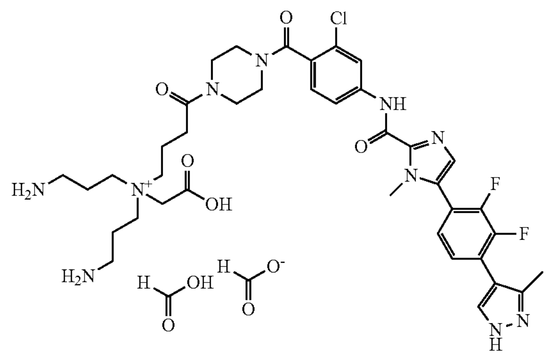 | 797.4 | Intermediate M1 and Intermediate R11: HCl |
| Example D42 | bis(azetidin-3-ylmethyl)-(carboxymethyl)-[4-[4-[2-chloro-4-[[5-[2,3-difluoro-4-(3-methyl-1H-pyrazol-4-yl)phenyl]-1-methyl-imidazole-2-carbonyl]amino]benzoyl]piperazin-1-yl]-4-oxo-butyl] ammonium; formic acid; formate | 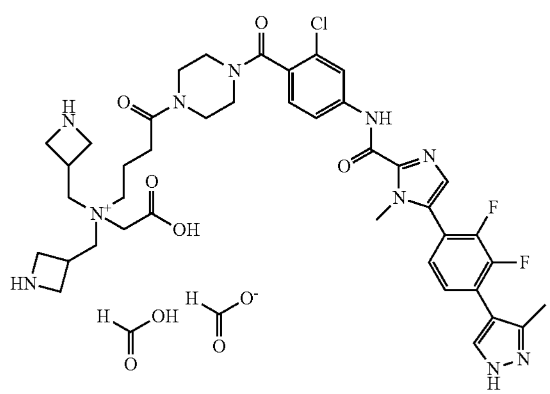 | 821.5 | Intermediate M1 and Intermediate R12: HCl |

Example D22
5-[2,3-difluoro-4-[1-(2-methoxyethyl)-3-methyl-pyrazol-4-yl]phenyl]-N-[4-[4-(3-hydroxypiperidine-4-carbonyl)piperazine-1-carbonyl]-3-methyl-phenyl]-1-methyl-imidazole-2-carboxamide; formic acid
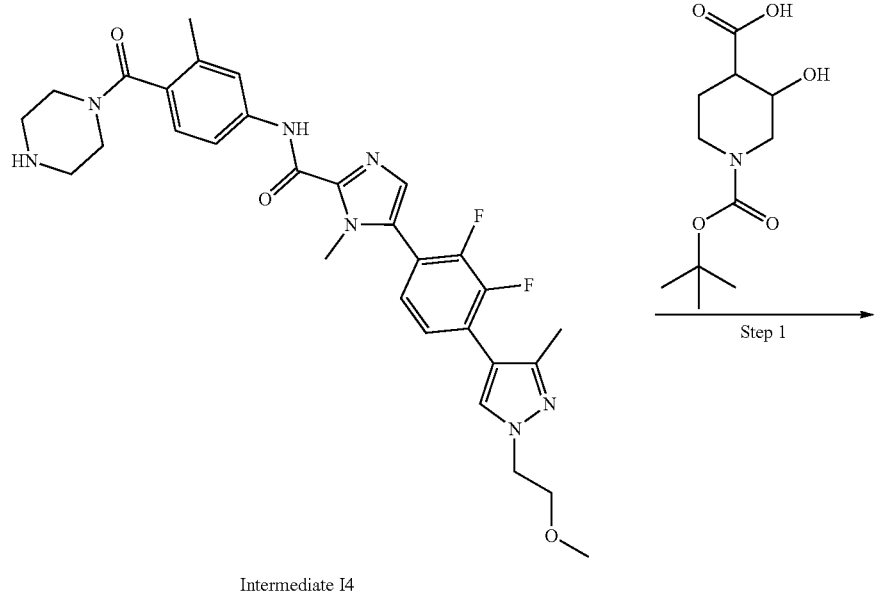
Intermediate I4
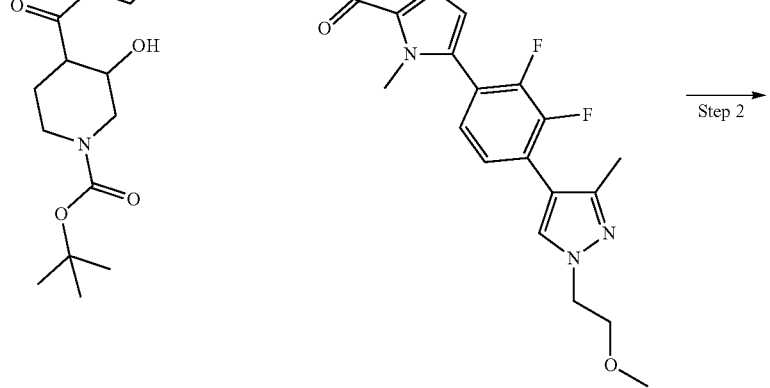

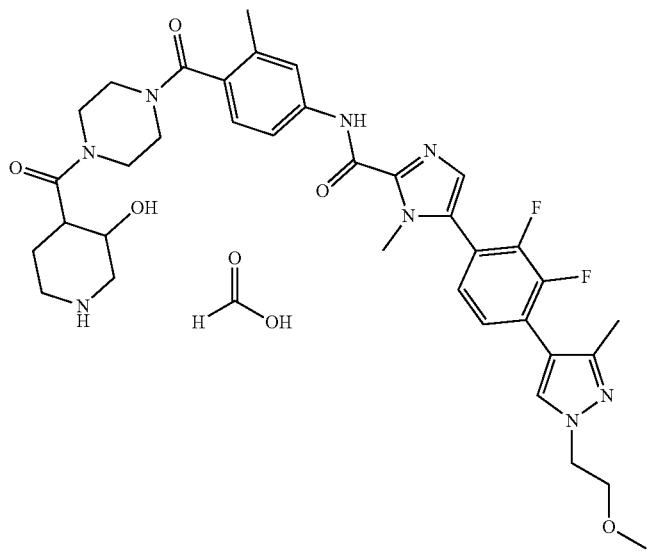

Example D22

Step 1: tert-butyl 4-[4-[4-[[5-[2,3-difluoro-4-[1-(2-methoxyethyl)-3-methyl-pyrazol-4-yl]phenyl]-1-methyl-imidazole-2-carbonyl]amino]-2-methyl-benzoyl]piperazine-1-carbonyl]-3-hydroxy-piperidine-1-carboxylate At room temperature, a mixture of 5-[2,3-difluoro-4-[1-(2-methoxyethyl)-3-methyl-pyrazol-4-yl]phenyl]-1-methyl-N-[3-methyl-4-(piperazine-1-carbonyl)phenyl]imidazole-2-carboxamide (300 mg, 519 µmol), 1-tert-butoxycarbonyl-3-hydroxy-piperidine-4-carboxylic acid (191 mg, 779 µmol), HATU (296 mg, 779 µmol) and DIPEA (201 mg, 1.56 mmol) in DMF (2 mL) was stirred for 16 h. Then the mixture was poured into water. The water layer was extracted with DCM. The combined organic layers were washed with water, dried over anhydrous Na₂SO₄ and concentrated in vacuum. The crude product tert-butyl 4-[4-[4-[[5-[2,3-difluoro-4-[1-(2-methoxyethyl)-3-methyl-pyrazol-4-yl]phenyl]-1-methyl-imidazole-2-carbonyl]amino]-2-methyl-benzoyl]piperazine-1-carbonyl]-3-hydroxy-piperidine-1-carboxylate was used into next step reaction directly. MS [M+H]⁺: 805.5.

Step 2: 5-[2,3-difluoro-4-[1-(2-methoxyethyl)-3-methyl-pyrazol-4-yl]phenyl]-N-[4-[4-(3-hydroxypiperidine-4-carbonyl)piperazine-1-carbonyl]-3-methyl-phenyl]-1-methyl-imidazole-2-carboxamide; formic acid At room temperature, a solution of tert-butyl 4-[4-[4-[[5-[2,3-difluoro-4-[1-(2-methoxyethyl)-3-methyl-pyrazol-4-yl]phenyl]-1-methyl-imidazole-2-carbonyl]amino]-2-methyl-benzoyl]piperazine-1-carbonyl]-3-hydroxy-piperidine-1-carboxylate (400 mg, 497 µmol) in DCM (10 mL) and TFA (5 mL) was stirred for 1 h. Then the mixture was concentrated in vacuum. The residue was basified by NH₃·H₂O to PH 8-9. The water layer was extracted with DCM. The organic layer was dried over anhydrous Na₂SO₄ and concentrated in vacuum. The residue was purified by Prep-HPLC to afford 5-[2,3-difluoro-4-[1-(2-methoxyethyl)-3-methyl-pyrazol-4-yl]phenyl]-N-[4-[4-(3-hydroxypiperidine-4-carbonyl)piperazine-1-carbonyl]-3-methyl-phenyl]-1-methyl-imidazole-2-carboxamide; formic acid. MS [M+H]⁺: 705.4.

The following examples were prepared in analogy to Example D22.

| Ex# | Name | Structure | MS ESI [M + H]+ | Starting Material |
|---|---|---|---|---|
| Example D23 | N-[3-chloro-4-[4-[[(2S,4R)-4-hydroxypyrrolidine-2-carbonyl]amino]piperidine-1-carbonyl]phenyl]-5-[2,3-difluoro-4-[1-(2-methoxyethyl)-3-methyl-pyrazol-4-yl]phenyl]-1-methyl-imidazole-2-carboxamide; formic acid | 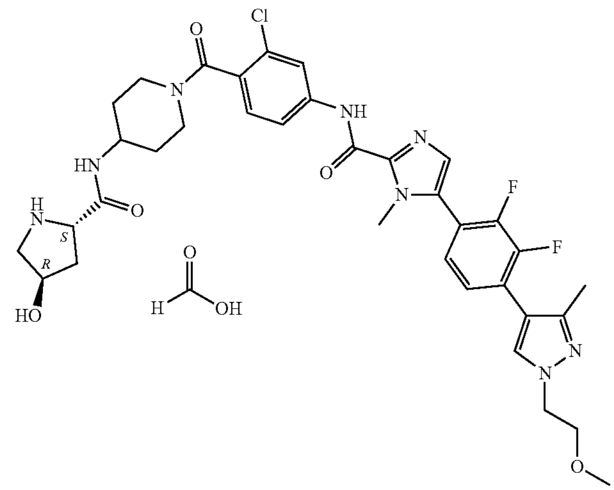 | 725.3 | Intermediate I5 and (2S,4R)-1-tert-butoxy-carbonyl-4-hydroxy-pyrrolidine-2-carboxylic acid; HCl |
| Example D24 | N-[3-chloro-4-[4-(4-hydroxypiperidine-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; formic acid | 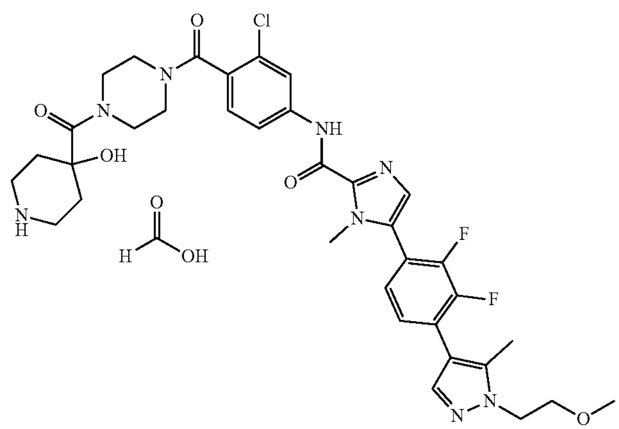 [SMILES: COCCn1ncc(-c2ccc(-c3cnc(C(=O)Nc4ccc(C(=O)N5CCN(C(=O)C6(O)CCNCC6)CC5)c(Cl)c4)n3C)c(F)c2F)c1C ; O=CO] | 725.2 | Intermediate I1 and 1-(tert-butoxy-carbonyl)-4-hydroxy-piperidine-4-carboxylic acid; HCl |
| Example D25 | N-[3-chloro-4-[4-(3-hydroxypiperidine-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; formic acid | 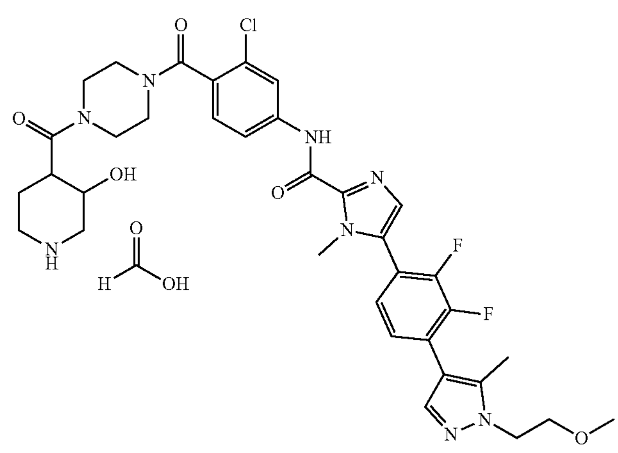 [SMILES: COCCn1ncc(-c2ccc(-c3cnc(C(=O)Nc4ccc(C(=O)N5CCN(C(=O)C6CCNCC6O)CC5)c(Cl)c4)n3C)c(F)c2F)c1C ; O=CO] | 725.2 | Intermediate I1 and 1-(tert-butoxy-carbonyl)-3-hydroxy-piperidine-4-carboxylic acid; HCl |

| Ex# | Name | Structure | MS ESI [M + H]+ | Starting Material |
|---|---|---|---|---|
| Example D26 | N-[3-chloro-4-[4-[(2S)-5-oxopyrrolidine-2-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; 2,2,2-trifluoroacetic acid | 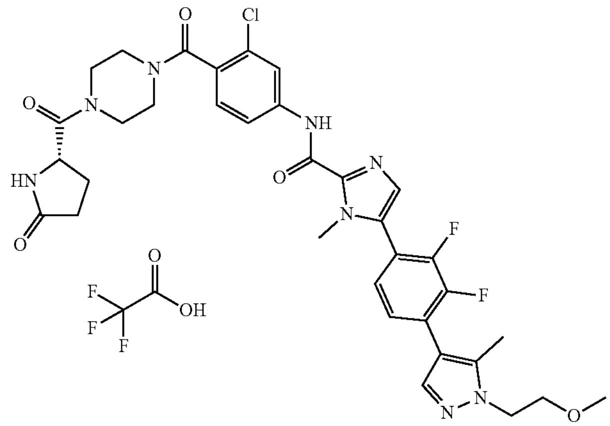 [SMILES: COCCn1ncc(-c2ccc(-c3cnc(C(=O)Nc4ccc(C(=O)N5CCN(C(=O)[C@@H]6CCC(=O)N6)CC5)c(Cl)c4)n3C)c(F)c2F)c1C ; O=C(O)C(F)(F)F] | 709.5 | Intermediate I1 and (S)-5-oxo-pyrrolidine-2-carboxylic acid |
| Example D27 | N-[3-chloro-4-[4-(2-oxopiperidine-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; 2,2,2-trifluoroacetic acid | 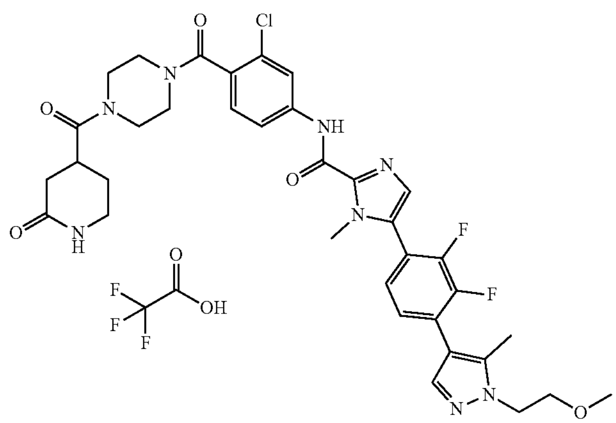 [SMILES: COCCn1ncc(-c2ccc(-c3cnc(C(=O)Nc4ccc(C(=O)N5CCN(C(=O)C6CCNC(=O)C6)CC5)c(Cl)c4)n3C)c(F)c2F)c1C ; O=C(O)C(F)(F)F] | 723.3 | Intermediate I1 and 2-oxopiperidine-4-carboxylic acid |
| Example D28 | N-[3-chloro-4-[4-(2-pyrrolidin-1-ylacetyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; 2,2,2-trifluoroacetic acid | 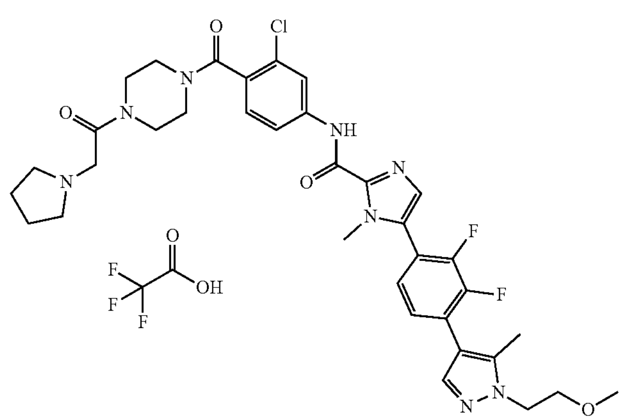 [SMILES: COCCn1ncc(-c2ccc(-c3cnc(C(=O)Nc4ccc(C(=O)N5CCN(C(=O)CN6CCCC6)CC5)c(Cl)c4)n3C)c(F)c2F)c1C ; O=C(O)C(F)(F)F] | 709.2 | Intermediate I1 and 2-(pyrrolidin-1-yl)acetic acid |

-continued

| Ex# | Name | Structure | MS ESI [M + H]+ | Starting Material |
|---|---|---|---|---|
| Example D29 | N-[3-chloro-4-[4-(pyrrolidine-2-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; 2,2,2-trifluoroacetic acid | 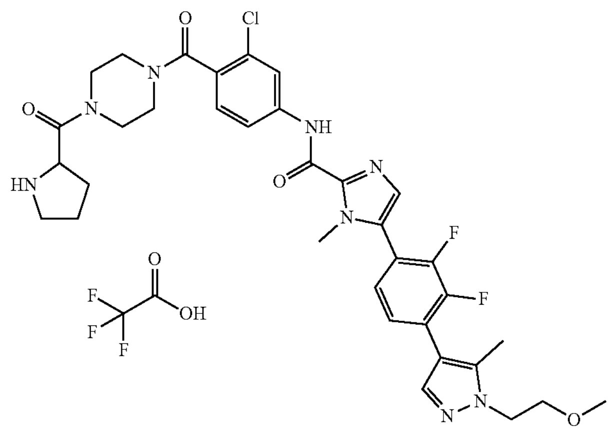 [SMILES: COCCn1ncc(-c2ccc(-c3cnc(C(=O)Nc4ccc(C(=O)N5CCN(C(=O)C6CCCN6)CC5)c(Cl)c4)n3C)c(F)c2F)c1C ; O=C(O)C(F)(F)F] | 695.3 | Intermediate I1 and (tert-butoxy-carbonyl) proline; HCl |
| Example D30 | N-[4-[4-(3-aminobicyclo[1.1.1]pentane-1-carbonyl)piperazine-1-carbonyl]-3-chloro-phenyl]-5-[2,3-difluoro-4-[1-(2-methoxyethyl)-5-methyl-pyrazol-4-yl]phenyl]-1-methyl-imidazole-2-carboxamide; 2,2,2-trifluoroacetic acid | 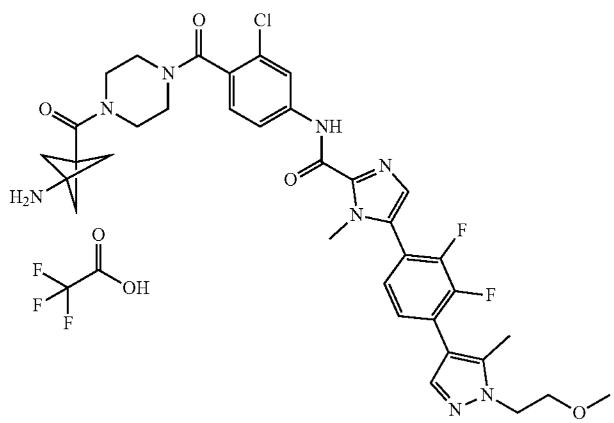 | 707.8 | Intermediate I1 and 3-(tert-butoxy-carbonyl-amino)bicyclo[1.1.1]pentane-1-carboxylic acid; HCl |
| Example D31 | N-[3-chloro-4-[4-[(2S,4R)-4-hydroxypyrrolidine-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide; formic acid | 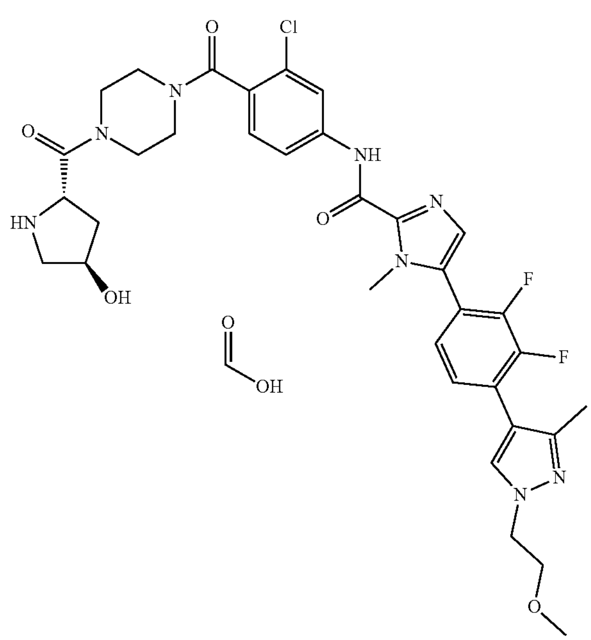 [SMILES: COCCn1cc(-c2ccc(-c3cnc(C(=O)Nc4ccc(C(=O)N5CCN(C(=O)[C@@H]6C[C@@H](O)CN6)CC5)c(Cl)c4)n3C)c(F)c2F)c(C)n1 ; O=CO] | 711.3 | Intermediate I2 and (2S,4R)-1-tert-butoxy-carbonyl-4-hydroxy-pyrrolidine-2-carboxylic acid; HCl |

| Ex# | Name | Structure | MS ESI [M + H]+ | Starting Material |
|---|---|---|---|---|
| Example D32 | N-[3-chloro-4-[4-[2-(dimethylamino)acetyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; 2,2,2-trifluoroacetic acid | 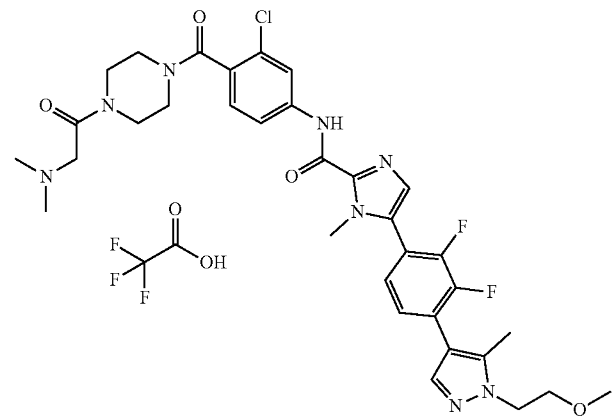 | 683.4 | Intermediate I1 and dimethylglycine |
| Example D33 | N-[3-chloro-4-[[1-[2-(dimethylamino)acetyl]-4-piperidyl]methylcarbamoyl]phenyl]-5-[2,3-difluoro-4-[1-(2-methoxyethyl)-5-methyl-pyrazol-4-yl]phenyl]-1-methyl-imidazole-2-carboxamide; 2,2,2-trifluoroacetic acid | 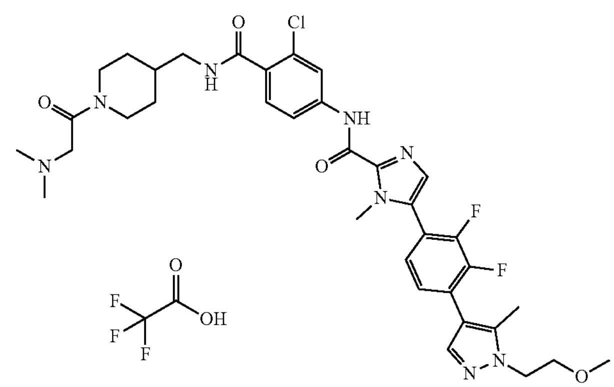 | 711.3 | Intermediate I7 and dimethylglycine |
| Example D34 | N-[3-chloro-4-[4-[2-(dimethylamino)acetyl]piperazine-1-carbonyl]phenyl]-5-[2,3-difluoro-4-(3-methyl-1H-pyrazol-4-yl)phenyl]-1-methyl-imidazole-2-carboxamide; formic acid | 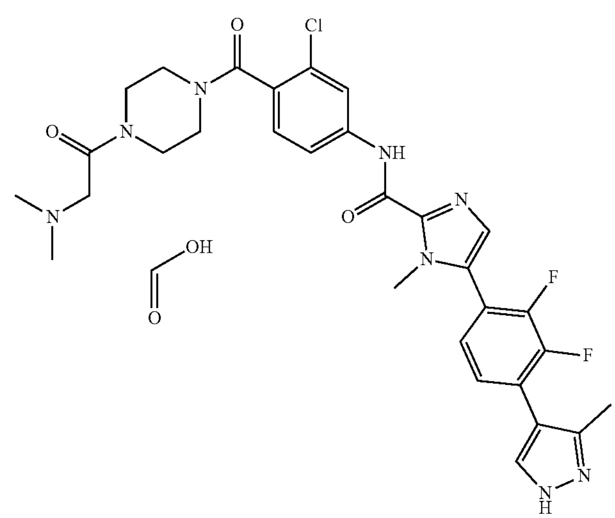 | 625.2 | Intermediate M1 and dimethylglycine |

| Ex# | Name | Structure | MS ESI [M + H]+ | Starting Material |
|---|---|---|---|---|
| Example D36 | N-[3-chloro-4-[4-[(2S,4R)-4-hydroxypyrrolidine-2-carbonyl]piperazine-1-carbonyl]phenyl]-5-[2,3-difluoro-4-(3-methyl-1H-pyrazol-4-yl)phenyl]-1-methyl-imidazole-2-carboxamide | 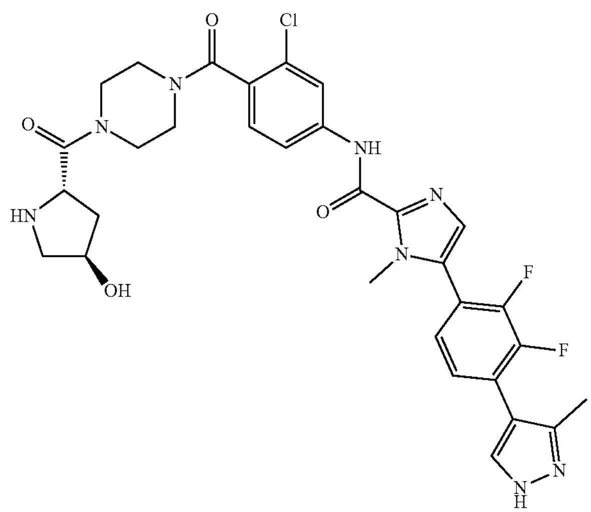 [SMILES: Cc1n[nH]cc1-c1ccc(-c2cnc(C(=O)Nc3ccc(C(=O)N4CCN(C(=O)[C@@H]5C[C@@H](O)CN5)CC4)c(Cl)c3)n2C)c(F)c1F] | 653.2 | Intermediate M1; Intermediate R3, and TFA |
| Example D44 | N-[3-chloro-4-[4-(4-methoxypiperidine-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide | 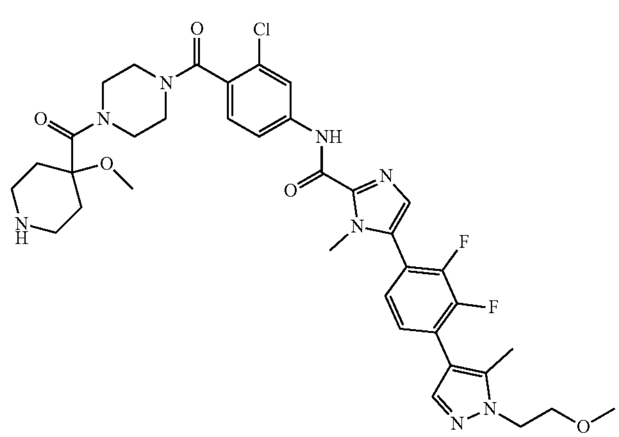 [SMILES: COCCn1ncc(-c2ccc(-c3cnc(C(=O)Nc4ccc(C(=O)N5CCN(C(=O)C6(OC)CCNCC6)CC5)c(Cl)c4)n3C)c(F)c2F)c1C] | 739.2 | Intermediate I1 and 1-(tert-butoxycarbonyl)-4-methoxy-piperidine-4-carboxylic acid and HCl |

Example D43
N-[3-chloro-4-[4-[(2S,4R)-4-hydroxy-1,1-dimethyl-pyrrolidin-1-ium-2-carbonyl]piperazine-1-carbonyl]phenyl]-5-[4-(3,5-dimethyl-1H-pyrazol-4-yl)-2,3-difluoro-phenyl]-1-methyl-imidazole-2-carboxamide; formate
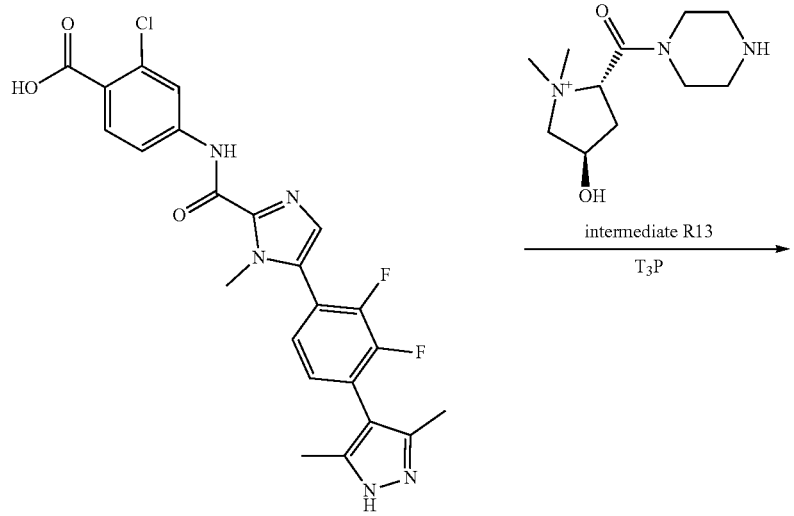
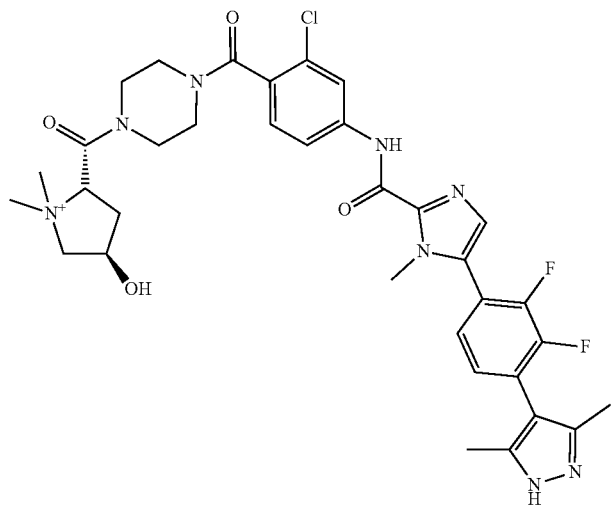

To a mixture of 2-chloro-4-[[5-[4-(3,5-dimethyl-1H-pyrazol-4-yl)-2,3-difluoro-phenyl]-1-methyl-imidazole-2-carbonyl]amino]benzoic acid (105.0 mg, 0.220 mmol) in THF (5 mL) and DMF (5 mL) was added [(2S,4R)-4-hydroxy-1,1-dimethyl-pyrrolidin-1-ium-2-yl]-piperazin-1-yl-methanone (49.34 mg, 0.220 mmol), N,N-diisopropylethylamine (0.4 mL, 2.3 mmol) and propylphosphonic anhydride (438.99 mg, 1.38 mmol). The reaction mixture was stirred at 25° C. for 16 h. The mixture was concentrated to remove solvent, purified by prep-HPLC (0.1% FA)-ACN to afford N-[3-chloro-4-[4-[(2S,4R)-4-hydroxy-1,1-dimethyl-pyrrolidin-1-ium-2-carbonyl]piperazine-1-carbonyl]phenyl]-5-[4-(3,5-dimethyl-1H-pyrazol-4-yl)-2,3-difluoro-phenyl]-1-methyl-imidazole-2-carboxamide; formate (2.5 mg). MS [M]$^+$: 695.3.

Example E1

N-[3-chloro-4-[4-(piperidine-4-carbonyl)piperazine-1-carbonyl]phenyl]-5-[4-[1-(2,2-difluoroethyl)-5-methyl-pyrazol-4-yl]-2,3-difluoro-phenyl]-1-methyl-imidazole-2-carboxamide

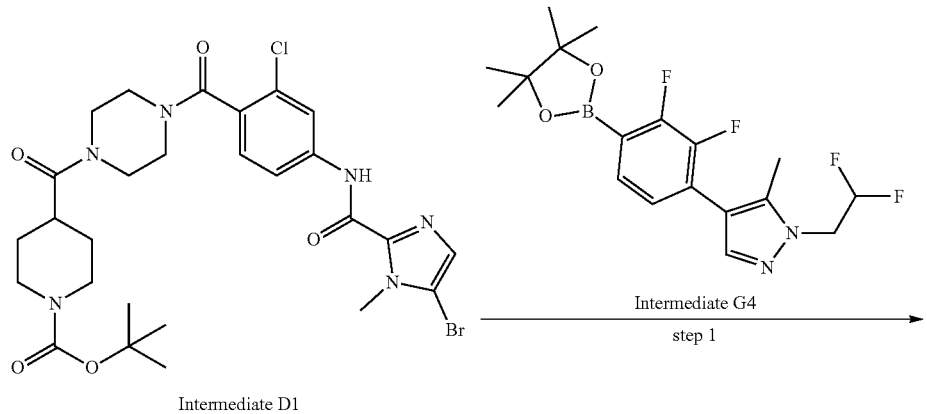

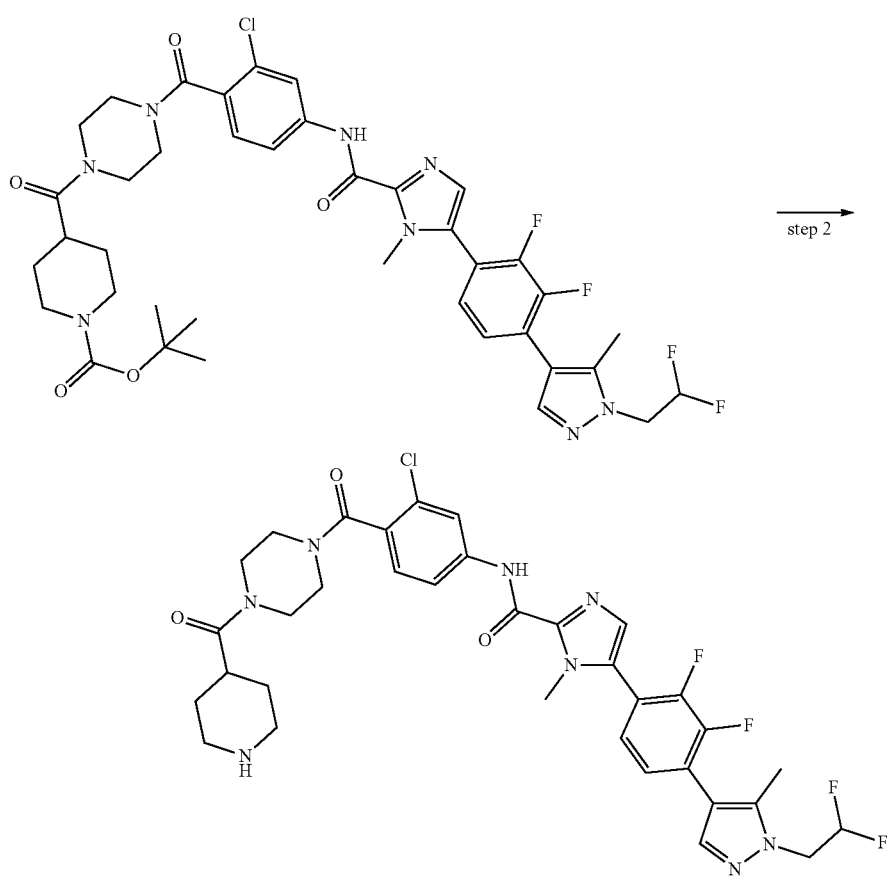

Example E1

Step 1: tert-butyl 4-[4-[2-chloro-4-[[5-[4-[1-(2,2-difluoroethyl)-5-methyl-pyrazol-4-yl]-2,3-difluoro-phenyl]-1-methyl-imidazole-2-carbonyl]amino]benzoyl]piperazine-1-carbonyl]piperidine-1-carboxylate To a 25 mL microwave vial was added tert-butyl 4-[4-[4-[[(5-bromo-1-methyl-imidazole-2-carbonyl)amino]-2-chloro-benzoyl]piperazine-1-carbonyl]piperidine-1-carboxylate (48 mg, 75.2 µmol), 4-(2,3-difluoro-4-(4,4,5,5-tetramethyl-1,3,2-dioxaborolan-2-yl)phenyl)-1-(2,2-difluoroethyl)-5-methyl-1H-pyrazole (31.8 mg, 82.8 µmol), 4-(2,3-difluoro-4-(4,4,5,5-tetramethyl-1,3,2-dioxaborolan-2-yl)phenyl)-1-(2,2-difluoroethyl)-5-methyl-1H-pyrazole (31.8 mg, 82.8 µmol) and Na$_2$CO$_3$ (23.9 mg, 226 µmol) in 1,4-Dioxane (10 mL)/Water (1 mL). The vial was capped and heated in the microwave at 100° C. for 3 h under N$_2$. The crude reaction mixture was concentrated in vacuum. The crude material was purified by flash chromatography to afford tert-butyl 4-[4-[2-chloro-4-[[5-[4-[1-(2,2-difluoroethyl)-5-methyl-pyrazol-4-yl]-2,3-difluoro-phenyl]-1-methyl-imidazole-2-carbonyl]amino]benzoyl]piperazine-1-carbonyl]piperidine-1-carboxylate (26 mg). MS [M−100]$^+$: 715.2.

Step 2: N-[3-chloro-4-[4-(piperidine-4-carbonyl)piperazine-1-carbonyl]phenyl]-5-[4-[1-(2,2-difluoroethyl)-5-methyl-pyrazol-4-yl]-2,3-difluoro-phenyl]-1-methyl-imidazole-2-carboxamide In a 50 mL round-bottomed flask, tert-butyl 4-(4-(2-chloro-4-(5-(4-(7-(2,2-difluoroethyl)-5-methyl-1H-pyrazol-4-yl)-2,3-difluorophenyl)-1-methyl-1H-imidazole-2-carboxamido)benzoyl)piperazine-1-carbonyl)piperidine-1-carboxylate (26 mg, 31.9 µmol) was combined with THF (2 mL) to give a light brown solution. HCl water solution (797 µL, 9.57 mmol) was added. The reaction was stirred at room temperature for 1 h. The crude reaction mixture was concentrated in vacuum. The crude material was purified by preparative HPLC to afford N-[3-chloro-4-[4-(piperidine-4-carbonyl)piperazine-1-carbonyl]phenyl]-5-[4-[1-(2,2-difluoroethyl)-5-methyl-pyrazol-4-yl]-2,3-difluoro-phenyl]-1-methyl-imidazole-2-carboxamide (1.4 mg). MS [M+H]$^+$: 715.4.

The following examples were prepared in analogy to Examples E1.

| Ex# | Name | Structure | MS ESI [M + H]$^+$ | Starting Material |
|---|---|---|---|---|
| Example E2 | N-[3-chloro-4-[4-[2-[(3S)-pyrrolidin-3-yl]acetyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; formic acid | 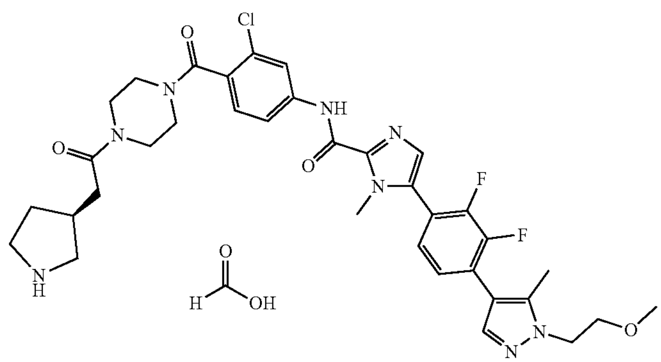 [SMILES: COCCn1ncc(-c2ccc(-c3cnc(C(=O)Nc4ccc(C(=O)N5CCN(C(=O)C[C@@H]6CCNC6)CC5)c(Cl)c4)n3C)c(F)c2F)c1C ; O=CO] | 709.3 | Intermediate D2; Intermediate G3 and HCl |
| Example E3 | N-[3-chloro-4-[4-(piperidine-4-carbonyl)piperazine-1-carbonyl]phenyl]-5-[2-fluoro-4-[1-(2-methoxyethyl)-5-methyl-pyrazol-4-yl]-3-methyl-phenyl]-1-methyl-imidazole-2-carboxamide; formic acid | 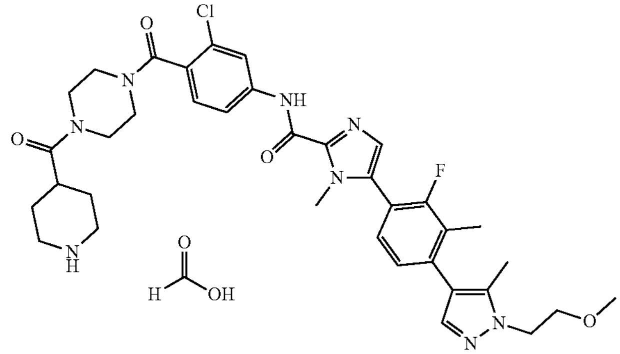 [SMILES: COCCn1ncc(-c2ccc(-c3cnc(C(=O)Nc4ccc(C(=O)N5CCN(C(=O)C6CCNCC6)CC5)c(Cl)c4)n3C)c(F)c2C)c1C ; O=CO] | 705.4 | Intermediate D1; Intermediate G10 and HCl |

-continued

| Ex# | Name | Structure | MS ESI [M + H]+ | Starting Material |
|---|---|---|---|---|
| Example E4 | 5-[2-chloro-3-fluoro-4-[1-(2-methoxyethyl)-5-methyl-pyrazol-4-yl]phenyl]-N-[3-chloro-4-[4-(piperidine-4-carbonyl)piperazine-1-carbonyl]phenyl]-1-methyl-imidazole-2-carboxamide; formic acid | 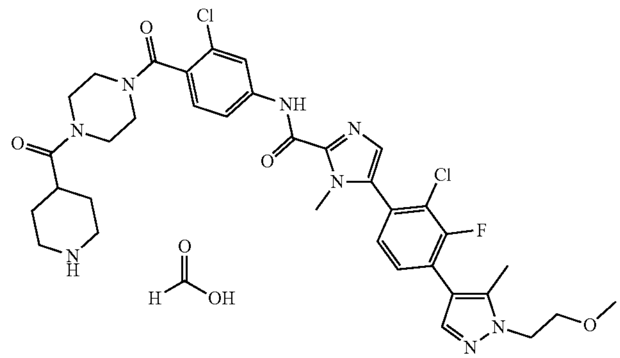 [SMILES: COCCn1ncc(-c2ccc(-c3cnc(C(=O)Nc4ccc(C(=O)N5CCN(C(=O)C6CCNCC6)CC5)c(Cl)c4)n3C)c(Cl)c2F)c1C ; O=CO] | 725.2 | Intermediate D1; Intermediate G11 and HCl |
| Example E5 | N-[3-chloro-4-[4-(piperidine-4-carbonyl)piperazine-1-carbonyl]phenyl]-5-[3-fluoro-4-[1-(2-methoxyethyl)-5-methyl-pyrazol-4-yl]-2-methyl-phenyl]-1-methyl-imidazole-2-carboxamide; formic acid | 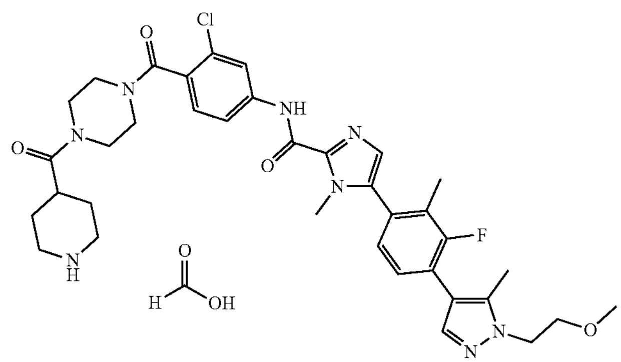 [SMILES: COCCn1ncc(-c2ccc(-c3cnc(C(=O)Nc4ccc(C(=O)N5CCN(C(=O)C6CCNCC6)CC5)c(Cl)c4)n3C)c(C)c2F)c1C ; O=CO] | 705.4 | Intermediate D1; Intermediate G13 and HCl |
| Example E6 | N-[3-chloro-4-[4-(piperidine-4-carbonyl)piperazine-1-carbonyl]phenyl]-5-[4-[1-[2-(difluoromethoxy)ethyl]-3-(trifluoromethyl)pyrazol-4-yl]-2,3-difluoro-phenyl]-1-methyl-imidazole-2-carboxamide; formic acid | 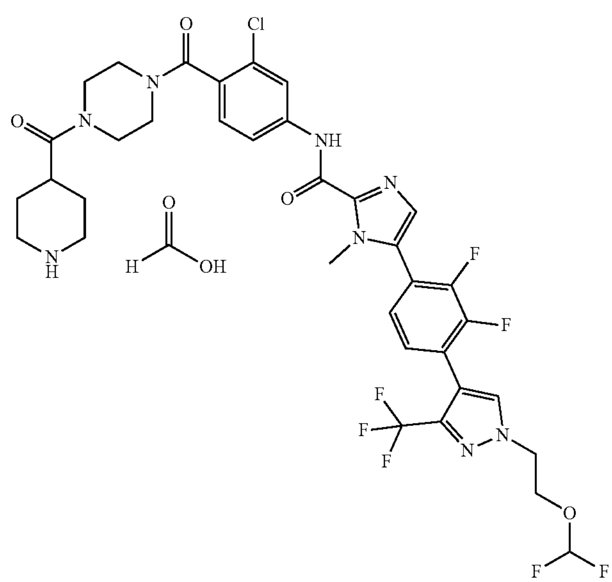 [SMILES: Cn1c(-c2ccc(-c3cn(CCOC(F)F)nc3C(F)(F)F)c(F)c2F)cnc1C(=O)Nc1ccc(C(=O)N2CCN(C(=O)C3CCNCC3)CC2)c(Cl)c1 ; O=CO] | 799.2 | Intermediate D1; Intermediate G46 and TFA |

-continued

| Ex# | Name | Structure | MS ESI [M + H]+ | Starting Material |
|---|---|---|---|---|
| Example E7 | N-[3-chloro-4-(piperazine-1-carbonyl)phenyl]-5-[2,3-difluoro-4-[1-(2-methoxyethyl)-5-methyl-pyrazol-4-yl]phenyl]-1-methyl-imidazole-2-carboxamide; 2,2,2-trifluoroacetic acid | 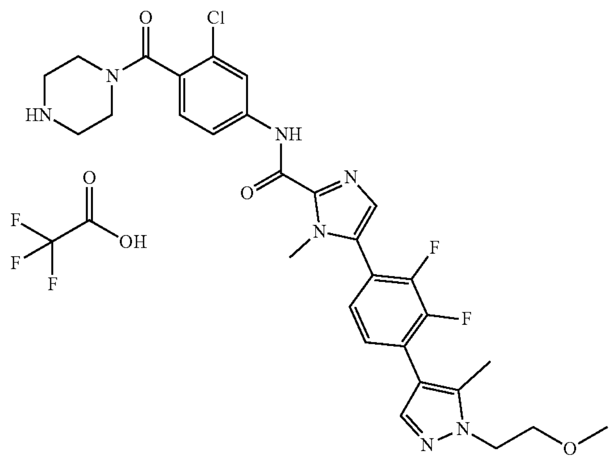 | 598.4 | Intermediate B1; Intermediate G3 and HCl |
| Example E8 | 5-[2,3-difluoro-4-[1-(2-methoxyethyl)-5-methyl-pyrazol-4-yl]phenyl]-N-[4-[4-[(2S,4R)-4-hydroxypyrrolidine-2-carbonyl]piperazine-1-carbonyl]-3-methyl-phenyl]-1-methyl-imidazole-2-carboxamide | 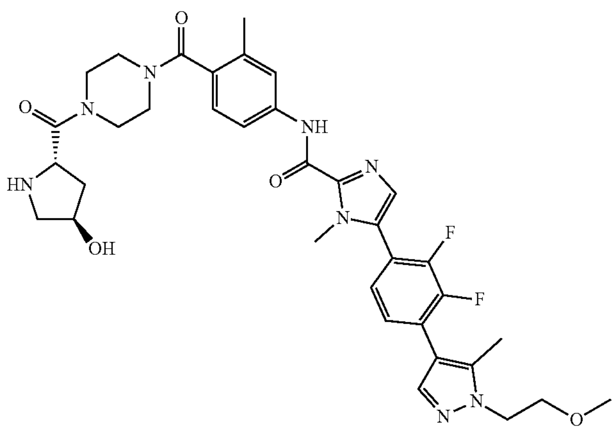 [SMILES: COCCn1ncc(-c2ccc(-c3cnc(C(=O)Nc4ccc(C(=O)N5CCN(C(=O)[C@@H]6C[C@@H](O)CN6)CC5)c(C)c4)n3C)c(F)c2F)c1C] | 691.4 | Intermediate D4; Intermediate G3 and HCl |
| Example E9 | N-[3-chloro-4-[4-[(2S,4R)-4-hydroxypyrrolidine-2-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; 2,2,2-trifluoroacetic acid | 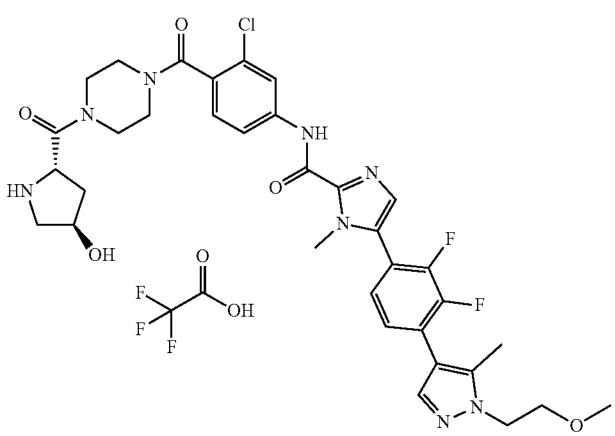 [SMILES: COCCn1ncc(-c2ccc(-c3cnc(C(=O)Nc4ccc(C(=O)N5CCN(C(=O)[C@@H]6C[C@@H](O)CN6)CC5)c(Cl)c4)n3C)c(F)c2F)c1C ; O=C(O)C(F)(F)F] | 711.3 | Intermediate D6; Intermediate G3 and HCl |

| Ex# | Name | Structure | MS ESI [M + H]+ | Starting Material |
|---|---|---|---|---|
| Example E10 | N-[3-chloro-4-(4-piperidylmethyl-carbamoyl)phenyl]-5-[2,3-difluoro-4-[1-(2-methoxyethyl)-5-methyl-pyrazol-4-yl]phenyl]-1-methyl-imidazole-2-carboxamide; 2,2,2-trifluoroacetic acid | 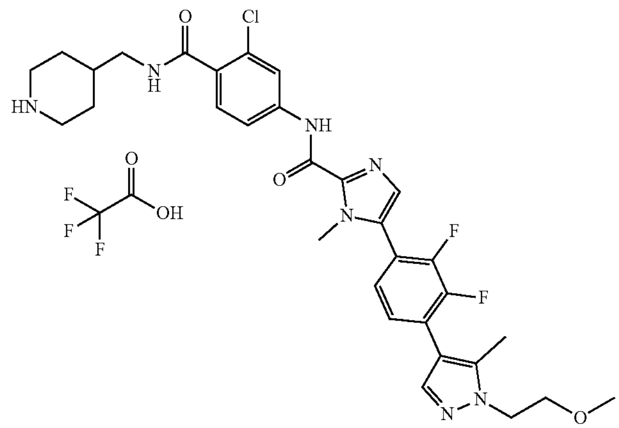 [SMILES: COCCn1ncc(-c2ccc(-c3cnc(C(=O)Nc4ccc(C(=O)NCC5CCNCC5)c(Cl)c4)n3C)c(F)c2F)c1C ; O=C(O)C(F)(F)F] | 626.4 | Intermediate B5; Intermediate G3 and HCl |
| Example E11 | N-[3-chloro-4-[4-(piperidine-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; 2,2,2-trifluoroacetic acid | 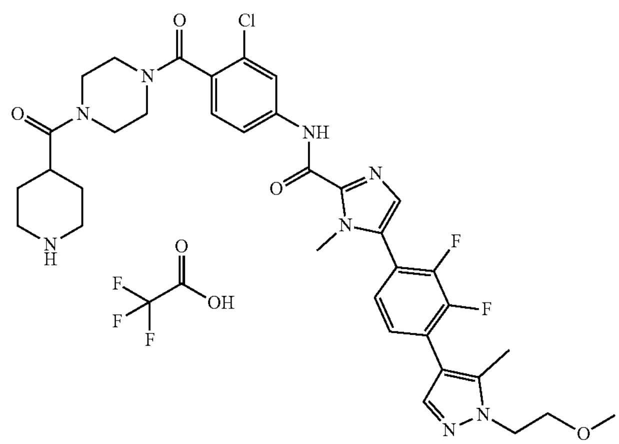 [SMILES: COCCn1ncc(-c2ccc(-c3cnc(C(=O)Nc4ccc(C(=O)N5CCN(C(=O)C6CCNCC6)CC5)c(Cl)c4)n3C)c(F)c2F)c1C ; O=C(O)C(F)(F)F] | 709.3 | Intermediate D1; Intermediate G3 and HCl |
| Example E12 | N-[4-[4-[1-(2-amino-2-oxo-ethyl)piperidine-4-carbonyl]piperazine-1-carbonyl]-3-chloro-phenyl]-5-[3-fluoro-4-[3-(trifluoromethyl)-1H-pyrazol-4-yl]phenyl]-1-methyl-imidazole-2-carboxamide; 2,2,2-trifluoroacetic acid | 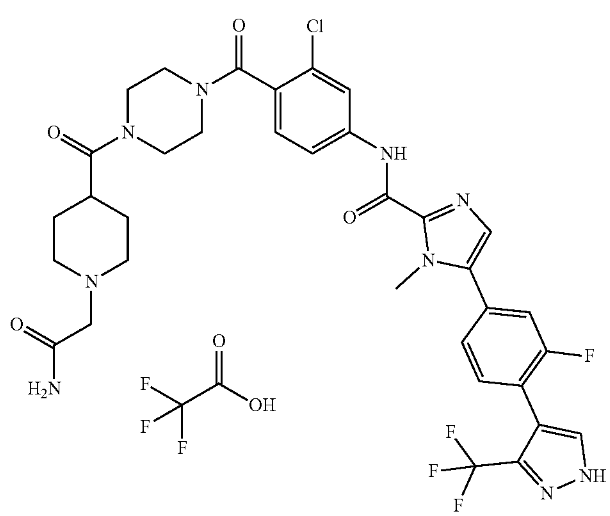 [SMILES: Cn1c(-c2ccc(-c3c[nH]nc3C(F)(F)F)c(F)c2)cnc1C(=O)Nc1ccc(C(=O)N2CCN(C(=O)C3CCN(CC(N)=O)CC3)CC2)c(Cl)c1 ; O=C(O)C(F)(F)F] | 744.2 | Intermediate G46; Intermediate P1 and HCl |

-continued

| Ex# | Name | Structure | MS ESI [M + H]+ | Starting Material |
|---|---|---|---|---|
| Example E13 | N-[3-chloro-4-[4-(piperidine-4-carbonyl)piperazine-1-carbonyl]phenyl]-5-[2,3-difluoro-4-[1-(2-methoxyethyl)-5-(methoxymethyl)pyrazol-4-yl]phenyl]-1-methyl-imidazole-2-carboxamide; formic acid | 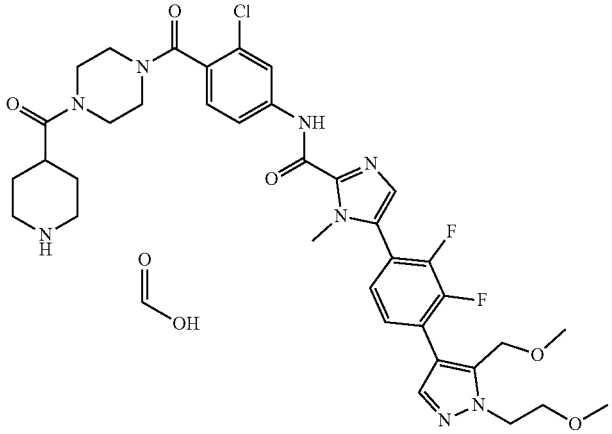 [SMILES: COCCn1ncc(-c2ccc(-c3cnc(C(=O)Nc4ccc(C(=O)N5CCN(C(=O)C6CCNCC6)CC5)c(Cl)c4)n3C)c(F)c2F)c1COC ; O=CO] | 739.3 | Intermediate D1; Intermediate G25 and HCl |
| Example E14 | N-[4-[4-[2-(dimethylamino)acetyl]piperazine-1-carbonyl]-3-methyl-phenyl]-5-[4-[1-(2-methoxyethyl)-5-methyl-pyrazol-4-yl]phenyl]-1-methyl-imidazole-2-carboxamide | 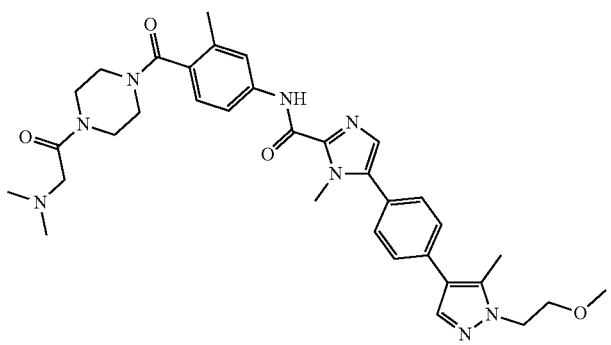 | 627.4 | Intermediate D5; Intermediate G12 |
| Example E15 | N-[3-chloro-4-[4-[2-(dimethylamino)acetyl]piperazine-1-carbonyl]phenyl]-1-methyl-5-[4-(3-methyl-1H-pyrazol-4-yl)phenyl]imidazole-2-carboxamide; formic acid | 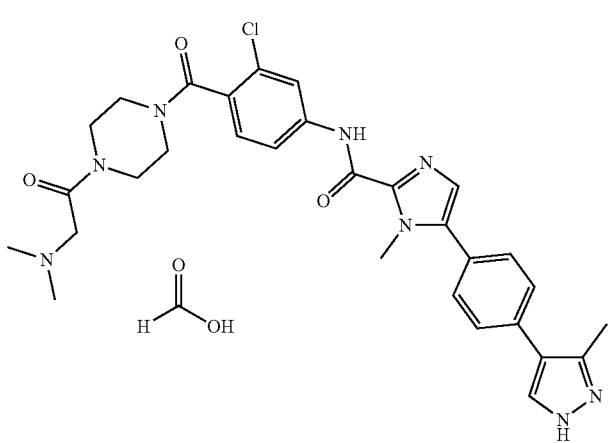 | 589.4 | Intermediate J1; TFA |

| Ex# | Name | Structure | MS ESI [M + H]+ | Starting Material |
|---|---|---|---|---|
| Example E16 | N-[3-chloro-4-[4-[2-(dimethylamino)acetyl]piperazine-1-carbonyl]phenyl]-5-[4-(3,5-dimethyl-1H-pyrazol-4-yl)phenyl]-1-methyl-imidazole-2-carboxamide | 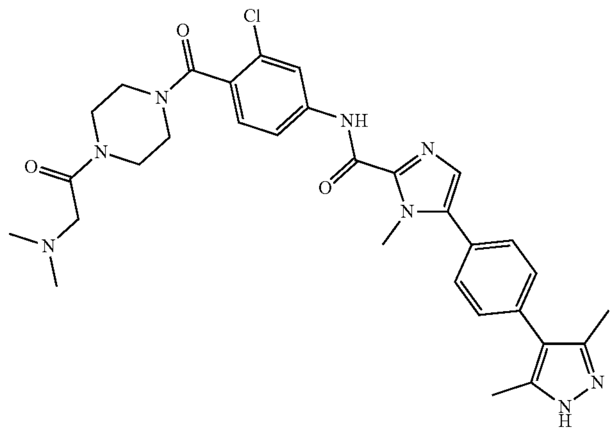 | 603.4 | Intermediate J2 and TFA |
| Example E17 | N-[3-chloro-4-[4-(piperidine-4-carbonyl)piperazine-1-carbonyl]phenyl]-5-[2-fluoro-6-[5-(4-methoxyphenyl)-1H-pyrazol-4-yl]-3-pyridyl]-1-methyl-imidazole-2-carboxamide; formic acid | 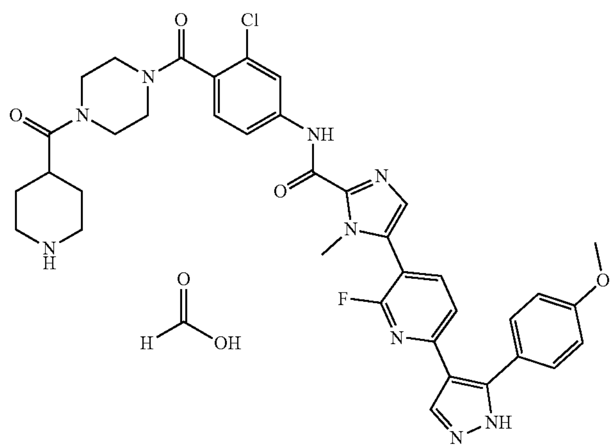 [SMILES: COc1ccc(-c2[nH]ncc2-c2ccc(-c3cnc(C(=O)Nc4ccc(C(=O)N5CCN(C(=O)C6CCNCC6)CC5)c(Cl)c4)n3C)c(F)n2)cc1 ; O=CO] | 726.3 | Intermediate D1 and Intermediate G75; HCl |
| Example E18 | N-[3-chloro-4-[4-(piperidine-4-carbonyl)piperazine-1-carbonyl]phenyl]-5-[2-fluoro-6-(1H-pyrazol-4-yl)-3-pyridyl]-1-methyl-imidazole-2-carboxamide | 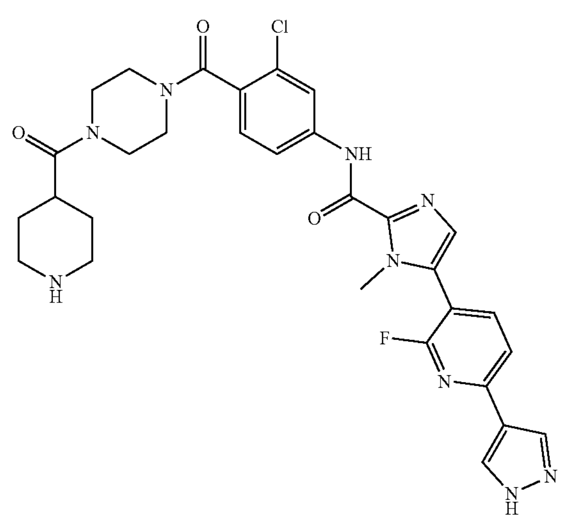 [SMILES: Cn1c(-c2ccc(-c3cn[nH]c3)nc2F)cnc1C(=O)Nc1ccc(C(=O)N2CCN(C(=O)C3CCNCC3)CC2)c(Cl)c1] | 620.2 | Intermediate D1 and Intermediate G81; HCl |

-continued

| Ex# | Name | Structure | MS ESI [M + H]+ | Starting Material |
|---|---|---|---|---|
| Example E19 | N-[3-chloro-4-[4-(piperidine-4-carbonyl)piperazine-1-carbonyl]phenyl]-5-[2,3-difluoro-4-(3-methyl-1H-pyrazol-4-yl)phenyl]-1-methyl-imidazole-2-carboxamide | 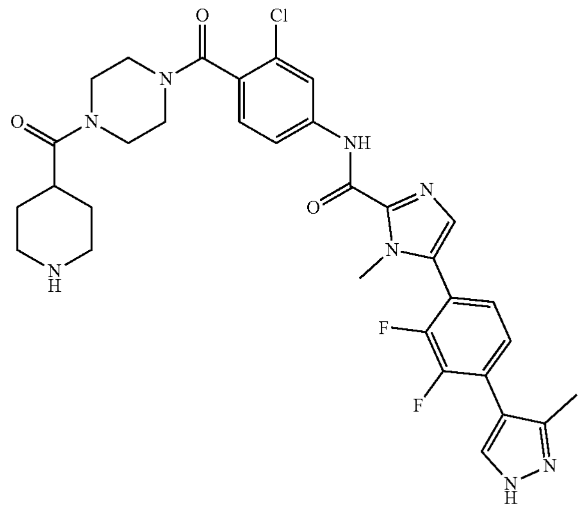 [SMILES: Cc1n[nH]cc1-c1ccc(-c2cnc(C(=O)Nc3ccc(C(=O)N4CCN(C(=O)C5CCNCC5)CC4)c(Cl)c3)n2C)c(F)c1F] | 651.1 | Intermediate D1 and Intermediate G1; HCl |
| Example E20 | N-[3-chloro-4-[4-(piperidine-4-carbonyl)piperazine-1-carbonyl]phenyl]-5-[2,3-difluoro-4-(1-methyl-pyrazol-4-yl)phenyl]-1-methyl-imidazole-2-carboxamide | 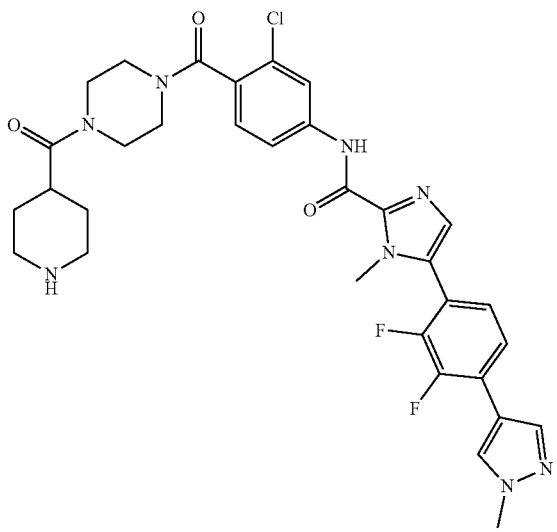 [SMILES: Cn1cc(-c2ccc(-c3cnc(C(=O)Nc4ccc(C(=O)N5CCN(C(=O)C6CCNCC6)CC5)c(Cl)c4)n3C)c(F)c2F)cn1] | 651.1 | Intermediate D1 and Intermediate G82; HCl |

-continued

| Ex# | Name | Structure | MS ESI [M + H]+ | Starting Material |
|---|---|---|---|---|
| Example E21 | N-[3-chloro-4-[4-(piperidine-4-carbonyl)piperazine-1-carbonyl]phenyl]-5-[2,3-difluoro-4-[1-(2-methoxyethyl)pyrazol-4-yl]phenyl]-1-methyl-imidazole-2-carboxamide | 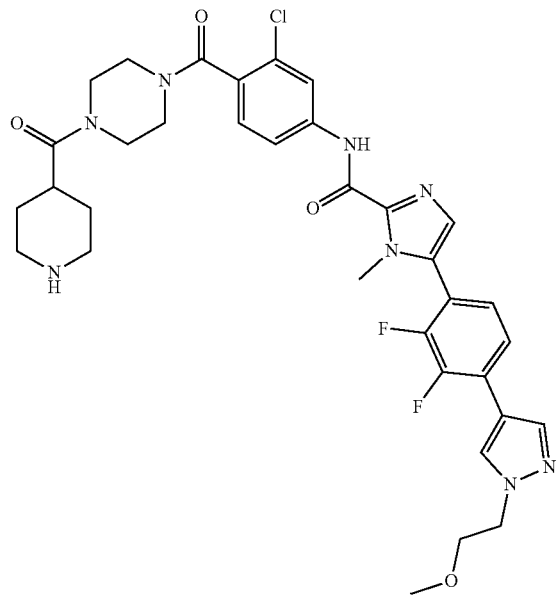 [SMILES: COCCn1cc(-c2ccc(-c3cnc(C(=O)Nc4ccc(C(=O)N5CCN(C(=O)C6CCNCC6)CC5)c(Cl)c4)n3C)c(F)c2F)cn1] | 695.2 | Intermediate D1 and Intermediate G83; HCl |
| Example E22 | (1S,5R)-6-[[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]amino]-N-[(3R,4R)-4-hydroxypyrrolidin-3-yl]-3-azabicyclo[3.1.0]hexane-3-carboxamide | 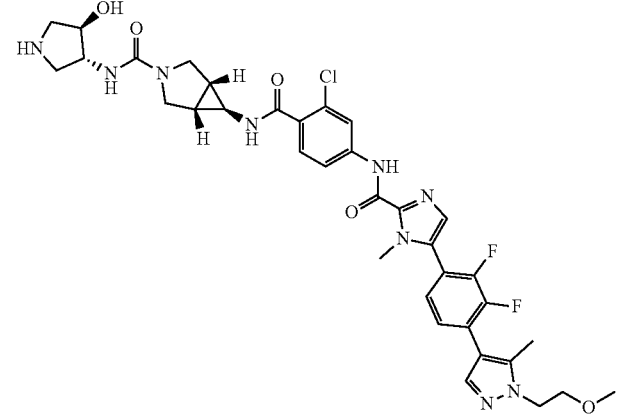 [SMILES: COCCn1ncc(-c2ccc(-c3cnc(C(=O)Nc4ccc(C(=O)N[C@H]5[C@@H]6CN(C(=O)N[C@@H]7CNC[C@H]7O)C[C@@H]65)c(Cl)c4)n3C)c(F)c2F)c1C] | 738.2 | Intermediate D11 and Intermediate G3; HCl |
| Example E23 | N-[3-chloro-4-[4-(piperidine-4-carbonyl)piperazine-1-carbonyl]phenyl]-1-methyl-5-[4-(1H-pyrazol-4-yl)phenyl]imidazole-2-carboxamide | 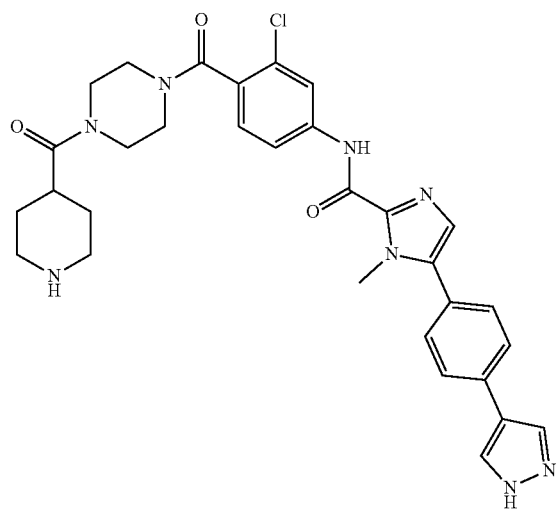 [SMILES: Cn1c(-c2ccc(-c3cn[nH]c3)cc2)cnc1C(=O)Nc1ccc(C(=O)N2CCN(C(=O)C3CCNCC3)CC2)c(Cl)c1] | 601.2 | Intermediate D1 and Intermediate G90; HCl |

Example F1
5-[4-[1-(3-amino-3-oxo-propyl)-3-(trifluoromethyl)pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide; formate
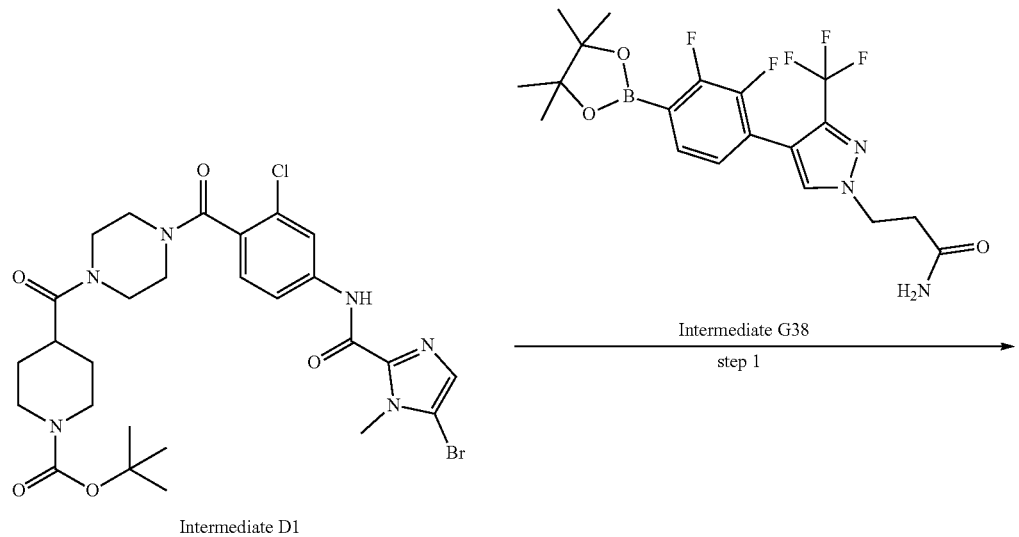
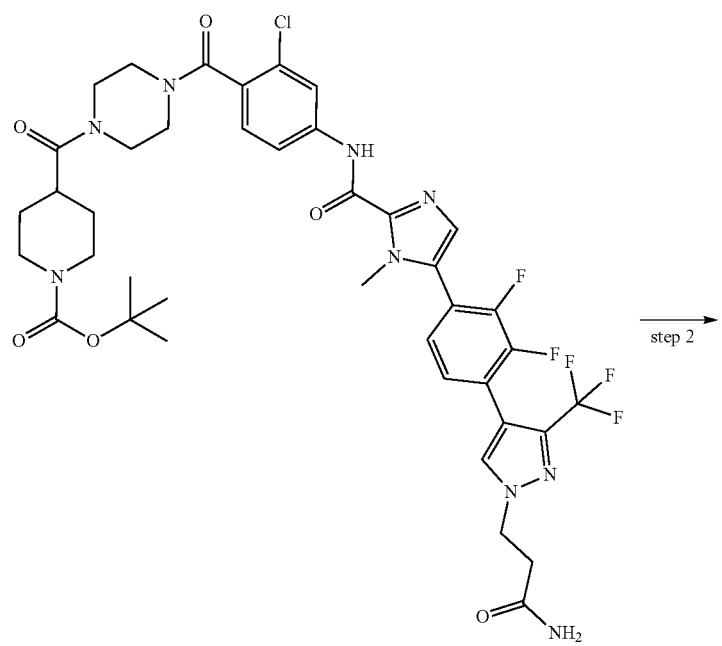

411

412

-continued

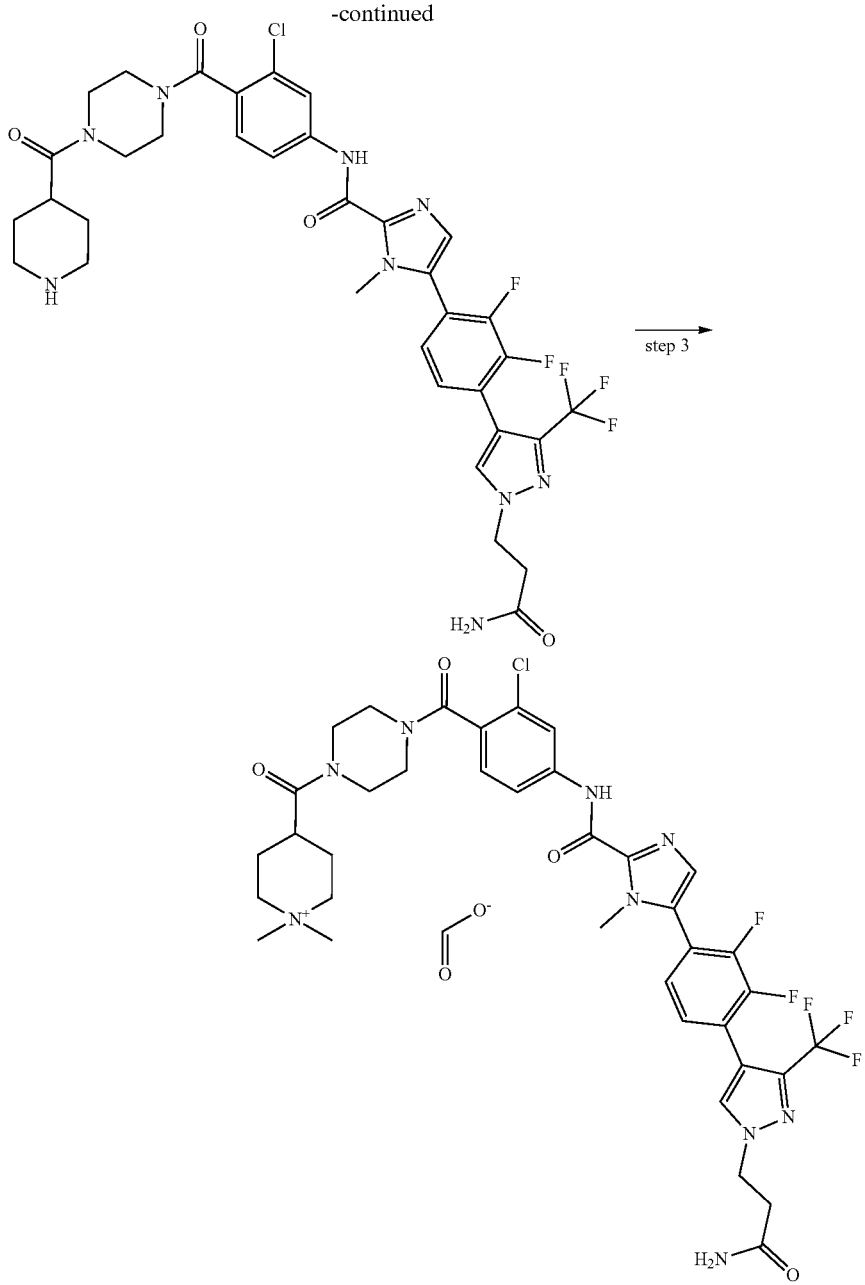

Example F1

Step 1: tert-butyl 4-[4-[4-[[5-[4-[1-(3-amino-3-oxo-propyl)-3-(trifluoromethyl)pyrazol-4-yl]-2,3-difluoro-phenyl]-1-methyl-imidazole-2-carbonyl]amino]-2-chloro-benzoyl]piperazine-1-carbonyl]piperidine-1-carboxylate 3-(4-(2,3-difluoro-4-(4,4,5,5-tetramethyl-1,3,2-dioxaborolan-2-yl)phenyl)-3-(trifluoromethyl)-1H-pyrazol-1-yl)propanamide (100 mg, 225 µmol), tert-butyl 4-(4-(4-(5-bromo-1-methyl-1H-imidazole-2-carboxamido)-2-chlorobenzoyl)piperazine-1-carbonyl)piperidine-1-carboxylate (129 mg, 202 µmol), sodium carbonate (71.4 mg, 674 µmol) and Pd-118 (29.3 mg, 44.9 µmol) were placed in water (408 µL) and dioxane (4.08 ml) in microwave tube. The tube was evacuated and backfilled with argon for 5 times. The mixture was then heated at 100° C. for 1 h. The mixture was cooled to room temperature, 100-200 mesh silica gel was added to absorb the material. The loaded sample was purified by flash chromatography to afford the product (98 mg). MS [M+H]$^+$: 876.3.

Step 2: 5-[4-[1-(3-amino-3-oxo-propyl)-3-(trifluoromethyl)pyrazol-4-yl]-2,3-difluoro-phenyl]-N-[3-chloro-4-[4-(piperidine-4-carbonyl)piperazine-1-carbonyl]phenyl]-1-methyl-imidazole-2-carboxamide tert-butyl 4-(4-(4-(5-(4-(1-(3-amino-3-oxopropyl)-3-(trifluoromethyl)-1H-pyrazol-4-yl)-2,3-difluorophenyl)-1-methyl-1H-imidazole-2-carboxamido)-2-chlorobenzoyl)

piperazine-1-carbonyl)piperidine-1-carboxylate (98 mg, 112 μmol) was dissolved in 2 mL 20% TFA/DCM solution and the resulting solution was stirred for 1 h at room temperature. After completion, the solvent was removed in vacuo to afford the product which was used without purification (70 mg). MS [M+H]⁺: 776.2.

Step 3: 5-[4-[1-(3-amino-3-oxo-propyl)-3-(trifluoromethyl)pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;formate 5-[4-[1-(3-amino-3-oxo-propyl)-3-(trifluoromethyl)pyrazol-4-yl]-2,3-difluoro-phenyl]-N-[3-chloro-4-[4-(piperidine-4-carbonyl)piperazine-1-carbonyl]phenyl]-1-methyl-imidazole-2-carboxamide (70 mg) was dissolved in DMA (2.24 mL), to this solution was added N-ethyl-N-isopropylpropan-2-amine (72.3 mg, 559 μmol) and iodomethane (31.7 mg, 224 μmol). The solution was stirred at rt for 2 h. After completion, the product was purified by preparative HPLC directly to afford the product (28.9 mg). MS [M]⁺: 804.3.

The following examples were prepared in analogy to Example F1.

| Ex# | Name | Structure | MS ESI [M]⁺ | Starting Material |
|---|---|---|---|---|
| Example F2 | N-[3-chloro-4-[4-(1,1-dimethylpiperidin-1-ium-4-carbonyl)piperazine-1-carbonyl]phenyl]-5-[2-chloro-3-fluoro-4-[1-(2-methoxyethyl)-5-methyl-pyrazol-4-yl]phenyl]-1-methyl-imidazole-2-carboxamide; formate | 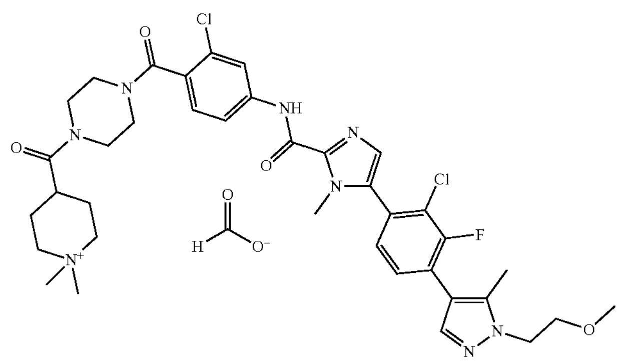 | 753.3 | Intermediate D1 and Intermediate G11; HCl; iodomethane. |
| Example F3 | N-[3-chloro-4-[4-(1,1-dimethylpiperidin-1-ium-4-carbonyl)piperazine-1-carbonyl]phenyl]-5-[3-fluoro-4-[1-(2-methoxyethyl)-5-methyl-pyrazol-4-yl]-2-methyl-phenyl]-1-methyl-imidazole-2-carboxamide; formate | 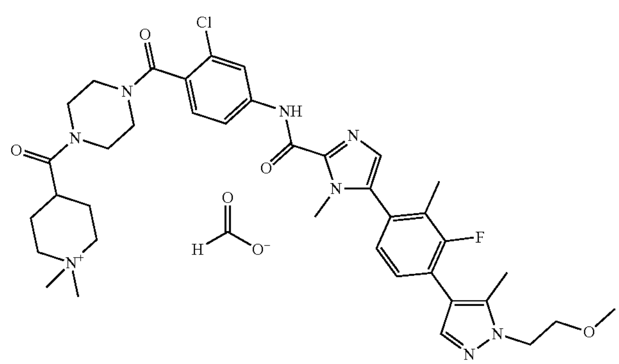 | 733.4 | Intermediate D1 and Intermediate G13; HCl; iodomethane. |

-continued

| Ex# | Name | Structure | MS ESI [M]+ | Starting Material |
|---|---|---|---|---|
| Example F4 | N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(3-hydroxy-3-methyl-butyl)-5-methyl-pyrazol-4-yl]phenyl]-1-methyl-imidazole-2-carboxamide; formate | 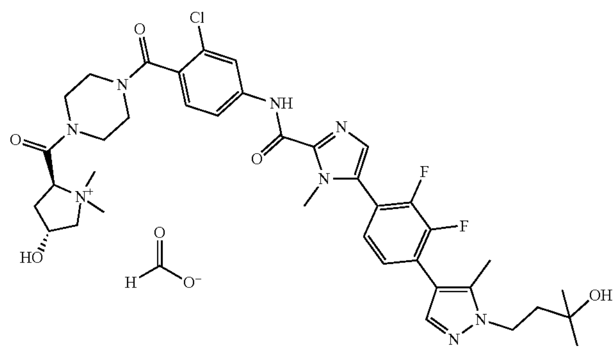 | 767.3 | Intermediate D6 and Intermediate G14; HCl; iodomethane. |
| Example F5 | N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[3-methyl-1-[2-(methylamino)-2-oxo-ethyl]pyrazol-4-yl]phenyl]-1-methyl-imidazole-2-carboxamide; formate | 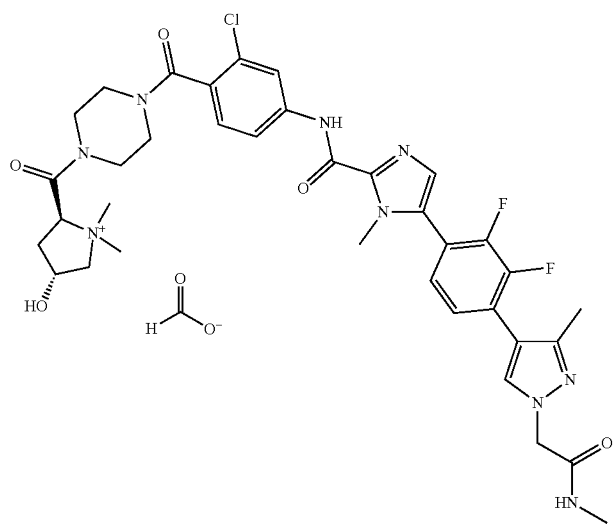 | 752.3 | Intermediate D6 and Intermediate G15; HCl; iodomethane. |
| Example F6 | N-[3-chloro-4-[4-(1,1-dimethylpiperidin-1-ium-4-carbonyl)piperazine-1-carbonyl]phenyl]-5-[4-[1-[2-(difluoromethoxy)ethyl]-3-(trifluoromethyl)pyrazol-4-yl]-2,3-difluoro-phenyl]-1-methyl-imidazole-2-carboxamide; formate | 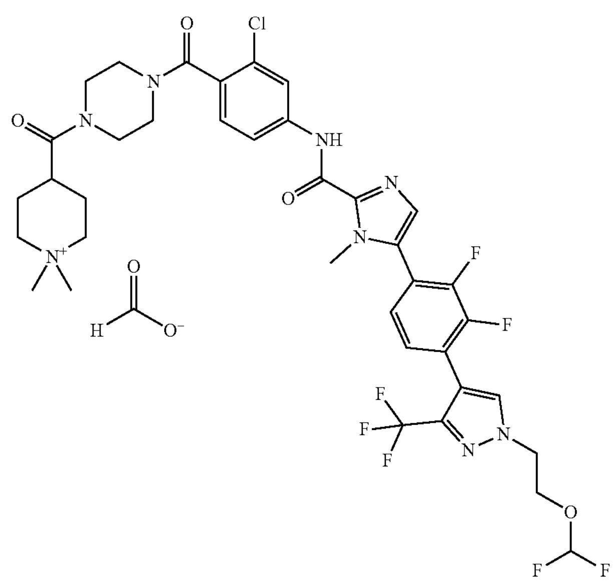 | 827.2 | Intermediate D1 and Intermediate G48; TFA; iodomethane. |

| Ex# | Name | Structure | MS ESI [M]+ | Starting Material |
|---|---|---|---|---|
| Example F7 | N-[3-chloro-4-[4-(1,1-dimethylpiperidin-1-ium-4-carbonyl)piperazine-1-carbonyl]phenyl]-5-[2,3-difluoro-4-[1-(3-hydroxy-2-methyl-propyl)-3-(trifluoro-methyl)pyrazol-4-yl]phenyl]-1-methyl-imidazole-2-carboxamide; formate | 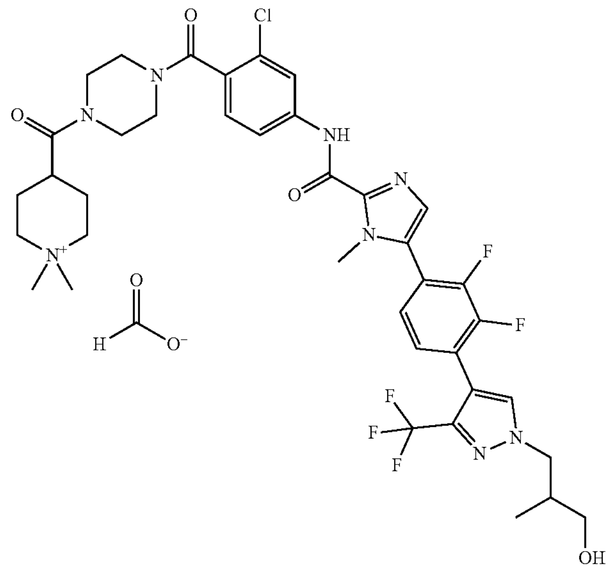 | 805.3 | Intermediate D1 and Intermediate G49; TFA; iodomethane. |
| Example F8 | N-[3-chloro-4-[4-(1,1-dimethylpiperidin-1-ium-4-carbonyl)piperazine-1-carbonyl]phenyl]-5-[4-[1-[(2S)-2,3-dihydroxypropyl]-3-(trifluoro-methyl)pyrazol-4-yl]-2,3-difluoro-phenyl]-1-methyl-imidazole-2-carboxamide; formate | 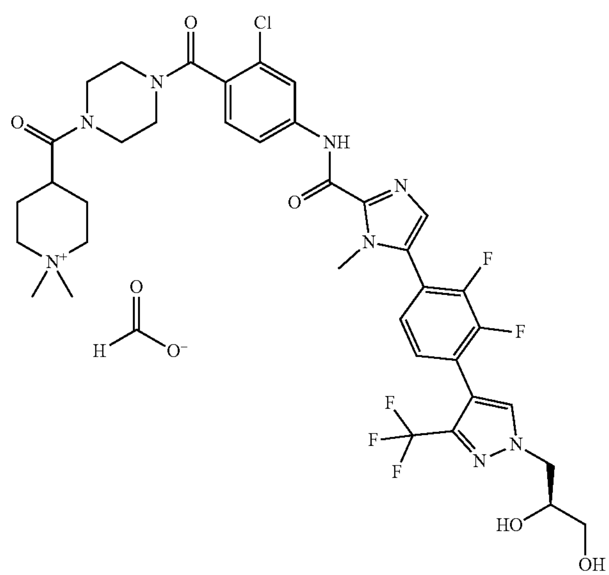 | 807.3 | Intermediate D1 and Intermediate G45; HCl; iodomethane. |

| Ex# | Name | Structure | MS ESI [M]+ | Starting Material |
|---|---|---|---|---|
| Example F9 | N-[3-chloro-4-[4-[(2S,4R)-4-hydroxy-1,1-dimethyl-pyrrolidin-1-ium-2-carbonyl]piperazine-1-carbonyl]phenyl]-5-[4-[1-[2-(difluoro-methoxy)ethyl]-3-methyl-pyrazol-4-yl]-2,3-difluoro-phenyl]-1-methyl-imidazole-2-carboxamide; formate | 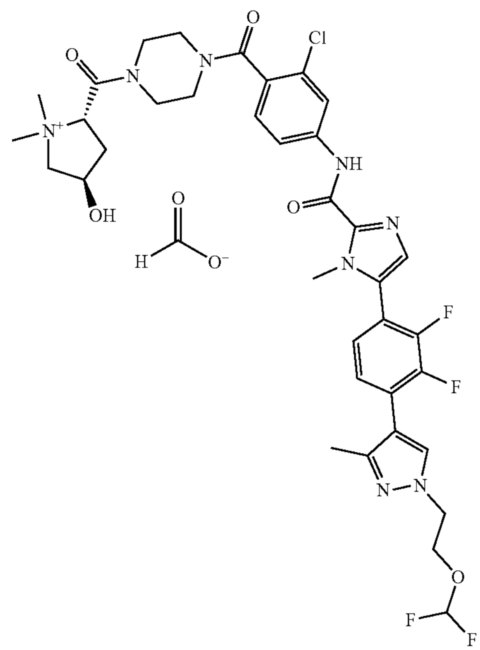 | 775.3 | Intermediate D6 and Intermediate G33; HCl; iodomethane. |
| Example F10 | N-[3-chloro-4-[4-[(2S,4R)-4-hydroxy-1,1-dimethyl-pyrrolidin-1-ium-2-carbonyl]piperazine-1-carbonyl]phenyl]-5-[4-[1-[2-(difluoro-methoxy)ethyl]-5-methyl-pyrazol-4-yl]-2,3-difluoro-phenyl]-1-methyl-imidazole-2-carboxamide; formate | 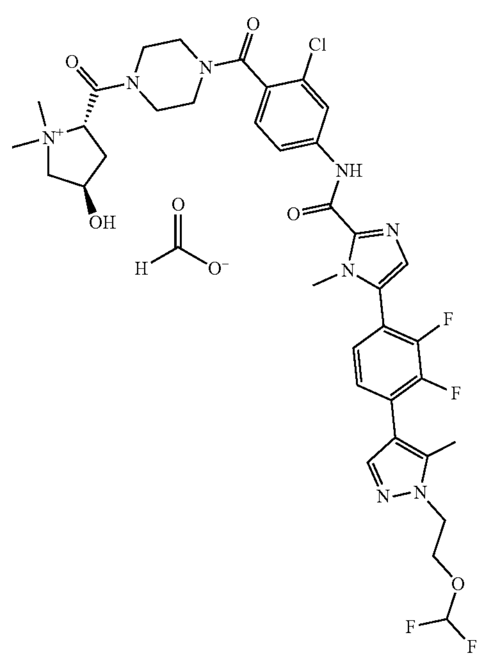 | 775.3 | Intermediate D6 and Intermediate G34; HCl; iodomethane. |

-continued

| Ex# | Name | Structure | MS ESI [M]+ | Starting Material |
|---|---|---|---|---|
| Example F11 | N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[3-isopropyl-1-(2-methoxyethyl)pyrazol-4-yl]phenyl]-1-methyl-imidazole-2-carboxamide; formate | 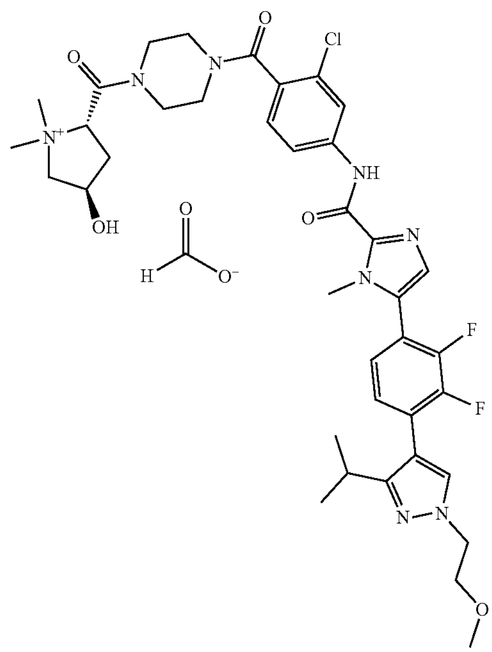 | 767.3 | Intermediate D6 and Intermediate G35; HCl; iodomethane. |
| Example F12 | N-[3-chloro-4-[4-[(2S,4R)-4-hydroxy-1,1-dimethyl-pyrrolidin-1-ium-2-carbonyl]piperazine-1-carbonyl]phenyl]-5-[4-[5-(difluoromethyl)-1-(2-methoxyethyl)pyrazol-4-yl]-2,3-difluoro-phenyl]-1-methyl-imidazole-2-carboxamide; formate | 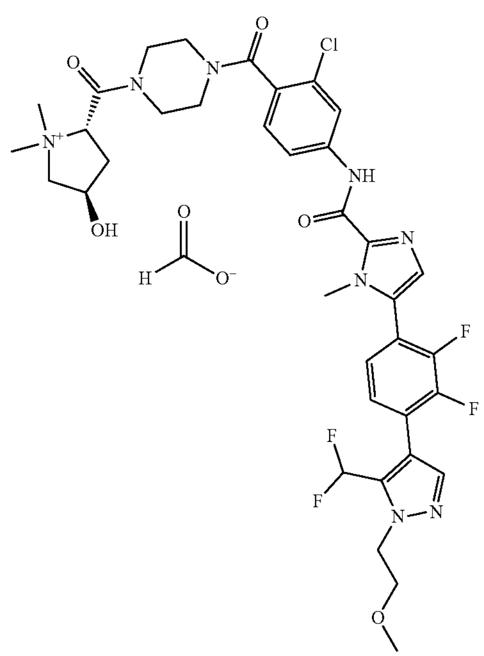 | 775.3 | Intermediate D6 and Intermediate G36; HCl; iodomethane. |

-continued

| Ex# | Name | Structure | MS ESI [M]+ | Starting Material |
|---|---|---|---|---|
| Example F14 | 5-[2,3-difluoro-4-[1-(2-methoxyethyl)-5-methyl-pyrazol-4-yl]phenyl]-N-[4-[4-[(2S,4R)-4-hydroxy-1,1-dimethyl-pyrrolidin-1-ium-2-carbonyl]piperazine-1-carbonyl]-3-methyl-phenyl]-1-methyl-imidazole-2-carboxamide; 2,2,2-trifluoroacetate | 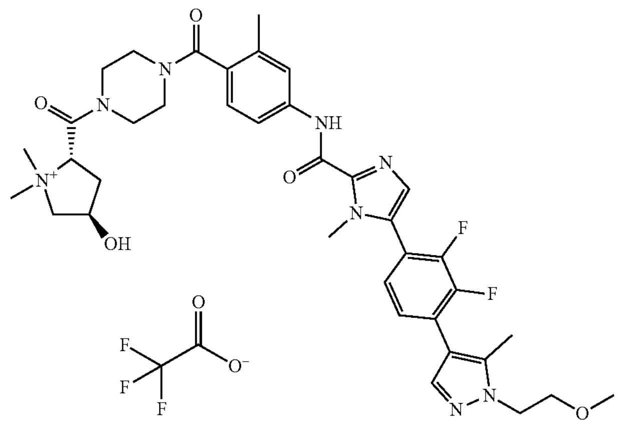 | 719.4 | Intermediate D4 and Intermediate G3; HCl; iodomethane. |
| Example F15 | N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; 2,2,2-trifluoroacetate | 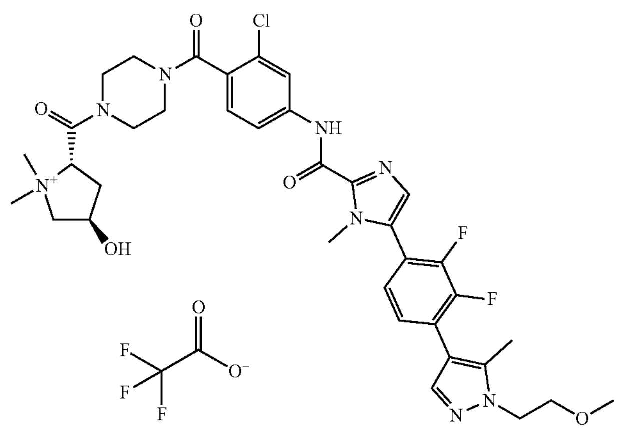 | 739.4 | Intermediate D6 and Intermediate G3; HCl; iodomethane. |
| Example F16 | N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(3-hydroxypropyl)-3-methyl-pyrazol-4-yl]phenyl]-1-methyl-imidazole-2-carboxamide; formate | 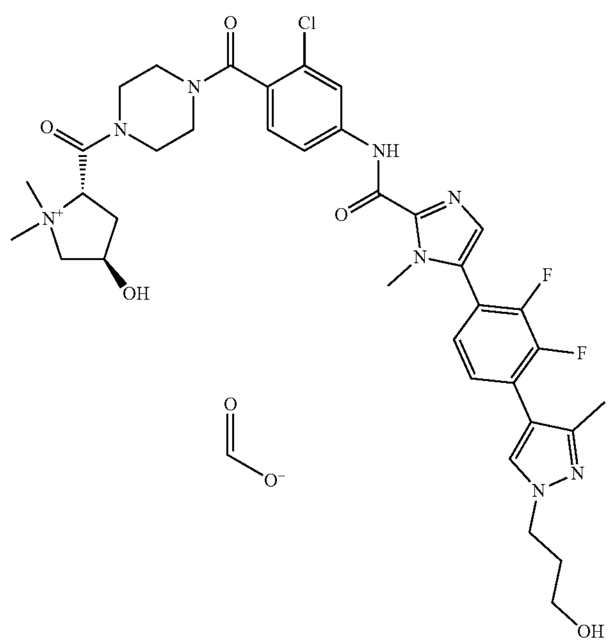 | 739.3 | Intermediate D6 and Intermediate G19; HCl; iodomethane. |

-continued

| Ex# | Name | Structure | MS ESI [M]+ | Starting Material |
|---|---|---|---|---|
| Example F17 | N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(3-hydroxypropyl)-5-methyl-pyrazol-4-yl]phenyl]-1-methyl-imidazole-2-carboxamide; formate | 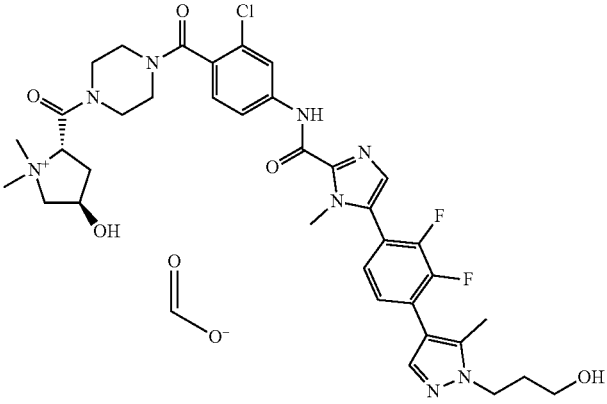 | 739.3 | Intermediate D6 and Intermediate G20; HCl; iodomethane. |
| Example F18 | N-[3-chloro-4-[4-(1,1-dimethylpiperidin-1-ium-4-carbonyl)piperazine-1-carbonyl]phenyl]-5-[2-methoxy-4-[1-(2-methoxyethyl)-5-methyl-pyrazol-4-yl]phenyl]-1-methyl-imidazole-2-carboxamide; formate | 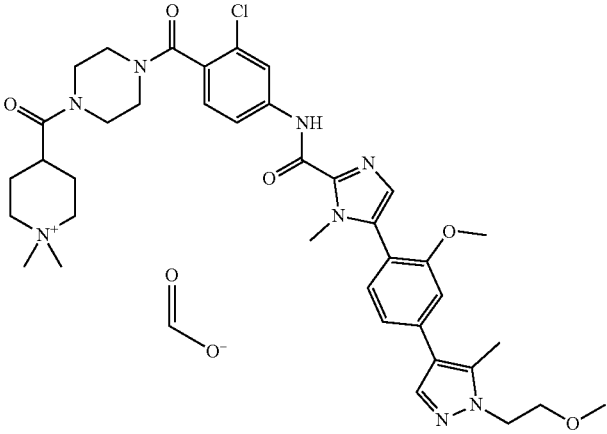 | 731.2 | Intermediate D1 and Intermediate G21; HCl; iodomethane. |
| Example F19 | N-[3-chloro-4-[4-(1,1-dimethylpiperidin-1-ium-4-carbonyl)piperazine-1-carbonyl]phenyl]-5-[4-[1-(2-methoxyethyl)-5-methyl-pyrazol-4-yl]-2-methyl-phenyl]-1-methyl-imidazole-2-carboxamide; formate | 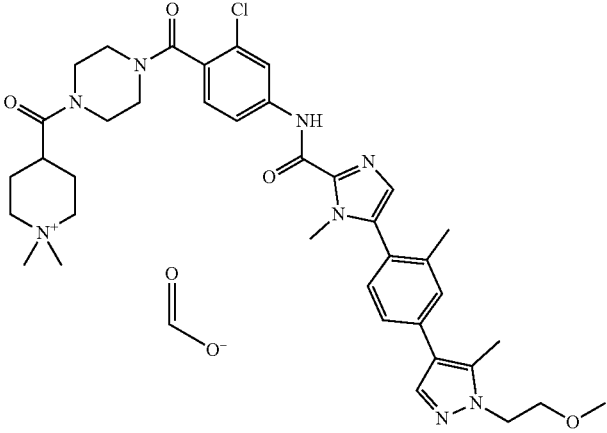 | 715.2 | Intermediate D1 and Intermediate G22; HCl; iodomethane. |

-continued

| Ex# | Name | Structure | MS ESI [M]+ | Starting Material |
|---|---|---|---|---|
| Example F20 | N-[3-chloro-4-[4-[(2S,4R)-4-hydroxy-1,1-dimethyl-pyrrolidin-1-ium-2-carbonyl]piperazine-1-carbonyl]phenyl]-5-[4-[5-ethyl-1-(2-methoxyethyl)pyrazol-4-yl]-2,3-difluoro-phenyl]-1-methyl-imidazole-2-carboxamide; formate | 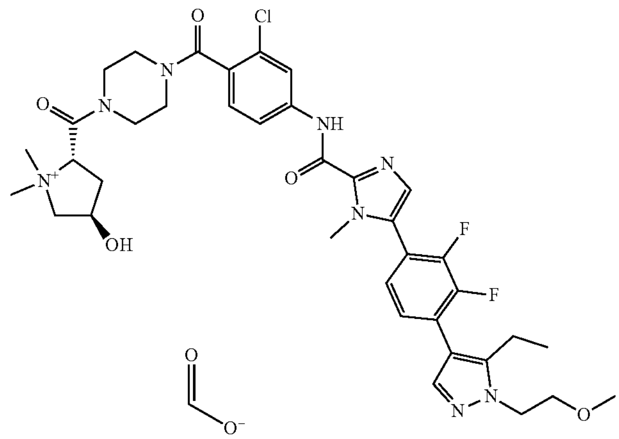 | 753.3 | Intermediate D6 and Intermediate G23; HCl; iodomethane. |
| Example F21 | N-[3-chloro-4-[4-(1,1-dimethylpiperidin-1-ium-4-carbonyl)piperazine-1-carbonyl]phenyl]-5-[2,3-difluoro-4-[5-(4-hydroxybutyl)-1H-pyrazol-4-yl]phenyl]-1-methyl-imidazole-2-carboxamide; formate | 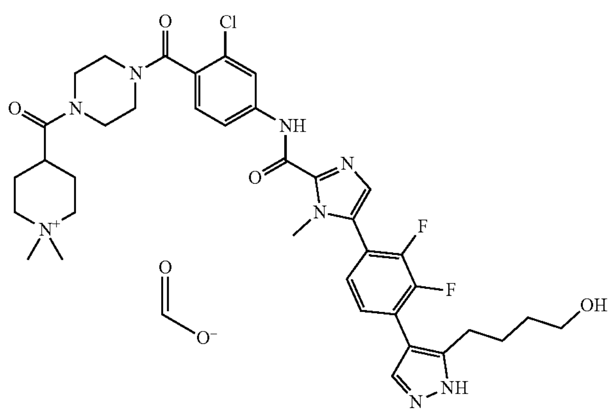 | 737.2 | Intermediate D1 and Intermediate G24; HCl; iodomethane. |
| Example F22 | N-[3-chloro-4-[4-(1,1-dimethylpiperidin-1-ium-4-carbonyl)piperazine-1-carbonyl]phenyl]-5-[2-chloro-4-[1-(2-methoxyethyl)-5-methyl-pyrazol-4-yl]phenyl]-1-methyl-imidazole-2-carboxamide; formate | 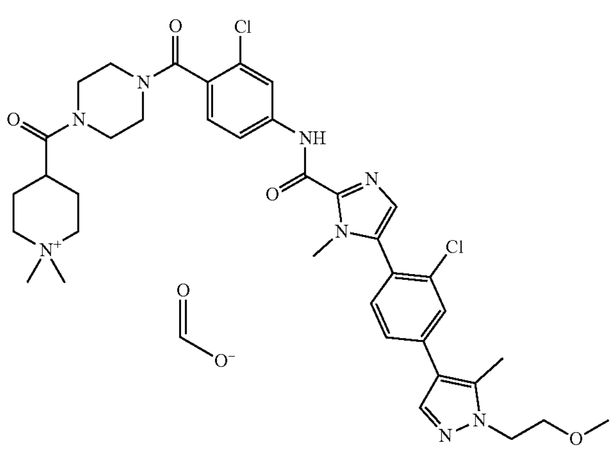 | 737.3 | Intermediate D1 and Intermediate G28; HCl; iodomethane. |

| Ex# | Name | Structure | MS ESI [M]+ | Starting Material |
|---|---|---|---|---|
| Example F23 | N-[3-chloro-4-[4-(1,1-dimethylpiperidin-1-ium-4-carbonyl)piperazine-1-carbonyl]phenyl]-5-[3-fluoro-2-methoxy-4-[1-(2-methoxyethyl)-5-methyl-pyrazol-4-yl]phenyl]-1-methyl-imidazole-2-carboxamide; formate | 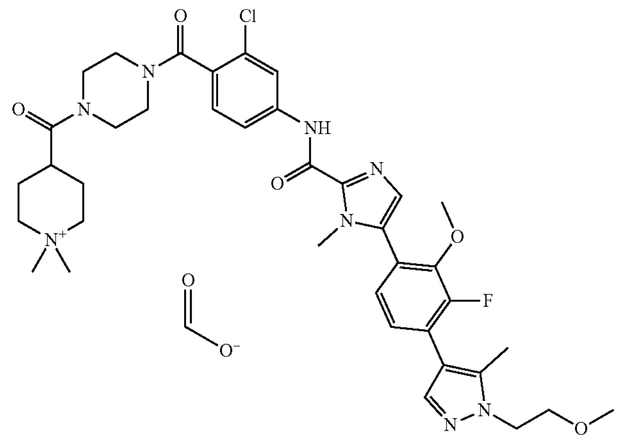 | 749.5 | Intermediate D1 and Intermediate G29; HCl; iodomethane. |
| Example F24 | N-[3-chloro-4-[4-[2-(4-hydroxy-1,1-dimethyl-piperidin-1-ium-4-yl)acetyl]piperazine-1-carbonyl]phenyl]-5-[4-[3-ethyl-1-(2-methoxyethyl)pyrazol-4-yl]-2,3-difluoro-phenyl]-1-methyl-imidazole-2-carboxamide; formate | 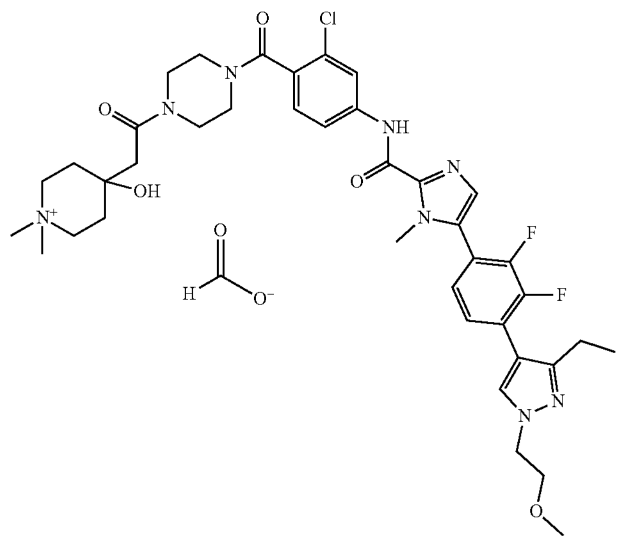 | 781.4 | Intermediate D8 and Intermediate G50; HCl; iodomethane. |
| Example F25 | N-[3-chloro-4-[4-(1,1-dimethylpiperidin-1-ium-4-carbonyl)piperazine-1-carbonyl]phenyl]-5-[2,3-difluoro-4-[3-(hydroxymethyl)-1-(2-methoxyethyl)pyrazol-4-yl]phenyl]-1-methyl-imidazole-2-carboxamide; formate | 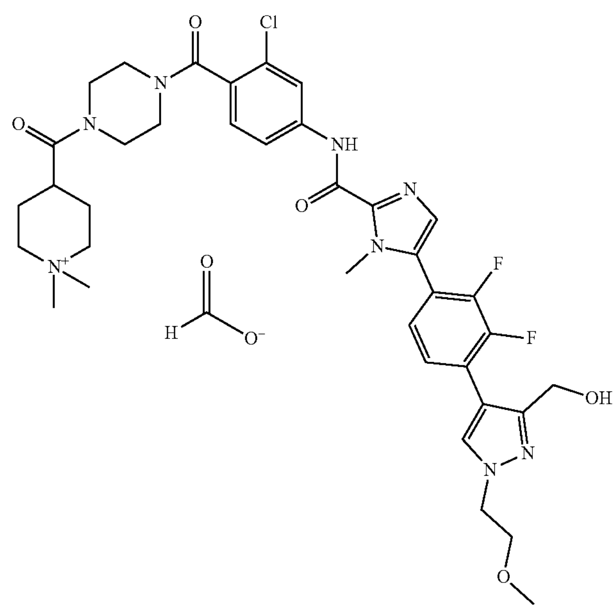 | 753.6 | Intermediate D1 and Intermediate G51; HCl; iodomethane. |

| Ex# | Name | Structure | MS ESI [M]+ | Starting Material |
|---|---|---|---|---|
| Example F26 | 5-[4-[3-amino-1-(2-methoxyethyl)pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide; formate | 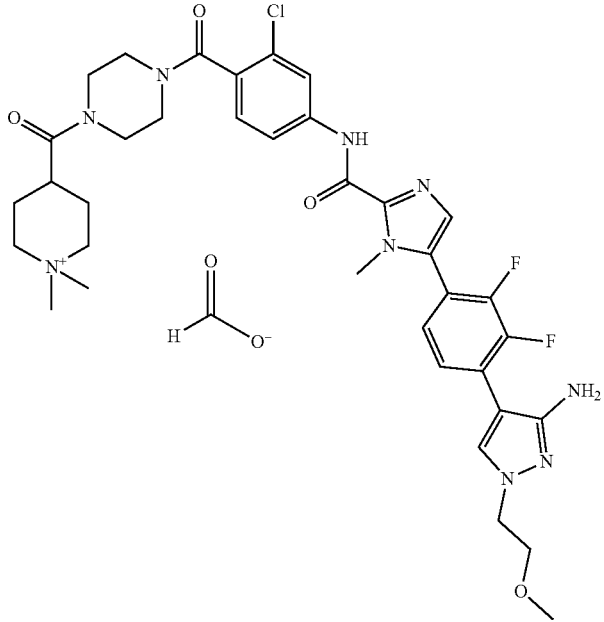 | 738.4 | Intermediate D1 and Intermediate G52; HCl; iodomethane. |
| Example F27 | N-[3-chloro-4-[4-(1,1-dimethylpiperidin-1-ium-4-carbonyl)piperazine-1-carbonyl]phenyl]-5-[2,3-difluoro-4-(3-phenyl-1H-pyrazol-4-yl)phenyl]-1-methyl-imidazole-2-carboxamide; formate | 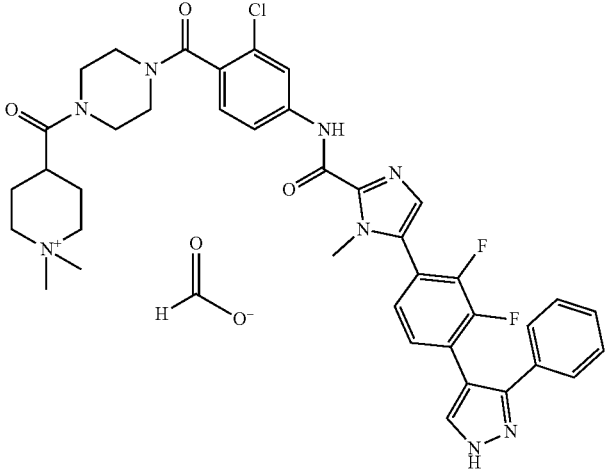 | 741.5 | Intermediate D1 and Intermediate G53; HCl; iodomethane. |

-continued

| Ex# | Name | Structure | MS ESI [M]+ | Starting Material |
|---|---|---|---|---|
| Example F28 | N-[3-chloro-4-[4-(1,1-dimethylpiperidin-1-ium-4-carbonyl)piperazine-1-carbonyl]phenyl]-5-[4-(5,6-dihydro-4H-pyrrolo[1,2-b]pyrazol-3-yl)-2,3-difluoro-phenyl]-1-methyl-imidazole-2-carboxamide; formate | 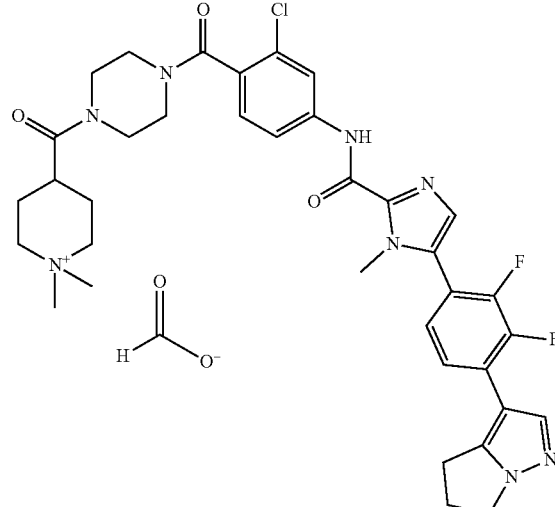 | 705.1 | Intermediate D1 and Intermediate G54; HCl; Iodomethane. |
| Example F29 | N-[3-chloro-4-[4-(1,1-dimethylpiperidin-1-ium-4-carbonyl)piperazine-1-carbonyl]phenyl]-5-[2,3-difluoro-4-[3-(fluoromethyl)-1-(2-methoxyethyl)pyrazol-4-yl]phenyl]-1-methyl-imidazole-2-carboxamide; chloride | 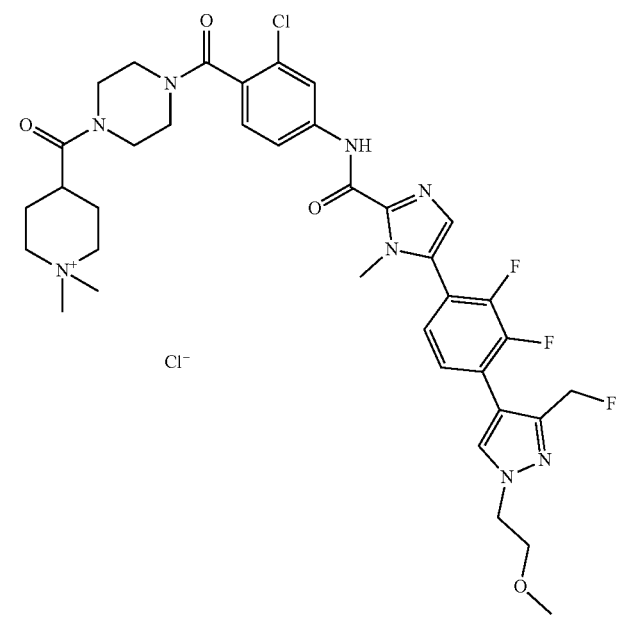 [SMILES: COCCn1cc(-c2ccc(-c3cnc(C(=O)Nc4ccc(C(=O)N5CCN(C(=O)C6CC[N+](C)(C)CC6)CC5)c(Cl)c4)n3C)c(F)c2F)c(CF)n1 ; [Cl-]] | 755.3 | Intermediate D1 and Intermediate G55; HCl; Iodomethane. |

-continued

| Ex# | Name | Structure | MS ESI [M]+ | Starting Material |
|---|---|---|---|---|
| Example F30 | N-[3-chloro-4-[4-(1,1-dimethylpiperidin-1-ium-4-carbonyl)piperazine-1-carbonyl]phenyl]-5-[4-[3-chloro-1-(2-methoxyethyl)pyrazol-4-yl]-2,3-difluoro-phenyl]-1-methyl-imidazole-2-carboxamide; formate | 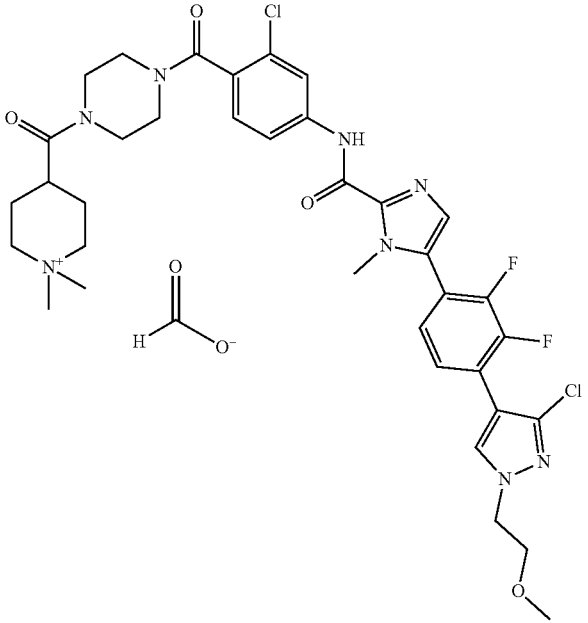 | 757.3 | Intermediate D1 and Intermediate G56; HCl; Iodomethane. |
| Example F31 | N-[3-chloro-4-[4-(1,1-dimethylpiperidin-1-ium-4-carbonyl)piperazine-1-carbonyl]phenyl]-5-[4-[5-chloro-1-(2-methoxyethyl)pyrazol-4-yl]-2,3-difluoro-phenyl]-1-methyl-imidazole-2-carboxamide; formate | 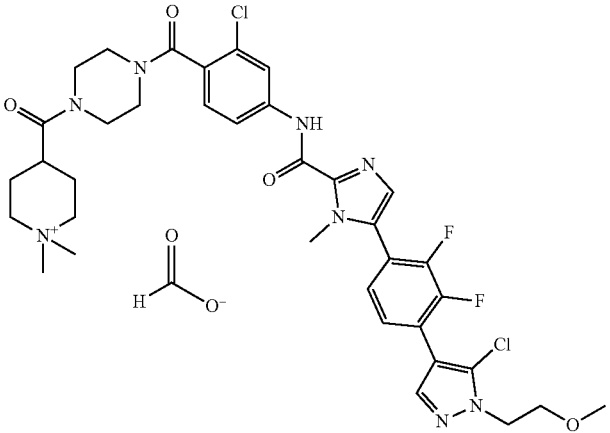 | 757.3 | Intermediate D1 and Intermediate G57; iodomethane. |

-continued

| Ex# | Name | Structure | MS ESI [M]+ | Starting Material |
|---|---|---|---|---|
| Example F32 | N-[3-chloro-4-[4-(1,1-dimethylpiperidin-1-ium-4-carbonyl)piperazine-1-carbonyl]phenyl]-5-[2,3-difluoro-4-[1-(2-methylsulfonylethyl)-3-(trifluoromethyl)pyrazol-4-yl]phenyl]-1-methyl-imidazole-2-carboxamide; formate | 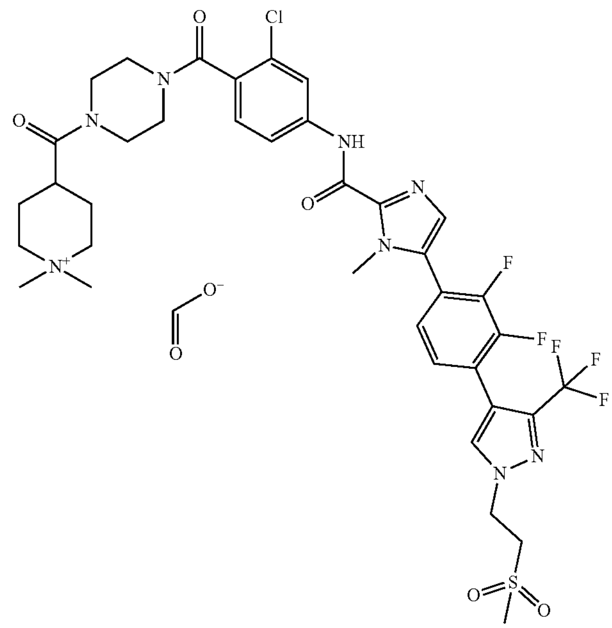 | 839.2 | Intermediate D1 and intermediate G39; then TFA and iodomethane. |
| Example F33 | N-[3-chloro-4-[4-(1,1-dimethylpiperidin-1-ium-4-carbonyl)piperazine-1-carbonyl]phenyl]-5-[2,3-difluoro-4-[1-(2-hydroxypropyl)-3-(trifluoromethyl)pyrazol-4-yl]phenyl]-1-methyl-imidazole-2-carboxamide; formate | 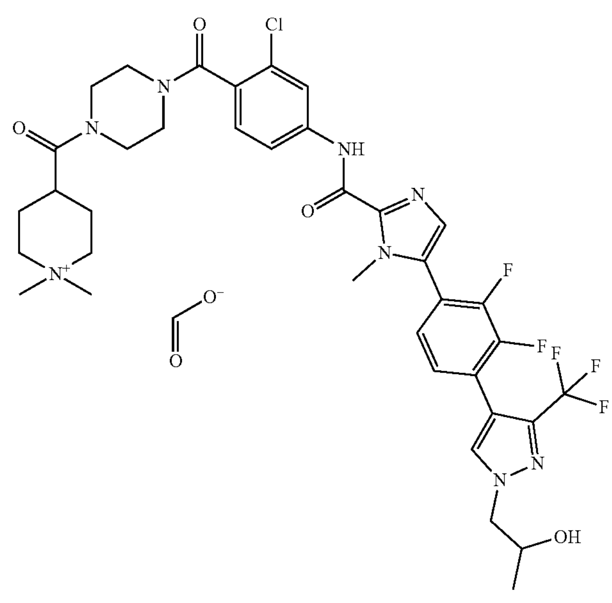 | 791.3 | Intermediate D1 and intermediate G47; then TFA and iodomethane. |

-continued

| Ex# | Name | Structure | MS ESI [M]+ | Starting Material |
|---|---|---|---|---|
| Example F34 | 5-[4-[1-(4-amino-4-oxo-butyl)-3-(trifluoromethyl)pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide; formate | 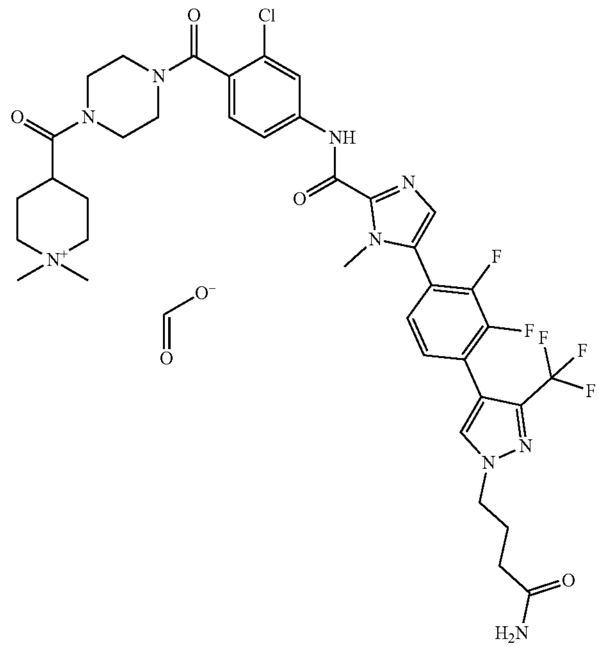 | 818.3 | Intermediate D1 and intermediate G40; then TFA and iodomethane. |
| Example F35 | 5-[4-[1-(2-amino-2-oxo-ethyl)-3-(trifluoromethyl)pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide; formate | 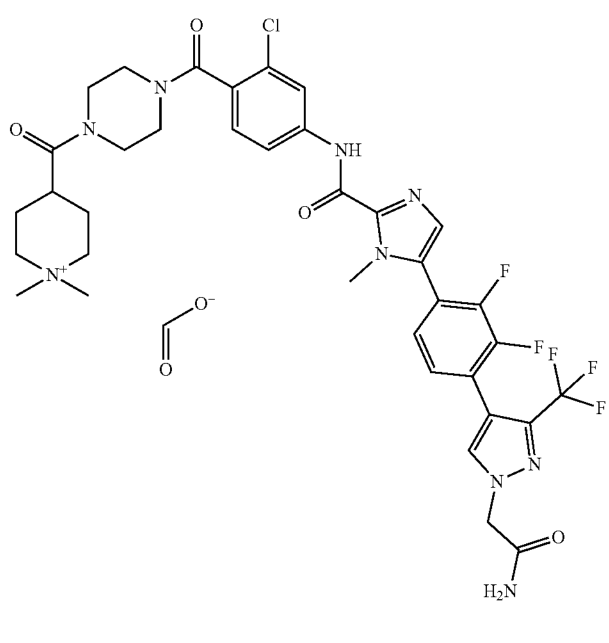 | 790.4 | Intermediate D1 and intermediate G41; then TFA and iodomethane. |

| Ex# | Name | Structure | MS ESI [M]+ | Starting Material |
|---|---|---|---|---|
| Example F36 | N-[3-chloro-4-[4-(1,1-dimethylpiperidin-1-ium-4-carbonyl)piperazine-1-carbonyl]phenyl]-5-[2,3-difluoro-4-[1-(2-methoxyethyl)-3-(trifluoromethyl)pyrazol-4-yl]phenyl]-1-methyl-imidazole-2-carboxamide; formate | 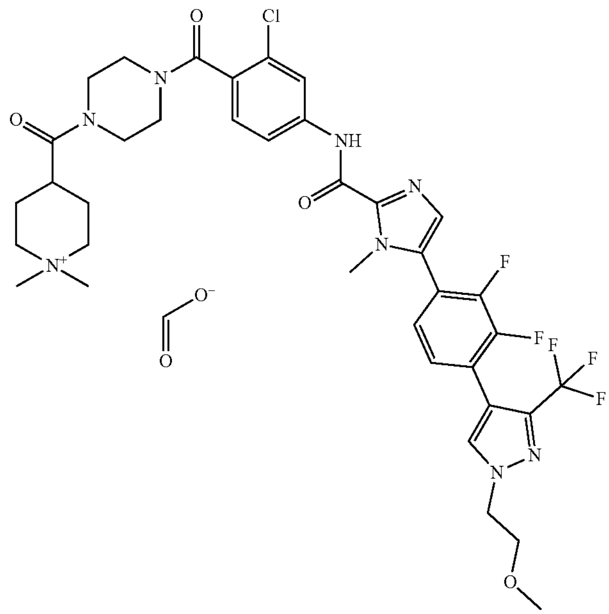 | 791.2 | Intermediate D1 and intermediate G42; then TFA and iodomethane. |
| Example F37 | N-[3-chloro-4-[4-(1,1-dimethylpiperidin-1-ium-4-carbonyl)piperazine-1-carbonyl]phenyl]-5-[2,3-difluoro-4-[1-(2-morpholinoethyl)-5-(trifluoromethyl)pyrazol-4-yl]phenyl]-1-methyl-imidazole-2-carboxamide; formate | 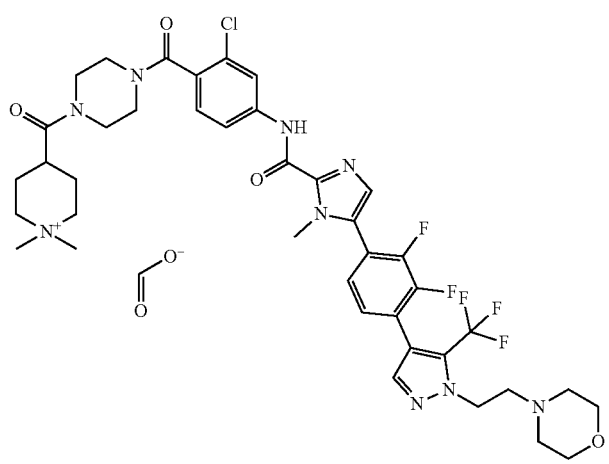 | 846.3 | Intermediate D1 and intermediate G43; then TFA and iodomethane. |

| Ex# | Name | Structure | MS ESI [M]+ | Starting Material |
|---|---|---|---|---|
| Example F38 | N-[3-chloro-4-[4-(1,1-dimethylpiperidin-1-ium-4-carbonyl)piperazine-1-carbonyl]phenyl]-5-[2,3-difluoro-4-[1-(3-methoxypropyl)-3-(trifluoromethyl)pyrazol-4-yl]phenyl]-1-methyl-imidazole-2-carboxamide; formate | 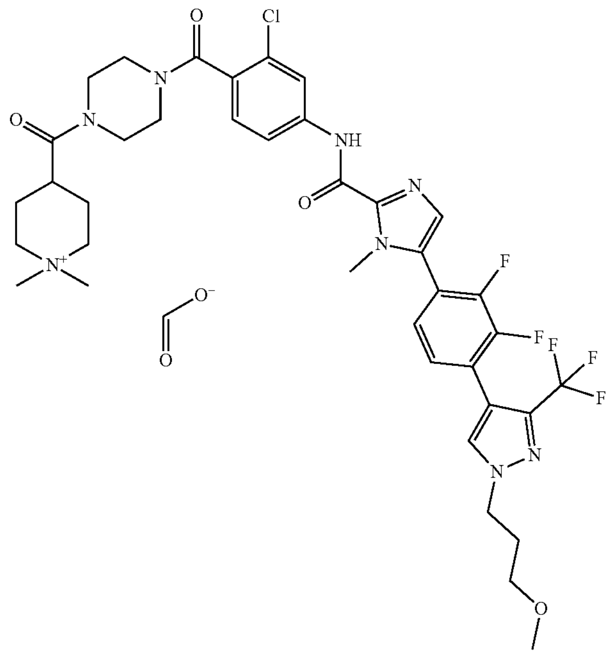 | 805.4 | Intermediate D1 and intermediate G44; then TFA and iodomethane. |
| Example F39 | N-[3-chloro-4-[4-(1,1-dimethylpiperidin-1-ium-4-carbonyl)piperazine-1-carbonyl]phenyl]-5-[2,3-difluoro-4-[3-methyl-1-(tetrahydropyran-4-ylmethyl)pyrazol-4-yl]phenyl]-1-methyl-imidazole-2-carboxamide; formate | 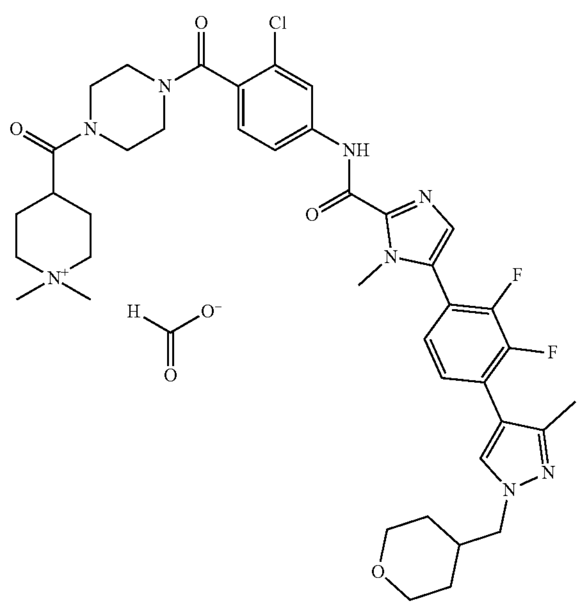 | 777.1 | Intermediate D1 and intermediate G31; TFA; iodomethane. |

-continued

| Ex# | Name | Structure | MS ESI [M]+ | Starting Material |
|---|---|---|---|---|
| Example F40 | 5-[4-[1-(5-amino-2-pyridyl)-3-methyl-pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide; chloride | 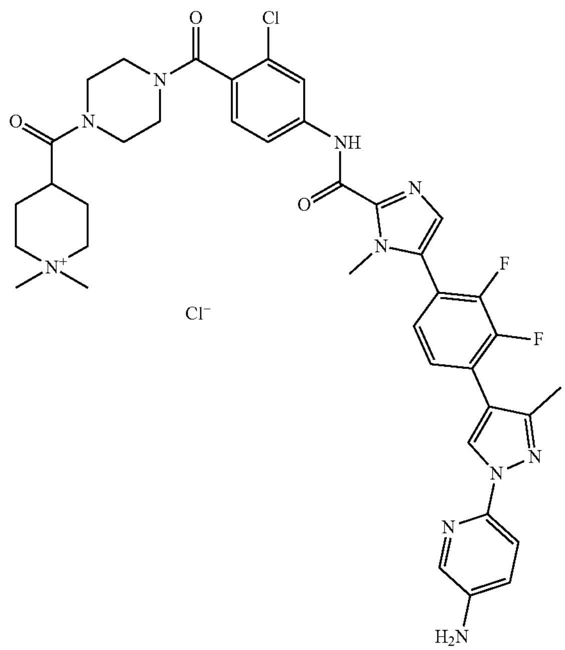 [SMILES: Cc1nn(-c2ccc(N)cn2)cc1-c1ccc(-c2cnc(C(=O)Nc3ccc(C(=O)N4CCN(C(=O)C5CC[N+](C)(C)CC5)CC4)c(Cl)c3)n2C)c(F)c1F ; [Cl-]] | 771.2 | Intermediate D1 and intermediate G70; HCl; iodomethane. |
| Example F41 | N-[3-chloro-4-[4-(1,1-dimethylpiperidin-1-ium-4-carbonyl)piperazine-1-carbonyl]phenyl]-5-[2,3-difluoro-4-[3-methyl-1-(2-pyridylmethyl)pyrazol-4-yl]phenyl]-1-methyl-imidazole-2-carboxamide; formate | 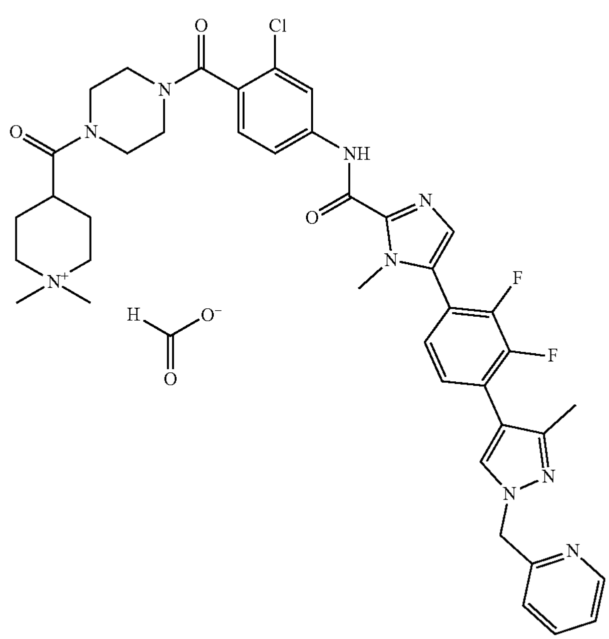 | 770.3 | Intermediate D1 and intermediate G32; HCl; iodomethane |

-continued

| Ex# | Name | Structure | MS ESI [M]+ | Starting Material |
|---|---|---|---|---|
| Example F42 | N-[3-chloro-4-[4-(1,1-dimethylpiperidin-1-ium-4-carbonyl)piperazine-1-carbonyl]phenyl]-5-[2,3-difluoro-4-[3-methyl-1-(1H-pyrazol-4-yl)pyrazol-4-yl]phenyl]-1-methyl-imidazole-2-carboxamide; formate | 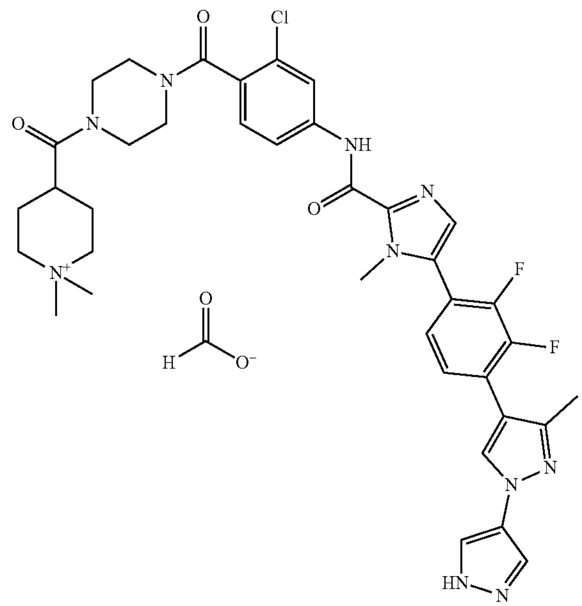 | 745.3 | Intermediate D1 and intermediate G71; HCl; iodomethane |
| Example F43 | 5-[4-[1-[(5-amino-2-pyridyl)methyl]-3-methyl-pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide; chloride | 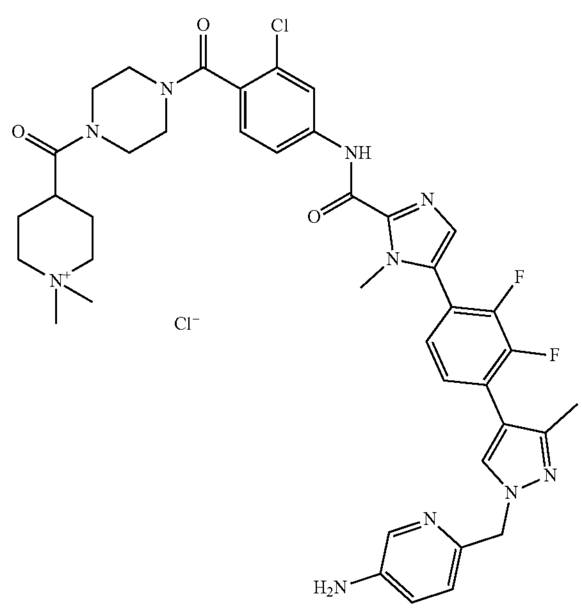 [SMILES: Cc1nn(Cc2ccc(N)cn2)cc1-c1ccc(-c2cnc(C(=O)Nc3ccc(C(=O)N4CCN(C(=O)C5CC[N+](C)(C)CC5)CC4)c(Cl)c3)n2C)c(F)c1F ; [Cl-]] | 785.5 | Intermediate D1 and intermediate G72; HCl; iodomethane |

| Ex# | Name | Structure | MS ESI [M]+ | Starting Material |
|---|---|---|---|---|
| Example F44 | N-[3-chloro-4-[4-(1,1-dimethylpiperidin-1-ium-4-carbonyl)piperazine-1-carbonyl]phenyl]-5-[2,3-difluoro-4-[3-(2-methylpyrazol-3-yl)-1H-pyrazol-4-yl]phenyl]-1-methyl-imidazole-2-carboxamide; formate | 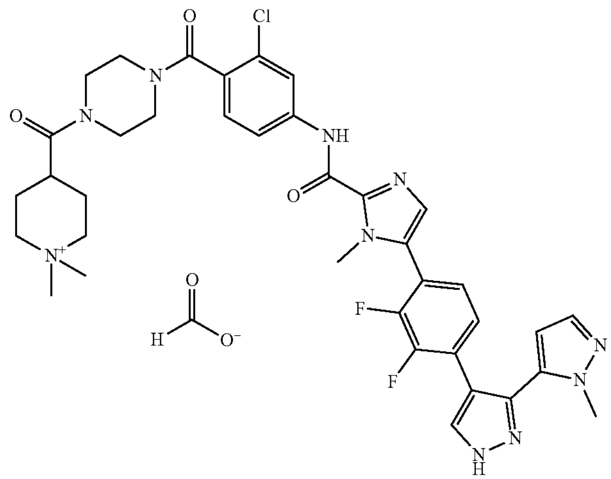 | 745.4 | Intermediate D1 and intermediate G65; HCl; iodomethane |
| Example F45 | N-[3-chloro-4-[4-(1,1-dimethylpiperidin-1-ium-4-carbonyl)piperazine-1-carbonyl]phenyl]-5-[2,3-difluoro-4-[3-(3-fluorophenyl)-1H-pyrazol-4-yl]phenyl]-1-methyl-imidazole-2-carboxamide; formate | 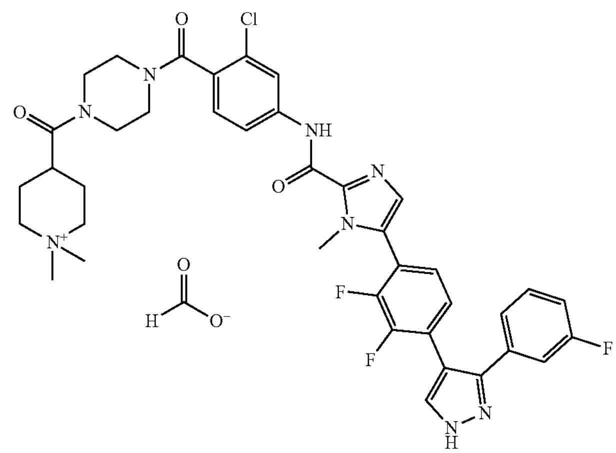 | 759.3 | Intermediate D1 and intermediate G66; HCl; iodomethane |
| Example F46 | N-[3-chloro-4-[4-(1,1-dimethylpiperidin-1-ium-4-carbonyl)piperazine-1-carbonyl]phenyl]-5-[2,3-difluoro-4-[3-methyl-1-[2-(2-oxo-1-pyridyl)ethyl]pyrazol-4-yl]phenyl]-1-methyl-imidazole-2-carboxamide; formate | 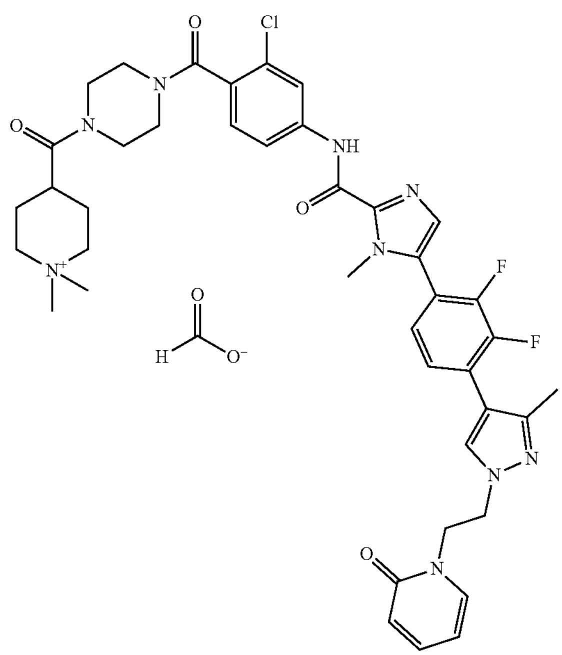 | 800.6 | Intermediate D1 and intermediate G73; HCl; iodomethane |

-continued

| Ex# | Name | Structure | MS ESI [M]+ | Starting Material |
|---|---|---|---|---|
| Example F47 | N-[3-chloro-4-[4-(1,1-dimethylpiperidin-1-ium-4-carbonyl)piperazine-1-carbonyl]phenyl]-5-[2,3-difluoro-4-[3-(1-methylpyrazol-4-yl)-1H-pyrazol-4-yl]phenyl]-1-methyl-imidazole-2-carboxamide; formate | 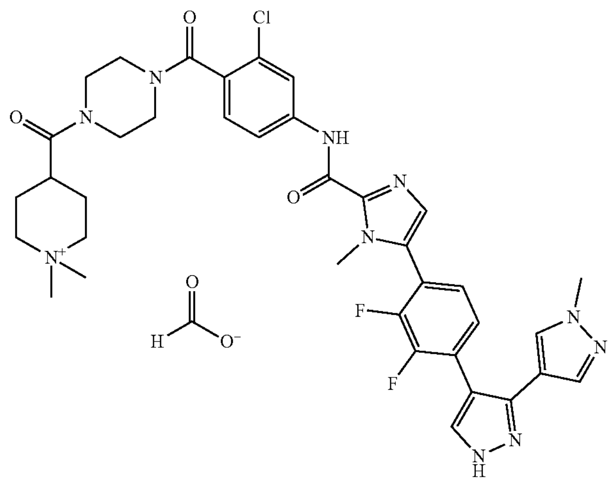 | 745.2 | Intermediate D1 and intermediate G67; HCl; iodomethane |
| Example F48 | N-[3-chloro-4-[4-(1,1-dimethylpiperidin-1-ium-4-carbonyl)piperazine-1-carbonyl]phenyl]-5-[2,3-difluoro-4-[3-(1H-pyrazol-4-yl)-1H-pyrazol-4-yl]phenyl]-1-methyl-imidazole-2-carboxamide; formate | 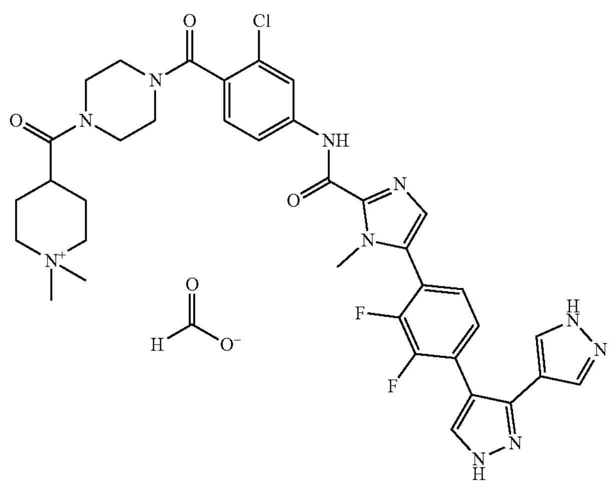 | 731.2 | Intermediate D1 and intermediate G68; HCl; iodomethane |
| Example F49 | N-[3-chloro-4-[4-(1,1-dimethylpiperidin-1-ium-4-carbonyl)piperazine-1-carbonyl]phenyl]-5-[2,3-difluoro-4-[1-(2-methoxyethyl)-3-phenyl-pyrazol-4-yl]phenyl]-1-methyl-imidazole-2-carboxamide; formate | 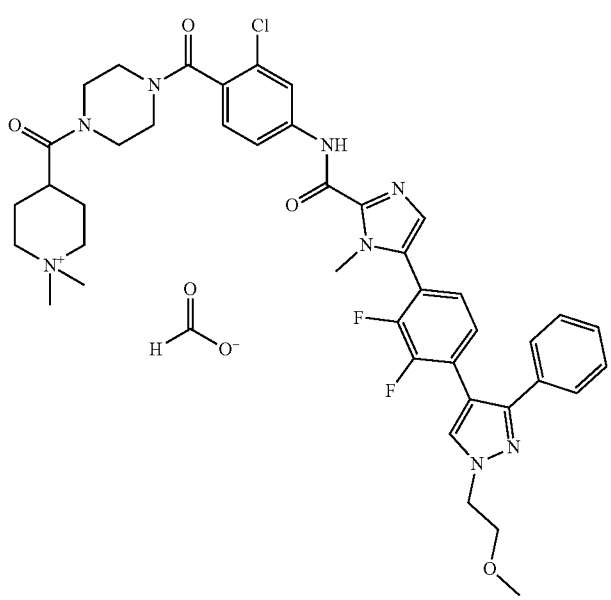 | 799.4 | Intermediate D1 and intermediate G69; HCl; iodomethane |

| Ex# | Name | Structure | MS ESI [M]+ | Starting Material |
|---|---|---|---|---|
| Example F50 | N-[3-chloro-4-[4-(1,1-dimethylpiperidin-1-ium-4-carbonyl)piperazine-1-carbonyl]phenyl]-5-[2,3-difluoro-4-[3-methyl-1-(2-pyridyl)pyrazol-4-yl]phenyl]-1-methyl-imidazole-2-carboxamide; formate | 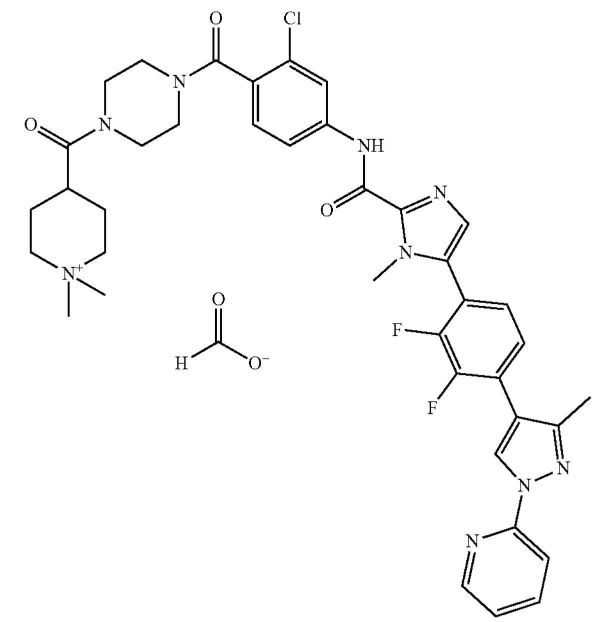 | 756.2 | Intermediate D1 and intermediate G74; HCl; iodomethane |
| Example F51 | [2-[4-[2-chloro-4-[[1-methyl-5-[4-(3-methyl-1H-pyrazol-4-yl)phenyl]imidazole-2-carbonyl]amino]benzoyl]piperazin-1-yl]-2-oxo-ethyl]-trimethyl-ammonium; formate | 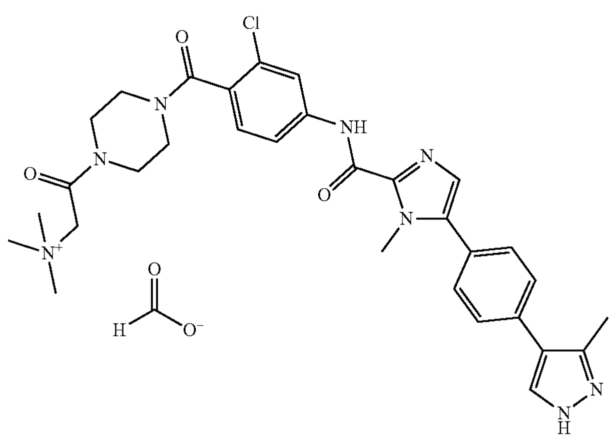 | 603.4 | Intermediate D3 and intermediate G8; HCl; iodomethane |
| Example F52 | [2-[4-[2-chloro-4-[[5-[4-(3,5-dimethyl-1H-pyrazol-4-yl)phenyl]-1-methyl-imidazole-2-carbonyl]amino]benzoyl]piperazin-1-yl]-2-oxo-ethyl]-trimethyl-ammonium; 2,2,2-trifluoroacetate | 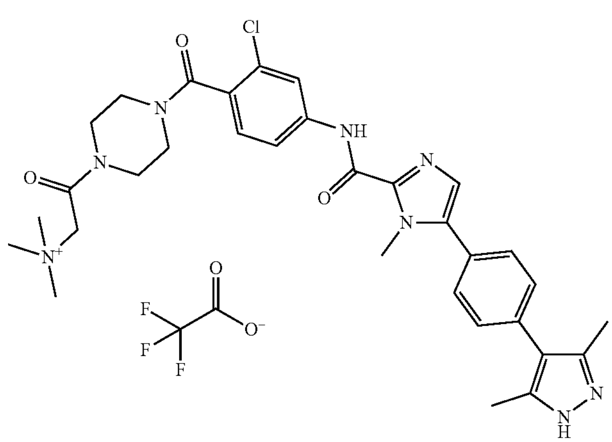 | 617.4 | Intermediate D3 and intermediate G9; HCl; iodomethane |

-continued

| Ex# | Name | Structure | MS ESI [M]+ | Starting Material |
|---|---|---|---|---|
| Example F53 | 4-chloro-N-[3-chloro-4-[4-(1,1-dimethylpiperidin-1-ium-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide; formate | 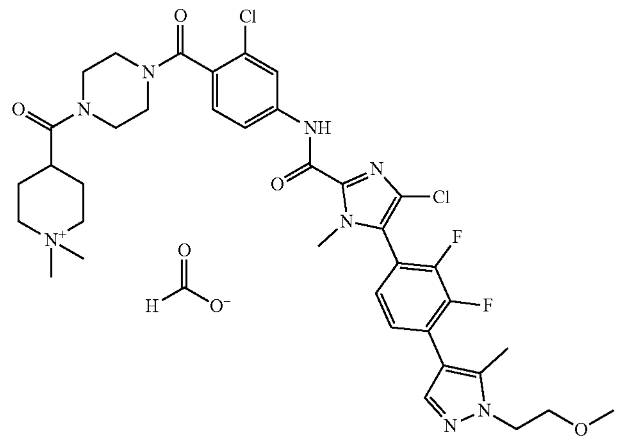 | 773.4 | Intermediate D10 and intermediate G3; HCl; iodomethane |
| Example F54 | N-[3-chloro-4-[4-(1,1-dimethylpiperidin-1-ium-4-carbonyl)piperazine-1-carbonyl]phenyl]-5-[2,3-difluoro-4-[1-[2-(6-methoxy-2-pyridyl)ethyl]-3-methyl-pyrazol-4-yl]phenyl]-1-methyl-imidazole-2-carboxamide; formate | 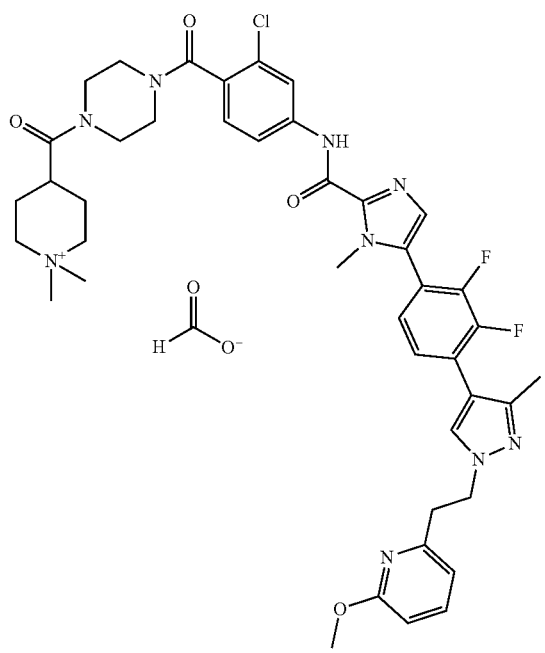 | 814.3 | Intermediate D1 and intermediate G76; HCl; iodomethane |

-continued

| Ex# | Name | Structure | MS ESI [M]+ | Starting Material |
|---|---|---|---|---|
| Example F55 | N-[3-chloro-4-[4-(1,1-dimethylpiperidin-1-ium-4-carbonyl)piperazine-1-carbonyl]phenyl]-5-[2,3-difluoro-4-[1-[(6-methoxy-2-pyridyl)methyl]-3-methyl-pyrazol-4-yl]phenyl]-1-methyl-imidazole-2-carboxamide; formate | 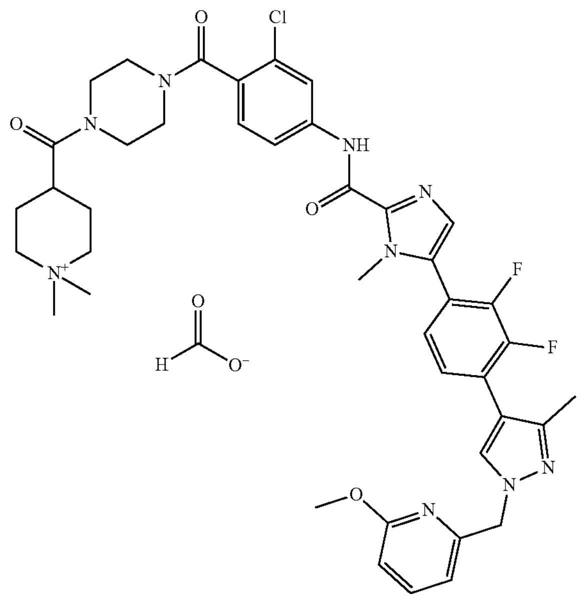 | 800.3 | Intermediate D1 and intermediate G77; HCl; iodomethane |
| Example F56 | N-[3-chloro-4-[4-(1,1-dimethylpiperidin-1-ium-4-carbonyl)piperazine-1-carbonyl]phenyl]-5-[2,3-difluoro-4-[3-methyl-1-(1H-triazol-4-ylmethyl)pyrazol-4-yl]phenyl]-1-methyl-imidazole-2-carboxamide; formate | 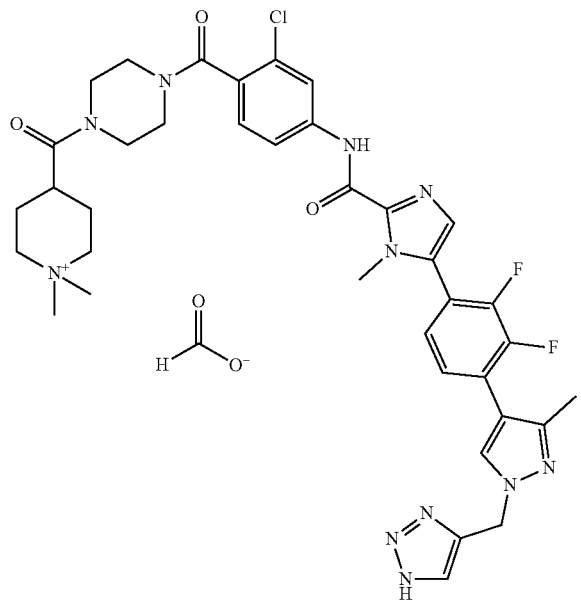 | 760.3 | Intermediate D1 and intermediate G78; HCl; iodomethane |

-continued

| Ex# | Name | Structure | MS ESI [M]+ | Starting Material |
|---|---|---|---|---|
| Example F57 | N-[3-chloro-4-[4-(1,1-dimethylpiperidin-1-ium-4-carbonyl)piperazine-1-carbonyl]phenyl]-5-[2-fluoro-6-[1-(2-methoxyethyl)-5-methyl-pyrazol-4-yl]-3-pyridyl]-1-methyl-imidazole-2-carboxamide; formate | 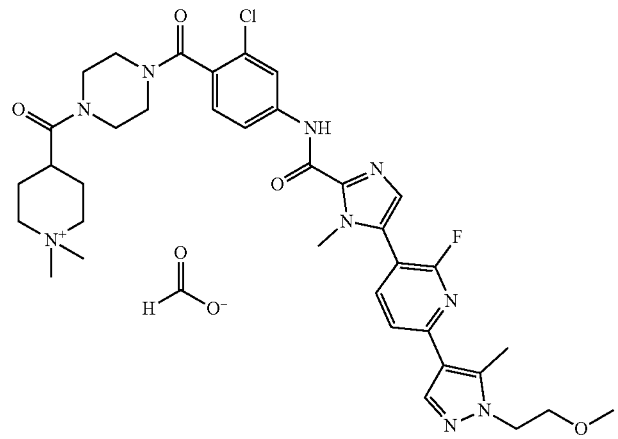 | 720.2 | Intermediate D1 and intermediate G79; HCl; iodomethane |
| Example F59 | N-[3-chloro-4-[4-(1,1-dimethylpiperidin-1-ium-4-carbonyl)piperazine-1-carbonyl]phenyl]-5-[2-fluoro-6-[5-(4-methoxyphenyl)-1H-pyrazol-4-yl]-3-pyridyl]-1-methyl-imidazole-2-carboxamide; formate | 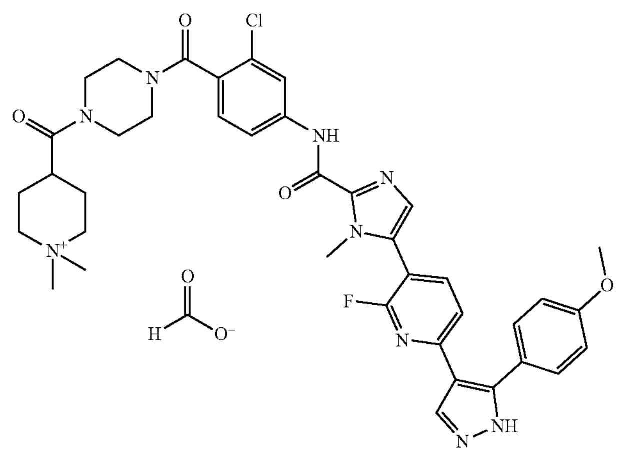 | 754.3 | Intermediate D1 and intermediate G75; HCl; iodomethane |
| Example F63 | 5-[4-[5-[(3-amino-3-oxo-propyl)amino]-2-pyridyl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide; formate | 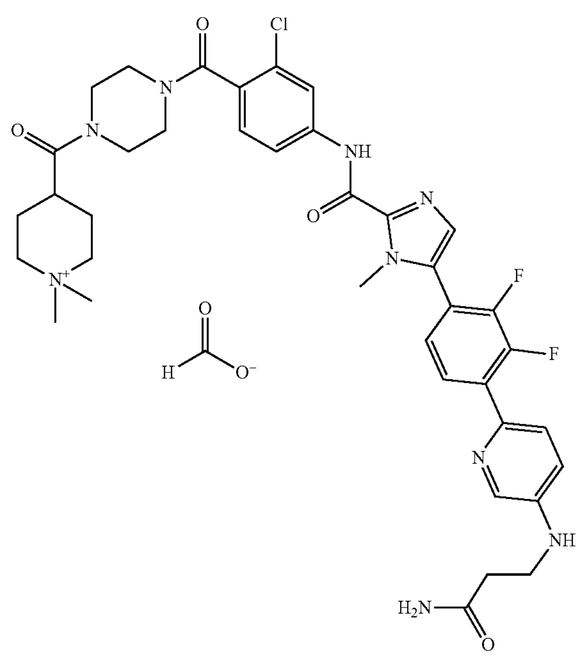 | 762.3 | Intermediate D1 and intermediate G86; HCl; iodomethane; piperidine |

-continued

| Ex# | Name | Structure | MS ESI [M]+ | Starting Material |
|---|---|---|---|---|
| Example F64 | 5-[4-(5-amino-3-methyl-2-pyridyl)-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide; formate | 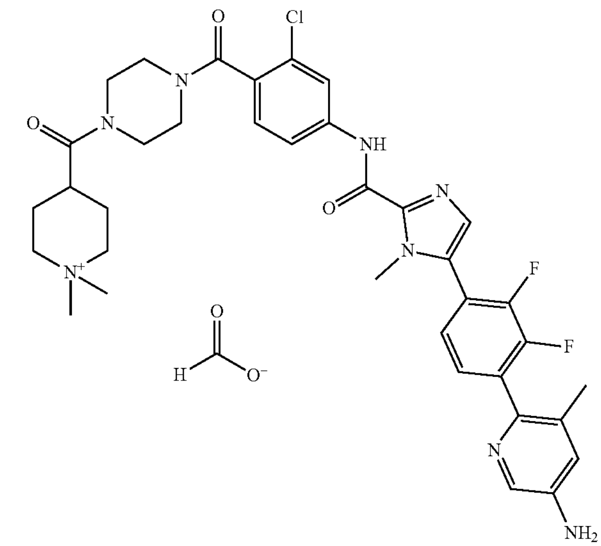 | 705.6 | Intermediate D1 and intermediate G87; HCl; iodomethane; piperidine |
| Example F65 | 5-[4-(5-amino-2-pyridyl)-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide; formate | 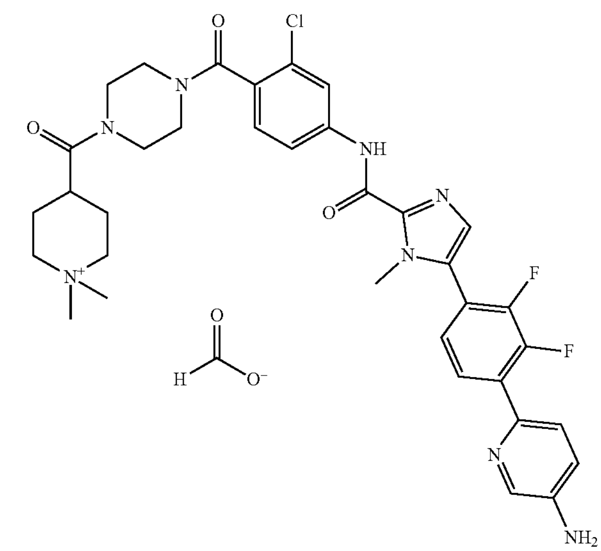 | 691.3 | Intermediate D1 and intermediate G88; HCl; iodomethane; piperidine |
| Example F66 | (1S,5R)-6-[[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]amino]-N-[(3R,4R)-4-hydroxy-1,1-dimethyl-pyrrolidin-1-ium-3-yl]-3-azabicyclo[3.1.0]hexane-3-carboxamide; formate | 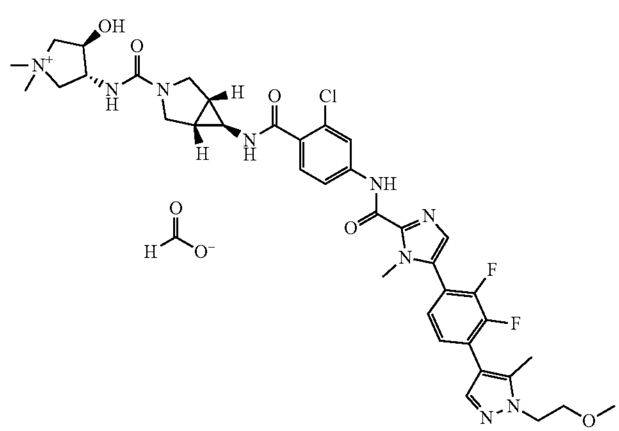 | 766.3 | Intermediate D11 and Intermediate G3; HCl; iodomethane |

| Ex# | Name | Structure | MS ESI [M]+ | Starting Material |
|---|---|---|---|---|
| Example F67 | N-[3-chloro-4-[4-(1,1-dimethylpiperidin-1-ium-4-carbonyl)piperazine-1-carbonyl]phenyl]-5-[2-fluoro-6-[1-(2-methoxyethyl)-3,5-dimethyl-pyrazol-4-yl]-3-pyridyl]-1-methyl-imidazole-2-carboxamide; formate | 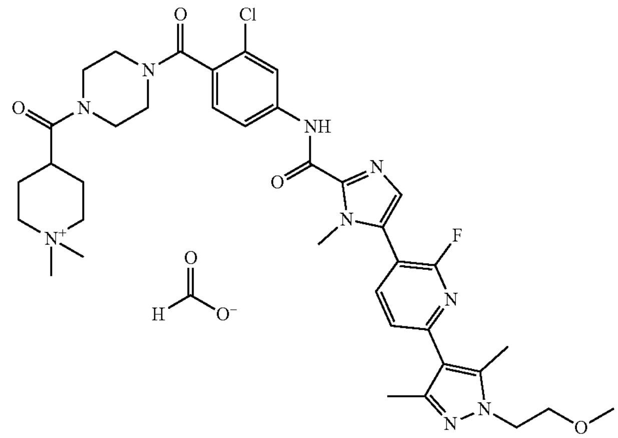 | 734.3 | Intermediate D1 and intermediate G91; HCl; iodomethane |

Example F58

N-[3-chloro-4-[4-[(2S,4R)-4-hydroxy-1,1-dimethyl-pyrrolidin-1-ium-2-carbonyl]piperazine-1-carbonyl]phenyl]-5-[4-[1-(3-cyanopropyl)-3,5-dimethyl-pyrazol-4-yl]-2,3-difluoro-phenyl]-1-methyl-imidazole-2-carboxamide; formate

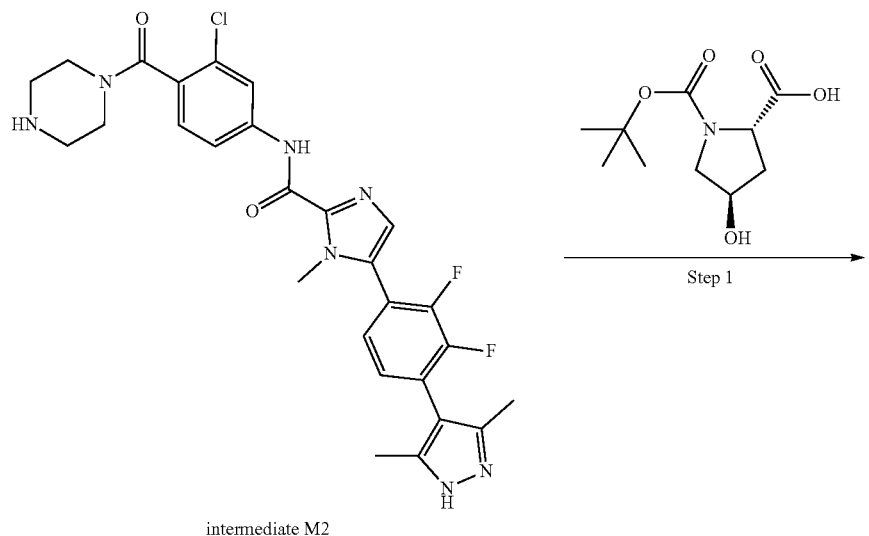

intermediate M2

Step 1

465
-continued
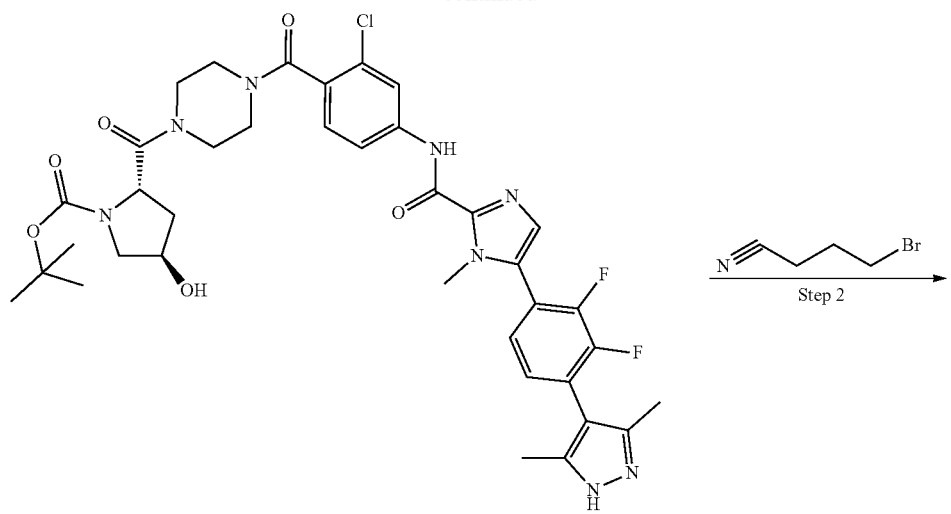
Step 2
466
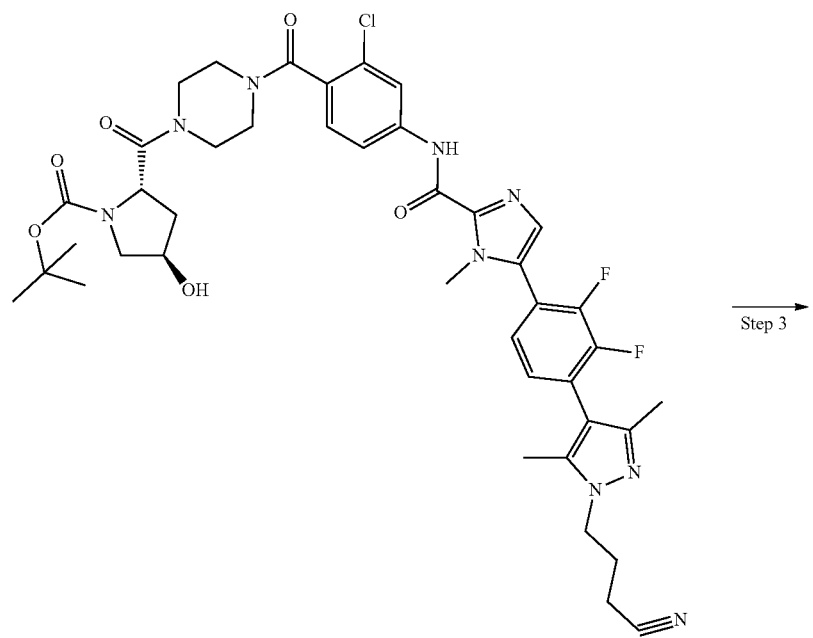
Step 3

-continued
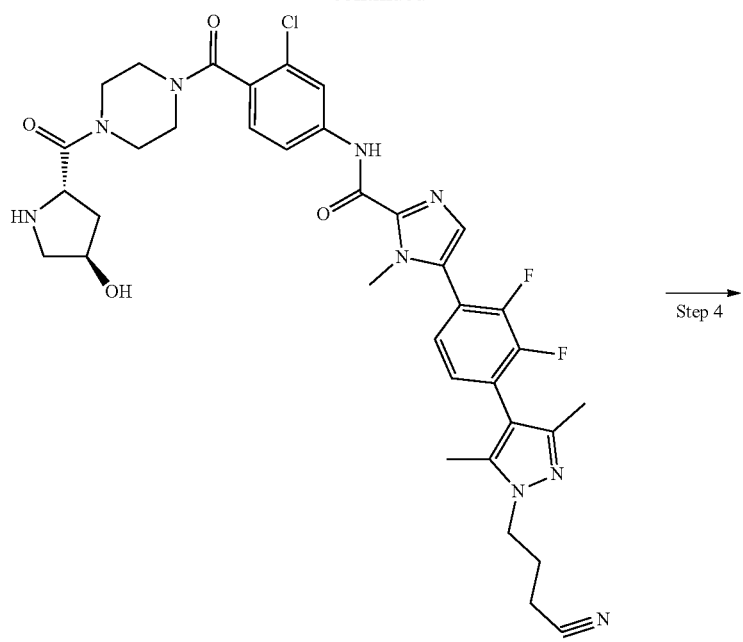
Step 4
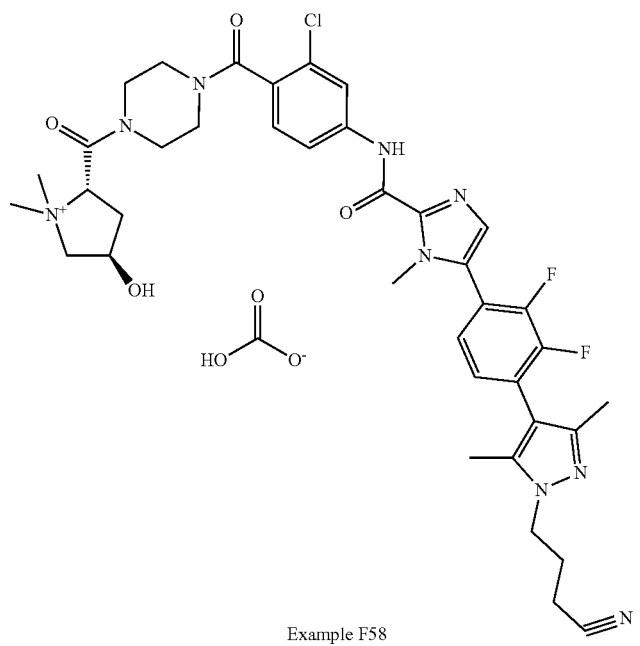
Example F58

Step 1: tert-butyl (2S,4R)-2-[4-[2-chloro-4-[[5-[4-(3,5-dimethyl-1H-pyrazol-4-yl)-2,3-difluoro-phenyl]-1-methyl-imidazole-2-carbonyl]amino]benzoyl]piperazine-1-carbonyl]-4-hydroxy-pyrrolidine-1-carboxylate To a mixture of N-[3-chloro-4-(piperazine-1-carbonyl)phenyl]-5-[4-(3,5-dimethyl-1H-pyrazol-4-yl)-2,3-difluoro-phenyl]-1-methyl-imidazole-2-carboxamide (1.0 g, 1.44 mmol) and BOC—HYP—OH (400.73 mg, 1.73 mmol) in THF (10 mL) was added N,N-diisopropylethylamine (0.56 g, 4.33 mmol) and PROPYLPHOSPHONIC ANHYDRIDE (1.19 g, 1.88 mmol). The reaction mixture was stirred at 25° C. for 4 h. The solution was extracted with water (10 mL) and EA (20 mL) and washed with sat.aq NaCl (10 mL), dried by anhydrous $Na_2SO_4$. The crude was purified by prep-HPLC(FA) to obtain the title compound (600 mg). MS $[M+H]^+$: 767.1.

Step 2: tert-butyl (2S,4R)-2-[4-[2-chloro-4-[[5-[4-[1-(3-cyanopropyl)-3,5-dimethyl-pyrazol-4-yl]-2,3-difluoro-phenyl]-1-methyl-imidazole-2-carbonyl]amino]benzoyl]piperazine-1-carbonyl]-4-hydroxy-pyrrolidine-1-carboxylate To a mixture of tert-butyl (2S,4R)-2-[4-[2-chloro-4-[[5-[4-(3,5-dimethyl-1H-pyrazol-4-yl)-2,3-difluoro-phenyl]-1-methyl-imidazole-2-carbonyl]amino]benzoyl]piperazine-1-carbonyl]-4-hydroxy-pyrrolidine-1-carboxylate (100.0 mg, 0.130 mmol) in DMF (3 mL) was added 4-bromo butyronitrile (28.94 mg, 0.200 mmol) and cesium carbonate (127.4 mg, 0.390 mmol). The reaction mixture was stirred at 80° C. for 16 h. The solution was purified by prep-HPLC(FA) directly to obtain the title compound (50 mg). MS $[M+H]^+$: 834.3. Step 3: N-[3-chloro-4-[4-[(2S,4R)-4-hydroxypyrrolidine-2-carbonyl]piperazine-1-carbonyl]phenyl]-5-[4-[1-(3-cyanopropyl)-3,5-dimethyl-pyrazol-4-yl]-2,3-difluoro-phenyl]-1-methyl-imidazole-2-carboxamide To a mixture of tert-butyl (2S,4R)-2-[4-[2-chloro-4-[[5-[4-[1-(3-cyanopropyl)-3,5-dimethyl-pyrazol-4-yl]-2,3-difluoro-phenyl]-1-methyl-imidazole-2-carbonyl]amino]benzoyl]piperazine-1-carbonyl]-4-hydroxy-pyrrolidine-1-carboxylate (30.0 mg, 0.040 mmol) in DCM (2 mL) was added TFA (2.0 mL, 0.110 mmol). The reaction mixture was stirred at 25° C. for 16 h. The solution was concentrated in vacuum directly to obtain the title compound (26.4 mg). MS $[M+H]^+$: 734.1.

Step 4: N-[3-chloro-4-[4-[(2S,4R)-4-hydroxy-1,1-dimethyl-pyrrolidin-1-ium-2-carbonyl]piperazine-1-carbonyl]phenyl]-5-[4-[1-(3-cyanopropyl)-3,5-dimethyl-pyrazol-4-yl]-2,3-difluoro-phenyl]-1-methyl-imidazole-2-carboxamide; formate To a mixture of N-[3-chloro-4-[4-[(2S,4R)-4-hydroxypyrrolidine-2-carbonyl]piperazine-1-carbonyl]phenyl]-5-[4-[1-(3-cyanopropyl)-3,5-dimethyl-pyrazol-4-yl]-2,3-difluoro-phenyl]-1-methyl-imidazole-2-carboxamide (26.4 mg, 0.040 mmol) in MeCN (2 mL) and water (0.200 mL) was added TEA (0.1 mL, 0.110 mmol) and iodomethane (0.1 mL, 0.040 mmol). The reaction mixture was stirred at 25° C. for 16 h. The solution was concentrared in vacuum and the crude was purified by prep-HPLC(FA) to obtain the title compound (16.9 mg). MS $[M]^+$: 762.2.

Example F60 rac-(1S,5R)-6-[[2-chloro-4-[[5-[2,3-difluoro-4-[1-(2-methoxyethyl)-3,5-dimethyl-pyrazol-4-yl]phenyl]-1-methyl-imidazole-2-carbonyl]amino]benzoyl]amino]-N-[(3R,4R)-4-hydroxy-1,1-dimethyl-pyrrolidin-1-ium-3-yl]-3-azabicyclo[3.1.0]hexane-3-carboxamide; formate

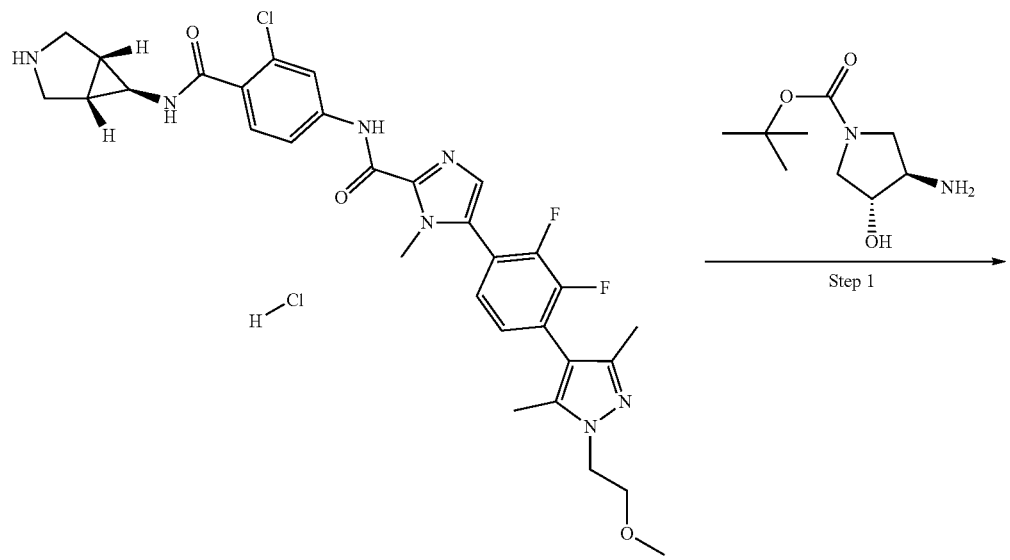

Step 1

-continued
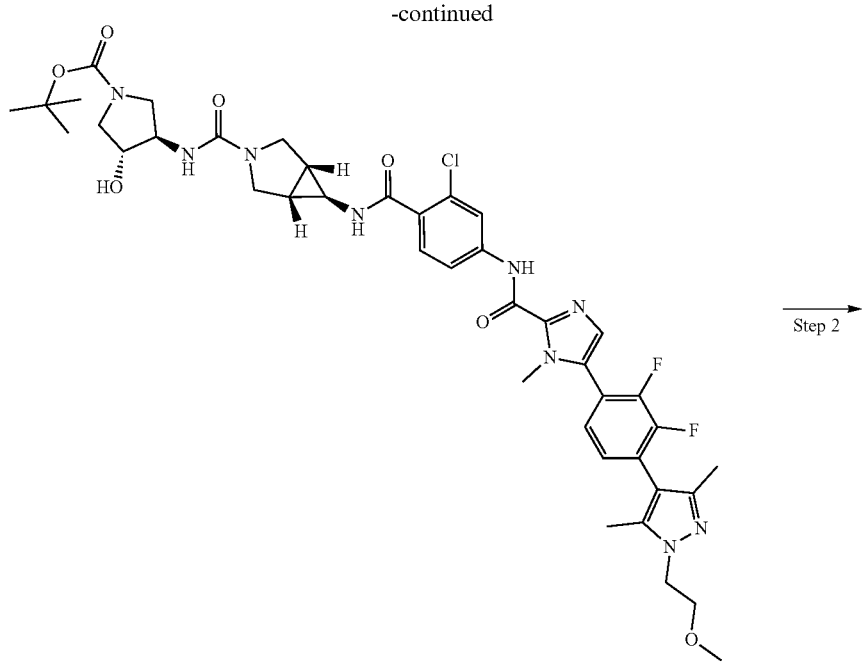
Step 2
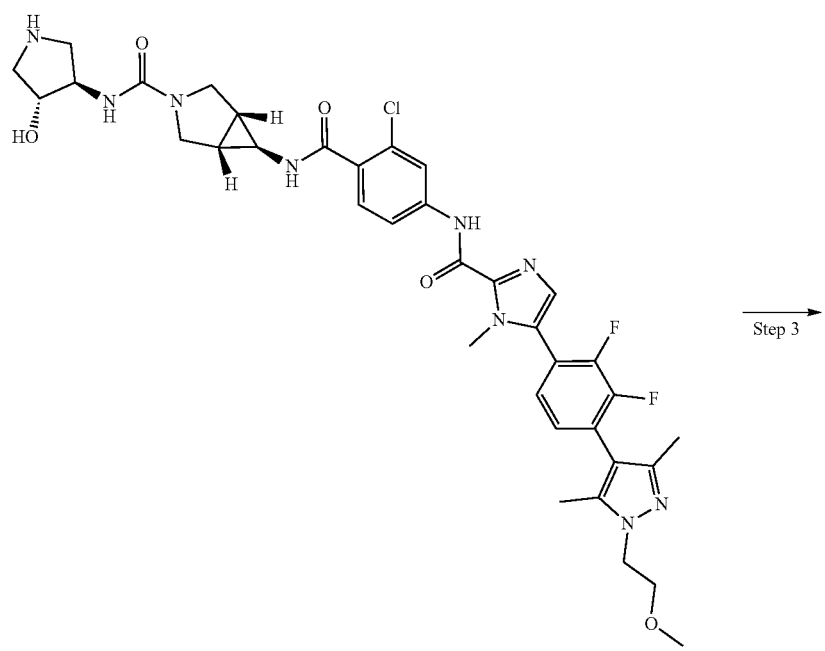
Step 3

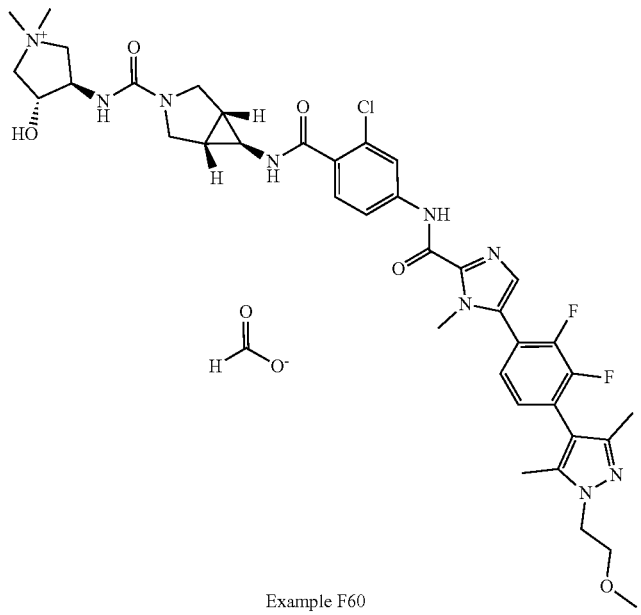

Example F60

Step 1: rac-tert-butyl (3R,4R)-3-[[(1S,5R)-6-[[2-chloro-4-[[5-[2,3-difluoro-4-[1-(2-methoxyethyl)-3,5-dimethyl-pyrazol-4-yl]phenyl]-1-methyl-imidazole-2-carbonyl]amino]benzoyl]amino]-3-azabicyclo[3.1.0]hexane-3-carbonyl]amino]-4-hydroxy-pyrrolidine-1-carboxylate In a 5 mL sealed, tert-butyl (trans)-3-amino-4-hydroxy-pyrrolidine-1-carboxylate (45.9 mg, 227 µmol) was combined with DMF (0.5 ml), TEA (38.3 mg, 52.8 µl, 378 µmol) and CDI (30.7 mg, 189 µmol) were added and the reaction mixture was stirred at RT for 20 min. Then N-(4-(((exo)-3-azabicyclo[3.1.0]hexan-6-yl)carbamoyl)-3-chlorophenyl)-5-(2,3-difluoro-4-(1-(2-methoxyethyl)-3,5-dimethyl-1H-pyrazol-4-yl)phenyl)-1-methyl-1H-imidazole-2-carboxamide hydrochloride (50 mg, 75.7 µmol) was added and the reaction was stirred at RT. The product was submitted for purification by prep HPLC. To afford the title compound (15.5 mg). MS [M+H]⁺: 852.3.

Step 2: rac-tert-butyl (3R,4R)-3-[[(1S,5R)-6-[[2-chloro-4-[[5-[2,3-difluoro-4-[1-(2-methoxyethyl)-3,5-dimethyl-pyrazol-4-yl]phenyl]-1-methyl-imidazole-2-carbonyl]amino]benzoyl]amino]-3-azabicyclo[3.1.0]hexane-3-carbonyl]amino]-4-hydroxy-pyrrolidine-1-carboxylate In a 5 mL round-bottomed flask, rac-tert-butyl (3R,4R)-3-[[(1S,5R)-6-[[2-chloro-4-[[5-[2,3-difluoro-4-[1-(2-methoxyethyl)-3,5-dimethyl-pyrazol-4-yl]phenyl]-1-methyl-imidazole-2-carbonyl]amino]benzoyl]amino]-3-azabicyclo[3.1.0]hexane-3-carbonyl]amino]-4-hydroxy-pyrrolidine-1-carboxylate (15 mg, 17.6 µmol) was combined with DCM (150 µL) to give a light brown solution. HCl 4 M in dioxane (22 µL, 88 µmol) was added and the reaction mixture was stirred at RT. The reaction mixture was concentrated to dryness then lyophilized. To afford the title compound (14.1 mg). MS [M+H]⁺ 752.3.

Step 3: rac-(1S,5R)-6-[[2-chloro-4-[[5-[2,3-difluoro-4-[1-(2-methoxyethyl)-3,5-dimethyl-pyrazol-4-yl]phenyl]-1-methyl-imidazole-2-carbonyl]amino]benzoyl]amino]-N-[(3R,4R)-4-hydroxy-1,1-dimethyl-pyrrolidin-1-ium-3-yl]-3-azabicyclo[3.1.0]hexane-3-carboxamide; formate In a 5 mL round-bottomed flask, rac-tert-butyl (3R,4R)-3-[[(1S,5R)-6-[[2-chloro-4-[[5-[2,3-difluoro-4-[1-(2-methoxyethyl)-3,5-dimethyl-pyrazol-4-yl]phenyl]-1-methyl-imidazole-2-carbonyl]amino]benzoyl]amino]-3-azabicyclo[3.1.0]hexane-3-carbonyl]amino]-4-hydroxy-pyrrolidine-1-carboxylate (14 mg, 17.8 µmol) was combined with acetonitrile (300 µL) to give a light brown suspension. DIPEA (6.88 mg, 9.3 µl, 53.3 µmol) and MeI (6.05 mg, 42.6 µmol) were added and the reaction mixture was stirred overnight at RT. The reaction mixture was concentrated to dryness and submitted for purification to prep HPLC. Finally the product was lyophilized to afford the title compound (6.8 mg). MS [M]⁺: 780.3.

Example G1

N-[3-chloro-4-[4-(1,1-dimethylpiperidin-1-ium-4-carbonyl)piperazine-1-carbonyl]phenyl]-5-[2,3-difluoro-4-[1-[2-(isopropylamino)-2-oxo-ethyl]-3-methyl-pyrazol-4-yl]phenyl]-1-methyl-imidazole-2-carboxamide; formate

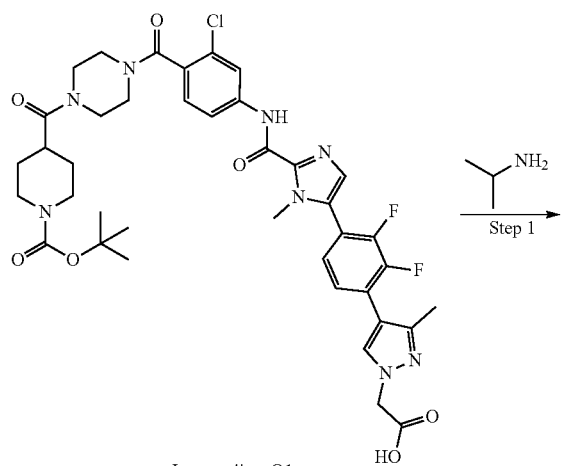

Intermediate O1

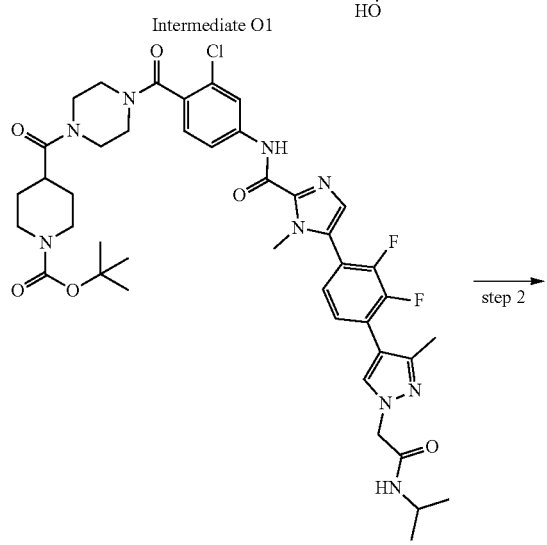

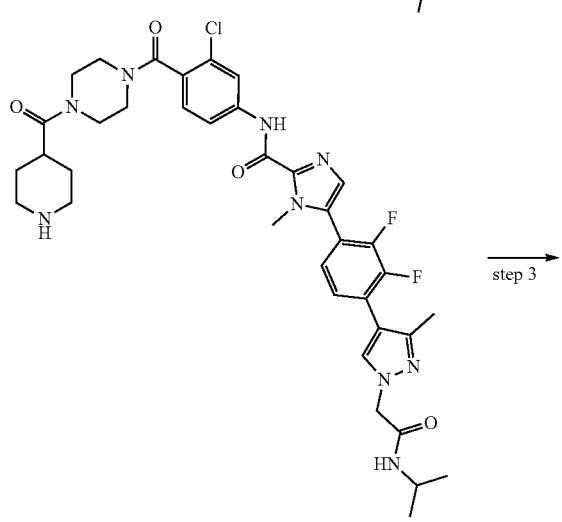

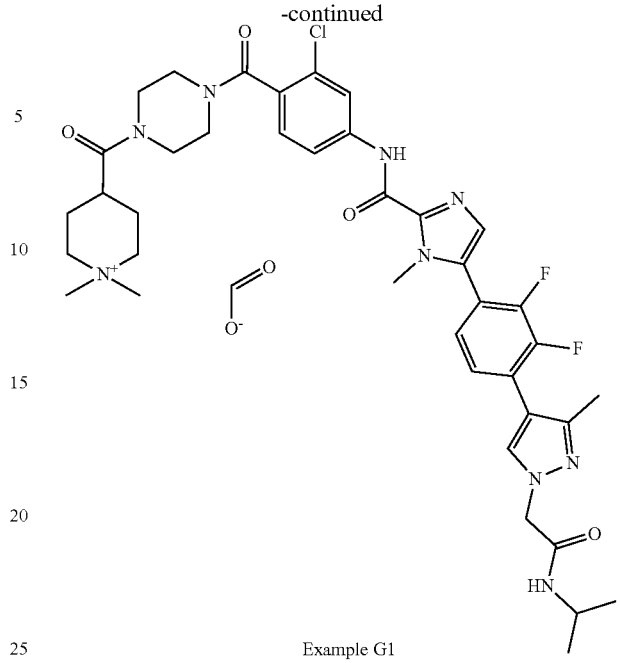

Example G1

Step 1: tert-butyl 4-[4-[2-chloro-4-[[5-[2,3-difluoro-4-[1-[2-(isopropylamino)-2-oxo-ethyl]-3-methyl-pyrazol-4-yl]phenyl]-1-methyl-imidazole-2-carbonyl]amino]benzoyl]piperazine-1-carbonyl]piperidine-1-carboxylate 2-[4-[4-[2-[[4-[4-(1-tert-butoxycarbonylisonipecotoyl)piperazine-1-carbonyl]-3-chloro-phenyl]carbamoyl]-3-methyl-imidazol-4-yl]-2,3-difluoro-phenyl]-3-methyl-pyrazol-1-yl]acetic acid (150 mg, 0.185 mmol), DIPEA (71.87 mg, 0.556 mmol) and isopropylamine (16.43 mg, 0.278 mmol) were dissolved in acetonitrile (1.85 mL). To this stirred solution was added HATU (84.57 mg, 0.222 mmol) in one portion. The resulting yellow solution was stirred at room temperature for 30 min. The solvent was removed in vacuo, and the residue was purified by flash chromatography to afford the product (141 mg). MS [M+H]$^+$: 850.8.

Step 2: N-[3-chloro-4-[4-(piperidine-4-carbonyl)piperazine-1-carbonyl]phenyl]-5-[2,3-difluoro-4-[1-[2-(isopropylamino)-2-oxo-ethyl]-3-methyl-pyrazol-4-yl]phenyl]-1-methyl-imidazole-2-carboxamide 4-[4-[2-chloro-4-[[5-[2,3-difluoro-4-[1-[2-(isopropylamino)-2-keto-ethyl]-3-methyl-pyrazol-4-yl]phenyl]-1-methyl-imidazole-2-carbonyl]amino]benzoyl]piperazine-1-carbonyl]piperidine-1-carboxylic acid tert-butyl ester (141 mg, 0.166 mmol) was stirred in 5 mL 1.5 N HCl/MeOH solution at room temperature for 5 h. The solvent was removed in vacuum, and the crude product (140 mg) was used without purification. MS [M+H]$^+$: 750.6.

Step 3: N-[3-chloro-4-[4-(1,1-dimethylpiperidin-1-ium-4-carbonyl)piperazine-1-carbonyl]phenyl]-5-[2,3-difluoro-4-[1-[2-(isopropylamino)-2-oxo-ethyl]-3-methyl-pyrazol-4-yl]phenyl]-1-methyl-imidazole-2-carboxamide; formate N-[3-chloro-4-[4-(piperidine-4-carbonyl)piperazine-1-carbonyl]phenyl]-5-[2,3-difluoro-4-[2-(isopropylamino)-

2-oxo-ethyl]-3-methyl-pyrazol-4-yl]phenyl]-1-methyl-imidazole-2-carboxamide (140 mg) was dissolved in N,N-dimethylacetamide (2 mL). To this solution was added DIPEA (214.3 mg, 1.66 mmol) and iodomethane (70.61 mg, 0.497 mmol). The solution was stirred at room temperature for 1 h. The product was purified by preparative HPLC directly to afford the product as amorphous powder (56 mg). MS [M]⁺: 778.5.

The following examples were prepared in analogy to Example G1.

| Ex# | Name | Structure | MS ESI [M]⁺ | Starting Material |
|---|---|---|---|---|
| Example G2 | 5-[4-[1-[2-(tert-butylamino)-2-oxo-ethyl]-3-methyl-pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide; formate | 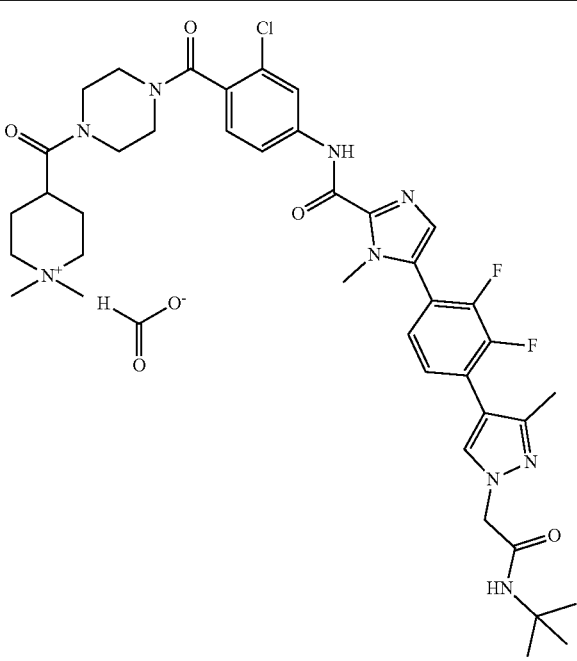 | 792.7 | Intermediate O1 and 2-methylpropan-2-amine; HCl; iodomethane. |
| Example G3 | 5-[4-[1-[2-(1-bicyclo[1.1.1]pentanylamino)-2-oxo-ethyl]-3-methyl-pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide; formate | 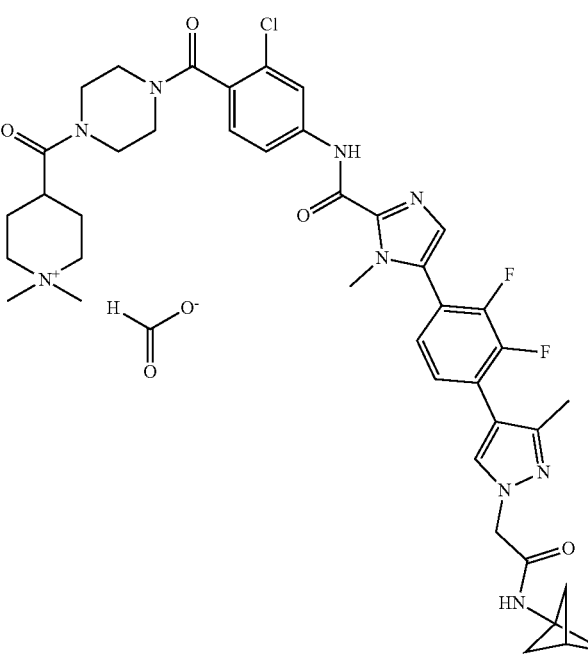 | 802.4 | Intermediate O1 and bicyclo[1.1.1]pentan-1-amine; HCl; iodomethane. |

-continued

| Ex# | Name | Structure | MS ESI [M]+ | Starting Material |
|---|---|---|---|---|
| Example G4 | N-[3-chloro-4-[4-(1,1-dimethylpiperidin-1-ium-4-carbonyl)piperazine-1-carbonyl]phenyl]-5-[4-[1-[2-[(3-cyano-1-bicyclo[1.1.1]pentanyl)amino]-2-oxo-ethyl]-3-methyl-pyrazol-4-yl]-2,3-difluoro-phenyl]-1-methyl-imidazole-2-carboxamide; formate | 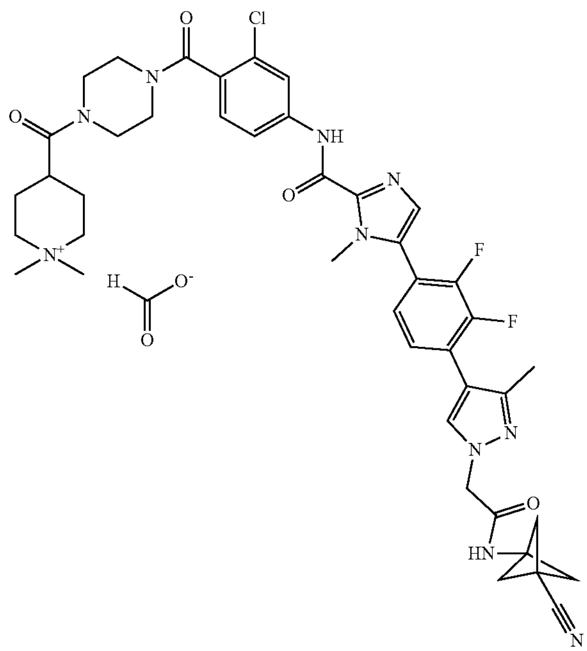 | 827.5 | Intermediate O1 and 3-aminobicyclo[1.1.1]pentane-1-carbonitrile; HCl; iodomethane. |
| Example G5 | 5-[4-[1-(2-anilino-2-oxo-ethyl)-3-methyl-pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide; formate | 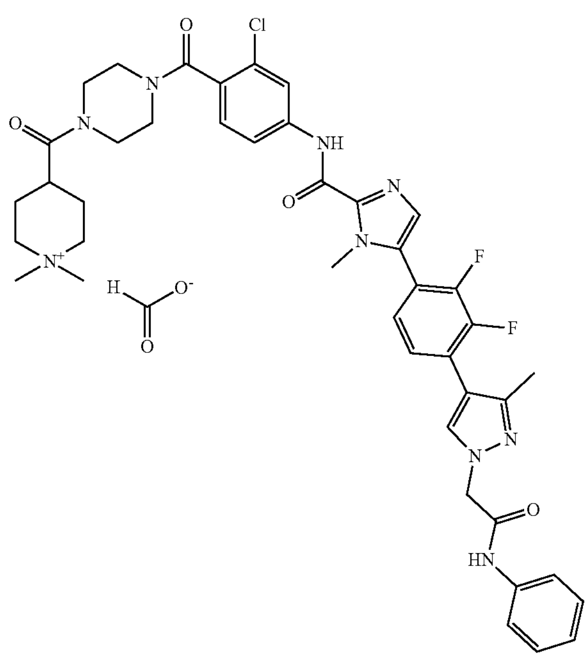 | 812.6 | Intermediate O1 and aniline; HCl; iodomethane. |

-continued

| Ex# | Name | Structure | MS ESI [M]+ | Starting Material |
|---|---|---|---|---|
| Example G6 | N-[3-chloro-4-[4-(1,1-dimethylpiperidin-1-ium-4-carbonyl)piperazine-1-carbonyl]phenyl]-5-[2,3-difluoro-4-[1-[2-(2-fluoroanilino)-2-oxo-ethyl]-3-methyl-pyrazol-4-yl]phenyl]-1-methyl-imidazole-2-carboxamide; formate | 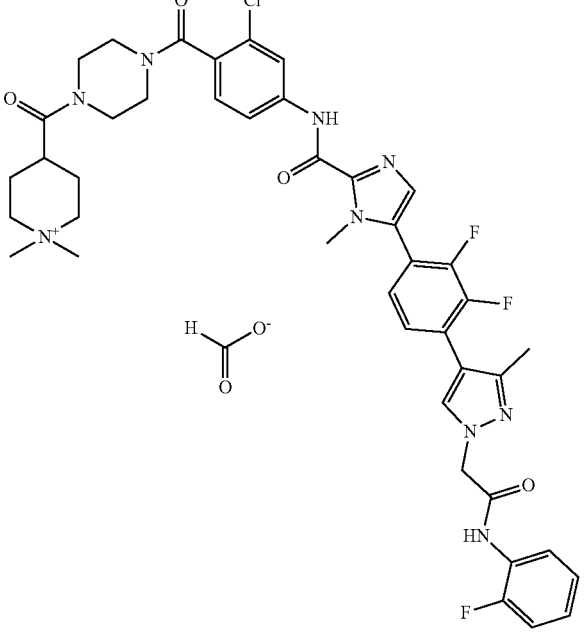 | 830.4 | Intermediate O1 and 2-fluoroaniline; HCl; iodomethane. |
| Example G7 | N-[3-chloro-4-[4-(1,1-dimethylpiperidin-1-ium-4-carbonyl)piperazine-1-carbonyl]phenyl]-5-[2,3-difluoro-4-[1-[2-(2-methoxyanilino)-2-oxo-ethyl]-3-methyl-pyrazol-4-yl]phenyl]-1-methyl-imidazole-2-carboxamide; formate | 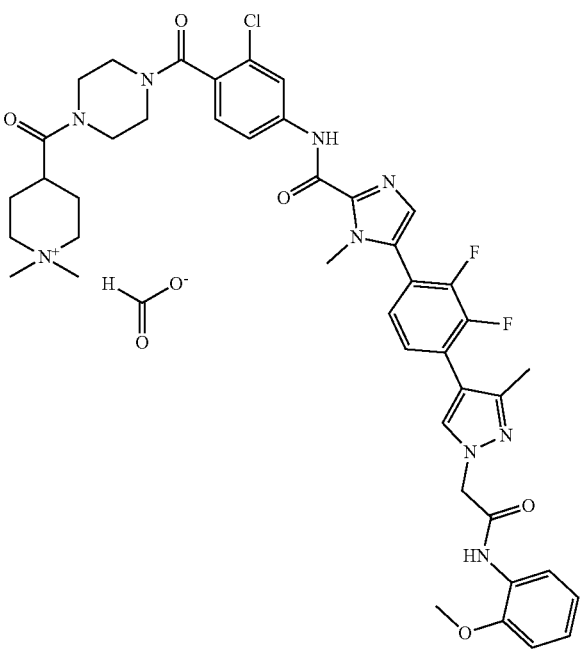 | 842.4 | Intermediate O1 and 2-methoxyaniline; HCl; iodomethane |

-continued

| Ex# | Name | Structure | MS ESI [M]+ | Starting Material |
|---|---|---|---|---|
| Example G8 | N-[3-chloro-4-[4-(1,1-dimethylpiperidin-1-ium-4-carbonyl)piperazine-1-carbonyl]phenyl]-5-[2,3-difluoro-4-[1-[2-(4-fluoroanilino)-2-oxo-ethyl]-3-methyl-pyrazol-4-yl]phenyl]-1-methyl-imidazole-2-carboxamide; formate | 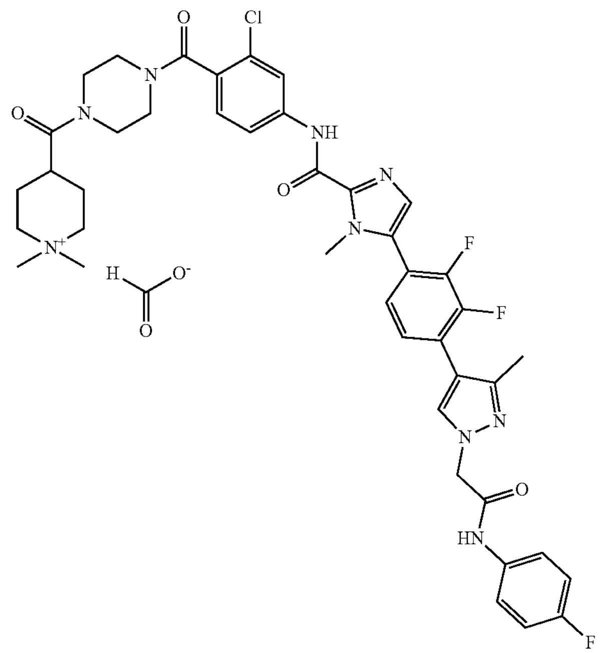 | 830.4 | Intermediate O1 and 4-fluoroaniline; HCl; iodomethane |
| Example G9 | N-[3-chloro-4-[4-(1,1-dimethylpiperidin-1-ium-4-carbonyl)piperazine-1-carbonyl]phenyl]-5-[4-[1-[2-(cyclohexylamino)-2-oxo-ethyl]-3-methyl-pyrazol-4-yl]-2,3-difluoro-phenyl]-1-methyl-imidazole-2-carboxamide; formate | 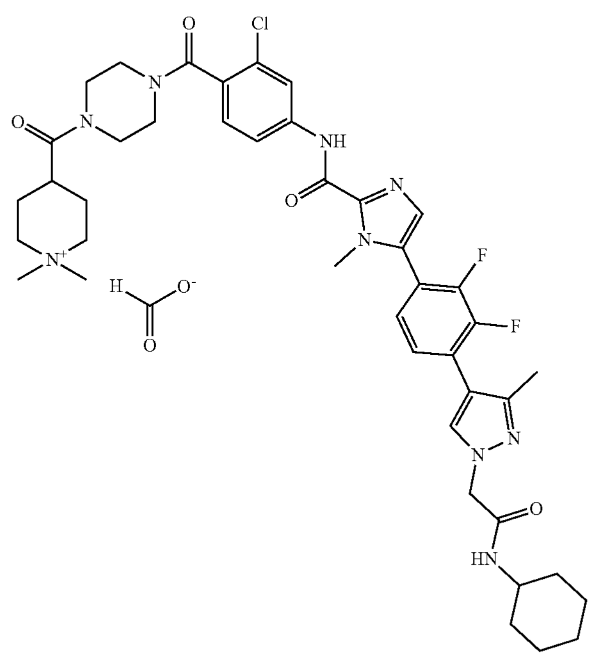 | 818.4 | Intermediate O1 and cyclo-hexanamine; HCl; iodomethane |

-continued

| Ex# | Name | Structure | MS ESI [M]+ | Starting Material |
|---|---|---|---|---|
| Example G10 | N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(thiazol-2-ylamino)ethyl]pyrazol-4-yl]phenyl]-1-methyl-imidazole-2-carboxamide; formate | 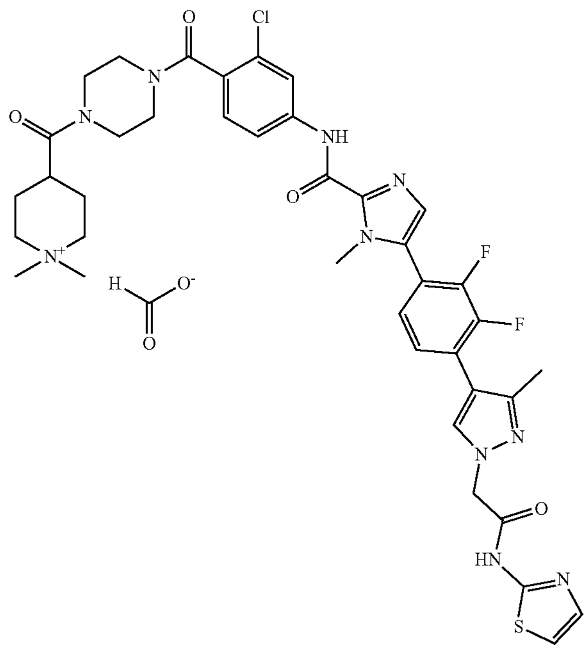 | 819.3 | Intermediate O1 and thiazol-2-amine; HCl; iodomethane |
| Example G11 | N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(1H-pyrazol-4-ylamino)ethyl]pyrazol-4-yl]phenyl]-1-methyl-imidazole-2-carboxamide; formate | 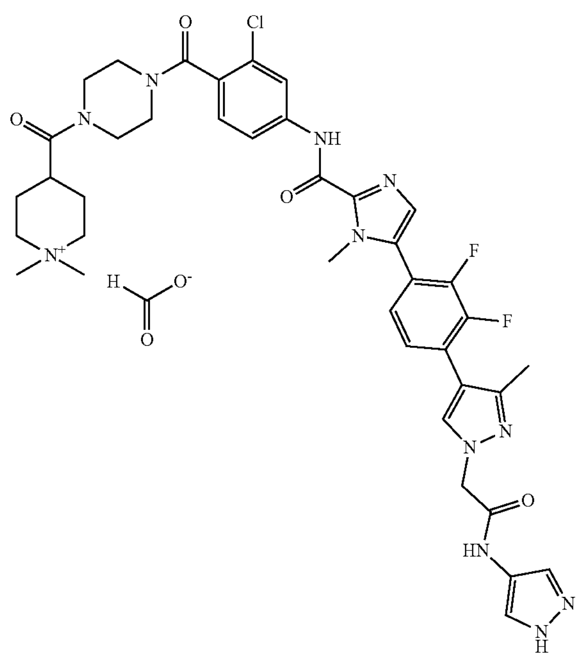 | 802.3 | Intermediate O1 and 1H-pyrazol-4-amine; HCl; iodomethane |

| Ex# | Name | Structure | MS ESI [M]+ | Starting Material |
|---|---|---|---|---|
| Example G12 | N-[3-chloro-4-[4-(1,1-dimethylpiperidin-1-ium-4-carbonyl)piperazine-1-carbonyl]phenyl]-5-[2,3-difluoro-4-[3-methyl-1-[2-[(1-methylpyrazol-4-yl)amino]-2-oxo-ethyl]pyrazol-4-yl]phenyl]-1-methyl-imidazole-2-carboxamide; formate | 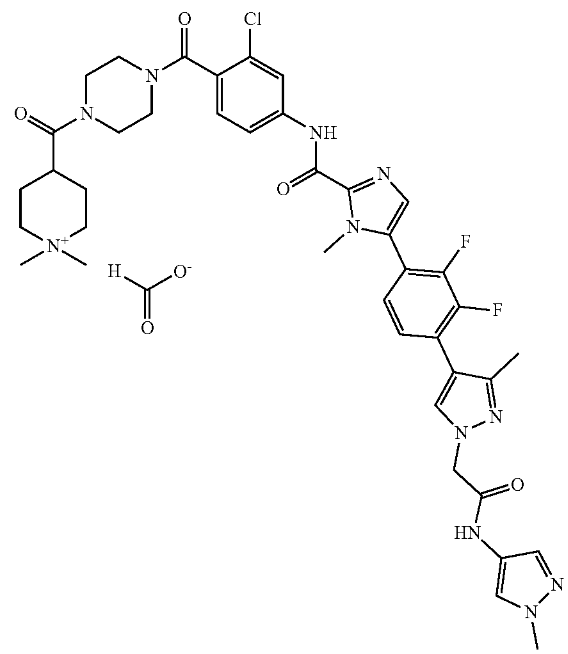 | 816.3 | Intermediate O1 and 1-methylpyrazol-4-amine; HCl; iodomethane |
| Example G13 | N-[3-chloro-4-[4-(1,1-dimethylpiperidin-1-ium-4-carbonyl)piperazine-1-carbonyl]phenyl]-5-[2,3-difluoro-4-[1-[2-(3-fluoroanilino)-2-oxo-ethyl]-3-methyl-pyrazol-4-yl]phenyl]-1-methyl-imidazole-2-carboxamide; chloride | 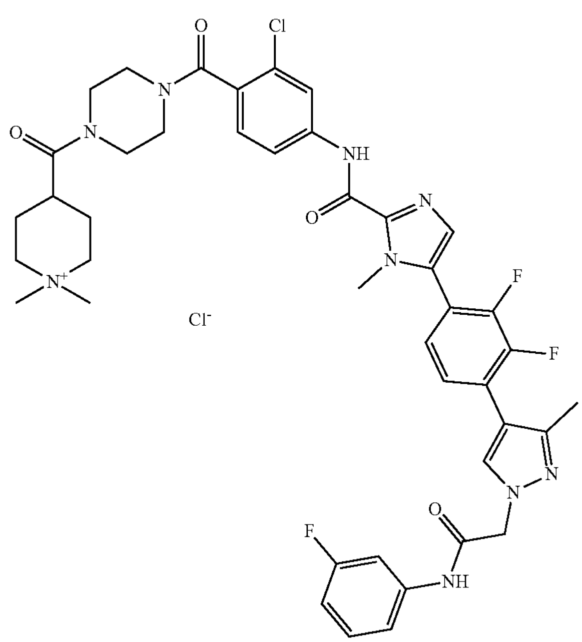 [SMILES: Cc1nn(CC(=O)Nc2cccc(F)c2)cc1-c1ccc(-c2cnc(C(=O)Nc3ccc(C(=O)N4CCN(C(=O)C5CC[N+](C)(C)CC5)CC4)c(Cl)c3)n2C)c(F)c1F ; [Cl-]] | 830.4 | Intermediate O1 and 3-fluoroaniline; HCl; iodomethane |

| Ex# | Name | Structure | MS ESI [M]+ | Starting Material |
|---|---|---|---|---|
| Example G14 | N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(2-pyridylamino)ethyl]pyrazol-4-yl]phenyl]-1-methyl-imidazole-2-carboxamide; formate | 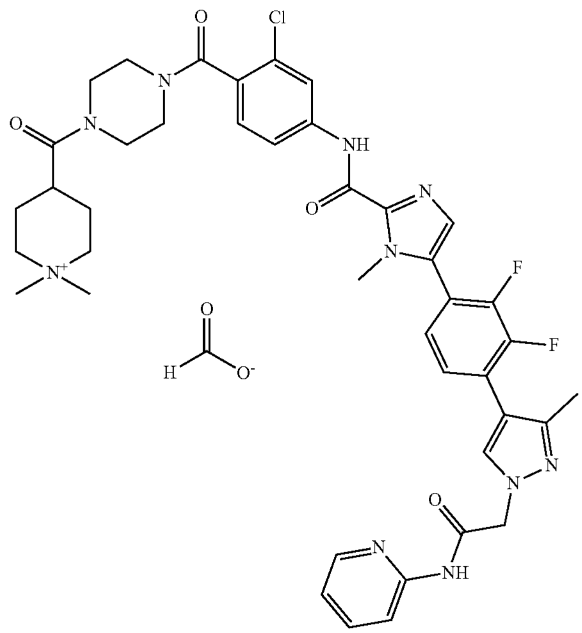 | 813.4 | Intermediate O1 and pyridin-2-amine; HCl; iodomethane |
| Example G15 | N-[3-chloro-4-[4-(1,1-dimethylpiperidin-1-ium-4-carbonyl)piperazine-1-carbonyl]phenyl]-5-[2,3-difluoro-4-[3-methyl-1-[2-[(1-methylpyridin-1-ium-3-yl)amino]-2-oxo-ethyl]pyrazol-4-yl]phenyl]-1-methyl-imidazole-2-carboxamide; diformate | 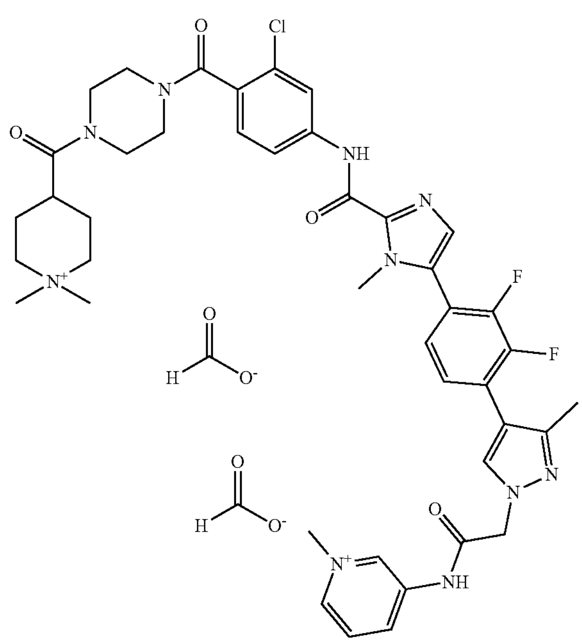 | 827.4 | Intermediate O1 and pyridin-3-amine; HCl; iodomethane |

-continued

| Ex# | Name | Structure | MS ESI [M]+ | Starting Material |
|---|---|---|---|---|
| Example G16 | N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(pyrimidin-2-ylamino)ethyl]pyrazol-4-yl]phenyl]-1-methyl-imidazole-2-carboxamide; formate | 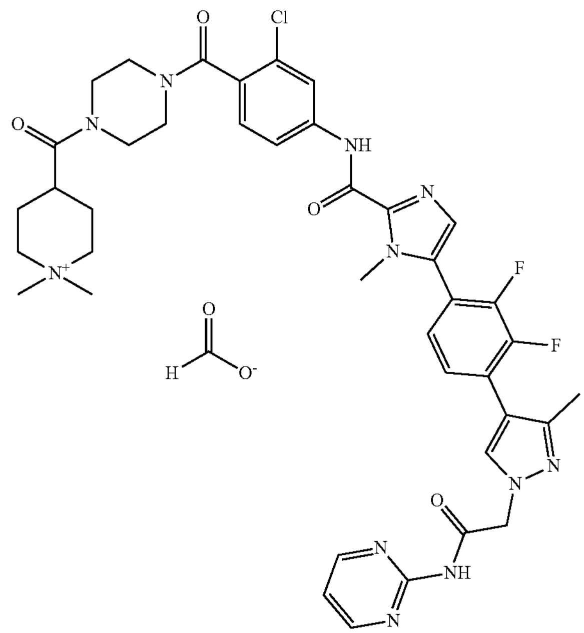 | 814.3 | Intermediate O1 and pyrimidin-2-amine; HCl; iodomethane |
| Example G17 | N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(4-pyridylamino)ethyl]pyrazol-4-yl]phenyl]-1-methyl-imidazole-2-carboxamide; chloride | 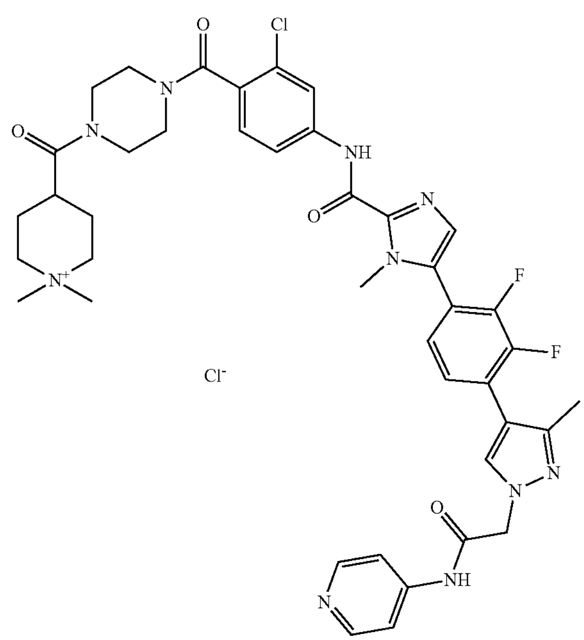 [SMILES: Cc1nn(CC(=O)Nc2ccncc2)cc1-c1ccc(-c2cnc(C(=O)Nc3ccc(C(=O)N4CCN(C(=O)C5CC[N+](C)(C)CC5)CC4)c(Cl)c3)n2C)c(F)c1F ; [Cl-]] | 813.2 | Intermediate O1 and pyridin-4-amine; HCl; iodomethane |

-continued

| Ex# | Name | Structure | MS ESI [M]+ | Starting Material |
|---|---|---|---|---|
| Example G18 | 5-[4-[1-[2-(tert-butylamino)-2-oxo-ethyl]-5-methyl-pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide; formate | 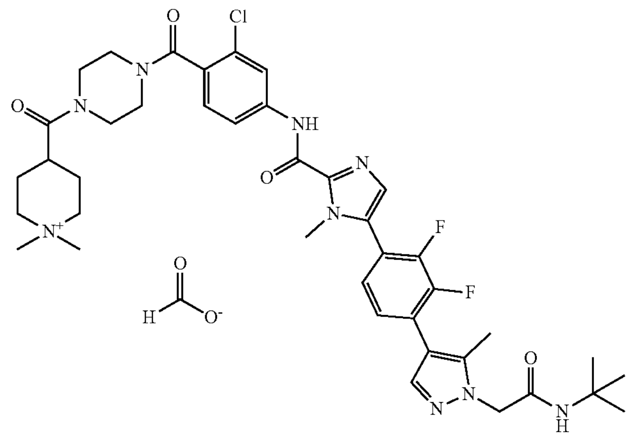 | 792.3 | Intermediate O2 and 2-methylpropan-2-amine; HCl; iodomethane |
| Example G19 | N-[3-chloro-4-[4-(1,1-dimethylpiperidin-1-ium-4-carbonyl)piperazine-1-carbonyl]phenyl]-5-[2,3-difluoro-4-[5-methyl-1-[2-oxo-2-(2-pyridylamino)ethyl]pyrazol-4-yl]phenyl]-1-methyl-imidazole-2-carboxamide; formate | 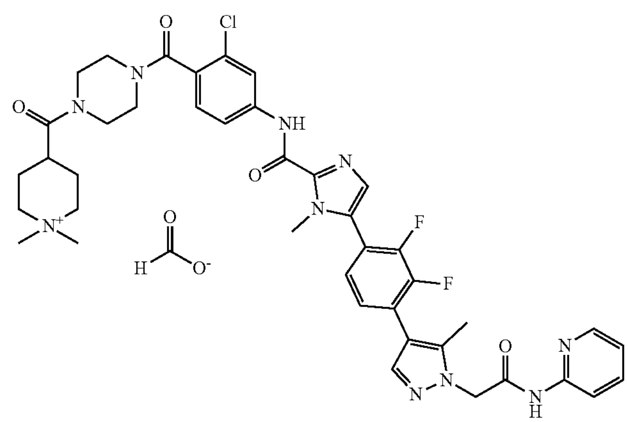 | 813.3 | Intermediate O2 and pyridin-2-amine; HCl; iodomethane |
| Example G20 | N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(tetrahydrofuran-3-ylamino)ethyl]pyrazol-4-yl]phenyl]-1-methyl-imidazole-2-carboxamide; formate | 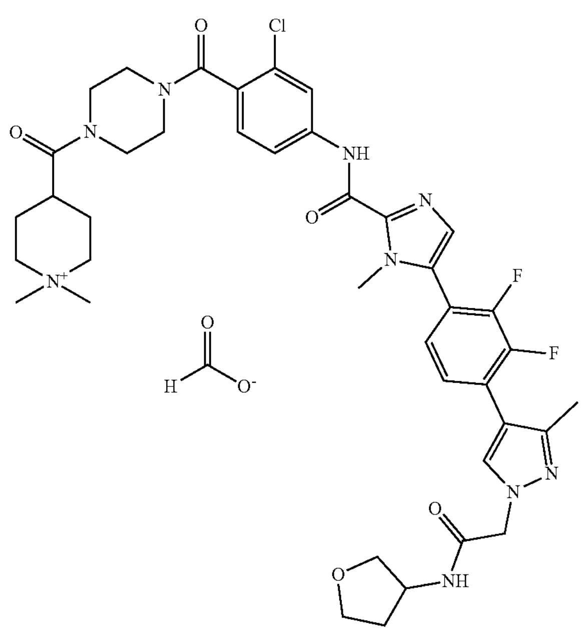 | 806.6 | Intermediate O1 and tetrahydrofuran-3-amine; HCl; iodomethane |

-continued

| Ex# | Name | Structure | MS ESI [M]+ | Starting Material |
|---|---|---|---|---|
| Example G21 | N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(tetrahydropyran-2-ylamino)ethyl]pyrazol-4-yl]phenyl]-1-methyl-imidazole-2-carboxamide; formate | 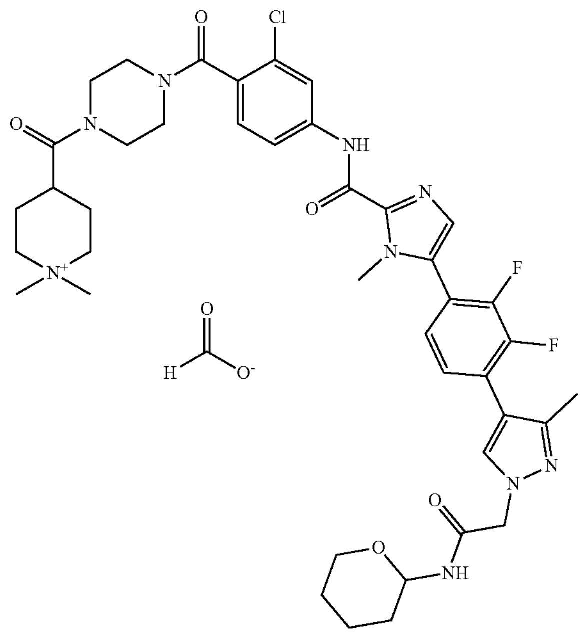 | 820.3 | Intermediate O1 and tetrahydropyran-2-amine; HCl; iodomethane |
| Example G22 | N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(tetrahydropyran-3-ylamino)ethyl]pyrazol-4-yl]phenyl]-1-methyl-imidazole-2-carboxamide; formate | 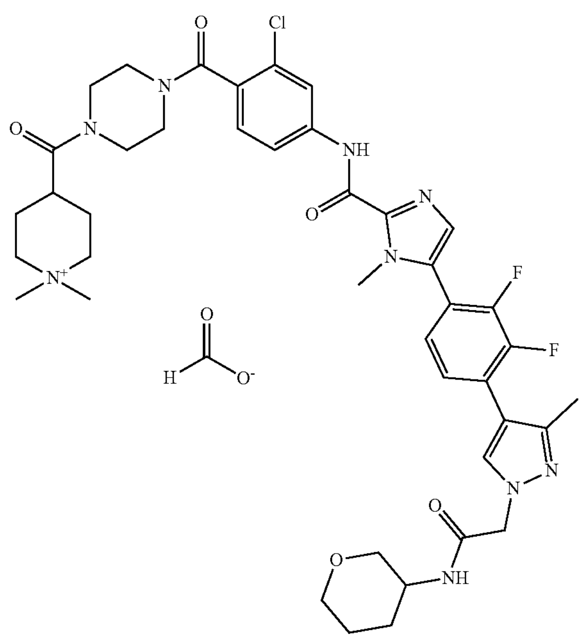 | 820.3 | Intermediate O1 and intermediate R8; HCl; iodomethane |

| Ex# | Name | Structure | MS ESI [M]+ | Starting Material |
|---|---|---|---|---|
| Example G23 | N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(pyridazin-3-ylamino)ethyl]pyrazol-4-yl]phenyl]-1-methyl-imidazole-2-carboxamide; formate | 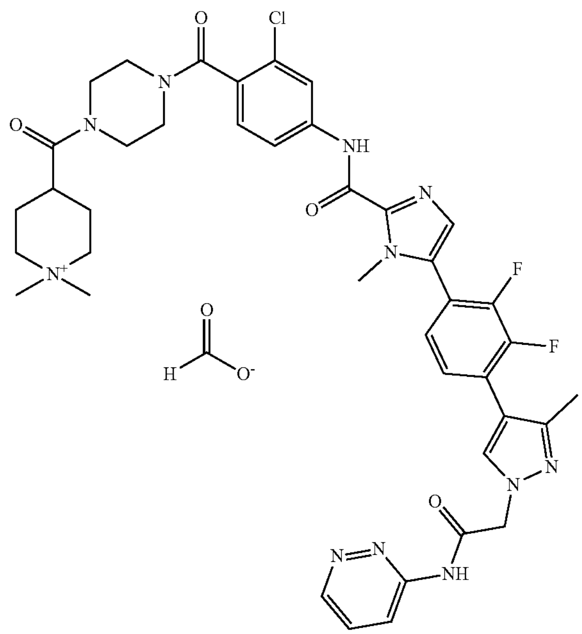 | 814.5 | Intermediate O1 and pyridazin-3-amine; HCl; iodomethane |
| Example G24 | N-[3-chloro-4-[4-(1,1-dimethylpiperidin-1-ium-4-carbonyl)piperazine-1-carbonyl]phenyl]-5-[4-[1-[2-[(0,1-dimethylpiperidin-1-ium-3-yl)amino]-2-oxo-ethyl]-3-methyl-pyrazol-4-yl]-2,3-difluoro-phenyl]-1-methyl-imidazole-2-carboxamide; diformate | 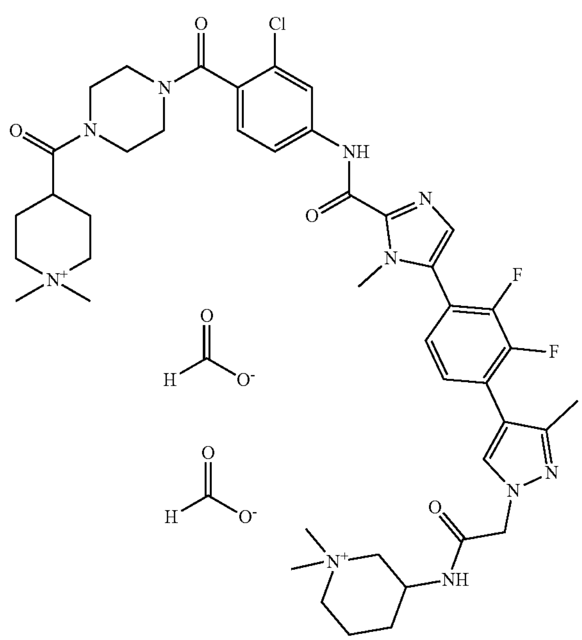 | 424.6 | Intermediate O1 and benzyl 3-aminopiperidine-1-carboxylate; HCl; iodomethane |

| Ex# | Name | Structure | MS ESI [M]+ | Starting Material |
|---|---|---|---|---|
| Example G25 | N-[3-chloro-4-[4-(1,1-dimethylpiperidin-1-ium-4-carbonyl)piperazine-1-carbonyl]phenyl]-5-[2,3-difluoro-4-[5-methyl-1-[2-oxo-2-(pyridazin-3-ylamino)ethyl]pyrazol-4-yl]phenyl]-1-methyl-imidazole-2-carboxamide; formate | 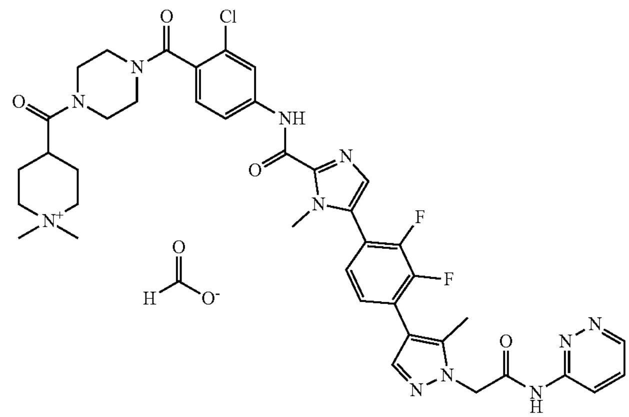 | 814.0 | Intermediate O2 and pyridazin-3-amine; HCl; iodomethane |
| Example G26 | N-[3-chloro-4-[4-(1,1-dimethylpiperidin-1-ium-4-carbonyl)piperazine-1-carbonyl]phenyl]-5-[4-[1-[2-[(4,4-difluorocyclohexyl)amino]-2-oxo-ethyl]-3-methyl-pyrazol-4-yl]-2,3-difluoro-phenyl]-1-methyl-imidazole-2-carboxamide; formate | 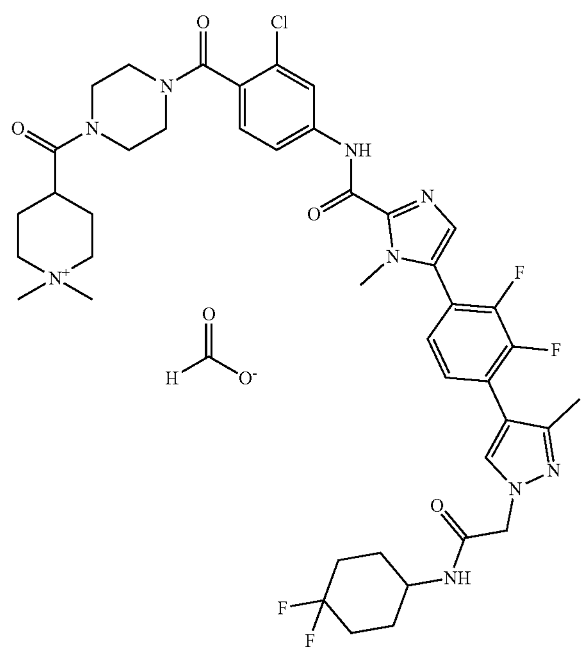 | 854.4 | Intermediate O1 and 4,4-difluorocyclohexanamine; HCl; iodomethane |

| Ex# | Name | Structure | MS ESI [M]+ | Starting Material |
|---|---|---|---|---|
| Example G27 | N-[3-chloro-4-[4-(1,1-dimethylpiperidin-1-ium-4-carbonyl)piperazine-1-carbonyl]phenyl]-5-[2,3-difluoro-4-[3-pyridylamino)ethyl]pyrazol-4-yl]phenyl]-1-methyl-imidazole-2-carboxamide; formate | 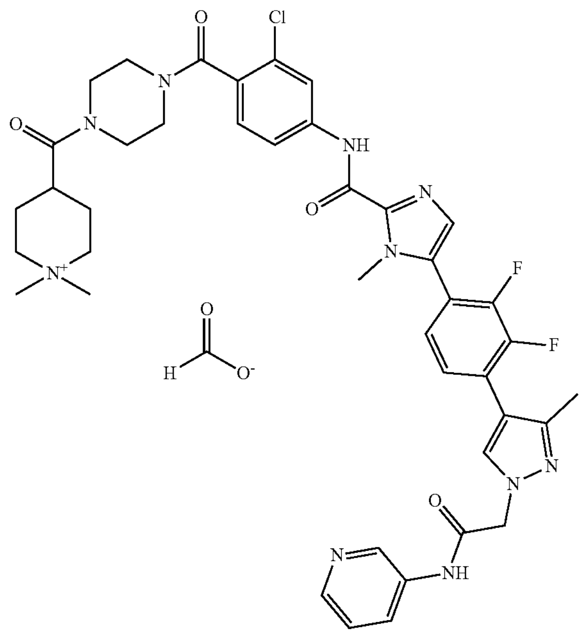 | 813.6 | Intermediate O1 and pyridin-3-amine; HCl; iodomethane |
| Example G28 | N-[3-chloro-4-[4-(1,1-dimethylpiperidin-1-ium-4-carbonyl)piperazine-1-carbonyl]phenyl]-5-[2,3-difluoro-4-[1-[2-[(5-methoxy-2-pyridyl)amino]-2-oxo-ethyl]-3-methyl-pyrazol-4-yl]phenyl]-1-methyl-imidazole-2-carboxamide; formate | 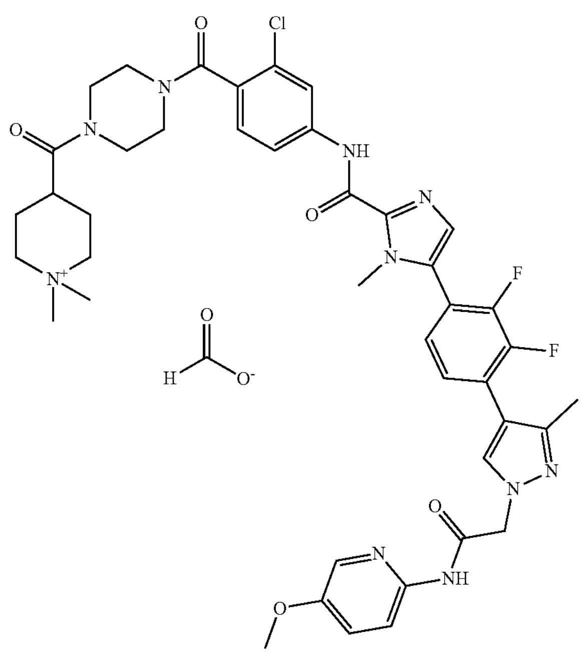 | 845.1 | Intermediate O1 and 5-methoxypyridin-2-amine; HCl; iodomethane |

-continued

| Ex# | Name | Structure | MS ESI [M]+ | Starting Material |
|---|---|---|---|---|
| Example G29 | N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(1-piperidyl)ethyl]pyrazol-4-yl]phenyl]-1-methyl-imidazole-2-carboxamide; formate | 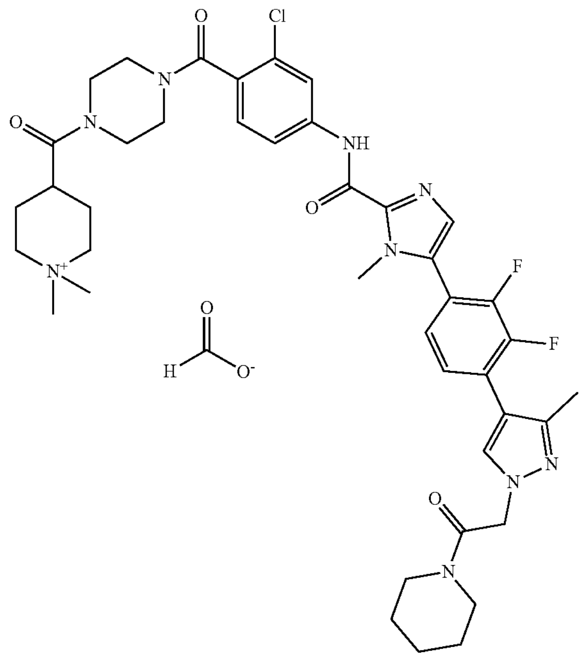 | 804.4 | Intermediate O1 and piperidine; HCl; iodomethane |
| Example G30 | N-[3-chloro-4-[4-(1,1-dimethylpiperidin-1-ium-4-carbonyl)piperazine-1-carbonyl]phenyl]-5-[4-[1-[2-[4-(4,4-dimethylpiperazin-4-ium-1-carbonyl)anilino]-2-oxo-ethyl]-3-methyl-pyrazol-4-yl]-2,3-difluoro-phenyl]-1-methyl-imidazole-2-carboxamide; diformate | 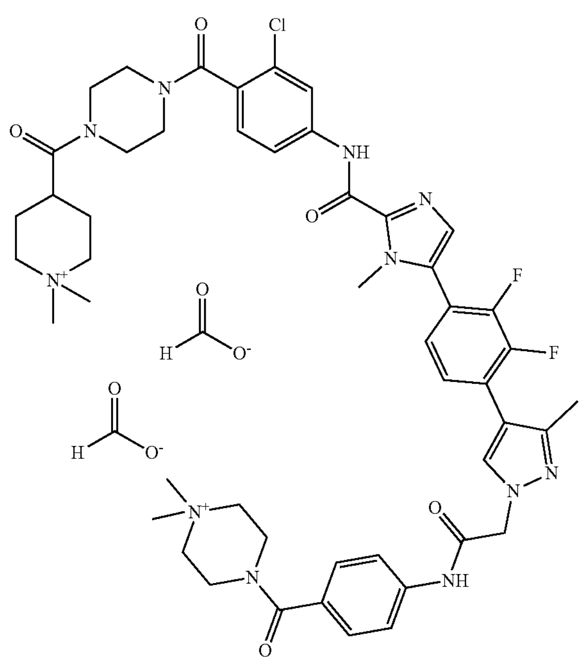 | 477.1 | Intermediate O1 and (4-aminophenyl)-(4-methylpiperazin-1-yl)methanone; HCl; iodomethane |

-continued

| Ex# | Name | Structure | MS ESI [M]+ | Starting Material |
|---|---|---|---|---|
| Example G31 | N-[3-chloro-4-[4-(1,1-dimethylpiperidin-1-ium-4-carbonyl)piperazine-1-carbonyl]phenyl]-5-[2,3-difluoro-4-[1-[2-[(6-fluoropyridazin-3-yl)amino]-2-oxo-ethyl]-3-methyl-pyrazol-4-yl]phenyl]-1-methyl-imidazole-2-carboxamide; formate | 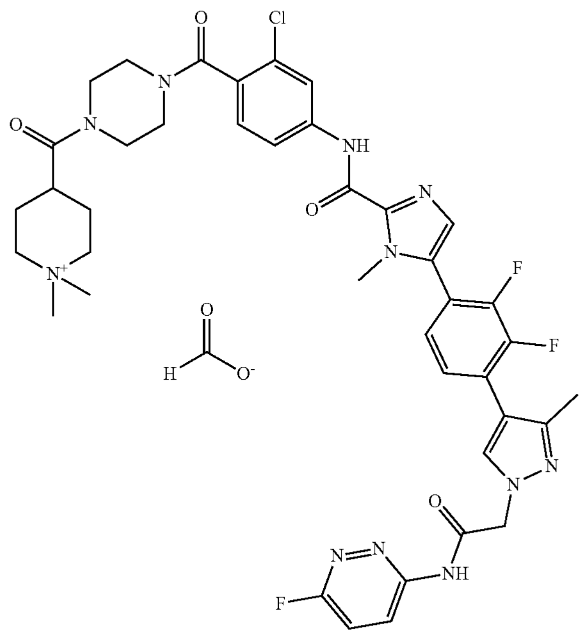 | 832.3 | Intermediate O1 and 6-fluoropyridazin-3-amine; HCl; iodomethane |
| Example G32 | N-[3-chloro-4-[4-(1,1-dimethylpiperidin-1-ium-4-carbonyl)piperazine-1-carbonyl]phenyl]-5-[2,3-difluoro-4-[1-[2-[[(1S,2S)-2-methoxycyclohexyl]amino]-2-oxo-ethyl]-3-methyl-pyrazol-4-yl]phenyl]-1-methyl-imidazole-2-carboxamide; formate | 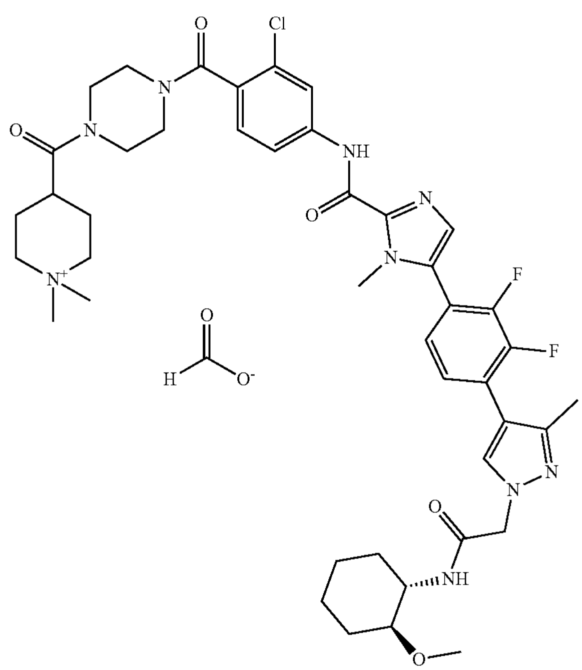 | 848.5 | Intermediate O1 and rac-(1S,2S)-2-methoxycyclohexanamine; HCl; iodomethane |

| Ex# | Name | Structure | MS ESI [M]+ | Starting Material |
|---|---|---|---|---|
| Example G33 | N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(pyridazin-4-ylamino)ethyl]pyrazol-4-yl]phenyl]-1-methyl-imidazole-2-carboxamide; formate | 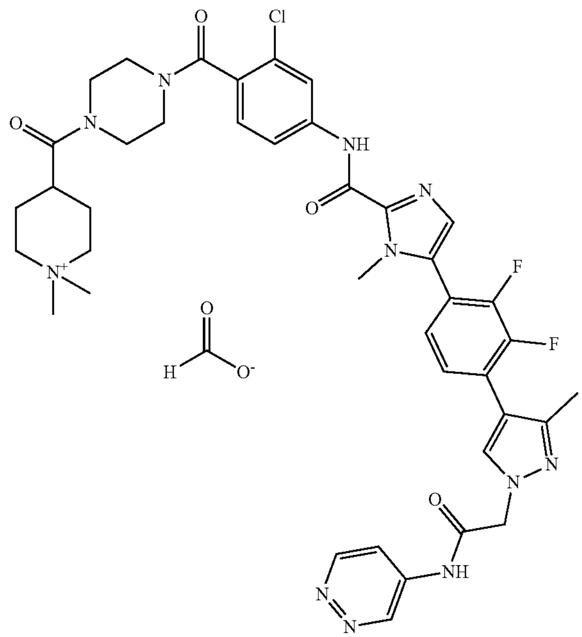 | 814.5 | Intermediate O1 and pyridazin-4-amine; HCl; iodomethane |
| Example G34 | N-[3-chloro-4-[4-(1,1-dimethylpiperidin-1-ium-4-carbonyl)piperazine-1-carbonyl]phenyl]-5-[4-[1-[2-[(6-cyano-3-pyridyl)amino]-2-oxo-ethyl]-3-methyl-pyrazol-4-yl]-2,3-difluoro-phenyl]-1-methyl-imidazole-2-carboxamide; formate | 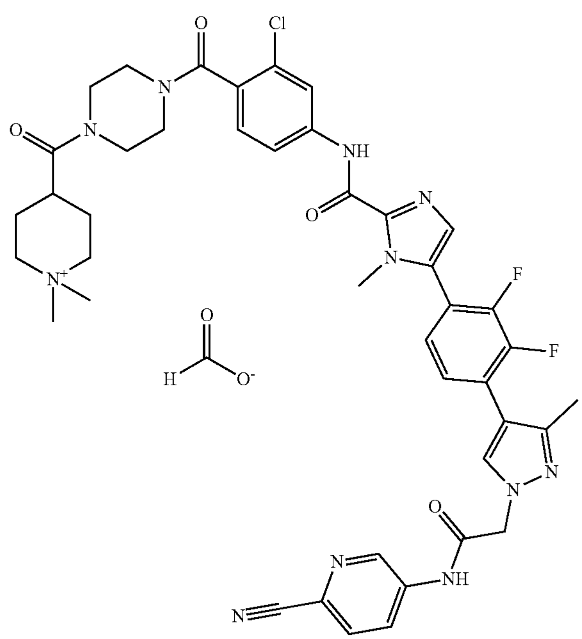 | 838.4 | Intermediate O1 and pyridazin-4-amine; HCl; iodomethane |

Example H1
N-[2-[4-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]-2,3-difluorophenyl]-5-methyl-pyrazol-1-yl]ethyl]pyridine-2-carboxamide formate
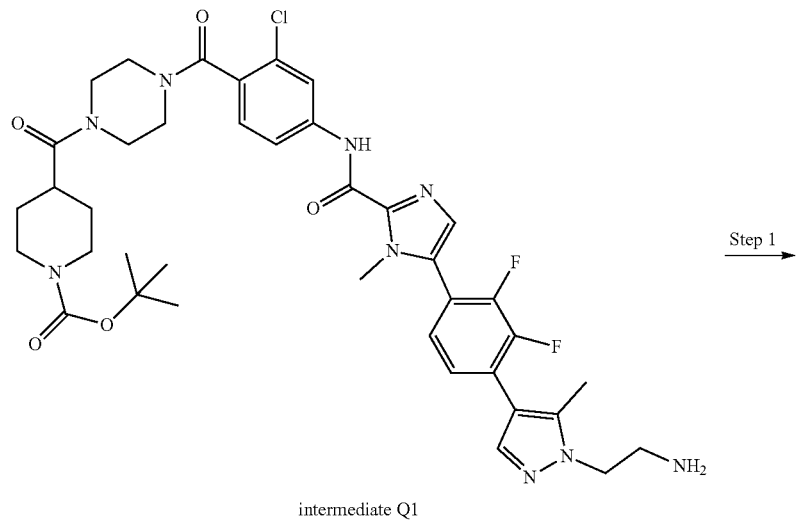
intermediate Q1
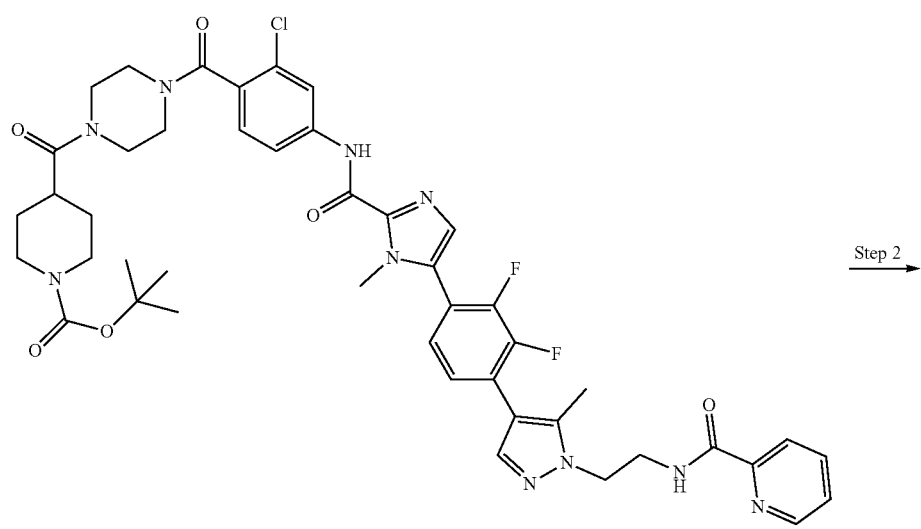

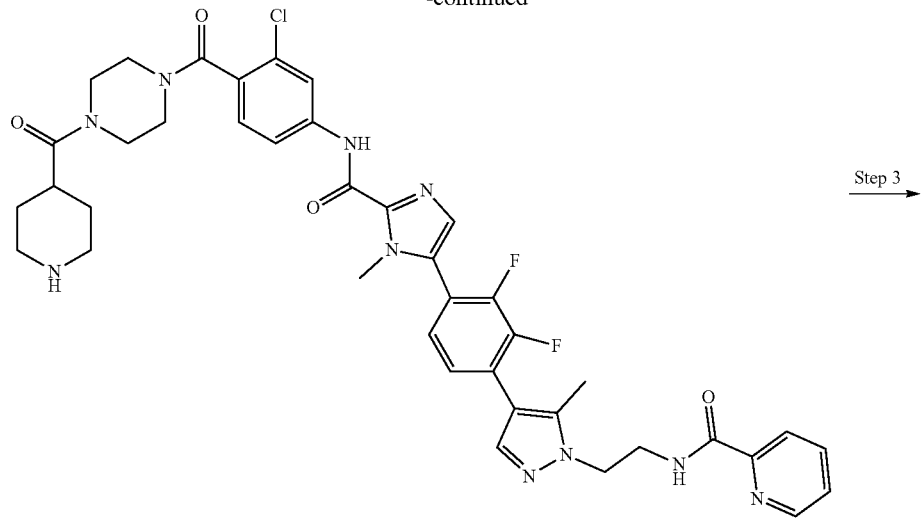

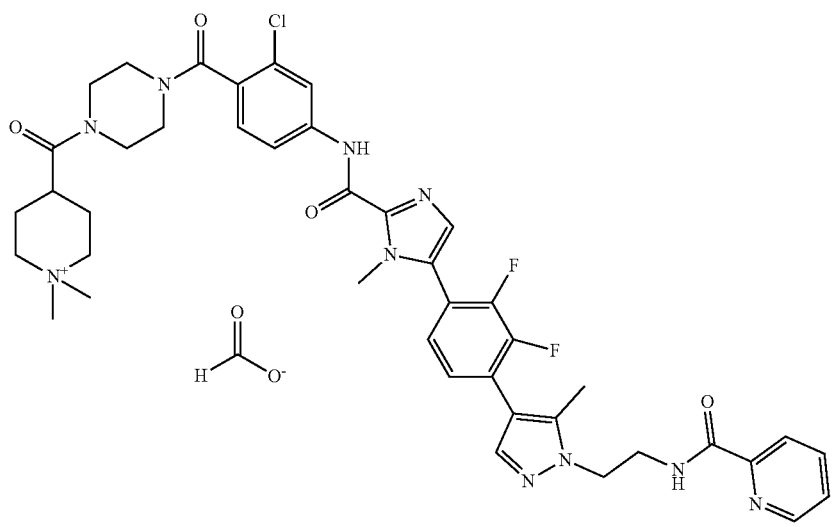

Example H1

Step 1: tert-butyl 4-[4-[2-chloro-4-[[5-[2,3-difluoro-4-[5-methyl-1-[2-(pyridine-2-carbonylamino)ethyl]pyrazol-4-yl]phenyl]-1-methyl-imidazole-2-carbonyl]amino]benzoyl]piperazine-1-carbonyl]piperidine-1-carboxylate tert-butyl 4-[4-[4-[[5-[4-[1-(2-aminoethyl)-5-methyl-pyrazol-4-yl]-2,3-difluoro-phenyl]-1-methyl-imidazole-2-carbonyl]amino]-2-chloro-benzoyl]piperazine-1-carbonyl]piperidine-1-carboxylate (100 mg, 0.126 mmol) was dissolved in dichloromethane (5 mL), 2-picolinic acid (18.6 mg, 0.151 mmol), HATU (57.44 mg, 0.151 mmol) and DIEA (32.54 mg, 0.252 mmol) were added at rt. The mixture was stirred at room temperature for 1 h. The reaction mixture was diluted with water (30 mL) and extracted two times with DCM (25 mL). The organic layers were washed with brine (20 mL), dried over $Na_2SO_4$ and concentrated to dryness. the crude product was directly used to the next step. to afford tert-butyl 4-[4-[2-chloro-4-[[5-[2,3-difluoro-4-[5-methyl-1-[2-(pyridine-2-carbonylamino)ethyl]pyrazol-4-yl]phenyl]-1-methyl-imidazole-2-carbonyl]amino]benzoyl]piperazine-1-carbonyl]piperidine-1-carboxylate (113 mg). MS $[M+H]^+$: 899.7.

Step 2: N-[2-[4-[4-[2-[[3-chloro-4-[(piperidine-4-carbonyl)piperazine-1-carbonyl]phenyl]carbamoyl]-3-methyl-imidazol-4-yl]-2,3-difluoro-phenyl]-5-methyl-pyrazol-1-yl]ethyl]pyridine-2-carboxamide tert-butyl 4-[4-[2-chloro-4-[[5-[2,3-difluoro-4-[5-methyl-1-[2-(pyridine-2-carbonylamino)ethyl]pyrazol-4-yl]phenyl]-1-methyl-imidazole-2-carbonyl]amino]benzoyl]piperazine-1-carbonyl]piperidine-1-carboxylate (113 mg, 0.126 mmol) was dissolved in tetrahydrofuran (2 mL) and 12 M HCl (in water) (628.21 mg, 6.28 mmol) was added at rt. The mixture was stirred at room temperature for 1 h. The reaction mixture was concentrated under vacuum, the crude product was directly used to the next step, to afford N-[2-[4-[4-[2-[[3-chloro-4-[4-(piperidine-4-carbonyl)piperazine-1-carbonyl]phenyl]carbamoyl]-3-methyl-imidazol-4-yl]-2,3-difluoro-phenyl]-5-methyl-pyrazol-1-yl]ethyl]pyridine-2-carboxamide (100 mg) as light brown solid. MS $[M+H]^+$: 799.9.

Step 3: N-[2-[4-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]-2,3-difluoro-phenyl]-5-methyl-pyrazol-1-yl]ethyl]pyridine-2-carboxamide; formate N-[2-[4-[4-[2-[[3-chloro-4-[4-(piperidine-4-carbonyl)piperazine-1-carbonyl]phenyl]carbamoyl]-3-methyl-imidazol-4-yl]-2,3-difluoro-phenyl]-5-methyl-pyrazol-1-yl]ethyl]pyridine-2-carboxamide (100 mg, 0.125 mmol) was dissolved in acetonitrile (6 mL), iodomethane (53.28 mg, 0.375 mmol) and DIEA (48.51 mg, 0.375 mmol) were added at rt. The mixture was stirred at room temperature for 1 h. The reaction was concentrated under vacuum, the crude product was purified by HPLC to afford N-[2-[4-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]-2,3-difluoro-phenyl]-5-methyl-pyrazol-1-yl]ethyl]pyridine-2-carboxamide;formate (56.6 mg) as white powder. MS [M]$^+$: 828.1.

The following examples were prepared in analogy to Examples H1.

| Ex# | Name | Structure | MS ESI [M]$^+$ | Starting Material |
|---|---|---|---|---|
| Example H2 | N-[2-[4-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]-2,3-difluoro-phenyl]-3-methyl-pyrazol-1-yl]ethyl]pyridine-2-carboxamide; formate | 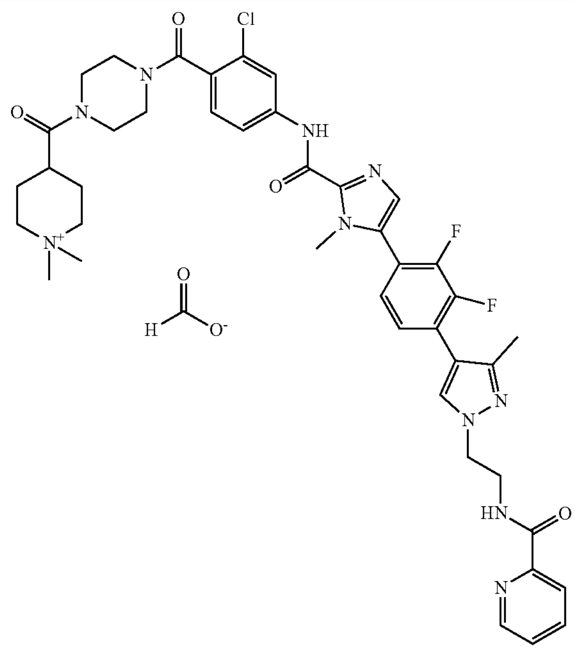 | 827.7 | Intermediate Q2 and 2-picolinic acid; HCl iodomethane |
| Example H3 | N-[3-chloro-4-[4-(1,1-dimethylpiperidin-1-ium-4-carbonyl)piperazine-1-carbonyl]phenyl]-5-[2,3-difluoro-4-[1-[2-[(4-fluorophenyl)sulfonylamino]ethyl]-3-methyl-pyrazol-4-yl]phenyl]-1-methyl-imidazole-2-carboxamide; formate | 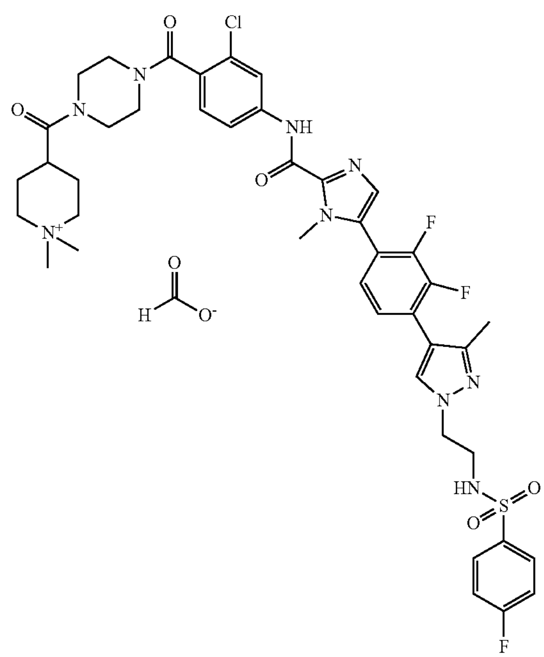 | 881.3 | Intermediate Q2; 4-fluorobenzene sulfonyl chloride; HCl iodomethane |

-continued

| Ex# | Name | Structure | MS ESI [M]+ | Starting Material |
|---|---|---|---|---|
| Example H4 | 5-[4-[1-[2-(tert-butylcarbamoylamino)ethyl]-5-methyl-pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide; formate | 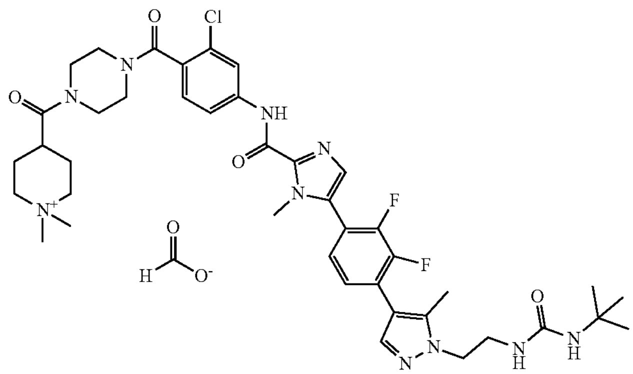 | 822.2 | Intermediate Q1; 2-isocyanato-2-methyl-propane; HCl iodomethane |
| Example H5 | 5-[4-[1-[2-(tert-butylcarbamoylamino)ethyl]-3-methyl-pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide; formate | 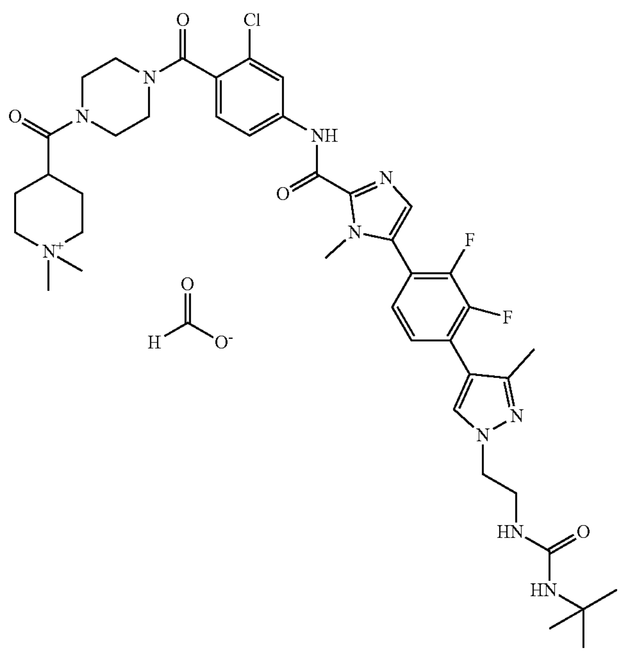 | 822.2 | Intermediate Q2; 2-isocyanato-2-methyl-propane; HCl iodomethane |
| Example H6 | N-[3-chloro-4-[4-(1,1-dimethylpiperidin-1-ium-4-carbonyl)piperazine-1-carbonyl]phenyl]-5-[2,3-difluoro-4-[5-methyl-1-[2-(2-pyridylcarbamoylamino)ethyl]pyrazol-4-yl]phenyl]-1-methyl-imidazole-2-carboxamide; formate | 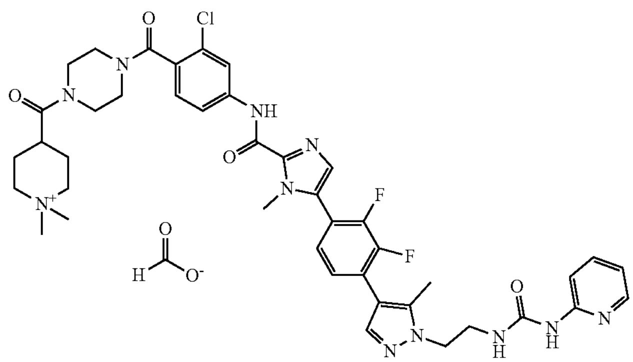 | 842.7 | Intermediate Q1; 2-isocyanato-pyridine; HCl iodomethane |

| Ex# | Name | Structure | MS ESI [M]+ | Starting Material |
|---|---|---|---|---|
| Example H7 | N-[3-chloro-4-[4-(1,1-dimethylpiperidin-1-ium-4-carbonyl)piperazine-1-carbonyl]phenyl]-5-[2,3-difluoro-4-[3-methyl-1-[2-(2-pyridylcarbamoylamino)ethyl]pyrazol-4-yl]phenyl]-1-methyl-imidazole-2-carboxamide; formate | 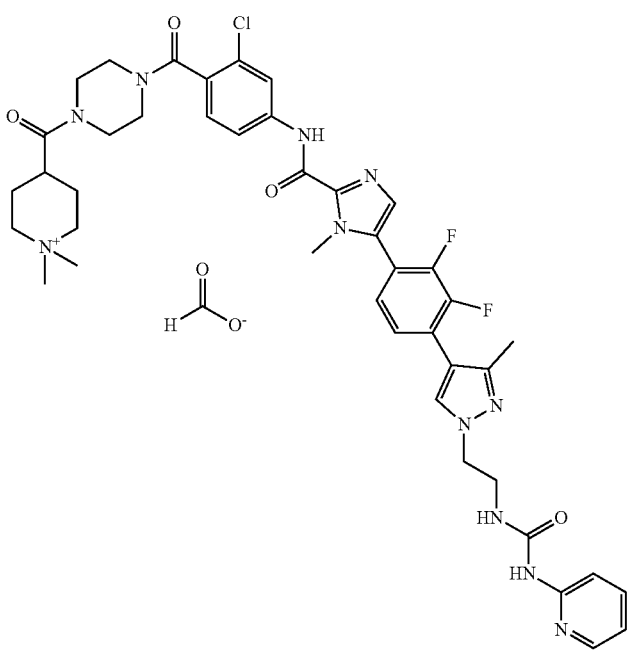 | 842.3 | Intermediate Q2; 2-isocyanato-pyridine; HCl iodomethane |
| Example H8 | N-[3-chloro-4-[4-(1,1-dimethylpiperidin-1-ium-4-carbonyl)piperazine-1-carbonyl]phenyl]-5-[2,3-difluoro-4-[3-methyl-1-[2-(pyrrolidine-1-carbonylamino)ethyl]pyrazol-4-yl]phenyl]-1-methyl-imidazole-2-carboxamide; formate | 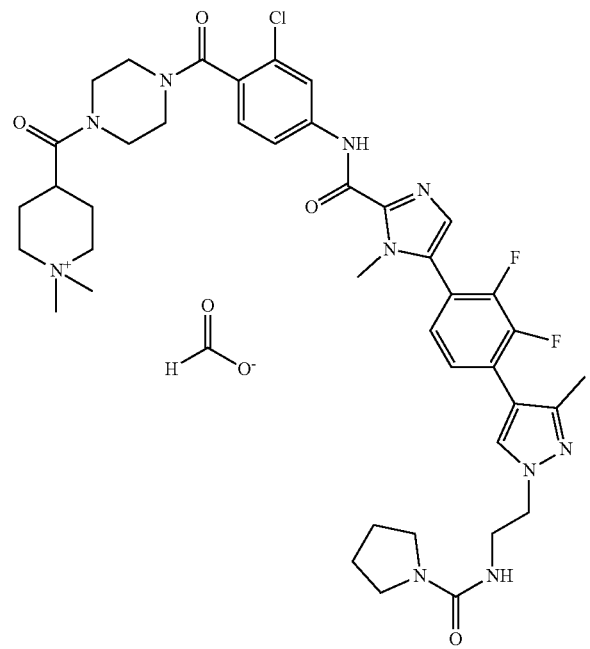 | 819.5 | Intermediate Q2; pyrrolidine-1-carbonyl chloride; HCl iodomethane |

Example 11
N-[3-chloro-4-[4-(1,1-dimethylpiperidin-1-ium-4-carbonyl)piperazine-1-carbonyl]phenyl]-5-[2,3-difluoro-4-[5-(2-pyridyl)-1H-pyrazol-4-yl]phenyl]-1-methyl-imidazole-2-carboxamide; formate
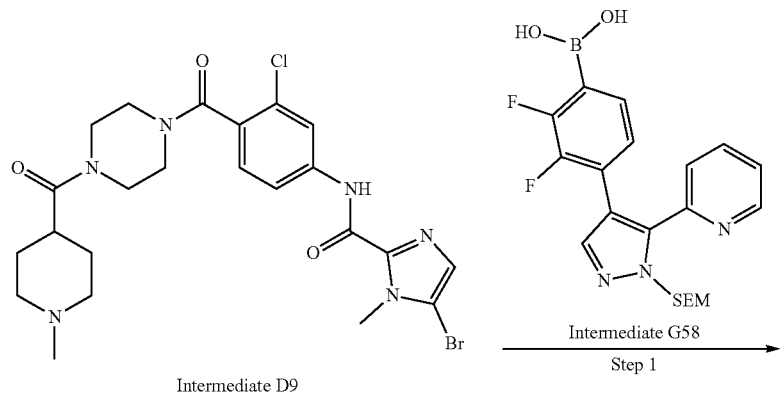
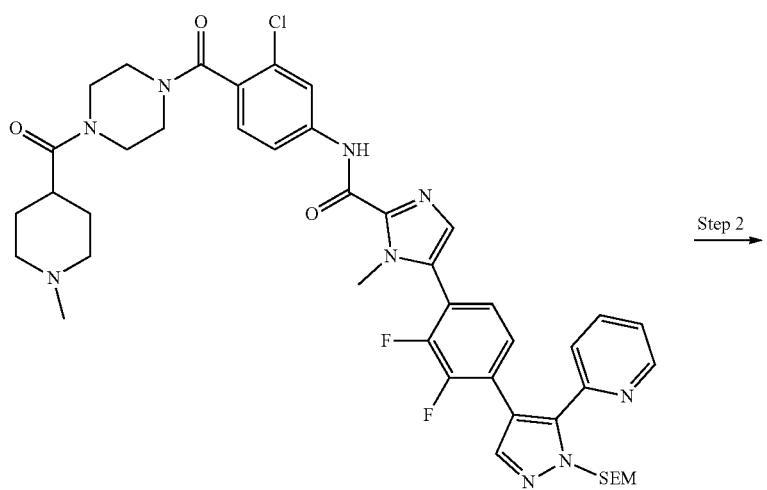
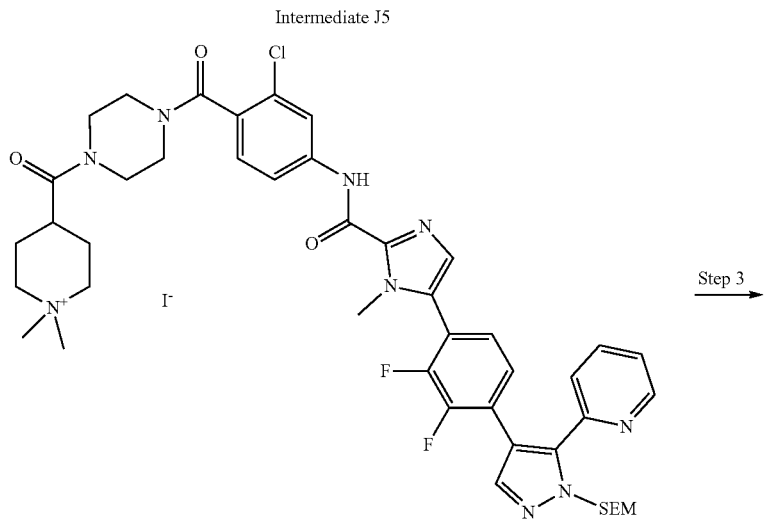

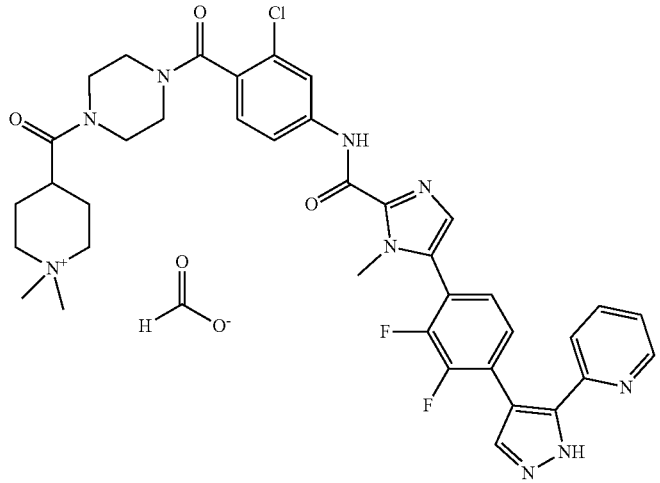

Example I1

Step 1: N-(3-chloro-4-(4-(1-methylpiperidine-4-carbonyl)piperazine-1-carbonyl)phenyl)-5-(2,3-difluoro-4-(5-(pyridin-2-yl)-1-((2-(trimethylsilyl)ethoxy)methyl)-1H-pyrazol-4-yl)phenyl)-1-methyl-1H-imidazole-2-carboxamide To a solution of 5-bromo-N-[3-chloro-4-[4-(1-methylpiperidine-4-carbonyl)piperazine-1-carbonyl]phenyl]-1-methyl-imidazole-2-carboxamide (80.0 mg, 0.14 mmol) in 1,4-dioxane (1.0 mL) was added [2,3-difluoro-4-[5-(2-pyridyl)-1-(2-trimethylsilylethoxymethyl)pyrazol-4-yl]phenyl]boronic acid (75.0 mg, 0.17 mmol), sodium carbonate (46.1 mg, 0.43 mmol), [1,1-Bis(di-tert-butylphosphino)ferrocene]palladium(II) Dichloride (19.2 mg, 0.02 mmol) and water (0.1 mL) in glove box, the mixture was stirred at 100° C. for 2 h. The mixture was diluted with 10 mL of DCM and filtered off, the filtrate was concentrated, the residue was purified by Prep-HPLC (FA as additive) to give N-[3-chloro-4-[4-(1-methylpiperidine-4-carbonyl)piperazine-1-carbonyl]phenyl]-5-[2,3-difluoro-4-[5-(2-pyridyl)-1-(2-trimethylsilylethoxymethyl)pyrazol-4-yl]phenyl]-1-methyl-imidazole-2-carboxamide (45 mg). MS [M+H]+: 858.4.

Step 2: N-[3-chloro-4-[4-(1,1-dimethylpiperidin-1-ium-4-carbonyl)piperazine-1-carbonyl]phenyl]-5-[2,3-difluoro-4-[5-(2-pyridyl)-1-(2-trimethylsilylethoxymethyl)pyrazol-4-yl]phenyl]-1-methyl-imidazole-2-carboxamide;iodide To a solution of N-[3-chloro-4-[4-(1-methylpiperidine-4-carbonyl)piperazine-1-carbonyl]phenyl]-5-[2,3-difluoro-4-[5-(2-pyridyl)-1-(2-trimethylsilylethoxymethyl)pyrazol-4-yl]phenyl]-1-methyl-imidazole-2-carboxamide (39.0 mg, 0.05 mmol) in DMF (1 mL) was added N,N-diisopropylethylamine (0.03 mL, 0.18 mmol) and iodomethane (25.8 mg, 0.18 mmol), the mixture was stirred at 25° C. for 0.5 h. The mixture was purified by Flash-HPLC and lyophilized to give N-[3-chloro-4-[4-(1,1-dimethylpiperidin-1-ium-4-carbonyl)piperazine-1-carbonyl]phenyl]-5-[2,3-difluoro-4-[5-(2-pyridyl)-1-(2-trimethylsilylethoxymethyl)pyrazol-4-yl]phenyl]-1-methyl-imidazole-2-carboxamide;iodide (35.0 mg). MS[M]+: 872.5.

Step 3: N-[3-chloro-4-[4-(1,1-dimethylpiperidin-1-ium-4-carbonyl)piperazine-1-carbonyl]phenyl]-5-[2,3-difluoro-4-[5-(2-pyridyl)-1H-pyrazol-4-yl]phenyl]-1-methyl-imidazole-2-carboxamide;formate The mixture of N-[3-chloro-4-[4-(1,1-dimethylpiperidin-1-ium-4-carbonyl)piperazine-1-carbonyl]phenyl]-5-[2,3-difluoro-4-[5-(2-pyridyl)-1-(2-trimethylsilylethoxymethyl)pyrazol-4-yl]phenyl]-1-methyl-imidazole-2-carboxamide;iodide (35.0 mg, 0.04 mmol) and HCl/MeOH (4.0 mL) was stirred at 25° C. for 16 h. The mixture was concentrated at 20° C. in vacuum, the residue was purified by Prep-HPLC (FA as additive) and lyophilized to give N-[3-chloro-4-[4-(1,1-dimethylpiperidin-1-ium-4-carbonyl)piperazine-1-carbonyl]phenyl]-5-[2,3-difluoro-4-[5-(2-pyridyl)-1H-pyrazol-4-yl]phenyl]-1-methyl-imidazole-2-carboxamide;formate (10.1 mg). MS [M]+: 742.4.

The following examples were prepared in analogy to Examples I1.

| Ex# | Name | Structure | MS ESI [M]+ | Starting Material |
|---|---|---|---|---|
| Example I2 | N-[3-chloro-4-[4-(1,1-dimethylpiperidin-1-ium-4-carbonyl)piperazine-1-carbonyl]phenyl]-5-[2,3-difluoro-4-[5-(4-methoxyphenyl)-1H-pyrazol-4-yl]phenyl]-1-methyl-imidazole-2-carboxamide; formate | 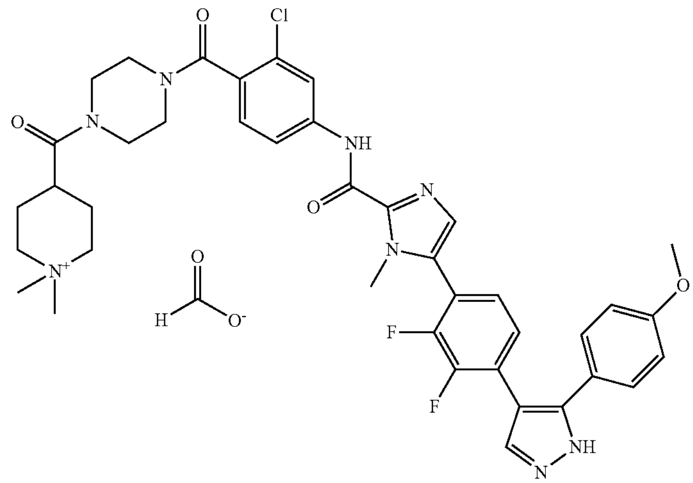 | 771.2 | Intermediate D9 and Intermediate G59; iodomethane; HCl |
| Example I3 | N-[3-chloro-4-[4-(1,1-dimethylpiperidin-1-ium-4-carbonyl)piperazine-1-carbonyl]phenyl]-5-[2,3-difluoro-4-[5-(3-methoxyphenyl)-1H-pyrazol-4-yl]phenyl]-1-methyl-imidazole-2-carboxamide; formate | 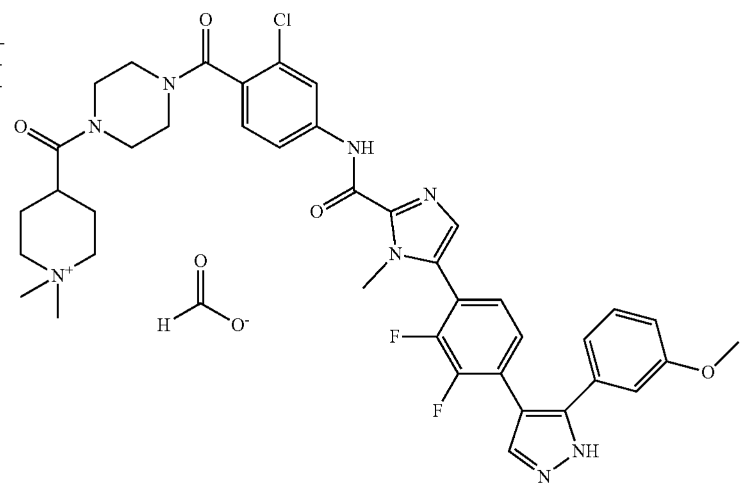 | 771.2 | Intermediate D9 and Intermediate G60; iodomethane; HCl |
| Example I4 | N-[3-chloro-4-[4-(1,1-dimethylpiperidin-1-ium-4-carbonyl)piperazine-1-carbonyl]phenyl]-5-[2,3-difluoro-4-[5-(2-methoxyphenyl)-1H-pyrazol-4-yl]phenyl]-1-methyl-imidazole-2-carboxamide; formate | 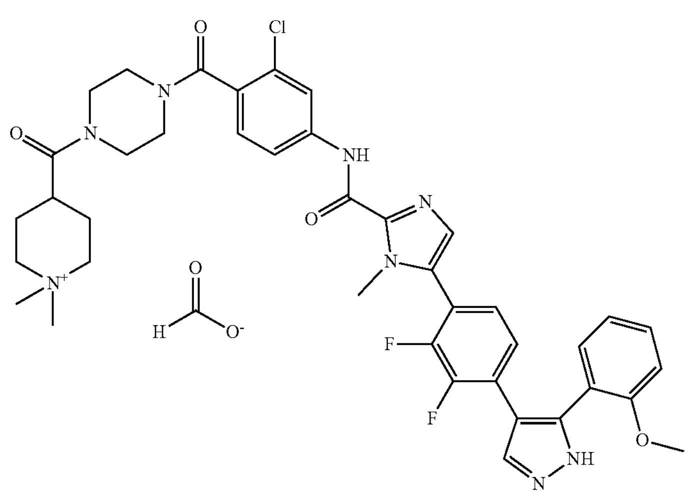 | 771.2 | Intermediate D9 and Intermediate G61; iodomethane; HCl |

-continued

| Ex# | Name | Structure | MS ESI [M]+ | Starting Material |
|---|---|---|---|---|
| Example I5 | N-[3-chloro-4-[4-(1,1-dimethylpiperidin-1-ium-4-carbonyl)piperazine-1-carbonyl]phenyl]-5-[2,3-difluoro-4-(5-thiazol-4-yl-1H-pyrazol-4-yl)phenyl]-1-methyl-imidazole-2-carboxamide; formate | 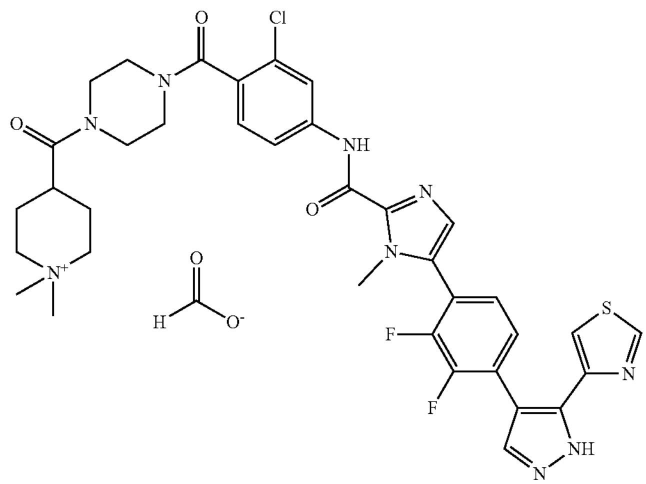 | 748.1 | Intermediate D9 and Intermediate G62; iodomethane; HCl |
| Example I6 | N-[3-chloro-4-[4-(1,1-dimethylpiperidin-1-ium-4-carbonyl)piperazine-1-carbonyl]phenyl]-5-[2,3-difluoro-4-(5-tetrahydropyran-4-yl-1H-pyrazol-4-yl)phenyl]-1-methyl-imidazole-2-carboxamide; formate | 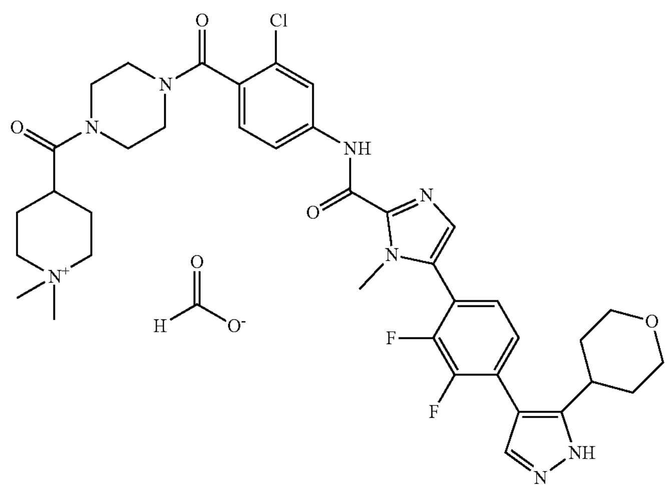 | 749.3 | Intermediate D9 and Intermediate G63; iodomethane; HCl |
| Example I7 | N-[3-chloro-4-[4-(1,1-dimethylpiperidin-1-ium-4-carbonyl)piperazine-1-carbonyl]phenyl]-5-[4-[5-(3,6-dihydro-2H-pyran-4-yl)-1H-pyrazol-4-yl]-2,3-difluoro-phenyl]-1-methyl-imidazole-2-carboxamide;formate | 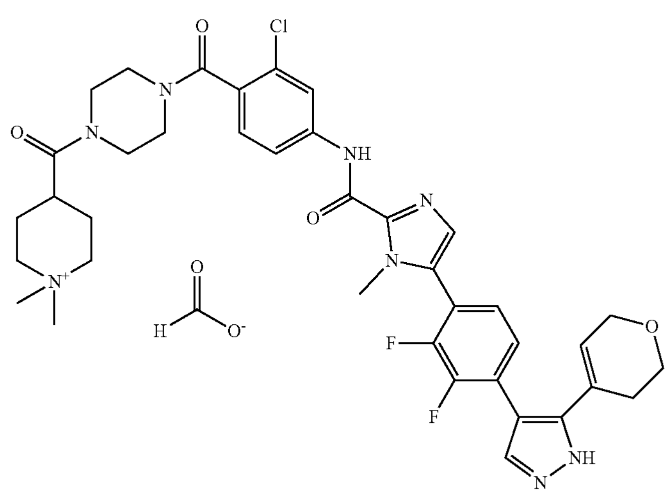 | 747.0 | Intermediate D9 and Intermediate G64; iodomethane; HCl |

Example J1
N-[4-[4-[1-(azetidin-3-ylmethyl)-1-methyl-piperidin-1-ium-4-carbonyl]piperazine-1-carbonyl]-3-chloro-phenyl]-5-[2,3-difluoro-4-(3-methyl-1H-pyrazol-4-yl)phenyl]-1-methyl-imidazole-2-carboxamide; formate
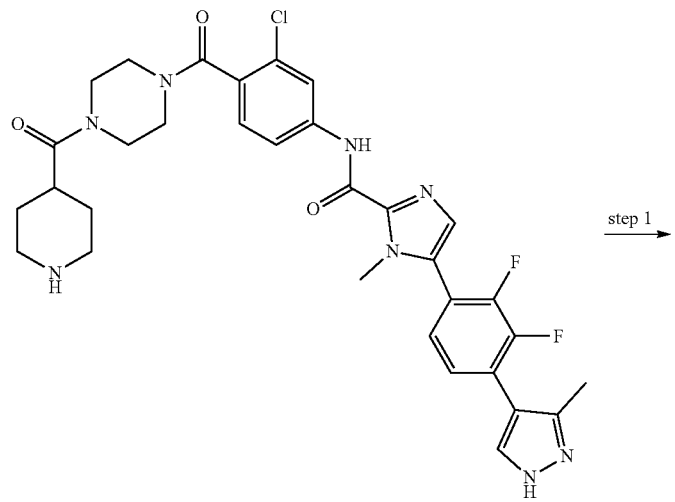
Intermediate K9
step 1
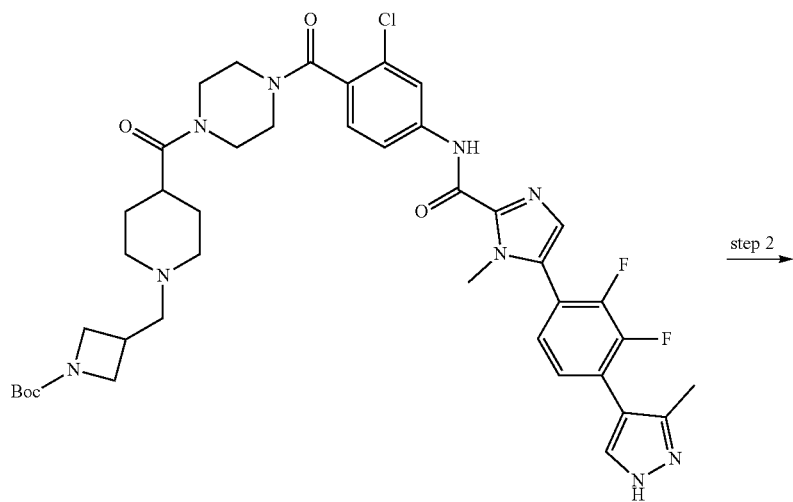
step 2

529
-continued
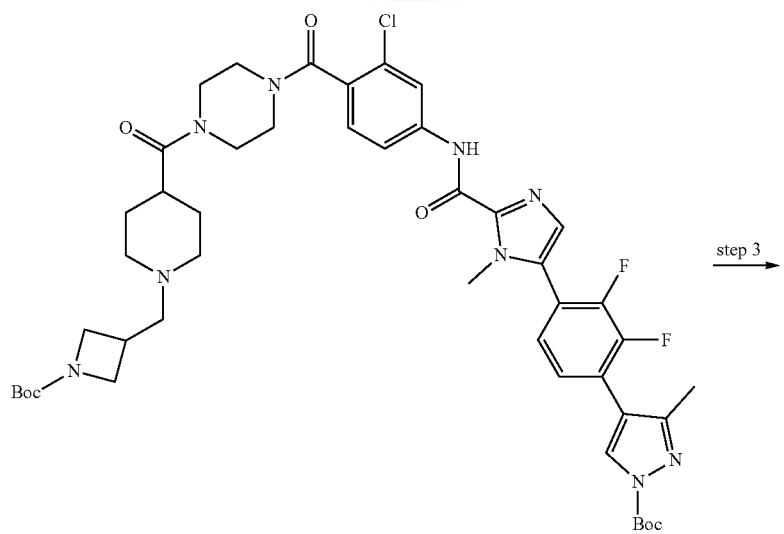
step 3
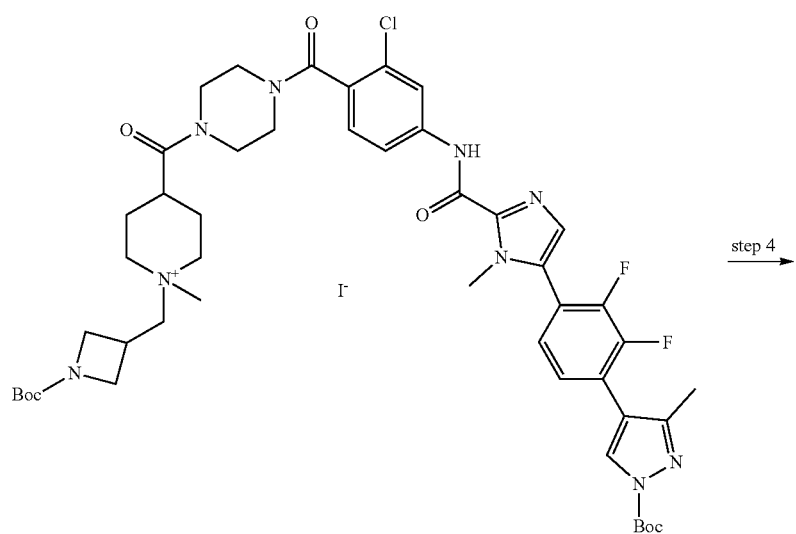
step 4
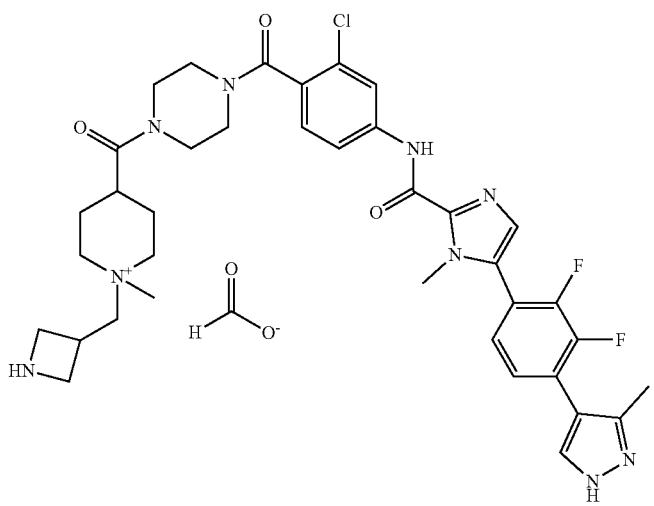
Example J1

Step 1: tert-butyl 3-[[4-[4-[2-chloro-4-[[5-[2,3-difluoro-4-(3-methyl-1H-pyrazol-4-yl)phenyl]-1-methyl-imidazole-2-carbonyl]amino]benzoyl]piperazine-1-carbonyl]-1-piperidyl]methyl]azetidine-1-carboxylate In a 50 mL round-bottomed flask, N-[3-chloro-4-[4-(piperidine-4-carbonyl)piperazine-1-carbonyl]phenyl]-5-[2,3-difluoro-4-(3-methyl-1H-pyrazol-4-yl)phenyl]-1-methyl-imidazole-2-carboxamide (88 mg, 135 μmol), tert-butyl 3-formylazetidine-1-carboxylate (50.1 mg, 270 μmol) and NaBH$_3$CN (25.5 mg, 405 μmol) were combined with MeOH (5 mL) to give a light brown solution. The reaction mixture was heated to 45° C. and stirred for 3 h. The crude reaction mixture was concentrated in vacuum. The reaction mixture was poured into 25 mL sat NaHCO$_3$ and extracted with EtOAc (3×25 mL). The organic layers were combined, washed with sat NaCl (1×25 mL), The organic layers were dried over Na$_2$SO$_4$ and concentrated in vacuum to afford tert-butyl 3-[[4-[4-[2-chloro-4-[[5-[2,3-difluoro-4-(3-methyl-1H-pyrazol-4-yl)phenyl]-1-methyl-imidazole-2-carbonyl]amino]benzoyl]piperazine-1-carbonyl]-1-piperidyl]methyl]azetidine-1-carboxylate (111 mg). MS [M+H]$^+$: 821.1.

Step 2: tert-butyl 4-[4-[2-[[4-[4-[1-[(1-tert-butoxycarbonylazetidin-3-yl)methyl]piperidine-4-carbonyl]piperazine-1-carbonyl]-3-chloro-phenyl]carbamoyl]-3-methyl-imidazol-4-yl]-2,3-difluoro-phenyl]-3-methyl-pyrazole-1-carboxylate In a 100 mL round-bottomed flask, tert-butyl 3-[[4-[4-[2-chloro-4-[[5-[2,3-difluoro-4-(3-methyl-1H-pyrazol-4-yl)phenyl]-1-methyl-imidazole-2-carbonyl]amino]benzoyl]piperazine-1-carbonyl]-1-piperidyl]methyl]azetidine-1-carboxylate (110 mg, 134 μmol), Boc$_2$O (43.9 mg, 201 μmol) and TEA (20.4 mg, 201 μmol) were combined with DCM (5 mL) to give a light brown solution. The reaction was stirred at room temperature for 1 h. The crude reaction mixture was concentrated in vacuum. The crude product was directly used to the next step to afford tert-butyl 4-[4-[2-[[4-[4-[1-[(1-tert-butoxycarbonylazetidin-3-yl)methyl]piperidine-4-carbonyl]piperazine-1-carbonyl]-3-chloro-phenyl]carbamoyl]-3-methyl-imidazol-4-yl]-2,3-difluoro-phenyl]-3-methyl-pyrazole-1-carboxylate (123 mg, 134 μmol). MS [M+H]$^+$: 920.8.

Step 3: tert-butyl 4-[4-[2-[[4-[4-[1-[(1-tert-butoxycarbonylazetidin-3-yl)methyl]-1-methyl-piperidin-1-ium-4-carbonyl]piperazine-1-carbonyl]-3-chloro-phenyl]carbamoyl]-3-methyl-imidazol-4-yl]-2,3-difluoro-phenyl]-3-methyl-pyrazole-1-carboxylate; iodide In a 100 mL round-bottomed flask, tert-butyl 4-[4-[2-[[4-[4-[1-[(1-tert-butoxycarbonylazetidin-3-yl)methyl]piperidine-4-carbonyl]piperazine-1-carbonyl]-3-chloro-phenyl]carbamoyl]-3-methyl-imidazol-4-yl]-2,3-difluoro-phenyl]-3-methyl-pyrazole-1-carboxylate (123 mg, 134 μmol), MeI (94.8 mg, 668 μmol) and DIPEA (86.4 mg, 668 μmol) were combined with MeCN (5 mL) to give a light brown solution. The reaction was stirred at room temperature for 15 h. The crude reaction mixture was concentrated in vacuum. The crude product was directly used to the next step to afford tert-butyl 4-[4-[2-[[4-[4-[1-[(1-tert-butoxycarbonylazetidin-3-yl)methyl]-1-methyl-piperidin-1-ium-4-carbonyl]piperazine-1-carbonyl]-3-chloro-phenyl]carbamoyl]-3-methyl-imidazol-4-yl]-2,3-difluoro-phenyl]-3-methyl-pyrazole-1-carboxylate; iodide (125 mg). MS [M]$^+$: 935.1.

Step 4: N-[4-[4-[1-(azetidin-3-ylmethyl)-1-methyl-piperidin-1-ium-4-carbonyl]piperazine-1-carbonyl]-3-chloro-phenyl]-5-[2,3-difluoro-4-(3-methyl-1H-pyrazol-4-yl)phenyl]-1-methyl-imidazole-2-carboxamide; 2,2,2-trifluoroacetate In a 100 mL round-bottomed flask, tert-butyl 4-[4-[2-[[4-[4-[1-[(1-tert-butoxycarbonylazetidin-3-yl)methyl]-1-methyl-piperidin-1-ium-4-carbonyl]piperazine-1-carbonyl]-3-chloro-phenyl]carbamoyl]-3-methyl-imidazol-4-yl]-2,3-difluoro-phenyl]-3-methyl-pyrazole-1-carboxylate;iodide (120 mg, 128 μmol) was combined with DCM (3 mL) to give a light brown solution. 2,2,2-trifluoroacetic acid (1.46 g, 12.8 mmol) was added. The reaction was stirred at room temperature for 1 h. The crude reaction mixture was concentrated in vacuum. The crude material was purified by preparative HPLC to afford N-[4-[4-[1-(azetidin-3-ylmethyl)-1-methyl-piperidin-1-ium-4-carbonyl]piperazine-1-carbonyl]-3-chloro-phenyl]-5-[2,3-difluoro-4-(3-methyl-1H-pyrazol-4-yl)phenyl]-1-methyl-imidazole-2-carboxamide; 2,2,2-trifluoroacetate (17.4 mg). MS [M]$^+$: 734.9.

Example K1

5-[4-[1-[2-(2-aminoethoxy)ethyl]-3,5-dimethyl-pyrazol-4-yl]-2,3-difluoro-phenyl]-N-[3-chloro-4-[4-[(2S,4R)-4-hydroxy-1,1-dimethyl-pyrrolidin-1-ium-2-carbonyl]piperazine-1-carbonyl]phenyl]-1-methyl-imidazole-2-carboxamide; 2,2,2-trifluoroacetate

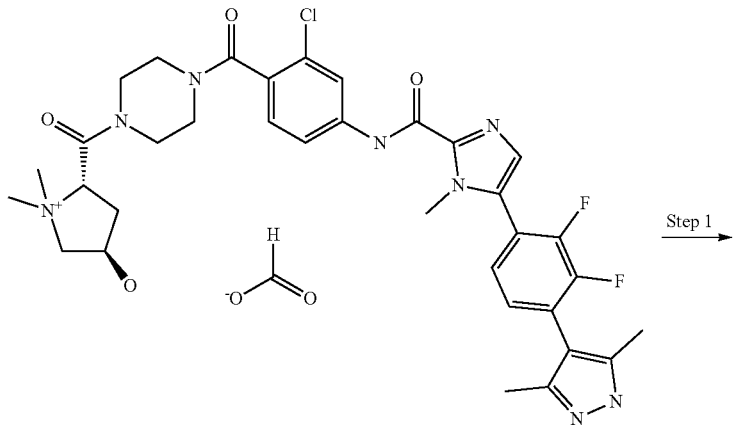

Example D43

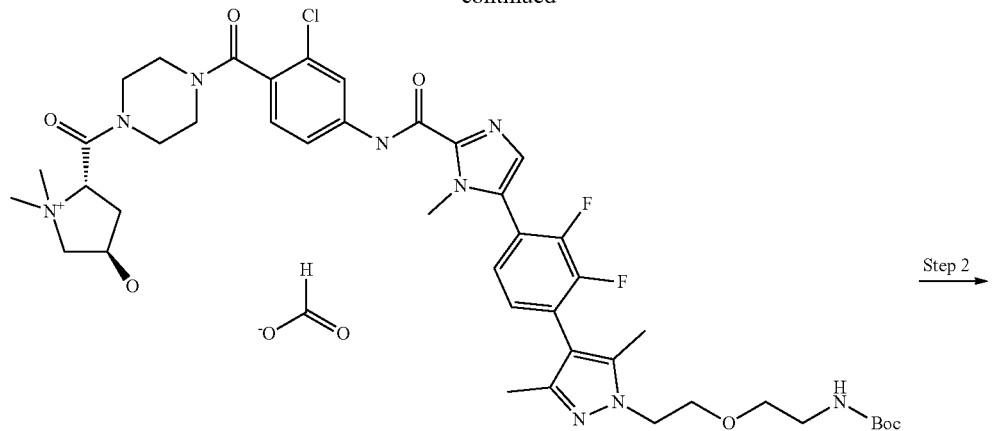

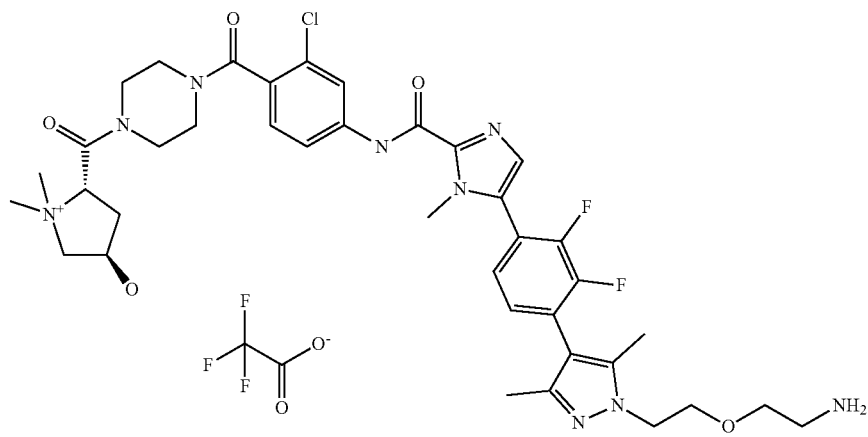

Example K1

Step 1: N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-[2-(2-hydrazinoethoxy)ethyl]-3,5-dimethyl-pyrazol-4-yl]phenyl]-1-methyl-imidazole-2-carboxamide; formate To a mixture of N-[3-chloro-4-[4-[(2S,4R)-4-hydroxy-1,1-dimethyl-pyrrolidin-1-ium-2-carbonyl]piperazine-1-carbonyl]phenyl]-5-[4-(3,5-dimethyl-1H-pyrazol-4-yl)-2,3-difluoro-phenyl]-1-methyl-imidazole-2-carboxamide;formate (100.0 mg, 0.140 mmol) in DMF (10 mL) was added tert-butyl N-[2-(2-bromoethoxy)ethyl]carbamate (385.18 mg, 1.44 mmol), and sodium borohydride (108.69 mg, 2.87 mmol). The reaction mixture was stirred at 80° C. for 16 h. The mixture was concentrated to remove solvent and purified by prep-HPLC (0.1% F A)-ACN to afford N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-[2-(2-hydrazinoethoxy)ethyl]-3,5-dimethyl-pyrazol-4-yl]phenyl]-1-methyl-imidazole-2-carboxamide; formate (60 mg). MS [M]$^+$: 882.3.

Step 2: 5-[4-[1-[2-(2-aminoethoxy)ethyl]-3,5-dimethyl-pyrazol-4-yl]-2,3-difluoro-phenyl]-N-[3-chloro-4-[4-[(2S,4R)-4-hydroxy-1,1-dimethyl-pyrrolidin-1-ium-2-carbonyl]piperazine-1-carbonyl]phenyl]-1-methyl-imidazole-2-carboxamide; 2,2,2-trifluoroacetate N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-[2-(2-hydrazinoethoxy)ethyl]-3,5-dimethyl-pyrazol-4-yl]phenyl]-1-methyl-imidazole-2-carboxamide;formate (60.0 mg, 0.070 mmol) was added into HCl/dioxane (5.0 mL, 0.070 mmol). The reaction mixture was stirred at 25° C. for 2 h. The mixture was concentrated to get crude product and purified by prep-HPLC (0.1% TFA)-ACN to obtain 5-[4-[1-[2-(2-aminoethoxy)ethyl]-3,5-dimethyl-pyrazol-4-yl]-2,3-difluoro-phenyl]-N-[3-chloro-4-[4-[(2S,4R)-4-hydroxy-1,1-dimethyl-pyrrolidin-1-ium-2-carbonyl]piperazine-1-carbonyl]phenyl]-1-methyl-imidazole-2-carboxamide; 2,2,2-trifluoroacetate (13.3 mg). MS [M]$^+$: 782.5.

The following examples were prepared in analogy to Examples K1.

| Ex# | Name | Structure | MS ESI [M]+ | Starting Material |
|---|---|---|---|---|
| Example K2 | N-[3-chloro-4-[4-[(4R)-4-hydroxy-1,1-dimethyl-pyrrolidin-1-ium-2-carbonyl]piperazine-1-carbonyl]phenyl]-5-[4-[1-2-(difluoromethoxy)ethyl]-3,5-dimethyl-pyrazol-4-yl]-2,3-difluoro-phenyl]-1-methyl-imidazole-2-carboxamide; formate | 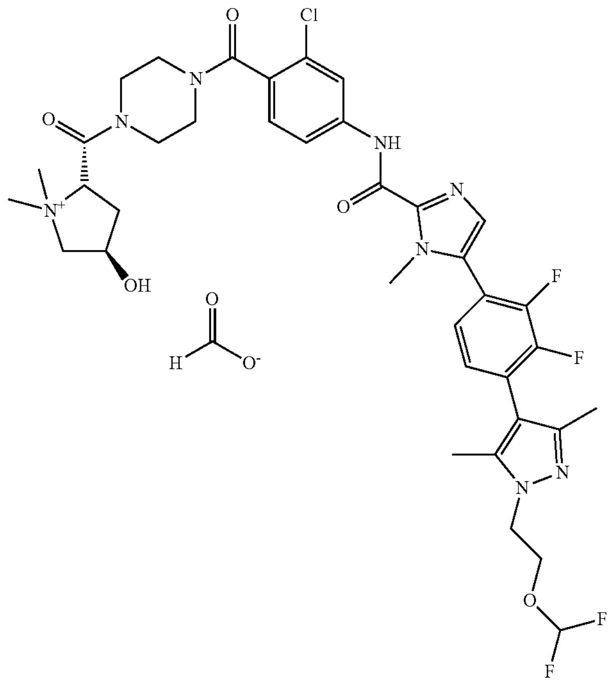 | 789.3 | Example D43 and 1-bromo-2-(difluoromethoxy)ethane |
| Example K3 | N-[3-chloro-4-[4-[(4R)-4-hydroxy-1,1-dimethyl-pyrrolidin-1-ium-2-carbonyl]piperazine-1-carbonyl]phenyl]-5-[4-[1-2,2-difluorocyclopropyl)methyl]-3,5-dimethyl-pyrazol-4-yl]-2,3-difluoro-phenyl]-1-methyl-imidazole-2-carboxamide; formate | 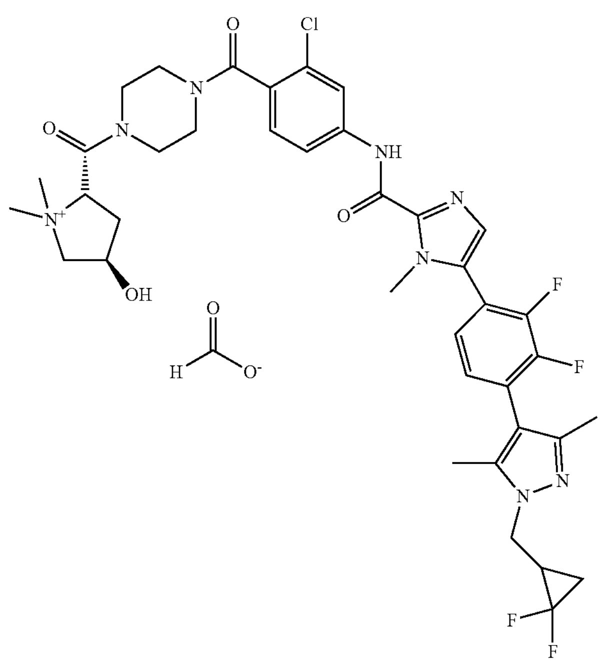 | 785.3 | Example D43 and 2-(bromomethyl)-1,1-difluoro-cyclopropane |

Intermediate G94 tert-butyl 2-[3-methyl-4-[4-(4,4,5,5-tetramethyl-1,3, 2-dioxaborolan-2-yl)phenyl]pyrazol-1-yl]acetate

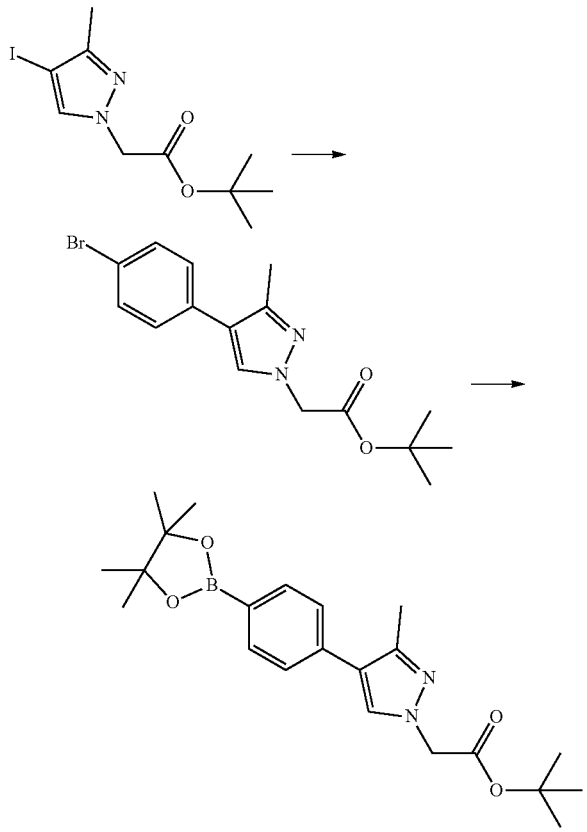

Intermediate G94

Step 1: tert-butyl 2-[4-(4-bromophenyl)-3-methyl-pyrazol-1-yl]acetate

A mixture of 4-bromophenylboronic acid (6.23 g, 31.04 mmol), tert-butyl 2-(4-iodo-3-methyl-pyrazol-1-yl)acetate (10.0 g, 31.04 mmol)(isomer mixture), sodium carbonate (6.58 g, 62.08 mmol) and Pd(dppf)Cl2 (2.27 g, 3.1 mmol) in 1,4-dioxane (200 mL)/Water (20 mL) was stirred under N2 at 85° C. for 16 h. The reaction mixture was filtered and the filtrate was concentrated in vacuum, purified by silica column (PE:EA=5:1) to afford tert-butyl 2-[4-(4-bromophenyl)-3-methyl-pyrazol-1-yl]acetate (3.3 g, 9.4 mmol, 30.27% yield)(isomer mixture) as yellow oil. MS [(M+2+H)+]: 353.0.

Step 2: tert-butyl 2-[3-methyl-4-[4-(4,4,5,5-tetramethyl-1,3,2-dioxaborolan-2-yl)phenyl]pyrazol-1-yl]acetate A mixture of tert-butyl 2-[4-(4-bromophenyl)-3-methyl-pyrazol-1-yl]acetate (3.3 g, 9.4 mmol)(isomer mixture), potassium acetate (1.84 g, 18.79 mmol), bis(pinacolato)diboron (7157.49 mg, 28.19 mmol) and Pd(dppf)Cl$_2$ (0.69 g, 0.94 mmol) in 1,4-dioxane (50 mL) was evacuated and backfilled with N2 (3×), then the mixture was stirred under N2 at 95° C. for 16 h. The mixture was cooled to room temperature, filtered and concentrated in vacuum to afford a residue. The residue was purified by silica column (PE:EA=10:1 to 1:1) to afford tert-butyl 2-[3-methyl-4-[4-(4,4,5,5-tetramethyl-1,3,2-dioxaborolan-2-yl)phenyl]pyrazol-1-yl]acetate (3.7 g, 9.29 mmol, 98.87% yield)(isomer mixture) as yellow solid. MS [(M+H)+]: 399.3.

The following examples were prepared in analogy to Intermediate G94.

| Ex# | Name | Structure | MS [M + H]+ | Starting Material |
|---|---|---|---|---|
| Intermediate G95 | tert-butyl 2-[4-[2-fluoro-4-(4,4,5,5-tetramethyl-1,3,2-dioxaborolan-2-yl)phenyl]-3-methyl-pyrazol-1-yl]acetate | 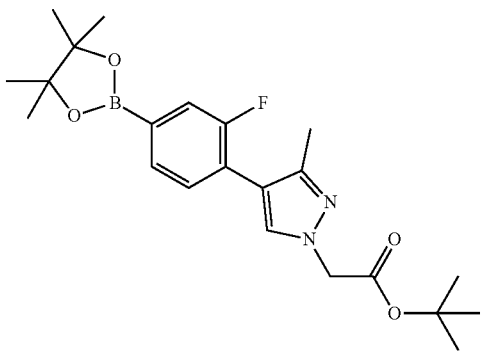 [SMILES: Cc1nn(CC(=O)OC(C)(C)C)cc1-c1ccc(B2OC(C)(C)C(C)(C)O2)cc1F] | 417.2 | 4-bromo-2-fluorobenzene boronic acid |

| Ex# | Name | Structure | MS [M + H]+ | Starting Material |
|---|---|---|---|---|
| Intermediate G96 | tert-butyl 2-[4-[2,3-difluoro-4-(4,4,5,5-tetramethyl-1,3,2-dioxaborolan-2-yl)phenyl]-3-methyl-pyrazol-1-yl]acetate | 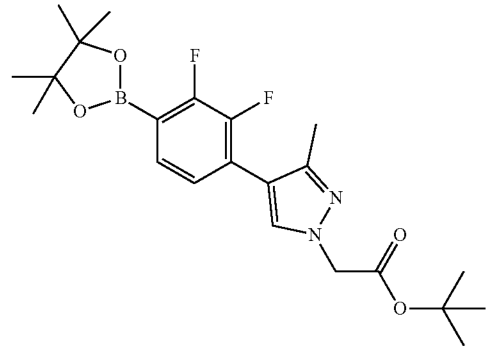 [SMILES: Cc1nn(CC(=O)OC(C)(C)C)cc1-c1ccc(B2OC(C)(C)C(C)(C)O2)c(F)c1F] | 435.1 | 4-bromo-2,3-difluorophenylboronic acid |

Intermediate G97

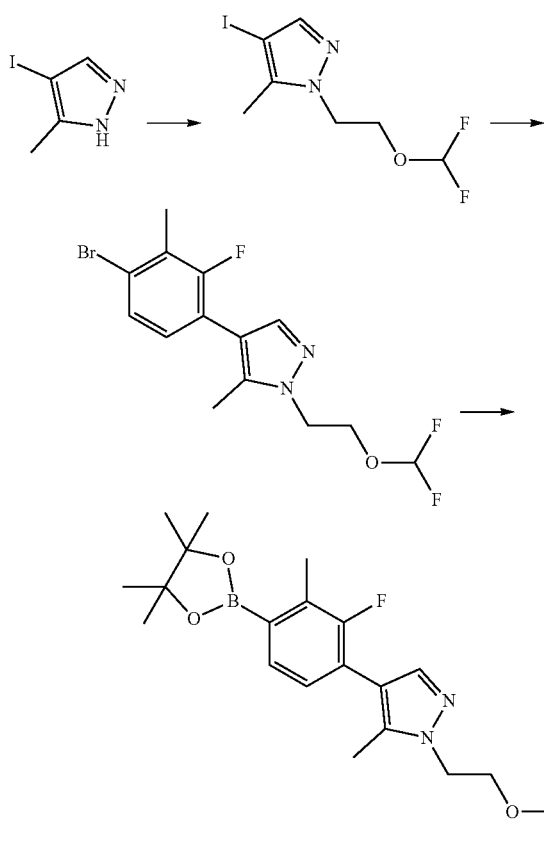

Intermediate G97

Step 1: 1-[2-(difluoromethoxy)ethyl]-4-iodo-5-methyl-pyrazole

To a mixture of 4-iodo-3-methyl-1H-pyrazole (13.0 g, 62.5 mmol) and 2-(difluoromethoxy)ethyl 4-methylbenzenesulfonate (14.98 g, 56.25 mmol) in DMF (150 mL) was added potassium carbonate (21.59 g, 156.25 mmol) at 25° C. Then the mixture was stirred at 65° C. for 16 h. The reaction mixture was pour into water (150 mL), extracted with EA (150 mL×2). The combined organic layer was washed with brine (200 mL), dry over sodium sulfate, concentrated in vacuum to give the residue, which was purified by column (PE:EA=10:1 to 3:1) to afford 1-[2-(difluoromethoxy)ethyl]-4-iodo-5-methyl-pyrazole (12.0 g, 39.72 mmol, 31.78% yield)(isomer mixture) as yellow oil. MS [(M+H)+]: 303.0.

Step 2: 4-(4-bromo-2-fluoro-3-methyl-phenyl)-1-[2-(difluoromethoxy)ethyl]-5-methyl-pyrazole To a mixture of 1-[2-(difluoromethoxy)ethyl]-4-iodo-5-methyl-pyrazole (12.98 g, 42.95 mmol)(isomer mixture), (4-bromo-2-fluoro-3-methyl-phenyl)boronic acid (10.0 g, 42.95 mmol) and sodium carbonate (11.38 g, 107.37 mmol) in 1,4-dioxane (200 mL)/Water (20 mL) was added Pd(dppf)Cl2 (3.14 g, 4.30 mmol) at 25° C., the mixture was evacuated, backfilled with N2 (3×) and stirred at 60° C. for 4 h under N2. The reaction mixture was filtered, the filtrate was concentrated in vacuum to give the residue, which was purified by column (PE:EA=10:1 to 2:1) to afford 4-(4-bromo-2-fluoro-3-methyl-phenyl)-1-[2-(difluoromethoxy)ethyl]-5-methyl-pyrazole (12.0 g, 33.04 mmol, 76.94% yield)(isomer mixture) as yellow oil. MS [(M+H)+]: 364.9.

Step 3: 1-[2-(difluoromethoxy)ethyl]-4-[2-fluoro-3-methyl-4-(4,4,5,5-tetramethyl-1,3,2-dioxaborolan-2-yl)phenyl]-5-methyl-pyrazole A stirred mixture of 4-(4-bromo-2-fluoro-3-methyl-phenyl)-1-[2-(difluoromethoxy)ethyl]-5-methyl-pyrazole (12.0 g, 33.04 mmol)(isomer mixture), Pd(dppf)Cl2 (2.42 g, 3.3 mmol), bis(pinacolato)diboron (12.59 g, 49.56 mmol) and potassium acetate (5.16 mL, 82.61 mmol) in 1,4-dioxane (200 mL) was evacuated and backfilled with N2 (3×) at 25° C. Then the mixture was stirred at 95° C. for 16 h under N2. The reaction mixture was cooled to room temperature, filtered, the filtrate was concentrated in vacuum to give the residue, which was purified by column (PE:EA=10:1 to 3:1) to afford 1-[2-(difluoromethoxy)ethyl]-4-[2-fluoro-3-methyl-4-(4,4,5,5-tetramethyl-1,3,2-dioxaborolan-2-yl)phenyl]-5-methyl-pyrazole (10.0 g, 24.38 mmol, 73.77% yield) (isomer mixture) as yellow solid. MS [(M+H)+]: 410.9.

The following examples were prepared in analogy to Intermediate G2.

| Ex# | Name | Structure | MS [M + H]+ | Starting Material |
|---|---|---|---|---|
| Intermediate G98 | 4-[2-fluoro-4-(4,4,5,5-tetramethyl-1,3,2-dioxaborolan-2-yl)phenyl]-1-(2-methoxyethyl)-5-methyl-pyrazole | 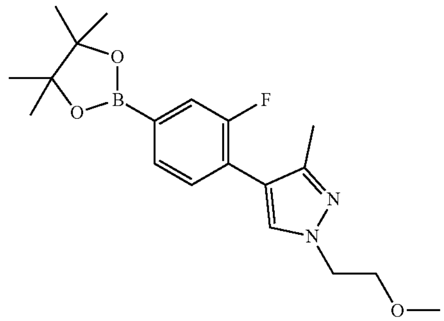 | 361.3 | 1-bromo-3-fluoro-4-iodobenzene and Intermediate E1 |
| Intermediate G99 | 4-[2-fluoro-4-(4,4,5,5-tetramethyl-1,3,2-dioxaborolan-2-yl)phenyl]-1-(2-methoxyethyl)-3-methyl-pyrazole | 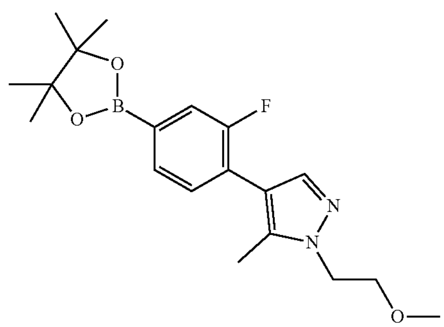 | 361.3 | 1-bromo-3-fluoro-4-iodobenzene and Intermediate E2 |

The following example were prepared in analogy to Intermediate H1.

| Ex# | Name | Structure | MS [M − H]− | Starting Material |
|---|---|---|---|---|
| Intermediate H12 | N-[3-chloro-4-(piperazine-1-carbonyl)phenyl]-5-[3-fluoro-4-[1-(2-methoxyethyl)-3-methyl-pyrazol-4-yl]phenyl]-1-methyl-imidazole-2-carboxamide hydrochloride | 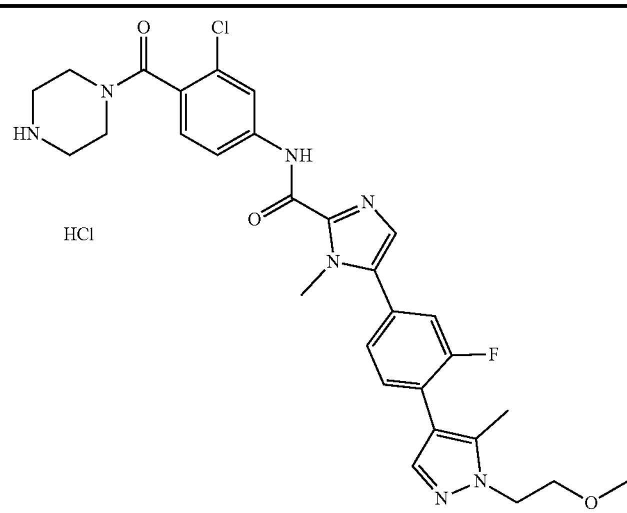 | 578.3 | Intermediate B1 and Intermediate G98 |

-continued

| Ex# | Name | Structure | MS [M − H]⁻ | Starting Material |
|---|---|---|---|---|
| Intermediate H13 | N-[3-chloro-4-(piperazine-1-carbonyl)phenyl]-5-[3-fluoro-4-[1-(2-methoxyethyl)-5-methyl-pyrazol-4-yl]phenyl]-1-methyl-imidazole-2-carboxamide hydrochloride | 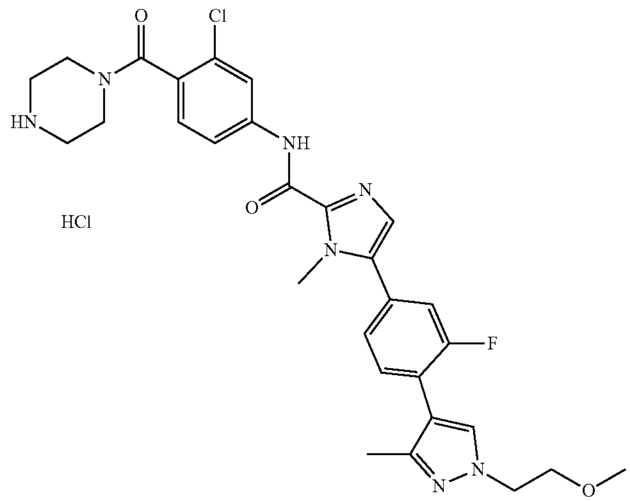 [SMILES: COCCn1cc(-c2ccc(-c3cnc(C(=O)Nc4ccc(C(=O)N5CCNCC5)c(Cl)c4)n3C)cc2F)c(C)n1 ; Cl] | 578.4 | Intermediate B1 and Intermediate G99 |
| Intermediate H14 | 5-[2,3-difluoro-4-[1-(2-methoxyethyl)-3-methyl-pyrazol-4-yl]phenyl]-1-methyl-N-[3-methyl-4-(piperazine-1-carbonyl)phenyl]imidazole-2-carboxamide hydrochloride | 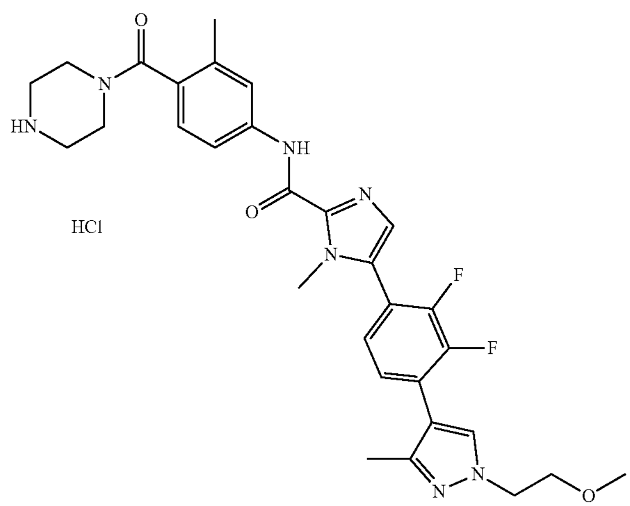 [SMILES: COCCn1cc(-c2ccc(-c3cnc(C(=O)Nc4ccc(C(=O)N5CCNCC5)c(C)c4)n3C)c(F)c2F)c(C)n1 ; Cl] | 578.3 | Intermediate B2 and Intermediate G2 |
| Intermediate H15 | 5-[3-fluoro-4-[1-(2-methoxyethyl)-3-methyl-pyrazol-4-yl]phenyl]-1-methyl-N-[3-methyl-4-(piperazine-1-carbonyl)phenyl]imidazole-2-carboxamide hydrochloride | 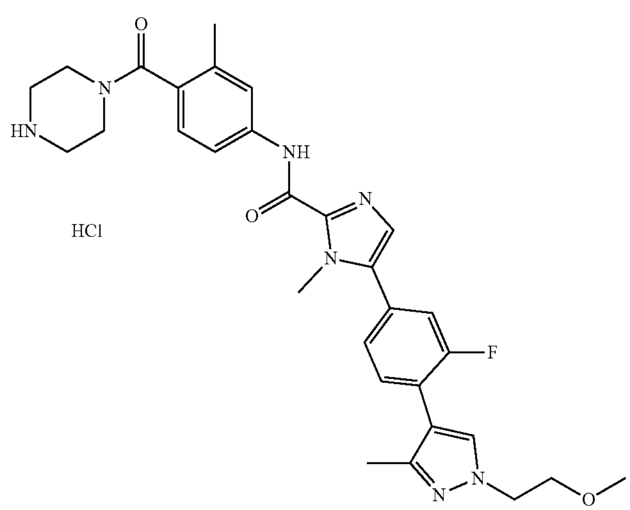 [SMILES: COCCn1cc(-c2ccc(-c3cnc(C(=O)Nc4ccc(C(=O)N5CCNCC5)c(C)c4)n3C)cc2F)c(C)n1 ; Cl] | 560.5 | Intermediate B2 and Intermediate G98 |

| Ex# | Name | Structure | MS [M − H]⁻ | Starting Material |
|---|---|---|---|---|
| Intermediate H16 | 5-[3-fluoro-4-[1-(2-methoxyethyl)-5-methyl-pyrazol-4-yl]-2-methyl-phenyl]-1-methyl-N-[3-methyl-4-(piperazine-1-carbonyl)phenyl]imidazole-2-carboxamide hydrochloride | 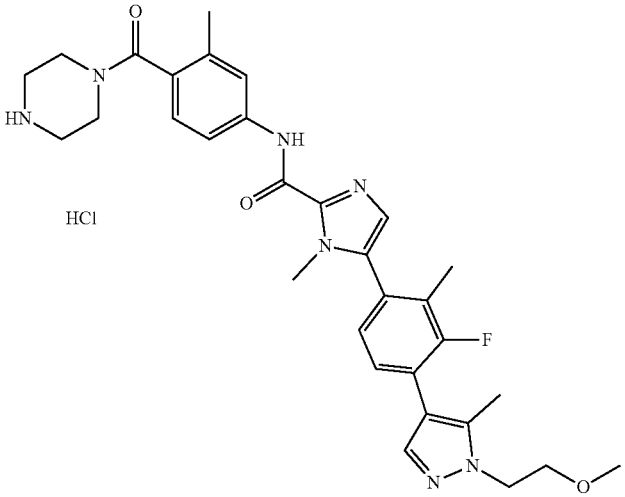 [SMILES: COCCn1ncc(-c2ccc(-c3cnc(C(=O)Nc4ccc(C(=O)N5CCNCC5)c(C)c4)n3C)c(C)c2F)c1C ; Cl] | 574.5 | Intermediate B2 and Intermediate G13 |

Intermediate 113

N-[3-chloro-4-[4-(methylamino)piperidine-1-carbonyl]phenyl]-5-[2,3-difluoro-4-[1-(2-methoxyethyl)-5-methyl-pyrazol-4-yl]phenyl]-1-methyl-imidazole-2-carboxamide; formic acid

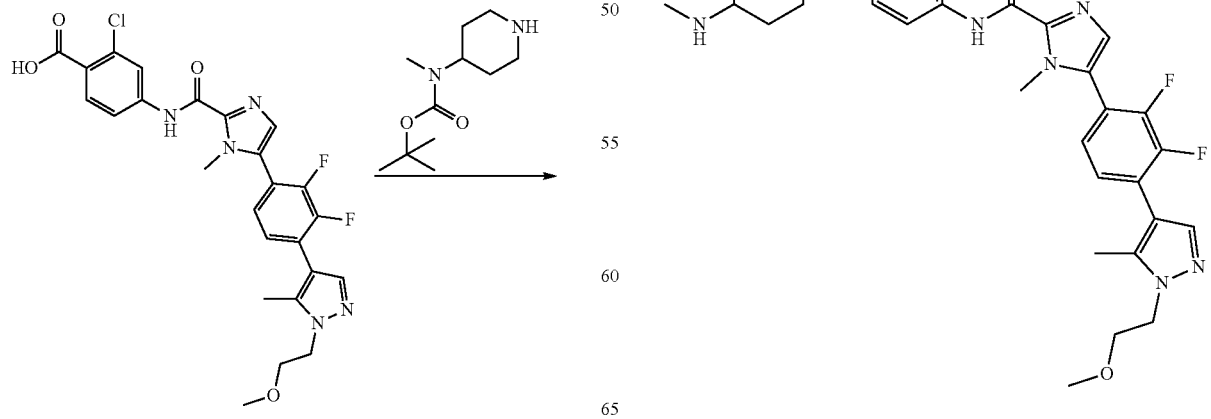

To 188 mg of 2-chloro-4-[[5-[2,3-difluoro-4-[1-(2-methoxyethyl)-5-methyl-pyrazol-4-yl]phenyl]-1-methyl-imidazole-2-carbonyl]amino]benzoic acid (23.5 mg, 0.0338 mmol) dissolved in 1 ml DMF was added HATU (15.4 mg, 0.041 mmol, 1.200 eq) and Et3N (24 uL, 0.169 mmol, 5.000 eq). The mixture was stirred at room temperature for 10 mi and then N-methyl-N-(4-piperidyl)carbamic acid tert-butyl ester (9.4 mg, 0.0439 mmol, 1.300 eq) was added and the mixture was stirred at room temperature over night. The mixture was then evaporated to dryness, dissolved in 1 ml DCM and treated with an excess of 4N HCl in dioxan (250 uL, 1.01 mmol, 30.000 eq) over night at RT. The mixtures was then evaporated to dryness and directly purified by preparative HPLC to afford the title compound (2 mg. 8.8% yield). MS [(M−H)−]: 624.3.

The following example was prepared in analogy to Intermediate 113.

| Ex# | Name | Structure | MS [M + H]$^+$ | Starting Material |
|---|---|---|---|---|
| Intermediate I14 | tert-butyl 4-[4-[[5-[4-[1-(2-tert-butoxy-2-oxo-ethyl)-3-methyl-pyrazol-4-yl]-3-fluoro-phenyl]-1-methyl-imidazole-2-carbonyl]amino]-2-chloro-benzoyl]piperazine-1-carboxylate | 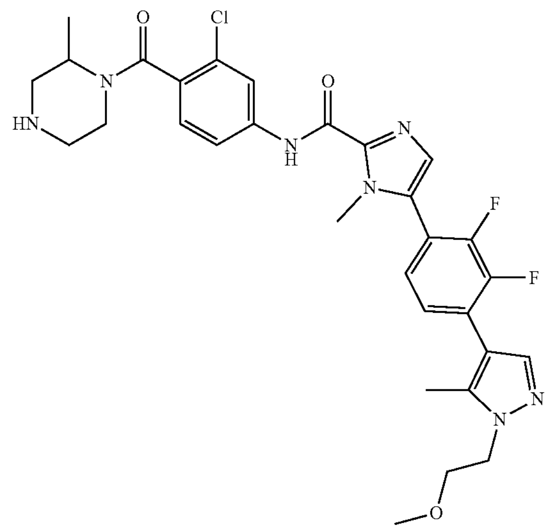 [SMILES: COCCn1ncc(-c2ccc(-c3cnc(C(=O)Nc4ccc(C(=O)N5CCNCC5C)c(Cl)c4)n3C)c(F)c2F)c1C] | 612.5 | 3-methylpiperazine-1-carboxylic acid tert-butyl ester |

Intermediate O4

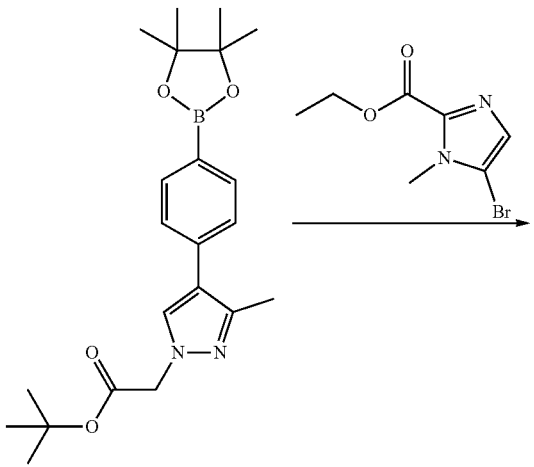

Intermediate G94

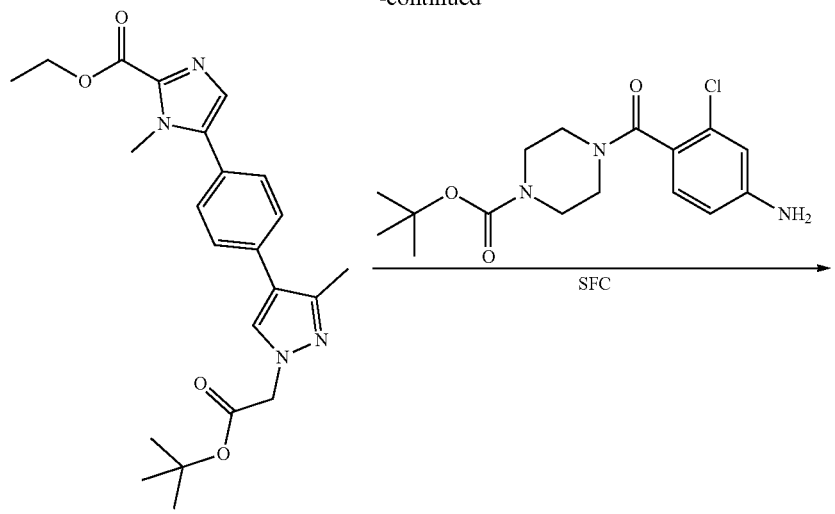

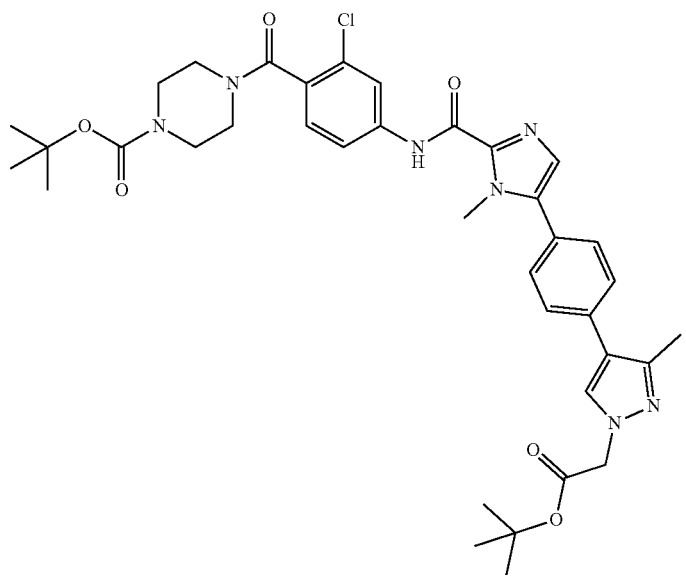

Intermediate O4

Step 1: ethyl 5-[4-[1-(2-tert-butoxy-2-oxo-ethyl)-3-methyl-pyrazol-4-yl]phenyl]-1-methyl-imidazole-2-carboxylate A mixture of tert-butyl 2-[3-methyl-4-[4-(4,4,5,5-tetramethyl-1,3,2-dioxaborolan-2-yl)phenyl]pyrazol-1-yl]acetate (3.7 g, 9.29 mmol)(isomer mixture), ethyl 5-bromo-1-methyl-imidazole-2-carboxylate (3.25 g, 13.93 mmol), potassium carbonate (2.57 g, 18.58 mmol), BrettPhos Pd G3 (843.03 mg, 0.93 mmol) in 1,4-dioxane (50 mL)/Water (5 mL) was stirred under N2 at 90° C. for 16 h. The mixture was concentrated in vacuum and purified by silica column (PE:EA=2:1) to afford ethyl 5-[4-[1-(2-tert-butoxy-2-oxo-ethyl)-3-methyl-pyrazol-4-yl]phenyl]-1-methyl-imidazole-2-carboxylate (1.2 g, 2.83 mmol, 30.43% yield)(isomer mixture) as yellow oil. MS [(M+H)+]: 425.1.

Step 2: tert-butyl 4-[4-[[5-[4-[1-(2-tert-butoxy-2-oxo-ethyl)-3-methyl-pyrazol-4-yl]phenyl]-1-methyl-imidazole-2-carbonyl]amino]-2-chloro-benzoyl]piperazine-1-carboxylate To a solution of tert-butyl 4-(4-amino-2-chloro-benzoyl)piperazine-1-carboxylate (800.54 mg, 2.36 mmol) and ethyl 5-[4-[1-(2-tert-butoxy-2-oxo-ethyl)-3-methyl-pyrazol-4-yl]phenyl]-1-methyl-imidazole-2-carboxylate (1.0 g, 2.36 mmol)(isomer mixture) in THF (20 mL) was added dropwise potassium bis(trimethylsilyl) amide (3.53 mL, 3.53 mmol, 1M in hexane) slowly at −35° C. and stirred for 0.5 h under N2. The solution was poured into sat.NH4Cl (100 ml) and extracted with EA (50 ml×2), washed with brine (100 ml), dried by anhydrous Na2SO4, then concentrated in vacuum to afford a residue. The residue was purified by silica column (55% EtOAc in PE) to afford the isomer mixture. The isomer mixture was purified by SFC [Column:

Chiralpak IG-3 50×4.6 mm I.D., 3 um Mobile phase: Phase A for CO2, and Phase B for MeOH+ACN (0.05% DEA); Gradient elution: 60% Methanol+ACN (0.05% DEA) in CO2 Flow rate: 3 mL/min; Detector: PDA Column Temp: 35° C.; Back Pressure: 100 Bar] to afford tert-butyl 4-[4-[[5-[4-[1-(2-tert-butoxy-2-oxo-ethyl)-3-methyl-pyrazol-4-yl]phenyl]-1-methyl-imidazole-2-carbonyl]amino]-2-chloro-benzoyl] piperazine-1-carboxylate (470.0 mg, 0.65 mmol, 27.78% yield) as light yellow solid MS (ESI+) [(M+H)+]: 718.3.

The following example were prepared in analogy to Intermediate O4.

| Ex# | Name | Structure | MS [M + H]⁺ | Starting Material |
|---|---|---|---|---|
| Intermediate O5 | tert-butyl 4-[4-[[5-[4-[1-(2-tert-butoxy-2-oxo-ethyl)-3-methyl-pyrazol-4-yl]-3-fluoro-phenyl]-1-methyl-imidazole-2-carbonyl]amino]-2-chloro-benzoyl]piperazine-1-carboxylate | 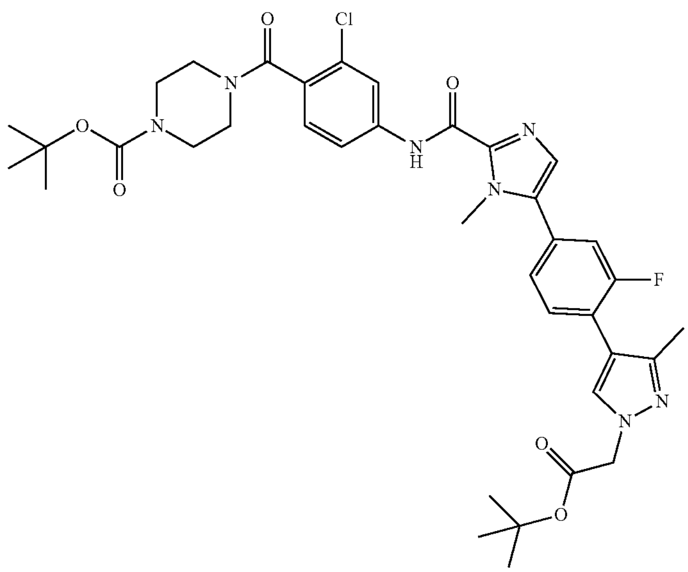 [SMILES: Cc1nn(CC(=O)OC(C)(C)C)cc1-c1ccc(-c2cnc(C(=O)Nc3ccc(C(=O)N4CCN(C(=O)OC(C)(C)C)CC4)c(Cl)c3)n2C)cc1F] | 736.2 | Intermediate G95 |
| Intermediate O6 | tert-butyl 4-[4-[[5-[4-[1-(2-tert-butoxy-2-oxo-ethyl)-3-methyl-pyrazol-4-yl]-2,3-difluoro-phenyl]-1-methyl-imidazole-2-carbonyl]amino]-2-chloro-benzoyl]piperazine-1-carboxylate | 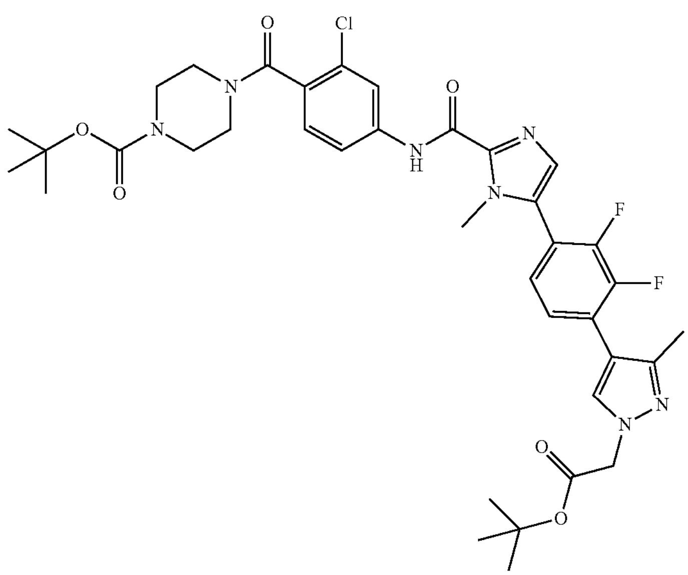 [SMILES: Cc1nn(CC(=O)OC(C)(C)C)cc1-c1ccc(-c2cnc(C(=O)Nc3ccc(C(=O)N4CCN(C(=O)OC(C)(C)C)CC4)c(Cl)c3)n2C)c(F)c1F] | 754.4 | Intermediate G96 |

| Ex# | Name | Structure | MS [M + H]+ | Starting Material |
|---|---|---|---|---|
| Intermediate O7 | tert-butyl 4-[2-chloro-4-[[5-[4-[1-[2-(difluoromethoxy)ethyl]-5-methyl-pyrazol-4-yl]-3-fluoro-2-methyl-phenyl]-1-methyl-imidazole-2-carbonyl]amino]benzoyl]piperazine-1-carboxylate | 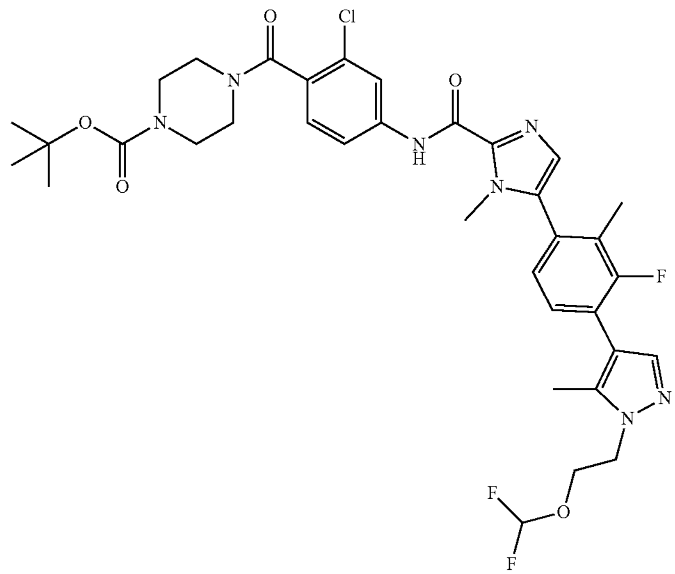 [SMILES: Cc1c(-c2cnc(C(=O)Nc3ccc(C(=O)N4CCN(C(=O)OC(C)(C)C)CC4)c(Cl)c3)n2C)ccc(-c2cnn(CCOC(F)F)c2C)c1F] | 730.0 | Intermediate G97 |

Intermediates R16 and R16' cis-1-(2-(tert-butoxy)-2-oxoethyl)-1-((1-(tert-butoxy-carbonyl)azetidin-3-yl)methyl)-4-carboxypiperidin-1-ium; 2,2,2-trifluoroacetate trans-1-(2-(tert-butoxy)-2-oxoethyl)-1-((1-(tert-bu-toxycarbonyl)azetidin-3-yl)methyl)-4-carboxypiperi-din-1-ium; 2,2,2-trifluoroacetate

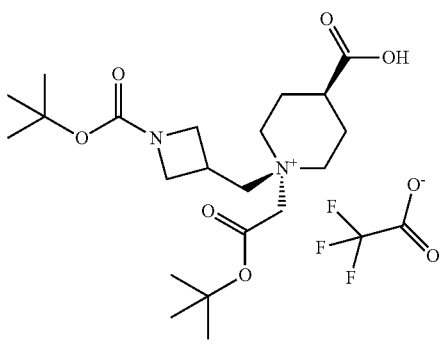

Intermediate R16'

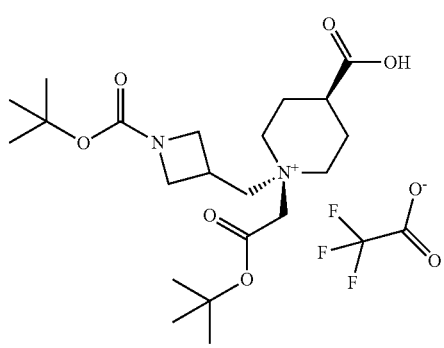

Intermediate R16

Intermediate R14 was purified by SFC (Column: DAI-CEL CHIRALCEL OD (250 mm×30 mm, 10 um); condition: 0.1% NH$_{13}$H2O MEOH; 20% B; Gradient Time(min): 6.5 min; FlowRate(ml/min): 50 mL/min) to give cis-1-(2-(tert-butoxy)-2-oxoethyl)-1-((1-(tert-butoxycarbonyl)azeti-din-3-yl)methyl)-4-carboxypiperidin-1-ium; 2,2,2-trifluoro-acetate (4.6 g, 11.15 mmol, 28.65% yield) as a white solid, MS [(M)+]: 413.0 and trans-1-(2-(tert-butoxy)-2-oxoethyl)-1-((1-(tert-butoxycarbonyl)azetidin-3-yl)methyl)-4-car-boxypiperidin-1-ium; 2,2,2-trifluoroacetate (4.6 g, 11.15 mmol, 28.65% yield) as a white solid MS [(M)+]: 413.0.

Intermediate R17

(1-tert-butoxycarbonylazetidin-3-yl)methyl-(2-tert-butoxy-2-oxo-ethyl)-(3-carboxypropyl)-methyl-ammonium; 2,2,2-trifluoroacetate

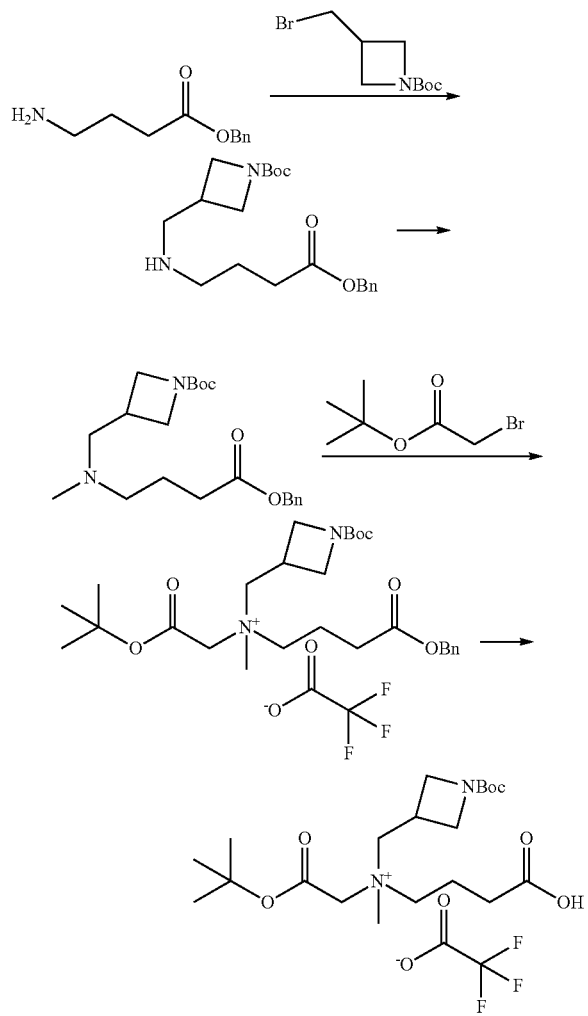

Step 1: tert-butyl 3-[[(4-benzyloxy-4-oxo-butyl)amino]methyl]azetidine-1-carboxylate To a mixture of benzyl 4-aminobutanoate;hydrochloride (4.5 g, 19.59 mmol) and potassium carbonate (8.12 g, 58.77 mmol), sodium iodide (146.83 mg, 0.98 mmol) in ACN (45 mL) was added 1-BOC-3-(bromomethyl)azetidine (6.37 g, 25.47 mmol) at 20° C. Then the mixture was stirred at 50° C. for 16 h. The mixture was filtered, the solid was washed with ACN (20 mL×3). The combined filtrate was concentrated under vacuum to give tert-butyl 3-[[(4-benzyloxy-4-oxo-butyl)amino]methyl]azetidine-1-carboxylate (12.0 g, 33.11 mmol, 99.71% yield) as a light yellow oil. MS [(M+H)+]: 363.2.

Step 2: tert-butyl 3-[[(4-benzyloxy-4-oxo-butyl)-methyl-amino]methyl]azetidine-1-carboxylate To a solution of tert-butyl 3-[[(4-benzyloxy-4-oxo-butyl)amino]methyl]azetidine-1-carboxylate (12.0 g, 33.11 mmol) in MeCN (100 mL) was added acetic acid (397.63 mg, 6.62 mmol) and formaldehyde (13.44 g, 165.54 mmol, 37% in water) at 30° C. and stirred for 2 h. Sodium cyan borohydride (4.16 g, 66.21 mmol) was added into the mixture in five portions at 30° C. and stirred at 30° C. for another 16 h. The mixture was concentrated under vacuum to afford a residue. The residue was dissolved in ACN (100 mL), filtered through the celite pad, The filtrate was concentrated under vacuum and purified by reversed phase-HPLC (water (0.1% FA)-ACN) and lyophilized to give tert-butyl 3-[[(4-benzyloxy-4-oxo-butyl)-methyl-amino]methyl]azetidine-1-carboxylate (1.9 g, 5.05 mmol, 15.24% yield) as light red oil. MS [(M+Na)+]: 399.2.

Step 3: (4-benzyloxy-4-oxo-butyl)-[(1-tert-butoxycarbonylazetidin-3-yl)methyl]-(2-tert-butoxy-2-oxo-ethyl)-methyl-ammonium;2,2,2-trifluoroacetate To a solution of tert-butyl 3-[[(4-benzyloxy-4-oxo-butyl)-methyl-amino]methyl]azetidine-1-carboxylate (1.7 g, 4.52 mmol) and DIEA (1.57 mL, 9.03 mmol) in ACN (20 mL) was added sodium iodide (67.68 mg, 0.45 mmol) and tert-butyl bromoacetate (1.32 g, 6.77 mmol). The mixture was stirred at 50° C. for 16 h. The mixture was concentrated under vacuum to afford a residue, which was purified by revered phase-HPLC (0water (0.1% TFA)-ACN), lyophilized to give (4-benzyloxy-4-oxo-butyl)-[(1-tert-butoxycarbonylazetidin-3-yl)methyl]-(2-tert-butoxy-2-oxo-ethyl)-methyl-ammonium;2,2,2-trifluoroacetate (2.3 g, 3.8 mmol, 81.35% yield) as light yellow gum. MS [(M)+]: 491.4.

Step 4: (1-tert-butoxycarbonylazetidin-3-yl)methyl-(2-tert-butoxy-2-oxo-ethyl)-(3-carboxypropyl)-methyl-ammonium; 2,2,2-trifluoroacetate To a solution of (4-benzyloxy-4-oxo-butyl)-[(1-tert-butoxycarbonylazetidin-3-yl)methyl]-(2-tert-butoxy-2-oxo-ethyl)-methyl-ammonium;2,2,2-trifluoroacetate (2.3 g, 3.8 mmol) in Methanol (30 mL) was added palladium on charcoal (460 mg, 0.43 mmol) and palladium hydroxide on charcoal (460.0 mg, 0.33 mmol) under N2. The mixture was degassed and then stirred at 30° C. for 3 h under hydrogen (760 mmHg). The mixture was filtered through celite pad, the solid was washed with MeOH (10 mL×3). The filtrate was concentrated under vacuum to give (1-tert-butoxycarbonylazetidin-3-yl)methyl-(2-tert-butoxy-2-oxo-ethyl)-(3-carboxypropyl)-methyl-ammonium; 2,2,2-trifluoroacetate (1.87 g, 3.63 mmol, 95.55% yield). MS [(M)+]: 401.1.

The following example was prepared in analogy to Intermediate R17.

| Ex# | Name | Structure | MS [M + H]+ | Starting Material |
|---|---|---|---|---|
| Intermediate R18 | 3-(tert-butoxycarbonyl-amino)propyl-(2-tert-butoxy-2-oxo-ethyl)-(3-carboxypropyl)-methyl-ammonium; bromide | 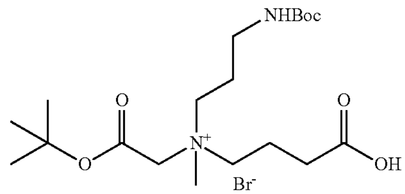 [SMILES: CC(C)(C)OC(=O)C[N+](C)(CCCNC(=O)OC(C)(C)C)CCCC(=O)O ; [Br-]] | 389.3 | benzyl 4-aminobutanoate; hydrochloride and 3-(Boc-amino)propyl bromide |
Intermediate R19
tert-butyl N-[3-[4-(3-aminopropyl)-2-pyridyl]propyl]carbamate; hydrochloride
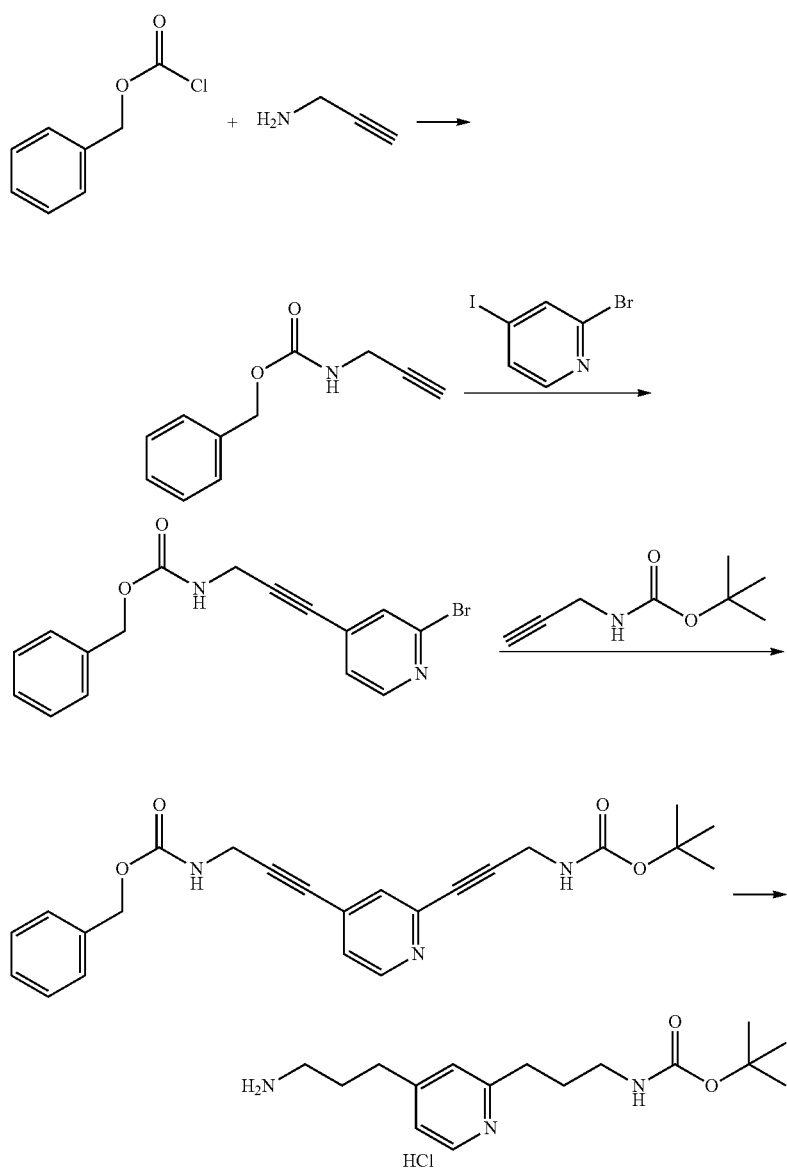

Step 1: benzyl N-prop-2-ynylcarbamate

To a mixture of propargylamine (5.0 g, 90.78 mmol, 1.0 eq) and sodium hydrogen carbonate (38.13 g, 453.89 mmol, 5.0 eq) in EtOAc (100 mL)/water (100 mL) was added dropwise benzyl chloroformate (14.25 mL, 99.85 mmol, 1.1 eq) at 0° C., then the mixture was stirred for 1 h at 0° C. The solution was poured into water (50 mL) and extracted with EtOAc, washed with brine, dried over Na₂SO₄, concentrated in vacuo and purified by flash chromatography to afford benzyl N-prop-2-ynylcarbamate (15.4 g, 81.39 mmol, 89.66% yield) as light yellow oil. MS [(M+H)+]: 189.9

Step 2: benzyl N-[3-(2-bromo-4-pyridyl)prop-2-ynyl]carbamate

A mixture of benzyl N-prop-2-ynylcarbamate (6.0 g, 31.7 mmol, 1.0 eq), copper(I) iodide (0.32 mL, 9.51 mmol, 0.3 eq) and tetrakis(triphenylphosphine)palladium(0) (1.83 g, 1.59 mmol, 0.05 eq) in toluene (20 mL) and was added 2-bromo-4-iodopyridine (9.0 g, 31.7 mmol, 1.0 eq), tetrabutylammonium fluoride in THF (31.7 mL, 31.7 mmol, 1.0 eq) and triethylamine (13.26 mL, 95.11 mmol, 3.0 eq) under N2, then the mixture was stirred at 25° C. for 16 h. The reaction was no further work-up and purified by flash chromatography to obtain benzyl N-[3-(2-bromo-4-pyridyl)prop-2-ynyl]carbamate (9.1 g, 26.36 mmol, 83.16% yield) as brown oil. MS [(M+H)+]: 345.0

Step 3: tert-butyl N-[3-[4-[3-(benzyloxycarbonylamino)prop-1-ynyl]-2-pyridyl]prop-2-ynyl]carbamate To a mixture of N—BOC-propargylamine (4.09 g, 26.36 mmol, 1.0 eq), copper(I) iodide (0.16 mL, 4.78 mmol, 0.18 eq) and bis(triphenylphosphine)palladium(II) chloride (0.93 g, 1.32 mmol, 0.05 eq) in DMF (10 mL) was added benzyl N-[3-(2-bromo-4-pyridyl)prop-2-ynyl]carbamate (9.1 g, 26.36 mmol, 1.0 eq) and triethylamine (91.0 mL, 652.89 mmol, 24.77 eq) under N2, then the mixture was stirred at 50° C. for 16 h. The reaction was concentrated under vacuum and purified by flash chromatography to obtain tert-butyl N-[3-[4-[3-(benzyloxycarbonylamino)prop-1-ynyl]-2-pyridyl]prop-2-ynyl]carbamate (9.4 g, 22.41 mmol, 85.0% yield) as brown oil. MS [(M+H)+]: 420.2

Step 4: tert-butyl N-[3-[4-(3-aminopropyl)-2-pyridyl]propyl]carbamate; hydrochloride To a mixture of tert-butyl N-[3-[4-[3-(benzyloxycarbonylamino)prop-1-ynyl]-2-pyridyl]prop-2-ynyl]carbamate (4.0 g, 9.54 mmol, 1.0 eq) and ammonium hydroxide (1.0 mL, 9.54 mmol, 1.0 eq) in methanol (50 mL) was added wet palladium 10% on activated carbon (400.0 mg, 9.54 mmol, 1.0 eq) at 25° C. The mixture was degassed and purged with H2 for 3 times. Then the mixture was stirred under hydrogen for 48 h. The reaction was filtered through a pad of celite and the filtrate was concentrated in vacuo. The residue was purified by prep-HPLC and lyophilized to obtain the white solid, then dissolved in HCl solution (5%, 100 mL) and lyophilized to afford tert-butyl N-[3-[4-(3-aminopropyl)-2-pyridyl]propyl]carbamate; hydrochloride (2090.86 mg, 6.34 mmol, 64.54% yield) as light yellow oil. MS [(M+H)+]: 294.2

Intermediate R19 bis [4-(tert-butoxycarbonylamino)butyl]-(2-tert-butoxy-2-oxo-ethyl)-(3-carboxypropyl)ammonium; bromide

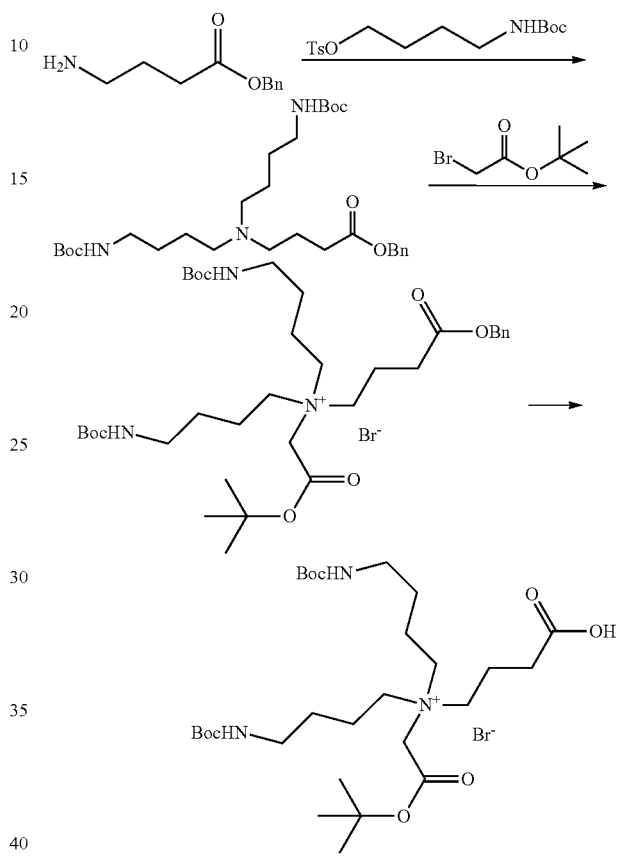

Step 1: benzyl 4-[bis[4-(tert-butoxycarbonylamino)butyl]amino]butanoate

To a mixture of 4-(tert-butoxycarbonylamino)butyl 4-methylbenzenesulfonate (4934.05 mg, 14.37 mmol) and benzyl 4-aminobutanoate;hydrochloride (1.5 g, 6.53 mmol) in ACN (60 mL) was added potassium carbonate (2707.56 mg, 19.59 mmol). The reaction mixture was stirred at 50° C. for 16 h. The reaction mixture was filtered, the filtrate was concentrated in vacuum to give the residue, which was purified by reversed phase-HPLC and lyophilized to afford benzyl 4-[bis[4-(tert-butoxycarbonylamino)butyl]amino] butanoate (2000.0 mg, 3.25 mmol, 57.17% yield) as yellow oil. MS [(M+H)+]: 536.4.

Step 2: (4-benzyloxy-4-oxo-butyl)-bis[4-(tert-butoxycarbonylamino)butyl]-(2-tert-butoxy-2-oxo-ethyl)ammonium; bromide To a mixture of benzyl 4-[bis[4-(tert-butoxycarbonylamino)butyl]amino]butanoate (2000.0 mg, 3.25 mmol) and N-ethyl-N-isopropylpropan-2-amine (839.74 mg, 6.5 mmol) in ACN (10 mL) was added tert-butyl bromoacetate (633.67 mg, 3.25 mmol) at 20° C. The reaction mixture was stirred at 50° C. for 16 h. The reaction mixture was filtered, the filtrate was concentrated in vacuum to give the residue, which was purified by reversed phase-HPLC and lyophilized to afford (4-benzyloxy-4-oxo-butyl)-bis[4-(tert-butoxycarbonylamino)butyl]-(2-tert-butoxy-2-oxo-ethyl)ammonium; bromide (400.0 mg, 0.55 mmol, 18.92% yield) as yellow solid. MS [(M)+]: 650.4.

Step 3: bis[4-(tert-butoxycarbonylamino)butyl]-(2-tert-butoxy-2-oxo-ethyl)-(3-carboxypropyl)ammonium; bromide To a solution of (4-benzyloxy-4-oxo-butyl)-bis[4-(tert-butoxycarbonylamino)butyl]-(2-tert-butoxy-2-oxo-ethyl)ammonium;bromide (500.0 mg, 0.68 mmol) in Methanol (20 mL) was added wet palladium on active carbon (50.0 mg, 10%) at 30° C. under N2, then the reaction mixture was stirred at 30° C. for 16 h under H2 (balloon, 15 psi). The reaction mixture was filtered, the filtrate was concentrated in vacuum to give bis[4-(tert-butoxycarbonylamino)butyl]-(2-tert-butoxy-2-oxo-ethyl)-(3-carboxypropyl)ammonium; bromide (250.0 mg, 0.39 mmol, 57.03% yield) as colorless oil. MS [(M)+]: 560.8.

Intermediate R20

4-[bis[3-(tert-butoxycarbonylamino)propyl]amino]butanoic acid

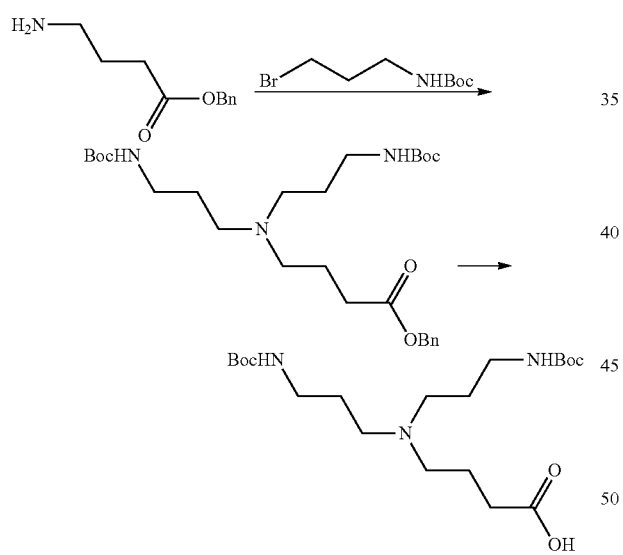

Step 1: benzyl 4-[bis[3-(tert-butoxycarbonylamino)propyl]amino]butanoate

To a stirred mixture of benzyl 4-aminobutanoate;hydrochloride (4.5 g, 19.59 mmol) and potassium carbonate (5.42 g, 39.18 mmol) in ACN (100 mL) was added 3-(BOC-amino)propyl bromide (11.66 g, 48.98 mmol) at 20° C., then the mixture was stirred at 60° C. for 16 h. The solution was cooled to room temperature and filtered. The filtrate was concentrated in vacuum, purified by reversed phase-HPLC and lyophilized to afford benzyl 4-[bis[3-(tert-butoxycarbonylamino)propyl]amino]butanoate (3.5 g, 6.89 mmol, 35.19% yield) as colorless oil. MS [(M+H)+]: 508.1.

Step 2: 4-[bis[3-(tert-butoxycarbonylamino)propyl]amino]butanoic acid

To a solution of benzyl 4-[bis[3-(tert-butoxycarbonylamino)propyl]amino]butanoate (1.3 g, 2.56 mmol) in Methanol (50 mL) was added wet palladium on active carbon (0.27 g, 0.26 mmol, 10%) at 20° C. under N2, then the mixture was stirred under H2 (balloon) at 20° C. for 16 h. The solution was filtered with diatomite and concentrated to afford 4-[bis[3-(tert-butoxycarbonylamino)propyl]amino]butanoic acid (706.0 mg, 1.69 mmol, 66.03% yield) as colorless oil. MS [(M+H)+]: 418.3.

Intermediate R21 bis[2-(tert-butoxycarbonylamino)ethyl]-(2-tert-butoxy-2-oxo-ethyl)-(3-carboxypropyl)ammonium; bromide

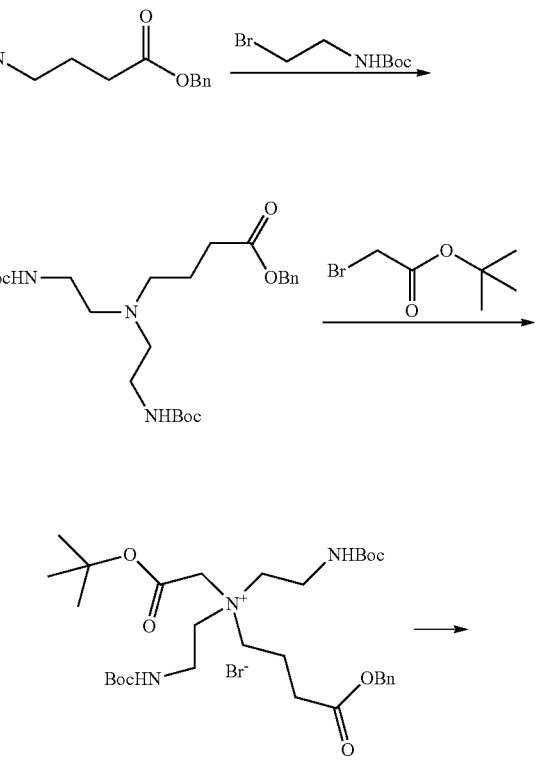

Step 1: benzyl 4-[bis[2-(tert-butoxycarbonylamino)ethyl]amino]butanoate

To a solution of benzyl 4-aminobutanoate;hydrochloride (11.0 g, 47.89 mmol) in ACN (100 mL) was added tert-butyl N-(2-bromoethyl)carbamate (32.2 g, 143.67 mmol) and DIEA (33.36 mL, 191.55 mmol) at 10° C., then the mixture was stirred at 50° C. for 48 h. The solution was concentrated, the residue was purified by reversed phase-HPLC and lyophilized to afford benzyl 4-[bis[2-(tert-butoxycarbonylamino)ethyl]amino]butanoate (6.5 g, 13.55 mmol, 28.3% yield) as light yellow oil. MS [(M+H)+]: 480.3.

Step 2: (4-benzyloxy-4-oxo-butyl)-bis[2-(tert-butoxycarbonylamino)ethyl]-(2-tert-butoxy-2-oxo-ethyl)ammonium;bromide To a mixture of benzyl 4-[bis[2-(tert-butoxycarbonylamino)ethyl]amino]butanoate (5.0 g, 10.43 mmol) in ACN (50 mL) was added tert-butyl bromoacetate (12.2 g, 62.55 mmol) and DIEA (5.45 mL, 31.28 mmol) at 10° C. The reaction mixture was stirred at 60° C. for 16 h. The mixture was concentrated under vacuum and the residue was purified by reversed phase-HPLC and lyophilized to afford (4-benzyloxy-4-oxo-butyl)-bis[2-(tert-butoxycarbonylamino)ethyl]-(2-tert-butoxy-2-oxo-ethyl)ammonium; bromide (5.5 g, 8.17 mmol, 78.33% yield) as white solid. MS [(M)+]: 594.3.

Step 3: bis[2-(tert-butoxycarbonylamino)ethyl]-(2-tert-butoxy-2-oxo-ethyl)-(3-carboxypropyl)ammonium; bromide To a solution of (4-benzyloxy-4-oxo-butyl)-bis[2-(tert-butoxycarbonylamino)ethyl]-(2-tert-butoxy-2-oxo-ethyl)ammonium;formate (2.5 g, 3.91 mmol) in Methanol (50 mL) was added wet palladium on active carbon (250 mg, 10%) under N2. Then the mixture was stirred under Hydrogen (15 Psi) at 20° C. for 16 h. The mixture was filtered with diatomite and the filtrate was concentrated to afford bis[2-(tert-butoxycarbonylamino)ethyl]-(2-tert-butoxy-2-oxo-ethyl)-(3-carboxypropyl)ammonium; bromide (1.2 g, 2.05 mmol, 52.54% yield) as white solid. MS [(M)+]: 504.4.

Intermediate R22 tert-butyl 2-[1-[3-(tert-butoxycarbonylamino)propyl]piperazin-1-ium-1-yl]acetate; formate

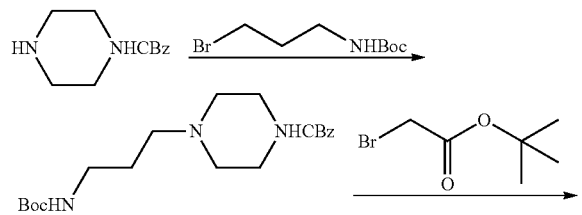

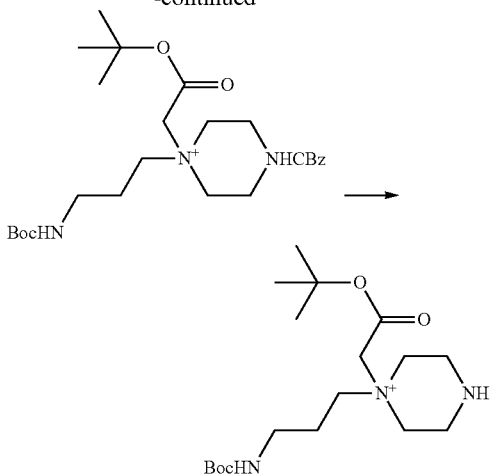

Step 1: benzyl 4-[3-(tert-butoxycarbonylamino)propyl]piperazine-1-carboxylate To a solution of 1-CBZ-piperazine (5.0 g, 22.7 mmol, 1.0 eq) in MeCN (100 mL) was added triethylamine (3.16 mL, 22.7 mmol, 1.0 eq) and 3-(BOC-amino)propyl bromide (5.68 g, 23.83 mmol, 1.05 eq), then the mixture was stirred at 25° C. for 16 h. The mixture was concentrated in vacuo and purified by flash chromatography to obtain benzyl 4-[3-(tert-butoxycarbonylamino)propyl]piperazine-1-carboxylate (5.2 g, 13.78 mmol, 60.69% yield) as light brown solid. MS [(M+H)+]: 378.3

Step 2: benzyl 4-[3-(tert-butoxycarbonylamino)propyl]piperazine-1-carboxylate To a solution of benzyl 4-[3-(tert-butoxycarbonylamino)propyl]piperazine-1-carboxylate (5.2 g, 13.78 mmol, 1 eq) in MeCN (100 mL) was added triethylamine (1.92 mL, 13.78 mmol, 1 eq) and tert-butyl bromoacetate (5.37 g, 27.55 mmol, 2 eq), then the mixture was stirred at 50° C. for 16 h. The mixture was concentrated in vacuo and purified by prep-HPLC to obtain benzyl 4-[3-(tert-butoxycarbonylamino)propyl]-4-(2-tert-butoxy-2-oxo-ethyl)piperazin-4-ium-1-carboxylate;formate (4.0 g, 7.44 mmol, 58.94% yield) as light yellow oil. MS [(M+]: 492.4

Step 3: tert-butyl 2-[1-[3-(tert-butoxycarbonylamino)propyl]piperazin-1-ium-1-yl]acetate; formate To a solution of benzyl 4-[3-(tert-butoxycarbonylamino)propyl]-4-(2-tert-butoxy-2-oxo-ethyl)piperazin-4-ium-1-carboxylate (4.0 g, 8.12 mmol, 1.0 eq) in THE (40 mL) with palladium (0.39 mL, 0.38 mmol, 0.05 eq) was treated under Hydrogen (16.24 mg, 8.12 mmol, 1.0 eq) at 25° C. for 16 h. The cat. was filtered and washed. The filtrate was concentrated in vacuo and purified by prep-HPLC to obtain tert-butyl 2-[1-[3-(tert-butoxycarbonylamino)propyl]piperazin-1-ium-1-yl]acetate (1.5 g, 3.72 mmol, 51.53% yield)tert-butyl 2-[1-[3-(tert-butoxycarbonylamino)propyl]piperazin-1-ium-1-yl]acetate; formate (1.5 g, 3.72 mmol, 51.53% yield) as white solid. MS [(M+]: 358.3

The following example was prepared in analogy to Intermediate R22.

| Ex# | Name | Structure | MS [M+] | Starting Material |
|---|---|---|---|---|
| Intermediate R23 | tert-butyl 3-[[1-(2-tert-butoxy-2-oxo-ethyl)piperazin-1-ium-1-yl]methyl]azetidine-1-carboxylate; formate | 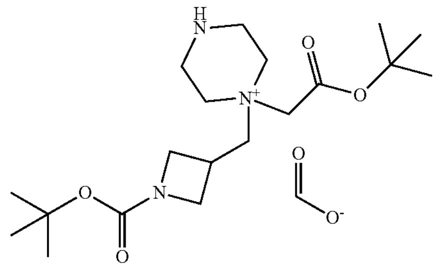 | 370.6 | 1-BOC-3-(bromomethyl) azetidine |

Intermediate R24

1-[2-(tert-butoxycarbonylamino)ethyl]-1-(2-tert-butoxy-2-oxo-ethyl)piperidin-1-ium-4-carboxylic acid; 2,2,2-trifluoroacetate

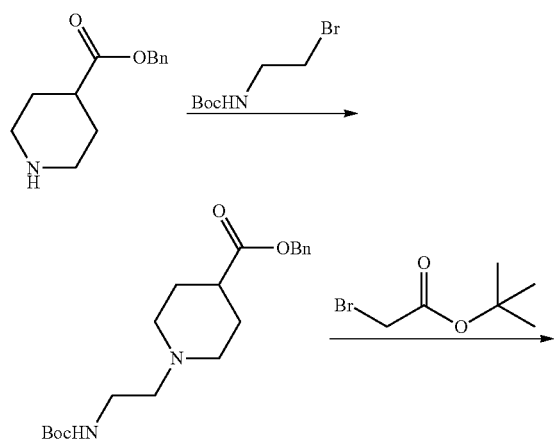

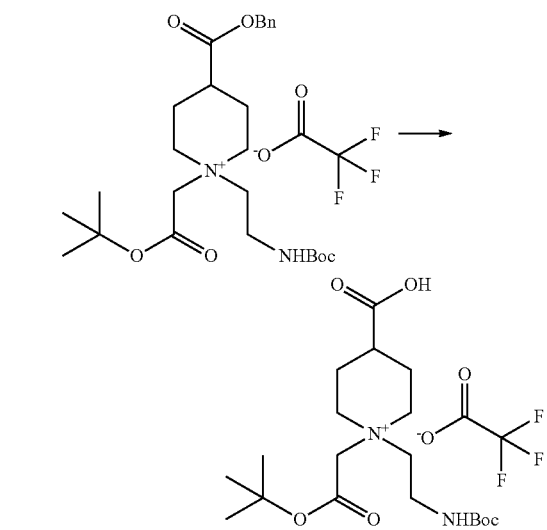

Step 1: benzyl 1-[2-(tert-butoxycarbonylamino) ethyl]piperidine-4-carboxylate To a solution of benzyl piperidine-4-carboxylate; hydrochloride (6.0 g, 23.46 mmol, 1.0 eq) and potassium carbonate (6.48 g, 46.92 mmol) in DMF (120 mL) was added tert-butyl N-(2-bromoethyl)carbamate (6.31 g, 28.15 mmol) at 20° C. and stirred at 20° C. for 16 h. The mixture was poured into water (200 mL) and then extracted with EtOAc (100 mL×3). The combined organic layers were washed with brine (80 mL×3), dried over sodium sulfate, filtered, the filtrate was concentrated under vacuum to give benzyl 1-[2-(tert-butoxycarbonylamino)ethyl]piperidine-4-carboxylate (9.23 g, 25.46 mmol, 97.69% yield) as a light yellow oil. MS [(M+H)+]: 363.2.

Step 2: benzyl 1-[2-(tert-butoxycarbonylamino) ethyl]-1-(2-tert-butoxy-2-oxo-ethyl)piperidin-1-ium-4-carboxylate; 2,2,2-trifluoroacetate To a solution of benzyl 1-[2-(tert-butoxycarbonylamino) ethyl]piperidine-4-carboxylate (9.23 g, 25.46 mmol), NaI (381.7 mg, 2.55 mmol) and DIEA (6.65 mL, 38.2 mmol) in DMF (90 mL) was added tert-butyl bromoacetate (5.96 g, 30.56 mmol) at 20° C. and stirred at 20° C. for 16 h. The mixture was concentrated under vacuum, the residue was purified by reversed phase-HPLC (water (0.1% TFA)-ACN) and lyophilized to give benzyl 1-[2-(tert-butoxycarbonylamino)ethyl]-1-(2-tert-butoxy-2-oxo-ethyl)piperidin-1-ium-4-carboxylate; 2,2,2-trifluoroacetate (5.7 g, 9.65 mmol, 46.87% yield) as a light yellow gum. MS [(M)+]: 477.2.

Step 3: 1-[2-(tert-butoxycarbonylamino)ethyl]-1-(2-tert-butoxy-2-oxo-ethyl)piperidin-1-ium-4-carboxylic acid; 2,2,2-trifluoroacetate To a solution of benzyl 1-[2-(tert-butoxycarbonylamino) ethyl]-1-(2-tert-butoxy-2-oxo-ethyl)piperidin-1-ium-4-carboxylate;2,2,2-trifluoroacetate (6.43 g, 10.89 mmol) in methanol (120 mL) was added palladium hydroxide on charcoal (1528.98 mg, 1.09 mmol, 10%) and palladium on charcoal (1.13 mL, 1.09 mmol, 10%) under N2. The mixture was degassed and then stirred under hydrogen (760 mmHg) at 25° C. for 4 h. The mixture was filtered through the celite pad, the solid was washed with MeOH (20 mL×4). The combined filtrate was concentrated under vacuum to give 1-[2-(tert-butoxycarbonylamino)ethyl]-1-(2-tert-butoxy-2-oxo-ethyl)piperidin-1-ium-4-carboxylic acid; 2,2,2-trifluoroacetate (4.1 g, 8.19 mmol, 67.71% yield) as a white solid. MS [(M)+]: 387.2.

Example L1
N-[3-chloro-4-[4-(1,1-dimethylpiperidin-1-ium-4-carbonyl)piperazine-1-carbonyl]phenyl]-5-[4-[1-[2-[(6-fluoropyridazin-3-yl)amino]-2-oxo-ethyl]-3-methyl-pyrazol-4-yl]phenyl]-1-methyl-imidazole-2-carboxamide; formate
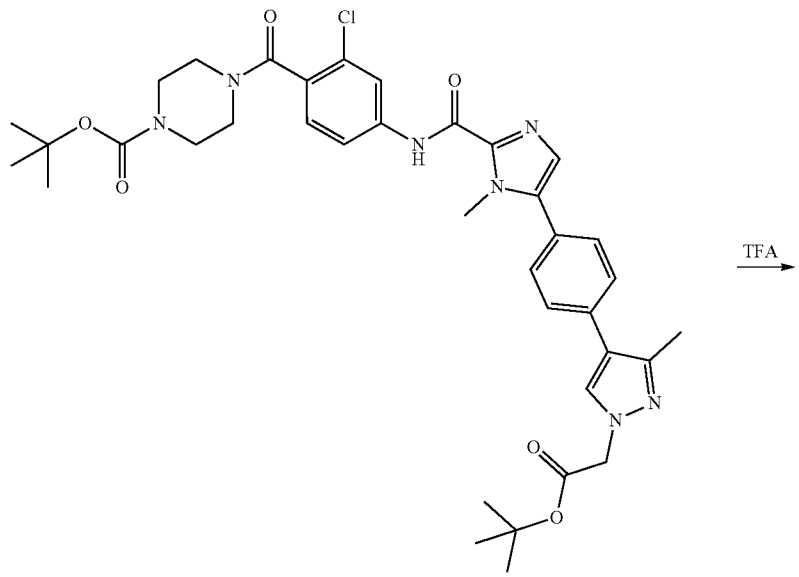
Intermediate O4
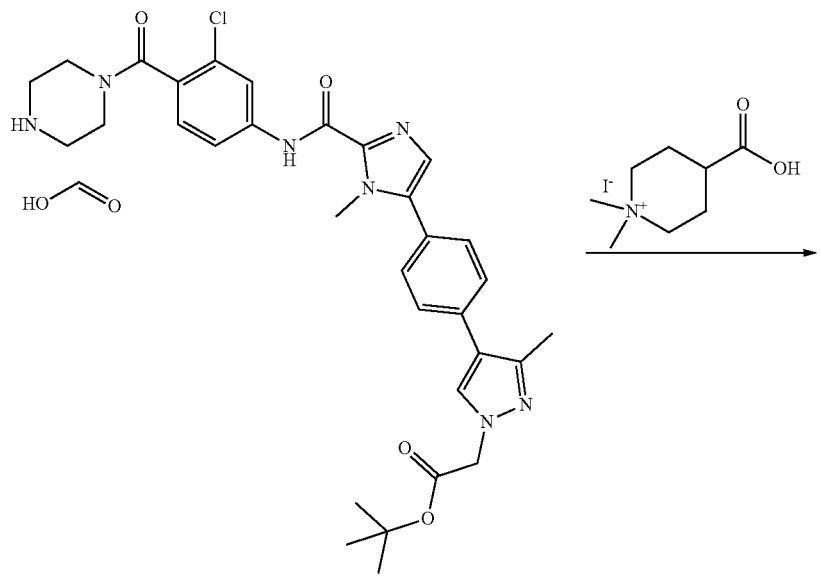

-continued
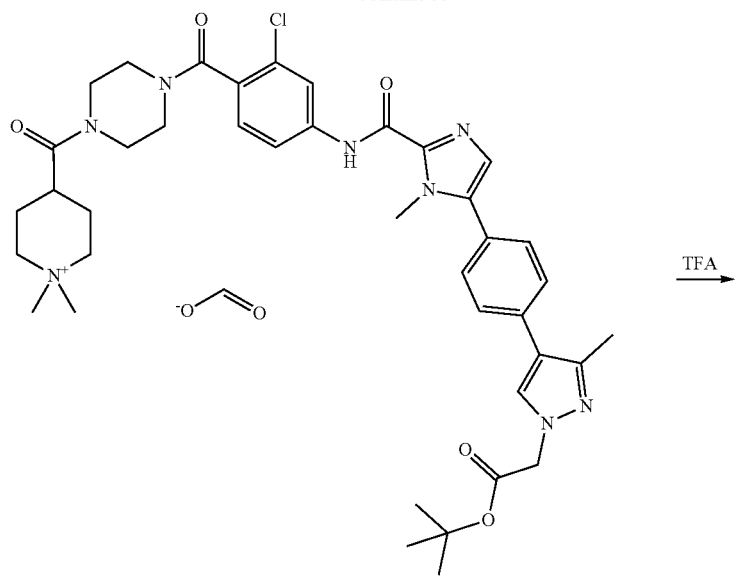
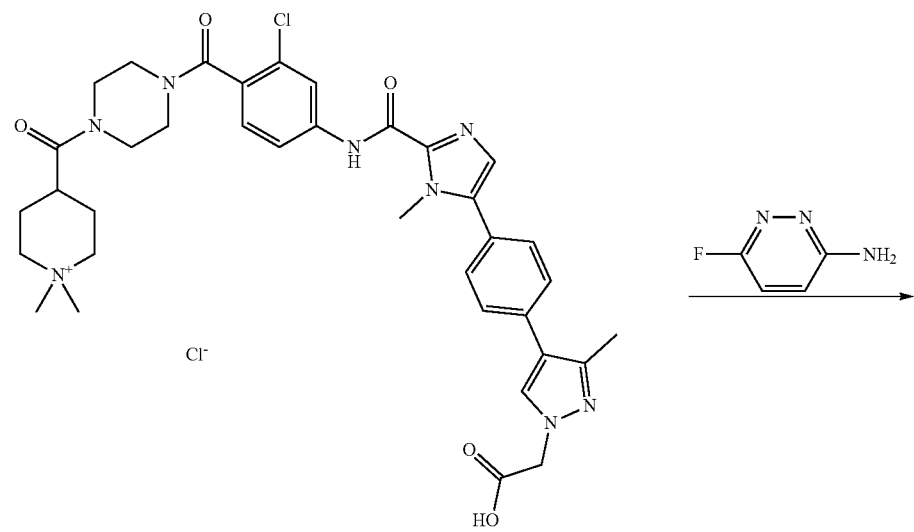

-continued

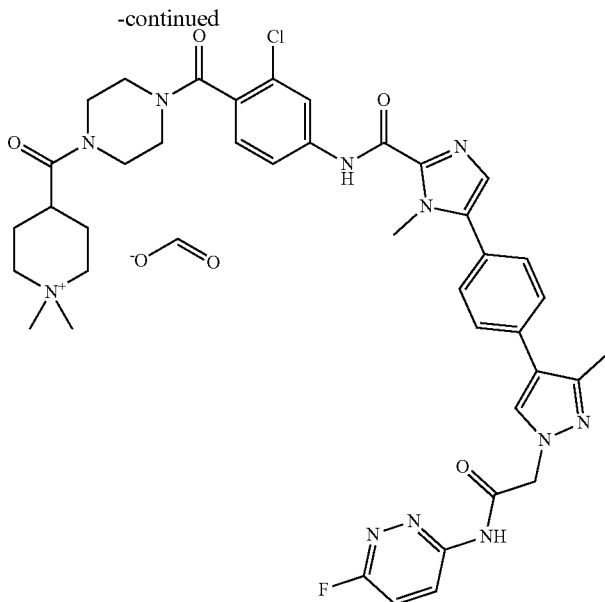

Example L1

Step 1: tert-butyl 2-[4-[4-[2-[[3-chloro-4-(piperazine-1-carbonyl)phenyl]carbamoyl]-3-methyl-imidazol-4-yl]phenyl]-3-methyl-pyrazol-1-yl]acetate; formic acid To a solution of tert-butyl 4-[4-[[5-[4-[1-(2-tert-butoxy-2-oxo-ethyl)-3-methyl-pyrazol-4-yl]phenyl]-1-methyl-imidazole-2-carbonyl]amino]-2-chloro-benzoyl]piperazine-1-carboxylate (200.0 mg, 0.28 mmol) in DCM (5 mL) was added TFA (0.25 mL, 3.24 mmol) at 25° C. and for 16 h. The mixture was concentrated in vacuum and purified by reversed phase HPLC (water (0.1% FA)-ACN) and lyophilized to afford tert-butyl 2-[4-[4-[2-[[3-chloro-4-(piperazine-1-carbonyl) phenyl] carbamoyl]-3-methyl-imidazol-4-yl]phenyl]-3-methyl-pyrazol-1-yl]acetate; formic acid (70.0 mg, 0.11 mmol, 40.67% yield) as white solid. MS [(M+H)+]: 618.3

Step 2: tert-butyl 2-[4-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]phenyl]-3-methyl-pyrazol-1-yl]acetate; formate To a solution of tert-butyl 2-[4-[4-[2-[[3-chloro-4-(piperazine-1-carbonyl)phenyl]carbamoyl]-3-methyl-imidazol-4-yl]phenyl]-3-methyl-pyrazol-1-yl]acetate;formic acid (70.0 mg, 0.11 mmol), 1,1-dimethylpiperidin-1-ium-4-carboxylic acid;iodide (60.1 mg, 0.21 mmol), DIEA (0.09 mL, 0.53 mmol) in DMF (2 mL) was added HATU (60.11 mg, 0.16 mmol) at 0° C. and stirred at 0° C. for 0.5 h. The mixture was purified by reversed phase-HPLC (water (0.1% FA)-ACN) and lyophilized to afford tert-butyl 2-[4-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]phenyl]-3-methyl-pyrazol-1-yl]acetate; formate (60.0 mg, 0.08 mmol, 75.07% yield) as yellow solid. MS [(M)+]: 757.4.

Step 3: 2-[4-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]phenyl]-3-methyl-pyrazol-1-yl]acetic acid; chloride To a solution of tert-butyl 2-[4-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]phenyl]-3-methyl-pyrazol-1-yl]acetate;formate (60.0 mg, 0.07 mmol) in DCM (2 mL) was added TFA (2.0 mL, 25.96 mmol) at 25° C. and stirred for 0.5 h. The mixture was concentrated in vacuum and purified by reversed phase HPLC (water (0.1% HCl)-ACN), lyophilized to afford 2-[4-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]phenyl]-3-methyl-pyrazol-1-yl]acetic acid; chloride (40.0 mg, 0.05 mmol, 76.27% yield) as white solid. MS [(M)+]: 701.4.

Step 4: N-[3-chloro-4-[4-(1,1-dimethylpiperidin-1-ium-4-carbonyl)piperazine-1-carbonyl]phenyl]-5-[4-[1-[2-[(6-fluoropyridazin-3-yl)amino]-2-oxo-ethyl]-3-methyl-pyrazol-4-yl]phenyl]-1-methyl-imidazole-2-carboxamide; formate To a solution of 2-[4-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]phenyl]-3-methyl-pyrazol-1-yl]acetic acid;chloride (70.0 mg, 0.09 mmol) in DMF (2 mL) was added DIEA (0.05 mL, 0.28 mmol) and 2-chloro-1-methylpyridinium iodide (36.36 mg, 0.14 mmol) at 25° C. and stirred for 20 min. Then 6-fluoropyridazin-3-amine (16.1 mg, 0.14 mmol) was added to the solution and stirred at 80° C. for 8 h. The mixture was purified by Prep-HPLC (Phenomenex Luna C18 75×30 mm×3 um, water (0.225 FA)-ACN, B=190%-39%; FowRat: 25 ml/min) to afford N-[3-chloro-4-[4-(1,1-dimethylpiperidin-1-ium-4-carbonyl)piperazine-1-carbonyl]phenyl]-5-[4-[1-[2-[(6-fluoropyridazin-3-yl)amino]-2-oxo-ethyl]-3-methyl-pyrazol-4-yl]phenyl]-1-methyl-imidazole-2-carboxamide; formate (28.9 mg, 0.03 mmol, 35.07% yield) as yellow solid. MS [(M)+]: 796.0.

The following examples were prepared in analogy to Examples L1.

| Ex# | Name | Structure | MS [M]+ | Starting Material |
|---|---|---|---|---|
| Example L2 | N-[3-chloro-4-[4-(1,1-dimethylpiperidin-1-ium-4-carbonyl)piperazine-1-carbonyl]phenyl]-5-[3-fluoro-4-[1-[2-[(6-fluoropyridazin-3-yl)amino]-2-oxo-ethyl]-3-methyl-pyrazol-4-yl]phenyl]-1-methyl-imidazole-2-carboxamide; formate | 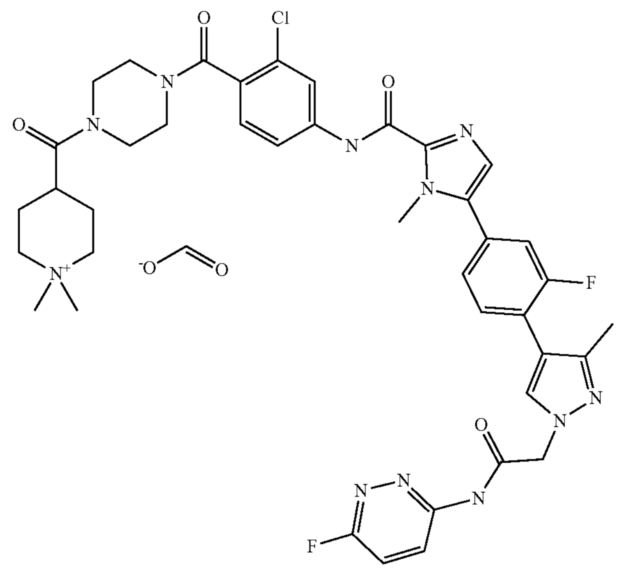 | 814.2 | Intermediate O5 and 6-fluoropyridazin-3-amine |
| Example L3 | N-[3-chloro-4-[4-(1,1-dimethylpiperidin-1-ium-4-carbonyl)piperazine-1-carbonyl]phenyl]-5-[2,3-difluoro-4-[3-methyl-1-[2-[(6-methylpyridazin-3-yl)amino]-2-oxo-ethyl]pyrazol-4-yl]phenyl]-1-methyl-imidazole-2-carboxamide; formate | 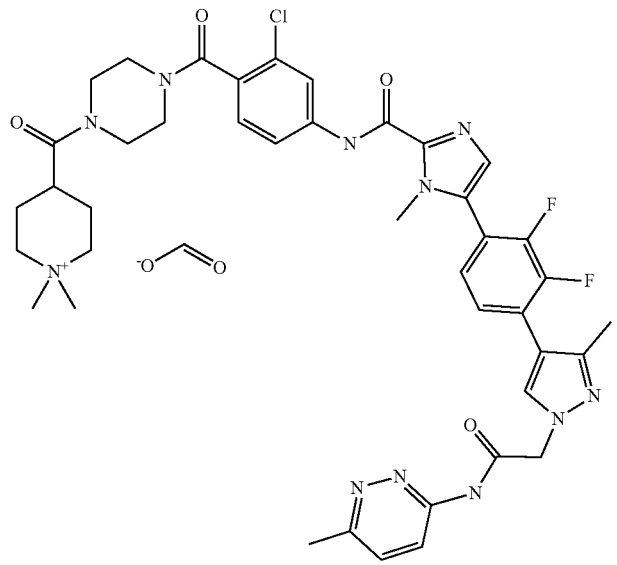 | 828.4 | Intermediate O6 and 3-amino-6-methylpyridazine |

| Ex# | Name | Structure | MS [M]+ | Starting Material |
|---|---|---|---|---|
| Example L4 | N-[3-chloro-4-[4-(1,1-dimethylpiperidin-1-ium-4-carbonyl)piperazine-1-carbonyl]phenyl]-5-[2,3-difluoro-4-[1-[2-[(6-methoxypyridazin-3-yl)amino]-2-oxo-ethyl]-3-methyl-pyrazol-4-yl]phenyl]-1-methyl-imidazole-2-carboxamide; formate | 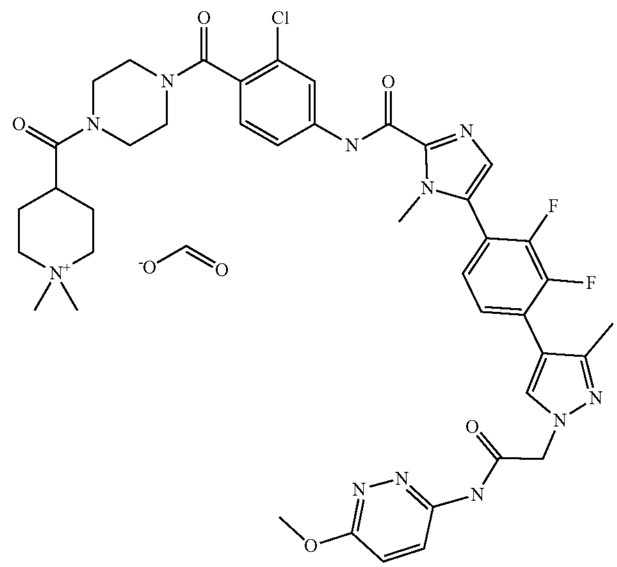 | 844.4 | Intermediate O6 and 3-amino-6-methoxypyridazine |
| Example L5 | N-[3-chloro-4-[4-(1,1-dimethylpiperidin-1-ium-4-carbonyl)piperazine-1-carbonyl]phenyl]-5-[2,3-difluoro-4-[3-methyl-1-[2-[(6-morpholinopyridazin-3-yl)amino]-2-oxo-ethyl]pyrazol-4-yl]phenyl]-1-methyl-imidazole-2-carboxamide; formate | 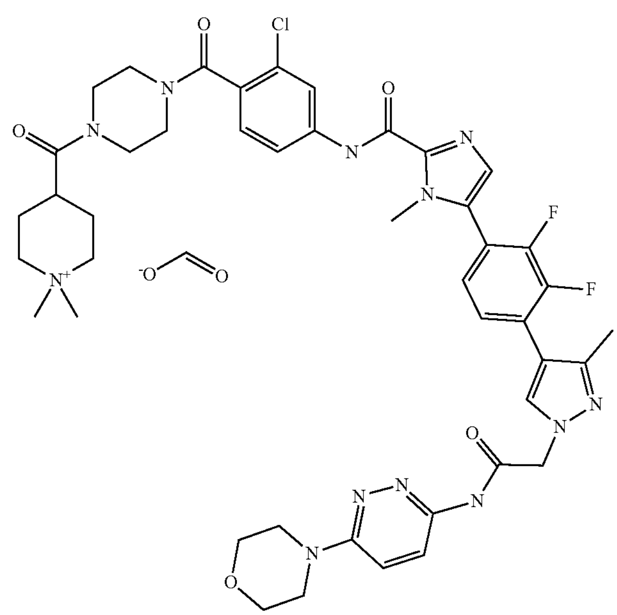 | 899.2 | Intermediate O6 and 6-morpholinopyridazin-3-amine |

Example L6
cis 2-[1-(azetidin-3-ylmethyl)-4-[4-[2-chloro-4-[[5-[2,3-difluoro-4-[1-[2-[(6-fluoropyridazin-3-yl)amino]-2-oxo-ethyl]-3-methyl-pyrazol-4-yl]phenyl]-methyl-imidazole-2-carbonyl]amino]benzoyl]piperazine-1-carbonyl]piperidin-1-ium-1-yl]acetic acid; formate
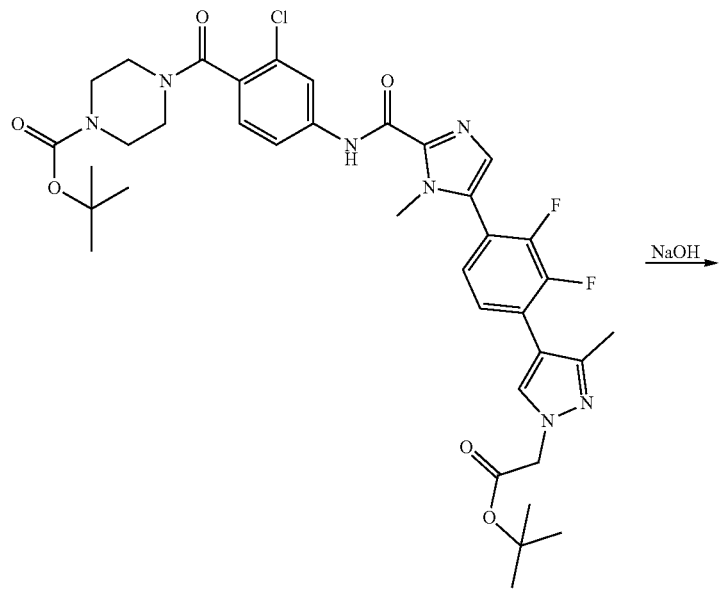
Intermediate O6
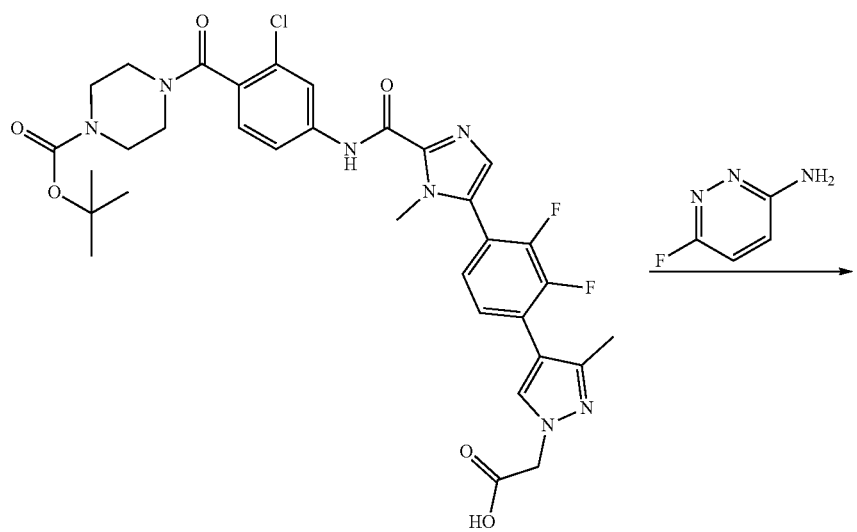

-continued
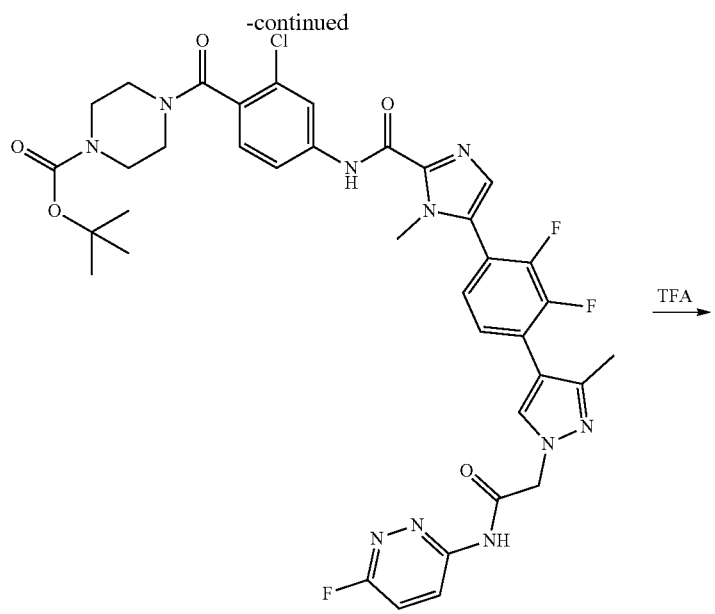
TFA →
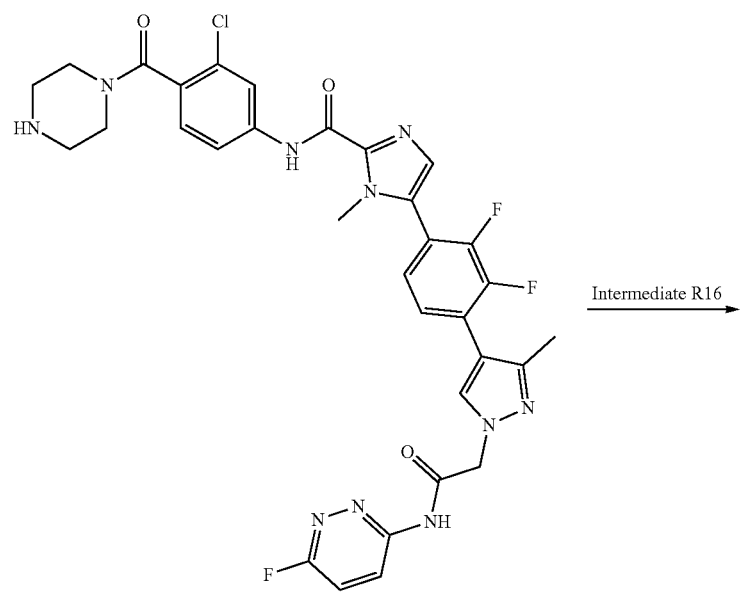
Intermediate R16 →

581
-continued
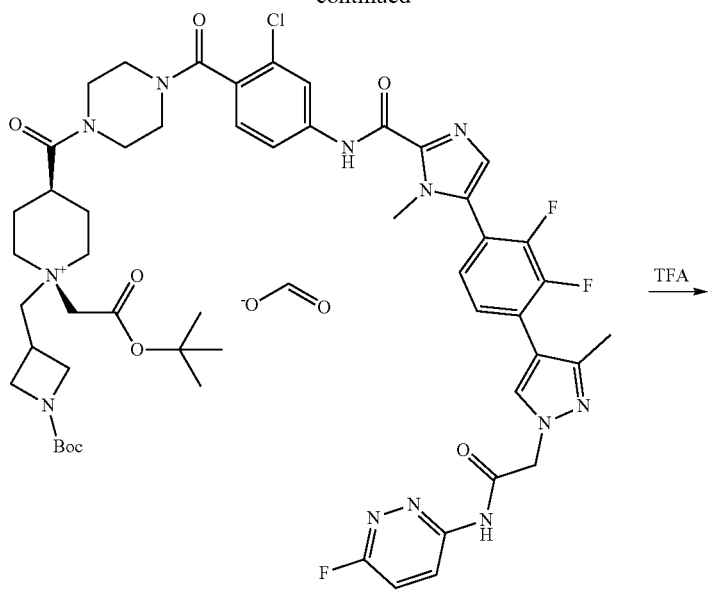
TFA →
582
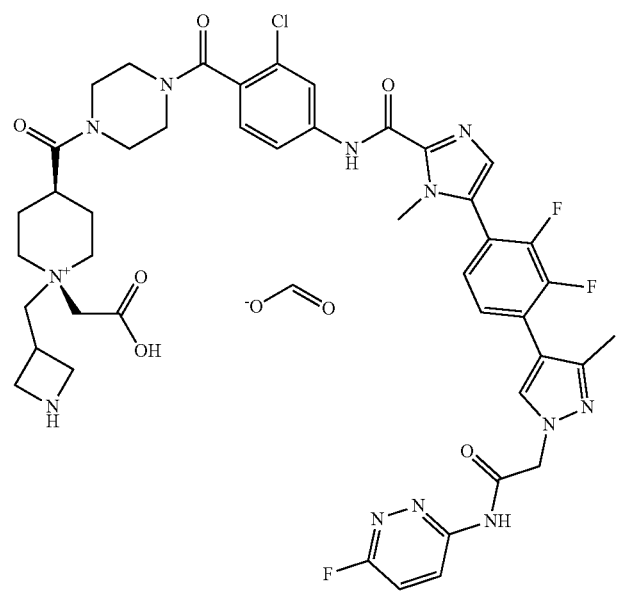

Step 1: 2-[4-[4-[2-[[4-(4-tert-butoxycarbonylpiperazine-1-carbonyl)-3-chloro-phenyl]carbamoyl]-3-methyl-imidazol-4-yl]-2,3-difluoro-phenyl]-3-methyl-pyrazol-1-yl]acetic acid To a solution of tert-butyl 4-[4-[[5-[4-[1-(2-tert-butoxy-2-oxo-ethyl)-3-methyl-pyrazol-4-yl]-2,3-difluoro-phenyl]-1-methyl-imidazole-2-carbonyl]amino]-2-chloro-benzoyl]piperazine-1-carboxylate (300.0 mg, 0.4 mmol) in Water (3 mL) and THF (3 mL) was added sodium hydroxide (47.7 mg, 1.19 mmol). The mixture was stirred at 10° C. and for 16 h. The reaction mixture was pour into water (10 mL), acidified with aq. HCl (1N) to pH=6, extracted with EA (10 mL×2). The combined organic layer was washed with brine, dried over sodium sulfate, concentrated in vacuum to afford 2-[4-[4-[2-[[4-(4-tert-butoxycarbonylpiperazine-1-carbonyl)-3-chloro-phenyl]carbamoyl]-3-methyl-imidazol-4-yl]-2,3-difluoro-phenyl]-3-methyl-pyrazol-1-yl]acetic acid (220.0 mg, 79.2% yield) as off-white solid. MS [(M+H)+]: 698.3.

Step 2: tert-butyl 4-[2-chloro-4-[[5-[2,3-difluoro-4-[1-[2-[(6-fluoropyridazin-3-yl)amino]-2-oxo-ethyl]-3-methyl-pyrazol-4-yl]phenyl]-1-methyl-imidazole-2-carbonyl]amino]benzoyl]piperazine-1-carboxylate To a solution of 2-[4-[4-[2-[[4-(4-tert-butoxycarbonylpiperazine-1-carbonyl)-3-chloro-phenyl]carbamoyl]-3-methyl-imidazol-4-yl]-2,3-difluoro-phenyl]-3-methyl-pyrazol-1-yl]acetic acid (220.0 mg, 0.32 mmol) and 6-fluoropyridazin-3-amine (142.55 mg, 1.26 mmol) in DMF (3 mL) was added DIEA (0.16 mL, 0.95 mmol) and BopCl (120.33 mg, 0.47 mmol). The mixture was stirred at 30° C. and for 1 h. The mixture was purified by reversed phase-HPLC (water (0.1% FA)-ACN, B=10%-60%) and lyophilized to afford tert-butyl 4-[2-chloro-4-[[5-[2,3-difluoro-4-[1-[2-[(6-fluoropyridazin-3-yl)amino]-2-oxo-ethyl]-3-methyl-pyrazol-4-yl]phenyl]-1-methyl-imidazole-2-carbonyl]amino]benzoyl]piperazine-1-carboxylate (200.0 mg, 0.25 mmol, 69.1% yield) as light yellow solid. MS [(M+H)+]: 793.2

Step 3: N-[3-chloro-4-(piperazine-1-carbonyl)phenyl]-5-[2,3-difluoro-4-[1-[2-[(6-fluoropyridazin-3-yl)amino]-2-oxo-ethyl]-3-methyl-pyrazol-4-yl]phenyl]-1-methyl-imidazole-2-carboxamide To a solution of tert-butyl 4-[2-chloro-4-[[5-[2,3-difluoro-4-[1-[2-[(6-fluoropyridazin-3-yl)amino]-2-oxo-ethyl]-3-methyl-pyrazol-4-yl]phenyl]-1-methyl-imidazole-2-carbonyl]amino]benzoyl]piperazine-1-carboxylate (200.0 mg, 0.25 mmol) in DCM (2 mL) was added TFA (0.4 mL, 5.19 mmol) at 30° C. and stirred at 30° C. for 3 h. The reaction mixture was pour into water, basified with aq.NaHCO3 to pH=8, extracted with EA (10 mL×2). The combined organic layer was washed with brine, dry over sodium sulfate, concentrated in vacuum to afford N-[3-chloro-4-(piperazine-1-carbonyl)phenyl]-5-[2,3-difluoro-4-[1-[2-[(6-fluoropyridazin-3-yl)amino]-2-oxo-ethyl]-3-methyl-pyrazol-4-yl]phenyl]-1-methyl-imidazole-2-carboxamide (120.0 mg, 0.17 mmol, 63.3% yield) as light yellow solid. MS [(M+H)+]: 693.2.

Step 4: tert-butyl 3-[[1-(2-tert-butoxy-2-oxo-ethyl)-4-[4-[2-chloro-4-[[5-[2,3-difluoro-4-[1-[2-[(6-fluoropyridazin-3-yl)amino]-2-oxo-ethyl]-3-methyl-pyrazol-4-yl]phenyl]-1-methyl-imidazole-2-carbonyl]amino]benzoyl]piperazine-1-carbonyl]piperidin-1-ium-1-yl]methyl]azetidine-1-carboxylate; formic acid To a mixture of N-[3-chloro-4-(piperazine-1-carbonyl)phenyl]-5-[2,3-difluoro-4-[1-[2-[(6-fluoropyridazin-3-yl)amino]-2-oxo-ethyl]-3-methyl-pyrazol-4-yl]phenyl]-1-methyl-imidazole-2-carboxamide (80.0 mg, 0.12 mmol) and (1s,4s)-1-(2-(tert-butoxy)-2-oxoethyl)-1-((1-(tert-butoxycarbonyl)azetidin-3-yl)methyl)-4-carboxypiperidin-1-ium; 2,2,2-trifluoroacetate (57.28 mg, 0.14 mmol) in DMF (1 mL) was added Bop-C₁ (29.32 mg, 0.12 mmol) and DIEA (0.06 mL, 0.35 mmol). The reaction mixture was stirred at 30° C. for 1 h. The reaction mixture was purified by reversed phase HPLC (water (0.1% FA)-ACN, B=60%-90%) and lyophilized to give tert-butyl 3-[[1-(2-tert-butoxy-2-oxo-ethyl)-4-[4-[2-chloro-4-[[5-[2,3-difluoro-4-[1-[2-[(6-fluoropyridazin-3-yl)amino]-2-oxo-ethyl]-3-methyl-pyrazol-4-yl]phenyl]-1-methyl-imidazole-2-carbonyl]amino]benzoyl]piperazine-1-carbonyl]piperidin-1-ium-1-yl]methyl]azetidine-1-carboxylate; formic acid (40.0 mg, 0.04 mmol, 25.5% yield) as light yellow solid. MS [(M)+]: 1087.5.

Example M1

N-[3-chloro-4-[4-(1,1-dimethylpiperidin-1-ium-4-carbonyl)piperazine-1-carbonyl]phenyl]-5-[2,3-difluoro-4-[3-methyl-1-[2-[(6-methyl-3-pyridyl)carbamoylamino]ethyl]pyrazol-4-yl]phenyl]-1-methyl-imidazole-2-carboxamide formate

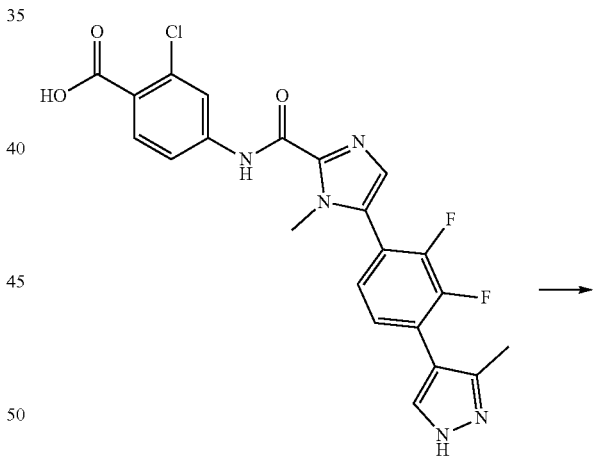

Intermediate L1

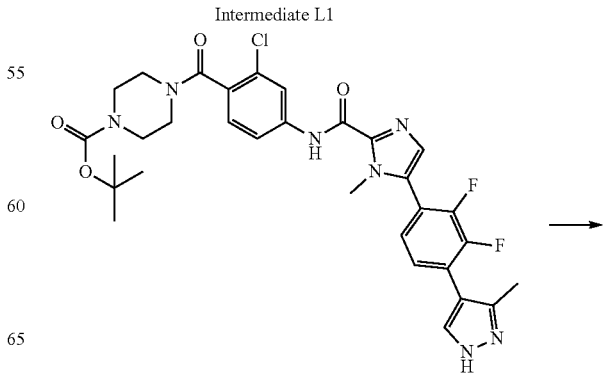

585
-continued
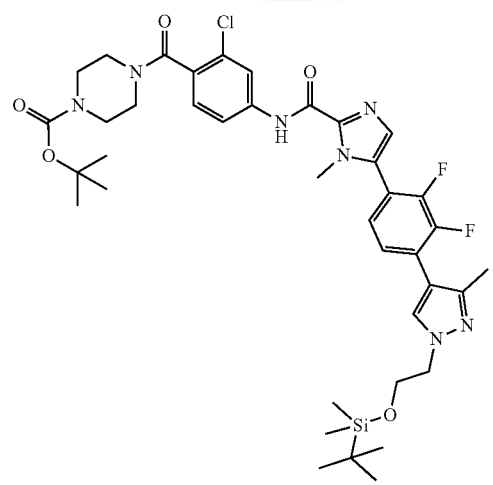
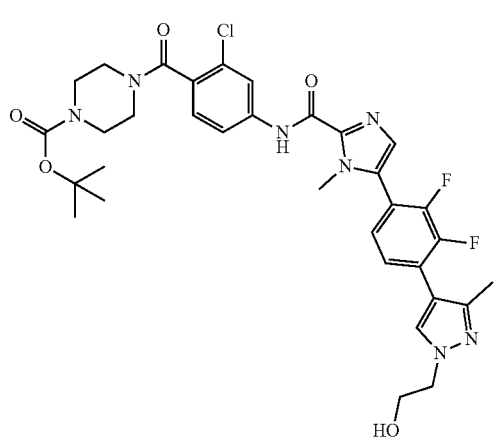
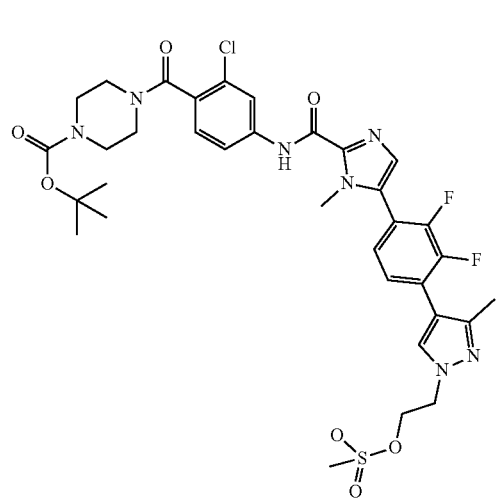
586
-continued
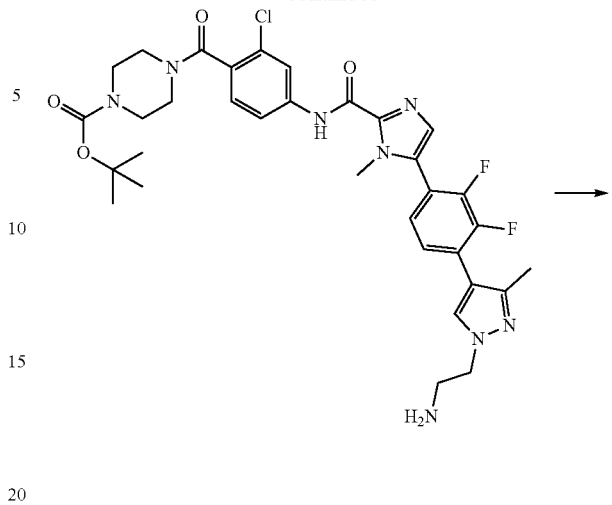
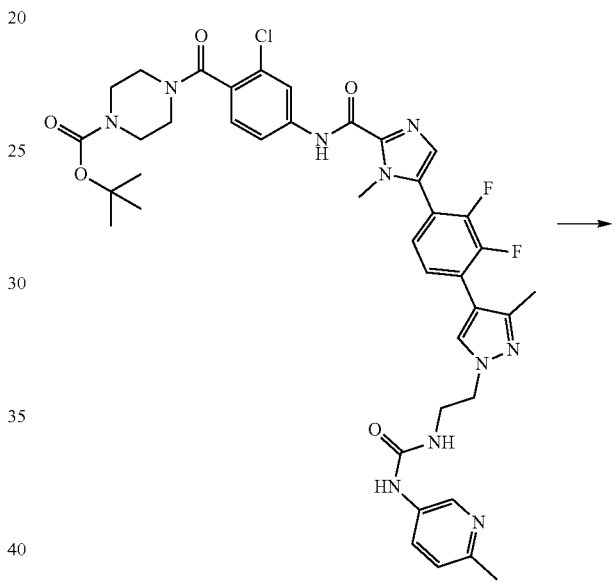
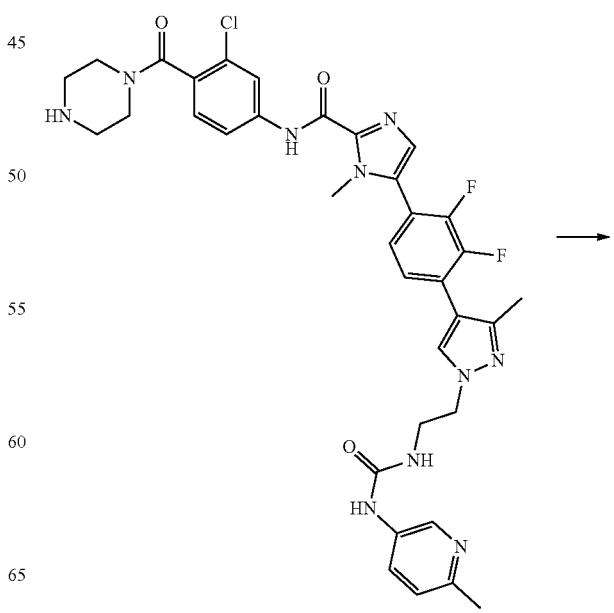

587

-continued

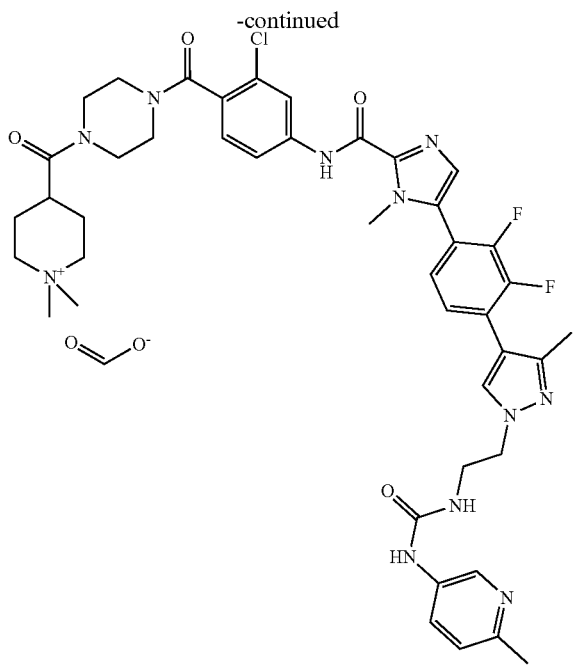

Step 1: tert-butyl 4-[2-chloro-4-[[5-[2,3-difluoro-4-(3-methyl-1H-pyrazol-4-yl)phenyl]-1-methyl-imidazole-2-carbonyl]amino]benzoyl]piperazine-1-carboxylate 3-(((ethylimino)methylene)amino)-N,N-dimethylpropan-1-amine hydrochloride (4.61 g, 24 mmol, Eq: 1.05) and N-ethyl-N-isopropylpropan-2-amine (14.8 g, 20 ml, 114 mmol, Eq: 5) were added to a solution of 2-chloro-4-(5-(2,3-difluoro-4-(3-methyl-1H-pyrazol-4-yl)phenyl)-1-methyl-1H-imidazole-2-carboxamido)benzoic acid (10.8 g, 22.9 mmol, Eq: 1) and 1H-benzo[d][1,2,3]triazol-1-ol (3.25 g, 24 mmol, Eq: 1.05) in DMA (57.2 ml) and stirred for 18 hours at room temperature. The mixture was poured into 100 mL and extracted with EtOAc (50 mL×4). The organic layer was washed with 50 mL with brine, dried over sodium sulfate, and concentrated in vacuo. The residue was used in the next step without purification.

Step 2: 4-[4-[[5-[4-[1-[2-[tert-butyl(dimethyl)silyl]oxyethyl]-3-methyl-pyrazol-4-yl]-2,3-difluoro-phenyl]-1-methyl-imidazole-2-carbonyl]amino]-2-chloro-benzoyl]piperazine-1-carboxylic acid tert-butyl ester 4-[2-chloro-4-[[5-[2,3-difluoro-4-(5-methyl-1H-pyrazol-4-yl)phenyl]-1-methyl-imidazole-2-carbonyl]amino]benzoyl]piperazine-1-carboxylic acid tert-butyl ester (1.9 g, 2.88 mmol, 1.000 eq) was dissolved in acetonitrile (60 mL). cesium carbonate (1.41 g, 4.32 mmol, 1.500 eq) was added followed by tert-butyl(2-iodoethoxy)dimethylsilane (1.07 g, 3.75 mmol, 1.300 eq). The mixture was heated at 70° C. over night. The cesium carbonate was filtered off. The mixture was purified by flash chromatography (100% heptane to 100% EtOAc). The mixture of regioisomers was separated by Prep-SFC chiral. The structures of regioisomers were elucidated by NMR. The title compound (814 mg, 32.9%) was isolated as colorless oil. MS [(M+H-Buten)+]: 742.2.

Step 3: 4-[2-chloro-4-[[5-[2,3-difluoro-4-[1-(2-hydroxyethyl)-3-methyl-pyrazol-4-yl]phenyl]-1-methyl-imidazole-2-carbonyl]amino]benzoyl]piperazine-1-carboxylic acid tert-butyl ester 4-[4-[[5-[4-[1-[2-[tert-butyl(dimethyl)silyl]oxyethyl]-3-methyl-pyrazol-4-yl]-2,3-difluoro-phenyl]-1-methyl-imidazole-2-carbonyl]amino]-2-chloro-benzoyl]piperazine-1-carboxylic acid tert-butyl ester (814 mg, 1.02 mmol, 1.000 eq) was dissolved in N,N-dimethylformamide (4 mL) and water (1 mL). Ammonium fluoride (377.61 mg, 10.2 mmol, 10.000 eq) was added at room temperature. The mixture was stirred at 60° C. over two days. The reaction mixture was poured into 100 mL brine and extracted two times with 100 mL EtOAc. The organic layers were combined, dried with $Na_2SO_4$, filtered and evaporated to dryness to afford the title compound (501.6 mg, 69.76%) as colorless waxy solid. MS [(M+H)+]: 684.3.

Step 4: 4-[2-chloro-4-[[5-[2,3-difluoro-4-[3-methyl-1-(2-methylsulfonyloxyethyl)pyrazol-4-yl]phenyl]-1-methyl-imidazole-2-carbonyl]amino]benzoyl]piperazine-1-carboxylic acid tert-butyl ester To 4-[2-chloro-4-[[5-[2,3-difluoro-4-[1-(2-hydroxyethyl)-3-methyl-pyrazol-4-yl]phenyl]-1-methyl-imidazole-2-carbonyl]amino]benzoyl]piperazine-1-carboxylic acid tert-butyl ester (468 mg, 0.664 mmol, 1.000 eq) dissolved in dichloromethane (30 mL) was added methanesulfonic anhydride (173.39 mg, 188.46 uL, 0.995 mmol, 1.500 eq) and DIEA (171.52 mg, 231.78 uL, 1.33 mmol, 2.000 eq). The mixture was stirred at room temperature for 3 h. The reaction mixture was poured into 30 mL brine and extracted three times with 30 mL DCM. The organic layers were combined, dried over MgSO4 and concentrated to dryness. The title compound was obtained as a light brown solid with an assumed purity of 85% and was used without further purification. MS [(M+H)+]: 762.4.

Step 5: 4-[4-[[5-[4-[1-(2-aminoethyl)-3-methyl-pyrazol-4-yl]-2,3-difluoro-phenyl]-1-methyl-imidazole-2-carbonyl]amino]-2-chloro-benzoyl]piperazine-1-carboxylic acid tert-butyl ester 4-[2-chloro-4-[[5-[2,3-difluoro-4-[3-methyl-1-(2-methylsulfonyloxyethyl)pyrazol-4-yl]phenyl]-1-methyl-imidazole-2-carbonyl]amino]benzoyl]piperazine-1-carboxylic acid tert-butyl ester (585 mg, 0.652 mmol, 1.000 eq) was treated with 2 M ammonia solution (2M in iPrOH) (12.61 g, 16.31 mL, 32.62 mmol, 50.000 eq) at 70° C. over 2 days. The title compound was obtained as a light brown gum with an assumed purity of 89% and was used without further purification. MS [(M+H)+]: 683.4

Step 6: tert-butyl 4-[2-chloro-4-[[5-[2,3-difluoro-4-[3-methyl-1-[2-[(6-methyl-3-pyridyl)carbamoylamino]ethyl]pyrazol-4-yl]phenyl]-1-methyl-imidazole-2-carbonyl]amino]benzoyl]piperazine-1-carboxylate 4-[4-[[5-[4-[1-(2-aminoethyl)-3-methyl-pyrazol-4-yl]-2,3-difluoro-phenyl]-1-methyl-imidazole-2-carbonyl]amino]-2-chloro-benzoyl]piperazine-1-carboxylic acid tert-butyl ester (33.7 mg, 0.044 mmol, 1.000 eq) was dissolved in N,N-dimethylformamide (1.5 mL). 5-isocyanato-2-methyl-pyridine (8.83 mg, 0.066 mmol, 1.500 eq) and DIEA (28.37 mg, 38.34 uL, 0.220 mmol, 5.000 eq) were added and the mixture was stirred over night at room temperature. The mixture was concentrated to dryness and used crude for next step.

Step 7: N-[3-chloro-4-(piperazine-1-carbonyl)phenyl]-5-[2,3-difluoro-4-[3-methyl-1-[2-[(6-methyl-3-pyridyl)carbamoylamino]ethyl]pyrazol-4-yl]phenyl]-1-methyl-imidazole-2-carboxamide Crude tert-butyl 4-[2-chloro-4-[[5-[2,3-difluoro-4-[3-methyl-1-[2-[(6-methyl-3-pyridyl)carbamoylamino]ethyl]pyrazol-4-yl]phenyl]-1-methyl-imidazole-2-carbonyl]amino]benzoyl]piperazine-1-carboxylate was treated with an excess of HCl 4N in dioxan (30 eq) at room temperature over night. The crude mixture was concentrated and purified by Prep-HPLC to afford the title compound (20 mg, 59.7%) as white amorph freeze-dried solid. MS [(M+H)+]: 717.2.

Step 8: N-[3-chloro-4-[4-(1,1-dimethylpiperidin-1-ium-4-carbonyl)piperazine-1-carbonyl]phenyl]-5-[2,3-difluoro-4-[3-methyl-1-[2-[(6-methyl-3-pyridyl)carbamoylamino]ethyl]pyrazol-4-yl]phenyl]-1-methyl-imidazole-2-carboxamide formate N-[3-chloro-4-(piperazine-1-carbonyl)phenyl]-5-[2,3-difluoro-4-[3-methyl-1-[2-[(6-methyl-3-pyridyl)carbamoylamino]ethyl]pyrazol-4-yl]phenyl]-1-methyl-imidazole-2-carboxamide (20 mg, 0.028 mmol, 1.000 eq) was dissolved in dichloromethane (1 mL). 1,1-dimethylpiperidin-1-ium-4-carboxylic acid iodide (24 mg, 0.069 mmol, 2.500 eq), DIEA (36.04 mg, 48.7 uL, 0.279 mmol, 10.000 eq) and propylphosphonic anhydride (50% solution) (53.24 mg, 0.084 mmol, 3.000 eq) were added and the mixture was stirred at room temperature over night. The crude mixture was concentrated, dissolved in MeOH and purified by Prep-HPLC to afford N-[3-chloro-4-[4-(1,1-dimethylpiperidin-1-ium-4-carbonyl)piperazine-1-carbonyl]phenyl]-5-[2,3-difluoro-4-[3-methyl-1-[2-[(6-methyl-3-pyridyl)carbamoylamino]ethyl]pyrazol-4-yl]phenyl]-1-methyl-imidazole-2-carboxamide formate (1.2 mg, 4.5% yield) as white amorph freeze-dried solid. MS [M+]: 856.5.

Example N1 azetidin-3-ylmethyl-(carboxymethyl)-[4-[4-[2-chloro-4-[[5-[4-[1-[2-(difluoromethoxy)ethyl]-5-methyl-pyrazol-4-yl]-3-fluoro-2-methyl-phenyl]-1-methyl-imidazole-2-carbonyl]amino]benzoyl]piperazin-1-yl]-4-oxo-butyl]-methyl-ammonium; formic acid; formate

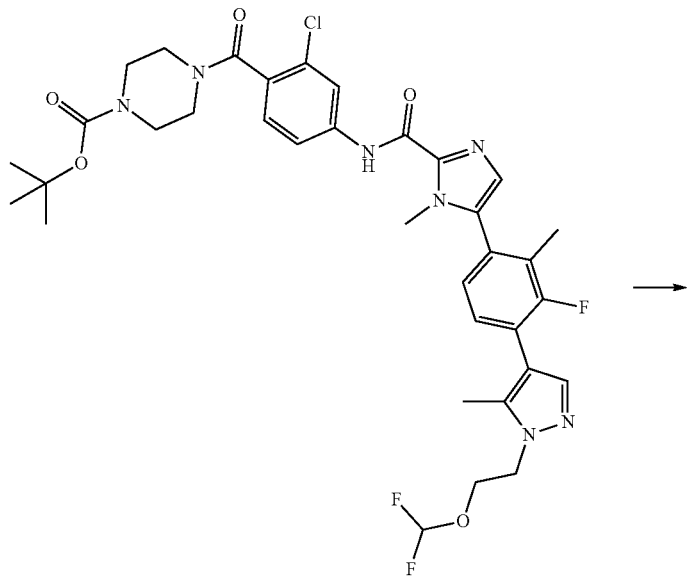

Intermediate O7

-continued
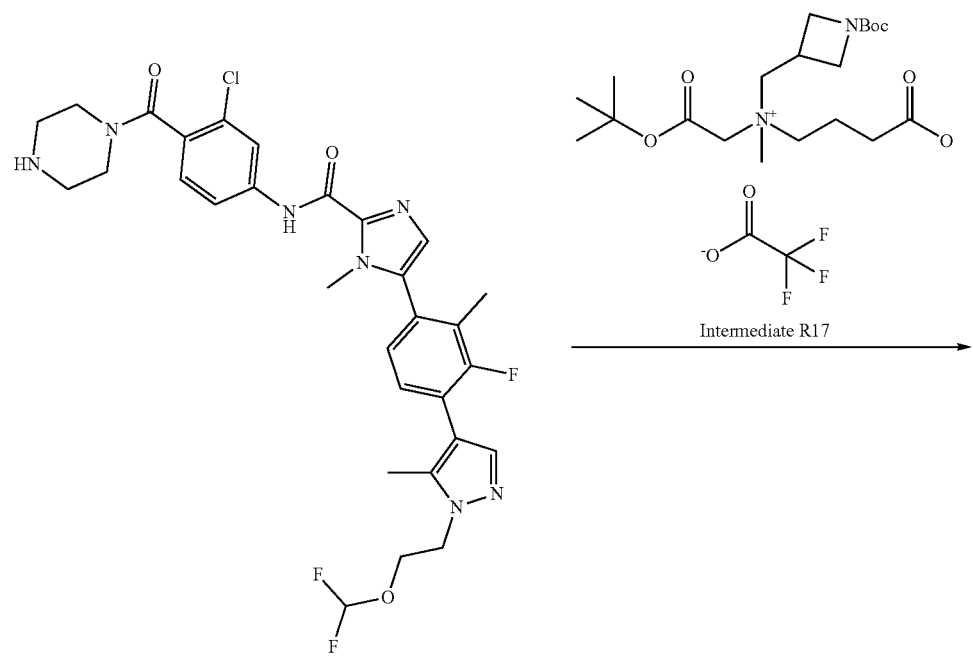
Intermediate R17
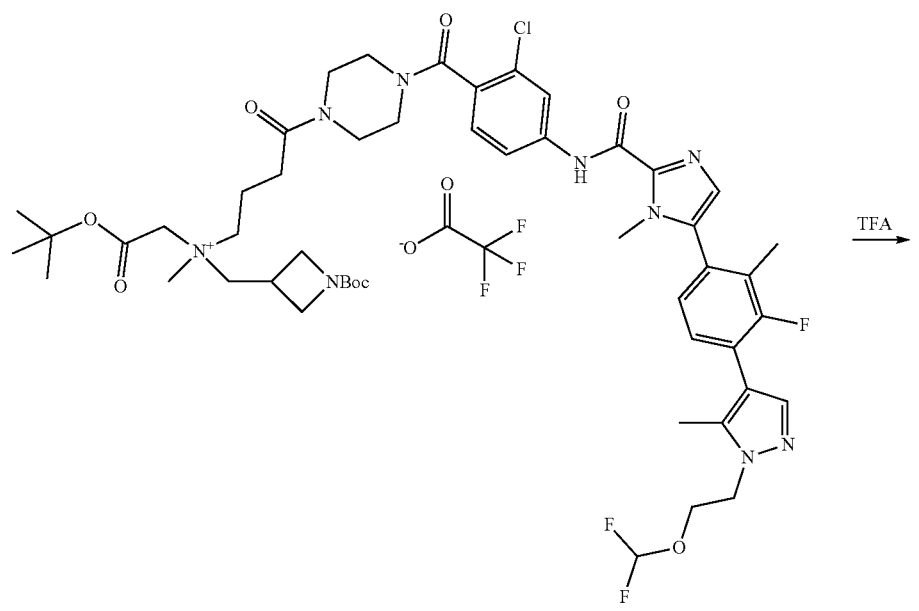
TFA

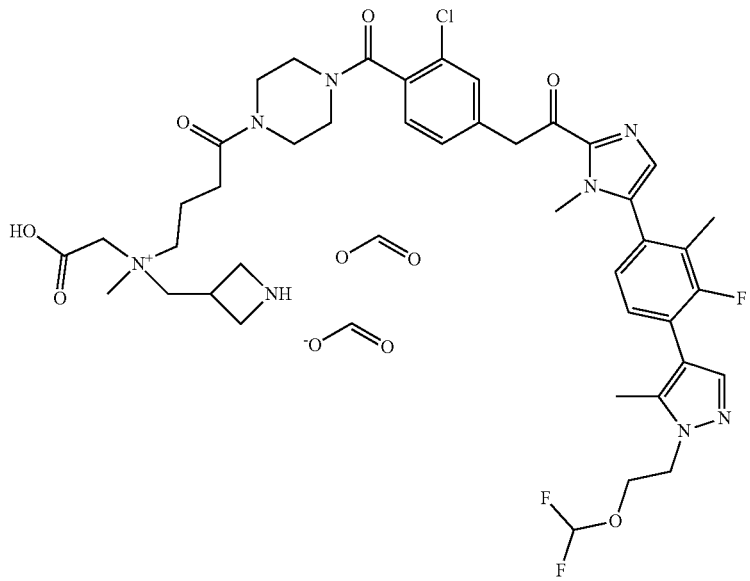

Step 1: N-[3-chloro-4-(piperazine-1-carbonyl)phenyl]-5-[4-[1-[2-(difluoromethoxy)ethyl]-5-methyl-pyrazol-4-yl]-3-fluoro-2-methyl-phenyl]-1-methyl-imidazole-2-carboxamide; hydrochloride To a mixture of tert-butyl 4-[2-chloro-4-[[5-[4-[1-[2-(difluoromethoxy)ethyl]-5-methyl-pyrazol-4-yl]-3-fluoro-2-methyl-phenyl]-1-methyl-imidazole-2-carbonyl]amino]benzoyl]piperazine-1-carboxylate (100.0 mg, 0.14 mmol) in 1,4-Dioxane (2 mL) was added HCl (0.5 mL, 2.0 mmol, 4M in 1,4-dioxane) at 30° C. and stirred at 30° C. for 4 h. The reaction mixture was concentrated in vacuum to afford crude N-[3-chloro-4-(piperazine-1-carbonyl)phenyl]-5-[4-[1-[2-(difluoromethoxy)ethyl]-5-methyl-pyrazol-4-yl]-3-fluoro-2-methyl-phenyl]-1-methyl-imidazole-2-carboxamide; hydrochloride (90.0 mg, 0.14 mmol, 98.6% yield) as light yellow solid. MS [(M+H)+]: 630.0.

Step 2: (1-tert-butoxycarbonylazetidin-3-yl)methyl-(2-tert-butoxy-2-oxo-ethyl)-[4-[4-[2-chloro-4-[[5-[4-[1-[2-(difluoromethoxy)ethyl]-5-methyl-pyrazol-4-yl]-3-fluoro-2-methyl-phenyl]-1-methyl-imidazole-2-carbonyl]amino]benzoyl]piperazin-1-yl]-4-oxo-butyl]-methyl-ammonium; 2,2,2-trifluoroacetate To a solution of N-[3-chloro-4-(piperazine-1-carbonyl)phenyl]-5-[4-[1-[2-(difluoromethoxy)ethyl]-5-methyl-pyrazol-4-yl]-3-fluoro-2-methyl-phenyl]-1-methyl-imidazole-2-carboxamide; hydrochloride (90.0 mg, 0.14 mmol), (1-tert-butoxycarbonylazetidin-3-yl)methyl-(2-tert-butoxy-2-oxo-ethyl)-(3-carboxypropyl)-methyl-ammonium;2,2,2-trifluoroacetate (115.79 mg, 0.23 mmol) and DIEA (0.1 mL, 0.6 mmol) in DMF (0.5 mL) was added HATU (85.57 mg, 0.23 mmol) at 0° C. The mixture was stirred at 0° C. for 0.5 h. The mixture was quenched with water (1 drop) and then concentrated under vacuum to afford a residue, which was purified by reversed phase and lyophilized to give (1-tert-butoxycarbonylazetidin-3-yl)methyl-(2-tert-butoxy-2-oxo-ethyl)-[4-[4-[2-chloro-4-[[5-[4-[1-[2-(difluoromethoxy)ethyl]-5-methyl-pyrazol-4-yl]-3-fluoro-2-methyl-phenyl]-1-methyl-imidazole-2-carbonyl]amino]benzoyl]piperazin-1-yl]-4-oxo-butyl]-methyl-ammonium; 2,2,2-trifluoroacetate (70 mg, 0.06 mmol, 41.4% yield) as a light yellow solid. MS [(M)+]: 1012.4.

Step 3: azetidin-3-ylmethyl-(carboxymethyl)-[4-[4-[2-chloro-4-[[5-[4-[1-[2-(difluoromethoxy)ethyl]-5-methyl-pyrazol-4-yl]-3-fluoro-2-methyl-phenyl]-1-methyl-imidazole-2-carbonyl]amino]benzoyl]piperazin-1-yl]-4-oxo-butyl]-methyl-ammonium; formic acid; formate To a solution of (1-tert-butoxycarbonylazetidin-3-yl)methyl-(2-tert-butoxy-2-oxo-ethyl)-[4-[4-[2-chloro-4-[[5-[4-[1-[2-(difluoromethoxy)ethyl]-5-methyl-pyrazol-4-yl]-3-fluoro-2-methyl-phenyl]-1-methyl-imidazole-2-carbonyl]amino]benzoyl]piperazin-1-yl]-4-oxo-butyl]-methyl-ammonium;2,2,2-trifluoroacetate (65.0 mg, 0.06 mmol) in DCM (0.5 mL) was added TFA (2.6 mL, 33.75 mmol) at 30° C. and stirred for 16 h. The mixture was concentrated under vacuum, the residue was purified by prep-HPLC (Column: Unisil 3-100 C18 Ultra 150×50 mm×3 um; Condition: water (0.225% FA)-ACN; Begin B=16%, End B=36%; Gradient Time(min) 10 min) and lyophilized to give azetidin-3-ylmethyl-(carboxymethyl)-[4-[4-[2-chloro-4-[[5-[4-[1-[2-(difluoromethoxy)ethyl]-5-methyl-pyrazol-4-yl]-3-fluoro-2-methyl-phenyl]-1-methyl-imidazole-2-carbonyl]amino]benzoyl]piperazin-1-yl]-4-oxo-butyl]-methyl-ammonium; formic acid; formate (33.1 mg, 0.03 mmol, 57.11% yield) as a white solid. MS [(M)+]: 856.1.

The following examples were prepared in analogy to Example N1.

| Ex# | Name | Structure | MS [M]+ | Starting Material |
|---|---|---|---|---|
| Example N2 | 2-[1-(azetidin-3-ylmethyl)-4-[4-[2-chloro-4-[[5-[4-[1-[2-(difluoromethoxy)ethyl]-5-methyl-pyrazol-4-yl]-3-fluoro-2-methyl-phenyl]-1-methyl-imidazole-2-carbonyl]amino]benzoyl]piperazine-1-carbonyl]piperidin-1-ium-1-yl]acetic acid; formate | 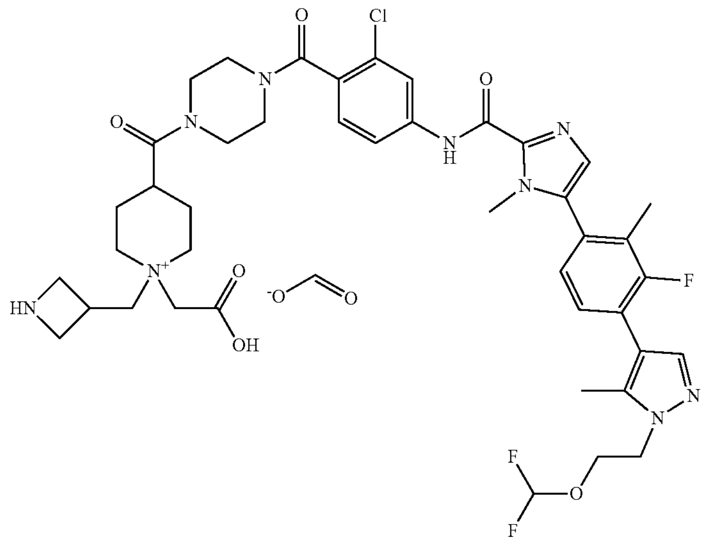 | 868.1 | Intermediate O7 and intermediate R14 |
| Example N3 | 3-aminopropyl-(carboxymethyl)-[4-[4-[2-chloro-4-[[5-[4-[1-[2-(difluoromethoxy)ethyl]-5-methyl-pyrazol-4-yl]-3-fluoro-2-methyl-phenyl]-1-methyl-imidazole-2-carbonyl]amino]benzoyl]piperazin-1-yl]-4-oxo-butyl]-methyl-ammonium; formate | 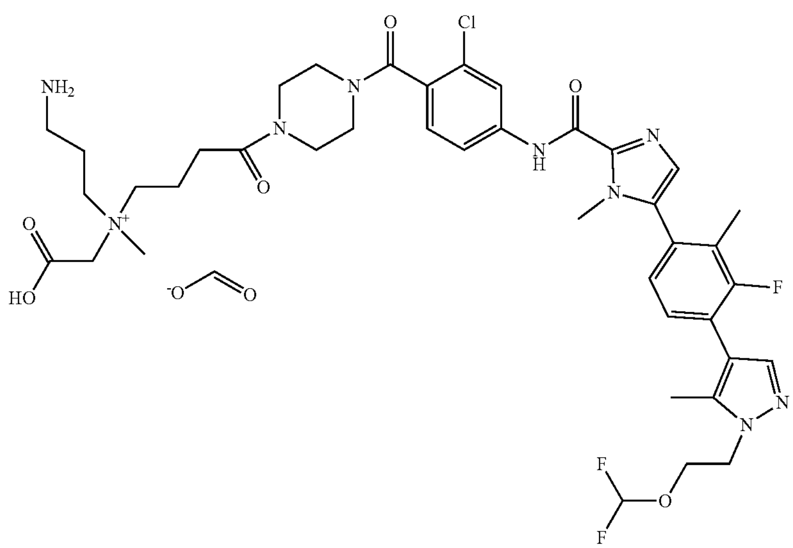 | 844.6 | Intermediate O7 and intermediate R18 |

Example N4
cis 2-[1-(azetidin-3-ylmethyl)-4-[4-[2-chloro-4-[[5-[4-[1-[2-(difluoromethoxy)ethyl]-3-methyl-pyrazol-4-yl]-2,3-difluoro-phenyl]-1-methyl-imidazole-2-carbonyl]amino]benzoyl]piperazine-1-carbonyl]piperidin-1-ium-1-yl]acetate
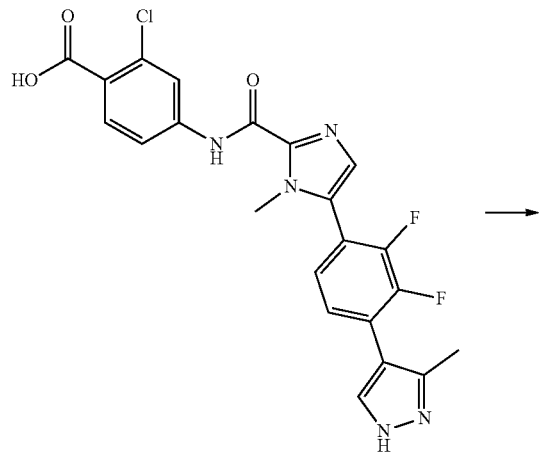
Intermediate L1
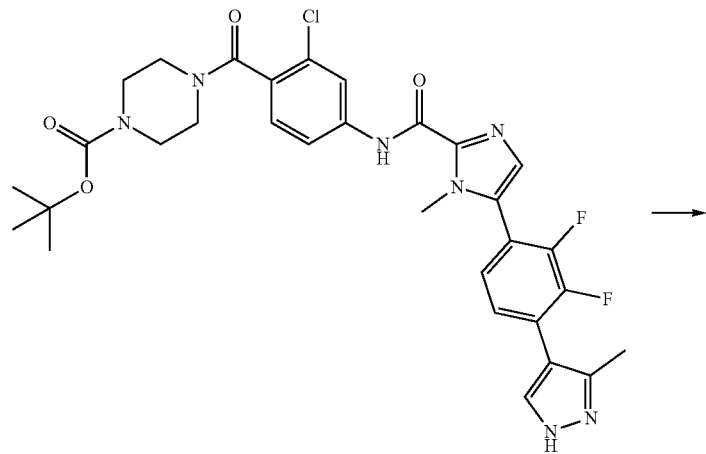

-continued
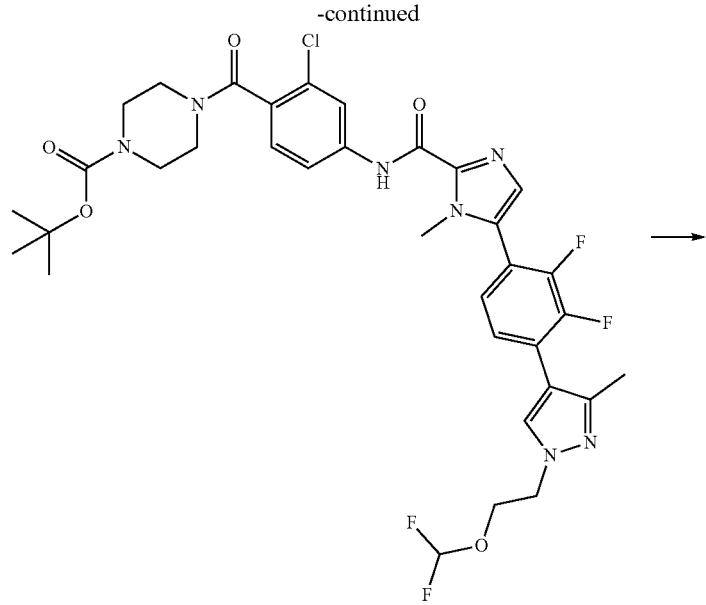
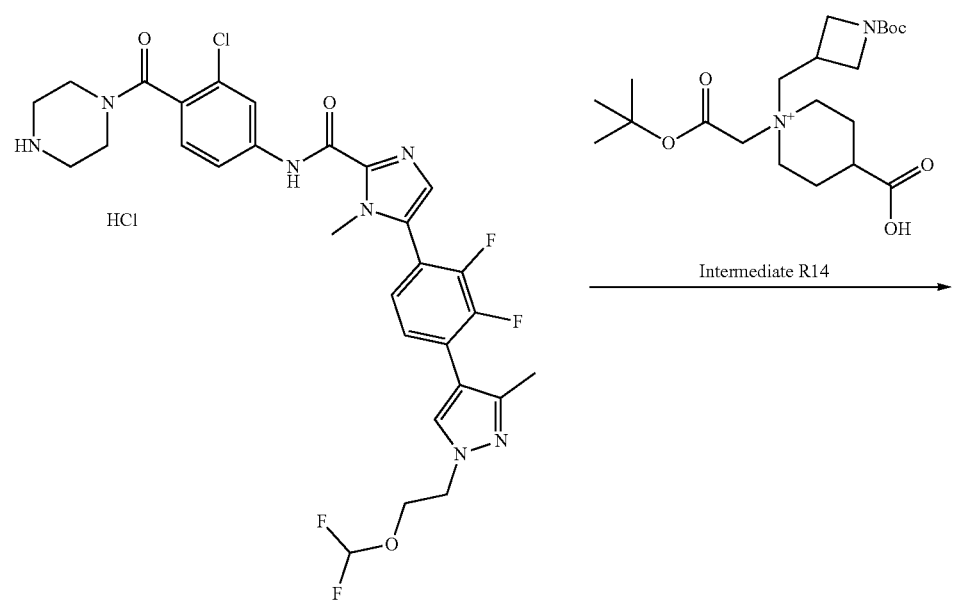
Intermediate R14

601

602

-continued

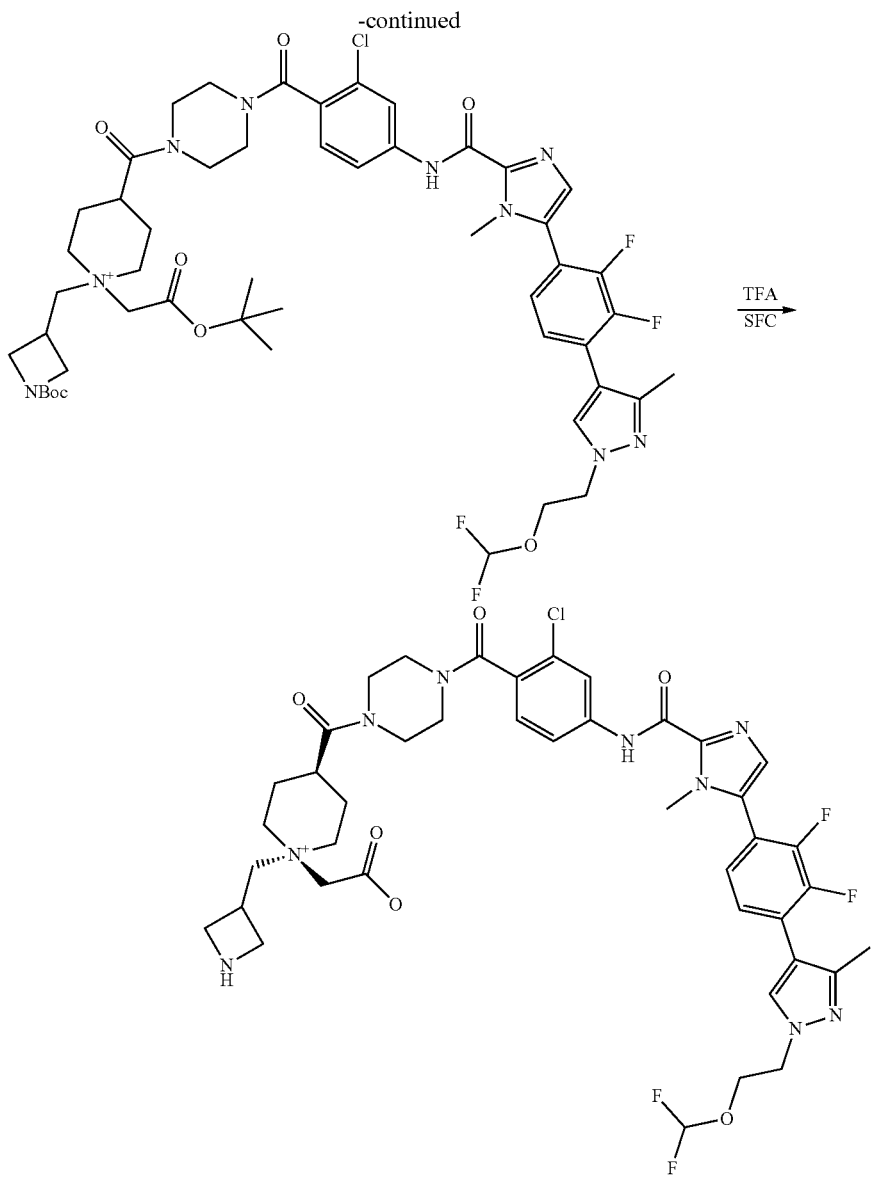

TFA
SFC →

Step 1: tert-butyl 4-[2-chloro-4-[[5-[2,3-difluoro-4-(3-methyl-1H-pyrazol-4-yl)phenyl]-1-methyl-imidazole-2-carbonyl]amino]benzoyl]piperazine-1-carboxylate 3-(((ethylimino)methylene)amino)-N,N-dimethylpropan-1-amine hydrochloride (4.61 g, 24 mmol, Eq: 1.05) and N-ethyl-N-isopropylpropan-2-amine (14.8 g, 20 ml, 114 mmol, Eq: 5) were added to a solution of 2-chloro-4-(5-(2,3-difluoro-4-(3-methyl-1H-pyrazol-4-yl)phenyl)-1-methyl-1H-imidazole-2-carboxamido)benzoic acid (10.8 g, 22.9 mmol, Eq: 1) and 1H-benzo[d][1,2,3]triazol-1-ol (3.25 g, 24 mmol, Eq: 1.05) in DMA (57.2 ml) and stirred for 18 hours at room temperature. The mixture was poured into 100 mL and extrated with EtOAc (50 mL×4). The organic layer was washed with 50 mL with brine, dried over sodium sulfate, and concentrated in vacuo. The residue was used in the next step without purification.

Step 2: tert-butyl 4-[2-chloro-4-[[5-[4-[1-[2-(difluoromethoxy)ethyl]-3-methyl-pyrazol-4-yl]-2,3-difluoro-phenyl]-1-methyl-imidazole-2-carbonyl]amino]benzoyl]piperazine-1-carboxylate To a mixture of tert-butyl 4-[2-chloro-4-[[5-[2,3-difluoro-4-(3-methyl-1H-pyrazol-4-yl)phenyl]-1-methyl-imidazole-2-carbonyl]amino]benzoyl]piperazine-1-carboxylate (700.0 mg, 1.09 mmol, 1.0 eq) and 2-(difluoromethoxy)ethyl 4-methylbenzenesulfonate (349.42 mg, 1.31 mmol, 1.2 eq) in DMF (10 mL) was added potassium carbonate (453.43 mg, 3.28 mmol, 3.0 eq). The reaction mixture was stirred at 60° C. for 16 h. The reaction mixture was filtered, the filtrate was purified by prep-HPLC (FA) to afford a mixture of isomers. The mixture was further purified by SFC to afford tert-butyl 4-[2-chloro-4-[[5-[4-[1-[2-(difluoromethoxy)ethyl]-3-methyl-pyrazol-4-yl]-2,3-difluoro-phenyl]-1-methyl-imidazole-2-carbonyl]amino]benzoyl]piperazine-1-carboxylate (125.0 mg, 0.17 mmol, 15.57% yield) as yellow solid and the title compound tert-butyl 4-[2-chloro-4-[[5-[4-

[1-[2-(difluoromethoxy)ethyl]-5-methyl-pyrazol-4-yl]-2,3-difluoro-phenyl]-1-methyl-imidazole-2-carbonyl]amino] benzoyl]piperazine-1-carboxylate (125.0 mg, 0.17 mmol, 15.57% yield) as yellow solid. MS [(M+H)+]: 734.3.

Step 3: N-[3-chloro-4-(piperazine-1-carbonyl)phenyl]-5-[4-[1-[2-(difluoromethoxy)ethyl]-3-methyl-pyrazol-4-yl]-2,3-difluoro-phenyl]-1-methyl-imidazole-2-carboxamide; hydrochloride A mixture of tert-butyl 4-[2-chloro-4-[[5-[4-[1-[2-(difluoromethoxy)ethyl]-3-methyl-pyrazol-4-yl]-2,3-difluoro-phenyl]-1-methyl-imidazole-2-carbonyl]amino]benzoyl]piperazine-1-carboxylate (125.0 mg, 0.17 mmol, 1.0 eq) in HCl (4N in dioxane) (5.0 mL, 5.0 mmol, 29.37 eq) was stirred at 30° C. for 15 h. The reaction mixture was concentrated in vacuum to afford N-[3-chloro-4-(piperazine-1-carbonyl) phenyl]-5-[4-[1-[2-(difluoromethoxy)ethyl]-3-methyl-pyrazol-4-yl]-2,3-difluoro-phenyl]-1-methyl-imidazole-2-carboxamide; hydrochloride (100.0 mg, 0.15 mmol, 92.63% yield) as yellow solid. MS [(M+H)+]: 634.1.

Step 4: tert-butyl 3-[[1-(2-tert-butoxy-2-oxo-ethyl)-4-[4-[2-chloro-4-[[5-[4-[1-[2-(difluoromethoxy) ethyl]-3-methyl-pyrazol-4-yl]-2,3-difluoro-phenyl]-1-methyl-imidazole-2-carbonyl]amino]benzoyl] piperazine-1-carbonyl]piperidin-1-ium-1-yl]methyl] azetidine-1-carboxylate To a mixture of 1-[(1-tert-butoxycarbonylazetidin-3-yl) methyl]-1-(2-tert-butoxy-2-oxo-ethyl)piperidin-1-ium-4-carboxylic acid (156.54 mg, 0.38 mmol, 1.2 eq) and N-ethyl-N-isopropylpropan-2-amine (0.16 mL, 0.95 mmol, 3.0 eq) in DMF (3 mL) was added 2-chloro-1-methylpyridin-1-ium iodide (96.71 mg, 0.38 mmol, 1.2 eq). The reaction mixture was stirred at 30° C. for 0.5 h. Then, N-[3-chloro-4-(piperazine-1-carbonyl)phenyl]-5-[4-[1-[2-(difluoromethoxy) ethyl]-3-methyl-pyrazol-4-yl]-2,3-difluoro-phenyl]-1-methyl-imidazole-2-carboxamide (200.0 mg, 0.32 mmol, 1.0 eq) was added to the above solution. The reaction mixture was stirred at 30° C. for another 3.5 h. The reaction mixture was purified by prep-HPLC (FA) to afford tert-butyl 3-[[1-(2-tert-butoxy-2-oxo-ethyl)-4-[4-[2-chloro-4-[[5-[4-[1-[2-(difluoromethoxy)ethyl]-3-methyl-pyrazol-4-yl]-2,3-difluoro-phenyl]-1-methyl-imidazole-2-carbonyl]amino] benzoyl]piperazine-1-carbonyl]piperidin-1-ium-1-yl] methyl]azetidine-1-carboxylate (170.0 mg, 0.17 mmol, 52.35% yield) as yellow solid. MS [(M+H)+]: 1028.5.

Step 5: cis 2-[1-(azetidin-3-ylmethyl)-4-[4-[2-chloro-4-[[5-[4-[1-[2-(difluoromethoxy)ethyl]-3-methyl-pyrazol-4-yl]-2,3-difluoro-phenyl]-1-methyl-imidazole-2-carbonyl]amino]benzoyl]piperazine-1-carbonyl]piperidin-1-ium-1-yl]acetate A solution of tert-butyl 3-[[1-(2-tert-butoxy-2-oxo-ethyl)-4-[4-[2-chloro-4-[[5-[4-[1-[2-(difluoromethoxy)ethyl]-3-methyl-pyrazol-4-yl]-2,3-difluoro-phenyl]-1-methyl-imidazole-2-carbonyl]amino]benzoyl]piperazine-1-carbonyl] piperidin-1-ium-1-yl]methyl]azetidine-1-carboxylate (150.0 mg, 0.15 mmol, 1.0 eq) in DCM (2 mL) was added trifluoroacetic acid (2.0 mL, 25.96 mmol, 178.18 eq). The reaction mixture was stirred at 30° C. for 16 h. The reaction mixture was concentrated in vacuum to give the residue, which was purified by prep-HPLC (FA) to afford 2-[1-(azetidin-3-ylmethyl)-4-[4-[2-chloro-4-[[5-[4-[1-[2-(difluoromethoxy) ethyl]-3-methyl-pyrazol-4-yl]-2,3-difluoro-phenyl]-1-methyl-imidazole-2-carbonyl]amino]benzoyl]piperazine-1-carbonyl]piperidin-1-ium-1-yl]acetic acid;formate (82.3 mg, 0.09 mmol, 58.8% yield) as white solid. Cis and trans isomers were separated by SFC chiral to afford the cis title compound (15.2 mg, 42.57%) as white powder. MS [(M+H)+]: 872.3

Example O1

2-[1-(azetidin-3-ylmethyl)-4-[[1-[2-chloro-4-[[5-[2,3-difluoro-4-[1-(2-methoxyethyl)-5-methyl-pyrazol-4-yl]phenyl]-1-methyl-imidazole-2-carbonyl]amino] benzoyl]-4-piperidyl]-methyl-carbamoyl]piperidin-1-ium-1-yl]acetic acid formate

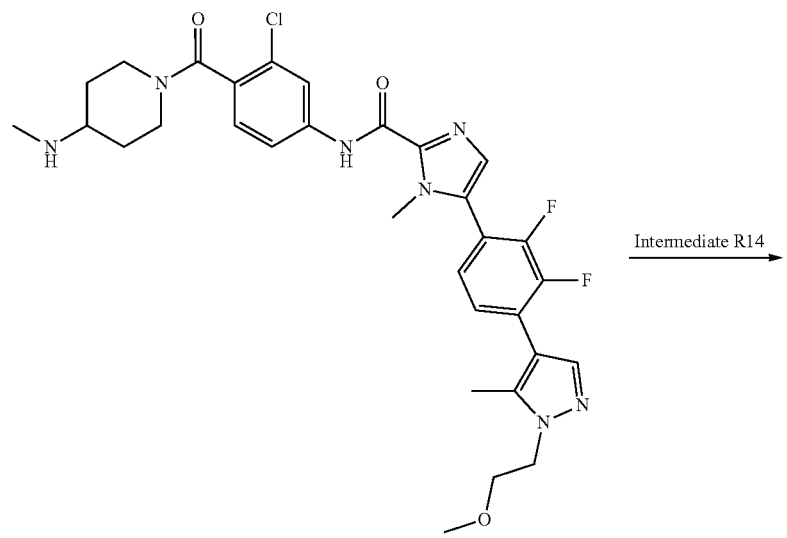

Intermediate I13

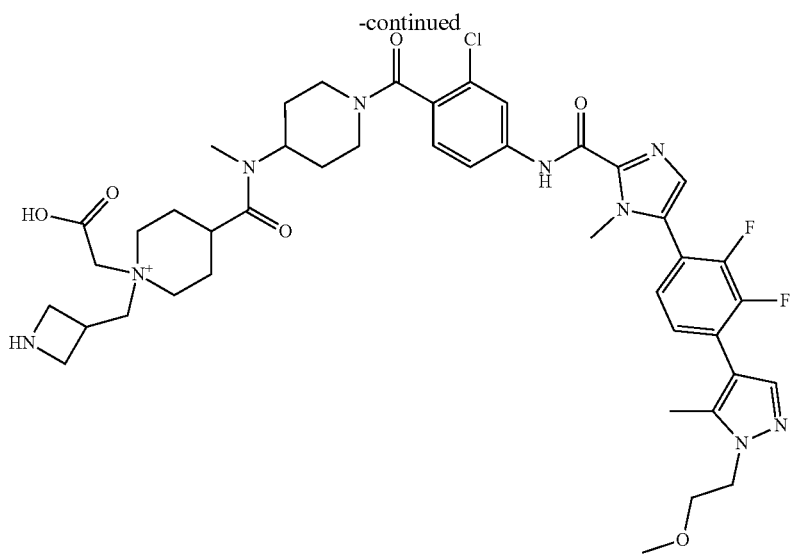

To N-[3-chloro-4-[4-(methylamino)piperidine-1-carbonyl]phenyl]-5-[2,3-difluoro-4-[1-(2-methoxyethyl)-5-methyl-pyrazol-4-yl]phenyl]-1-methyl-imidazole-2-carboxamide (8.7 mg, 0.014 mmol, 1 eq) dissolved in dichloromethane (2 mL), was added PyAOP reagent (9.49 mg, 0.018 mmol, 1.300 eq) and DIEA (7.24 mg, 9.8 uL, 0.056 mmol, 4.000 eq) followed by 1-[(1-tert-butoxycarbonylazetidin-3-yl)methyl]-1-(2-tert-butoxy-2-keto-ethyl)piperidin-1-ium-4-carboxylic acid;2,2,2-trifluoroacetate (11.8 mg, 0.0224 mmol, 1.6 eq). The mixture was stirred at room temperature over night. The mixture was then treated with an excess of HCl 4N in dioxane (15.31 mg, 12.76 uL, 0.420 mmol, 30.000 eq) over night at room temperature The mixture was then concentrated and directly purified by preparative HPLC to afford the title compound (1.7 mg, 13.3% yield). MS [M-]: 862.5.

The following examples were prepared in analogy to Example 01.

| Ex# | Name | Structure | MS | Starting Material |
|---|---|---|---|---|
| Example O2 | 2-[1-(azetidin-3-ylmethyl)-4-[(1S,5R) 6-[[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]amino]-3-azabicyclo[3.1.0]hexane-3-carbonyl]piperidin-1-ium-1-yl]acetic acid formate | 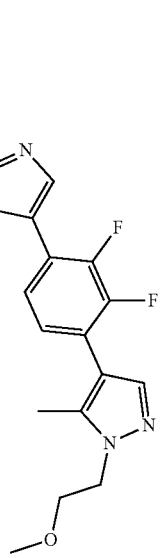 | MS [M]− 846.4 | Intermediate I12 and Intermediate R14 |

-continued

| Ex# | Name | Structure | MS | Starting Material |
|---|---|---|---|---|
| Example O3 | bis(4-aminobutyl)-(carboxymethyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]-3-methyl-piperazino]-4-keto-butyl] ammonium formate | 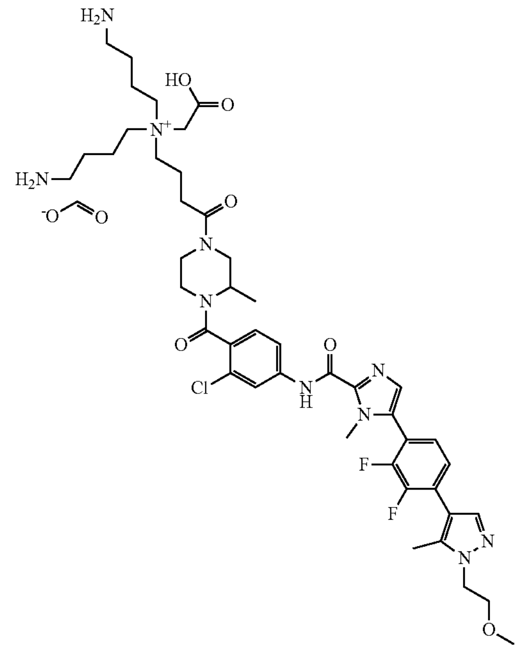 | MS [M]⁻ 895.9 | Intermediate 114 and Intermediate R19 |
| Example O4 | cis 2-[1-(azetidin-3-ylmethyl)-4-[4-[2-chloro-4-[[5-[3-fluoro-4-[1-(2-methoxyethyl)-5-methyl-pyrazol-4-yl]-2-methyl-phenyl]-1-methyl-imidazole-2-carbonyl]amino]benzoyl]piperazine-1-carbonyl]piperidin-1-ium-1-yl]acetic acid formate | 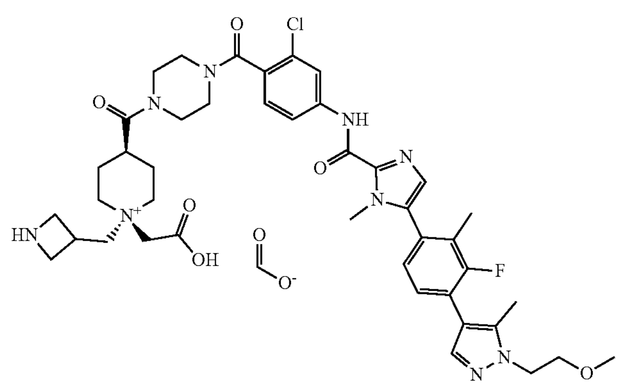 | MS [M]⁻ 830.3 | Intermediate H9 and Intermediate R16 |
| Example O5 | 3-aminopropyl-(carboxymethyl)-[4-[4-[2-chloro-4-[[5-[3-fluoro-4-[1-(2-methoxyethyl)-5-methyl-pyrazol-4-yl]-2-methyl-phenyl]-1-methyl-imidazole-2-carbonyl]amino]benzoyl]piperazino]-4-keto-butyl]-methyl-ammonium. 1:1 2,2,2-trifluoroacetic acid; 2,2,2-trifluoroacetate | 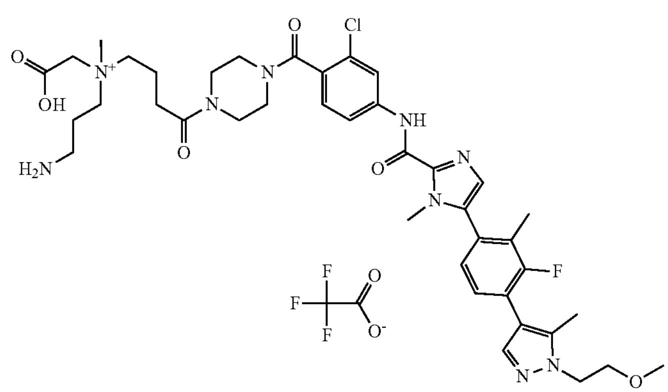 [SMILES: COCCn1ncc(-c2ccc(-c3cnc(C(=O)Nc4ccc(C(=O)N5CCN(C(=O)CCC[N+](C)(CCCN)CC(=O)O)CC5)c(Cl)c4)n3C)c(C)c2F)c1C ; O=C([O-])C(F)(F)F] | MS [M]⁻ 806.7 | Intermediate H9 and Intermediate R18 |

-continued

| Ex# | Name | Structure | MS | Starting Material |
|---|---|---|---|---|
| Example O6 | 2-[1-(azetidin-3-ylmethyl)-4-[4-[2-chloro-4-[[5-[3-fluoro-4-[1-(2-methoxyethyl)-5-methyl-pyrazol-4-yl]phenyl]-1-methyl-imidazole-2-carbonyl]amino]benzoyl]piperazine-1-carbonyl]piperidin-1-ium-1-yl]acetic acid; 2,2,2-trifluoroacetate | 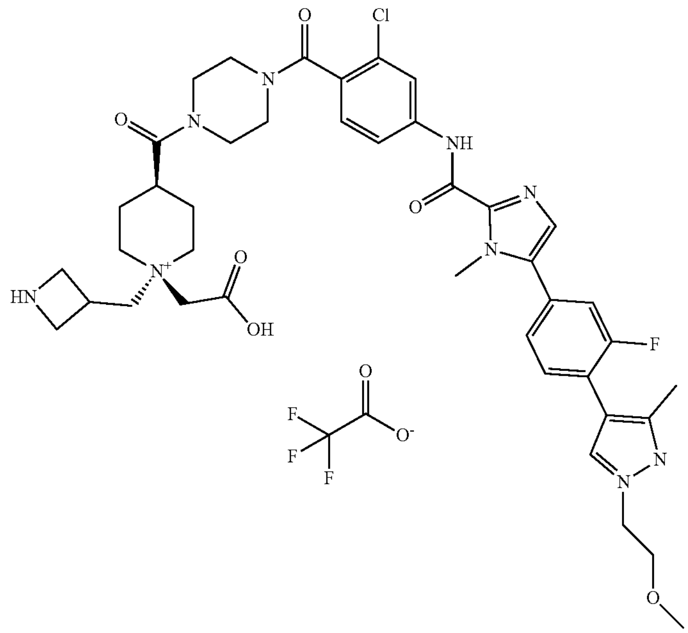 | MS [M]⁻ 818.3 | Intermediate H12 and Intermediate R14 |
| Example O7 | cis 2-[1-(azetidin-3-ylmethyl)-4-[4-[2-chloro-4-[[5-[3-fluoro-4-[1-(2-methoxyethyl)-3-methyl-pyrazol-4-yl]phenyl]-1-methyl-imidazole-2-carbonyl]amino]benzoyl]piperazine-1-carbonyl]piperidin-1-ium-1-yl]acetic acid; 2,2,2-trifluoroacetate | 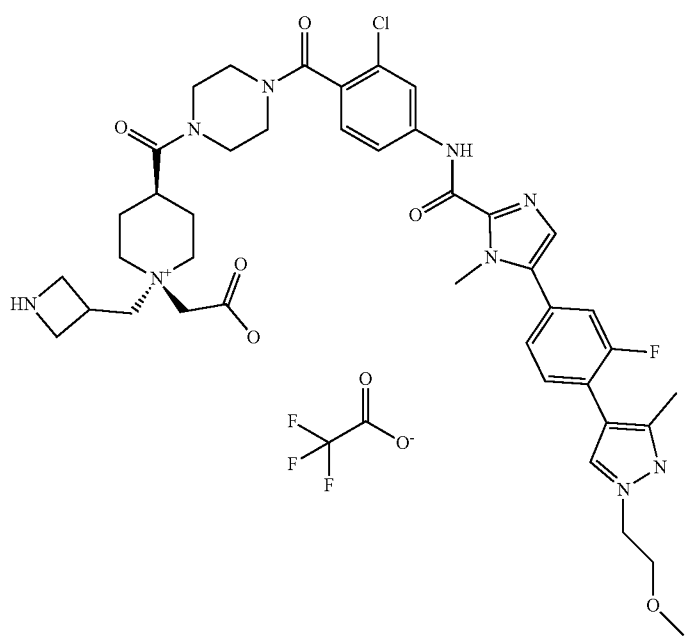 | MS [M]⁺ 818.8 | Intermediate H13 and Intermediate R16 |

| Ex# | Name | Structure | MS | Starting Material |
|---|---|---|---|---|
| Example O8 | cis 2-[1-(azetidin-3-ylmethyl)-4-[4-[[5-[2,3-difluoro-4-[1-(2-methoxyethyl)-3-methylpyrazol-4-yl]phenyl]-1-methylimidazole-2-carbonyl]amino]-2-methylbenzoyl]piperazine-1-carbonyl]piperidin-1-ium-1-yl]acetic acid formate | 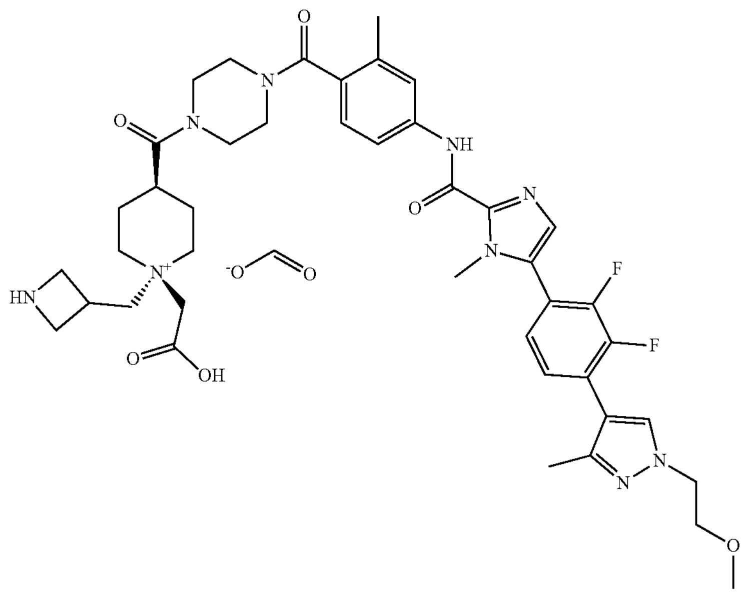 | MS [M]+ 816.4 | Intermediate H14 and Intermediate R16 |
| Example O9 | cis 2-[1-(azetidin-3-ylmethyl)-4-[4-[[5-[3-fluoro-4-[1-(2-methoxyethyl)-3-methyl-pyrazol-4-yl]phenyl]-1-methyl-imidazole-2-carbonyl]amino]-2-methyl-benzoyl]piperazine-1-carbonyl]piperidin-1-ium-1-yl]acetic acid formate | 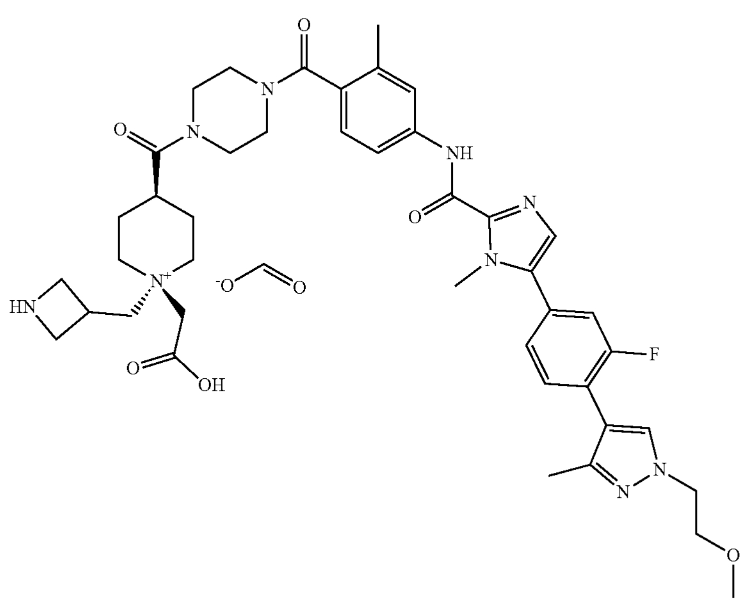 | MS [M]+ 798.6 | Intermediate H15 and Intermediate R16 |

-continued

| Ex# | Name | Structure | MS | Starting Material |
|---|---|---|---|---|
| Example O10 | cis 2-[1-(azetidin-3-ylmethyl)-4-[4-[[5-[3-fluoro-4-[1-(2-methoxyethyl)-5-methylpyrazol-4-yl]-2-methylphenyl]-1-methylimidazole-2-carbonyl]amino]-2-methylbenzoyl]piperazine-1-carbonyl]piperidin-1-ium-1-yl]acetic acid; formate | 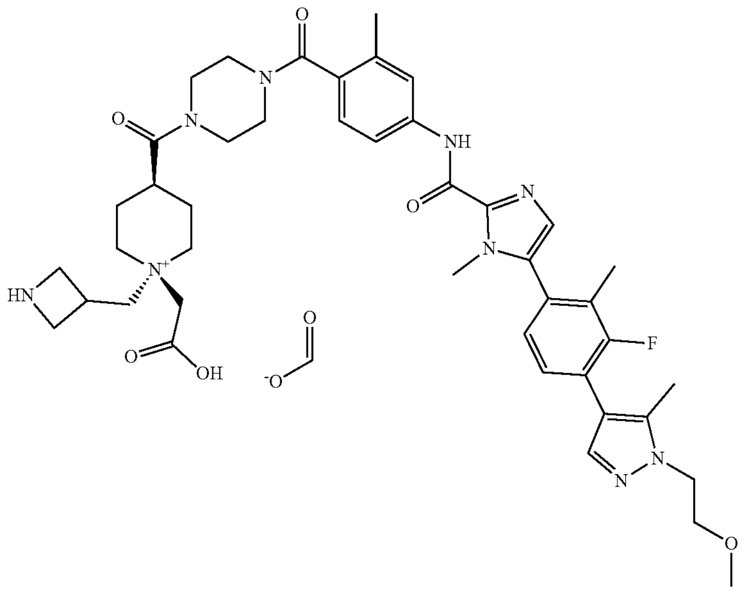 | MS [M]⁺ 812.6 | Intermediate H16 and Intermediate R16 |

Example O11

N-[3-chloro-4-[4-[(2S,4R)-4-hydroxy-1,1-dimethyl-pyrrolidin-1-ium-2-carbonyl]piperazine-1-carbonyl]phenyl]-5-[3-fluoro-4-[1-(2-methoxyethyl)-5-methyl-pyrazol-4-yl]-2-methyl-phenyl]-1-methyl-imidazole-2-carboxamide; 2,2,2-trifluoroacetate

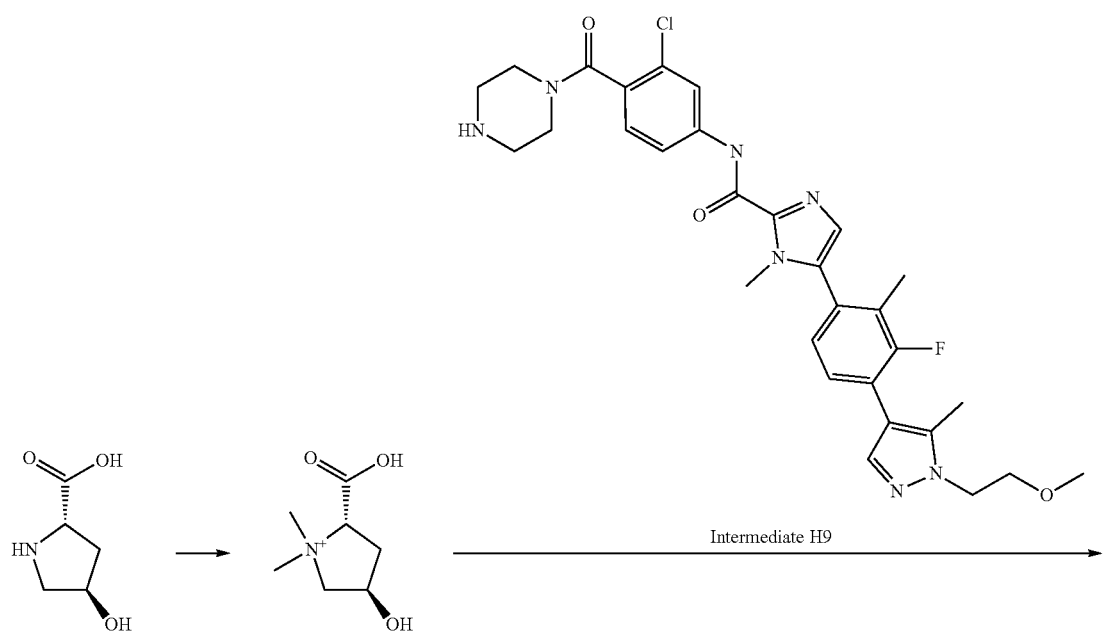

Intermediate H9

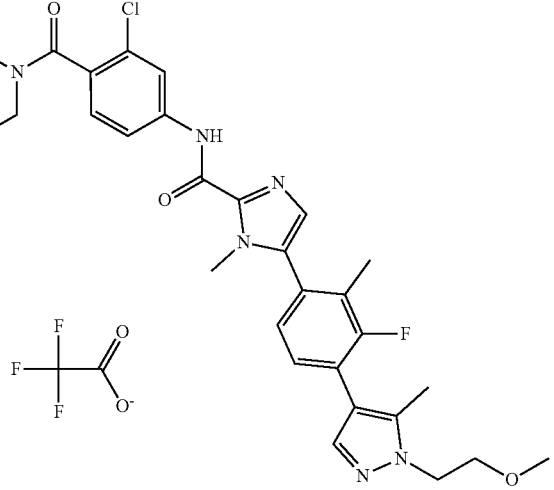

Step 1: (2S,4R)-4-hydroxy-1,1-dimethyl-pyrrolidin-1-ium-2-carboxylic acid trans-4-hydroxy-L-proline (8 g, 61.01 mmol, 1 eq) is dispensed in methanol (50 mL). 1,3-diisopropyl-2-methyl-isourea (10.62 g, 67.11 mmol, 1.1 eq) was added and the suspension is stirred at 22° C. for 18 hr. Mother liquor is evaporated to dryness to afford crude (2S,4R)-4-hydroxy-1,1-dimethyl-pyrrolidin-1-ium-2-carboxylic acid (15.011 g, 99.8% yield, purity 65%) which was used crude for next step. MS [M+]: 160.1

Step 2: N-[3-chloro-4-[4-[(2S,4R)-4-hydroxy-1,1-dimethyl-pyrrolidin-1-ium-2-carbonyl]piperazine-1-carbonyl]phenyl]-5-[3-fluoro-4-[1-(2-methoxyethyl)-5-methyl-pyrazol-4-yl]-2-methyl-phenyl]-1-methyl-imidazole-2-carboxamide; 2,2,2-trifluoroacetate (2S,4R)-4-hydroxy-1,1-dimethyl-pyrrolidin-1-ium-2-carboxylic acid (13.9 mg, 0.039 mmol, 1.179 eq) was dissolved in N,N-dimethylformamide (1 mL), DIEA (12.58 mg, 17 μL, 0.097 mmol, 2.937 eq) and HATU (15 mg, 0.039 mmol, 1.190 eq) were added and the mixture was stirred for 2 min before N-[3-chloro-4-(piperazine-1-carbonyl)phenyl]-5-[3-fluoro-4-[1-(2-methoxyethyl)-5-methyl-pyrazol-4-yl]-2-methyl-phenyl]-1-methyl-imidazole-2-carboxamide 0.1:1 2,2,2-trifluoroacetic acid (24.7 mg, 0.033 mmol, 1.000 eq) was added. The reaction mixture was stirred at room temperature for 1.5 h. an excess of 4 M HCl in dioxane (1.03 g, 855.73 uL, 3.42 mmol, 42.82 eq) was added and the mixture was stirring for 5 h at room temperature. The crude reaction mixture was directly purified by preparative HPLC and lyophilized to afford the title compound (14.6 mg, 52% yield) a colourless lyoph powder. MS [M+]: 735.5.

Example O12

2-[2-(3-aminopropyl)-4-[3-[[1-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]isonipecotoyl]amino]-propyl]pyridin-1-ium-1-yl]acetic acid; formate

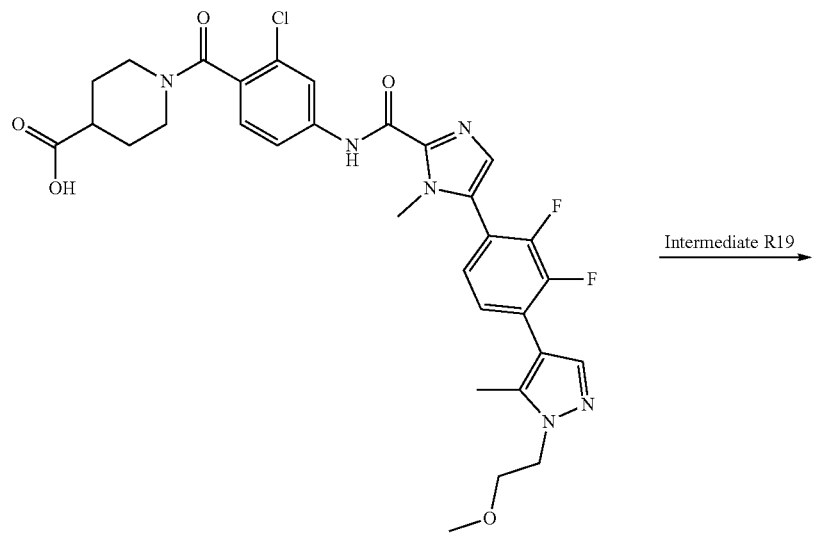

Intermediate I6 → Intermediate R19

617
-continued
618
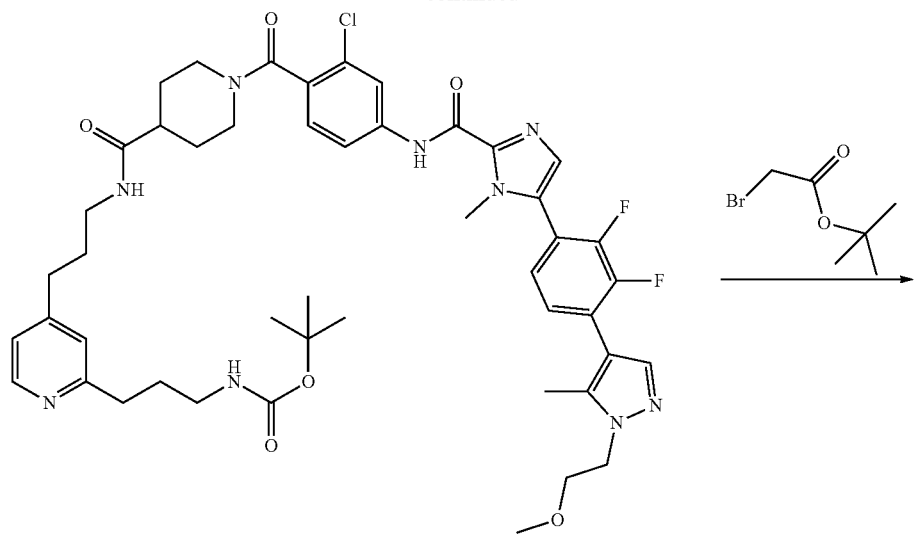
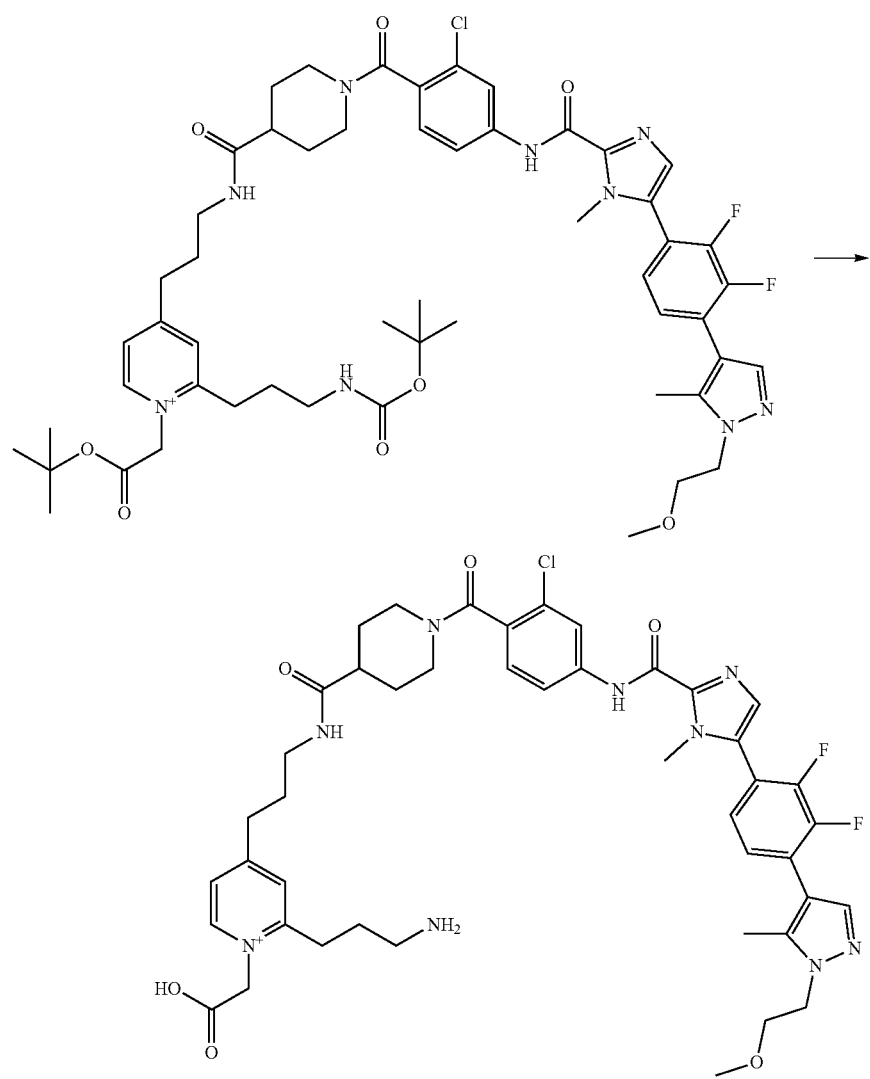

Step 1: N-[3-[4-[3-[[1-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]isonipecotoyl]amino]propyl]-2-pyridyl]propyl]carbamic acid tert-butyl ester To a solution of 1-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]isonipecotic acid (105.7 mg, 0.165 mmol, 1.000 eq) and N-[3-[4-(3-amino-propyl)-2-pyridyl]propyl]carbamic acid tert-butyl ester;hydrochloride (92 mg, 0.279 mmol, 1.691 eq) in N,N-dimethylformamide (1 mL) was added DIPEA (127.86 mg, 172.78 uL, 0.989 mmol, 6.000 eq) and HATU (81.5 mg, 0.214 mmol, 1.300 eq), the reaction mixture was stirred at room temperature overnight. The solvent was removed in vacuo and the residue purified via preparative HPLC to afford the title compound (95.7 mg, 63.33% yield) as off-white lyoph powder. MS [(M+H)+]: 916.9.

Step 2: 2-[2-[3-(tert-butoxycarbonylamino)propyl]-4-[3-[[1-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]isonipecotoyl]amino]propyl]pyridin-1-ium-1-yl]acetic acid tert-butyl ester To a solution of N-[3-[4-[3-[[1-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]isonipecotoyl]amino]-propyl]-2-pyridyl]propyl]carbamic acid tert-butyl ester (95.7 mg, 0.104 mmol, 1.000 eq) in acetonitrile (2 mL) was added tert-butyl bromoacetate (162.94 mg, 123.44 uL, 0.835 mmol, 8.000 eq) and DIPEA (107.97 mg, 145.9 uL, 0.835 mmol, 8.000 eq), and the reaction mixture stirred at 50° C. overnight. The solvent was removed in vacuo to afford crude 2-[2-[3-(tert-butoxycarbonylamino)propyl]-4-[3-[[1-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]isonipecotoyl]-amino]propyl]pyridin-1-ium-1-yl]acetic acid tert-butyl ester (243.8 mg, 99.58%) as yellow viscous oil, which was used without further purification. MS [M+]: 1030.9.

Step 3: 2-[2-(3-aminopropyl)-4-[3-[[1-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]isonipecotoyl]-amino]propyl]pyridin-1-ium-1-yl]acetic acid; formate To a solution of 2-[2-[3-(tert-butoxycarbonylamino)propyl]-4-[3-[[1-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]isonipecotoyl]amino]propyl]pyridin-1-ium-1-yl]acetic acid tert-butyl ester (243.8 mg, 0.104 mmol, 1.000 eq) in dichloromethane (2 mL) was added 4 M HCl in Dioxane (249.57 mg, 207.97 uL, 0.832 mmol, 8.000 eq) and the reaction mixture was stirred at room temperature overnight. The solvent was removed in vacuo and the residue purified via preparative HPLC to afford the title compound as light yellow lyoph powder. MS [M+]: 874.8.

Example P1 azetidin-3-ylmethyl-(carboxymethyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]-methyl-ammonium; formate

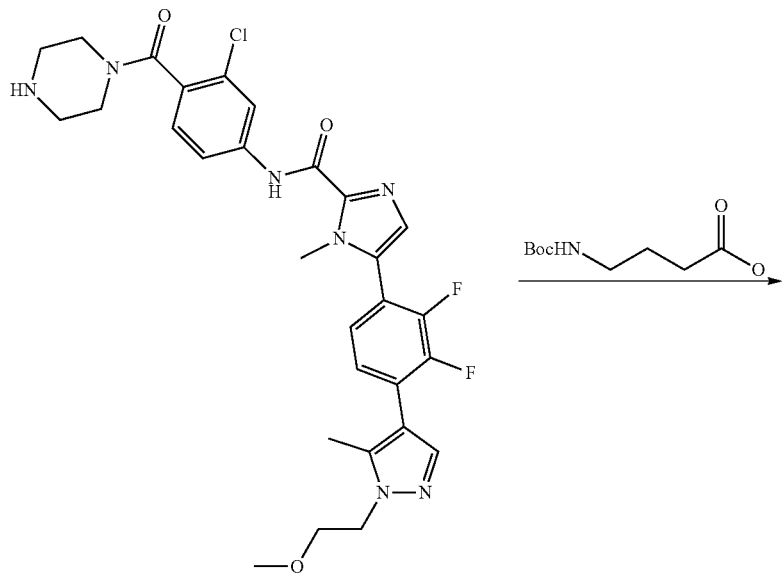

Intermediate H8

621
-continued
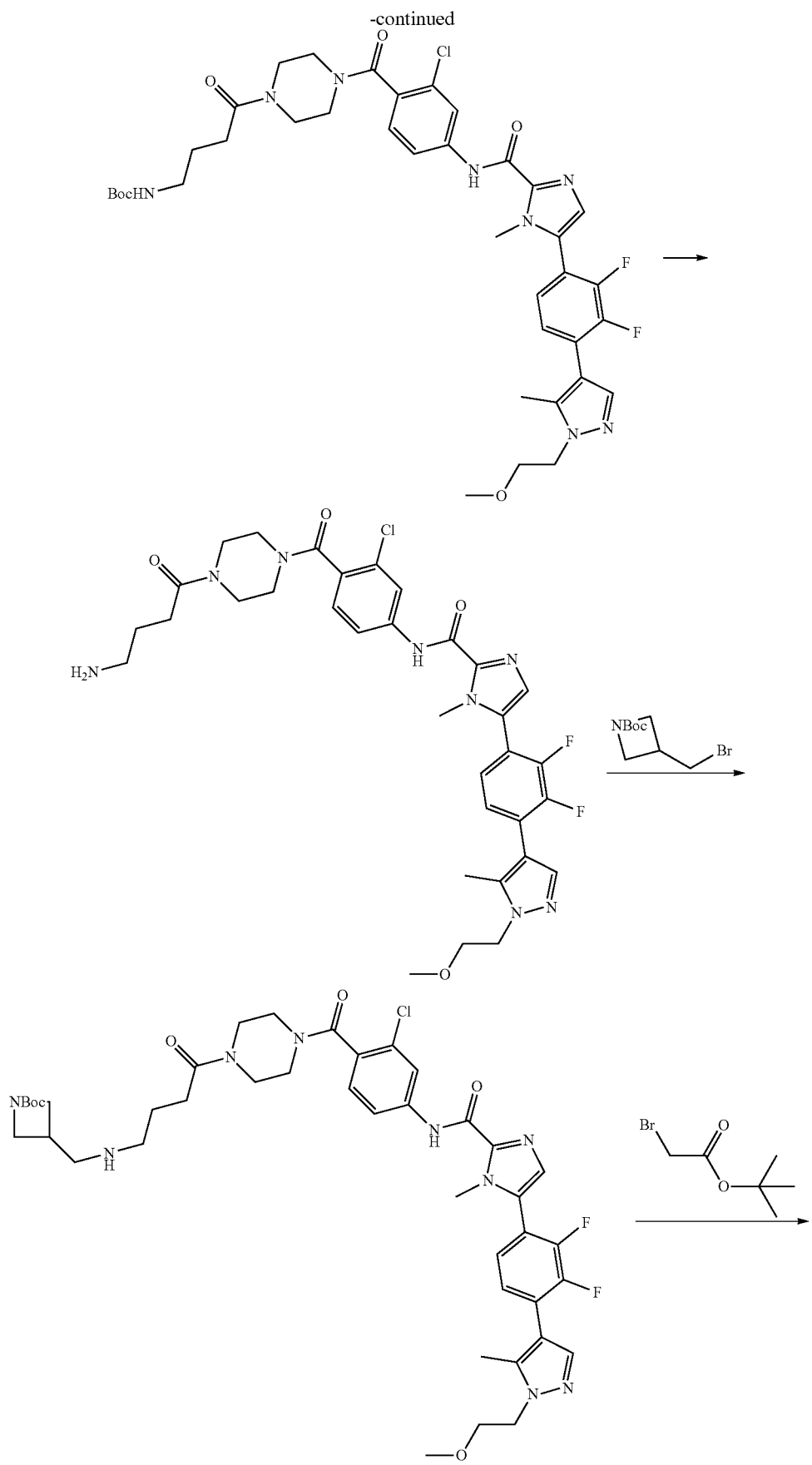
622

623
-continued
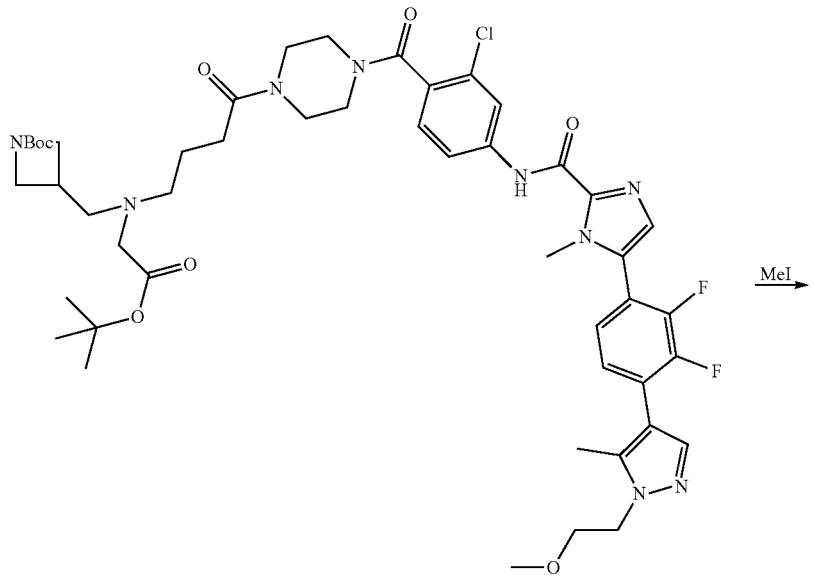
624
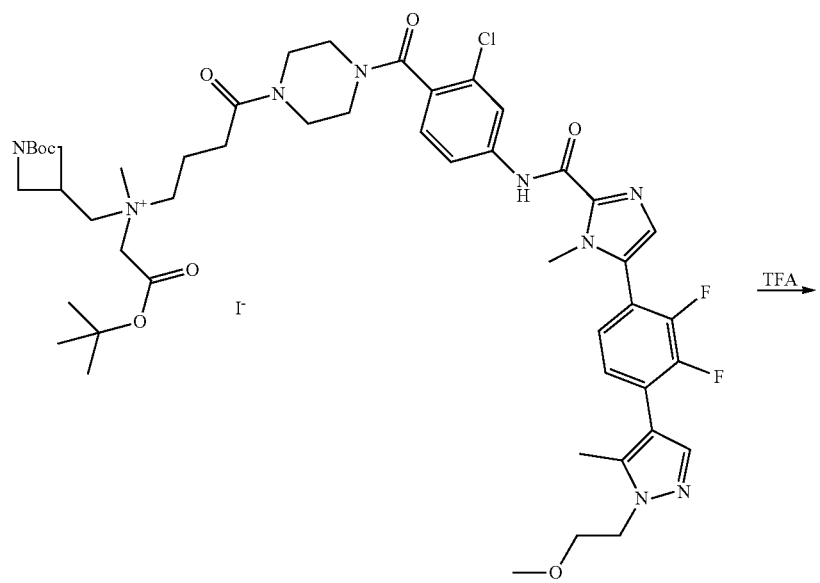

-continued

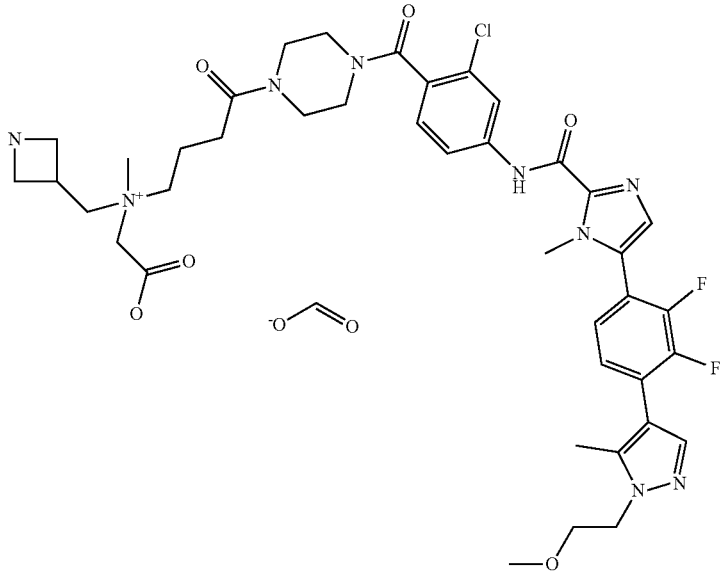

Step 1: tert-butyl N-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]carbamate To a stirred mixture of N-[3-chloro-4-(piperazine-1-carbonyl)phenyl]-5-[2,3-difluoro-4-[1-(2-methoxyethyl)-5-methyl-pyrazol-4-yl]phenyl]-1-methyl-imidazole-2-carboxamide (633.0 mg, 1.0 mmol), DIEA (0.52 mL, 3.01 mmol) and BOC-gamma-abu-OH (0.2 g, 1.0 mmol) in DMF (10 mL) was added HATU (0.76 g, 2.01 mmol) at 15° C. The reaction mixture was stirred at 15° C. for 1h. The mixture was poured into water, extracted with EtOAc, washed with brine, dried over Na2SO4 and concentrated in vacuum to afford crude tert-butyl N-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]carbamate (500.0 mg, 0.64 mmol, 63.63% yield) as black oil. MS [(M+H)+]: 783.5.

Step 2: N-[4-[4-(4-aminobutanoyl)piperazine-1-carbonyl]-3-chloro-phenyl]-5-[2,3-difluoro-4-[1-(2-methoxyethyl)-5-methyl-pyrazol-4-yl]phenyl]-1-methyl-imidazole-2-carboxamide A solution of tert-butyl N-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]carbamate (500.0 mg, 0.64 mmol) in hydrochloric acid (6.0 mL, 4 M in 1,4-dioxane) was stirred at 15° C. for 1 h. The mixture was concentrated in vacuum, the residue was purified by reversed phase HPLC and lyophilized to afford N-[4-[4-(4-aminobutanoyl)piperazine-1-carbonyl]-3-chloro-phenyl]-5-[2,3-difluoro-4-[1-(2-methoxyethyl)-5-methyl-pyrazol-4-yl]phenyl]-1-methyl-imidazole-2-carboxamide (320.0 mg, 0.47 mmol, 73.38% yield) as white solid MS [(M+H)+]: 683.1.

Step 3: tert-butyl 3-[[[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]amino]methyl]azetidine-1-carboxylate To a solution of N-[4-[4-(4-aminobutanoyl)piperazine-1-carbonyl]-3-chloro-phenyl]-5-[2,3-difluoro-4-[1-(2-methoxyethyl)-5-methyl-pyrazol-4-yl]phenyl]-1-methyl-imidazole-2-carboxamide (110.0 mg, 0.16 mmol) in ACN (5 mL) was added 1-BOC-3-(bromomethyl)azetidine (40.28 mg, 0.16 mmol,), sodium iodide (24.14 mg, 0.16 mmol) and potassium carbonate (33.38 mg, 0.24 mmol, 1.5 eq) at 20° C. Then the reaction mixture was heated to 50° C. and stirred for 16 h. The mixture was filtered and the filtrate was concentrated in vacuum. The residue was purified by Prep-HPLC, lyophilized to afford tert-butyl 3-[[[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]amino]methyl]azetidine-1-carboxylate (40.0 mg, 0.05 mmol, 29.14% yield) as white solid. MS [(M+H)+]: 852.2.

Step 4: tert-butyl 3-[[(2-tert-butoxy-2-oxo-ethyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]amino]methyl]azetidine-1-carboxylate To a solution of tert-butyl 3-[[[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]amino]methyl]azetidine-1-carboxylate (40.0 mg, 0.05 mmol) and TEA (0.02 mL, 0.14 mmol) in ACN (5 mL) was added tert-butyl bromoacetate (0.01 mL, 0.06 mmol) at 20° C., then the solution was stirred at 35° C. for 16 h. The reaction mixture was concentrated, purified by reversed phase-HPLC and concentrated to afford tert-butyl 3-[[(2-tert-butoxy-2-oxo-ethyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]amino]methyl]azetidine- 1-carboxylate (40.0 mg, 0.04 mmol, 88.19% yield) as yellow oil. MS [(M+H)+]: 966.2.

Step 5: (1-tert-butoxycarbonylazetidin-3-yl)methyl-(2-tert-butoxy-2-oxo-ethyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]-methyl-ammonium; iodide To a solution of tert-butyl 3-[[(2-tert-butoxy-2-oxo-ethyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]amino]methyl]azetidine-1-carboxylate (40.0 mg, 0.04 mmol) and TEA (0.02 mL, 0.12 mmol) in ACN (2 mL) was added iodomethane (0.03 mL, 0.41 mmol) at 15° C., then the solution was stirred at 15° C. for 2 h. The reaction mixture was concentrated in vacuum, the residue was purified by reversed phase HPLC and lyophilized to afford (1-tert-butoxycarbonylazetidin-3-yl)methyl-(2-tert-butoxy-2-oxo-ethyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]-methyl-ammonium; iodide (30.0 mg, 0.03 mmol, 98.47% yield) as white solid. MS [(M)+]: 980.2.

Step 6: azetidin-3-ylmethyl-(carboxymethyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]-methyl-ammonium; formate A solution of (1-tert-butoxycarbonylazetidin-3-yl)methyl-(2-tert-butoxy-2-oxo-ethyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]-methyl-ammonium;iodide (30.0 mg, 0.03 mmol) in DCM (1 mL) was added TFA (1.0 mL, 12.98 mmol) at 15° C. and stirred at 15° C. for 16 h. The reaction mixture was concentrated in vacuum, the residue was purified by Prep-HPLC and lyophilized to afford azetidin-3-ylmethyl-(carboxymethyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]-methyl-ammonium; formate (13.7 mg, 0.02 mmol) as white solid. MS [(M)+]: 824.1.

Example P2 bis(4-aminobutyl)-(carboxymethyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl] ammonium; formate

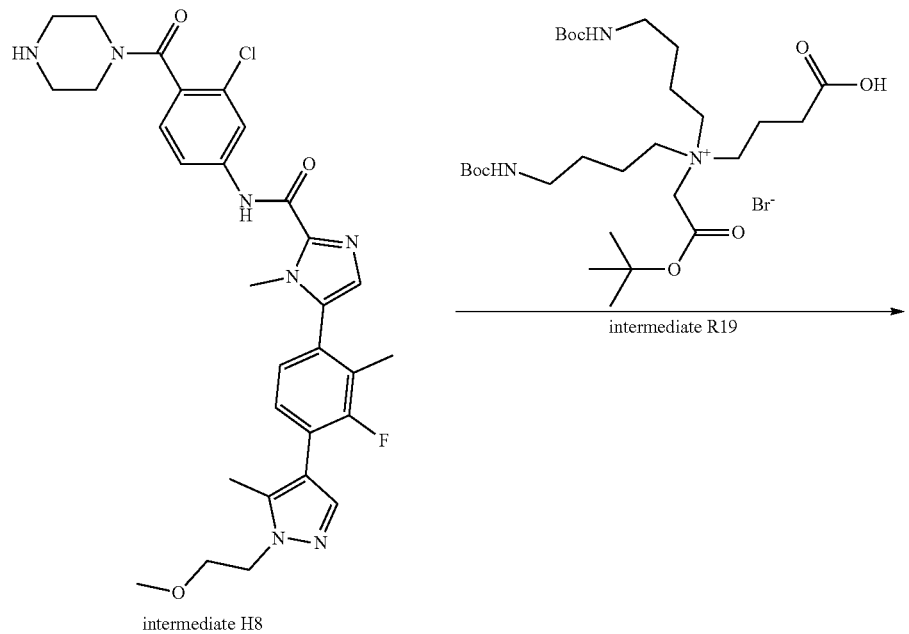

intermediate H8  intermediate R19

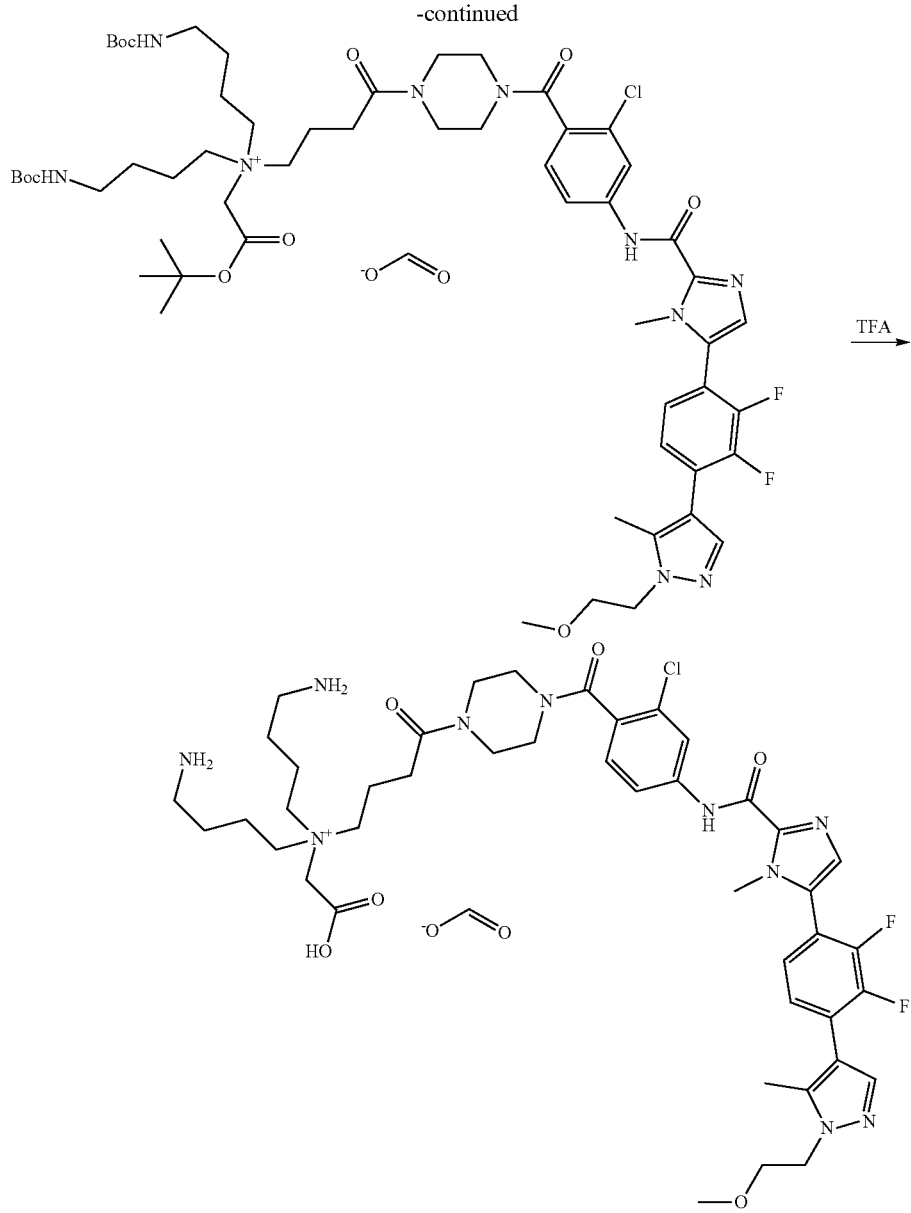

Step 1: bis[4-(tert-butoxycarbonylamino)butyl]-(2-tert-butoxy-2-oxo-ethyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]ammonium; formate To a mixture of bis[4-(tert-butoxycarbonylamino)butyl]-(2-tert-butoxy-2-oxo-ethyl)-(3-carboxypropyl)ammonium; bromide (128.55 mg, 0.2 mmol) and DIEA (64.83 mg, 0.5 mmol) in DMF (2 mL) was added CMPI (51.26 mg, 0.2 mmol) at 30° C. and stirred at 30° C. for 0.5 h. Then, N-[3-chloro-4-(piperazine-1-carbonyl)phenyl]-5-[2,3-difluoro-4-[1-(2-methoxyethyl)-5-methyl-pyrazol-4-yl]phenyl]-1-methyl-imidazole-2-carboxamide (100.0 mg, 0.17 mmol) was added to the above solution and stirred at 30° C. for another 3.5 h. The reaction mixture was purified by reversed phase-HPLC (water (0.1% FA)-ACN, B=85%~90%) and lyophilized to afford bis[4-(tert-butoxycarbonylamino)butyl]-(2-tert-butoxy-2-oxo-ethyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]ammonium; formate (80.0 mg, 0.07 mmol, 41.94% yield) as yellow solid. MS [(M)+]: 1139.5.

Step 2: bis(4-aminobutyl)-(carboxymethyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]ammonium; formate To a mixture of bis[4-(tert-butoxycarbonylamino)butyl]-(2-tert-butoxy-2-oxo-ethyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]ammonium;formate (60.0 mg, 0.05 mmol) in DCM (2 mL) was added TFA (2.0 mL, 25.96 mmol) at 30° C. and stirred for 16 h. The reaction mixture was concentrated in vacuum to give the residue, which was purified by prep-HPLC (Phenomenex Synergi C18 150×25 mm×10 um, water (0.225% FA)-ACN, B=9%-39% Flow-Rate: 25 ml/min) to afford bis(4-aminobutyl)-(carboxymethyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl] ammonium; formate (30.0 mg, 0.03 mmol) as white solid. MS [(M)+]: 883.5.

Example P3 bis(3-aminopropyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]-methyl-ammonium; formate

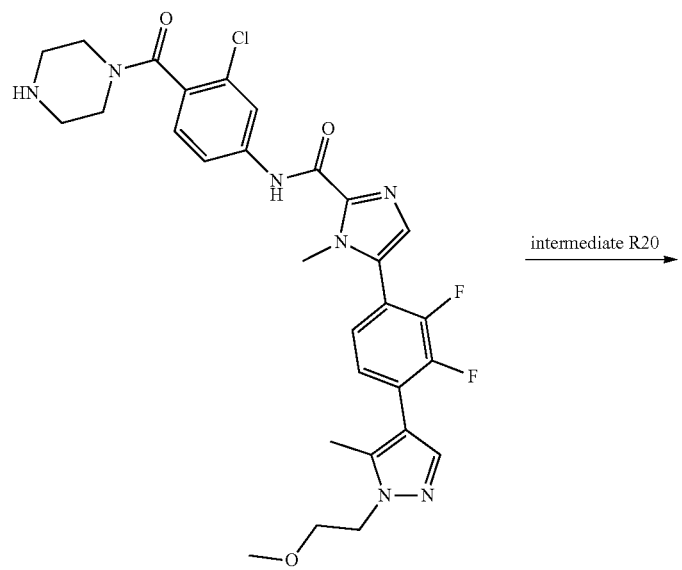

intermediate H8 intermediate R20

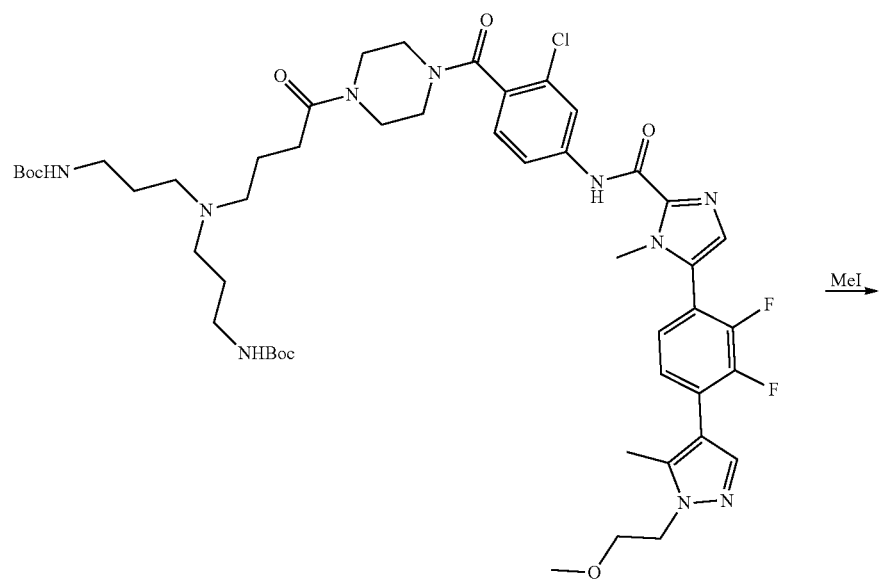

MeI

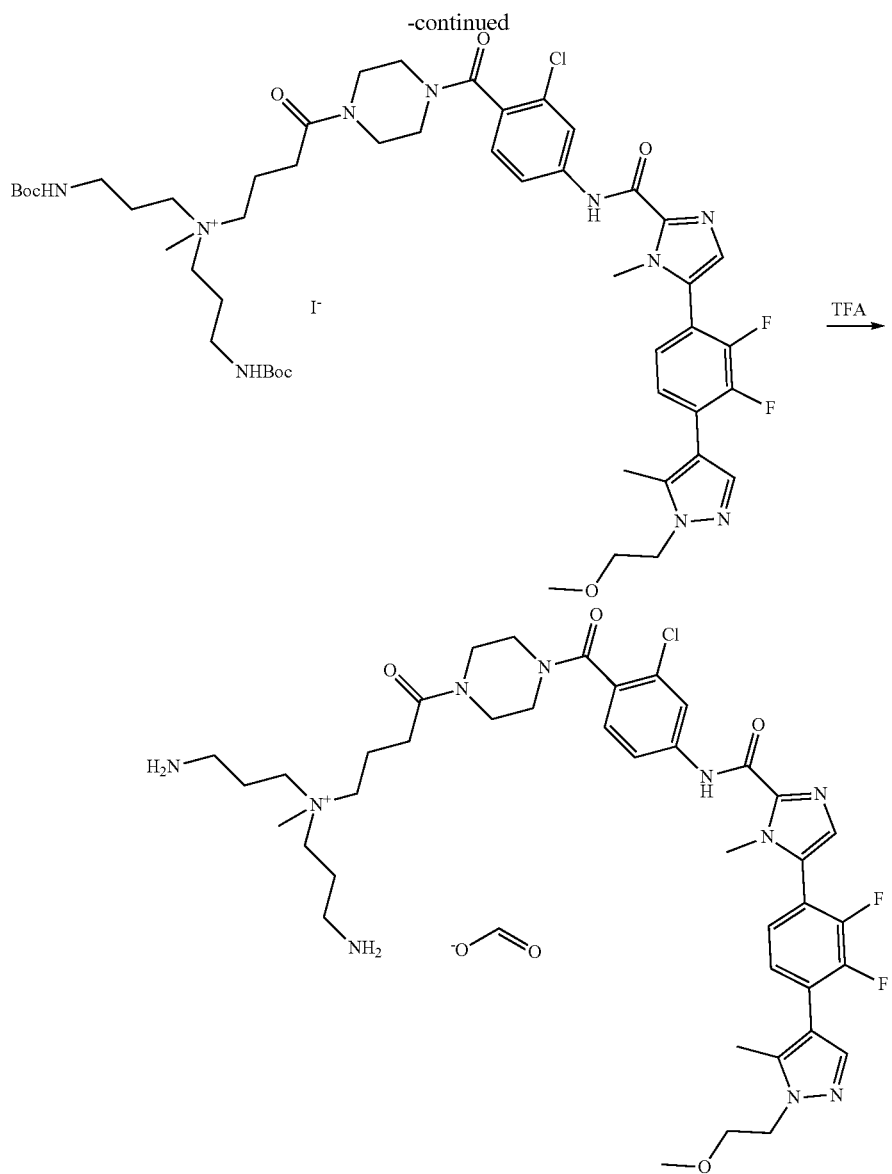

Step 1: tert-butyl N-[3-[3-(tert-butoxycarbonylamino)propyl-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]amino]propyl]carbamate To a stirred mixture of N-[3-chloro-4-(piperazine-1-carbonyl)phenyl]-5-[2,3-difluoro-4-[1-(2-methoxyethyl)-5-methyl-pyrazol-4-yl]phenyl]-1-methyl-imidazole-2-carboxamide (100.0 mg, 0.17 mmol), DIEA (0.09 mL, 0.5 mmol) and 4-[bis[3-(tert-butoxycarbonylamino)propyl]amino]butanoic acid (69.82 mg, 0.17 mmol) in DMF (3 mL) was added HATU (0.13 g, 0.33 mmol) at 15° C. Then the solution was stirred at 15° C. for 12 h. The mixture was poured into water (40 ml), extracted with EtOAc (40 ml), washed with brine (30 ml), dried over Na₂SO₄ and concentrated in vacuum to afford a residue. The residue was purified by reversed phase HPLC and lyophilized to afford tert-butyl N-[3-[3-(tert-butoxycarbonylamino)propyl-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]amino]propyl]carbamate (60.0 mg, 0.06 mmol, 35.97% yield) as white solid. MS [(M+H)+]: 997.2.

Step 2: bis[3-(tert-butoxycarbonylamino)propyl]-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]-methyl-ammonium; iodide To a solution of tert-butyl N-[3-[3-(tert-butoxycarbonylamino)propyl-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]amino]propyl]carbamate (60.0 mg, 0.06 mmol) and TEA (0.03 mL, 0.18 mmol) in ACN (3 mL) was added iodomethane (0.04 mL, 0.6 mmol) at 15° C. and stirred for 16 h. The reaction mixture was concentrated in vacuum, purified by reversed phase and lyophilized to afford bis[3-

(tert-butoxycarbonylamino)propyl]-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]-methyl-ammonium; iodide (25.0 mg, 0.02 mmol, 36.48% yield) as white solid. MS [(M)+]: 1011.3.

Step 3: bis(3-aminopropyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]-methyl-ammonium; formate To a solution of bis[3-(tert-butoxycarbonylamino)propyl]-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]-methyl-ammonium;iodide (50.0 mg, 0.04 mmol) in DCM (3 mL) was added TFA (3.0 mL, 38.94 mmol), the solution was stirred at 25° C. for 2 h. The reaction mixture was concentrated in vacuum and purified by Prep-HPLC, lyophilized to afford bis(3-aminopropyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]-methyl-ammonium; formate (15.7 mg, 0.02 mmol) as white solid. MS [(M)+]: 811.5.

Example P4 carboxymethyl-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]-bis[2-(dimethylamino)ethyl]ammonium; 2,2,2-trifluoroacetate

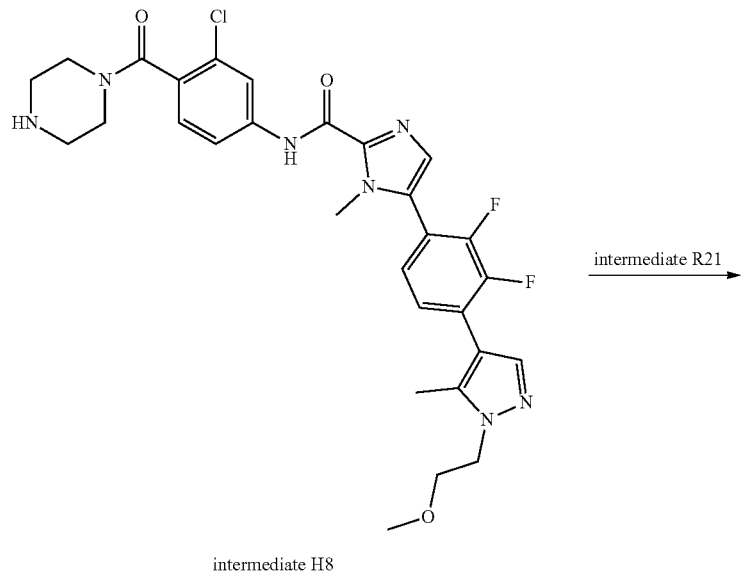

intermediate H8

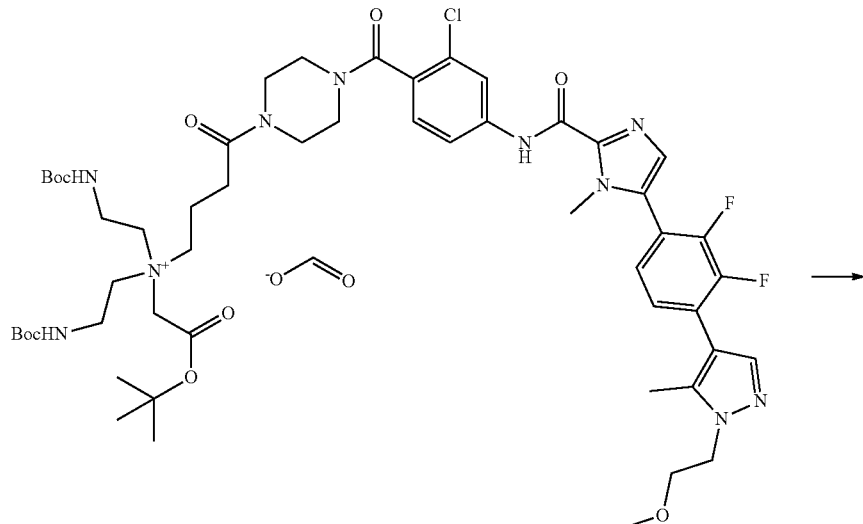

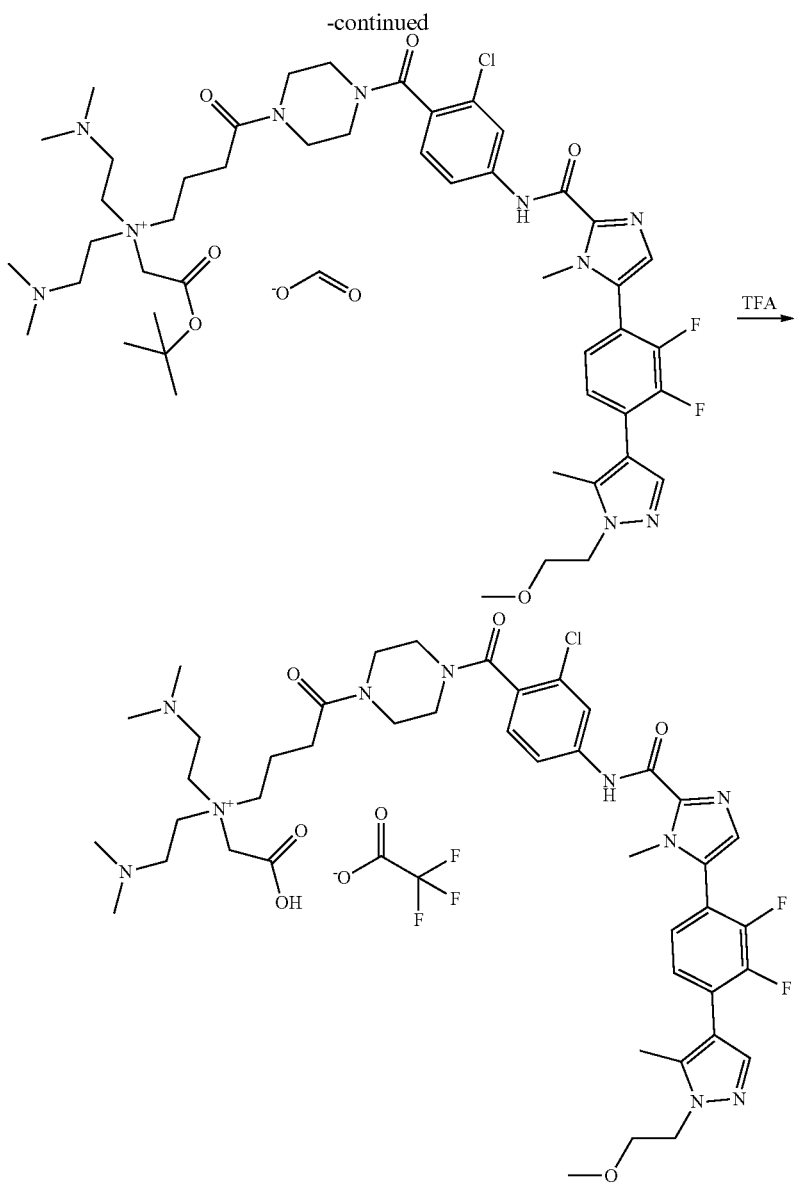

Step 1: bis[2-(tert-butoxycarbonylamino)ethyl]-(2-tert-butoxy-2-oxo-ethyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]ammonium; formate To a solution of N-[3-chloro-4-(piperazine-1-carbonyl)phenyl]-5-[2,3-difluoro-4-[1-(2-methoxyethyl)-5-methyl-pyrazol-4-yl]phenyl]-1-methyl-imidazole-2-carboxamide (200.0 mg, 0.33 mmol), DIEA (0.17 mL, 1.0 mmol) and bis[2-(tert-butoxycarbonylamino)ethyl]-(2-tert-butoxy-2-oxo-ethyl)-(3-carboxypropyl)ammonium;bromide (195.49 mg, 0.33 mmol) in DMF (5 mL) was added HATU (0.25 g, 0.67 mmol) at 15° C. Then the solution was stirred at 15° C. for 16 h. The mixture was purified by reversed phase-HPLC and lyophilized to afford bis[2-(tert-butoxycarbonylamino)ethyl]-(2-tert-butoxy-2-oxo-ethyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]ammonium; formate (300.0 mg, 0.27 mmol, 82.7% yield) as light brown solid. MS [(M)+]: 1083.5.

Step 2: (2-tert-butoxy-2-oxo-ethyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]-bis[2-(dimethylamino)ethyl]-ammonium; formate To a solution of bis[2-(tert-butoxycarbonylamino)ethyl]-(2-tert-butoxy-2-oxo-ethyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]ammonium;formate (245.0 mg, 0.22 mmol) and formaldehyde (1.0 mL, 37% in water) in DCM (4 mL) was added TFA (1.0 mL, 12.98 mmol) and stirred at 20° C. for 16 h. NaBH(OAc)₃ (229.82 mg, 1.08 mmol) was added to the solution and stirred at 20° C. for 1 h. The reaction mixture was concentrated in vacuum and the residue was purified by reversed phase-HPLC and lyophilized to obtain (2-tert-butoxy-2-oxo-ethyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]-bis[2-(dimethylamino)ethyl]ammonium; formate (60.0 mg, 0.06 mmol, 28.07% yield) as light brown solid. MS [(M)+]: 939.6.

Step 3: carboxymethyl-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]-bis[2-(dimethylamino)ethyl]ammonium; 2,2,2-trifluoroacetate To a solution of (2-tert-butoxy-2-oxo-ethyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]-bis[2-(dimethylamino)ethyl]ammonium;formate (60.0 mg, 0.06 mmol) in DCM (1 mL) was added TFA (1.0 mL, 12.98 mmol) and stirred at 20° C. for 16 h. The reaction mixture was concentrated in vacuum and the residue was purified by prep-HPLC to obtain carboxymethyl-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]-bis[2-(dimethylamino)ethyl]ammonium; 2,2,2-trifluoroacetate (11.86 mg, 0.01 mmol) as white solid. MS [(M)+]: 883.6.

Example P5

2-[1-(3-aminopropyl)-4-[5-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazino]-5-keto-pentanoyl]piperazin-1-ium-1-yl]acetic acid; formate

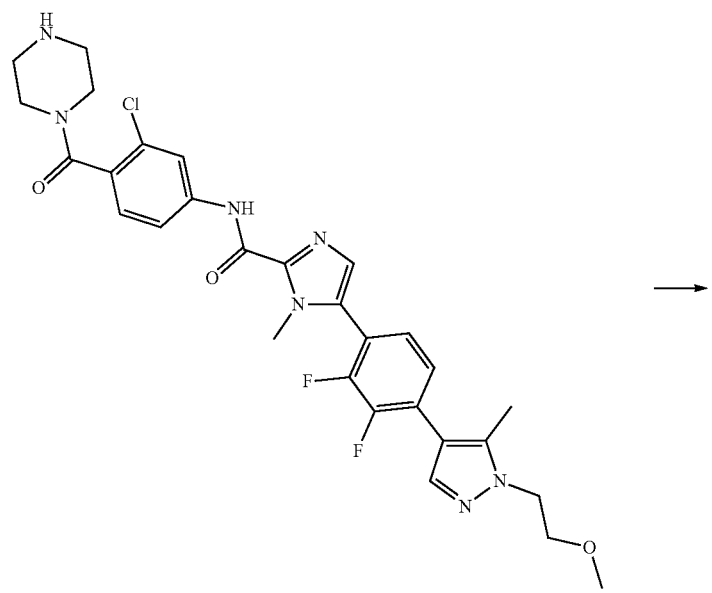

intermediate H8

641
-continued
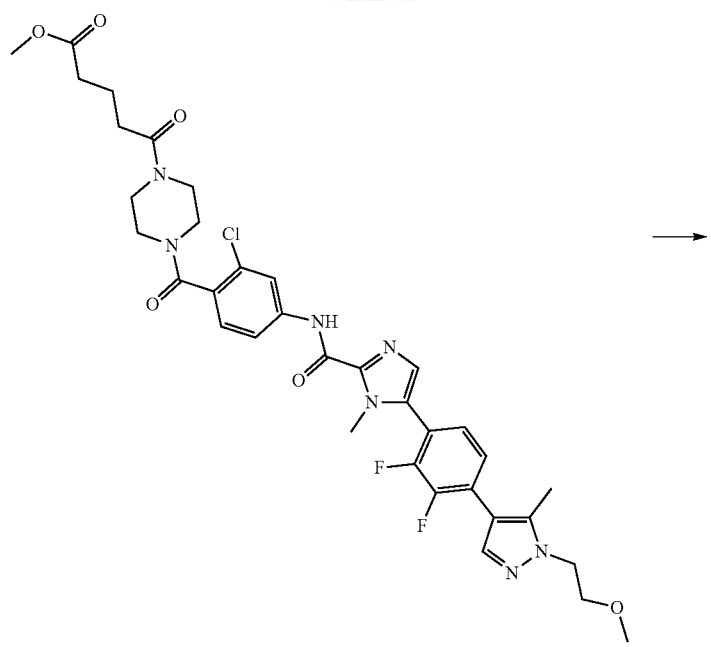
→
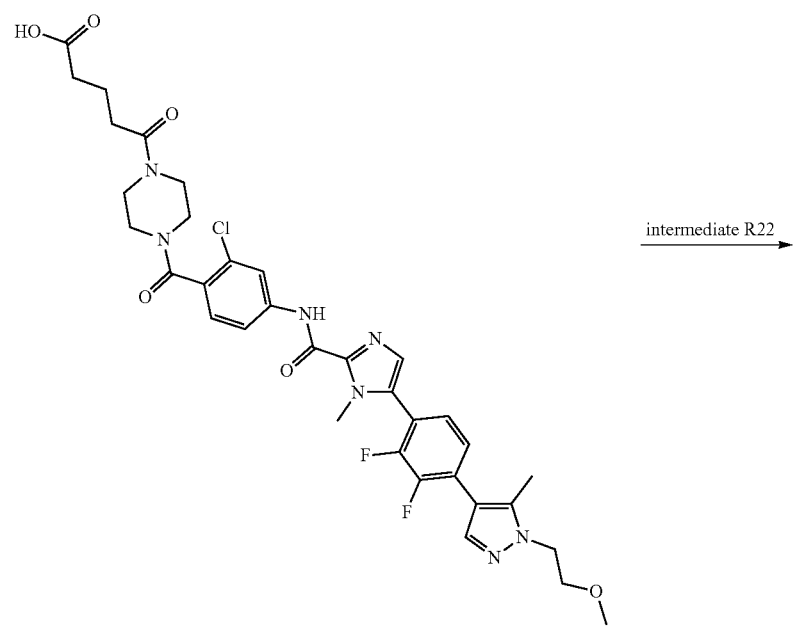
intermediate R22 →
642

-continued

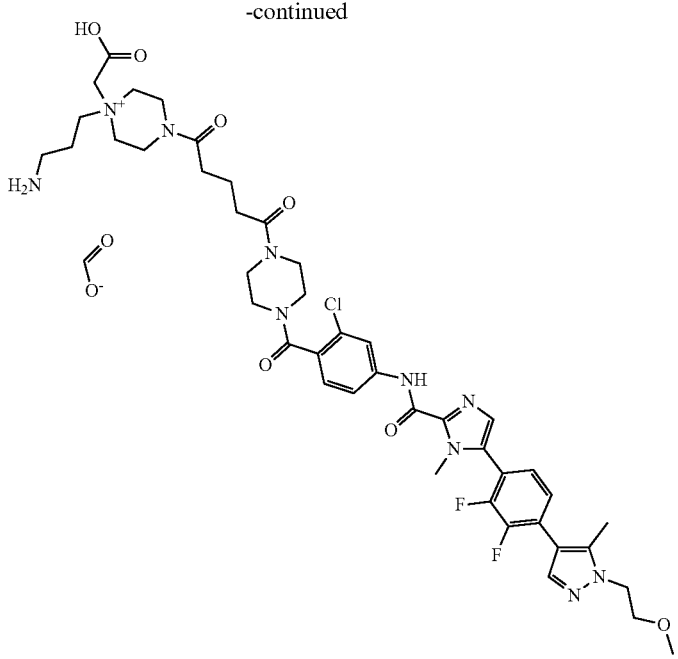

Step 1: 5-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazino]-5-keto-valeric acid methyl ester 5-keto-5-methoxy-valeric acid (35.93 mg, 0.246 mmol, 1.300 eq), HATU (107.87 mg, 0.284 mmol, 1.500 eq) and DIEA (122.21 mg, 165.15 uL, 0.946 mmol, 5.000 eq) are dissolved in N,N-dimethylformamide (1.2 mL). The mixture is stirred for 10 min. N-[3-chloro-4-(piperazine-1-carbonyl)phenyl]-5-[2,3-difluoro-4-[1-(2-methoxyethyl)-5-methyl-pyrazol-4-yl]phenyl]-1-methyl-imidazole-2-carboxamide; hydrochloride (120 mg, 0.189 mmol, 1.000 eq) is then added and the mixture was stirred at room temperature over night. The mixture was poured into 50 mL water and extracted 2× with EtOAc. The organic phases were combined and evaporated to dryness to give 5-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazino]-5-keto-valeric acid methyl ester 0.1:1 hydrogen chloride (299.5 mg, 99.67%) as light brown solid and used crude for next step. [(M+H)+]: 726.3.

Step 2: 5-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazino]-5-keto-valeric acid 5-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazino]-5-keto-valeric acid methyl ester (299.5 mg, 0.189 mmol, 1.000 eq) was dissolved in methanol (5 mL) and water (2 mL). lithium hydroxide monohydrate (79.1 mg, 1.89 mmol, 10.000 eq) was added and the reaction is stirred at 22° C. for 18 hr. The clear solution was acidified with 4M aq. HCl solution. The product is extracted two times with ethylacetate. Both organic layers were combined, dried with sodium sulfate, filtered and evaporated to dryness. The crude product purified via prep HPLC to afford after lyophilization 5-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazino]-5-keto-valeric acid (50.6 mg, 37.32%) as white solid. [(M+H)+]: 712.2.

Step 3: 2-[1-(3-aminopropyl)-4-[5-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazino]-5-keto-pentanoyl]piperazin-1-ium-1-yl]acetic acid; formate To a solution of 5-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazino]-5-keto-valeric acid (12.5 mg, 0.017 mmol, 1.000 eq) and 2-[1-[3-(tert-butoxycarbonylamino)propyl]piperazin-1-ium-1-yl]acetic acid tert-butyl ester;formate (10.37 mg, 0.024 mmol, 1.477 eq) in dichloromethane (1.04 mL) was added DIEA (10.68 mg, 14.44 uL, 0.083 mmol, 5.000 eq) and then PyAOP reagent (11.2 mg, 0.021 mmol, 1.300 eq). The reaction mixture was stirred at room temperature for 2 hr. Boc and t-butyl were then deprotected with 4N HCl in dioxane (247.96 mg, 206.64 uL, 0.827 mmol, 50.000 eq) over night at room temperature. Volatiles were removed in vacuo and the residue was purified via prep HPLC to yield the desired compound 2-[1-(3-aminopropyl)-4-[5-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazino]-5-keto-pentanoyl]piperazin-1-ium-1-yl]acetic acid; formate (5.8 mg, 37.27%) as white powder. MS [M-]: 940.5.

The following example was prepared in analogy to Example P5.

| Ex# | Name | Structure | MS [M] | Starting Material |
|---|---|---|---|---|
| Example P6 | 2-[1-(azetidin-3-ylmethyl)-4-[5-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazino]-5-keto-pentanoyl]piperazin-1-ium-1-yl]acetic acid; 1:1 formate | 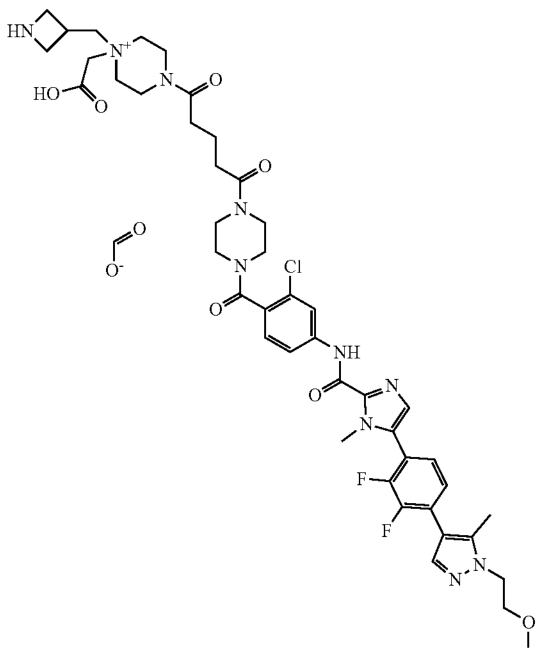 | 852.5 | Intermediate R23 |

Example Q1

N-[3-chloro-4-[4-(4-oxo-3-aza-6-azoniaspiro[5.5]undecane-9-carbonyl)piperazine-1-carbonyl]phenyl]-5-[2,3-difluoro-4-[1-(2-methoxyethyl)-3-methyl-pyrazol-4-yl]phenyl]-1-methyl-imidazole-2-carboxamide; 2,2,2-trifluoroacetate

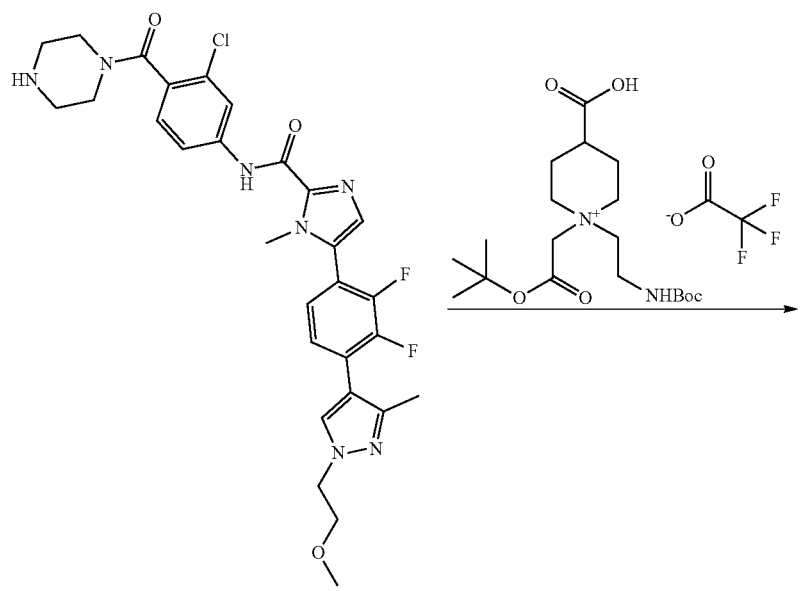

Intermediate I2

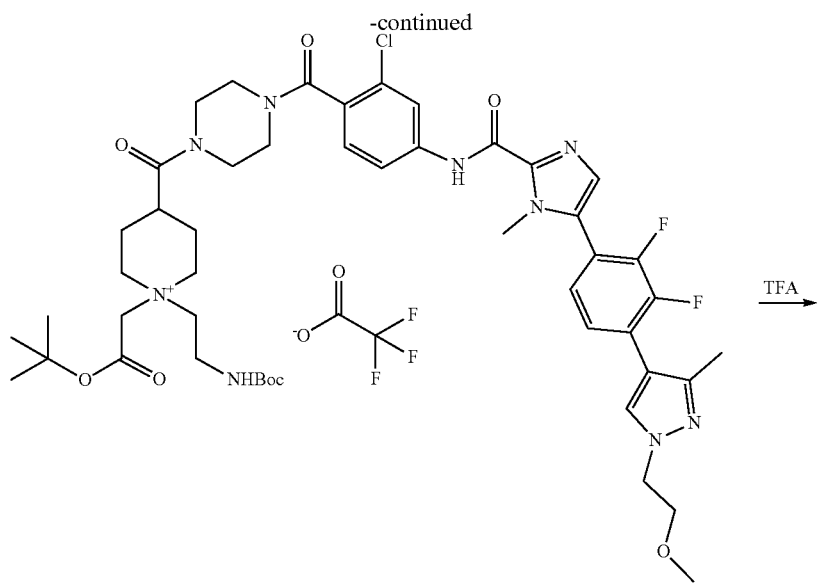

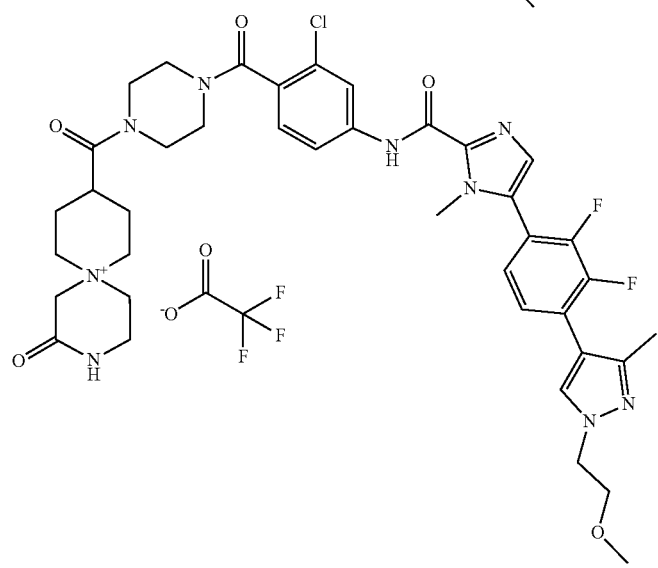

Step 1 tert-butyl 2-[1-[2-(tert-butoxycarbonylamino)ethyl]-4-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]piperidin-1-ium-1-yl]acetate; 2,2,2-trifluoroacetate To a solution of N-[3-chloro-4-(piperazine-1-carbonyl)phenyl]-5-[2,3-difluoro-4-[1-(2-methoxyethyl)-3-methyl-pyrazol-4-yl]phenyl]-1-methyl-imidazole-2-carboxamide; hydrochloride (200.0 mg, 0.32 mmol), DIEA (0.16 mL, 0.95 mmol) and 1-[2-(tert-butoxycarbonylamino)ethyl]-1-(2-tert-butoxy-2-oxo-ethyl)piperidin-1-ium-4-carboxylic acid;2,2,2-trifluoroacetate (205.09 mg, 0.41 mmol) in DMF (4 mL) was added HATU (179.78 mg, 0.47 mmol, 1.5 eq) at 0° C. and stirred at 0° C. for 1 h. The solution was purified by reversed phase-HPLC and lyophilized to afford tert-butyl 2-[1-[2-(tert-butoxycarbonylamino)ethyl]-4-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]piperidin-1-ium-1-yl]acetate; 2,2,2-trifluoroacetate (251.0 mg, 0.23 mmol, 73.7% yield) as white solid. MS [(M)+]: 966.6.

Step 2: N-[3-chloro-4-[4-(4-oxo-3-aza-6-azoniaspiro[5.5]undecane-9-carbonyl)piperazine-1-carbonyl]phenyl]-5-[2,3-difluoro-4-[1-(2-methoxyethyl)-3-methyl-pyrazol-4-yl]phenyl]-1-methyl-imidazole-2-carboxamide; 2,2,2-trifluoroacetate To a solution of tert-butyl 2-[1-[2-(tert-butoxycarbonylamino)ethyl]-4-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]piperidin-1-ium-1-yl]acetate;2,2,2-trifluoroacetate (51.0 mg, 0.05 mmol) in DCM (2 mL) was added TFA (4.0 mL, 51.92 mmol) in one portion at 10° C. and stirred at 10° C. for 16 h. The solution was concentrated, purified by Prep-HPLC and lyophilized to afford N-[3-chloro-4-[4-(4-oxo-3-aza-6-azoniaspiro[5.5]undeACNe-9-carbonyl)piperazine-1-carbonyl]phenyl]-5-[2,3-difluoro-4-[1-(2-methoxyethyl)-3-methyl-pyrazol-4-yl]phenyl]-1-methylimidazole-2-carboxamide; 2,2,2-trifluoroacetate (17.4 mg, 0.02 mmol) as white solid. MS [(M)+]: 792.3.

Example Q2

N-[4-[4-(3-benzyl-3-aza-6-azoniaspiro[5.5]undecane-9-carbonyl)piperazine-1-carbonyl]-3-chlorophenyl]-5-[2,3-difluoro-4-[1-(2-methoxyethyl)-3-methyl-pyrazol-4-yl]phenyl]-1-methyl-imidazole-2-carboxamide

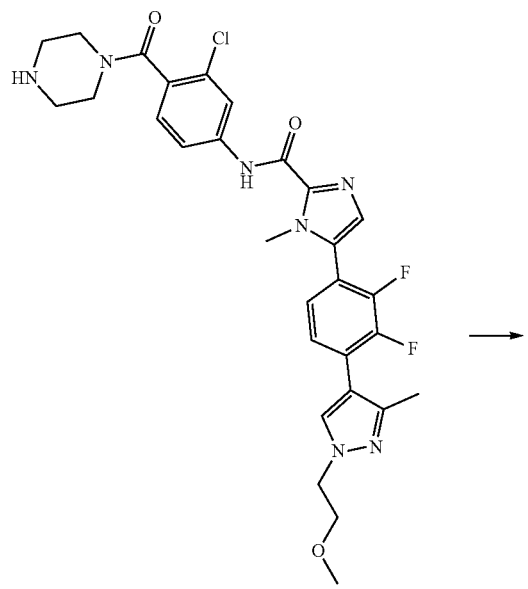

Intermediate I2

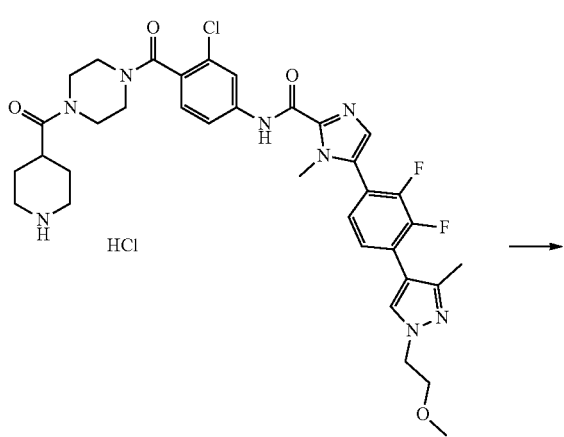

HCl

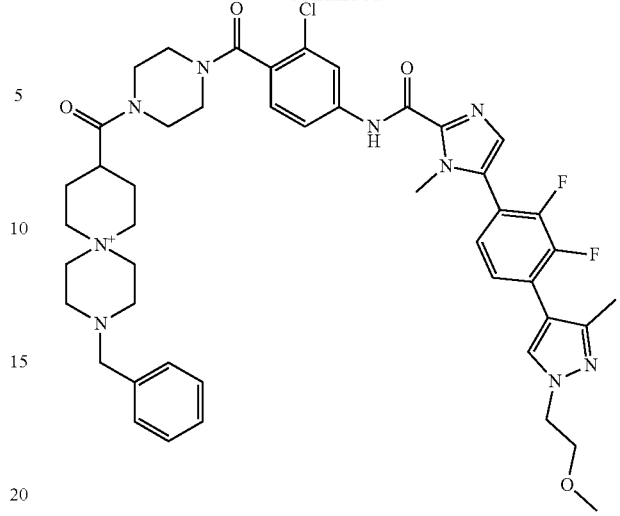

Step 1: 4-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]piperidine-1-carboxylic acid tert-butyl ester To a solution of 1-tert-butoxycarbonylisonipecotic acid (20.93 mg, 91.3 umol, 1.200 eq), N-[3-chloro-4-(piperazine-1-carbonyl)phenyl]-5-[2,3-difluoro-4-[1-(2-methoxyethyl)-3-methyl-pyrazol-4-yl]phenyl]-1-methyl-imidazole-2-carboxamide (50 mg, 76.08 umol, 1.000 eq), HATU (43.39 mg, 114.12 umol, 1.500 eq) and N,N-dimethylformamide, extra dry (400 uL) was added DIEA (29.5 mg, 39.86 uL, 228.25 umol, 3.000 eq) and the reaction mixture was stirred at room temperature for 2 h. The reaction mixture was diluted in EtOAc, and then washed with water and brine, filtered over MgSO4 and then concentrated under vacuo.

The crude material was purified by flash chromatography to yield 4-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]piperidine-1-carboxylic acid tert-butyl ester (41.8 mg, 67.89%) as yellow waxy solid. MS [(M+H)+]: 809.4

Step 2: N-[3-chloro-4-(4-isonipecotoylpiperazine-1-carbonyl)phenyl]-5-[2,3-difluoro-4-[1-(2-methoxyethyl)-3-methyl-pyrazol-4-yl]phenyl]-1-methyl-imidazole-2-carboxamide; hydrochloride 4-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]piperidine-1-carboxylic acid tert-butyl ester (41.8 mg, 0.052 mmol, 1.000 eq) was treated with an excess of 4 M HCl in dioxane (129.12 uL, 516.5 umol, 10.000 eq) in 1,4-dioxane (1.0 mL) and was stirred at room temperature over 4 days. Diethyl ether was added so the product was crash out. The solvent was evaporated to yield N-[3-chloro-4-(4-isonipecotoylpiperazine-1-carbonyl)phenyl]-5-[2,3-difluoro-4-[1-(2-methoxyethyl)-3-methyl-pyrazol-4-yl]phenyl]-1-methyl-imidazole-2-carboxamide hydrochloride (40.8 mg, 100%) as white solid. MS [(M+H)+]: 709.3.

Step 3: N-[4-[4-(3-benzyl-3-aza-6-azoniaspiro[5.5]undecane-9-carbonyl)piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide Benzyl-bis(2-bromoethyl)amine (9.47 mg, 6.06 uL, 29.5 umol, 1.100 eq), N-[3-chloro-4-(4-isonipecotoylpiperazine-1-carbonyl)phenyl]-5-[2,3-difluoro-4-[1-(2-methoxyethyl)-3-methyl-pyrazol-4-yl]phenyl]-1-methyl-imidazole-2-carboxamide (20 mg, 26.82 umol, 1.000 eq), potassium carbonate (12.23 mg, 88.51 umol, 3.300 eq) and potassium iodide (890.51 ug, 5.36 umol, 0.200 eq) were combined in N,N-dimethylformamide (500 uL). The reaction mixture was then stirred at room temperature over night. The mixture was purified over prep HPLC to afford N-[4-[4-(3-benzyl-3-aza-6-azoniaspiro[5.5]undecane-9-carbonyl)piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide (5.1 mg, 20.56%) as colorless solid. MS [(M)+]: 868.5.

The following examples were prepared in analogy to Example 01.

| Ex# | Name | Structure | MS [M]+ | Starting Material |
|---|---|---|---|---|
| Example Q3 | trans 2-[1-(azetidin-3-ylmethyl)-4-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]piperidin-1-ium-1-yl]acetic acid; formate | 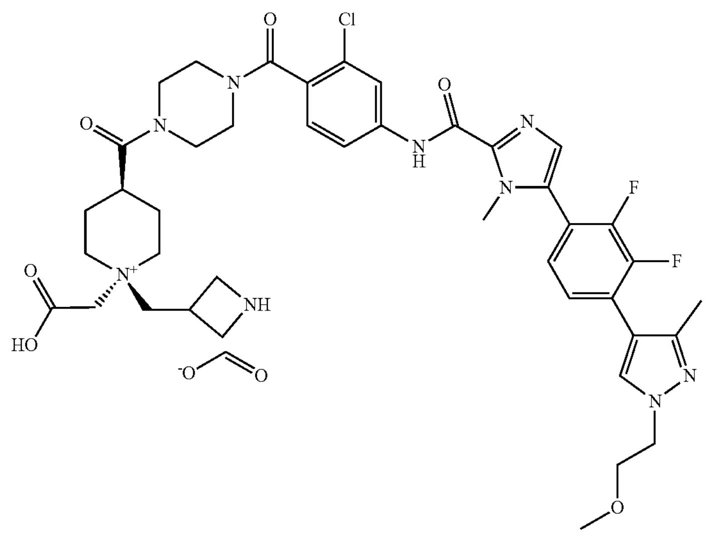 | 836.6 | Intermediate I2 and Intermediate R16' |
| Example Q4 | cis 2-[1-(azetidin-3-ylmethyl)-4-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]piperidin-1-ium-1-yl]acetic acid formate; | 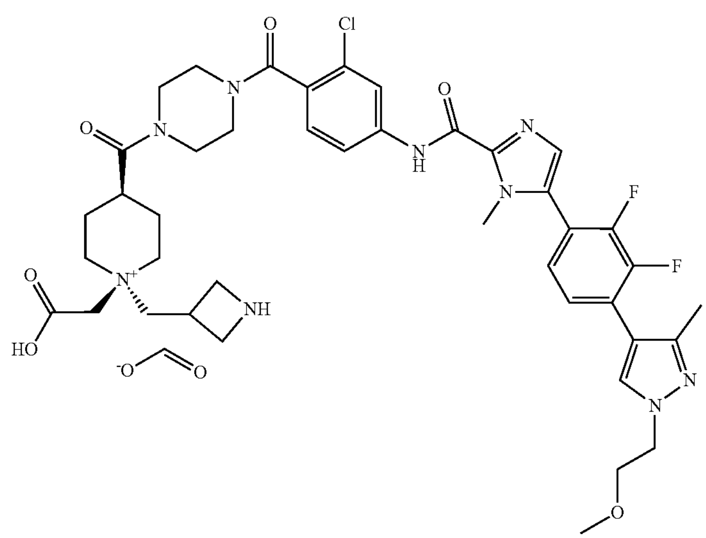 | 836.6 | Intermediate I2 and Intermediate R16 |

Assay Procedures
Antimicrobial Susceptibility Testing:
90% Growth Inhibitory Concentration (IC90) Determination The in vitro antimicrobial activity of the compounds was determined according to the following procedure:

The assay used a 10-points Iso-Sensitest broth medium to measure quantitatively the in vitro activity of the compounds against *Acinetobacter baumannii* ATCC17961.

Stock compounds in DMSO were serially twofold diluted (e.g. range from 50 to 0.097 µM final concentration) in 384 wells microtiter plates and inoculated with 49 µl the bacterial suspension in Iso-Sensitest medium to have a final cell concentration of ~5×10$^{(5)}$ CFU/ml in a final volume/well of 50 ul/well. Microtiter plates were incubated at 35±2° C.

Bacterial cell growth was determined with the measurement of optical density at λ=600 nm each 20 minutes over a time course of 16h. Growth inhibition was calculated during the logarithmic growth of the bacterial cells with determination of the concentration inhibiting 50% (IC50) and 90% (IC90) of the growth.

Table 1 provides the 90% growth inhibitory concentrations (IC90) in micromoles per liter of the compounds of present invention obtained against the strain *Acinetobacter baumannii* ATCC17961.

Particular compounds of the present invention exhibit an IC90 (*Acinetobacter baumannii* ATCC17961)≤25 µmol/l.

More particular compounds of the present invention exhibit an IC90 (*Acinetobacter baumannii* ATCC17961)≤5 µmol/l.

Most particular compounds of the present invention exhibit an IC90 (*Acinetobacter baumannii* ATCC17961)≤1 µmol/l.

TABLE 1

| Example | ATCC 17961 IC90 [µM] |
|---|---|
| Example A1 | 0.12 |
| Example A2 | 0.23 |
| Example A3 | 0.23 |
| Example A4 | 0.11 |
| Example A5 | 0.055 |
| Example A6 | 0.058 |
| Example A7 | 0.055 |
| Example A8 | 0.053 |
| Example A9 | 0.16 |
| Example A10 | 0.098 |
| Example A11 | 0.36 |
| Example A12 | 0.21 |
| Example A13 | 0.11 |
| Example B1 | 0.19 |
| Example B2 | 0.12 |
| Example B3 | 0.13 |
| Example B4 | 0.23 |
| Example B5 | 0.18 |
| Example B6 | 0.12 |
| Example B7 | 0.17 |
| Example B8 | 0.28 |
| Example B9 | 0.51 |
| Example B10 | 0.2 |
| Example B11 | 0.17 |
| Example B12 | 0.11 |
| Example B13 | 0.81 |
| Example B14 | 0.68 |
| Example B15 | 0.17 |
| Example B16 | 0.3 |
| Example B17 | 0.26 |
| Example B18 | 0.43 |
| Example B19 | 0.057 |
| Example B20 | 0.22 |
| Example B21 | 0.1 |
| Example B22 | 0.33 |
| Example B23 | 0.098 |
| Example B24 | 0.095 |
| Example B25 | 0.27 |
| Example B26 | 0.064 |
| Example B27 | 0.24 |
| Example B28 | 0.23 |
| Example B29 | 0.34 |
| Example B30 | 0.19 |
| Example B31 | 0.071 |
| Example B32 | 0.058 |
| Example B33 | 0.82 |
| Example B34 | / |
| Example B35 | 0.13 |
| Example B36 | 0.11 |
| Example B37 | 0.2 |
| Example B38 | 0.3 |
| Example B39 | 0.25 |
| Example B40 | 1.8 |
| Example C1 | 0.045 |
| Example C2 | 0.041 |
| Example C3 | 0.1 |
| Example C4 | 0.16 |
| Example C5 | 0.24 |
| Example C6 | 0.14 |
| Example C7 | 0.14 |
| Example C8 | 0.21 |
| Example C9 | 0.26 |
| Example C10 | 0.28 |
| Example C11 | 0.32 |
| Example C12 | 0.153 |
| Example C13 | / |
| Example C14 | 0.082 |
| Example D1 | 0.28 |
| Example D2 | 0.21 |
| Example D3 | 0.39 |
| Example D4 | 0.178 |
| Example D6 | 0.085 |
| Example D7 | 0.15 |
| Example D8 | 0.3 |
| Example D9 | 0.3 |
| Example D10 | 0.21 |
| Example D11 | 0.27 |
| Example D12 | 0.2 |
| Example D13 | 0.34 |
| Example D14 | 0.11 |
| Example D15 | 0.1 |
| Example D16 | 0.15 |
| Example D17 | 0.26 |
| Example D18 | 0.058 |
| Example D19 | / |
| Example D20 | 0.064 |
| Example D21 | 0.2 |
| Example D22 | 0.199 |
| Example D23 | 0.68 |
| Example D24 | 0.073 |
| Example D25 | 0.051 |
| Example D26 | 0.19 |
| Example D27 | 0.23 |
| Example D28 | 0.03 |
| Example D29 | <0.02 |
| Example D30 | 0.24 |
| Example D31 | 0.22 |
| Example D32 | 0.052 |
| Example D33 | 0.21 |
| Example D34 | 0.11 |
| Example D35 | 0.17 |
| Example D36 | 0.088 |
| Example D37 | 0.15 |
| Example D38 | 0.15 |
| Example D40 | 0.077 |
| Example D41 | 0.061 |
| Example D42 | 0.06 |
| Example D43 | 0.81 |
| Example D44 | 0.16 |

TABLE 1-continued

| Example | ATCC 17961 IC90 [μM] |
|---|---|
| Example E1 | / |
| Example E2 | 0.048 |
| Example E3 | 0.49 |
| Example E4 | / |
| Example E5 | 0.18 |
| Example E6 | 0.95 |
| Example E7 | 0.21 |
| Example E8 | 0.2 |
| Example E9 | 0.065 |
| Example E10 | 0.17 |
| Example E11 | 0.061 |
| Example E12 | 0.15 |
| Example E13 | 0.38 |
| Example E14 | 0.27 |
| Example E15 | 0.18 |
| Example E16 | 0.23 |
| Example E17 | 0.71 |
| Example E18 | 0.82 |
| Example E19 | 0.13 |
| Example E20 | 0.53 |
| Example E21 | 0.29 |
| Example E22 | 0.059 |
| Example E23 | 0.14 |
| Example F1 | 0.33 |
| Example F2 | 0.065 |
| Example F3 | 0.12 |
| Example F4 | 0.83 |
| Example F5 | 0.28 |
| Example F6 | 0.57 |
| Example F7 | 0.52 |
| Example F8 | / |
| Example F9 | 0.16 |
| Example F10 | 0.075 |
| Example F11 | 0.8 |
| Example F12 | 0.17 |
| Example F14 | 0.1 |
| Example F15 | 0.055 |
| Example F16 | 0.24 |
| Example F17 | 0.27 |
| Example F18 | 1.1 |
| Example F19 | 0.33 |
| Example F20 | 0.18 |
| Example F21 | / |
| Example F22 | 0.17 |
| Example F23 | 0.75 |
| Example F24 | 0.59 |
| Example F25 | 1.2 |
| Example F26 | 1.4 |
| Example F27 | 0.4 |
| Example F28 | 0.27 |
| Example F29 | 0.28 |
| Example F30 | 0.097 |
| Example F31 | 0.067 |
| Example F32 | 0.58 |
| Example F33 | 0.36 |
| Example F34 | 0.23 |
| Example F35 | / |
| Example F36 | 0.58 |
| Example F37 | 0.69 |
| Example F38 | 0.76 |
| Example F39 | 0.34 |
| Example F40 | 0.61 |
| Example F41 | 0.15 |
| Example F42 | 0.21 |
| Example F43 | 0.57 |
| Example F44 | 0.73 |
| Example F45 | 0.31 |
| Example F46 | 1.1 |
| Example F47 | 0.53 |
| Example F48 | 0.47 |
| Example F49 | 1.52 |
| Example F50 | 1.1 |
| Example F51 | 0.21 |
| Example F52 | 0.27 |
| Example F53 | 0.11 |
| Example F54 | 0.59 |
| Example F55 | 0.27 |
| Example F56 | 0.33 |
| Example F57 | 0.88 |
| Example F58 | 0.48 |
| Example F59 | 0.75 |
| Example F60 | 0.15 |
| Example K2 | 0.36 |
| Example K3 | 0.3 |
| Example F63 | 0.56 |
| Example F64 | 0.25 |
| Example F65 | 0.37 |
| Example F66 | 0.029 |
| Example F67 | 1.1 |
| Example G1 | 0.29 |
| Example G2 | 0.32 |
| Example G3 | 0.1 |
| Example G4 | 0.19 |
| Example G5 | / |
| Example G6 | 0.14 |
| Example G7 | 0.55 |
| Example G8 | 0.084 |
| Example G9 | 0.21 |
| Example G10 | 0.12 |
| Example G11 | 0.71 |
| Example G12 | 0.45 |
| Example G13 | 0.13 |
| Example G14 | 0.089 |
| Example G15 | 0.3 |
| Example G16 | 1.1 |
| Example G17 | 0.72 |
| Example G18 | 0.51 |
| Example G19 | / |
| Example G20 | / |
| Example G21 | / |
| Example G22 | 0.67 |
| Example G23 | 0.27 |
| Example G24 | 0.508 |
| Example G25 | 1 |
| Example G26 | 0.1 |
| Example G27 | 0.12 |
| Example G28 | 0.088 |
| Example G29 | 0.33 |
| Example G30 | 1 |
| Example G31 | 0.14 |
| Example G32 | 0.185 |
| Example G33 | 0.44 |
| Example G34 | 0.068 |
| Example H1 | 0.15 |
| Example H2 | 0.19 |
| Example H3 | 0.18 |
| Example H4 | 0.16 |
| Example H5 | 0.17 |
| Example H6 | 0.17 |
| Example H7 | 0.19 |
| Example H8 | 0.54 |
| Example I1 | 0.432 |
| Example I2 | 0.608 |
| Example I3 | 0.398 |
| Example I4 | 1.5 |
| Example I5 | / |
| Example I6 | 0.82 |
| Example I7 | 0.76 |
| Example J1 | 0.022 |
| Example K1 | 0.6 |
| Example L1 | 0.206 |
| Example L2 | 0.168 |
| Example L3 | 0.264 |
| Example L4 | 0.106 |
| Example L5 | 0.374 |
| Example L6 | 0.197 |
| Example M1 | 0.152 |
| Example N1 | 0.189 |
| Example N2 | 0.183 |
| Example N3 | 0.352 |

TABLE 1-continued

| Example | ATCC 17961 IC90 [μM] |
|---|---|
| Example N4 | 0.108 |
| Example O1 | 0.354 |
| Example O2 | 0.362 |
| Example O3 | 0.113 |
| Example O4 | 0.118 |
| Example O5 | 0.200 |
| Example O6 | 0.134 |
| Example O7 | 0.140 |
| Example O8 | 0.245 |
| Example O9 | 0.284 |
| Example O10 | 0.231 |
| Example O11 | 0.156 |
| Example O12 | 0.339 |
| Example P1 | 0.191 |
| Example P2 | 0.066 |
| Example P3 | 0.293 |
| Example P4 | 0.657 |
| Example P5 | 0.295 |
| Example P6 | 0.310 |
| Example Q1 | 0.165 |
| Example Q2 | 0.705 |
| Example Q3 | 0.359 |
| Example Q4 | 0.195 |

Minimal Inhibitory Concentration Protocol (MIC) Assay:

Table 2 provides the in vitro potency of the compounds of present invention obtained against the strain *Acinetobacter baumannii* ATCC17978, which was assessed by an MIC (Minimal Inhibitory Concentration) assay as follows.

Test compounds were prepared from 10 mM DMSO stock solutions. The top dose was diluted from 10 mM to 2.5 mM by DMSO, followed by serial 2-fold 11 points dilutions in DMSO in a master plate (Greiner, Cat No: 651201). 2 μL compounds were transferred from the master plate into a new 96-well assay plate (Costar, 3599).

The growth medium Caution-Adjusted Mueller Hinton Broth (CAMHIB) was prepared by adding 22 g powder (BD, 212322) in 1 L purified water, autoclaved, and supplemented with sterilized $CaCl_2$ (20 mg per liter) and $MgCl_2$ (10 mg per liter).

Vials of each of the test microorganisms were maintained frozen in the vapor phase of a liquid nitrogen freezer. Took out the bacterial strain ATCC 17978 from liquid nitrogen freezer, thawed it at room temperature, and diluted the bacterial in the CAMHB medium to achieve a final inoculum of $2\times10^5$ CFU/mL. 98 μL of the adjusted bacteria suspension was dispensed to the assay plate and pipetted 5 times.

Then the assay plates were incubated for 20 hours at 35±2° C. in ambient air with humidity. Following incubation, MIC (g/mL) value, the lowest concentration of drug that inhibits visible growth of the microorganism, was recorded by visual judgment of bacterial growth through magnification mirror of MIC reader, and the assay plates were photographed with Qcount system as image raw data. Meanwhile, the D600 of assay plates was recorded with SpectraMax Plus384 as GD raw data.

TABLE 2

| Example | MIC AB. ATCC17978 [μM] |
|---|---|
| Example B34 | 0.65 |
| Example C12 | 1.20 |
| Example C13 | 1.22 |
| Example D04 | 1.56 |
| Example D18 | 1.23 |
| Example D19 | 1.07 |
| Example D22 | 1.10 |
| Example D29 | 0.45 |
| Example E01 | 0.56 |
| Example E04 | 0.57 |
| Example F8 | 1.41 |
| Example F21 | 2.31 |
| Example F29 | 4.73 |
| Example F30 | 1.19 |
| Example F35 | 1.24 |
| Example F49 | 2.50 |
| Example F53 | 0.60 |
| Example G5 | 0.32 |
| Example G19 | 0.32 |
| Example G20 | 2.52 |
| Example G21 | 2.57 |
| Example G24 | 3.85 |
| Example G32 | 0.66 |
| Example I1 | 2.32 |
| Example I2 | 2.41 |
| Example I3 | 1.81 |
| Example I5 | 0.58 |

Example 1

A compound of formula (I) can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example 2

A compound of formula (I) can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Example 3

A compound of formula (I) can be used in a manner known per se as the active ingredient for the production of an infusion solution of the following composition:

| | |
|---|---|
| Active ingredient | 100 mg |
| Lactic acid 90% | 100 mg |
| NaOH q.s. or HCl q.s. for adjustment to pH 4.0 | |
| Sodium chloride q.s. or glucose q.s. for adjustment of the osmolality to 290 mOsm/kg | |
| Water for injection (WFI) | ad 100 ml |

Example 4

A compound of formula (I) can be used in a manner known per se as the active ingredient for the production of an infusion solution of the following composition:

| | |
|---|---|
| Active ingredient | 100 mg |
| Hydroxypropyl-beta-cyclodextrin | 10 g |
| NaOH q.s. or HCl q.s. for adjustment to pH 7.4 | |
| Sodium chloride q.s. or glucose q.s. for adjustment of the osmolality to 290 mOsm/kg | |
| Water for injection (WFI) | ad 100 ml |

The invention claimed is:

1. A compound of formula (I)

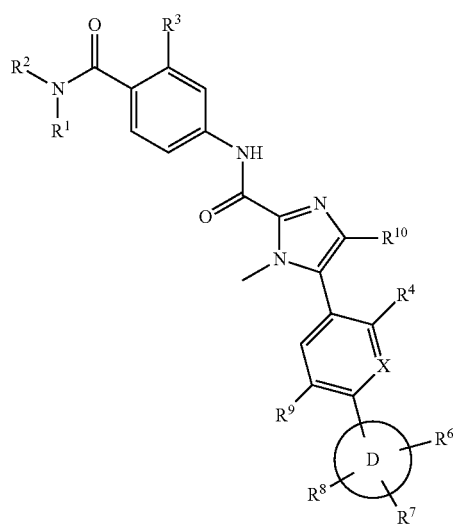

(I)

or a pharmaceutically acceptable salt thereof, wherein:

X is N or C—$R^5$;

$R^1$ and $R^2$, taken together with the nitrogen atom to which they are attached, form a group

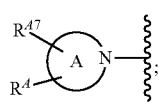

or $R^1$ is a group

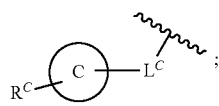

and $R^2$ is hydrogen;

$R^3$ is halogen or $C_1$-$C_6$-alkyl;

$R^4$ is selected from hydrogen, halogen, $C_1$-$C_6$-alkyl, and $C_1$-$C_6$-alkoxy;

$R^5$ is selected from hydrogen, halogen, and $C_1$-$C_6$-alkyl;

$R^6$ is selected from hydrogen, $C_1$-$C_6$-alkyl, carbamoyl-$C_1$-$C_6$-alkyl-NH—, amino, halogen, hydroxy-$C_1$-$C_6$-alkyl, halo-$C_1$-$C_6$-alkyl, and a group

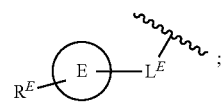

$R^7$ is selected from hydrogen, $C_1$-$C_6$-alkyl, $C_1$-$C_6$-alkoxy-$C_1$-$C_6$-alkyl-, hydroxy-$C_1$-$C_6$-alkyl, halo-$C_1$-$C_6$-alkyl, carbamoyl-$C_1$-$C_6$-alkyl, $C_1$-$C_6$-alkyl-NH—C(O)—$C_1$-$C_6$-alkyl-, $C_1$-$C_6$-alkyl-NH—C(O)—NH—$C_1$-$C_6$-alkyl-, cyano-$C_1$-$C_6$-alkyl, $C_1$-$C_6$-alkyl-SO$_2$—$C_1$-$C_6$-alkyl-, halo-$C_1$-$C_6$-alkoxy-$C_1$-$C_6$-alkyl-, amino-$C_1$-$C_6$-alkoxy-$C_1$-$C_6$-alkyl-, and a group

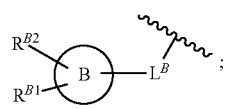

and $R^8$ is selected from hydrogen, halogen, $C_1$-$C_6$-alkyl, halo-$C_1$-$C_6$-alkyl, and $C_1$-$C_6$-alkoxy-$C_1$-$C_6$-alkyl; or $R^7$ and $R^8$, taken together with the atoms to which they are attached, form a 3- to 14-membered heterocycle;

$R^9$ and $R^{10}$ are each independently hydrogen or halogen;

$R^A$ is selected from hydrogen, $(C_1$-$C_6$-alkyl)$_2$N—$C_1$-$C_6$-alkyl-C(O)—, $(R^{A6})_3$N$^+$—$C_1$-$C_6$-alkyl-C(O)—, and a group;

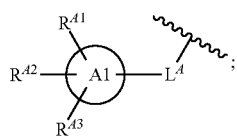

$R^{A1}$ is selected from hydrogen, hydroxy, amino, $C_1$-$C_6$-alkyl, halo-$C_1$-$C_6$-alkyl, hydoxy-$C_1$-$C_6$-alkyl, amino-$C_1$-$C_6$-alkyl, carbamoyl-$C_1$-$C_6$-alkyl, $C_1$-$C_6$-alkoxy-$C_1$-$C_6$-alkyl, H$_2$N—SO$_2$—$C_1$-$C_6$-alkyl-, H$_2$N—NH—C(O)—$C_1$-$C_6$-alkyl-, $C_1$-$C_6$-alkoxy, oxo, carbamoyl, and a group

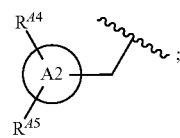

$R^{A2}$ is selected from hydrogen, hydroxy, amino, $C_1$-$C_6$-alkyl, carboxy-$C_1$-$C_6$-alkyl, and carbamoyl-$C_1$-$C_6$-alkyl;

$R^{A3}$, $R^{A4}$, $R^{A5}$, $R^{C2}$, and $R^{C3}$ are each independently selected from hydrogen and $C_1$-$C_6$-alkyl;

each $R^{46}$ is independently selected from $C_1$-$C_6$-alkyl, amino-$C_1$-$C_6$-alkyl, $C_1$-$C_6$-alkyl-NH—$C_1$-$C_6$-alkyl-, ($C_1$-$C_6$-alkyl)$_2$N—$C_1$-$C_6$-alkyl-, carboxy-$C_1$-$C_6$-alkyl, and (3- to 14-membered heterocyclyl)-$C_1$-$C_6$-alkyl-;

$R^{47}$ is selected from hydrogen and $C_1$-$C_6$-alkyl;

$R^{B1}$ is selected from hydrogen, halogen, cyano, amino, oxo, $C_1$-$C_6$-alkyl, $C_1$-$C_6$-alkoxy, and 3- to 14-membered heterocyclyl;

$R^{B2}$ is selected from hydrogen, halogen, and $C_1$-$C_6$-alkyl;

$R^C$ is selected from hydrogen, ($C_1$-$C_6$-alkyl)$_2$N—$C_1$-$C_6$-alkyl-C(O)—, ($C_1$-$C_6$-alkyl)$_3$N$^+$—$C_1$-$C_6$-alkyl-C(O)—, and a group

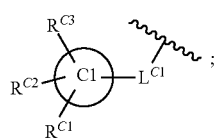

$R^{C1}$ is hydroxy;

$R^E$ is selected from $C_1$-$C_6$-alkyl, $C_1$-$C_6$-alkoxy, and halogen;

$L^A$ is selected from —$C_1$-$C_6$-alkyldiyl-, carbonyl, —C(O)—NH—, —NH—C(O)—, —C(O)—N($C_1$-$C_6$-alkyl)-, —N($C_1$-$C_6$-alkyl)-C(O)—, —$C_1$-$C_6$-alkyldiyl-NH—C(O)—, —SO$_2$—NH—, —NH—SO$_2$—, —$C_1$-$C_6$-alkyldiyl-C(O)—, and —C(O)—$C_1$-$C_6$-alkyldiyl-C(O)—;

$L^B$ is selected from a covalent bond, —$C_1$-$C_6$-alkyldiyl-, —NH—C(O)—$C_1$-$C_6$-alkyldiyl-, —C(O)—NH—$C_1$-$C_6$-alkyldiyl-, —NH—C(O)—NH—$C_1$-$C_6$-alkyldiyl-, —C(O)—$C_1$-$C_6$-alkyldiyl-, and —SO$_2$—NH—$C_1$-$C_6$-alkyldiyl-;

$L^C$ and $L^E$ are each independently a covalent bond or —$C_1$-$C_6$-alkyldiyl-;

$L^{C1}$ is —NH—C(O)— or carbonyl;

A, C, and C1 are each independently a 3- to 14-membered heterocyclyl;

A2 is selected from 3- to 14-membered heterocyclyl and $C_6$-$C_{10}$-aryl;

A1 is selected from 3- to 14-membered heterocyclyl, 5- to 14-membered heteroaryl, and $C_3$-$C_{10}$-cycloalkyl;

B is selected from 5- to 14-membered heteroaryl, 3- to 14-membered heterocyclyl, $C_3$-$C_{10}$-cycloalkyl, and $C_6$-$C_{10}$-aryl;

D is a 5- to 14-membered heteroaryl;

E is selected from 5- to 14-membered heteroaryl, 3- to 14-membered heterocyclyl, and $C_6$-$C_{10}$-aryl; and a wavy line represents the point of attachment of the respective R group to the remainder of formula (I).

2. The compound of formula (I) according to claim 1, or a pharmaceutically acceptable salt thereof, wherein:

$R^1$ and $R^2$, taken together with the nitrogen atom to which they are attached, form a group

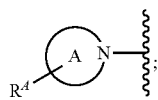

$R^A$ is selected from ($R^{46}$)$_3$N$^+$—$C_1$-$C_6$-alkyl-C(O)—, and a group

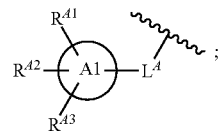

$R^{A1}$ is selected from hydroxy, $C_1$-$C_6$-alkyl, carbamoyl-$C_1$-$C_6$-alkyl, and a group

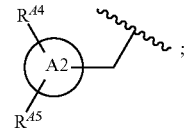

$R^{A2}$ is selected from $C_1$-$C_6$-alkyl, carboxy-$C_1$-$C_6$-alkyl, and carbamoyl-$C_1$-$C_6$-alkyl;

$R^{A3}$ is selected from hydrogen and $C_1$-$C_6$-alkyl;

$R^{A4}$ and $R^{A5}$ are hydrogen;

each $R^{46}$ is independently selected from amino-$C_1$-$C_6$-alkyl and carboxy-$C_1$-$C_6$-alkyl;

$L^A$ is carbonyl; and

A, A1 and A2 are each independently a 3- to 14-membered heterocyclyl.

3. The compound of formula (I) according to claim 2, or a pharmaceutically acceptable salt thereof, wherein:

$R^1$ and $R^2$, taken together with the nitrogen atom to which they are attached, form a group

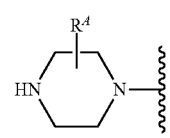

or a group

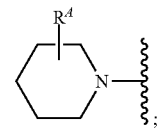

$R^A$ is selected from ($R^{46}$)$_3$N$^+$—(CH$_2$)$_3$—C(O)—, and a group

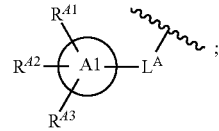

$R^{A1}$ is selected from hydroxy, methyl, 2-amino-2-oxoethyl, and a group

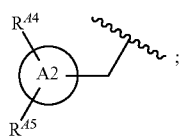

$R^{A2}$ is selected from methyl, carboxymethyl, and 2-amino-2-oxo-ethyl;
$R^{A3}$ is selected from hydrogen and methyl;
$R^{A4}$ and $R^{A5}$ are hydrogen;
each $R^{A6}$ is independently selected from aminopropyl and carboxymethyl;
$L^A$ is carbonyl;
A1 is selected from pyrrolidinyl, piperazinyl, piperidinyl, and 3-azabicyclo[3.1.0]hexan-6-yl; and
A2 is azetidinyl.

4. Me compound of formula (I) according to claim 1, or a pharmaceutically acceptable salt thereof, wherein $R^3$ is halogen.

5. The compound of formula (I) according to claim 4, or a pharmaceutically acceptable salt thereof, wherein $R^3$ is chloro.

6. The compound of formula (I) according to claim 1, or a pharmaceutically acceptable salt thereof, wherein:
X is C—$R^5$;
$R^4$ is selected from halogen and $C_1$-$C_6$-alkyl;
$R^5$ is halogen; and
$R^9$ is hydrogen.

7. He compound of formula (I) according to claim 6, or a pharmaceutically acceptable salt thereof, wherein:
X is C—$R^5$;
$R^4$ is selected from methyl, fluoro and chloro;
$R^5$ is fluoro; and
$R^9$ is hydrogen.

8. The compound of formula (I) according to claim 1, or a pharmaceutically acceptable salt thereof, wherein:
$R^6$ is selected from hydrogen, $C_1$-$C_6$-alkyl, and a group

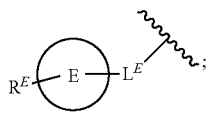

$R^7$ is selected from hydrogen, $C_1$-$C_6$-alkoxy-$C_1$-$C_6$-alkyl-, and a group

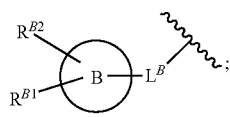

$R^8$ is selected from hydrogen, halogen, $C_1$-$C_6$-alkyl, and halo-$C_1$-$C_6$-alkyl;
$R^{B1}$ is selected from hydrogen and halogen;
$R^{B2}$ is hydrogen;
$R^E$ is halogen;
$L^B$ is selected from —$C_1$-$C_6$-alkyldiyl- and —NH—C(O)—$C_1$-$C_6$-alkyldiyl-;
$L^E$ is a covalent bond;
B and D are each independently a 5- to 14-membered heteroaryl; and
E is $C_6$-$C_{10}$-aryl.

9. The compound of formula (I) according to claim 8, or a pharmaceutically acceptable salt thereof, wherein:
$R^6$ is selected from hydrogen, methyl, and a group

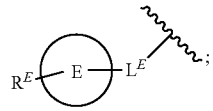

$R^7$ is selected from hydrogen, 2-methoxyethyl, and a group

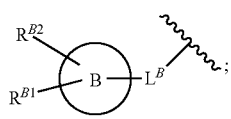

$R^8$ is selected from hydrogen, chloro, methyl, and difluoromethyl;
$R^{B1}$ is selected from hydrogen and fluoro;
$R^{B2}$ is hydrogen;
$R^E$ is fluoro;
$L^B$ is selected from —$CH_2$— and —NH—C(O)—$CH_2$—;
$L^E$ is a covalent bond;
B is selected from pyridyl and pyridazinyl;
D is pyrazolyl; and
E is phenyl.

10. Me compound of formula (I) according to claim 1, or a pharmaceutically acceptable salt thereof, wherein $R^{10}$ is hydrogen.

11. The compound of formula (I) according to claim 1, or a pharmaceutically acceptable salt thereof, wherein:
X is C—$R^5$;
$R^1$ and $R^2$, taken together with the nitrogen atom to which they are attached, form a group

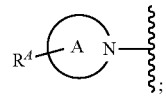

$R^3$, $R^4$, $R^5$ and $R^E$ are each independently halogen;
$R^6$ is selected from hydrogen, $C_1$-$C_6$-alkyl, and a group

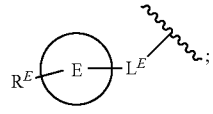

$R^7$ is selected from hydrogen, $C_1$-$C_6$-alkoxy-$C_1$-$C_6$-alkyl-, and a group

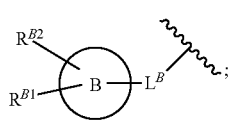

$R^8$ is selected from hydrogen, halogen, $C_1$-$C_6$-alkyl, and halo-$C_1$-$C_6$-alkyl;

$R^9$, $R^{10}$, $R^{A4}$, $R^{A5}$, and $R^{B2}$ are hydrogen;

$R^A$ is selected from $(R^{A6})_3N^+\text{—}C_1\text{-}C_6\text{-alkyl-}C(O)\text{—}$, and a group

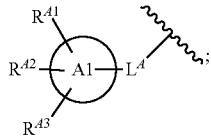

$R^{A1}$ is selected from hydroxy, $C_1$-$C_6$-alkyl, carbamoyl-$C_1$-$C_6$-alkyl, and a group

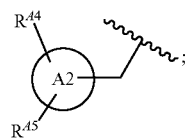

$R^{A2}$ is selected from $C_1$-$C_6$-alkyl, carboxy-$C_1$-$C_6$-alkyl, and carbamoyl-$C_1$-$C_6$-alkyl;

$R^{A3}$ is selected from hydrogen and $C_1$-$C_6$-alkyl;

each $R^{A6}$ is independently selected from amino-$C_1$-$C_6$-alkyl and carboxy-$C_1$-$C_6$-alkyl;

$R^{B1}$ is selected from hydrogen and halogen;

$L^A$ is carbonyl;

$L^B$ is selected from —$C_1$-$C_6$-alkyldiyl- and —NH—C(O)—$C_1$-$C_6$-alkyldiyl-;

$L^E$ is a covalent bond;

A, A1 and A2 are each independently a 3- to 14-membered heterocyclyl;

B and D are each independently a 5- to 14-membered heteroaryl; and

E is $C_6$-$C_{10}$-aryl.

12. The compound of formula (I) according to claim 1, or a pharmaceutically acceptable salt thereof, wherein:

X is C—$R^5$;

$R^1$ and $R^2$, taken together with the nitrogen atom to which they are attached, form a group

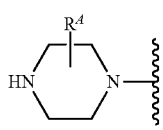

or a group

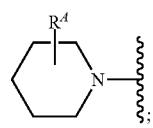

$R^3$ is chloro;

$R^4$ is fluoro or chloro;

$R^5$ and $R^E$ are fluoro;

$R^6$ is selected from hydrogen, methyl, and a group

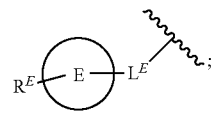

$R^7$ is selected from hydrogen, 2-methoxyethyl, and a group

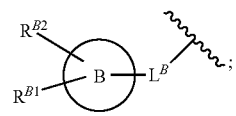

$R^8$ is selected from hydrogen, chloro, methyl, and difluoromethyl;

$R^9$, $R^{10}$, $R^{A4}$, $R^{A5}$, and $R^{B2}$ are hydrogen;

$R^A$ is selected from $(R^{A6})_3N^+\text{—}(CH_2)_3\text{—}C(O)\text{—}$, and a group

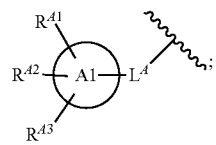

$R^{A1}$ is selected from hydroxy, methyl, 2-amino-2-oxo-ethyl, and a group

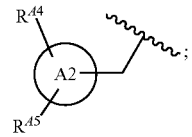

$R^{A2}$ is selected from methyl, carboxymethyl, and 2-amino-2-oxo-ethyl;

$R^{A3}$ is selected from hydrogen and methyl;

each $R^{A6}$ is independently selected from aminopropyl and carboxymethyl;

$R^{B1}$ is selected from hydrogen and fluoro;

$L^A$ is carbonyl;

$L^B$ is selected from —$CH_2$— and —NH—C(O)—$CH_2$—;

$L^E$ is a covalent bond;

A1 is selected from pyrrolidinyl, piperazinyl, piperidinyl, and 3-azabicyclo[3.1.0]hexan-6-yl;

A2 is azetidinyl;

B is selected from pyridyl and pyridazinyl;

D is pyrazolyl; and

E is phenyl.

13. The compound of formula (I) according to claim 1, or a pharmaceutically acceptable salt thereof, wherein said compound of formula (I) is selected from:

N-[3-chloro-4-[4-(1,1-dimethylpiperidin-1-ium-4-carbonyl)piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[4-[1-(2-methoxyethyl)-3,5-dimethyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[2-[(3S)-1,1-dimethylpyrrolidin-1-ium-3-yl]acetyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-(4-hydroxy-1,1-dimethyl-piperidin-1-ium-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-(3-hydroxy-1,1-dimethyl-piperidin-1-ium-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

[2-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-2-oxo-ethyl]-trimethyl-ammonium;

[2-[4-[[[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]amino]methyl]-1-piperidyl]-2-oxo-ethyl]-trimethyl-ammonium;

N-[3-chloro-4-[4-(4,4-dimethylpiperazin-4-ium-1-carbonyl)piperidine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[(2S,3S)-3-hydroxy-1,1-dimethyl-pyrrolidin-1-ium-2-carbonyl]piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide;

N-[3-chloro-4-[4-[(2S)-4-(hydroxymethyl)-1,1-dimethyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-(4-methoxy-1,1-dimethyl-piperidin-1-ium-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[4-[4-[1-(2-amino-2-oxo-ethyl)-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide;

N-[4-[4-[1-(2-amino-2-oxo-ethyl)-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide;

N-[4-[4-[1-(2-amino-2-oxo-ethyl)-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[1-(2-hydroxyethyl)-1-methyl-piperidin-1-ium-4-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[4-[4-[1-(azetidin-3-ylmethyl)-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide;

N-[4-[4-[1-(2-amino-2-oxo-ethyl)-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide;

N-[4-[4-[1-(2-amino-2-oxo-ethyl)-1-methyl-piperidin-1-ium-4-carbonyl]piperazine-1-carbonyl]-3-chloro-phenyl]-5-[4-[1-(2,2-difluoroethyl)-3-methyl-pyrazol-4-yl]-2,3-difluoro-phenyl]-1-methyl-imidazole-2-carboxamide;

N-[3-chloro-4-[4-[1-(2-hydroxyethyl)-1-methyl-piperidin-1-ium-4-carbonyl]piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide;

N-[3-chloro-4-[4-[1-(2-hydroxyethyl)-1-methyl-piperidin-1-ium-4-carbonyl]piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide;

N-[3-chloro-4-[4-[1-(2-methoxyethyl)-1-methyl-piperidin-1-ium-4-carbonyl]piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide;

N-[4-[4-[1-(2-amino-2-oxo-ethyl)-1-methyl-piperidin-1-ium-4-carbonyl]piperazine-1-carbonyl]-3-chloro-phenyl]-5-[4-[1-(2-methoxyethyl)-3,5-dimethyl-pyrazol-4-yl]phenyl]-1-methyl-imidazole-2-carboxamide;

N-[3-chloro-4-[4-[1-(2-hydroxyethyl)-1-methyl-piperidin-1-ium-4-carbonyl]piperazine-1-carbonyl]phenyl]-5-[4-[1-(2-methoxyethyl)-3,5-dimethyl-pyrazol-4-yl]phenyl]-1-methyl-imidazole-2-carboxamide;

2-[4-[1-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperidine-4-carbonyl]-1-methyl-piperazin-1-ium-1-yl]acetic acid;

2-[1-(2-amino-2-oxo-ethyl)-4-[1-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperidine-4-carbonyl]piperazin-1-ium-1-yl]acetic acid;

N-[4-[4-[4-(2-amino-2-oxo-ethyl)-4-methyl-piperazin-4-ium-1-carbonyl]piperidine-1-carbonyl]-3-chloro-phenyl]-5-[2,3-difluoro-4-[1-(2-methoxyethyl)-5-methyl-pyrazol-4-yl]phenyl]-1-methyl-imidazole-2-carboxamide;

N-[4-[4-[1-(2-amino-2-oxo-ethyl)-4-hydroxy-1-methyl-piperidin-1-ium-4-carbonyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[1-(2-hydrazino-2-oxo-ethyl)-1-methyl-piperidin-1-ium-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

2-[1-(azetidin-3-ylmethyl)-4-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]piperidin-1-ium-1-yl]acetic acid;

N-[3-chloro-4-[4-[1-[(1,1-dimethylazetidin-1-ium-3-yl)methyl]-1-methyl-piperidin-1-ium-4-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;diformate;

2-[1-(azetidin-3-ylmethyl)-4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]piperidin-1-ium-1-yl]acetic acid;

N-[4-[4-[1-(azetidin-3-ylmethyl)-1-methyl-piperidin-1-ium-4-carbonyl]piperazine-1-carbonyl]-3-chloro-phenyl]-5-[2,3-difluoro-4-[1-(2-methoxyethyl)-5-methyl-pyrazol-4-yl]phenyl]-1-methyl-imidazole-2-carboxamide;

2-[1-(azetidin-3-ylmethyl)-4-[1-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperidine-4-carbonyl]piperazin-1-ium-1-yl]acetic acid;

N-[4-[4-[4-(azetidin-3-ylmethyl)-4-methyl-piperazin-4-ium-1-carbonyl]piperidine-1-carbonyl]-3-chloro-phenyl]-5-[2,3-difluoro-4-[1-(2-methoxyethyl)-5-methyl-pyrazol-4-yl]phenyl]-1-methyl-imidazole-2-carboxamide;

N-[4-[4-[4-(2-amino-2-oxo-ethyl)-4-(azetidin-3-ylmethyl)piperazin-4-ium-1-carbonyl]piperidine-1-carbonyl]-3-chloro-phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[(1R,5S)-3,3-dimethyl-3-azoniabicyclo[3.1.0]hexane-6-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[(1R,5S)-3,3-dimethyl-3-azoniabicyclo[3.1.0]hexane-6-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[(2S,4R)-4-hydroxy-1-(3-hydroxypropyl)-1-methyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;iodide;

2-[1-(azetidin-3-ylmethyl)-4-[4-[2-chloro-4-[[5-[3-chloro-2-fluoro-4-[1-(2-methoxyethyl)-5-methyl-pyrazol-4-yl]phenyl]-1-methyl-imidazole-2-carbonyl]amino]benzoyl]piperazine-1-carbonyl]piperidin-1-ium-1-yl]acetic acid;

2-[1-(azetidin-3-ylmethyl)-4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]piperidin-1-ium-1-yl]acetic acid;

N-[3-chloro-4-[4-[1-[(1,1-dimethylazetidin-1-ium-3-yl)methyl]piperidine-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[1-(2,2-difluoroethyl)-1-methyl-piperidin-1-ium-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[1-(2-sulfamoylethyl)piperidine-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[1-methyl-1-(2-sulfamoylethyl)piperidin-1-ium-4-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[1-(2-hydroxyethyl)-1-methyl-pyrrolidin-1-ium-2-carbonyl]piperazine-1-carbonyl]phenyl]-5-[2,3-difluoro-4-(3-methyl-1H-pyrazol-4-yl)phenyl]-1-methyl-imidazole-2-carboxamide;

N-[3-chloro-4-[4-[(2S,4R)-4-hydroxy-1-(2-hydroxyethyl)-1-methyl-pyrrolidin-1-ium-2-carbonyl]piperazine-1-carbonyl]phenyl]-5-[2,3-difluoro-4-(3-methyl-1H-pyrazol-4-yl)phenyl]-1-methyl-imidazole-2-carboxamide;

2-[1-(azetidin-3-ylmethyl)-4-[4-[2-chloro-4-[[5-[2-chloro-3-fluoro-4-[1-(2-methoxyethyl)-5-methyl-pyrazol-4-yl]phenyl]-1-methyl-imidazole-2-carbonyl]amino]benzoyl]piperazine-1-carbonyl]piperidin-1-ium-1-yl]acetic acid;

2-[1-(azetidin-3-ylmethyl)-4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazine-1-carbonyl]piperazin-1-ium-1-yl]acetic acid;

2-[1-(azetidin-3-ylmethyl)-4-[4-[2-chloro-4-[[5-[3-fluoro-4-[1-(2-methoxyethyl)-5-methyl-pyrazol-4-yl]-2-methyl-phenyl]-1-methyl-imidazole-2-carbonyl]amino]benzoyl]piperazine-1-carbonyl]piperidin-1-ium-1-yl]acetic acid;

2-[1-(azetidin-3-ylmethyl)-4-[4-[2-chloro-4-[[5-[5-chloro-4-[1-(2-methoxyethyl)-5-methyl-pyrazol-4-yl]-2-methyl-phenyl]-1-methyl-imidazole-2-carbonyl]amino]benzoyl]piperazine-1-carbonyl]piperidin-1-ium-1-yl]acetic acid;

N-[3-chloro-4-[4-[2-(3-hydroxy-1-methyl-pyrrolidin-1-ium-1-yl)acetyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[4-[4-[2-(3-amino-1-methyl-pyrrolidin-1-ium-1-yl)acetyl]piperazine-1-carbonyl]-3-chloro-phenyl]-5-[2,3-difluoro-4-[1-(2-methoxyethyl)-5-methyl-pyrazol-4-yl]phenyl]-1-methyl-imidazole-2-carboxamide;

N-[4-[4-[2-(3-amino-1-methyl-pyrrolidin-1-ium-1-yl)acetyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[2-(3-hydroxy-1-methyl-pyrrolidin-1-ium-1-yl)acetyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[4-[4-[2-[(3S,4S)-3-amino-4-methoxy-1-methyl-pyrrolidin-1-ium-1-yl]acetyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide;

N-[4-[4-[2-[3-(aminomethyl)-3-hydroxy-1-methyl-pyrrolidin-1-ium-1-yl]acetyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide;

N-[4-[4-[2-(3-carbamoyl-1-methyl-pyrrolidin-1-ium-1-yl)acetyl]piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[2-[(3R)-3-hydroxy-1-methyl-pyrrolidin-1-ium-1-yl]acetyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[2-[(3S)-3-hydroxy-1-methyl-pyrrolidin-1-ium-1-yl]acetyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[2-[(3R,4R)-3,4-dihydroxy-1-methyl-pyrrolidin-1-ium-1-yl]acetyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[2-(3-hydroxy-1-methyl-pyrrolidin-1-ium-1-yl)acetyl]piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide;

N-[3-chloro-4-[4-[2-[(3R,4R)-3,4-dihydroxy-1-methyl-pyrrolidin-1-ium-1-yl]acetyl]piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide;

N-[4-[4-[2-[(3R,4R)-3-amino-4-methoxy-1-methyl-pyrrolidin-1-ium-1-yl]acetyl]piperazine-1-carbonyl]-3-chloro-phenyl]-5-[2,3-difluoro-4-[1-(2-methoxyethyl)-3,5-dimethyl-pyrazol-4-yl]phenyl]-1-methyl-imidazole-2-carboxamide;

N-[3-chloro-4-[4-[2-(1-methylpyrrolidin-1-ium-1-yl)acetyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[(2S,3S)-3-hydroxy-1,1-dimethyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-(3-hydroxy-1,1-dimethyl-piperidin-1-ium-4-carbonyl)piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide;

N-[3-chloro-4-[4-(3-hydroxy-1,1-dimethyl-piperidin-1-ium-4-carbonyl)piperazine-1-carbonyl]phenyl]-5-[2,3-difluoro-4-[1-(2-methoxyethyl)-3,5-dimethyl-pyrazol-4-yl]phenyl]-1-methyl-imidazole-2-carboxamide;

N-[3-chloro-4-[4-[3-(hydroxymethyl)-4,4-dimethyl-piperazin-4-ium-1-carbonyl]piperidine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[(2R,4S)-4-hydroxy-1,1-dimethyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[(2R,4R)-4-hydroxy-1,1-dimethyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[(2S,4S)-4-hydroxy-1,1-dimethyl-pyrrolidin-1-ium-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(3-methoxypropyl)-3-methyl-pyrazol-4-yl]phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(3-methoxypropyl)-5-methyl-pyrazol-4-yl]phenyl]-1-methyl-imidazole-2-carboxamide;

N-[3-chloro-4-[4-[(3S)-4,4-dimethylmorpholin-4-ium-3-carbonyl]piperazine-1-carbonyl]phenyl]-5-[2,3-difluoro-4-[1-(3-methoxypropyl)-3-methyl-pyrazol-4-yl]phenyl]-1-methyl-imidazole-2-carboxamide;

N-[3-chloro-4-[4-[(4,4-dimethyl-2-oxo-piperazin-4-ium-1-yl)methyl]piperidine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[2-(1-methylpyrrolidin-1-ium-1-yl)acetyl]piperazine-1-carbonyl]phenyl]-5-[2,3-difluoro-4-(3-methyl-1H-pyrazol-4-yl)phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-(3-methyl-1H-pyrazol-4-yl)phenyl]-1-methyl-imidazole-2-carboxamide;

N-[3-chloro-4-[4-[2-(4-hydroxy-1,1-dimethyl-piperidin-1-ium-4-yl)acetyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[2-[4-hydroxy-4-(hydroxymethyl)-1-methyl-piperidin-1-ium-1-yl]acetyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-(3-methyl-1H-pyrazol-4-yl)phenyl]-1-methyl-imidazole-2-carboxamide;

N-[4-[4-(4-amino-1,1-dimethyl-piperidin-1-ium-4-carbonyl)piperazine-1-carbonyl]-3-chloro-phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[(4,4-dimethyl-2-oxo-piperazin-4-ium-1-yl)methyl]piperidine-1-carbonyl]phenyl]-5-[2,3-difluoro-4-(3-methyl-1H-pyrazol-4-yl)phenyl]-1-methyl-imidazole-2-carboxamide;

5-[2,3-difluoro-4-[1-(2-methoxyethyl)-3-methyl-pyrazol-4-yl]phenyl]-N-[4-[4-(3-hydroxypiperidine-4-carbonyl)piperazine-1-carbonyl]-3-methyl-phenyl]-1-methyl-imidazole-2-carboxamide;

N-[3-chloro-4-[4-[[(2S,4R)-4-hydroxypyrrolidine-2-carbonyl]amino]piperidine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-(4-hydroxypiperidine-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-(3-hydroxypiperidine-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[(2S)-5-oxopyrrolidine-2-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-(2-oxopiperidine-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-(2-pyrrolidin-1-ylacetyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-(pyrrolidine-2-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[4-[4-(3-aminobicyclo[1.1.1]pentane-1-carbonyl)piperazine-1-carbonyl]-3-chloro-phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[(2S,4R)-4-hydroxypyrrolidine-2-carbonyl]piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-[2-(dimethylamino)acetyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[[1-[2-(dimethylamino)acetyl]-4-piperidyl]methylcarbamoyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[2-(dimethylamino)acetyl]piperazine-1-carbonyl]phenyl]-5-[2,3-difluoro-4-(3-methyl-1H-pyrazol-4-yl)phenyl]-1-methyl-imidazole-2-carboxamide;

[2-[4-[2-chloro-4-[[5-[2,3-difluoro-4-(3-methyl-1H-pyrazol-4-yl)phenyl]-1-methyl-imidazole-2-carbonyl]amino]benzoyl]piperazin-1-yl]-2-oxo-ethyl]-trimethyl-ammonium;

N-[3-chloro-4-[4-[(2S,4R)-4-hydroxypyrrolidine-2-carbonyl]piperazine-1-carbonyl]phenyl]-5-[2,3-difluoro-4-(3-methyl-1H-pyrazol-4-yl)phenyl]-1-methyl-imidazole-2-carboxamide;

N-[3-chloro-4-[4-[(1,1-dimethylpiperidin-1-ium-4-yl)sulfonylamino]piperidine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[[(1R,5S)-3-[(2S,4R)-4-hydroxy-1,1-dimethyl-pyrrolidin-1-ium-2-carbonyl]-3-azabicyclo[3.1.0]hexan-6-yl]carbamoyl]phenyl]-5-[2,3-difluoro-4-[1-(2-methoxyethyl)-3,5-dimethyl-pyrazol-4-yl]phenyl]-1-methyl-imidazole-2-carboxamide;

N-[3-chloro-4-[[(1S,5R)-3-[(2S,4R)-4-hydroxy-1,1-dimethyl-pyrrolidin-1-ium-2-carbonyl]-3-azabicyclo[3.1.0]hexan-6-yl]carbamoyl]phenyl]-5-[2,3-difluoro-4-[1-(2-methoxyethyl)-3,5-dimethyl-pyrazol-4-yl]phenyl]-1-methyl-imidazole-2-carboxamide;

bis(3-aminopropyl)-(carboxymethyl)-[4-[4-[2-chloro-4-[[5-[2,3-difluoro-4-(3-methyl-1H-pyrazol-4-yl)phenyl]-1-methyl-imidazole-2-carbonyl]amino]benzoyl]piperazin-1-yl]-4-oxo-butyl]ammonium;

bis(azetidin-3-ylmethyl)-(carboxymethyl)-[4-[4-[2-chloro-4-[[5-[2,3-difluoro-4-(3-methyl-1H-pyrazol-4-yl)phenyl]-1-methyl-imidazole-2-carbonyl]amino]benzoyl]piperazin-1-yl]-4-oxo-butyl]ammonium;

N-[3-chloro-4-[4-[(2S,4R)-4-hydroxy-1,1-dimethyl-pyrrolidin-1-ium-2-carbonyl]piperazine-1-carbonyl]phenyl]-5-[4-(3,5-dimethyl-1H-pyrazol-4-yl)-2,3-difluoro-phenyl]-1-methyl-imidazole-2-carboxamide;

N-[3-chloro-4-[4-(4-methoxypiperidine-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-(piperidine-4-carbonyl)piperazine-1-carbonyl]phenyl]-5-[4-[1-(2,2-difluoroethyl)-5-methyl-pyrazol-4-yl]-2,3-difluoro-phenyl]-1-methyl-imidazole-2-carboxamide;

N-[3-chloro-4-[4-[2-[(3S)-pyrrolidin-3-yl]acetyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-(piperidine-4-carbonyl)piperazine-1-carbonyl]phenyl]-5-[2-fluoro-4-[1-(2-methoxyethyl)-5-methyl-pyrazol-4-yl]-3-methyl-phenyl]-1-methyl-imidazole-2-carboxamide;

5-[2-chloro-3-fluoro-4-[1-(2-methoxyethyl)-5-methyl-pyrazol-4-yl]phenyl]-N-[3-chloro-4-[4-(piperidine-4-carbonyl)piperazine-1-carbonyl]phenyl]-1-methyl-imidazole-2-carboxamide;

N-[3-chloro-4-[4-(piperidine-4-carbonyl)piperazine-1-carbonyl]phenyl]-5-[3-fluoro-4-[1-(2-methoxyethyl)-5-methyl-pyrazol-4-yl]-2-methyl-phenyl]-1-methyl-imidazole-2-carboxamide;

N-[3-chloro-4-[4-(piperidine-4-carbonyl)piperazine-1-carbonyl]phenyl]-5-[4-[1-[2-(difluoromethoxy)ethyl]-3-(trifluoromethyl)pyrazol-4-yl]-2,3-difluoro-phenyl]-1-methyl-imidazole-2-carboxamide;

N-[3-chloro-4-(piperazine-1-carbonyl)phenyl]-5-[2,3-difluoro-4-[1-(2-methoxyethyl)-5-methyl-pyrazol-4-yl]phenyl]-1-methyl-imidazole-2-carboxamide;

5-[2,3-difluoro-4-[1-(2-methoxyethyl)-5-methyl-pyrazol-4-yl]phenyl]-N-[4-[4-[(2S,4R)-4-hydroxypyrrolidine-2-carbonyl]piperazine-1-carbonyl]-3-methyl-phenyl]-1-methyl-imidazole-2-carboxamide;

N-[3-chloro-4-[4-[(2S,4R)-4-hydroxypyrrolidine-2-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-(4-piperidylmethylcarbamoyl)phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-(piperidine-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[4-[4-[1-(2-amino-2-oxo-ethyl)piperidine-4-carbonyl]piperazine-1-carbonyl]-3-chloro-phenyl]-5-[3-fluoro-4-[3-(trifluoromethyl)-1H-pyrazol-4-yl]phenyl]-1-methyl-imidazole-2-carboxamide;

N-[3-chloro-4-[4-(piperidine-4-carbonyl)piperazine-1-carbonyl]phenyl]-5-[2,3-difluoro-4-[1-(2-methoxyethyl)-5-(methoxymethyl)pyrazol-4-yl]phenyl]-1-methyl-imidazole-2-carboxamide;

N-[4-[4-[2-(dimethylamino)acetyl]piperazine-1-carbonyl]-3-methyl-phenyl]-5-[4-[1-(2-methoxyethyl)-5-methyl-pyrazol-4-yl]phenyl]-1-methyl-imidazole-2-carboxamide;

N-[3-chloro-4-[4-[2-(dimethylamino)acetyl]piperazine-1-carbonyl]phenyl]-1-methyl-5-[4-(3-methyl-1H-pyrazol-4-yl)phenyl]imidazole-2-carboxamide;

N-[3-chloro-4-[4-[2-(dimethylamino)acetyl]piperazine-1-carbonyl]phenyl]-5-[4-(3,5-dimethyl-1H-pyrazol-4-yl)phenyl]-1-methyl-imidazole-2-carboxamide;

N-[3-chloro-4-[4-(piperidine-4-carbonyl)piperazine-1-carbonyl]phenyl]-5-[2-fluoro-6-[5-(4-methoxyphenyl)-1H-pyrazol-4-yl]-3-pyridyl]-1-methyl-imidazole-2-carboxamide;

N-[3-chloro-4-[4-(piperidine-4-carbonyl)piperazine-1-carbonyl]phenyl]-5-[2-fluoro-6-(1H-pyrazol-4-yl)-3-pyridyl]-1-methyl-imidazole-2-carboxamide;

N-[3-chloro-4-[4-(piperidine-4-carbonyl)piperazine-1-carbonyl]phenyl]-5-[2,3-difluoro-4-(3-methyl-1H-pyrazol-4-yl)phenyl]-1-methyl-imidazole-2-carboxamide;

N-[3-chloro-4-[4-(piperidine-4-carbonyl)piperazine-1-carbonyl]phenyl]-5-[2,3-difluoro-4-(1-methylpyrazol-4-yl)phenyl]-1-methyl-imidazole-2-carboxamide;

N-[3-chloro-4-[4-(piperidine-4-carbonyl)piperazine-1-carbonyl]phenyl]-5-[2,3-difluoro-4-[1-(2-methoxyethyl)pyrazol-4-yl]phenyl]-1-methyl-imidazole-2-carboxamide;

(1S,5R)-6-[[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]amino]-N-[(3R,4R)-4-hydroxypyrrolidin-3-yl]-3-azabicyclo[3.1.0]hexane-3-carboxamide;

N-[3-chloro-4-[4-(piperidine-4-carbonyl)piperazine-1-carbonyl]phenyl]-1-methyl-5-[4-(1H-pyrazol-4-yl)phenyl]imidazole-2-carboxamide;

5-[4-[1-(3-amino-3-oxo-propyl)-3-(trifluoromethyl)pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2-chloro-3-fluoro-4-[1-(2-methoxyethyl)-5-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[3-fluoro-4-[1-(2-methoxyethyl)-5-methyl-pyrazol-4-yl]-2-methyl-phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(3-hydroxy-3-methyl-butyl)-5-methyl-pyrazol-4-yl]phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[3-methyl-1-[2-(methylamino)-2-oxo-ethyl]pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[4-[1-[2-(difluoromethoxy)ethyl]-3-(trifluoromethyl)pyrazol-4-yl]-2,3-difluoro-phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-(3-hydroxy-2-methyl-propyl)-3-(trifluoromethyl)pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[4-[1-[(2S)-2,3-dihydroxypropyl]-3-(trifluoromethyl)pyrazol-4-yl]-2,3-difluoro-phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[4-[1-[2-(difluoromethoxy)ethyl]-3-methyl-pyrazol-4-yl]-2,3-difluoro-phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[4-[1-[2-(difluoromethoxy)ethyl]-5-methyl-pyrazol-4-yl]-2,3-difluoro-phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[3-isopropyl-1-(2-methoxyethyl)pyrazol-4-yl]phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[4-[5-(difluoromethyl)-1-(2-methoxyethyl)pyrazol-4-yl]-2,3-difluoro-phenyl]-1-methyl-imidazole-2-carboxamide;

5-[2,3-difluoro-4-[1-(2-methoxyethyl)-5-methyl-pyrazol-4-yl]phenyl]-N-[4-[4-[(2S,4R)-4-hydroxy-1,1-dimethyl-pyrrolidin-1-ium-2-carbonyl]piperazine-1-carbonyl]-3-methyl-phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(3-hydroxypropyl)-3-methyl-pyrazol-4-yl]phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[2,3-difluoro-4-[1-(3-hydroxypropyl)-5-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2-methoxy-4-[1-(2-methoxyethyl)-5-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[4-[1-(2-methoxyethyl)-5-methyl-pyrazol-4-yl]-2-methyl-phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[4-[5-ethyl-1-(2-methoxyethyl)pyrazol-4-yl]-2,3-difluoro-phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[5-(4-hydroxybutyl)-1H-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2-chloro-4-[1-(2-methoxyethyl)-5-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[3-fluoro-2-methoxy-4-[1-(2-methoxyethyl)-5-methyl-pyrazol-4-yl]phenyl]-1-methyl-imidazole-2-carboxamide;

N-[3-chloro-4-[4-[2-(4-hydroxy-1,1-dimethyl-piperidin-1-ium-4-yl)acetyl]piperazine-1-carbonyl]phenyl]-5-[4-

[3-ethyl-1-(2-methoxyethyl)pyrazol-4-yl]-2,3-difluoro-phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-(hydroxymethyl)-1-(2-methoxyethyl)pyrazol-4-yl]phenyl]-1-methyl-imidazole-2-carboxamide;

5-[4-[3-amino-1-(2-methoxyethyl)pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-(3-phenyl-1H-pyrazol-4-yl)phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[4-(5,6-dihydro-4H-pyrrolo[1,2-b]pyrazol-3-yl)-2,3-difluoro-phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-(fluoromethyl)-1-(2-methoxyethyl)pyrazol-4-yl]phenyl]-1-methyl-imidazole-2-carboxamide;chloride;

N-[3-chloro-4-[4-(1,1-dimethylpiperidin-1-ium-4-carbonyl)piperazine-1-carbonyl]phenyl]-5-[4-[3-chloro-1-(2-methoxyethyl)pyrazol-4-yl]-2,3-difluoro-phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[4-[5-chloro-1-(2-methoxyethyl)pyrazol-4-yl]-2,3-difluoro-phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-(2-methylsulfonylethyl)-3-(trifluoromethyl)pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-(2-hydroxypropyl)-3-(trifluoromethyl)pyrazol-4-yl]phenyl]-1-methyl-imidazole-2-carboxamide;

5-[4-[1-(4-amino-4-oxo-butyl)-3-(trifluoromethyl)pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;

5-[4-[1-(2-amino-2-oxo-ethyl)-3-(trifluoromethyl)pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-(2-methoxyethyl)-3-(trifluoromethyl)pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-(2-morpholinoethyl)-5-(trifluoromethyl)pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-(3-methoxypropyl)-3-(trifluoromethyl)pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-(tetrahydropyran-4-ylmethyl)pyrazol-4-yl]phenyl]-1-methyl-imidazole-2-carboxamide;

5-[4-[1-(5-amino-2-pyridyl)-3-methyl-pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;chloride;

N-[3-chloro-4-[4-(1,1-dimethylpiperidin-1-ium-4-carbonyl)piperazine-1-carbonyl]phenyl]-5-[2,3-difluoro-4-[3-methyl-1-(2-pyridylmethyl)pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-(1H-pyrazol-4-yl)pyrazol-4-yl]phenyl]-1-methyl-imidazole-2-carboxamide;

5-[4-[1-[(5-amino-2-pyridyl)methyl]-3-methyl-pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide; chloride;

N-[3-chloro-4-[4-(1,1-dimethylpiperidin-1-ium-4-carbonyl)piperazine-1-carbonyl]phenyl]-5-[2,3-difluoro-4-[3-(2-methylpyrazol-3-yl)-1H-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-(3-fluorophenyl)-1H-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-[2-(2-oxo-1-pyridyl)ethyl]pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-(1-methylpyrazol-4-yl)-1H-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-(1H-pyrazol-4-yl)-1H-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-(2-methoxyethyl)-3-phenyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-(2-pyridyl)pyrazol-4-yl]phenyl]-1-methyl-imidazole-2-carboxamide;

[2-[4-[2-chloro-4-[[1-methyl-5-[4-(3-methyl-1H-pyrazol-4-yl)phenyl]imidazole-2-carbonyl]amino]benzoyl]piperazin-1-yl]-2-oxo-ethyl]-trimethyl-ammonium;

[2-[4-[2-chloro-4-[[5-[4-(3,5-dimethyl-1H-pyrazol-4-yl)phenyl]-1-methyl-imidazole-2-carbonyl]amino]benzoyl]piperazin-1-yl]-2-oxo-ethyl]-trimethyl-ammonium;

4-chloro-N-[3-chloro-4-[4-(1,1-dimethylpiperidin-1-ium-4-carbonyl)piperazine-1-carbonyl]phenyl]-5-[2,3-difluoro-4-[1-(2-methoxyethyl)-5-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-[2-(6-methoxy-2-pyridyl)ethyl]-3-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-[(6-methoxy-2-pyridyl)methyl]-3-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-(1H-triazol-4-ylmethyl)pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2-fluoro-6-[1-

(2-methoxyethyl)-5-methyl-pyrazol-4-yl]-3-pyridyl]-1-methyl-imidazole-2-carboxamide;
N-[3-chloro-4-[4-[(2S,4R)-4-hydroxy-1,1-dimethyl-pyrrolidin-1-ium-2-carbonyl]piperazine-1-carbonyl]phenyl]-5-[4-[1-(3-cyanopropyl)-3,5-dimethyl-pyrazol-4-yl]-2,3-difluoro-phenyl]-1-methyl-imidazole-2-carboxamide;
N-[3-chloro-4-[4-(1,1-dimethylpiperidin-1-ium-4-carbonyl)piperazine-1-carbonyl]phenyl]-5-[2-fluoro-6-[5-(4-methoxyphenyl)-1H-pyrazol-4-yl]-3-pyridyl]-1-methyl-imidazole-2-carboxamide;
(1R,5S)-6-[[2-chloro-4-[[5-[2,3-difluoro-4-[1-(2-methoxyethyl)-3,5-dimethyl-pyrazol-4-yl]phenyl]-1-methyl-imidazole-2-carbonyl]amino]benzoyl]amino]-N-[(3R,4R)-4-hydroxy-1,1-dimethyl-pyrrolidin-1-ium-3-yl]-3-azabicyclo[3.1.0]hexane-3-carboxamide;
5-[4-[5-[(3-amino-3-oxo-propyl)amino]-2-pyridyl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;
5-[4-(5-amino-3-methyl-2-pyridyl)-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;
5-[4-(5-amino-2-pyridyl)-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;
(1S,5R)-6-[[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]amino]-N-[(3R,4R)-4-hydroxy-1,1-dimethyl-pyrrolidin-1-ium-3-yl]-3-azabicyclo[3.1.0]hexane-3-carboxamide;
N-[3-chloro-4-[4-(1,1-dimethylpiperidin-1-ium-4-carbonyl)piperazine-1-carbonyl]phenyl]-5-[2-fluoro-6-[1-(2-methoxyethyl)-3,5-dimethyl-pyrazol-4-yl]-3-pyridyl]-1-methyl-imidazole-2-carboxamide;
N-[3-chloro-4-[4-(1,1-dimethylpiperidin-1-ium-4-carbonyl)piperazine-1-carbonyl]phenyl]-5-[2,3-difluoro-4-[1-[2-(isopropylamino)-2-oxo-ethyl]-3-methyl-pyrazol-4-yl]phenyl]-1-methyl-imidazole-2-carboxamide;
5-[4-[1-[2-(tert-butylamino)-2-oxo-ethyl]-3-methyl-pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;
5-[4-[1-[2-(1-bicyclo[1.1.1]pentanylamino)-2-oxo-ethyl]-3-methyl-pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;
N-[3-chloro-4-[4-(1,1-dimethylpiperidin-1-ium-4-carbonyl)piperazine-1-carbonyl]phenyl]-5-[4-[1-[2-[(3-cyano-1-bicyclo[1.1.1]pentanyl)amino]-2-oxo-ethyl]-3-methyl-pyrazol-4-yl]-2,3-difluoro-phenyl]-1-methyl-imidazole-2-carboxamide;
5-[4-[1-(2-anilino-2-oxo-ethyl)-3-methyl-pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;
N-[3-chloro-4-[4-(1,1-dimethylpiperidin-1-ium-4-carbonyl)piperazine-1-carbonyl]phenyl]-5-[2,3-difluoro-4-[1-[2-(2-fluoroanilino)-2-oxo-ethyl]-3-methyl-pyrazol-4-yl]phenyl]-1-methyl-imidazole-2-carboxamide;
N-[3-chloro-4-[4-(1,1-dimethylpiperidin-1-ium-4-carbonyl)piperazine-1-carbonyl]phenyl]-5-[2,3-difluoro-4-[1-[2-(2-methoxyanilino)-2-oxo-ethyl]-3-methyl-pyrazol-4-yl]phenyl]-1-methyl-imidazole-2-carboxamide;
N-[3-chloro-4-[4-(1,1-dimethylpiperidin-1-ium-4-carbonyl)piperazine-1-carbonyl]phenyl]-5-[2,3-difluoro-4-[1-[2-(4-fluoroanilino)-2-oxo-ethyl]-3-methyl-pyrazol-4-yl]phenyl]-1-methyl-imidazole-2-carboxamide;
N-[3-chloro-4-[4-(1,1-dimethylpiperidin-1-ium-4-carbonyl)piperazine-1-carbonyl]phenyl]-5-[4-[1-[2-(cyclohexylamino)-2-oxo-ethyl]-3-methyl-pyrazol-4-yl]-2,3-difluoro-phenyl]-1-methyl-imidazole-2-carboxamide;
N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(thiazol-2-ylamino)ethyl]pyrazol-4-yl]phenyl]-1-methyl-imidazole-2-carboxamide;
N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(1H-pyrazol-4-ylamino)ethyl]pyrazol-4-yl]phenyl]-1-methyl-imidazole-2-carboxamide;
N-[3-chloro-4-[4-(1,1-dimethylpiperidin-1-ium-4-carbonyl)piperazine-1-carbonyl]phenyl]-5-[2,3-difluoro-4-[3-methyl-1-[2-[(1-methylpyrazol-4-yl)amino]-2-oxo-ethyl]pyrazol-4-yl]phenyl]-1-methyl-imidazole-2-carboxamide;
N-[3-chloro-4-[4-(1,1-dimethylpiperidin-1-ium-4-carbonyl)piperazine-1-carbonyl]phenyl]-5-[2,3-difluoro-4-[1-[2-(3-fluoroanilino)-2-oxo-ethyl]-3-methyl-pyrazol-4-yl]phenyl]-1-methyl-imidazole-2-carboxamide; chloride;
N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(2-pyridylamino)ethyl]pyrazol-4-yl]phenyl]-1-methyl-imidazole-2-carboxamide;
N-[3-chloro-4-[4-(1,1-dimethylpiperidin-1-ium-4-carbonyl)piperazine-1-carbonyl]phenyl]-5-[2,3-difluoro-4-[3-methyl-1-[2-[(1-methylpyridin-1-ium-3-yl)amino]-2-oxo-ethyl]pyrazol-4-yl]phenyl]-1-methyl-imidazole-2-carboxamide;diformate;
N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(pyrimidin-2-ylamino)ethyl]pyrazol-4-yl]phenyl]-1-methyl-imidazole-2-carboxamide;
N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(4-pyridylamino)ethyl]pyrazol-4-yl]phenyl]-1-methyl-imidazole-2-carboxamide; chloride;
5-[4-[1-[2-(tert-butylamino)-2-oxo-ethyl]-5-methyl-pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;
N-[3-chloro-4-[4-(1,1-dimethylpiperidin-1-ium-4-carbonyl)piperazine-1-carbonyl]phenyl]-5-[2,3-difluoro-4-[5-methyl-1-[2-oxo-2-(2-pyridylamino)ethyl]pyrazol-4-yl]phenyl]-1-methyl-imidazole-2-carboxamide;
N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(tetrahydrofuran-3-ylamino)ethyl]pyrazol-4-yl]phenyl]-1-methyl-imidazole-2-carboxamide;
N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(tetrahydropyran-2-ylamino)ethyl]pyrazol-4-yl]phenyl]-1-methyl-imidazole-2-carboxamide;
N-[3-chloro-4-[4-(1,1-dimethylpiperidin-1-ium-4-carbonyl)piperazine-1-carbonyl]phenyl]-5-[2,3-difluoro-4-

[3-methyl-1-[2-oxo-2-(tetrahydropyran-3-ylamino) ethyl]pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(pyridazin-3-ylamino)ethyl] pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[4-[1-[2-[(1,1-dimethylpiperidin-1-ium-3-yl)amino]-2-oxo-ethyl]-3-methyl-pyrazol-4-yl]-2,3-difluoro-phenyl]-1-methyl-imidazole-2-carboxamide;diformate;

N-[3-chloro-4-[4-(1,1-dimethylpiperidin-1-ium-4-carbonyl)piperazine-1-carbonyl]phenyl]-5-[2,3-difluoro-4-[5-methyl-1-[2-oxo-2-(pyridazin-3-ylamino)ethyl] pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[4-[1-[2-[(4,4-difluorocyclohexyl)amino]-2-oxo-ethyl]-3-methyl-pyrazol-4-yl]-2,3-difluoro-phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(3-pyridylamino)ethyl]pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-[2-[(5-methoxy-2-pyridyl)amino]-2-oxo-ethyl]-3-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(1-piperidyl)ethyl]pyrazol-4-yl] phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[4-[1-[2-[4-(4,4-dimethylpiperazin-4-ium-1-carbonyl)anilino]-2-oxo-ethyl]-3-methyl-pyrazol-4-yl]-2,3-difluoro-phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-[2-[(6-fluoropyridazin-3-yl)amino]-2-oxo-ethyl]-3-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-[2-[[(1S,2S)-2-methoxycyclohexyl]amino]-2-oxo-ethyl]-3-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-[2-oxo-2-(pyridazin-4-ylamino)ethyl] pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[4-[1-[2-[(6-cyano-3-pyridyl)amino]-2-oxo-ethyl]-3-methyl-pyrazol-4-yl]-2,3-difluoro-phenyl]-1-methyl-imidazole-2-carboxamide;

N-[2-[4-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]-2,3-difluoro-phenyl]-5-methyl-pyrazol-1-yl]ethyl]pyridine-2-carboxamide;

N-[2-[4-[4-[2-[[3-chloro-4-[4-(1,1-dimethylpiperidin-1-ium-4-carbonyl)piperazine-1-carbonyl]phenyl]carbamoyl]-3-methyl-imidazol-4-yl]-2,3-difluoro-phenyl]-3-methyl-pyrazol-1-yl]ethyl]pyridine-2-carboxamide;

N-[3-chloro-4-[4-(1,1-dimethylpiperidin-1-ium-4-carbonyl)piperazine-1-carbonyl]phenyl]-5-[2,3-difluoro-4-[1-[2-[(4-fluorophenyl)sulfonylamino]ethyl]-3-methyl-pyrazol-4-yl]phenyl]-1-methyl-imidazole-2-carboxamide;

5-[4-[1-[2-(tert-butylcarbamoylamino)ethyl]-5-methyl-pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;

5-[4-[1-[2-(tert-butylcarbamoylamino)ethyl]-3-methyl-pyrazol-4-yl]-2,3-difluoro-phenyl]-N-[3-chloro-4-[4-(1,1-dimethylpiperidin-1-ium-4-carbonyl)piperazine-1-carbonyl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[5-methyl-1-[2-(2-pyridylcarbamoylamino)ethyl]pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-[2-(2-pyridylcarbamoylamino)ethyl]pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-[2-(pyrrolidine-1-carbonylamino)ethyl] pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[5-(2-pyridyl)-1H-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[5-(4-methoxyphenyl)-1H-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[5-(3-methoxyphenyl)-1H-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[5-(2-methoxyphenyl)-1H-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-(5-thiazol-4-yl-1H-pyrazol-4-yl)phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-(5-tetrahydropyran-4-yl-1H-pyrazol-4-yl)phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[4-[5-(3,6-dihydro-2H-pyran-4-yl)-1H-pyrazol-4-yl]-2,3-difluoro-phenyl]-1-methyl-imidazole-2-carboxamide;

N-[4-[4-[1-(azetidin-3-ylmethyl)-1-methyl-piperidin-1-ium-4-carbonyl]piperazine-1-carbonyl]-3-chloro-phenyl]-5-[2,3-difluoro-4-(3-methyl-1H-pyrazol-4-yl)phenyl]-1-methyl-imidazole-2-carboxamide;

5-[4-[1-[2-(2-aminoethoxy)ethyl]-3,5-dimethyl-pyrazol-4-yl]-2,3-difluoro-phenyl]-N-[3-chloro-4-[4-[(2S,4R)-

4-hydroxy-1,1-dimethyl-pyrrolidin-1-ium-2-carbonyl]piperazine-1-carbonyl]phenyl]-1-methyl-imidazole-2-carboxamide;

N-[3-chloro-4-[4-[(2S,4R)-4-hydroxy-1,1-dimethyl-1$\lambda^5$-azolidine-2-carbonyl]piperazine-1-carbonyl]phenyl]-5-[4-[1-[2-(difluoromethoxy)ethyl]-3,5-dimethyl-pyrazol-4-yl]-2,3-difluoro-phenyl]-1-methyl-imidazole-2-carboxamide;

N-[3-chloro-4-[4-[(2S,4R)-4-hydroxy-1,1-dimethyl-pyrrolidin-1-ium-2-carbonyl]piperazine-1-carbonyl]phenyl]-5-[4-[1-[(2,2-difluorocyclopropyl)methyl]-3,5-dimethyl-pyrazol-4-yl]-2,3-difluoro-phenyl]-1-methyl-imidazole-2-carboxamide;

N-[4-[4-(3-benzyl-3-aza-6-azoniaspiro[5.5]undecane-9-carbonyl)piperazine-1-carbonyl]-3-chloro-phenyl]-5-[2,3-difluoro-4-[1-(2-methoxyethyl)-3-methyl-pyrazol-4-yl]phenyl]-1-methyl-imidazole-2-carboxamide;

cis 2-[1-(azetidin-3-ylmethyl)-4-[4-[2-chloro-4-[[5-[2,3-difluoro-4-[1-[2-[(6-fluoropyridazin-3-yl)amino]-2-oxo-ethyl]-3-methyl-pyrazol-4-yl]phenyl]-1-methyl-imidazole-2-carbonyl]amino]benzoyl]piperazine-1-carbonyl]piperidin-1-ium-1-yl]acetic acid;

N-[3-chloro-4-[4-(1,1-dimethylpiperidin-1-ium-4-carbonyl)piperazine-1-carbonyl]phenyl]-5-[2,3-difluoro-4-[3-methyl-1-[2-[(6-methyl-3-pyridyl)carbamoylamino]ethyl]pyrazol-4-yl]phenyl]-1-methyl-imidazole-2-carboxamide;

N-[3-chloro-4-[4-(4-oxo-3-aza-6-azoniaspiro[5.5]undecane-9-carbonyl)piperazine-1-carbonyl]phenyl]-5-[2,3-difluoro-4-[1-(2-methoxyethyl)-3-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[3-fluoro-4-[1-[2-[(6-fluoropyridazin-3-yl)amino]-2-oxo-ethyl]-3-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[4-[1-[2-[(6-fluoropyridazin-3-yl)amino]-2-oxo-ethyl]-3-methyl-pyrazol-4-yl]phenyl]-1-methyl-imidazole-2-carboxamide;

bis(4-aminobutyl)-(carboxymethyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]-3-methyl-piperazino]-4-keto-butyl]ammonium;

N-[3-chloro-4-[4-(1,1-dimethylpiperidin-1-ium-4-carbonyl)piperazine-1-carbonyl]phenyl]-5-[2,3-difluoro-4-[3-methyl-1-[2-[(6-methylpyridazin-3-yl)amino]-2-oxo-ethyl]pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[1-[2-[(6-methoxypyridazin-3-yl)amino]-2-oxo-ethyl]-3-methyl-pyrazol-4-yl]phenyl]-1-methyl-imidazole-2-carboxamide;

N-[3-chloro-4-[4-(1,1-dimethylpiperidin-1-ium-4-carbonyl)piperazine-1-carbonyl]phenyl]-5-[2,3-difluoro-4-[3-methyl-1-[2-[(6-morpholinopyridazin-3-yl)amino]-2-oxo-ethyl]pyrazol-4-yl]phenyl]-1-methyl-imidazole-2-carboxamide;

cis 2-[1-(azetidin-3-ylmethyl)-4-[4-[2-chloro-4-[[5-[3-fluoro-4-[1-(2-methoxyethyl)-3-methyl-pyrazol-4-yl]phenyl]-1-methyl-imidazole-2-carbonyl]amino]benzoyl]piperazine-1-carbonyl]piperidin-1-ium-1-yl]acetic acid;

cis 2-[1-(azetidin-3-ylmethyl)-4-[4-[2-chloro-4-[[5-[3-fluoro-4-[1-(2-methoxyethyl)-5-methyl-pyrazol-4-yl]-2-methyl-phenyl]-1-methyl-imidazole-2-carbonyl]amino]benzoyl]piperazine-1-carbonyl]piperidin-1-ium-1-yl]acetic acid;

2-[2-(3-aminopropyl)-4-[3-[[1-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]isonipecotoyl]amino]propyl]pyridin-1-ium-1-yl]acetic acid;

azetidin-3-ylmethyl-(carboxymethyl)-[4-[4-[2-chloro-4-[[5-[4-[1-[2-(difluoromethoxy)ethyl]-5-methyl-pyrazol-4-yl]-3-fluoro-2-methyl-phenyl]-1-methyl-imidazole-2-carbonyl]amino]benzoyl]piperazin-1-yl]-4-oxo-butyl]-methyl-ammonium;formic acid;

2-[1-(azetidin-3-ylmethyl)-4-[4-[2-chloro-4-[[5-[4-[1-[2-(difluoromethoxy)ethyl]-5-methyl-pyrazol-4-yl]-3-fluoro-2-methyl-phenyl]-1-methyl-imidazole-2-carbonyl]amino]benzoyl]piperazine-1-carbonyl]piperidin-1-ium-1-yl]acetic acid;

3-aminopropyl-(carboxymethyl)-[4-[4-[2-chloro-4-[[5-[4-[1-[2-(difluoromethoxy)ethyl]-5-methyl-pyrazol-4-yl]-3-fluoro-2-methyl-phenyl]-1-methyl-imidazole-2-carbonyl]amino]benzoyl]piperazin-1-yl]-4-oxo-butyl]-methyl-ammonium;

2-[1-(azetidin-3-ylmethyl)-4-[4-[2-chloro-4-[[5-[3-fluoro-4-[1-(2-methoxyethyl)-5-methyl-pyrazol-4-yl]phenyl]-1-methyl-imidazole-2-carbonyl]amino]benzoyl]piperazine-1-carbonyl]piperidin-1-ium-1-yl]acetic acid;

carboxymethyl-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]-bis[2-(dimethylamino)ethyl]ammonium;

cis 2-[1-(azetidin-3-ylmethyl)-4-[4-[2-chloro-4-[[5-[4-[1-[2-(difluoromethoxy)ethyl]-3-methyl-pyrazol-4-yl]-2,3-difluoro-phenyl]-1-methyl-imidazole-2-carbonyl]amino]benzoyl]piperazine-1-carbonyl]piperidin-1-ium-1-yl]acetate;

bis(3-aminopropyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]-methyl-ammonium;

N-[3-chloro-4-[4-[(2S,4R)-4-hydroxy-1,1-dimethyl-pyrrolidin-1-ium-2-carbonyl]piperazine-1-carbonyl]phenyl]-5-[3-fluoro-4-[1-(2-methoxyethyl)-5-methyl-pyrazol-4-yl]-2-methyl-phenyl]-1-methyl-imidazole-2-carboxamide;

3-aminopropyl-(carboxymethyl)-[4-[4-[2-chloro-4-[[5-[3-fluoro-4-[1-(2-methoxyethyl)-5-methyl-pyrazol-4-yl]-2-methyl-phenyl]-1-methyl-imidazole-2-carbonyl]amino]benzoyl]piperazino]-4-keto-butyl]-methyl-ammonium 0.1:1 2,2,2-trifluoroacetic acid;

bis(4-aminobutyl)-(carboxymethyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]ammonium;

cis 2-[1-(azetidin-3-ylmethyl)-4-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]piperidin-1-ium-1-yl]acetic acid;

trans 2-[1-(azetidin-3-ylmethyl)-4-[4-[2-chloro-4-[[5-[2,3-difluoro-4-[1-(2-methoxyethyl)-3-methyl-pyrazol-4-yl]phenyl]-1-methyl-imidazole-2-carbonyl]amino]benzoyl]piperazine-1-carbonyl]piperidin-1-ium-1-yl]acetic acid;

2-[1-(azetidin-3-ylmethyl)-4-[5-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazino]-5-keto-pentanoyl]piperazin-1-ium-1-yl]acetic acid;

2-[1-(3-aminopropyl)-4-[5-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazino]-5-keto-pentanoyl]piperazin-1-ium-1-yl]acetic acid;

2-[1-(azetidin-3-ylmethyl)-4-[(1S,5R)-6-[[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]amino]-3-azabicyclo[3.1.0]hexane-3-carbonyl]piperidin-1-ium-1-yl]acetic acid;

2-[1-(azetidin-3-ylmethyl)-4-[[1-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]-4-piperidyl]-methyl-carbamoyl]piperidin-1-ium-1-yl]acetic acid;

azetidin-3-ylmethyl-(carboxymethyl)-[4-[4-[2-chloro-4-[[5-[2,3-difluoro-4-[1-(2-methoxyethyl)-5-methyl-pyrazol-4-yl]phenyl]-1-methyl-imidazole-2-carbonyl]amino]benzoyl]piperazin-1-yl]-4-oxo-butyl]-methyl-ammonium;

cis 2-[1-(azetidin-3-ylmethyl)-4-[4-[4-[[5-[2,3-difluoro-4-[1-(2-methoxyethyl)-3-methylpyrazol-4-yl]phenyl]-1-methylimidazole-2-carbonyl]amino]-2-methylbenzoyl]piperazine-1-carbonyl]piperidin-1-ium-1-yl]acetic acid;

cis 2-[1-(azetidin-3-ylmethyl)-4-[4-[4-[[5-[3-fluoro-4-[1-(2-methoxyethyl)-3-methyl-pyrazol-4-yl]phenyl]-1-methyl-imidazole-2-carbonyl]amino]-2-methyl-benzoyl]piperazine-1-carbonyl]piperidin-1-ium-1-yl]acetic acid; and cis 2-[1-(azetidin-3-ylmethyl)-4-[4-[4-[[5-[3-fluoro-4-[1-(2-methoxyethyl)-5-methylpyrazol-4-yl]-2-methylphenyl]-1-methylimidazole-2-carbonyl]amino]-2-methyl-benzoyl]piperazine-1-carbonyl]piperidin-1-ium-1-yl]acetic acid.

14. A pharmaceutical composition comprising a compound of formula (I) according to claim 1, or a pharmaceutically acceptable salt thereof, and a therapeutically inert carrier.

15. A method for the treatment of infections caused by *Enterococcus faecium, Staphylococcus aureus, Klebsiella pneumoniae, Acinetobacter baumannii, Pseudomonas aeruginosa, Enterobacter* species or *E. coli*, or a combination thereof, which method comprises administering a compound of formula (I) according to claim 1, or a pharmaceutically acceptable salt thereof, to a mammal.

* * * * *